US012520720B2

(12) United States Patent
Jeon et al.

(10) Patent No.: US 12,520,720 B2
(45) Date of Patent: Jan. 6, 2026

(54) HETEROCYCLIC COMPOUND AND ORGANIC LIGHT-EMITTING DEVICE

(71) Applicant: Samsung Electronics Co., Ltd., Suwon-si (KR)

(72) Inventors: Soonok Jeon, Suwon-si (KR); Yeonsook Chung, Seoul (KR); Hasup Lee, Seoul (KR); Myungsun Sim, Suwon-si (KR); Sooghang Ihn, Hwaseong-si (KR); Yasushi Koishikawa, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 1199 days.

(21) Appl. No.: 16/549,614

(22) Filed: Aug. 23, 2019

(65) Prior Publication Data

US 2020/0083458 A1 Mar. 12, 2020

(30) Foreign Application Priority Data

Aug. 27, 2018 (KR) ........................ 10-2018-0100569

(51) Int. Cl.

| | |
|---|---|
| ***H10K 85/60*** | (2023.01) |
| ***C07D 401/14*** | (2006.01) |
| ***C07D 403/10*** | (2006.01) |
| ***C07D 403/14*** | (2006.01) |
| ***C07D 491/048*** | (2006.01) |
| ***C09K 11/06*** | (2006.01) |
| ***H10K 50/11*** | (2023.01) |

(52) U.S. Cl.

CPC ......... *H10K 85/654* (2023.02); *C07D 401/14* (2013.01); *C07D 403/10* (2013.01); *C07D 403/14* (2013.01); *C07D 491/048* (2013.01); *C09K 11/06* (2013.01); *H10K 85/657* (2023.02); *H10K 85/6572* (2023.02); *C09K 2211/1018* (2013.01); *H10K 50/11* (2023.02)

(58) Field of Classification Search

CPC .. C07D 401/14; C07D 403/10; C07D 403/14; C07D 491/048; H10K 85/649; H10K 85/654; H10K 85/657; H01L 51/0062; H01L 51/0067; H01L 51/0071; H01L 51/5012; C09K 11/06

See application file for complete search history.

(56) References Cited

U.S. PATENT DOCUMENTS

| | | | | |
|---|---|---|---|---|
| 8,324,403 | B2 | 12/2012 | Yabe et al. | |
| 9,312,499 | B1 | 4/2016 | Zeng | |
| 2005/0202278 | A1 * | 9/2005 | Mishima | H10K 50/12 313/506 |
| 2008/0145699 | A1 * | 6/2008 | Yabe | C07D 401/14 546/276.7 |
| 2009/0066223 | A1 | 3/2009 | Yabe et al. | |
| 2009/0134779 | A1 | 5/2009 | Kawami et al. | |
| 2009/0191426 | A2 | 7/2009 | Yabe et al. | |
| 2012/0126692 | A1 | 5/2012 | Ise et al. | |
| 2012/0153816 | A1 * | 6/2012 | Takizawa | C07D 409/04 546/4 |
| 2013/0240796 | A1 | 9/2013 | Parham et al. | |
| 2013/0264561 | A1 * | 10/2013 | Dobbs | H10K 85/6576 257/40 |
| 2016/0293850 | A1 | 10/2016 | Lee | |
| 2017/0186962 | A1 | 6/2017 | Ren et al. | |
| 2017/0200902 | A1 * | 7/2017 | Lee | C09K 11/06 |
| 2018/0053901 | A1 | 2/2018 | Yoshida et al. | |
| 2018/0123049 | A1 | 5/2018 | Lee et al. | |
| 2018/0145262 | A1 | 5/2018 | Zeng et al. | |
| 2019/0181359 | A1 * | 6/2019 | Seifermann | C07D 403/14 |
| 2019/0214570 | A1 * | 7/2019 | Inayama | C07D 487/04 |
| 2019/0284174 | A1 | 9/2019 | Bergmann et al. | |
| 2020/0212314 | A1 * | 7/2020 | Numata | H10K 50/11 |

FOREIGN PATENT DOCUMENTS

| | | | |
|---|---|---|---|
| CN | 101087776 | A | 12/2007 |
| CN | 106187861 | A | 12/2016 |
| CN | 107935914 | A | 4/2018 |
| CN | 107954922 | A | 4/2018 |
| CN | 107987009 | A | 5/2018 |
| EP | 1829871 | A1 | 9/2007 |
| EP | 2166584 | A1 | 3/2010 |
| EP | 3476915 | A1 | 5/2019 |
| JP | 2006199679 | A | 8/2006 |

(Continued)

OTHER PUBLICATIONS

Lee C et al., machine translation of KR-20170113808-A (2017) pp. 1-17. (Year: 2017).*

Dong Ryun Lee, et al., "Bis(diphenyltriazine) as a new acceptor of efficient thermally activated delayed fluorescent emitters", School of Chemical Engineering, Sungkyunkwan University, 31 pp.

Extended European search report issued by the European Patent Office on Dec. 10, 2019 in the examination of the European Patent Application No. 19192772.2, which corresponds to the U.S. Application above.

Yuanyuan Wang, et al., A Series of Bipolar CBP Derivatives with Introduction of a Electron-deficient Moiety for Efficient Green Organic Light-Emitting Diodes, Organic Electronics, vol. 61, Apr. 26, 2018 (Apr. 26, 2018), pp. 142-150, KP055646445.

(Continued)

*Primary Examiner* — Dylan C Kershner

(74) *Attorney, Agent, or Firm* — CANTOR COLBURN LLP

(57) ABSTRACT

A heterocyclic compound represented by Formula 1:

Formula 1

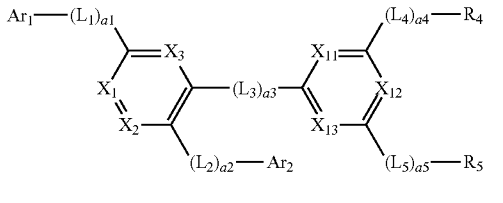

wherein, in Formula 1, groups and variables are the same as described in the specification.

15 Claims, 1 Drawing Sheet

(56) References Cited

FOREIGN PATENT DOCUMENTS

| | | | | |
|---|---|---|---|---|
| JP | 200788433 A | | 4/2007 | |
| JP | 4474493 B1 | | 3/2010 | |
| JP | 2019156843 A | | 9/2019 | |
| JP | 2019175999 A | | 10/2019 | |
| KR | 20070090952 A | | 9/2007 | |
| KR | 1020140083898 A | | 7/2014 | |
| KR | 1020140120975 A | | 10/2014 | |
| KR | 1020150002072 A | | 1/2015 | |
| KR | 1020150129282 A | | 11/2015 | |
| KR | 1020160126792 A | | 11/2016 | |
| KR | 20170113808 A | * | 10/2017 | |
| KR | 1020170113808 A | | 10/2017 | |
| KR | 20170134264 A | | 12/2017 | |
| KR | 101926771 B1 | | 12/2018 | |
| KR | 1020170134264 A | | 9/2019 | |
| WO | 2006095539 A1 | | 9/2006 | |
| WO | 2006126542 A1 | | 11/2006 | |
| WO | 2009008100 A1 | | 1/2009 | |
| WO | 2010074422 A1 | | 7/2010 | |
| WO | 2012069121 A1 | | 5/2012 | |
| WO | WO-2016024745 A2 | * | 2/2016 | C07D 213/06 |
| WO | 2016158540 A1 | | 10/2016 | |
| WO | 2016159479 A1 | | 10/2016 | |
| WO | 2017171420 A1 | | 10/2017 | |
| WO | 2018043761 A1 | | 3/2018 | |
| WO | 2019038448 A1 | | 2/2019 | |
| WO | 2019086667 A1 | | 5/2019 | |
| WO | 2019101594 A1 | | 5/2019 | |
| WO | WO-2019162332 A1 | * | 8/2019 | C07D 401/14 |
| WO | WO-2020091521 A1 | * | 5/2020 | C07D 403/04 |

OTHER PUBLICATIONS

English Abstract of KR 101926771.
English Abstract of KR 10-2017-0113808.
English Translation of Office Action issued Apr. 6, 2023, in corresponding KR Patent Application No. 10-2018-0100569, 10 pp.
Office Action issued Apr. 6, 2023, in corresponding KR Patent Application No. 10-2018-0100569, 10 pp.
"A Series of new bipolar CBP derivatives with introduction of a electron deficient moiety for efficient green organic light-emitting diodes", Organic Electronics, Apr. 26, 2018, vol. 61, p. 142-150.
English Abstract of CN107935914.
English Abstract of JP2019-175999.
English Abstract of KR20170134264.
English Abstract of WO2017-171420.
English Translation of Office Action dated Jul. 18, 2023, issued in corresponding JP Patent Application No. 2019-154369, 16 pp.
Office Action dated Jul. 18, 2023, issued in corresponding JP Patent Application No. 2019-154369, 9 pp.
English Abstract of CN 106187861.
English Abstract of KR 10-2017-0134264.

* cited by examiner

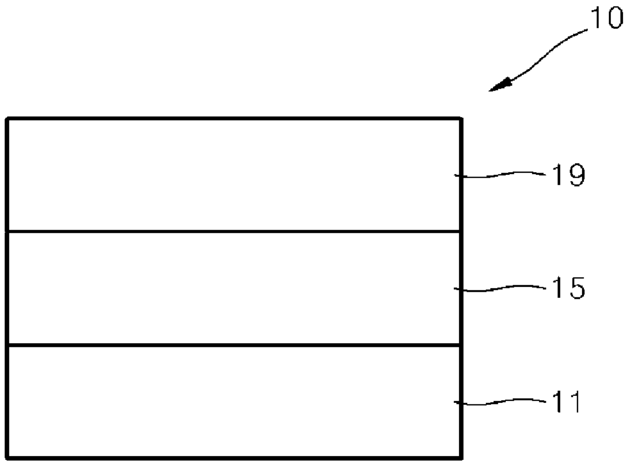
10
19
15
11

HETEROCYCLIC COMPOUND AND ORGANIC LIGHT-EMITTING DEVICE

CROSS-REFERENCE TO RELATED APPLICATION

This application claims priority to Korean Patent Application No. 10-2018-0100569, filed on Aug. 27, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to a heterocyclic compound and an organic light-emitting device including the same.

2. Description of the Related Art

Organic light-emitting devices (OLEDs) are self-emission devices that produce full-color images, and that also have wide viewing angles, high contrast ratios, short response times, and excellent characteristics in terms of brightness, driving voltage, and response speed, compared to the devices in the art.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a novel heterocyclic compound and an organic light-emitting device including the same.

Additional aspects will be set forth in part in the description which follows and, in part, will be apparent from the description, or may be learned by practice of the presented embodiments.

An aspect of the present disclosure provides a heterocyclic compound represented by Formula 1:

Formula 1

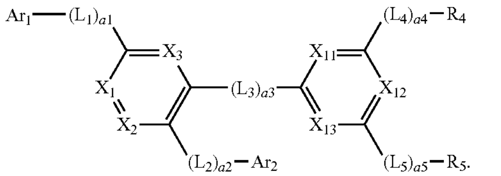

In Formula 1, $X_1$ may be N or $C(R_1)$, $X_2$ may be N or $C(R_2)$, and $X_3$ may be N or $C(R_3)$, wherein i) one selected from $X_1$ to $X_3$ may be N, and the others thereof may not be N; or ii) each of $X_1$ to $X_3$ may not be N, $R_1$ to $R_3$ may each independently be hydrogen, deuterium, a $C_1$-$C_{20}$ alkyl group, a $C_1$-$C_{20}$ alkyl group substituted with at least one deuterium, a $C_1$-$C_{20}$ alkoxy group, a $C_1$-$C_{20}$ alkoxy group substituted with at least one deuterium, or —$Si(Q_{101})(Q_{102})(Q_{103})$, $L_1$ and $L_2$ may each independently be selected from:

a single bond; and a $C_5$-$C_{60}$ carbocyclic group, a pyridine group, and a π electron-rich $C_1$-$C_{10}$ heterocyclic group, each unsubstituted or substituted with at least one $R_{10a}$, $L_3$ to $L_5$ may each independently be selected from:

a single bond; and a $C_5$-$C_{60}$ carbocyclic group and a $C_1$-$C_{60}$ heterocyclic group, each unsubstituted or substituted with at least one $R_{10a}$, a1 to a5 may each independently be an integer from 1 to 5, and $Ar_1$ and $Ar_2$ may each independently be a group represented by Formula 3A, a group represented by Formula 3B, a group represented by Formula 3C, a group represented by Formula 3D, a group represented by Formula 3E, a group represented by Formula 3F, or a $C_6$-$C_{60}$ aryl group unsubstituted or substituted with at least one $Z_{31}$:

3A

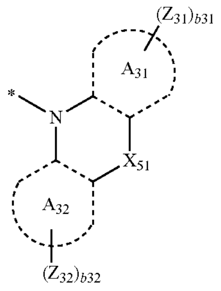

3B

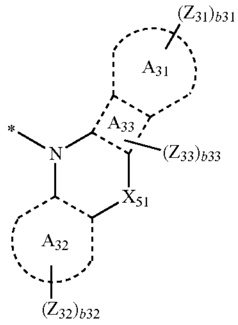

3C

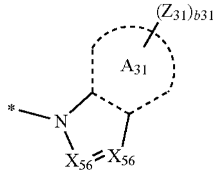

-continued

3D

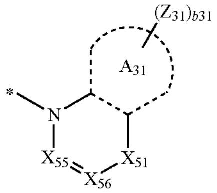

3E

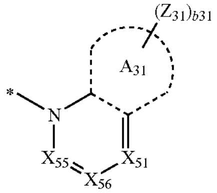

3F

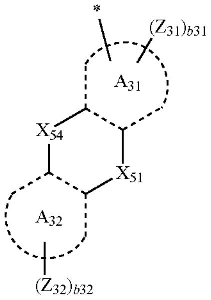

In Formulae 3A to 3F, ring $A_{31}$ to ring $A_{33}$ may each independently be a $C_5$-$C_{60}$ carbocyclic group or a π electron-rich $C_1$-$C_{60}$ heterocyclic group, $X_{51}$ may be a single bond, $N(Z_{51a})$, $C(Z_{51a})(Z_{51b})$, $Si(Z_{51a})(Z_{51b})$, O, or S, $X_{54}$ may be $N(Z_{54a})$, $C(Z_{54a})(Z_{54b})$, $Si(Z_{54a})(Z_{54b})$, O, or S, $X_{55}$ may be N or $C(Z_{55})$, $X_{56}$ may be N or $C(Z_{56})$, $X_{57}$ may be N or $C(Z_{57})$, $Z_{31}$ to $Z_{33}$, $Z_{51a}$, $Z_{51b}$, $Z_{54a}$, $Z_{54b}$, and $Z_{55}$ to $Z_{57}$ may each independently be selected from:

hydrogen, deuterium, a cyano group, a $C_1$-$C_{20}$ alkyl group, and a $C_1$-$C_{20}$ alkoxy group; and a $C_5$-$C_{60}$ carbocyclic group, a pyridine group, and a π electron-rich $C_1$-$C_{60}$ heterocyclic group, each unsubstituted or substituted with at least one $R_{10}$, b31 to b33 may each independently be an integer from 0 to 10,

* indicates a binding site to a neighboring atom, $X_{11}$ to $X_{13}$ may each independently be N or C(CN), $R_4$ and $R_5$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —$Si(Q_{111})(Q_{112})(Q_{113})$, $R_{10a}$ and $R_{10b}$ may each independently be deuterium, a cyano group, a $C_1$-$C_{20}$ alkyl group, a $C_1$-$C_{20}$ alkoxy group, a phenyl group, a ($C_1$-$C_{20}$ alkyl)phenyl group, a di($C_1$-$C_{20}$ alkyl)phenyl group, a tri($C_1$-$C_{20}$ alkyl)phenyl group, a ($C_6$-$C_{20}$ aryl)phenyl group, a di($C_6$-$C_{20}$ aryl)phenyl group, a tri($C_6$-$C_{20}$ aryl)phenyl group, a terphenyl group, a tetraphenyl group (or, a quaterphenyl group), a fluorenyl group, a ($C_1$-$C_{20}$ alkyl)fluorenyl group, a di($C_1$-$C_{20}$ alkyl)fluorenyl group, a tri($C_1$-$C_{20}$ alkyl)fluorenyl group, a ($C_6$-$C_{20}$ aryl)fluorenyl group, a di($C_6$-$C_{20}$ aryl)fluorenyl group, a tri($C_6$-$C_{20}$ aryl)fluorenyl group, a carbazolyl group, a ($C_1$-$C_{20}$ alkyl)carbazolyl group, a di($C_1$-$C_{20}$ alkyl)carbazolyl group, a tri($C_1$-$C_{20}$ alkyl)carbazolyl group, a ($C_6$-$C_{20}$ aryl)carbazolyl group, a di($C_6$-$C_{20}$ aryl)carbazolyl group, a tri($C_6$-$C_{20}$ aryl)carbazolyl group, a dibenzofuranyl group, a ($C_1$-$C_{20}$ alkyl)dibenzofuranyl group, a di($C_1$-$C_{20}$ alkyl)dibenzofuranyl group, a tri($C_1$-$C_{20}$ alkyl)dibenzofuranyl group, a ($C_6$-$C_{20}$ aryl)dibenzofuranyl group, a di($C_6$-$C_{20}$ aryl)dibenzofuranyl group, a tri($C_6$-$C_{20}$ aryl)dibenzofuranyl group, a dibenzothiophenyl group, a ($C_1$-$C_{20}$ alkyl)dibenzothiophenyl group, a di($C_1$-$C_{20}$ alkyl)dibenzothiophenyl group, a tri($C_1$-$C_{20}$ alkyl)dibenzothiophenyl group, a ($C_6$-$C_{20}$ aryl)dibenzothiophenyl group, a di($C_6$-$C_{20}$ aryl)dibenzothiophenyl group, a tri($C_6$-$C_{20}$ aryl)dibenzothiophenyl group, or —$Si(Q_{121})(Q_{122})(Q_{123})$, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cycloalkyl group, the substituted $C_1$-$C_{60}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_5$-$C_{60}$ aryl group, a $C_5$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{38})(Q_{37})$, and —$P(=O)(Q_{38})(Q_{39})$, and $Q_{101}$ to $Q_{103}$, $Q_{111}$ to $Q_{113}$, $Q_{121}$ to $Q_{123}$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

Another aspect of the present disclosure provides an organic light-emitting device including:

a first electrode;

a second electrode; and an organic layer disposed between the first electrode and the second electrode, wherein the organic layer includes an emission layer and the organic layer includes at least one heterocyclic compound represented by Formula 1.

BRIEF DESCRIPTION OF THE DRAWING

These and/or other aspects will become apparent and more readily appreciated from the following description of the embodiments, taken in conjunction with the FIGURE which is a schematic diagram of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

In an embodiment, a heterocyclic compound is provided. The heterocyclic compound according to an embodiment may be represented by Formula 1 below:

Formula 1

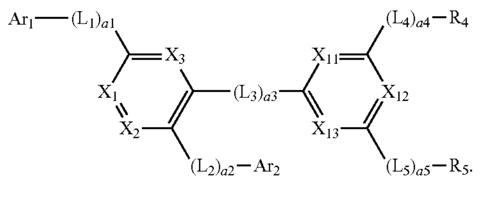

In Formula 1, $X_1$ may be N or $C(R_1)$, $X_2$ may be N or $C(R_2)$, and $X_3$ may be N or $C(R_3)$, i) wherein one selected from $X_1$ to $X_3$ may be N, and the others thereof may not be N; or ii) each of $X_1$ to $X_3$ may not be N.

In an embodiment, $X_1$ may be $C(R_1)$, $X_2$ may be $C(R_2)$, and $X_3$ may be $C(R_3)$;

$X_1$ may be N, $X_2$ may be $C(R_2)$, and $X_3$ may be $C(R_3)$; or $X_1$ may be $C(R_1)$, $X_2$ may be N, and $X_3$ may be $C(R_3)$, but embodiments of the present disclosure are not limited thereto.

$R_1$ to $R_3$ may each independently be hydrogen, deuterium, a $C_1$-$C_{20}$ alkyl group (for example, a methyl group, an ethyl group, a propyl group, a butyl group, or a pentyl group), a $C_1$-$C_{20}$ alkyl group substituted with at least one deuterium, a $C_1$-$C_{20}$ alkoxy group (for example, a methoxy group, an ethoxy group, a propoxy group, a butoxy group, or a pentoxy group), a $C_1$-$C_{20}$ alkoxy group substituted with at least one deuterium, or —$Si(Q_{101})(Q_{102})(Q_{103})$. $Q_{101}$ to $Q_{103}$ may each independently be the same as described herein.

In Formula 1, $L_1$ and $L_2$ may each independently be selected from:

a single bond; and a $C_5$-$C_{60}$ carbocyclic group, a pyridine group, and a π electron-rich $C_1$-$C_{10}$ heterocyclic group, each unsubstituted or substituted with at least one $R_{10a}$, and $L_3$ to $L_5$ may each independently be selected from:

a single bond; and a $C_5$-$C_{60}$ carbocyclic group and a $C_1$-$C_{60}$ heterocyclic group, each unsubstituted or substituted with at least one $R_{10a}$. $R_{10a}$ may be the same as described herein.

In an embodiment, $L_1$ to $L_5$ may each independently be selected from:

a single bond; and a benzene group, a fluorene group, a pyridine group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, an acridine group, and a dihydroacridine group, each unsubstituted or substituted with least one $R_{10a}$.

In one or more embodiments, $L_3$ in Formula 1 may each independently be selected from a single bond and groups represented by Formulae 2-1 to 2-4, but embodiments of the present disclosure are not limited thereto:

2-1

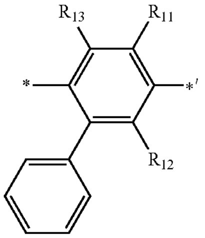

2-2

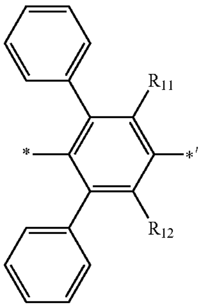

2-3

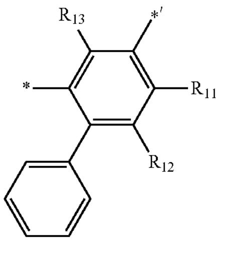

-continued 2-4

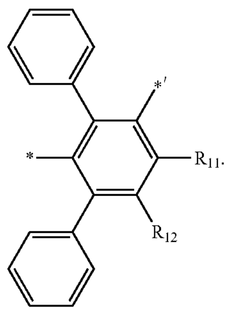

In Formulae 2-1 to 2-4, $R_{11}$ to $R_{13}$ may each independently be hydrogen, deuterium, or a $C_1$-$C_{10}$ alkyl group,

* indicate a binding site to a 6-membered ring on the left side in Formula 1, and

*' indicates a binding site to a 6-membered ring on the right side in Formula 1.

a1 to a5 in Formula 1 respectively indicate the number of groups $L_1$ to groups $L_5$, and may each independently be an integer from 1 to 5. When a1 to a5 are two or more, two or more groups $L_1$ to groups $L_5$ may be identical to or different from each other, respectively. a1 to a5 may each independently be 1 or 2, but embodiments of the present disclosure are not limited thereto.

$Ar_1$ and $Ar_2$ may each independently be a group represented by Formula 3A, a group represented by Formula 3B, a group represented by Formula 3C, a group represented by Formula 3D, a group represented by Formula 3E, a group represented by Formula 3F, or a $C_6$-$C_{60}$ aryl group unsubstituted or substituted with at least one $Z_{31}$:

3A

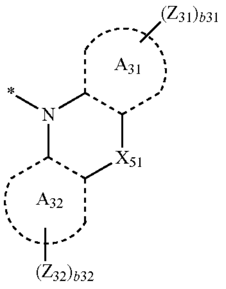

3B

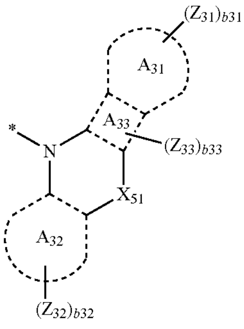

-continued

3C

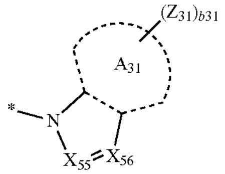

3D

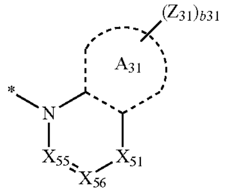

3E

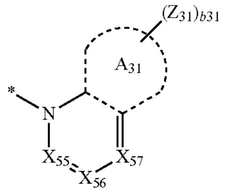

3F

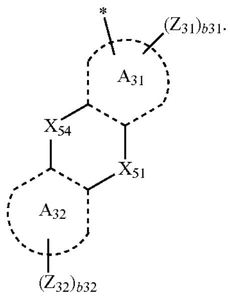

In an embodiment, $Ar_1$ and $Ar_2$ in Formula 1 may be identical to each other.

In one or more embodiments, $Ar_1$ and $Ar_2$ in Formula 1 may be different from each other.

In one or more embodiments, each of at least one selected from $Ar_1$ and $Ar_2$ in Formula 1 may independently be selected from groups represented by Formulae 3A to 3C.

ring $A_{31}$ to ring $A_{33}$ in Formulae 3A to 3F may each independently be a $C_5$-$C_{60}$ carbocyclic group or a π electron-rich $C_1$-$C_{60}$ heterocyclic group.

For example, ring $A_{31}$ to ring $A_{33}$ may each independently be a benzene group, a naphthalene group, an anthracene group, a phenanthrene group, a triphenylene group, a chrysene group, an indene group, an indole group, a benzofuran group, a benzothiophene group, a benzosilole group, a fluorene group, a carbazole group, a dibenzofuran group, a dibenzothiophene group, a dibenzosilole group, an indenocarbazole group, an indolocarbazole group, a benzofurocarbazole group, a benzothienocarbazole group, a benzosilolocarbazole group, an acridine group, or a dihydroacridine group, but embodiments of the present disclosure are not limited thereto.

In Formulae 3A to 3F, $X_{51}$ may be a single bond, $N(Z_{51a})$, $C(Z_{51a})(Z_{51b})$, $Si(Z_{51a})(Z_{51b})$, O, or S, $X_{54}$ may be $N(Z_{54a})$, $C(Z_{54a})(Z_{54b})$, $Si(Z_{54a})(Z_{54b})$, O, or S, $X_{55}$ may be N or $C(Z_{55})$, $X_{56}$ may be N or $C(Z_{56})$, and $X_{57}$ may be N or $C(Z_{57})$.

In an embodiment, in Formulae 3A and 3B, $X_{51}$ may be a single bond, and $X_{54}$ may be $N(Z_{54a})$, O, or S, but embodiments of the present disclosure are not limited thereto.

In Formulae 3A to 3F, $Z_{31}$ to $Z_{33}$, $Z_{51a}$, $Z_{51b}$, $Z_{54a}$, $Z_{54b}$, and $Z_{55}$ to $Z_{57}$ may each independently be selected from:

hydrogen, deuterium, a cyano group, a $C_1$-$C_{20}$ alkyl group, and a $C_1$-$C_{20}$ alkoxy group; and a $C_5$-$C_{60}$ carbocyclic group, a pyridine group, and a π electron-rich $C_1$-$C_{60}$ heterocyclic group, each unsubstituted or substituted with at least one $R_{10b}$. $R_{10b}$ may be the same as described below.

For example, $Z_{31}$ to $Z_{33}$, $Z_{51a}$, $Z_{51b}$, $Z_{54a}$, $Z_{54b}$, and $Z_{55}$ to $Z_{57}$ may each independently be selected from:

hydrogen, deuterium, a cyano group, a $C_1$-$C_{20}$ alkyl group, and a $C_1$-$C_{20}$ alkoxy group; and a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, and a dihydroacridinyl group, each unsubstituted or substituted with at least one $R_{10b}$.

b31 to b33 respectively indicate the number of groups $Z_{31}$ to groups $Z_{33}$ and may each independently be an integer from 0 to 10 (for example, 0, 1, 2, 3, or 4). When b31 to b33 are two or more, two or more groups $Z_{31}$ to groups $Z_{33}$ may be identical to or different from each other, respectively. b31 to b33 are each independently 0, 1, or 2, but embodiments of the present disclosure are not limited thereto.

* in Formulae 3A to 3F indicates a binding site to a neighboring atom.

In an embodiment, a ring represented by

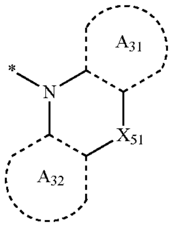

in Formula 3A may be selected from groups represented by Formulae 3A-1 to 3A-49, a ring represented by

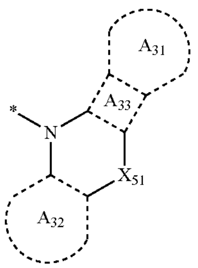

in Formula 3B may be selected from groups represented by Formulae 3B-1 to 3B-40, and a ring represented by

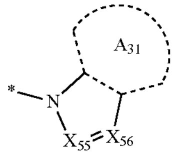

in Formula 3C may be a group represented by Formula 3C-1, but embodiments of the present disclosure are not limited thereto:

3A-1

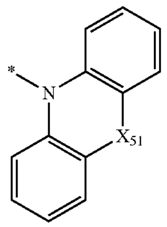

3A-2

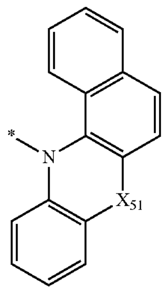

3A-3

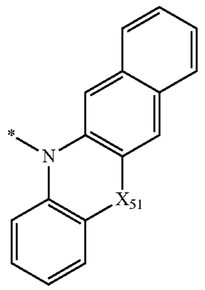

3A-4

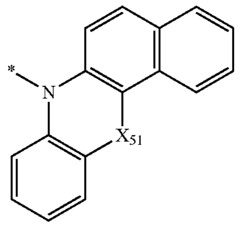

-continued
3A-5
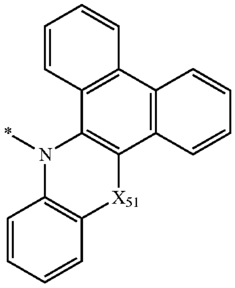
3A-6
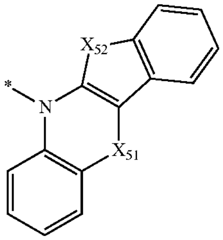
3A-7
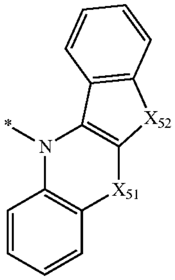
3A-8
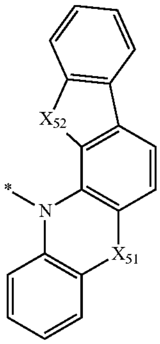
3A-9
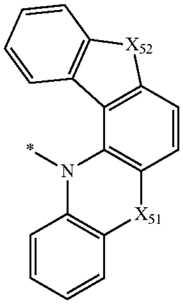
-continued
3A-10
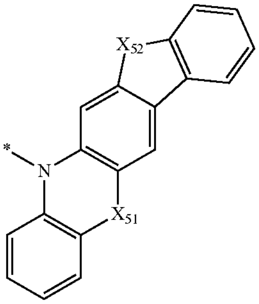
3A-11
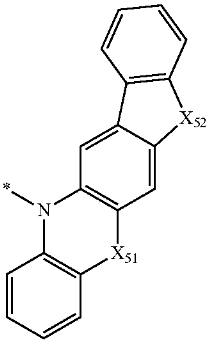
3A-12
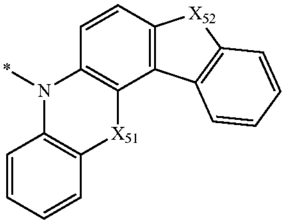
3A-13
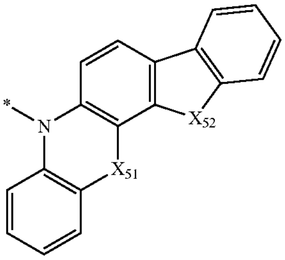
3A-14
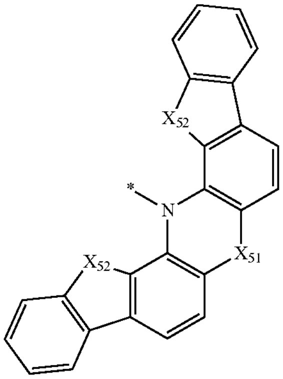

-continued
3A-15
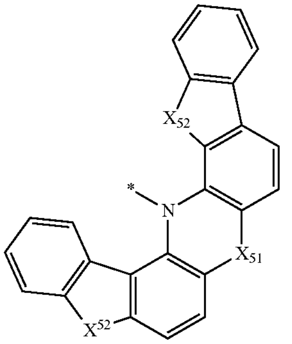
3A-16
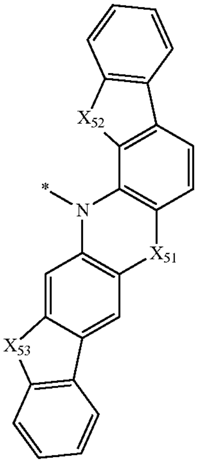
3A-17
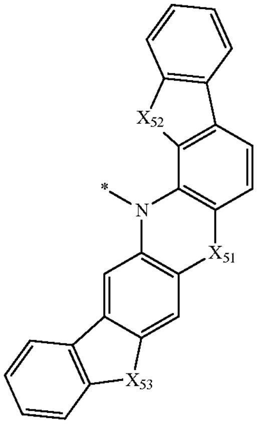
-continued
3A-18
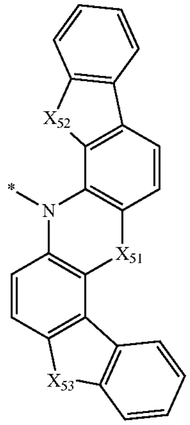
3A-19
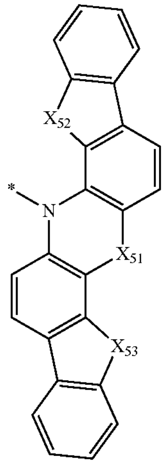
3A-20
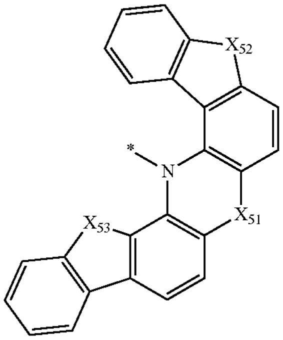
3A-21
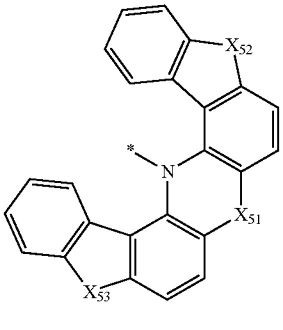

-continued
3A-22
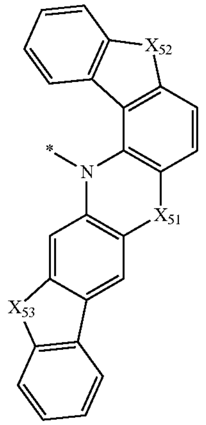
3A-23
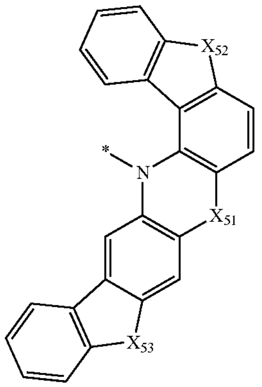
3A-24
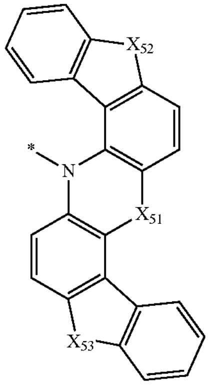
3A-25
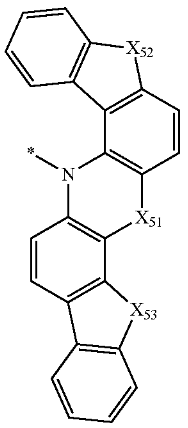
-continued
3A-26
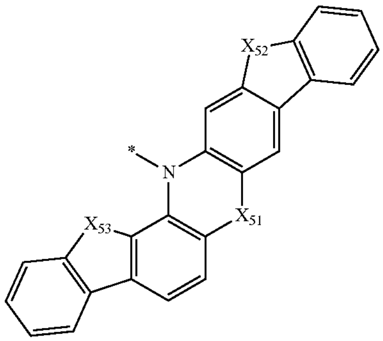
3A-27
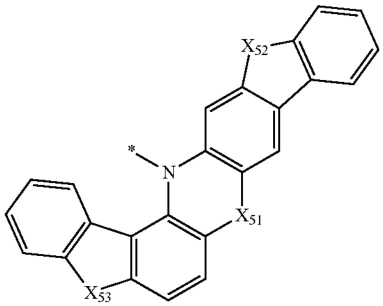
3A-28
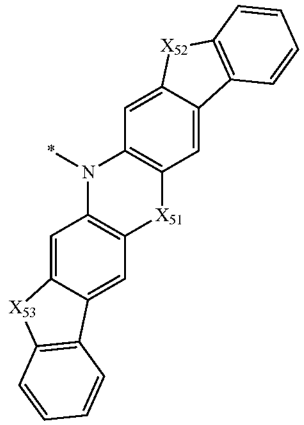
3A-29
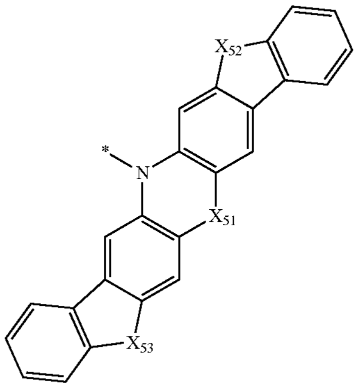

-continued
3A-30
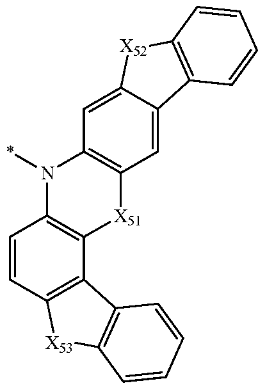
3A-31
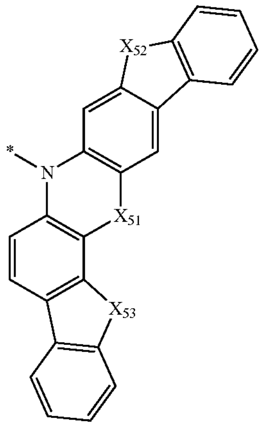
3A-32
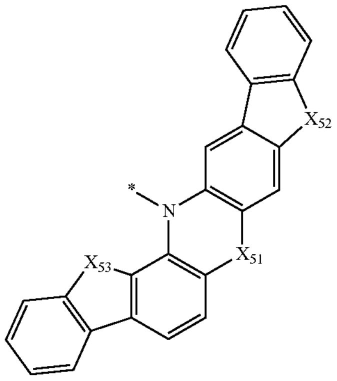
3A-33
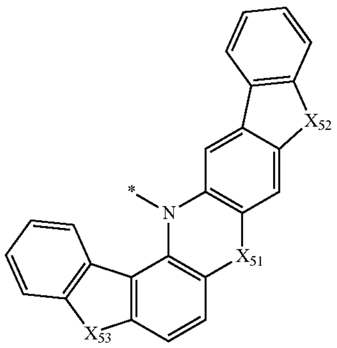
-continued
3A-34
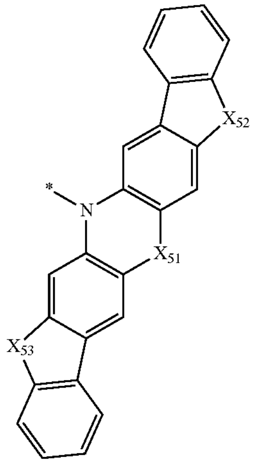
3A-35
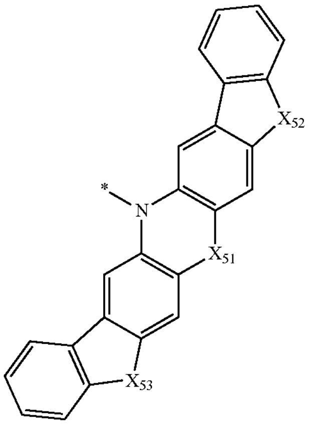
3A-36
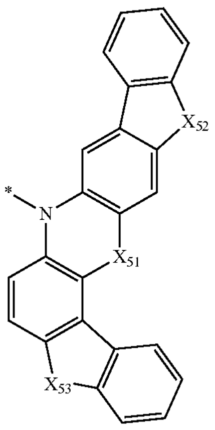

-continued
3A-37
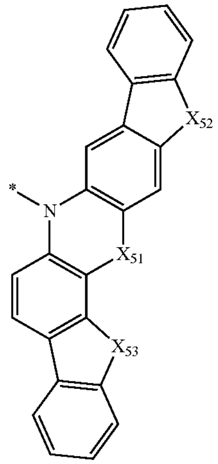
3A-38
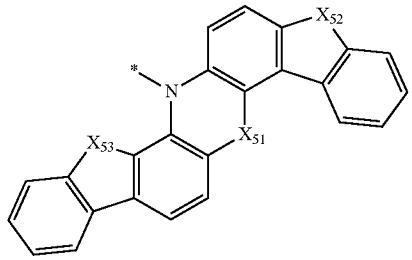
3A-39
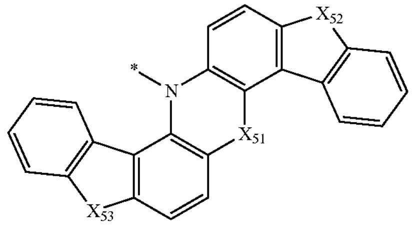
3A-40
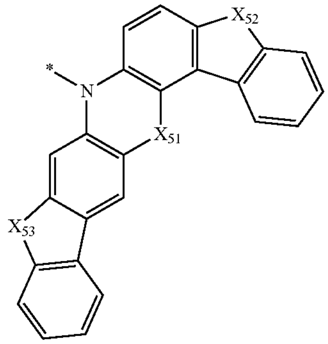
3A-41
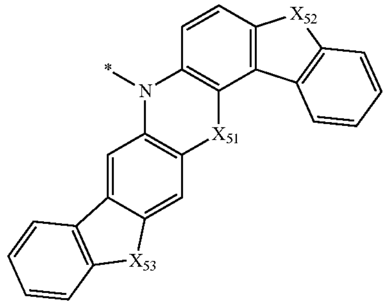
-continued
3A-42
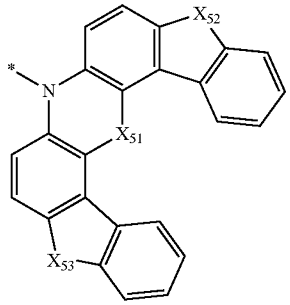
3A-43
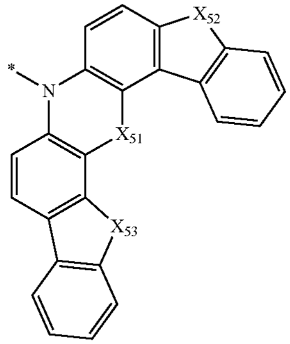
3A-44
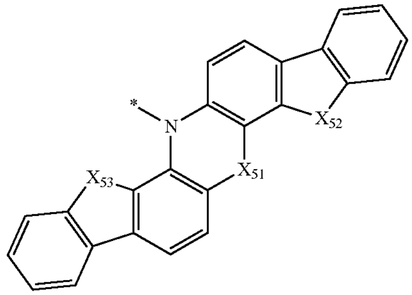
3A-45
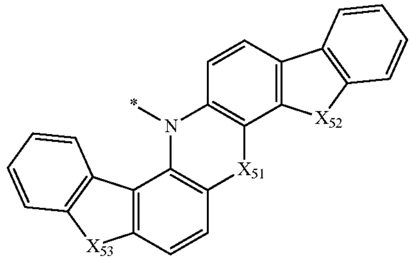
3A-46
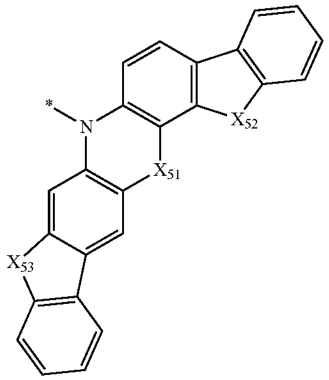

3A-47
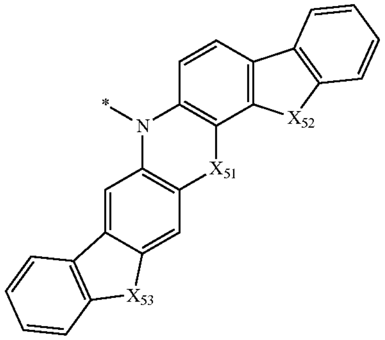
3A-48
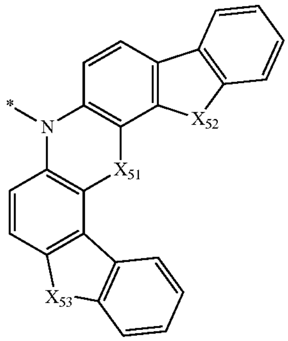
3A-49
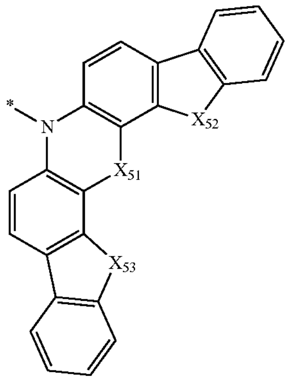
3B-1
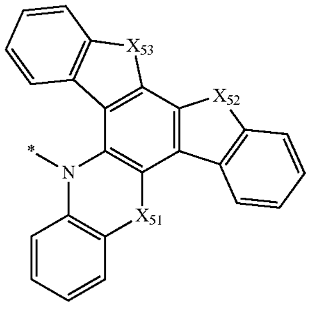
3B-2
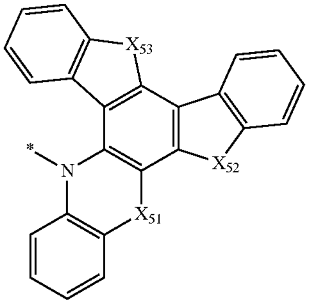
3B-3
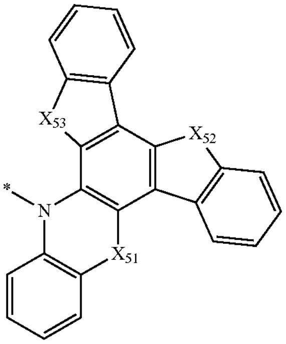
3B-4
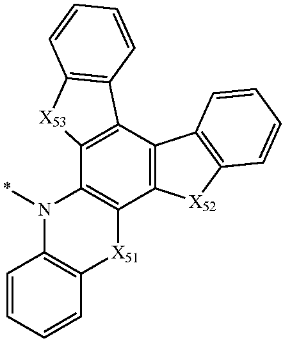
3B-5
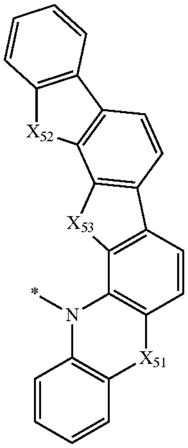

-continued
3B-6
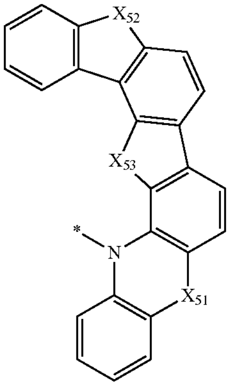
3B-7
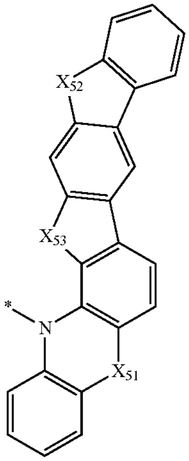
3B-8
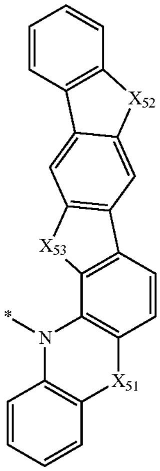
-continued
3B-9
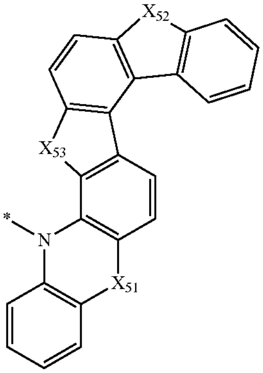
3B-10
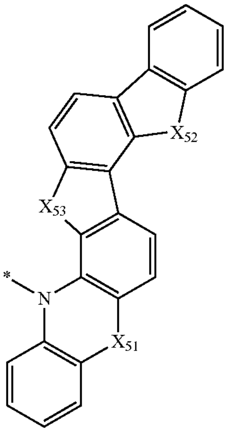
3B-11
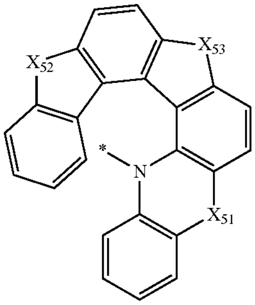
3B-12
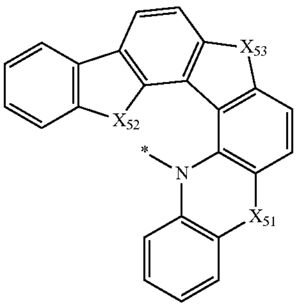

-continued
3B-13
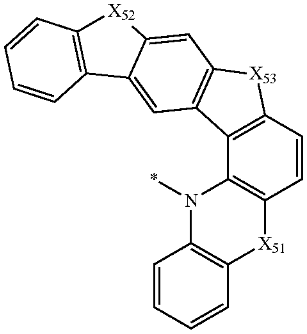
3B-14
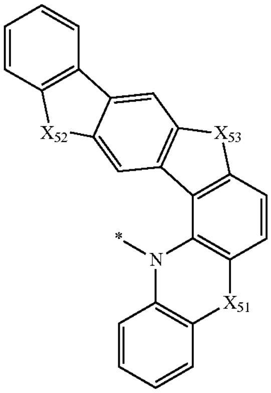
3B-15
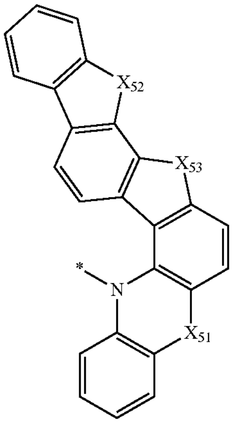
3B-16
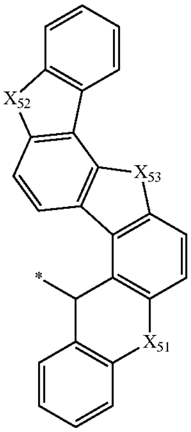
-continued
3B-17
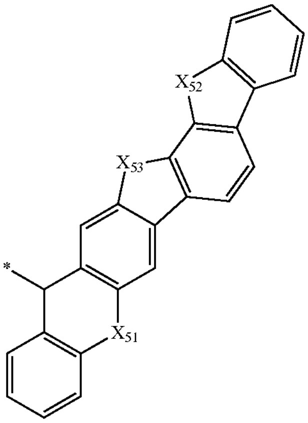
3B-18
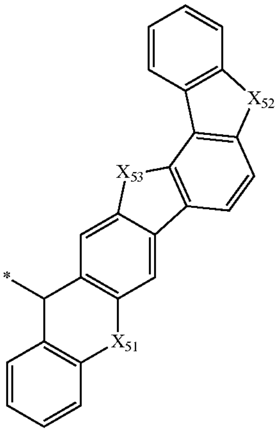
3B-19
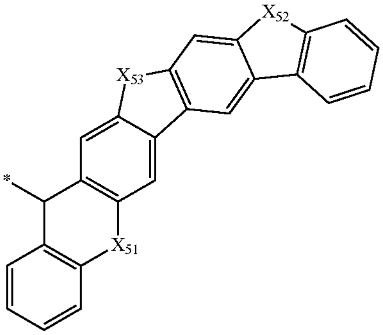
3B-20
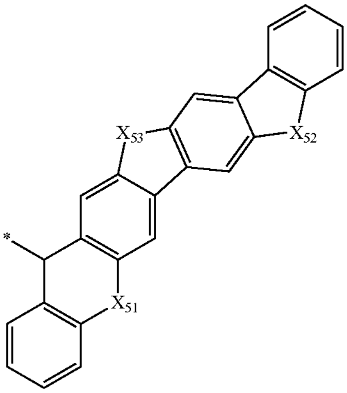

-continued
3B-21
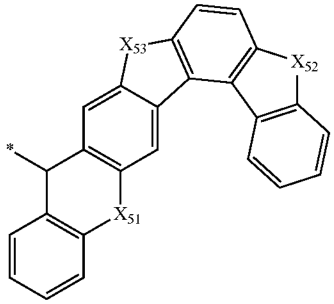
3B-22
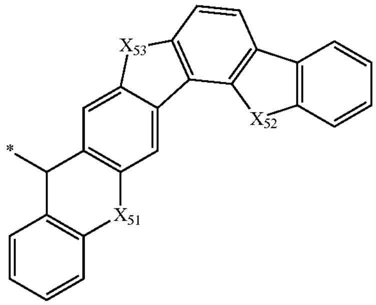
3B-23
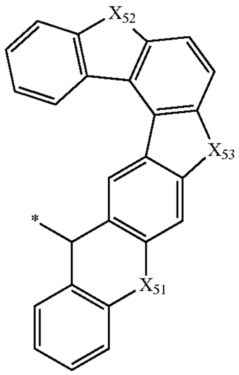
3B-24
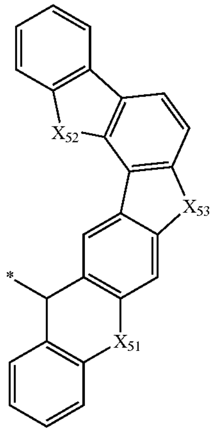
-continued
3B-25
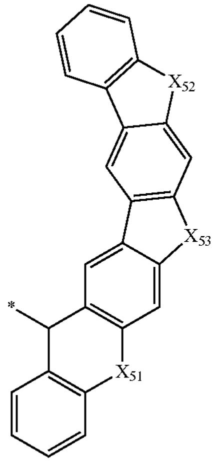
3B-26
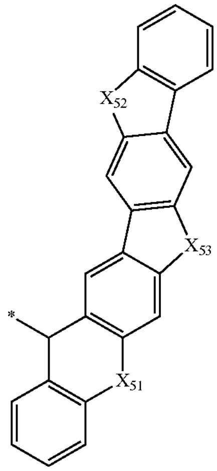
3B-27
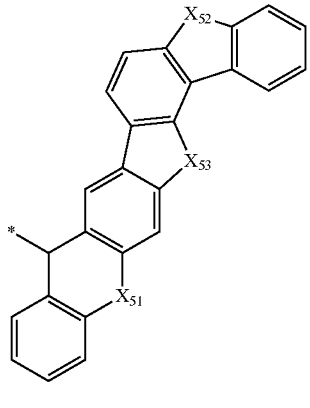

-continued
3B-28
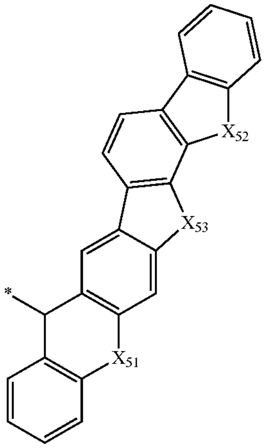
3B-29
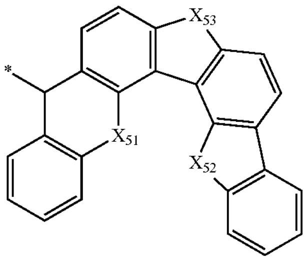
3B-30
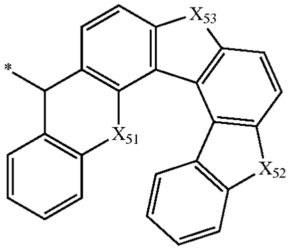
3B-31
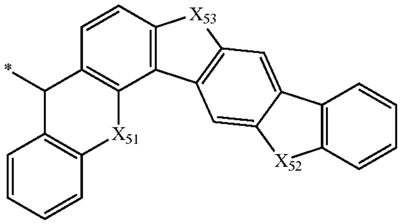
3B-32
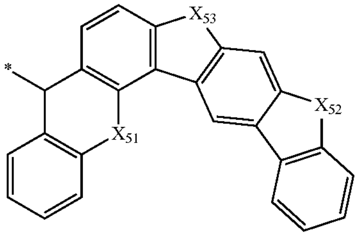
-continued
3B-33
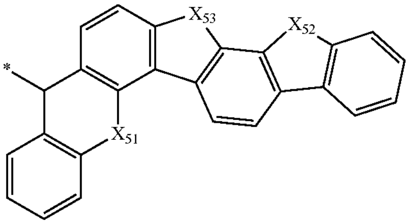
3B-34
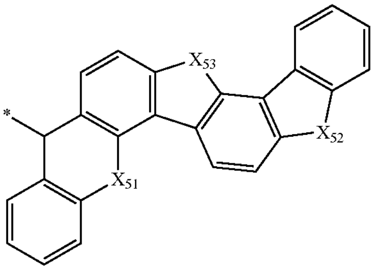
3B-35
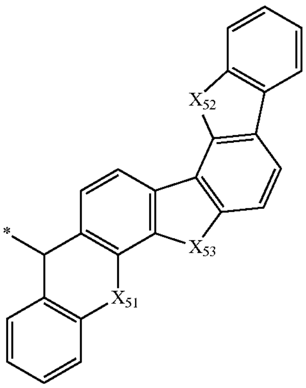
3B-36
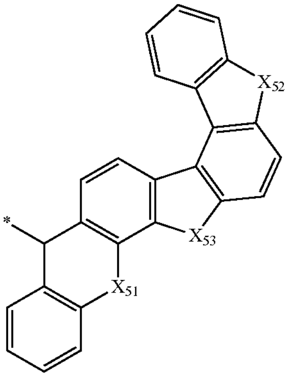
3B-37
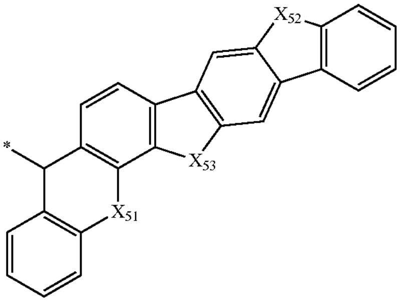

-continued 3B-38

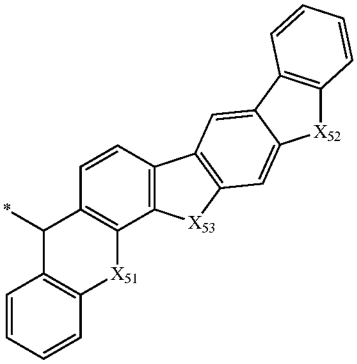

3B-39

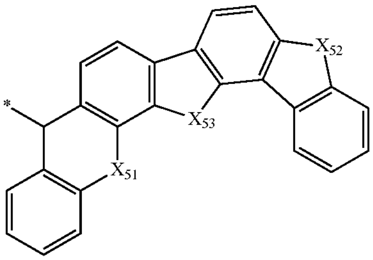

3B-40

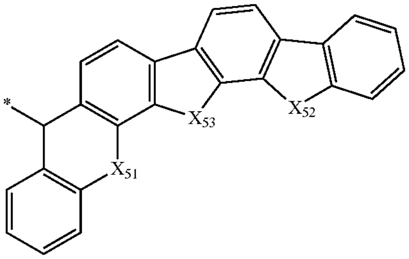

3C-1

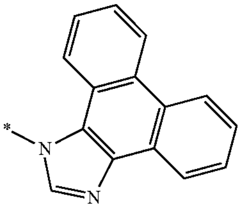

In Formulae 3A-1 to 3A-49, 3B-1 to 3B-40 and 3C-1, $X_{51}$ and * may each independently be the same as described herein, $X_{52}$ may be $N(Z_{52a})$, $C(Z_{52a})(Z_{52b})$, $Si(Z_{52a})(Z_{52b})$, O, or S, $X_{53}$ may be $N(Z_{53a})$, $C(Z_{53a})(Z_{53b})$, $Si(Z_{53a})(Z_{53b})$, O, or S, and $Z_{52a}$, $Z_{52b}$, $Z_{53a}$, and $Z_{53b}$ may each independently be the same as described in connection with $Z_{51a}$.

In one or more embodiments, each of at least one selected from $Ar_1$ and $Ar_2$ may independently be selected from groups represented by Formulae 3G-1 to 3G-10:

3G-1

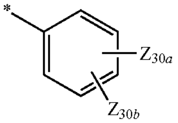

-continued 3G-2

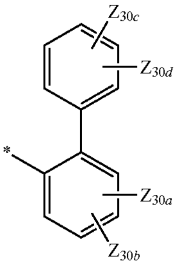

3G-3

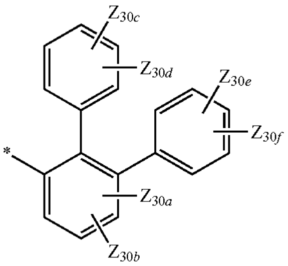

3G-4

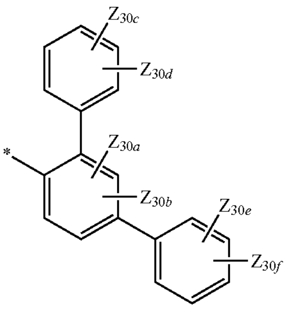

3G-5

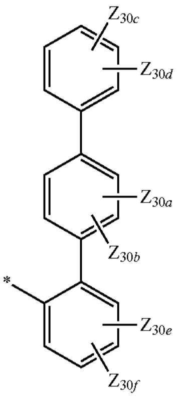

3G-6

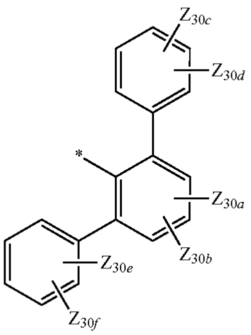

-continued 3G-7

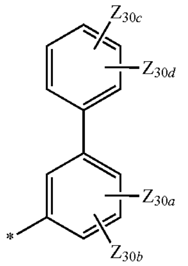

3G-8

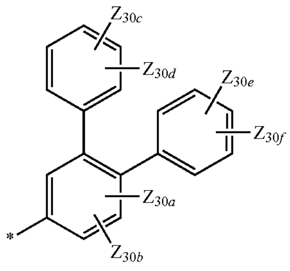

3G-9

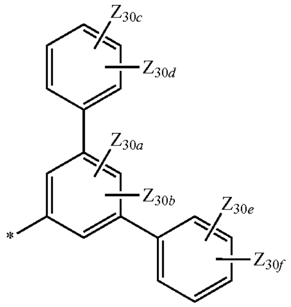

3G-10

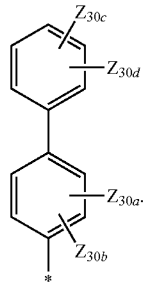

In Formulae 3G-1 to 3G-10, $Z_{30a}$, to $Z_{30f}$ or may each independently be the same as described in connection with $Z_{31}$, and

* indicates a binding site to a neighboring atom.

In Formula 1, $X_{11}$ to $X_{13}$ may each independently be N or C(CN).

In an embodiment, $X_{11}$ to $X_{13}$ may each independently be N.

In Formula 1, $R_4$ and $R_5$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{10}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —Si($Q_{111}$)($Q_{112}$)($Q_{113}$), wherein $Q_{111}$ to $Q_{113}$ may each independently be the same as described above.

For example, $R_4$ and $R_5$ may each independently be a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, and a dihydroacridinyl group, each unsubstituted or substituted with at least one $R_{10c}$, wherein $R_{10c}$ may be the same as $R_{10a}$ described herein.

$R_{10a}$ and $R_{10b}$ may each independently be deuterium, a cyano group, a $C_1$-$C_{20}$ alkyl group, a $C_1$-$C_{20}$ alkoxy group, a phenyl group, a ($C_1$-$C_{20}$ alkyl)phenyl group, a di($C_1$-$C_{20}$ alkyl)phenyl group, a tri($C_1$-$C_{20}$ alkyl)phenyl group, a ($C_6$-$C_{20}$ aryl)phenyl group, a di($C_6$-$C_{20}$ aryl)phenyl group, a tri($C_6$-$C_{20}$ aryl)phenyl group, a terphenyl group, a tetraphenyl group, a fluorenyl group, a ($C_1$-$C_{20}$ alkyl)fluorenyl group, a di($C_1$-$C_{20}$ alkyl)fluorenyl group, a tri($C_1$-$C_{20}$ alkyl) fluorenyl group, a ($C_6$-$C_{20}$ aryl)fluorenyl group, a di($C_6$-$C_{20}$ aryl)fluorenyl group, a tri($C_6$-$C_{20}$ aryl)fluorenyl group, a carbazolyl group, a ($C_1$-$C_{20}$ alkyl)carbazolyl group, a di($C_1$-$C_{20}$ alkyl)carbazolyl group, a tri($C_1$-$C_{20}$ alkyl)carbazolyl group, a ($C_6$-$C_{20}$ aryl)carbazolyl group, a di($C_6$-$C_{20}$ aryl) carbazolyl group, a tri($C_6$-$C_{20}$ aryl)carbazolyl group, a dibenzofuranyl group, a ($C_1$-$C_{20}$ alkyl)dibenzofuranyl group, a di($C_1$-$C_{20}$ alkyl)dibenzofuranyl group, a tri($C_1$-$C_{20}$ alkyl)dibenzofuranyl group, a ($C_6$-$C_{20}$ aryl)dibenzofuranyl group, a di($C_6$-$C_{20}$ aryl)dibenzofuranyl group, a tri($C_6$-$C_{20}$ aryl)dibenzofuranyl group, a dibenzothiophenyl group, a ($C_1$-$C_{20}$ alkyl)dibenzothiophenyl group, a di($C_1$-$C_{20}$ alkyl) dibenzothiophenyl group, a tri($C_1$-$C_{20}$ alkyl)dibenzothiophenyl group, a ($C_6$-$C_{20}$ aryl)dibenzothiophenyl group, a di($C_6$-$C_{20}$ aryl)dibenzothiophenyl group, a tri($C_6$-$C_{20}$ aryl) dibenzothiophenyl group, or —Si($Q_{121}$)($Q_{122}$)($Q_{123}$), wherein $Q_{122}$ to $Q_{123}$ may each independently be the same as described above. The term "$C_1$-$C_{20}$ alkyl group" as used herein refers to a methyl group, an ethyl group, a propyl group, a butyl group, a pentyl group, a hexyl group, a heptyl group, or an octyl group, and the term "$C_6$-$C_{20}$ aryl group" as used herein refers to a phenyl group, a naphthyl group, or a triphenylenyl group.

In an embodiment, $R_{10a}$ which may be included in $L_1$ to $L_3$ may not be a cyano group.

In one or more embodiments, in Formula 1, $Ar_1$ and $Ar_2$ may each independently be a group represented by one selected from Formulae D'-1 to D'-7 and D001 to D279, and/or a group represented by *-($L_3$)$_{a3}$-*' may be a single bond or a group represented by one selected from Formulae L-1 to L-5, and/or a group represented by

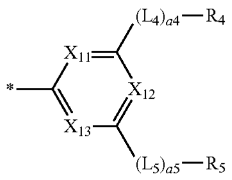

may be represented by one selected from Formulae A1 to A38,

* in a group represented by

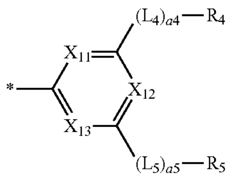

indicates a binding site to a neighboring atom, and in a group represented by *-$(L_3)_{a3}$-*', * indicates a binding site to a 6-membered ring on the left side in Formula 1, and *' indicates a binding site to a 6-membered ring on the right side in Formula 1, but embodiments of the present disclosure are not limited thereto:

D'-1

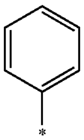

D'-2

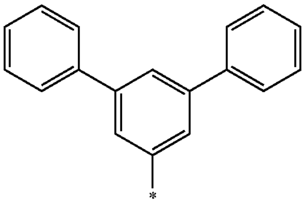

D'-3

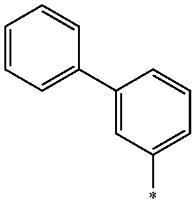

D'-4

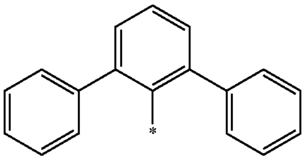

-continued

D'-5

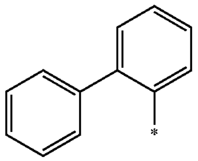

D'-6

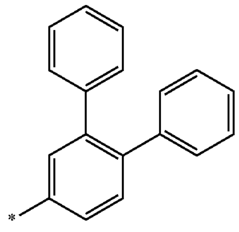

D'-7

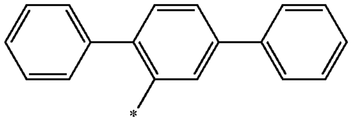

D001

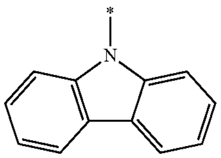

D002

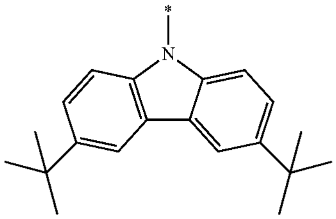

D003

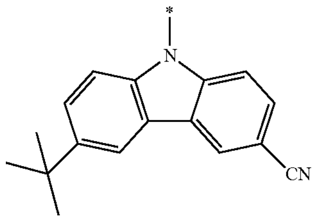

D004

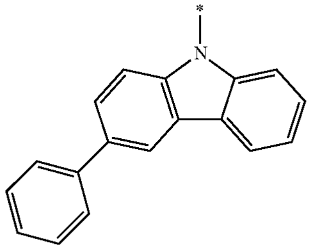

-continued
D005
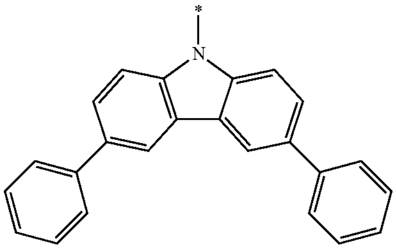
D006
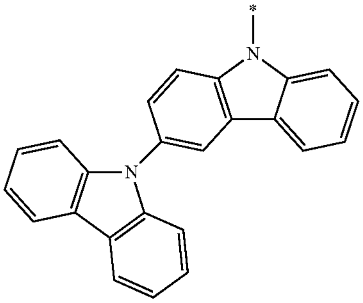
D007
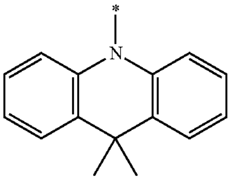
D008
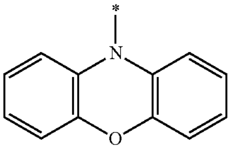
D009
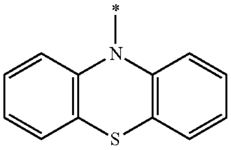
D010
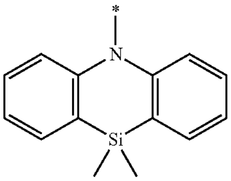
D011
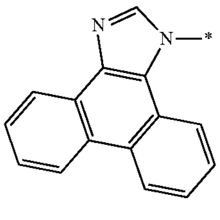
-continued
D012
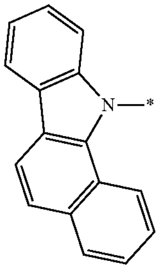
D013
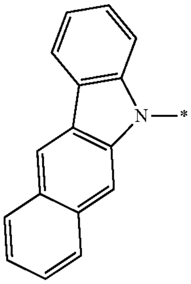
D014
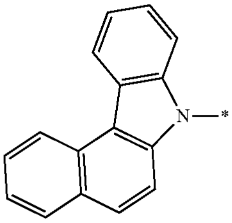
D015
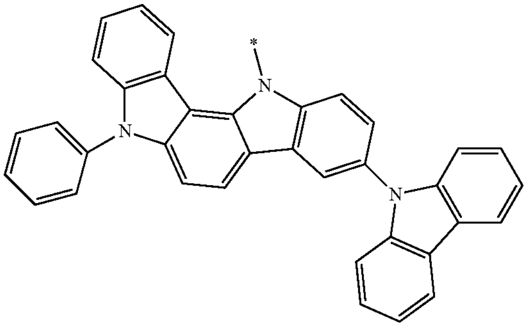
D016
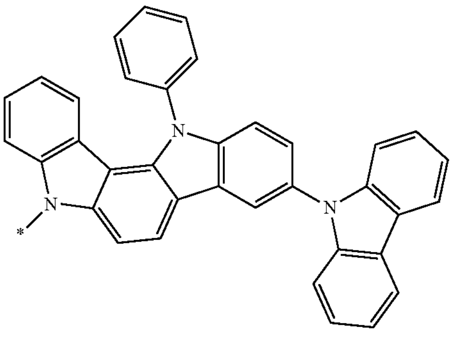

-continued
D017
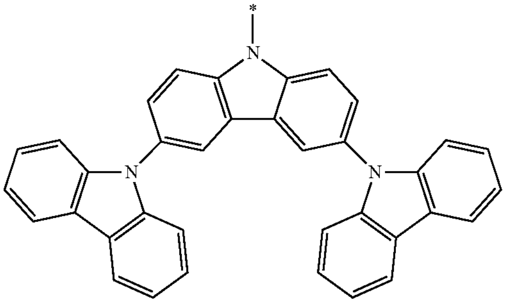
D018
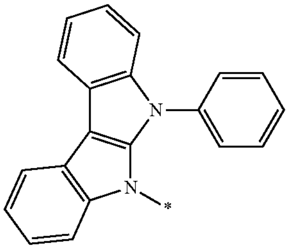
D019
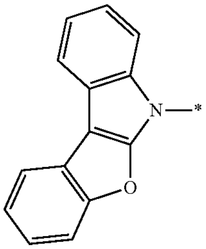
D020
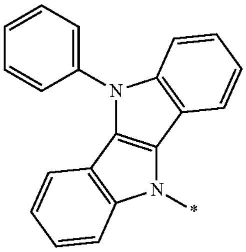
D021
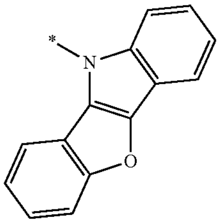
D022
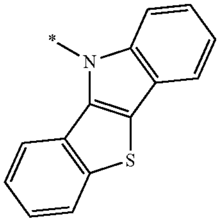
-continued
D023
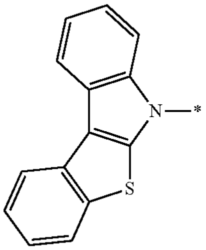
D024
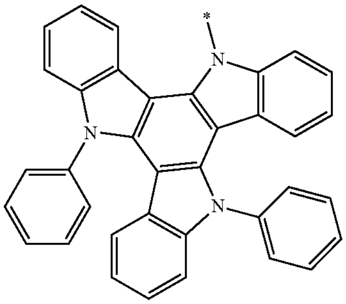
D025
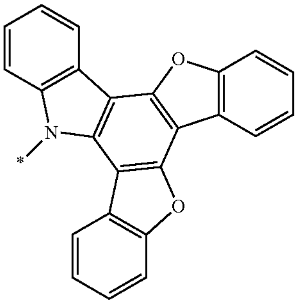
D026
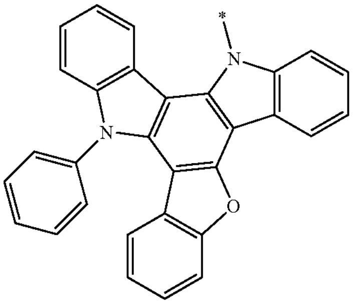
D027
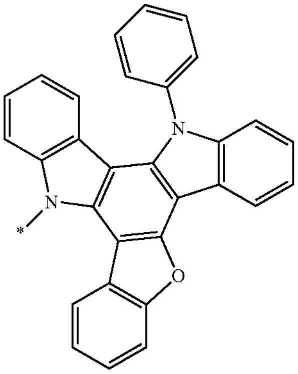

-continued
D028
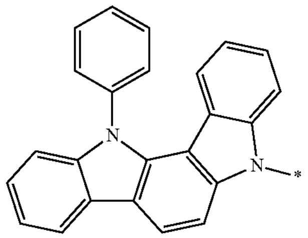
D029
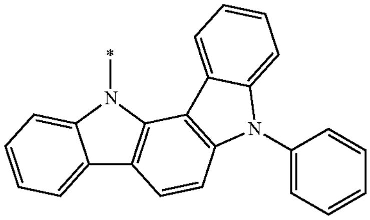
D030
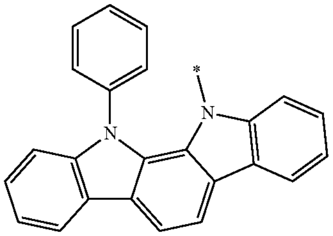
D031
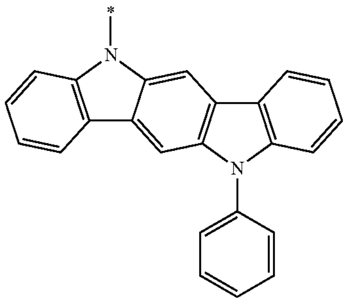
D032
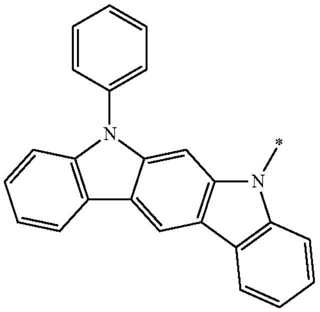
-continued
D033
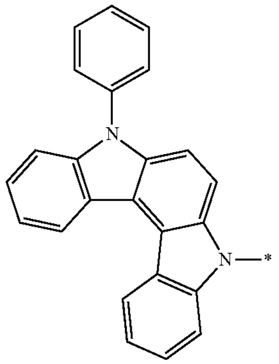
D034
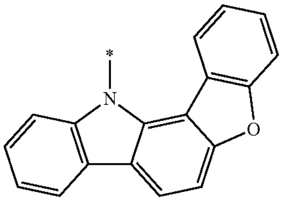
D035
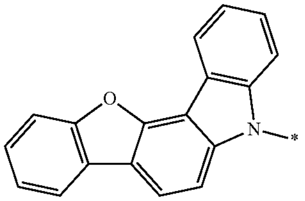
D036
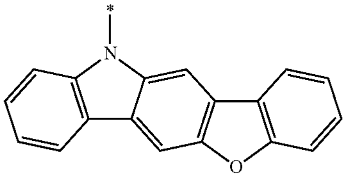
D037
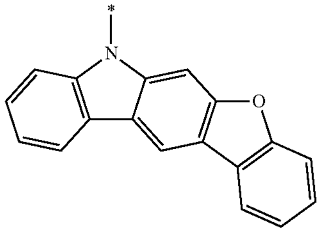
D038
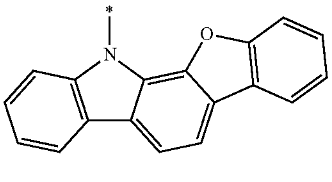

-continued
D039
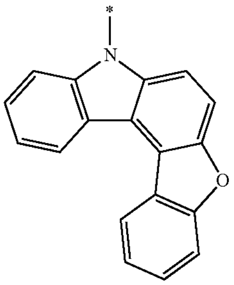
D040
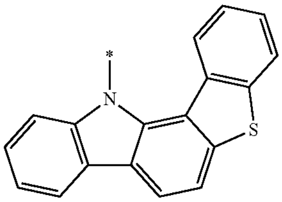
D041
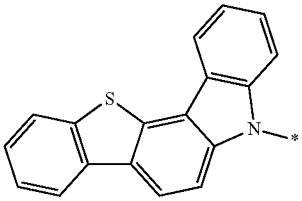
D042
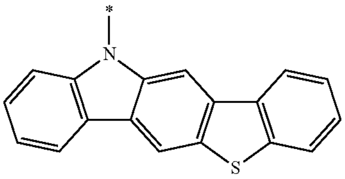
D043
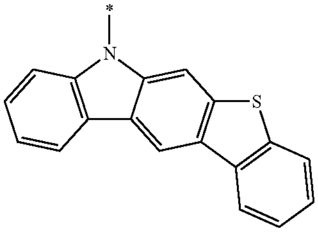
D044
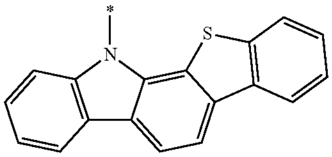
D045
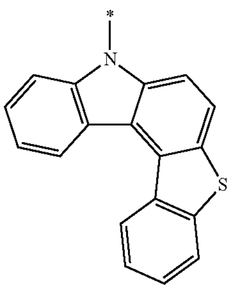
-continued
D046
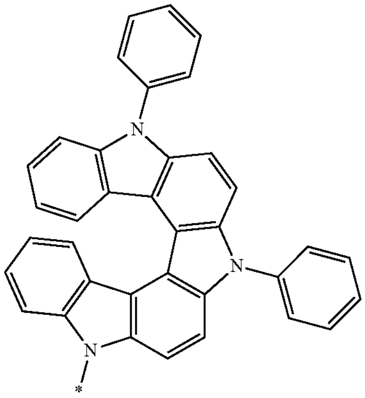
D047
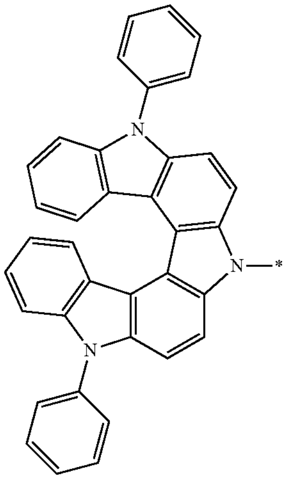
D048
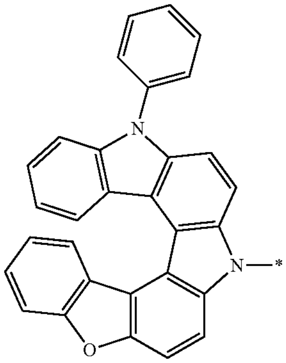
D049
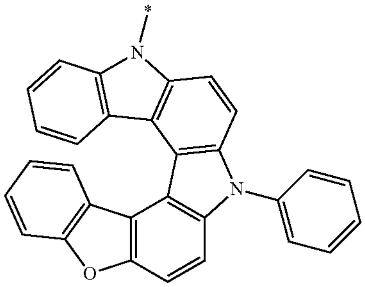

-continued
D050
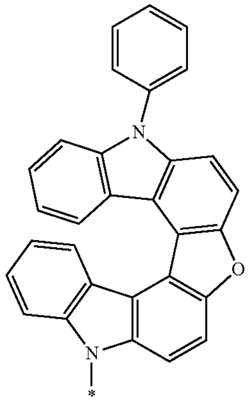
D051
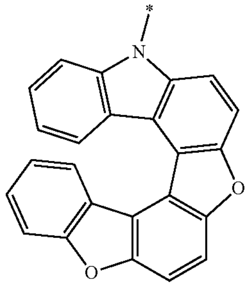
D052
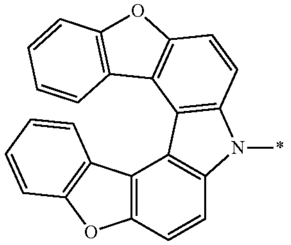
D053
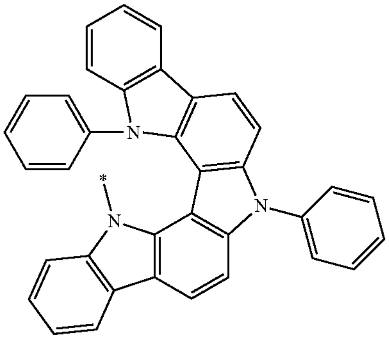
D054
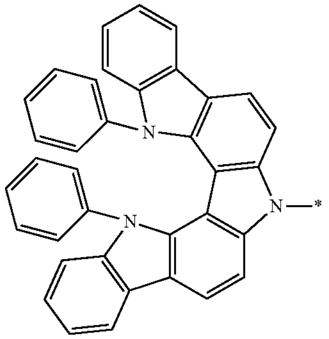
-continued
D055
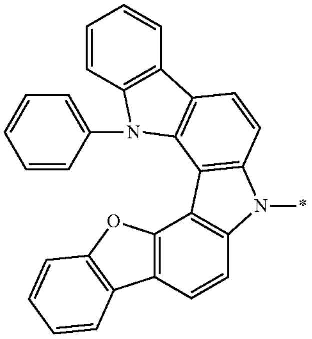
D056
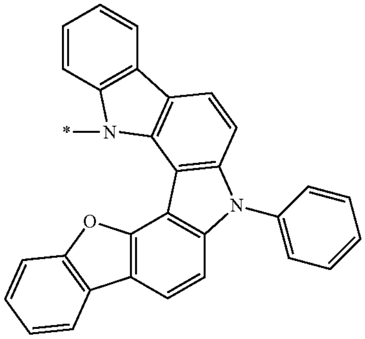
D057
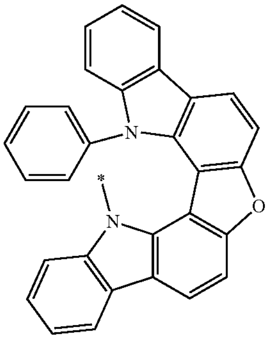
D058
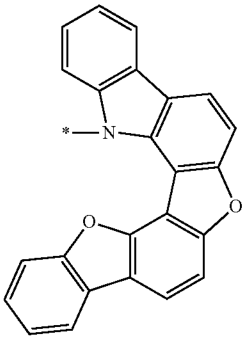

-continued
D059
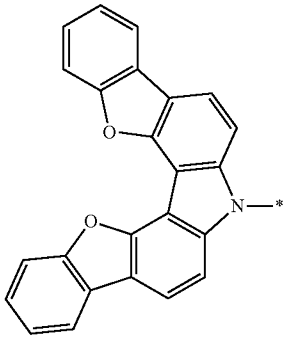
D060
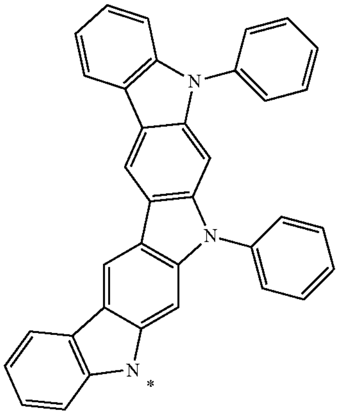
D061
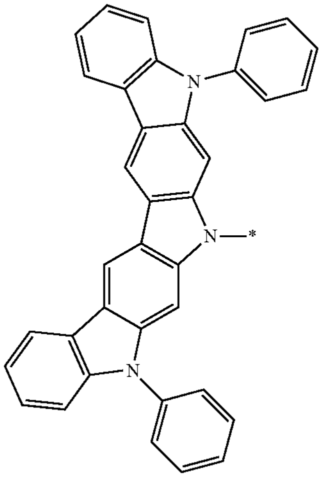
D062
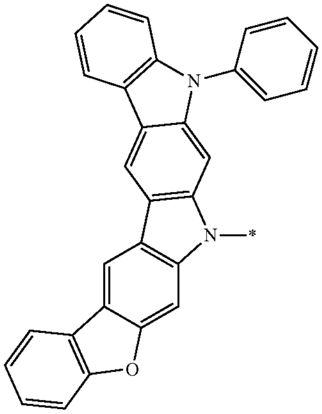
-continued
D063
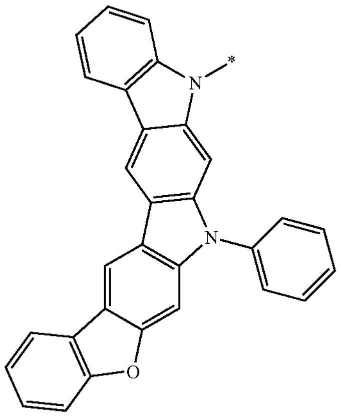
D064
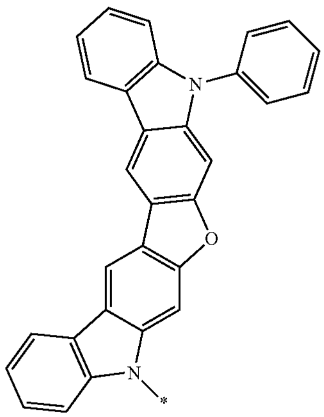
D065
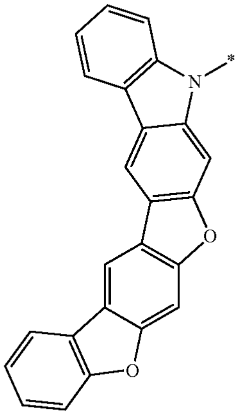

-continued
D066
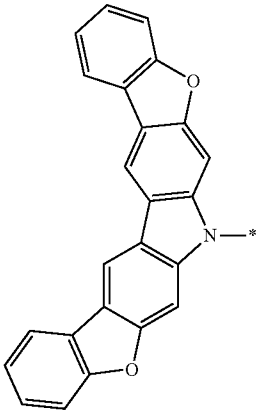
D067
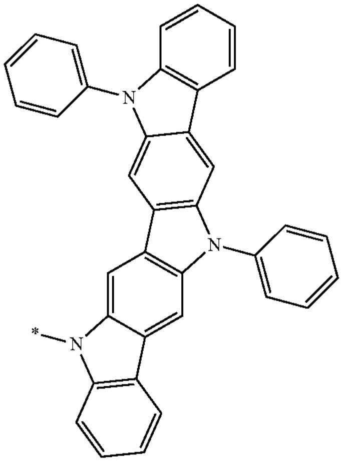
D068
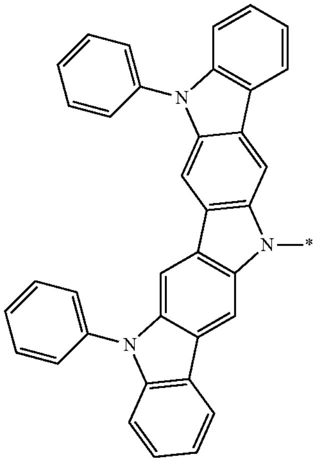
-continued
D069
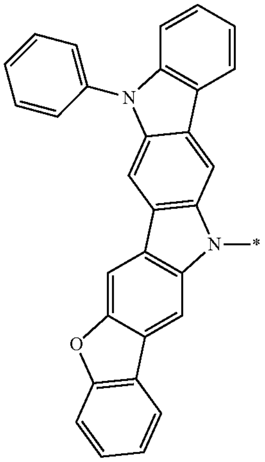
D070
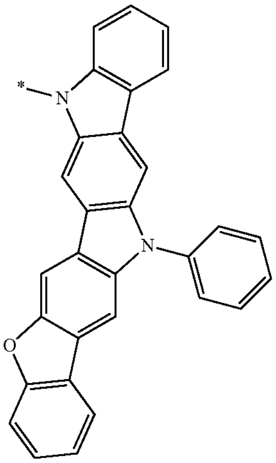
D071
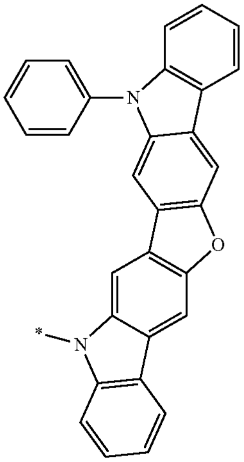

-continued
D072
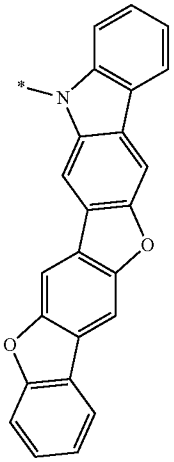
D073
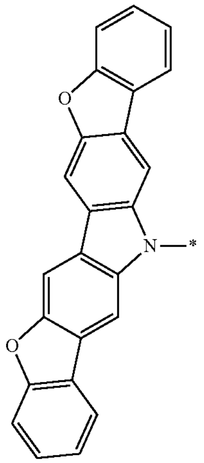
D074
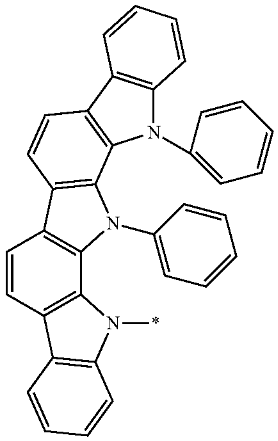
-continued
D075
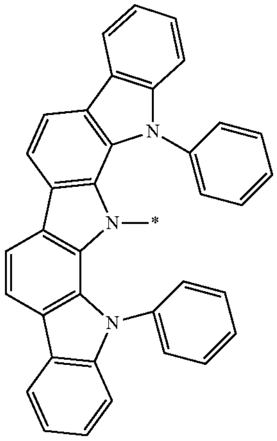
D076
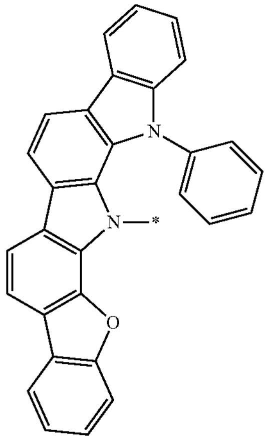
D077
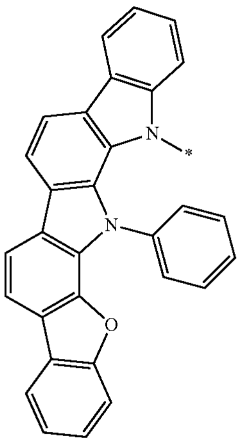

-continued
D078
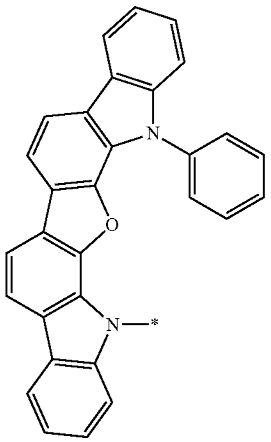
D079
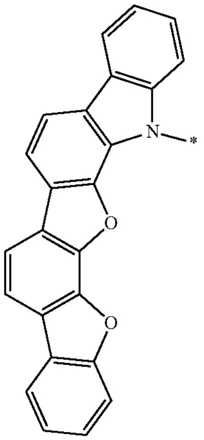
D080
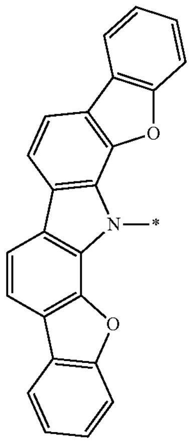
-continued
D081
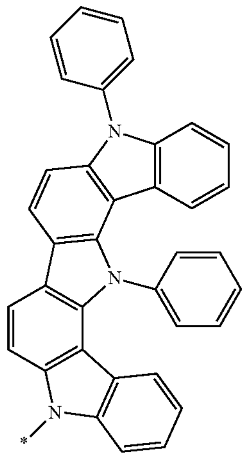
D082
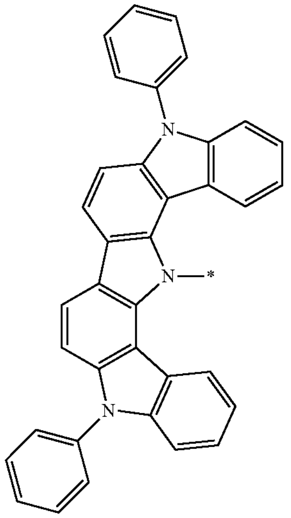
D083
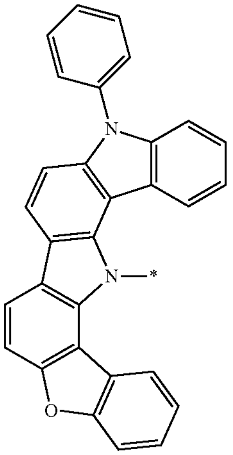

-continued
D084
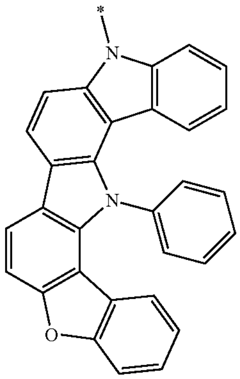
D085
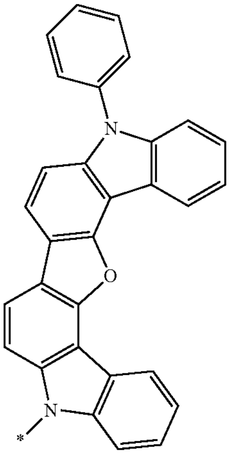
D086
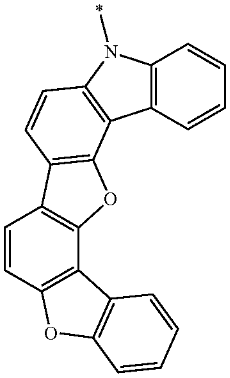
D087
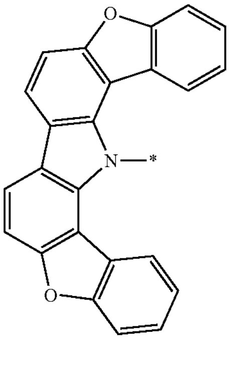
-continued
D088
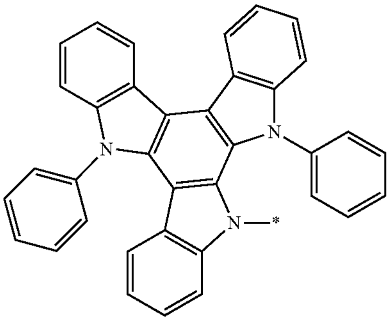
D089
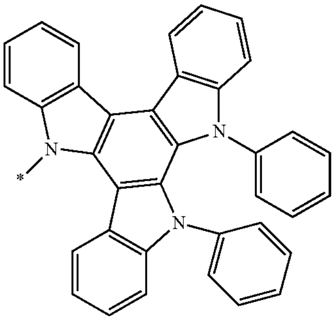
D090
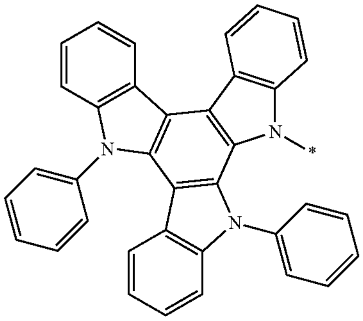
D091
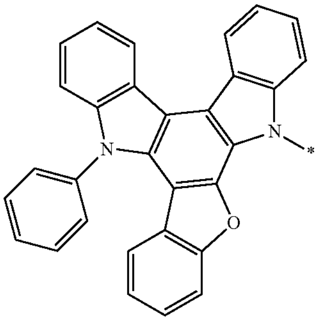
D092
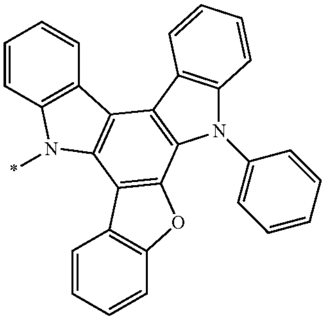

-continued
D093
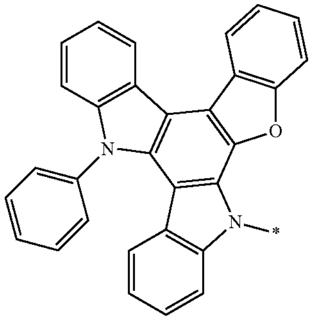
D094
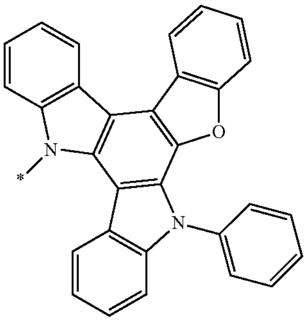
D095
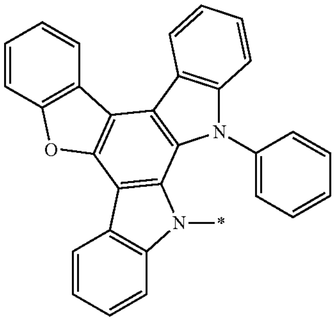
D096
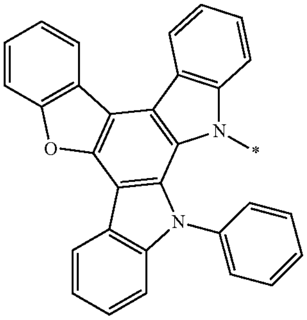
D097
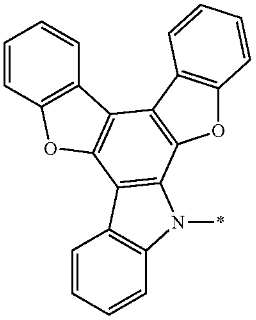
-continued
D098
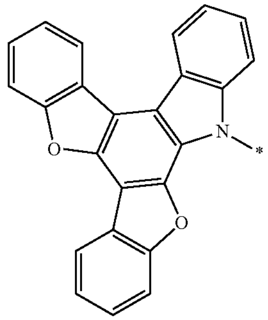
D099
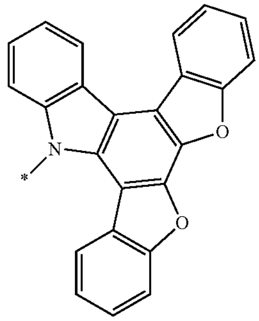
D100
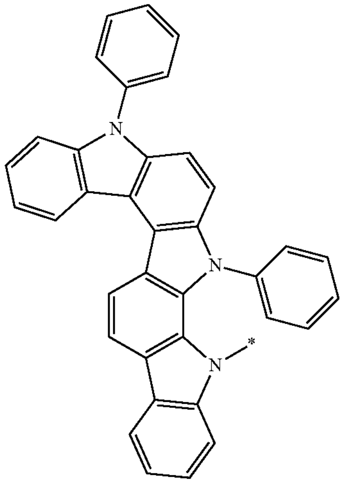
D101
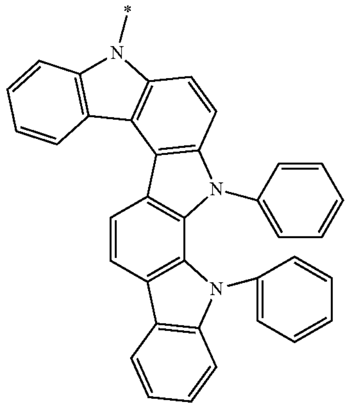

-continued
D102
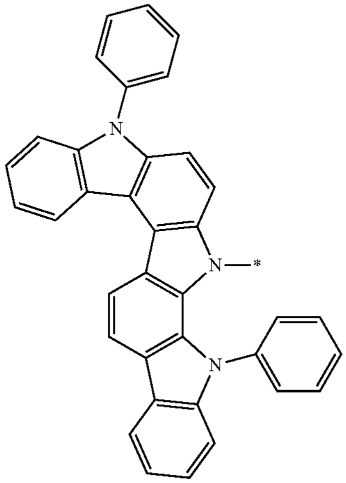
D103
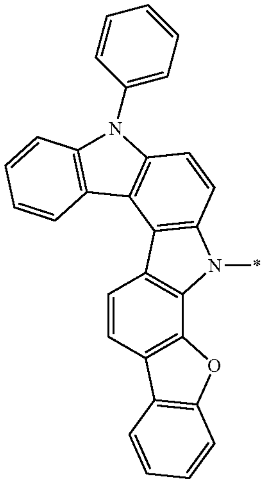
D104
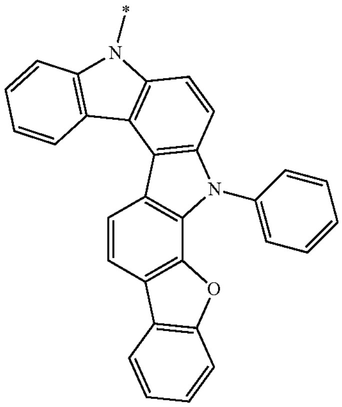
-continued
D105
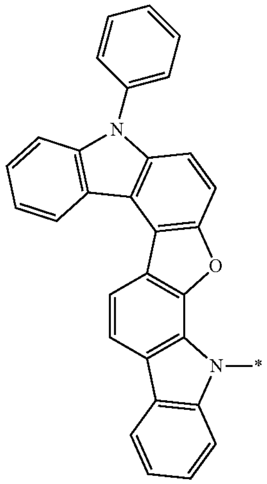
D106
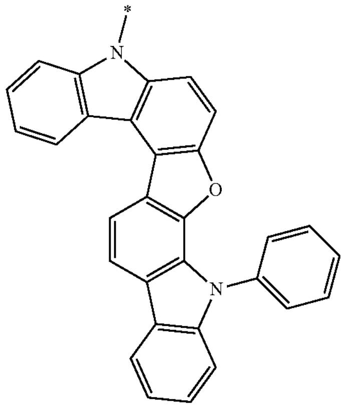
D107
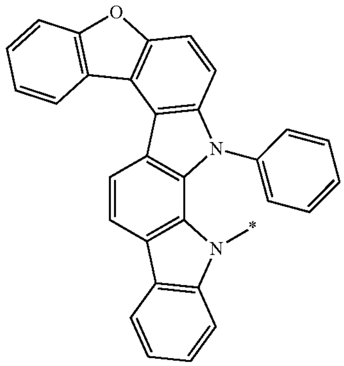
D108
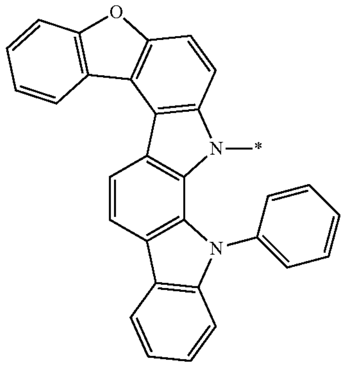

-continued
D109
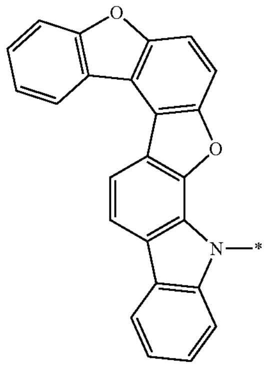
D110
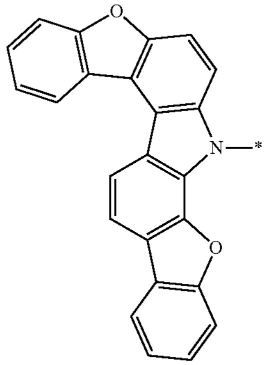
D111
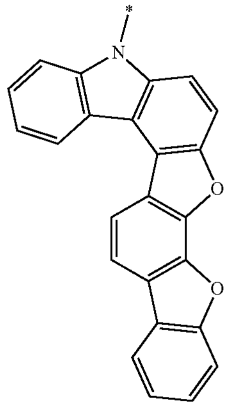
D112
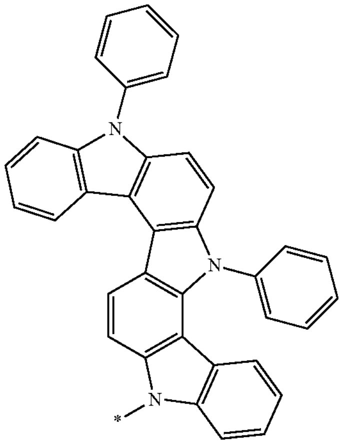
-continued
D113
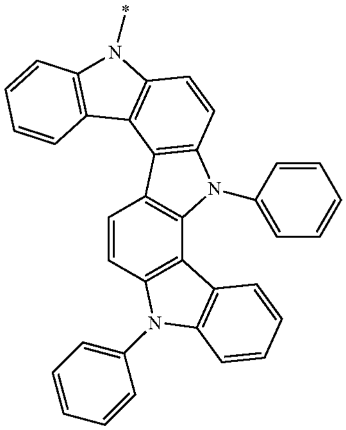
D114
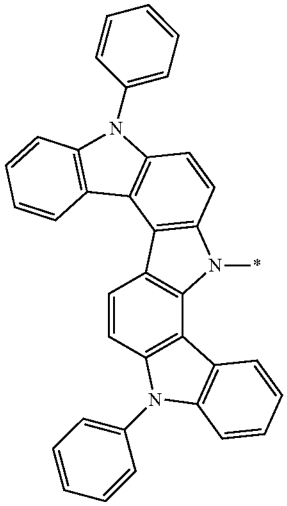
D115
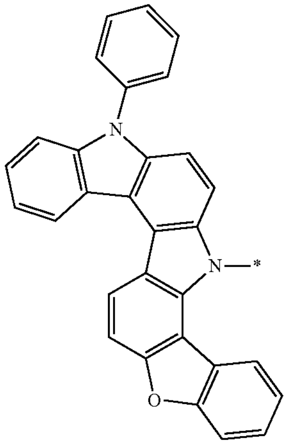

-continued
D116
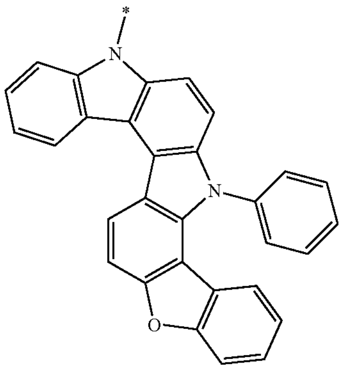
D117
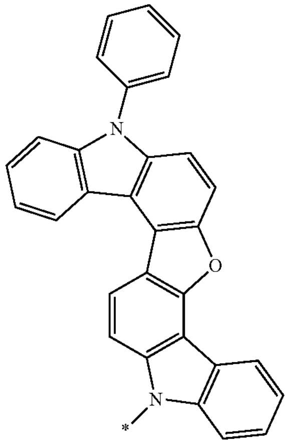
D118
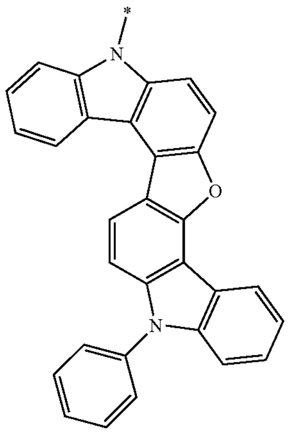
D119
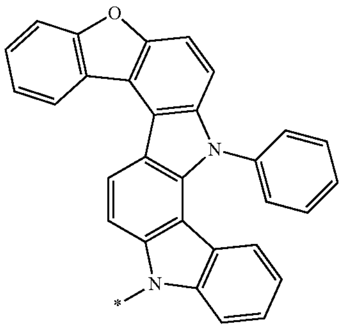
-continued
D120
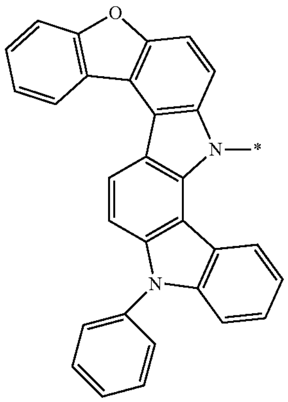
D121
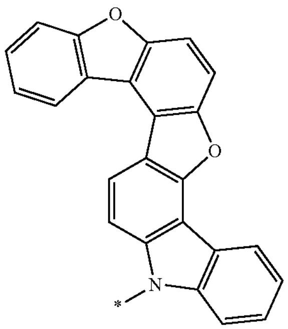
D122
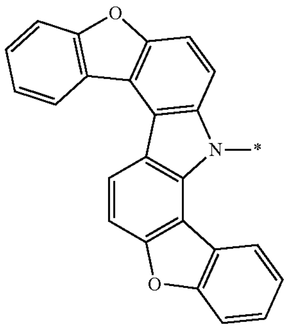
D123
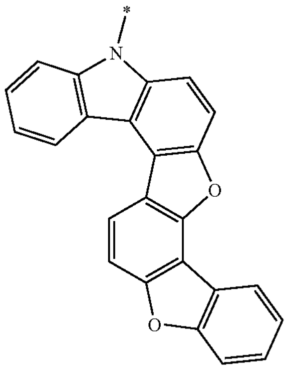

-continued
D124
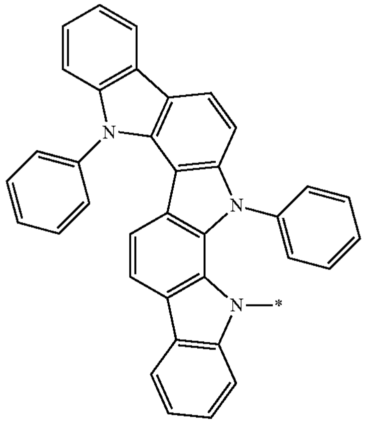
D125
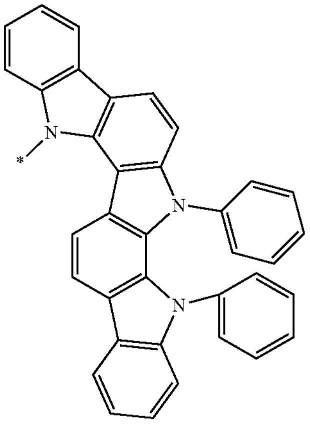
D126
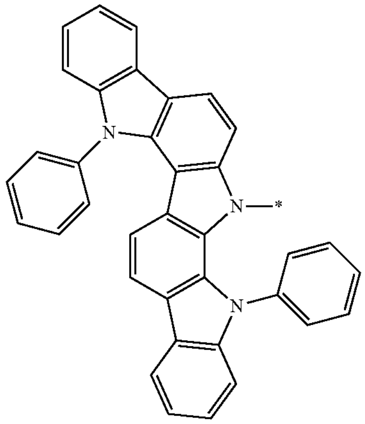
-continued
D127
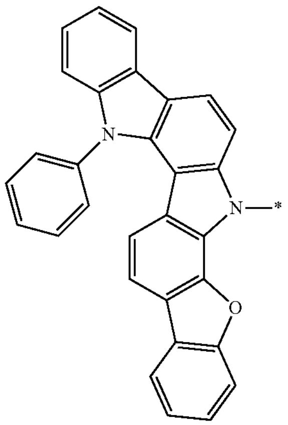
D128
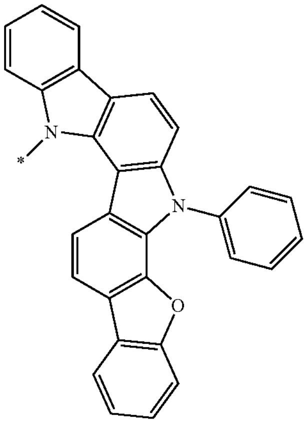
D129
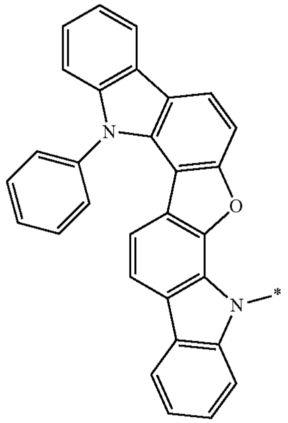

D130
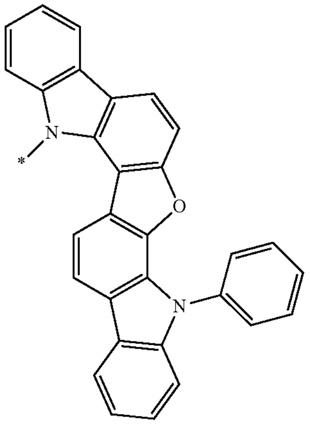
D131
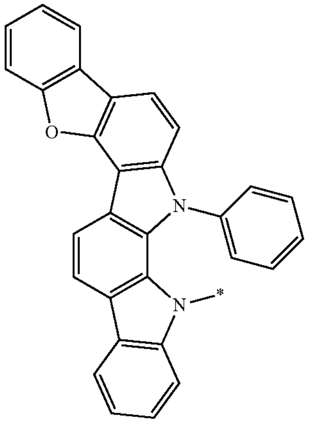
D132
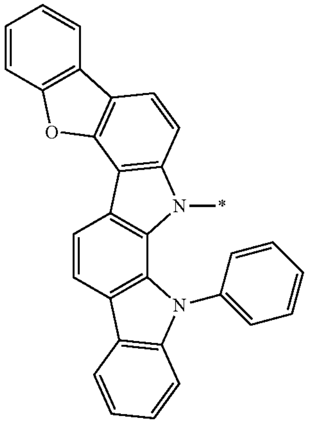
D133
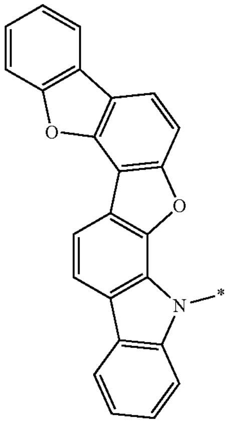
D134
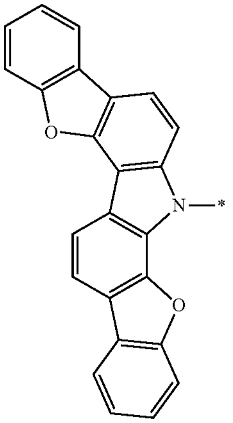
D135
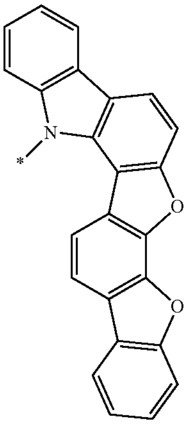

-continued
D136
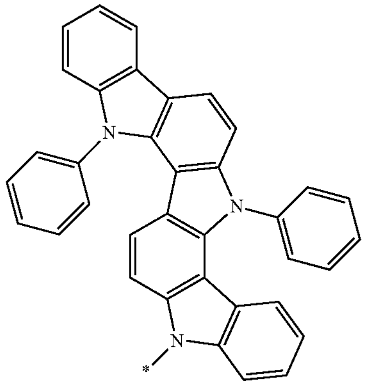
D137
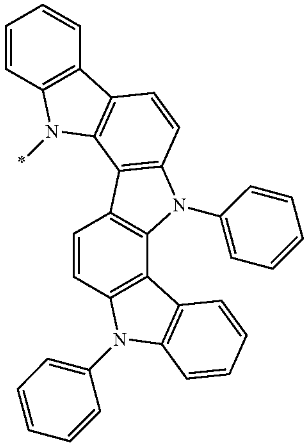
D138
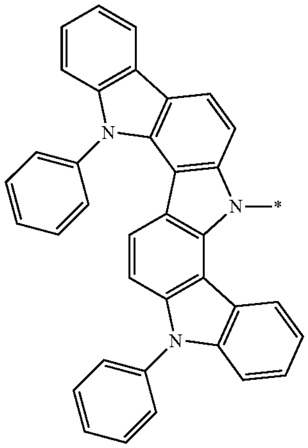
-continued
D139
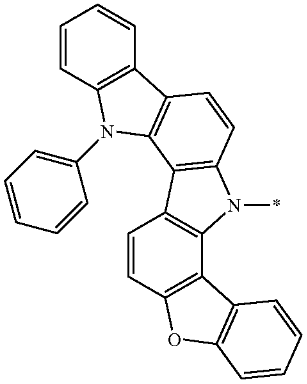
D140
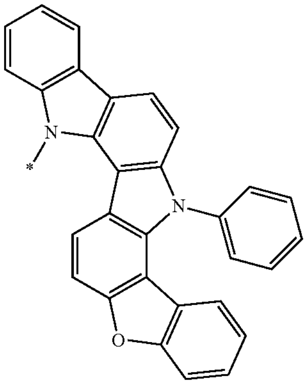
D141
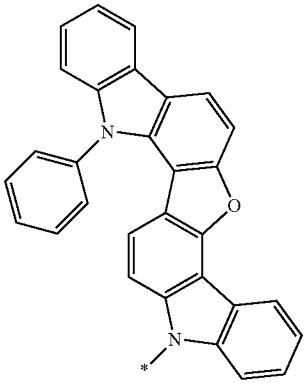
D142
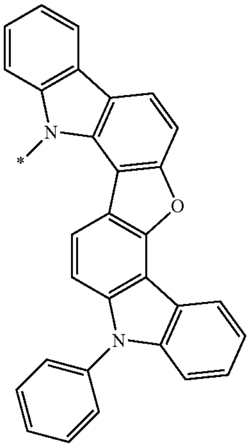

-continued
D143
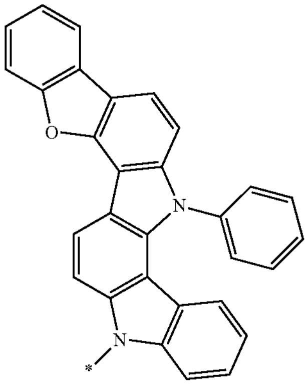
D144
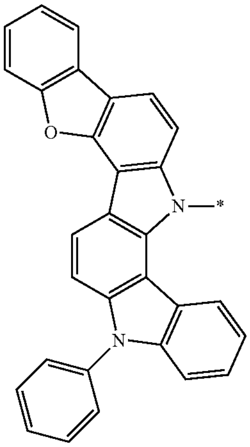
D145
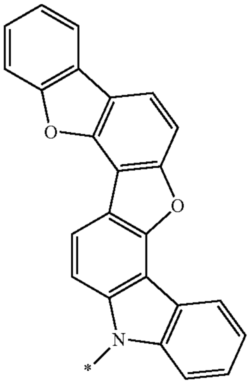
D146
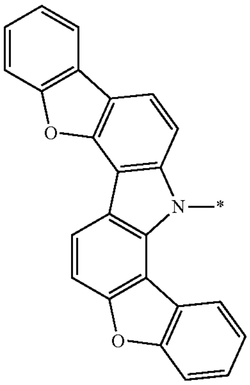
-continued
D147
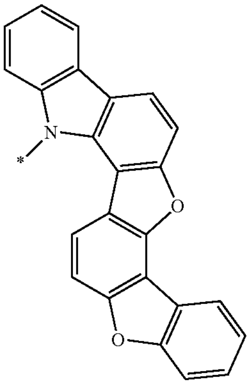
D148
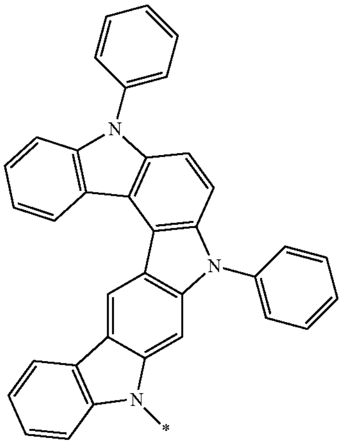
D149
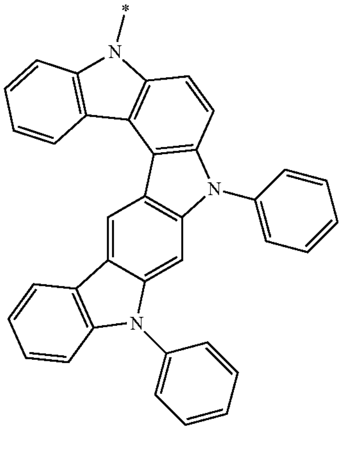

-continued
D150
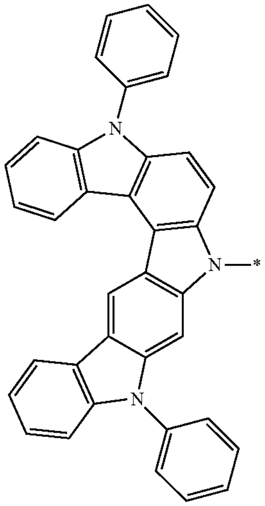
D151
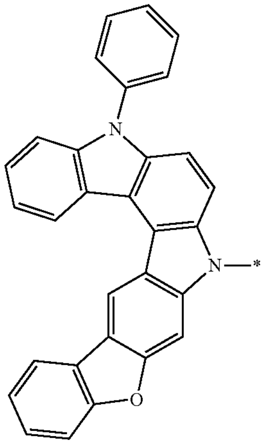
D152
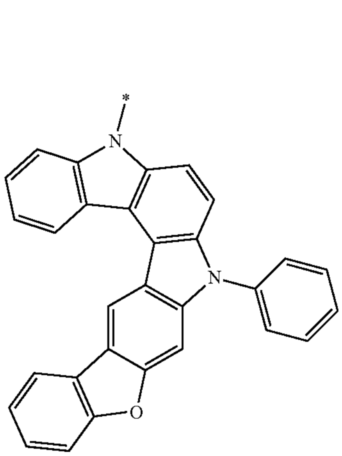
-continued
D153
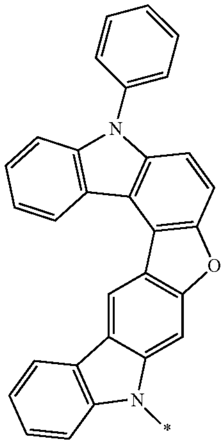
D154
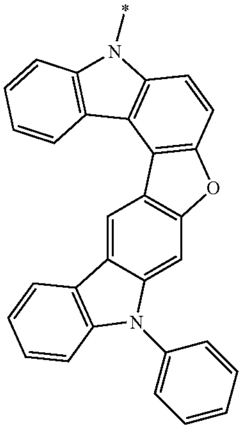
D155
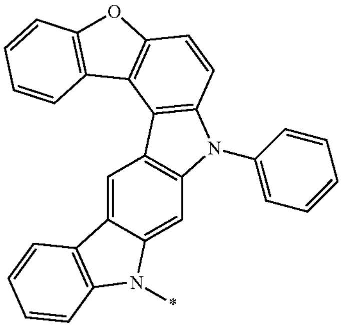
D156
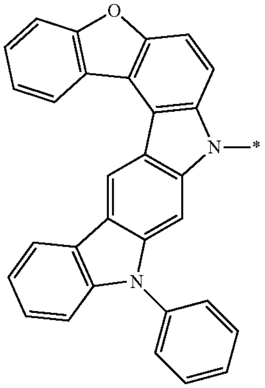

-continued
D157
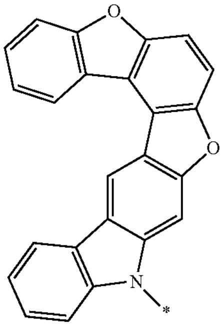
D158
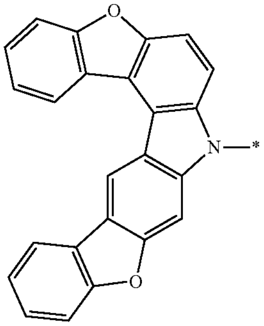
D159
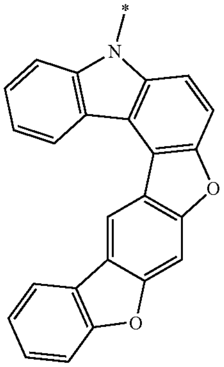
D160
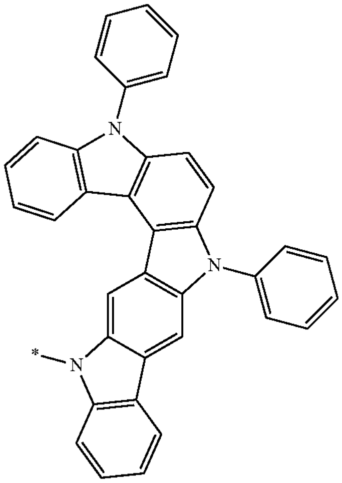
-continued
D161
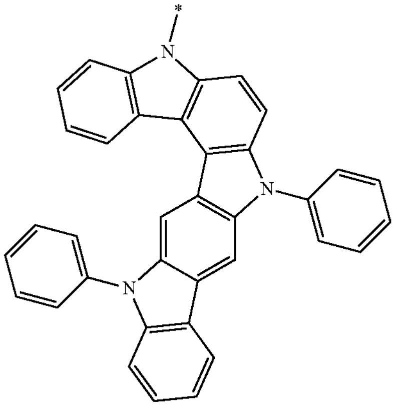
D162
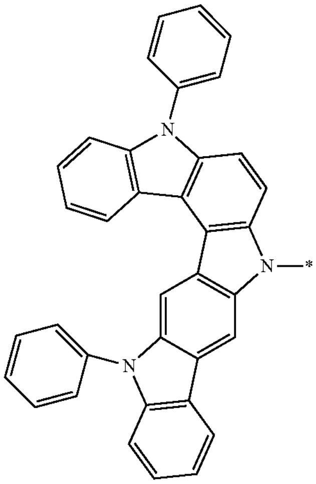
D163
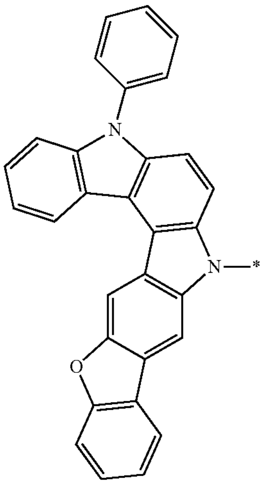

-continued
D164
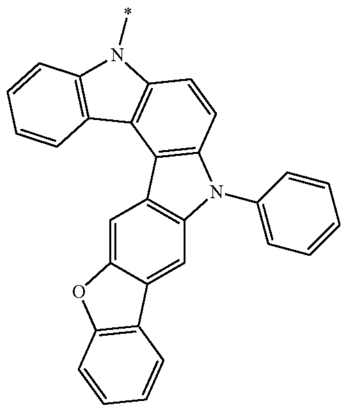
D165
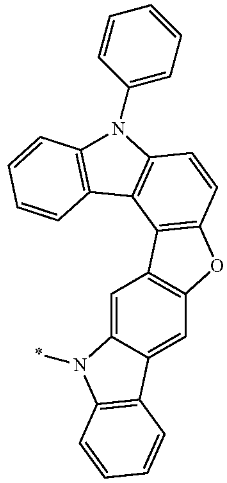
D166
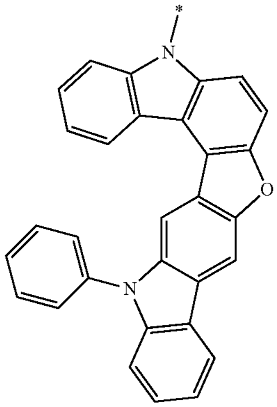
-continued
D167
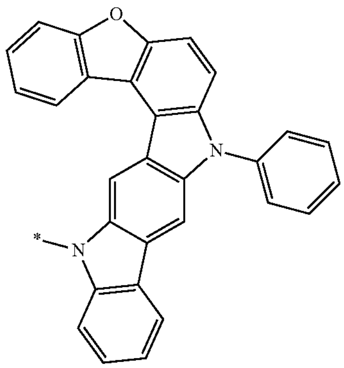
D168
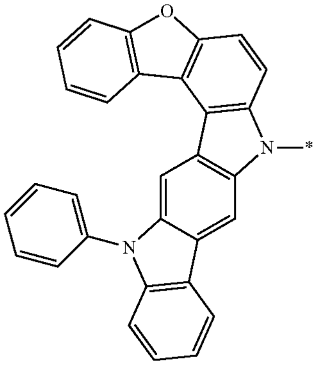
D169
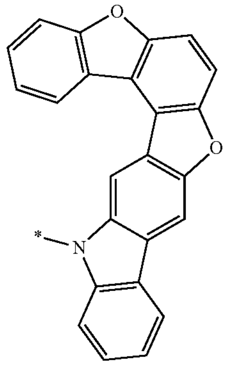
D170
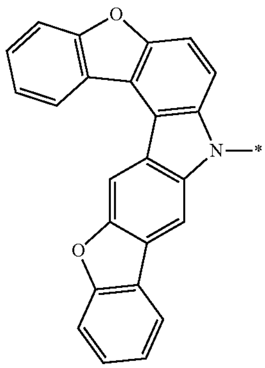

-continued
D171
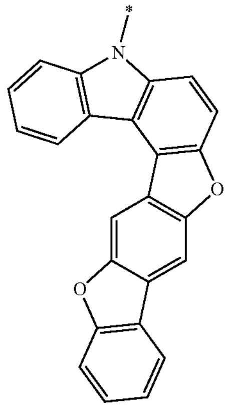
D172
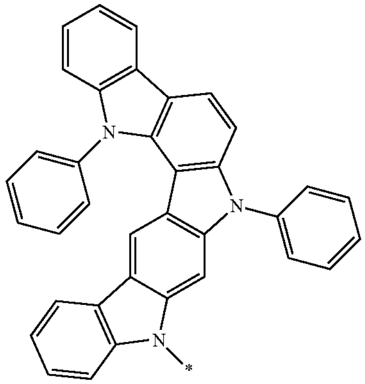
D173
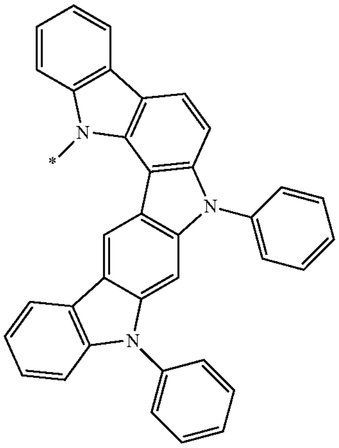
-continued
D174
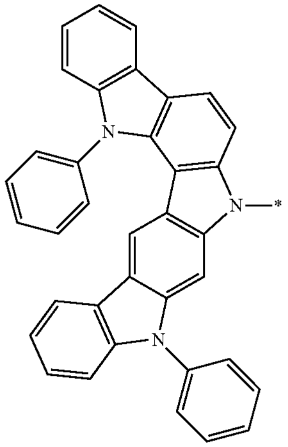
D175
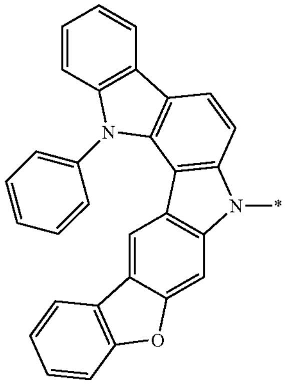
D176
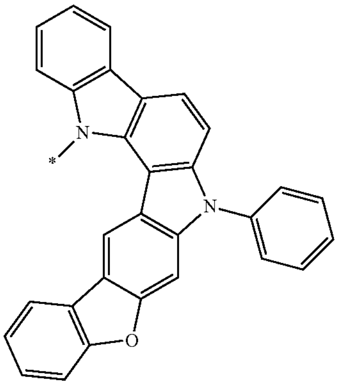
D177
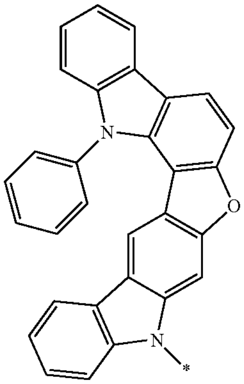

-continued
D178
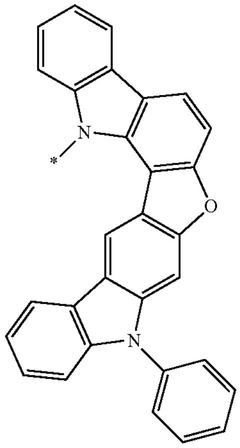
D179
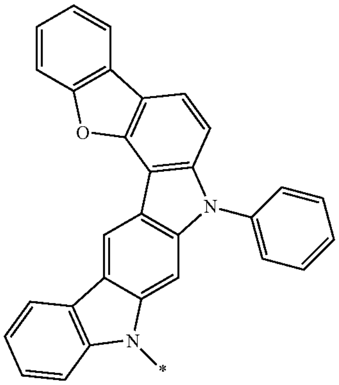
D180
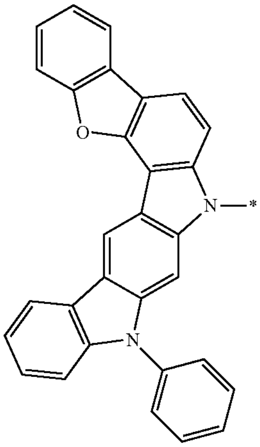
-continued
D181
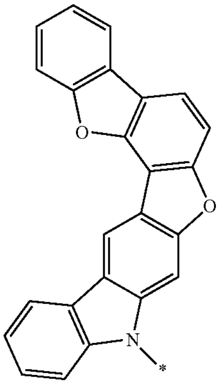
D182
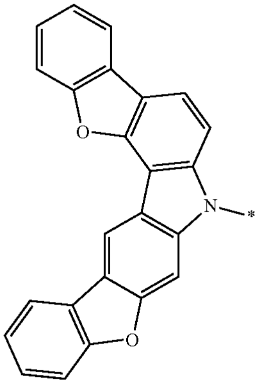
D183
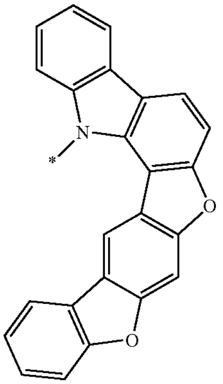
D184
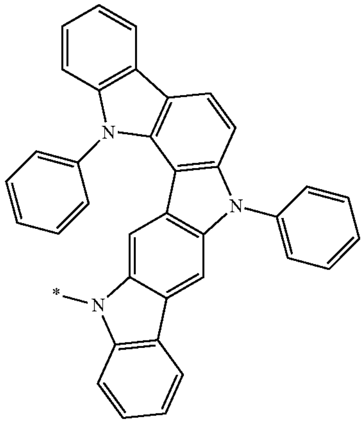

-continued
D185
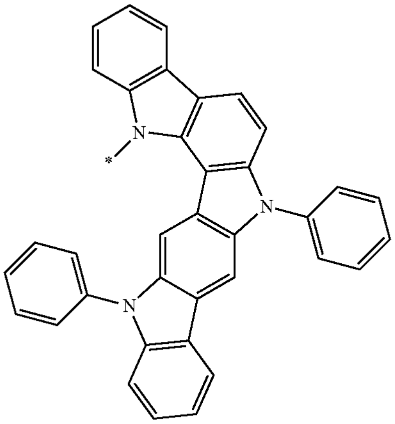
D186
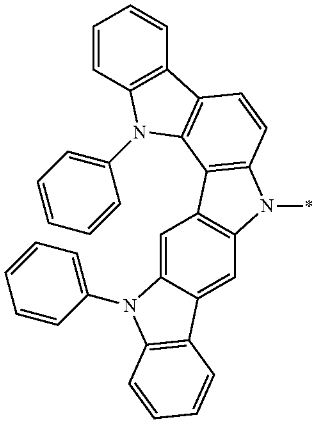
D187
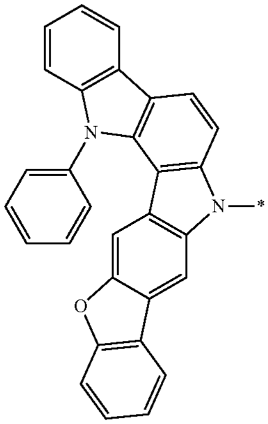
-continued
D188
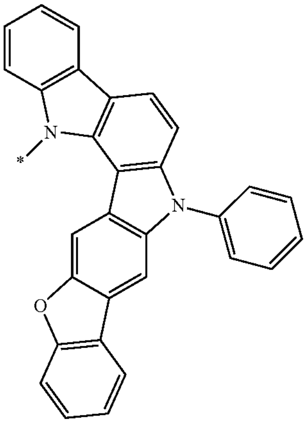
D189
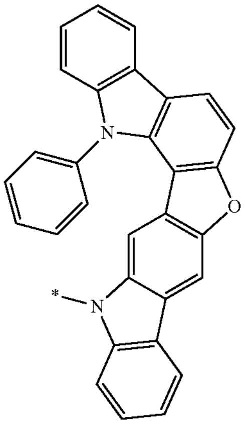
D190
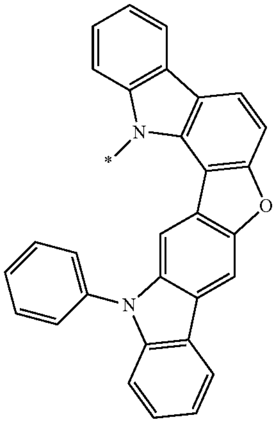

-continued
D191
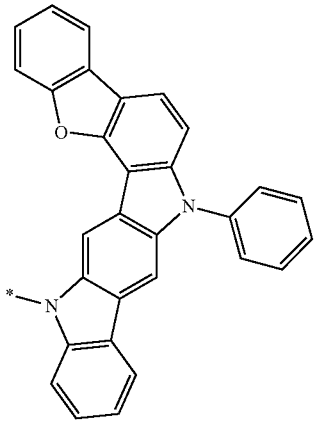
D192
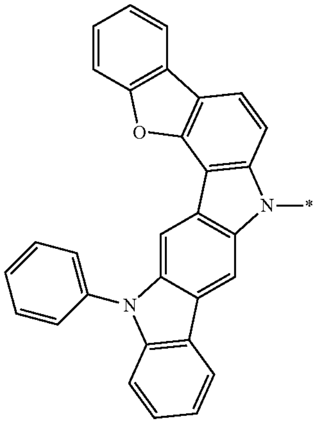
D193
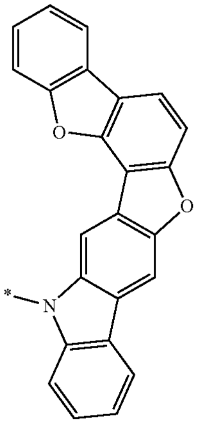
-continued
D194
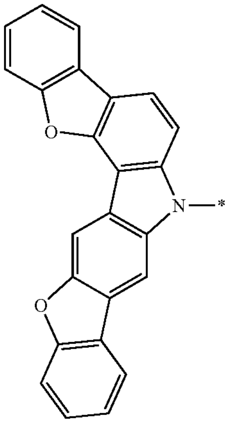
D195
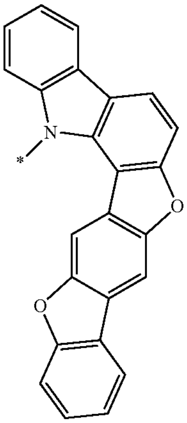
D196
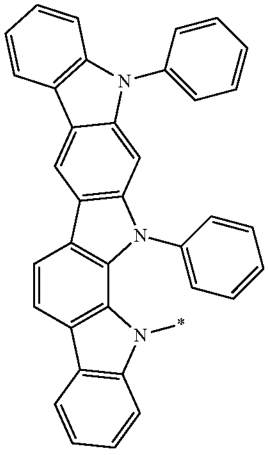

-continued
D197
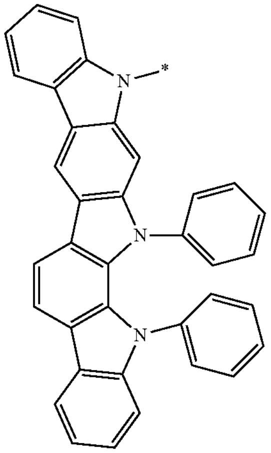
D198
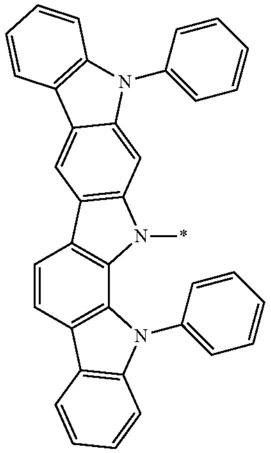
D199
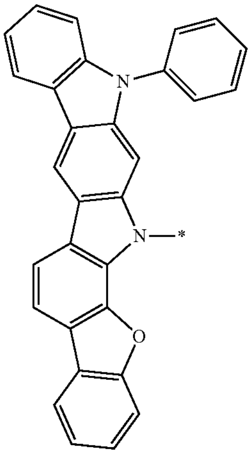
-continued
D200
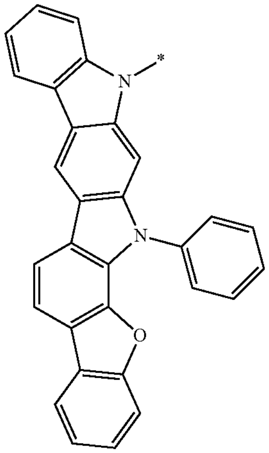
D201
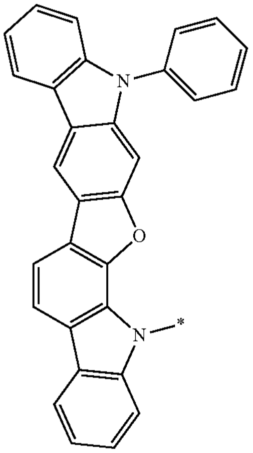
D202
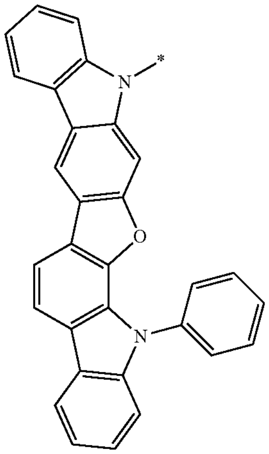

-continued
D203
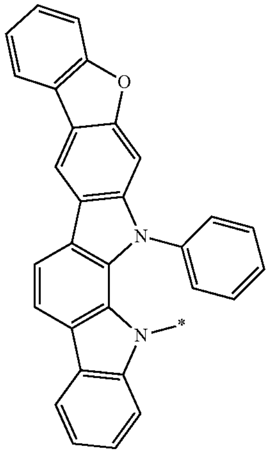
D204
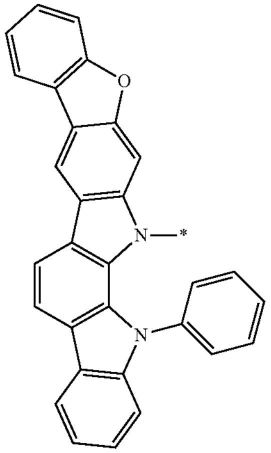
D205
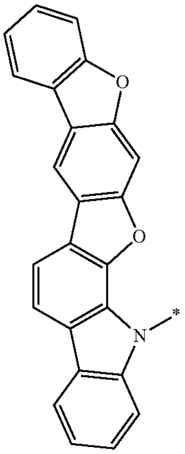
-continued
D206
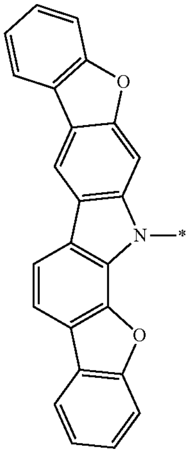
D207
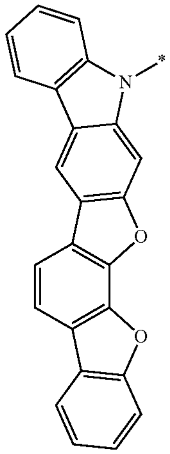
D208
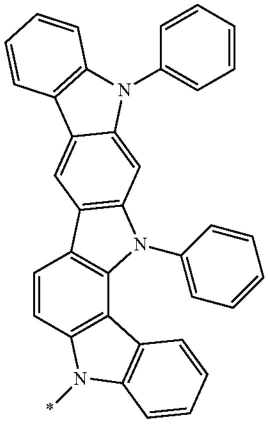

-continued
D209
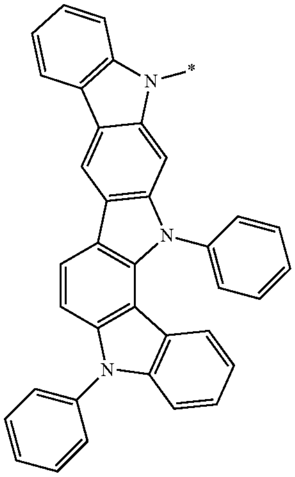
D210
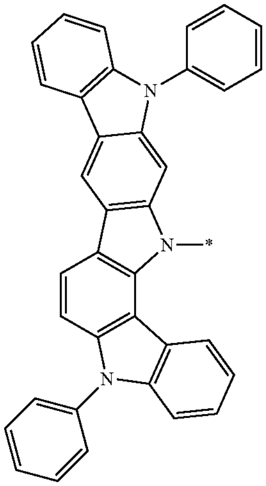
D211
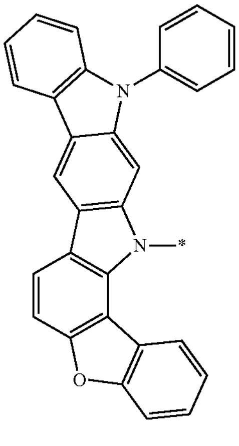
-continued
D212
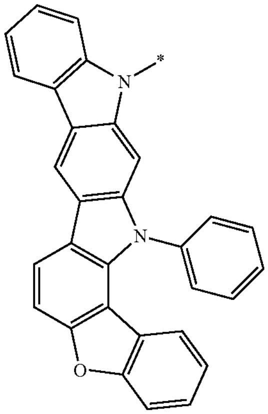
D213
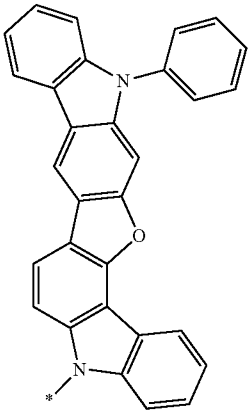
D214
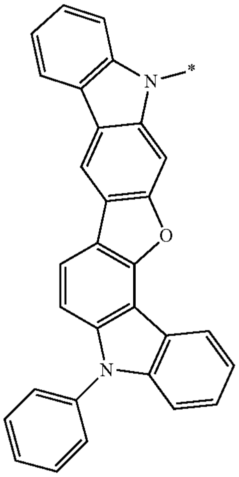

D215
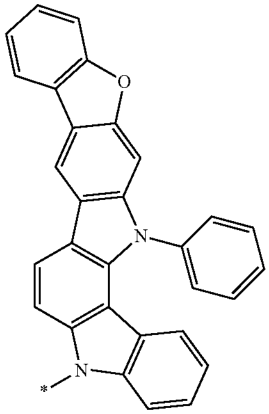
D216
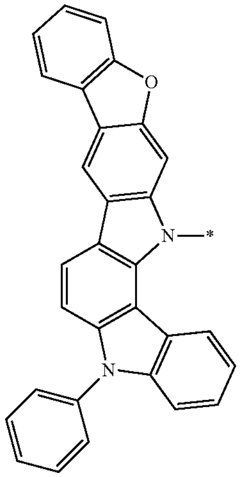
D217
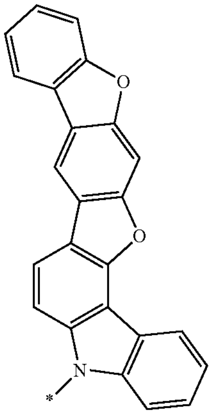
D218
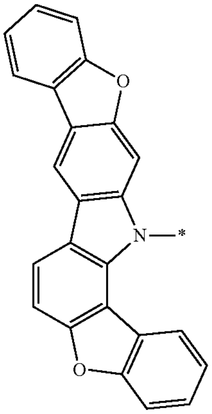
D219
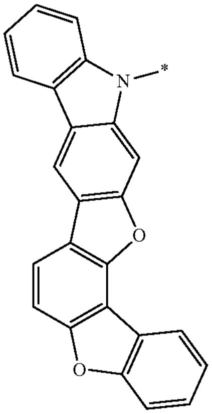
D220
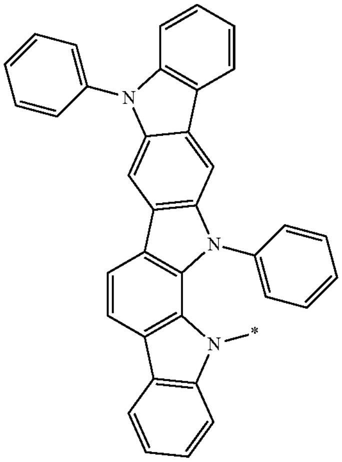

-continued
D221
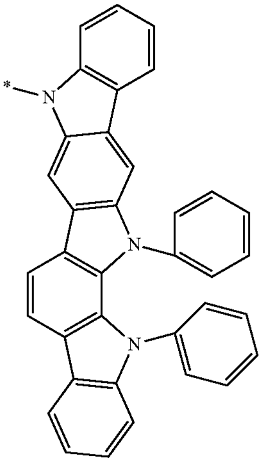
D222
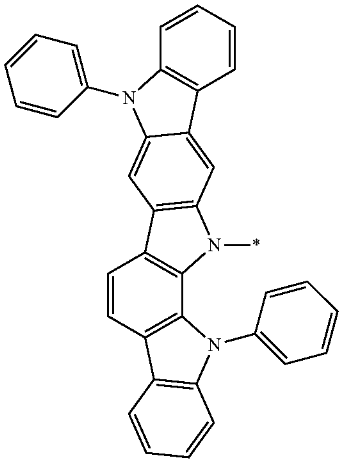
D223
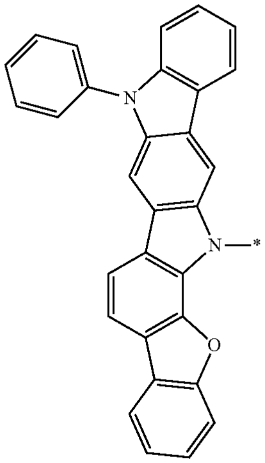
-continued
D224
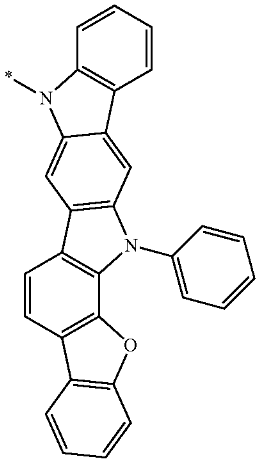
D225
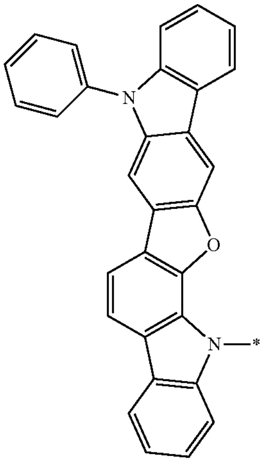
D226
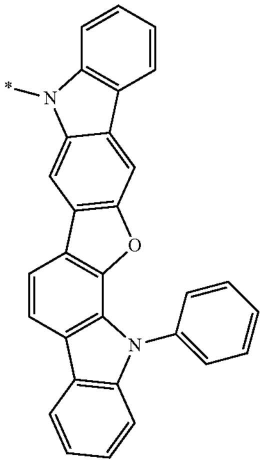

-continued
D227
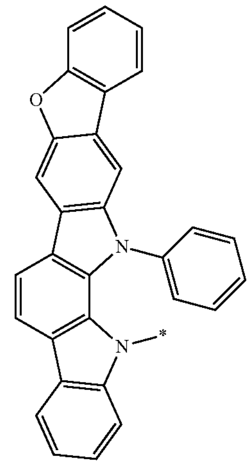
D228
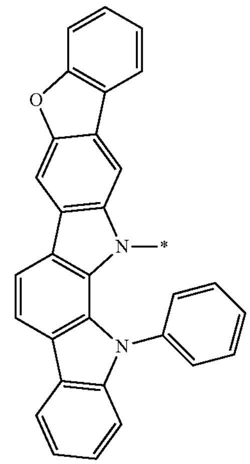
D229
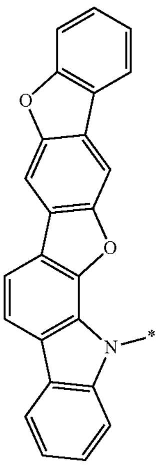
-continued
D230
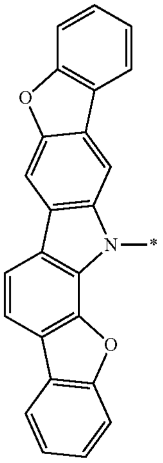
D231
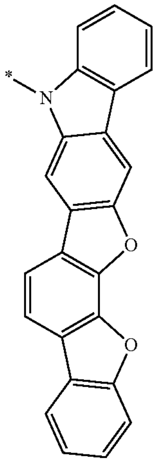
D232
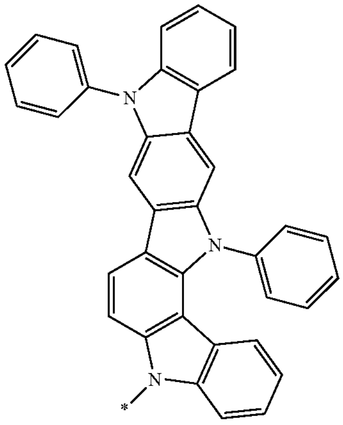

-continued
D233
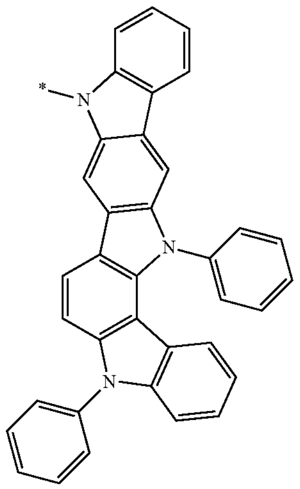
D234
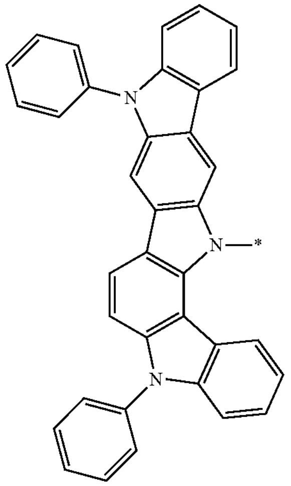
D235
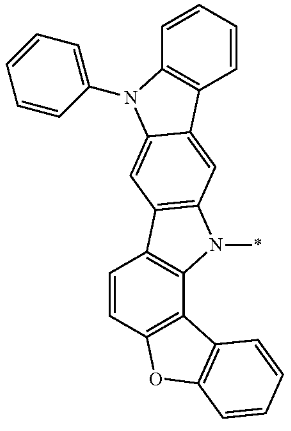
-continued
D236
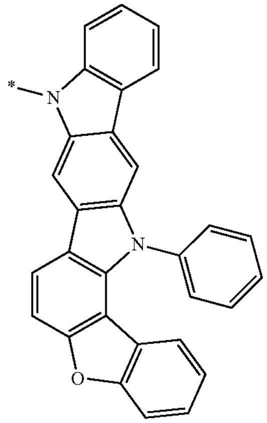
D237
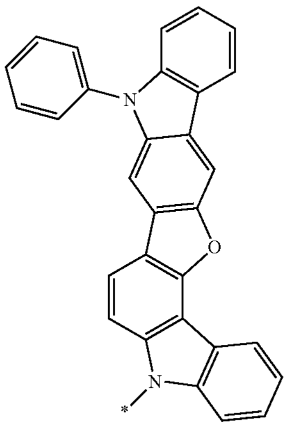
D238
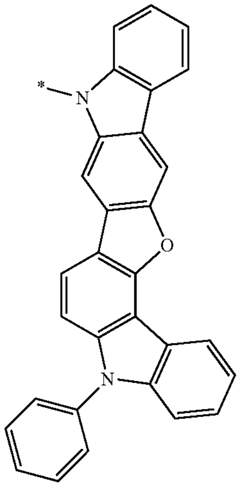

D239
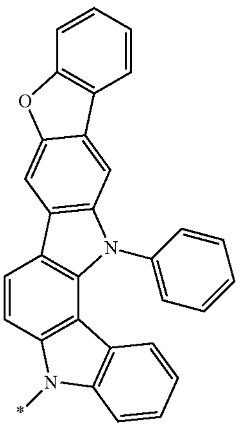
D240
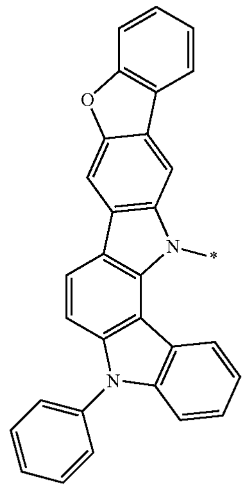
D241
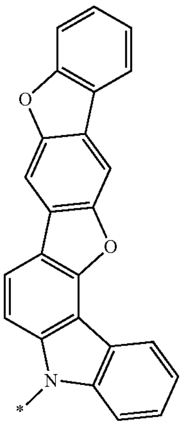
D242
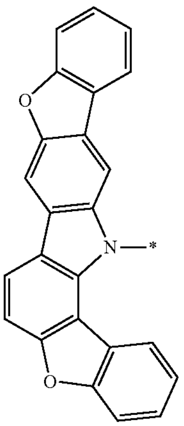
D243
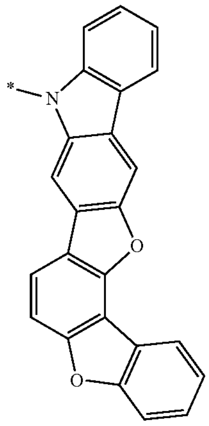
D244
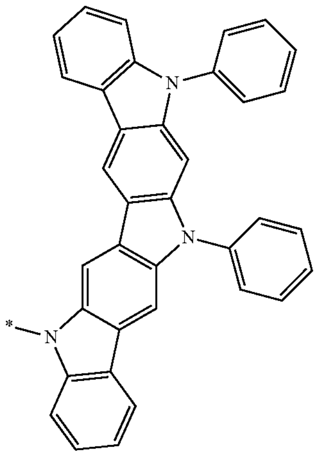

-continued
D245
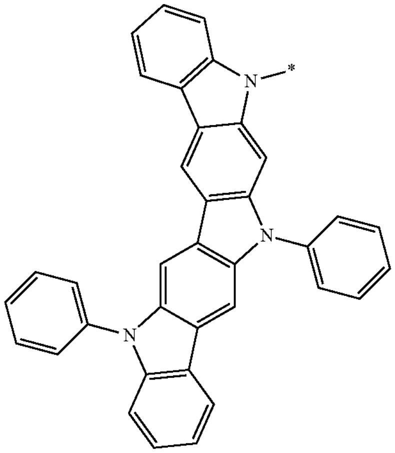
D246
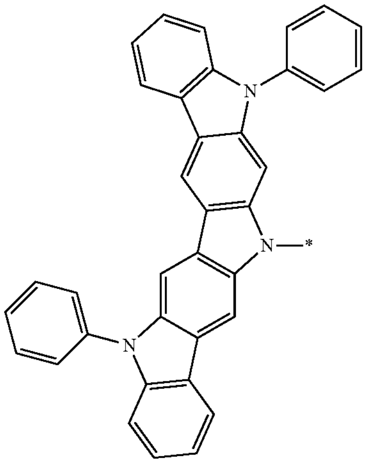
D247
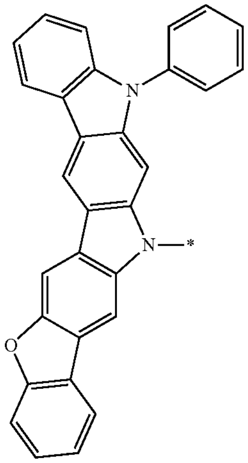
-continued
D248
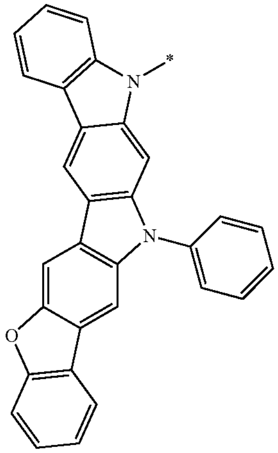
D249
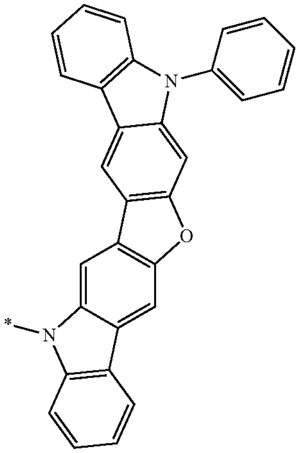
D250
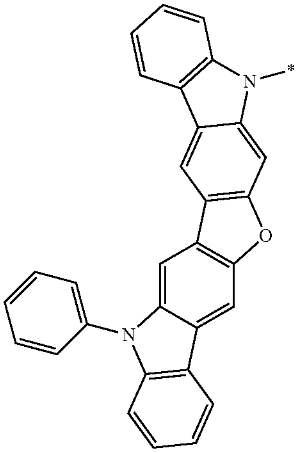

-continued
D251
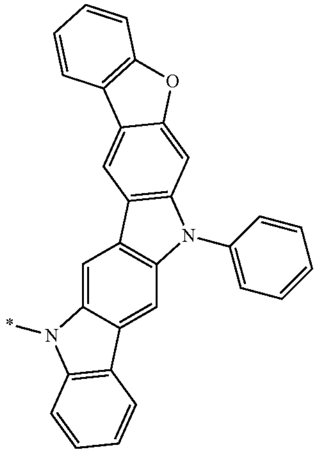
D252
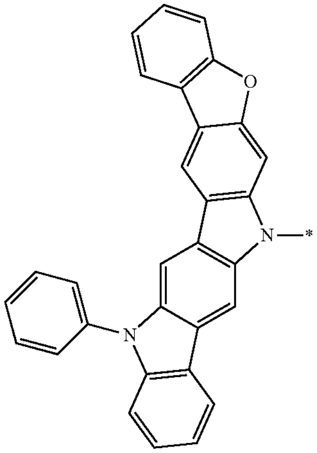
D253
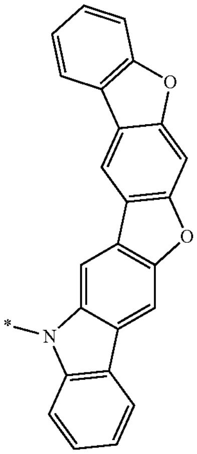
-continued
D254
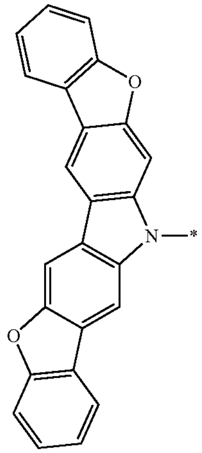
D255
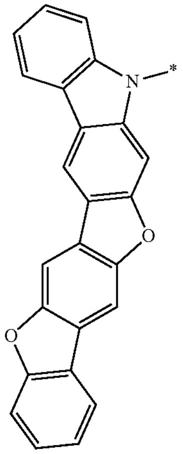
D256
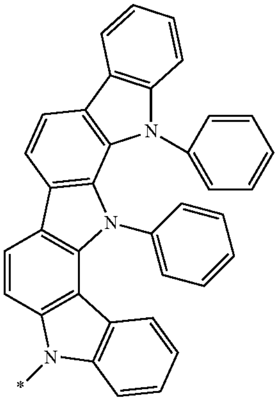

-continued
D257
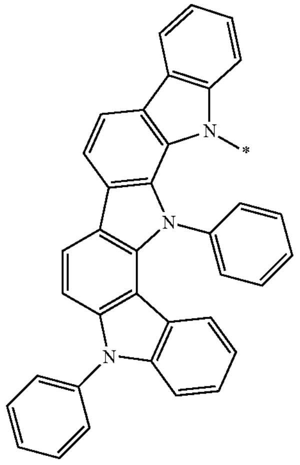
D258
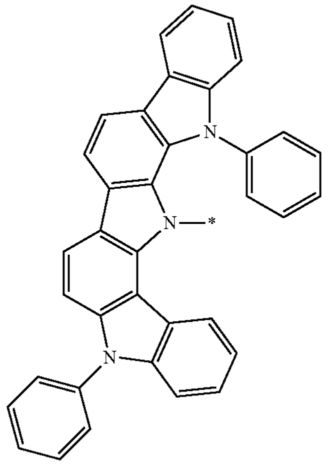
D259
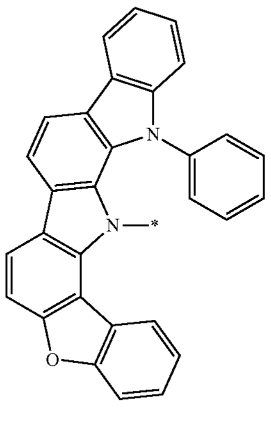
-continued
D260
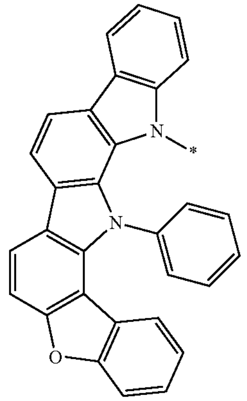
D261
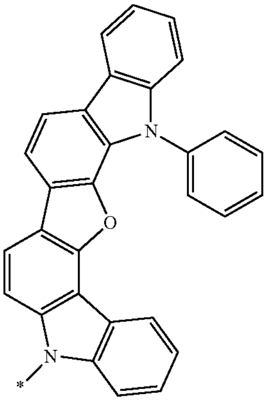
D262
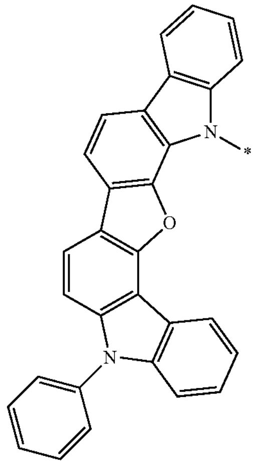

-continued
D263
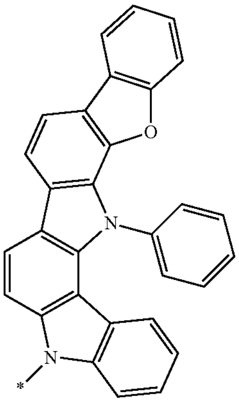
D264
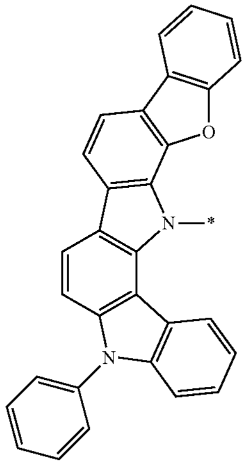
D265
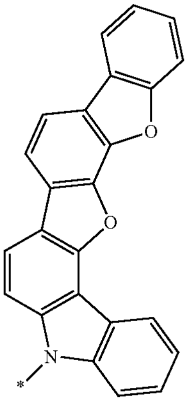
-continued
D266
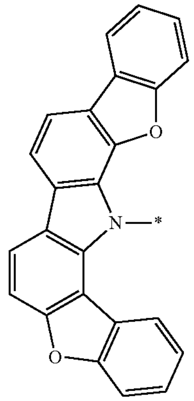
D267
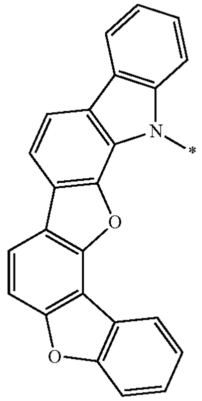
D268
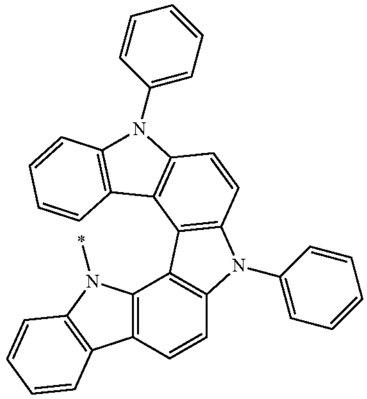
D269
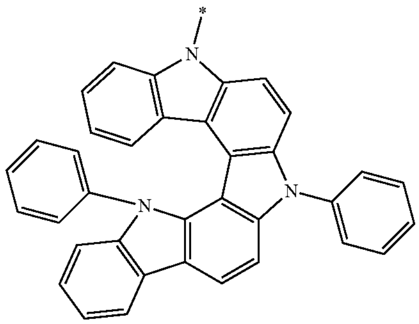

-continued
D270
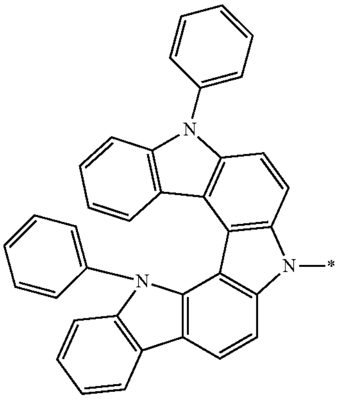
D271
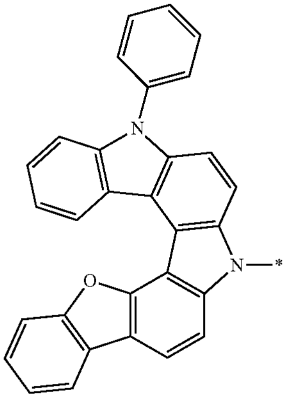
D272
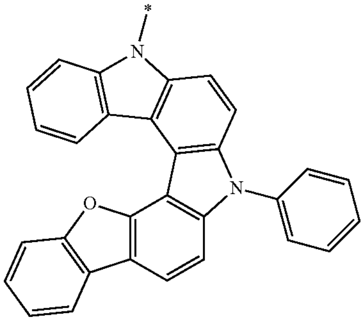
D273
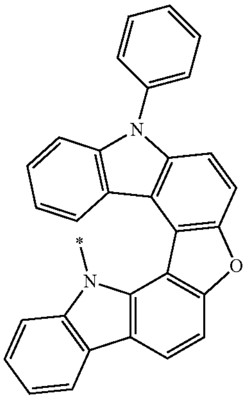
-continued
D274
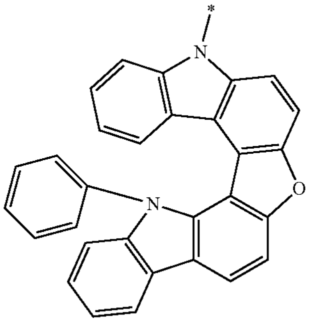
D275
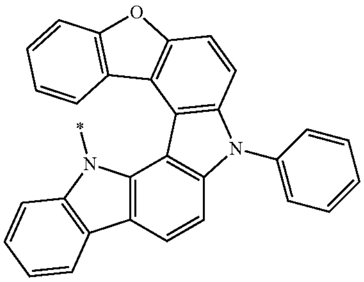
D276
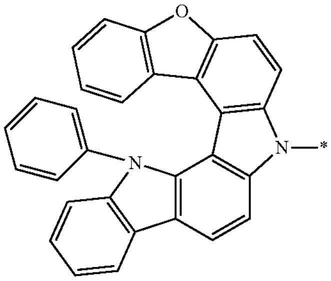
D277
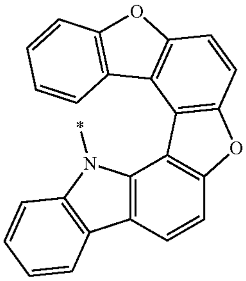
D278
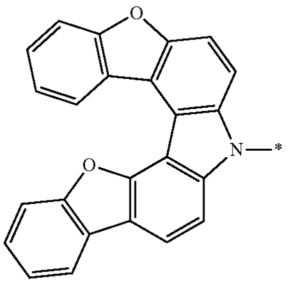

-continued
D279
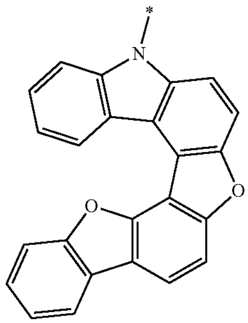
L-1
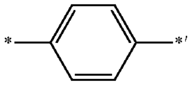
L-2
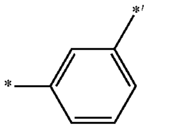
L-3
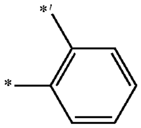
L-4
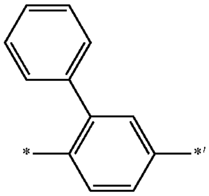
L-5
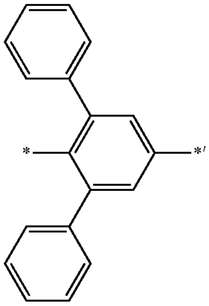
A1
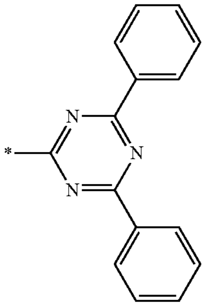
-continued
A2
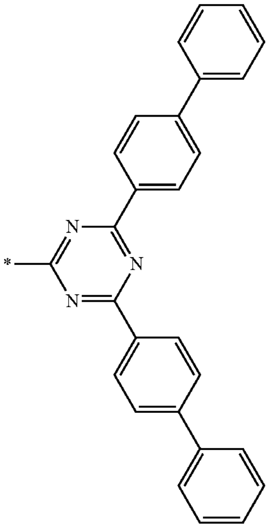
A3
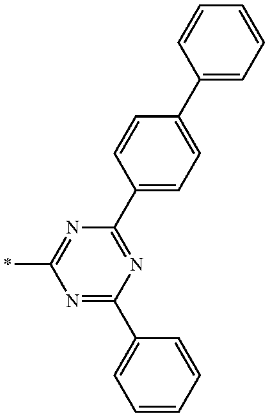
A4
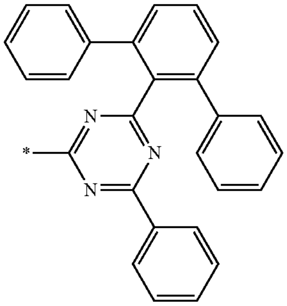

-continued
A5
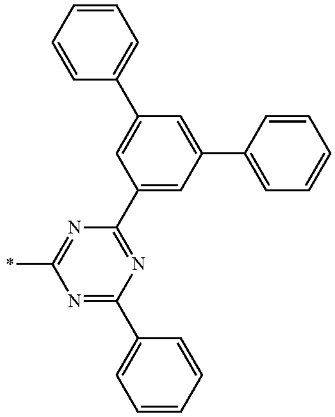
A6
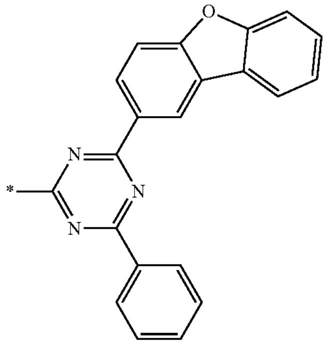
A7
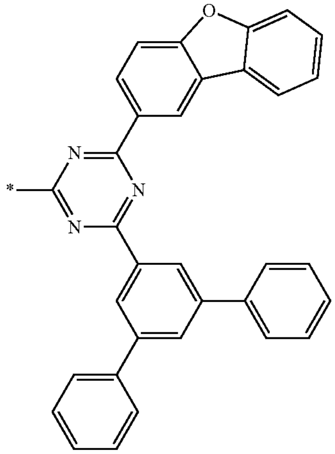
A8
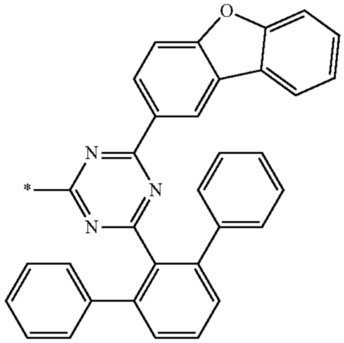
-continued
A9
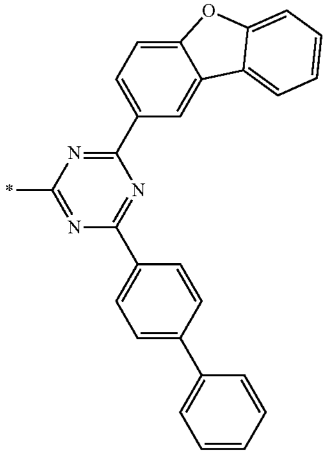
A10
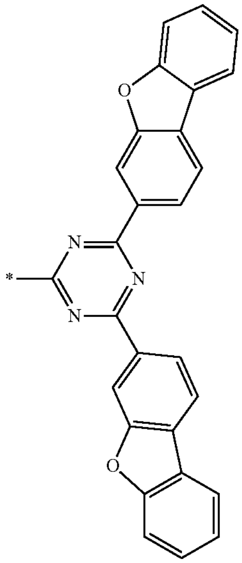
A11
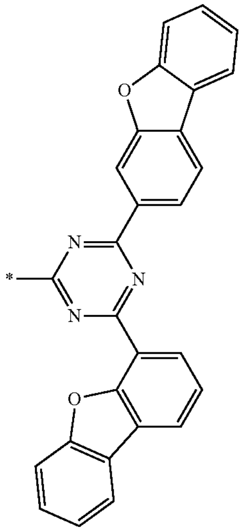

A12
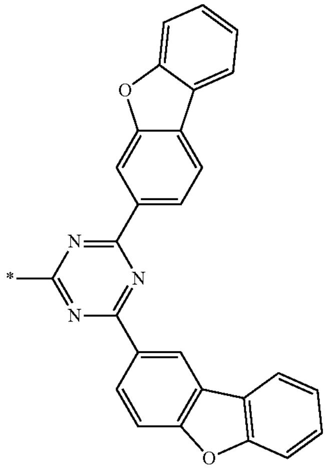
A13
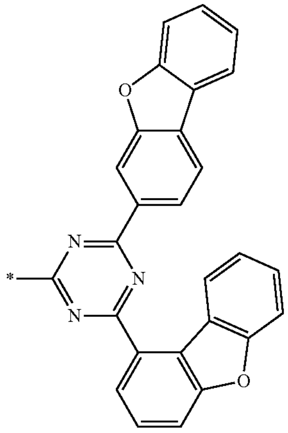
A14
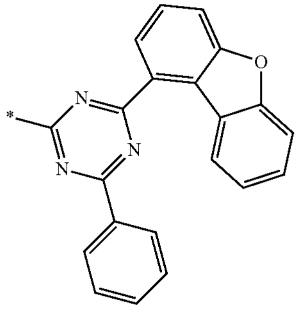
A15
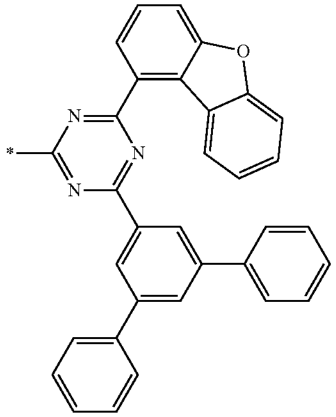
A16
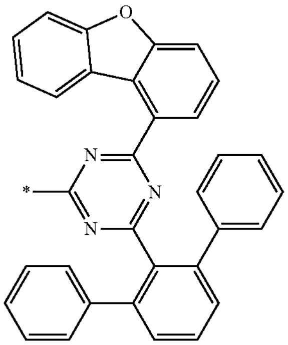
A17
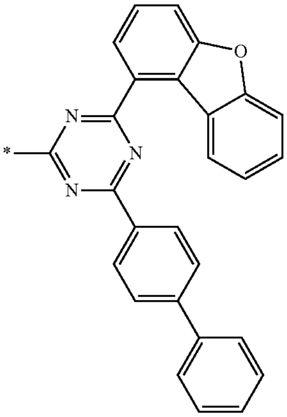
A18
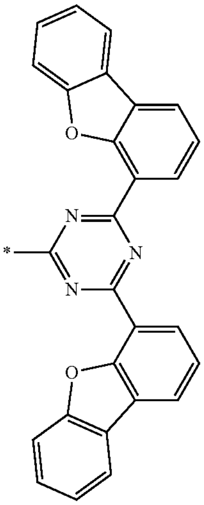

-continued
A19
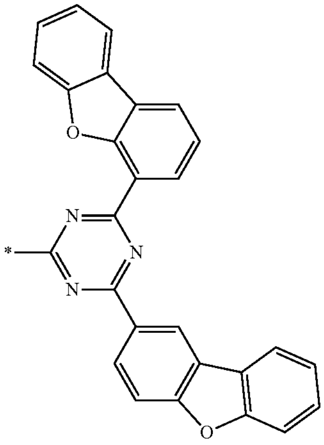
A20
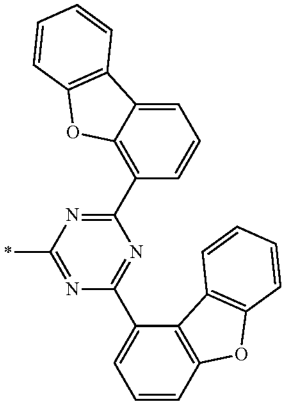
A21
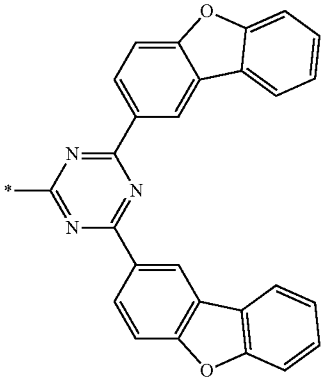
A22
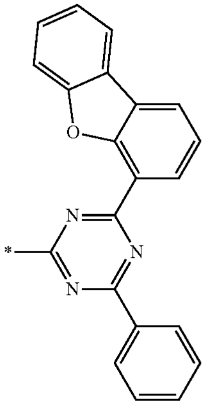
-continued
A23
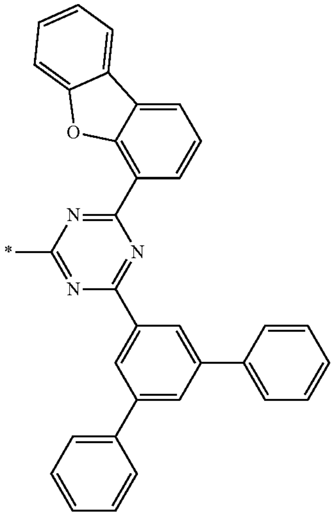
A24
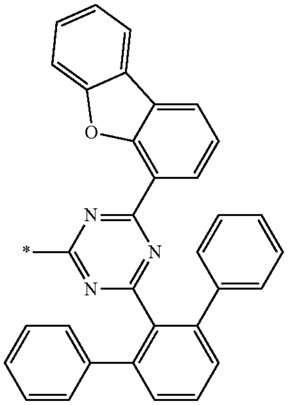
A25
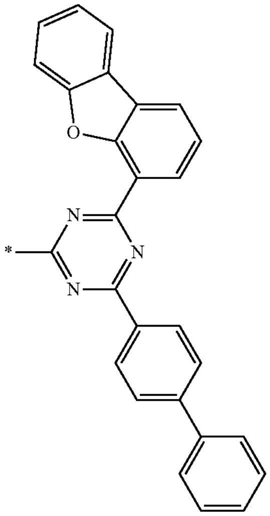

-continued
A26
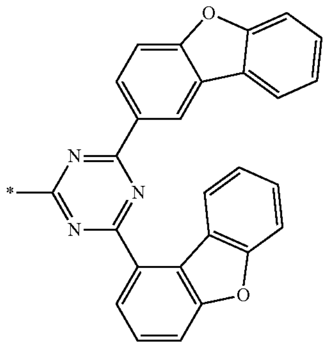
A27
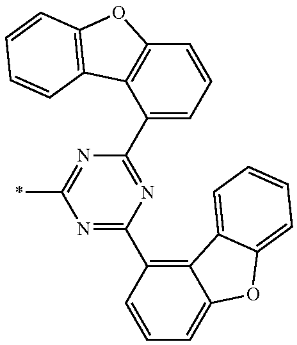
A28
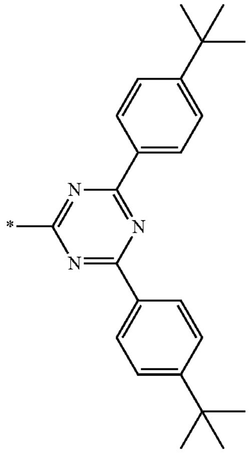
A29
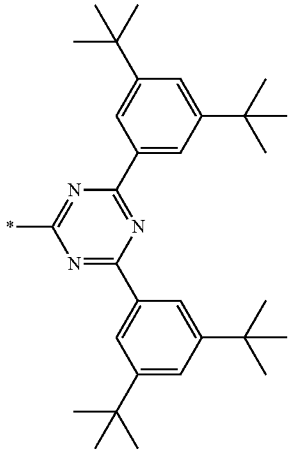
-continued
A30
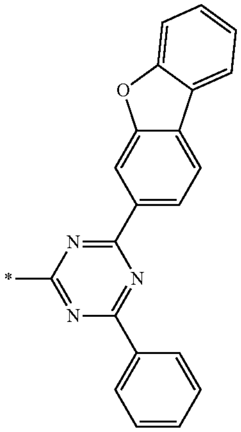
A31
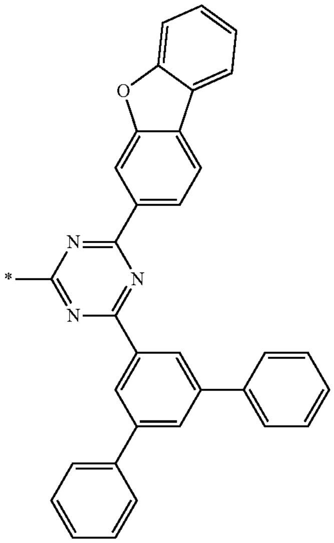
A32
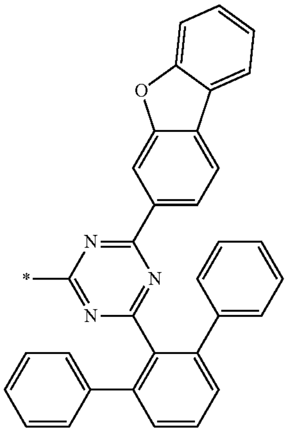

-continued
A33
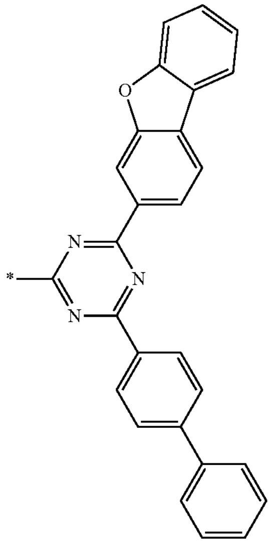
A34
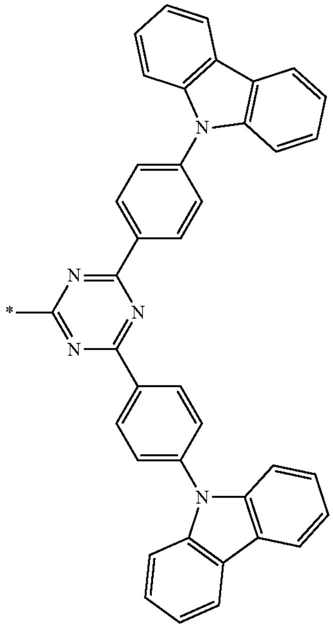
A35
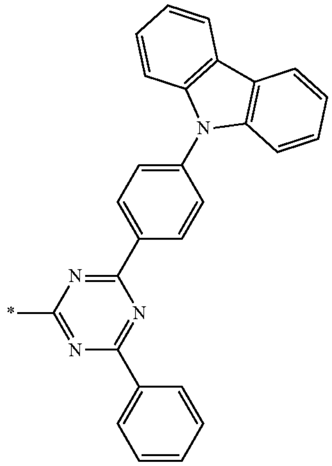
-continued
A36
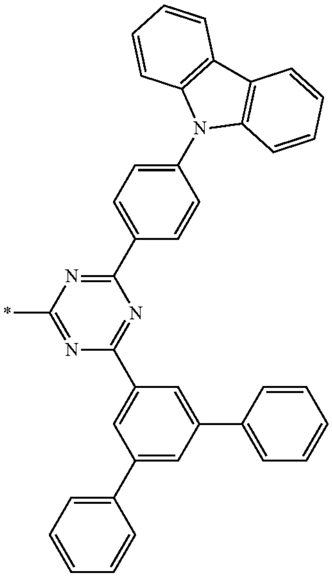
A37
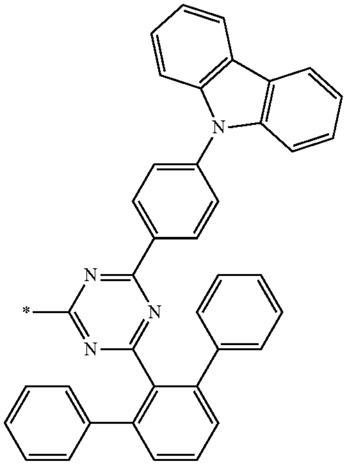
A38
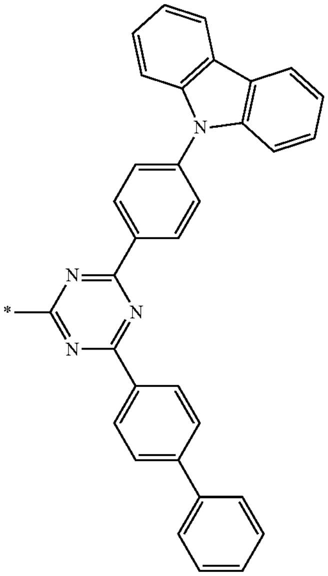

In the formulae above, * and *' each indicate a binding site to a neighboring atom.
In one or more embodiments, the heterocyclic compound may be one selected from Compounds 1 to 1078:
1
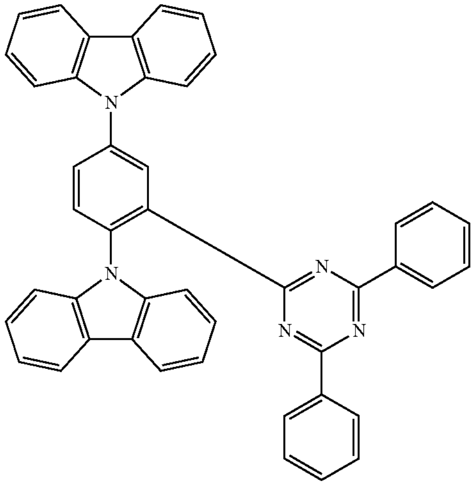
2
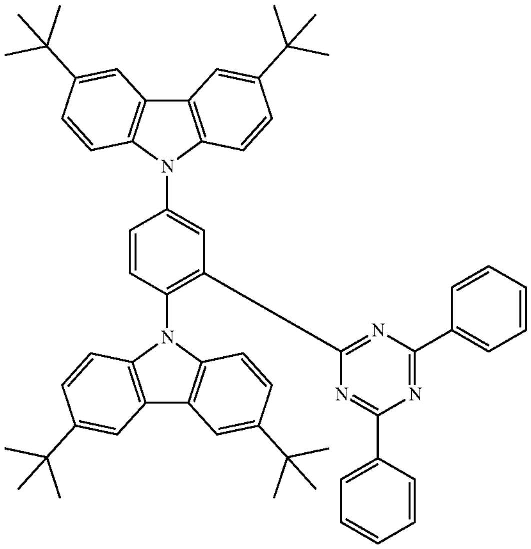
-continued
3
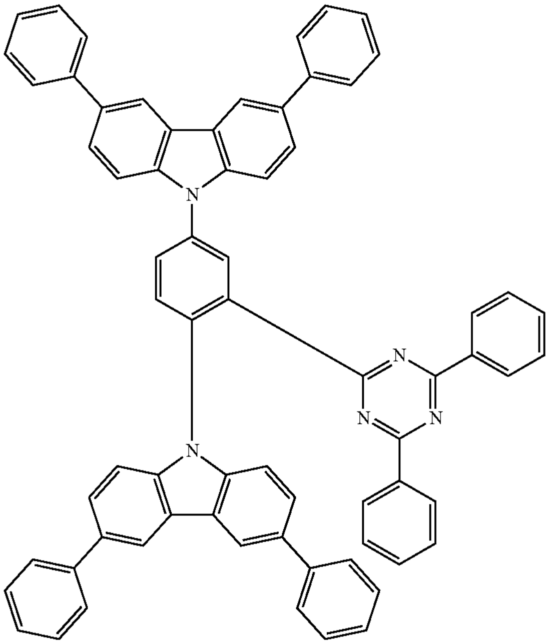
4
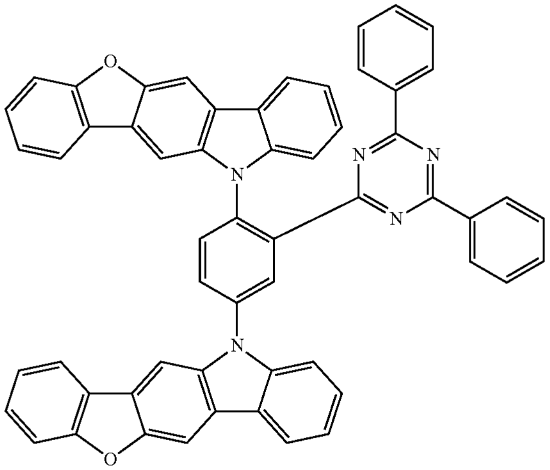
5
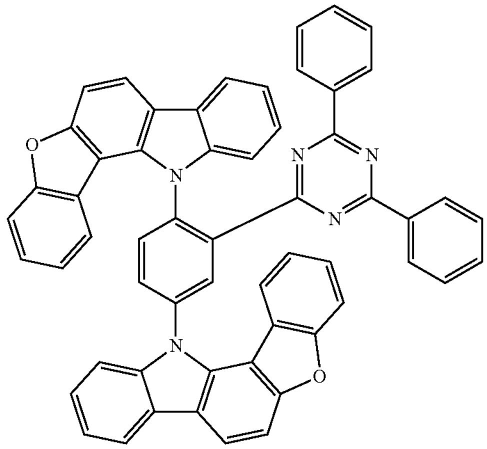

-continued
6
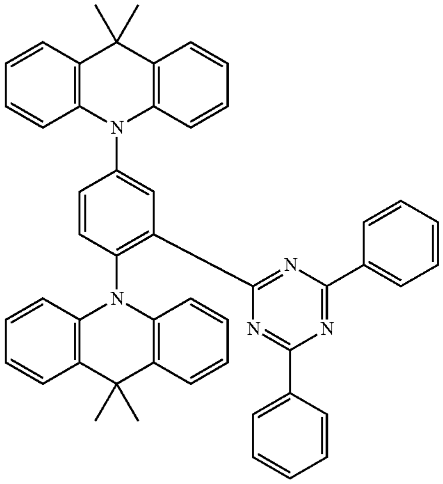
7
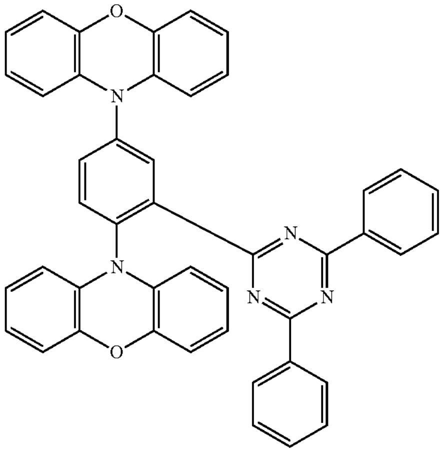
8
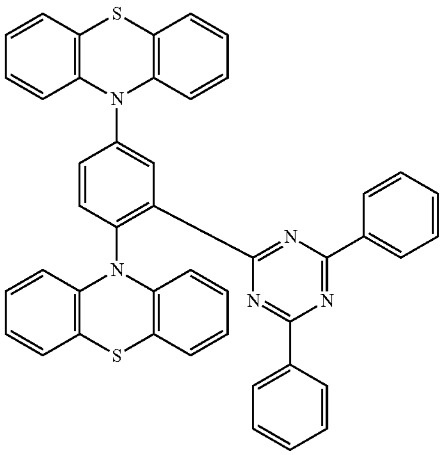
-continued
9
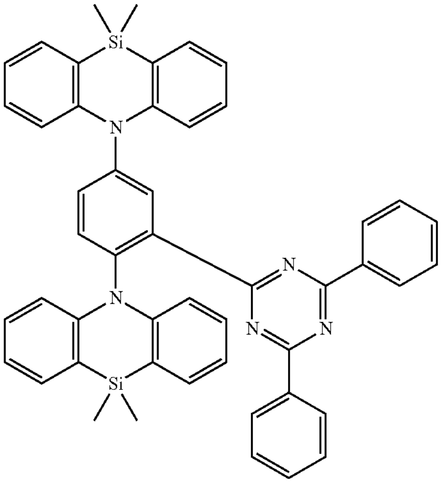
10
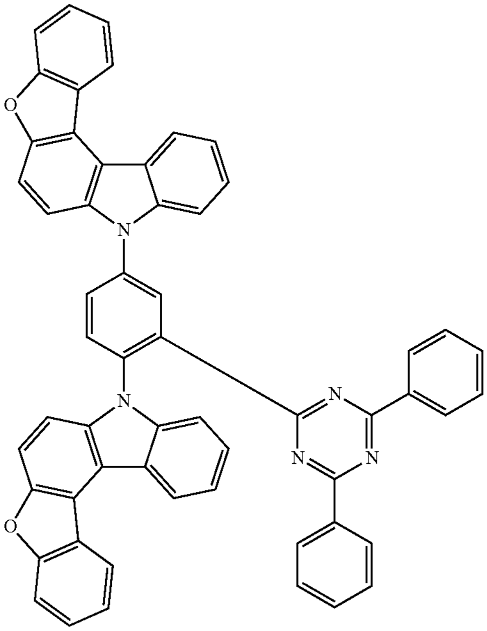

-continued
11
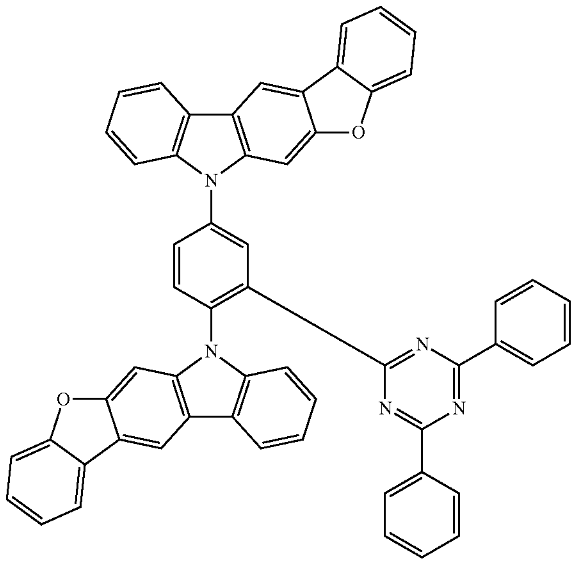
12
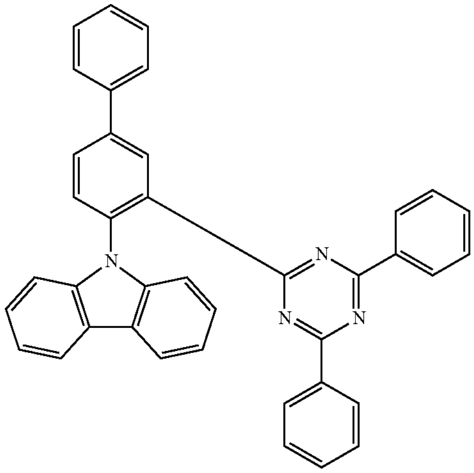
13
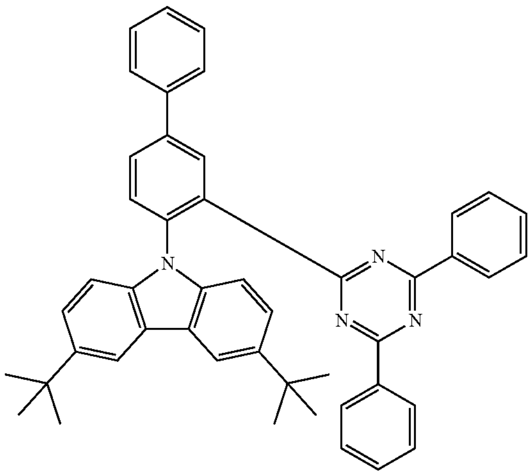
-continued
14
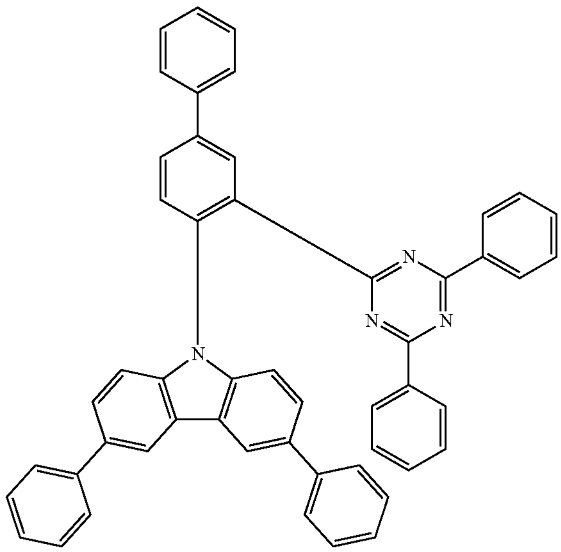
15
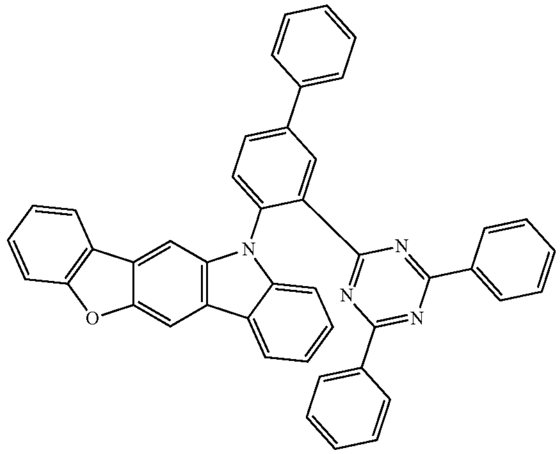
16
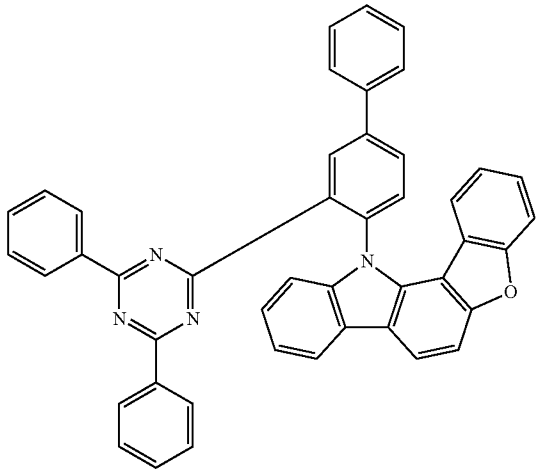

-continued
17
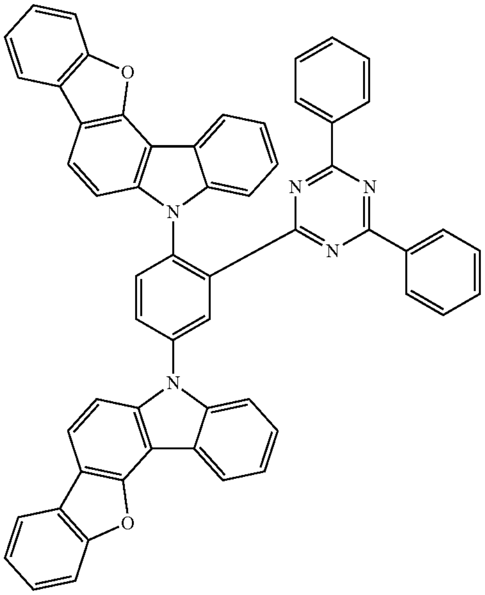
18
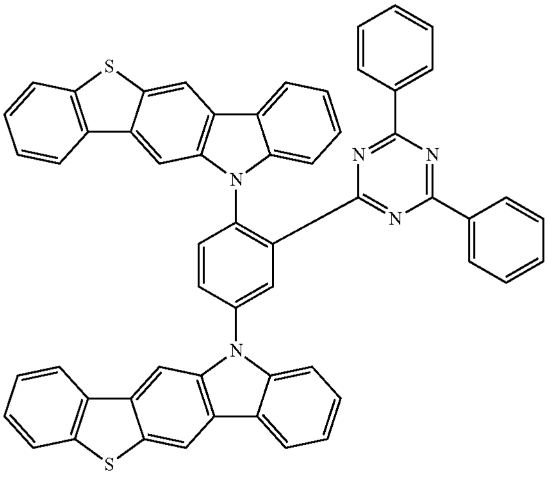
19
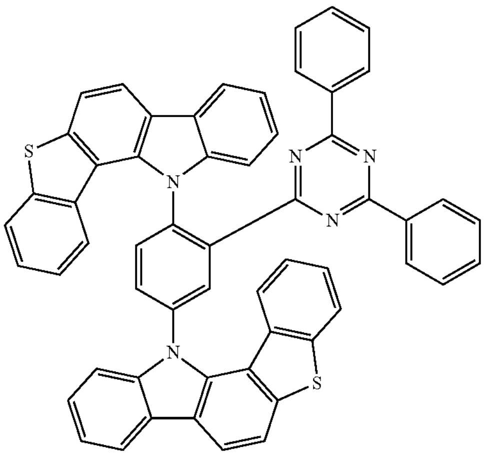
-continued
20
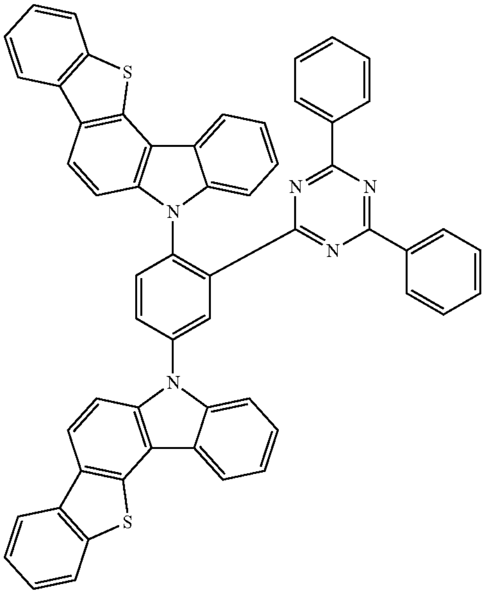
21
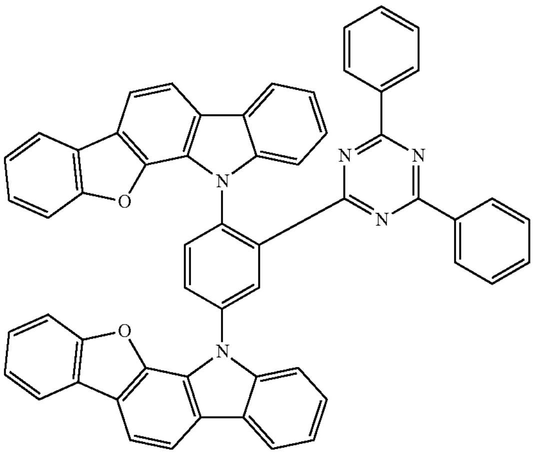

-continued
22
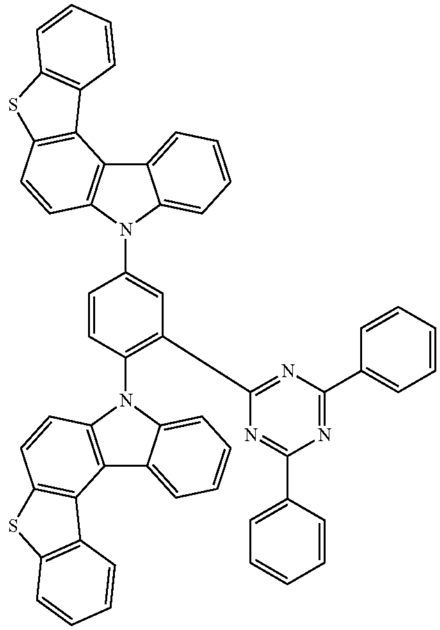
23
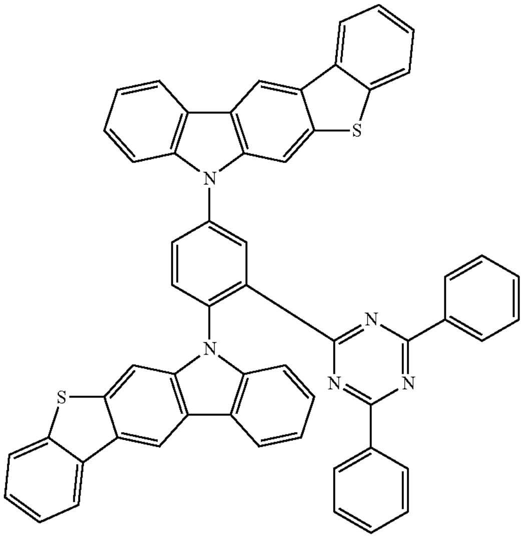
24
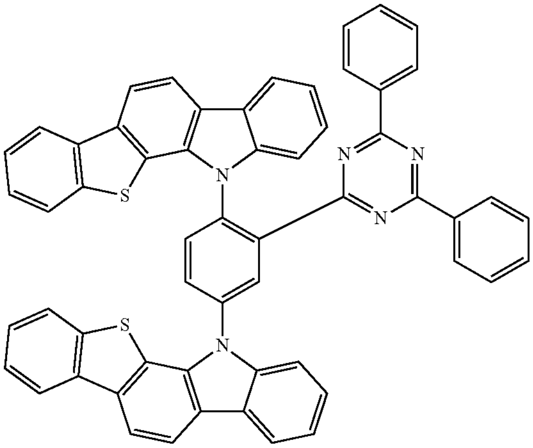
-continued
25
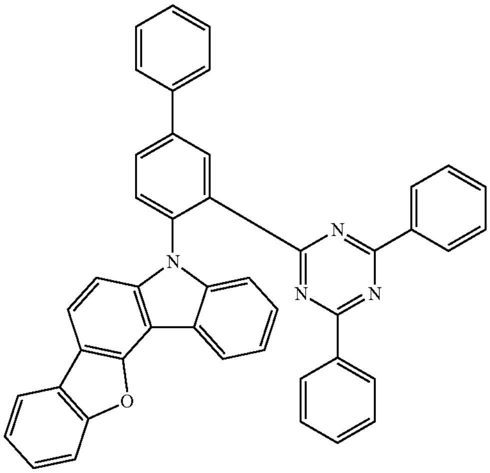
26
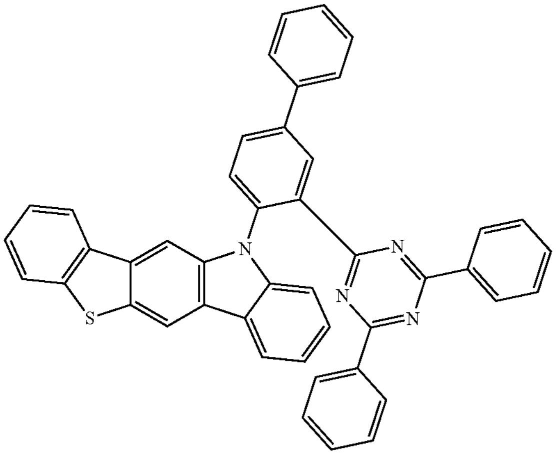
27
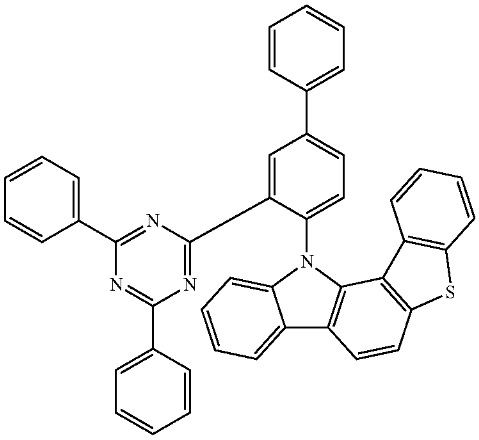

-continued
28
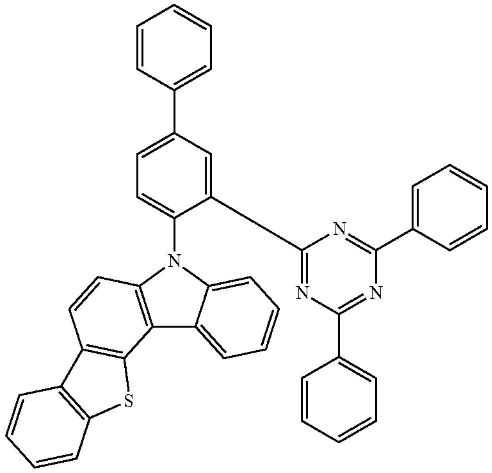
29
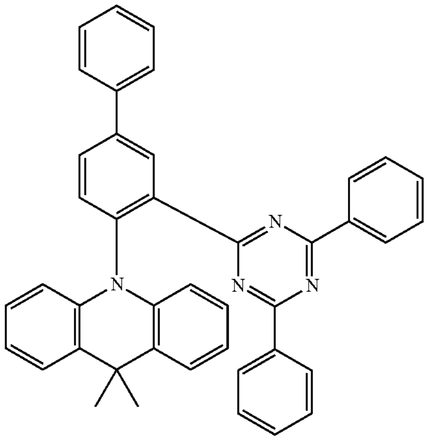
30
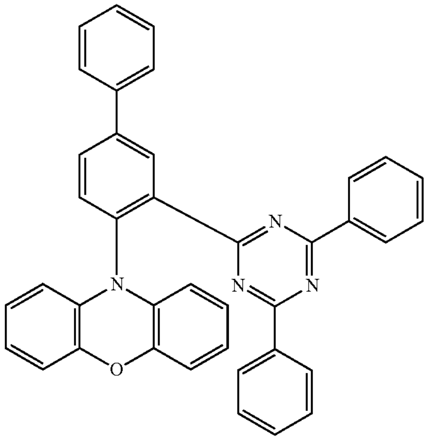
-continued
31
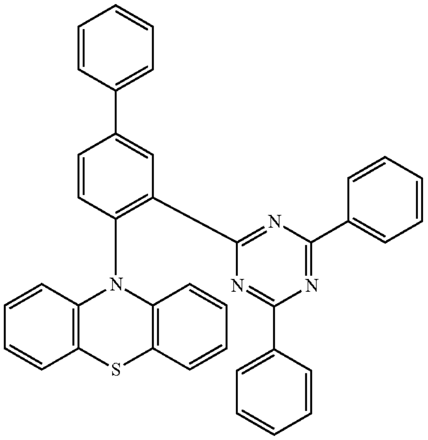
32
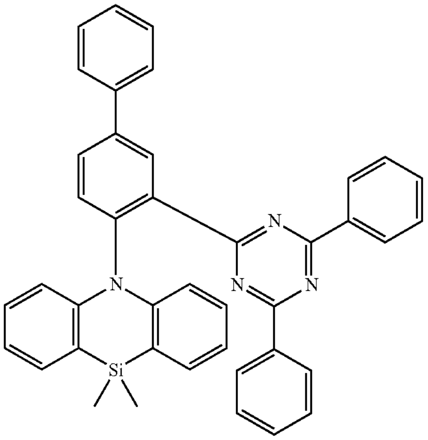
33
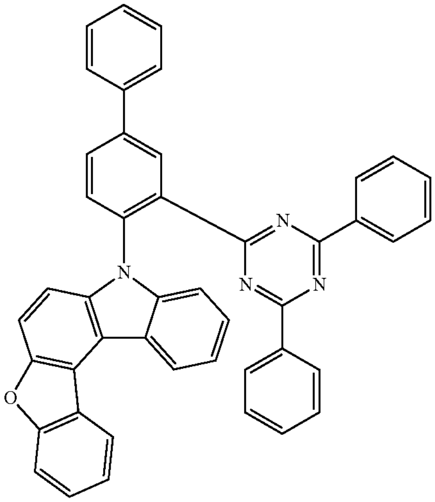

-continued
34
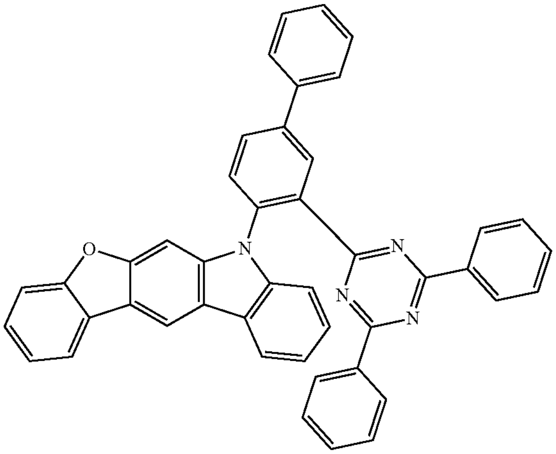
35
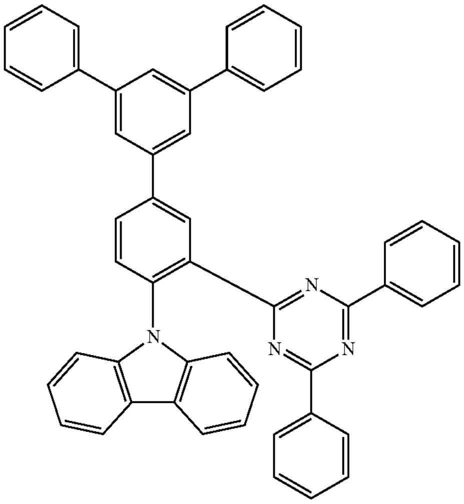
36
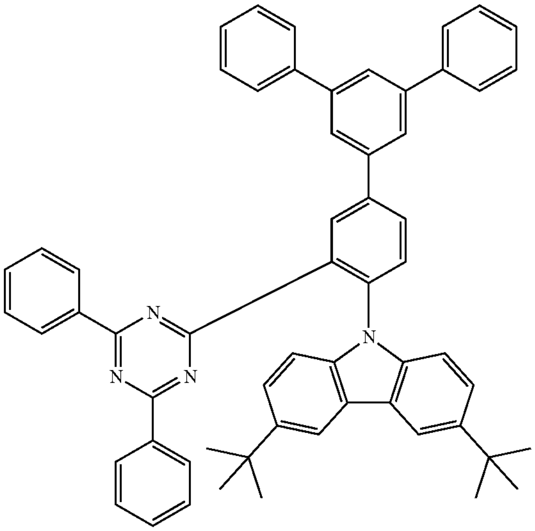
-continued
37
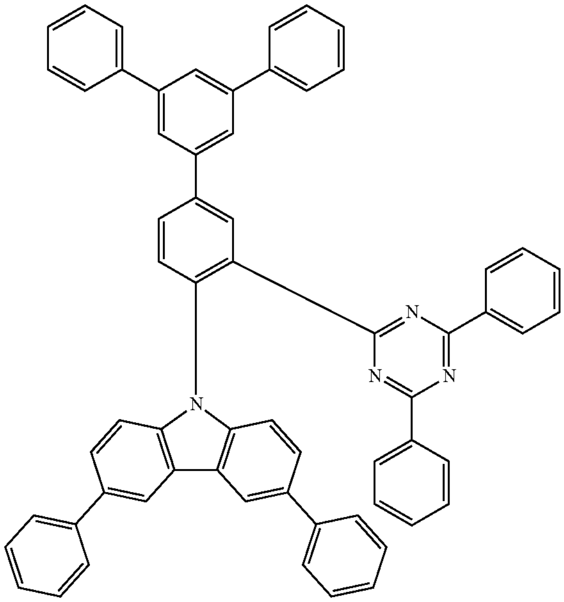
38
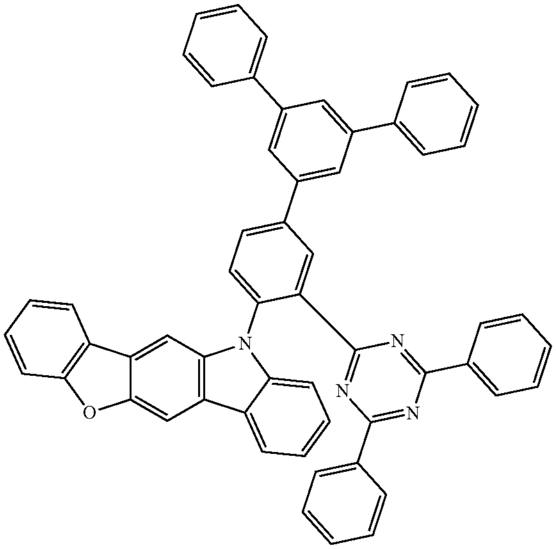

-continued
39
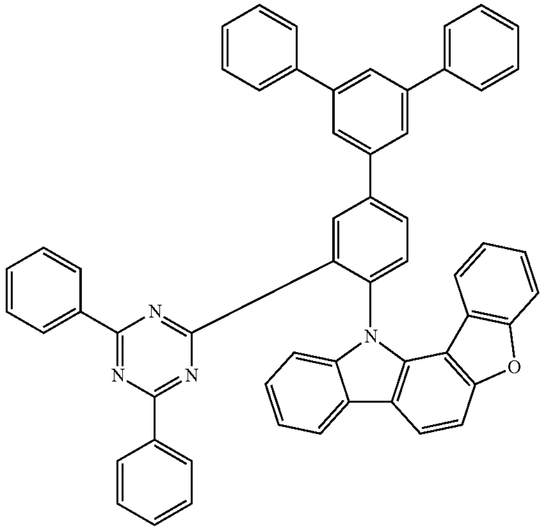
40
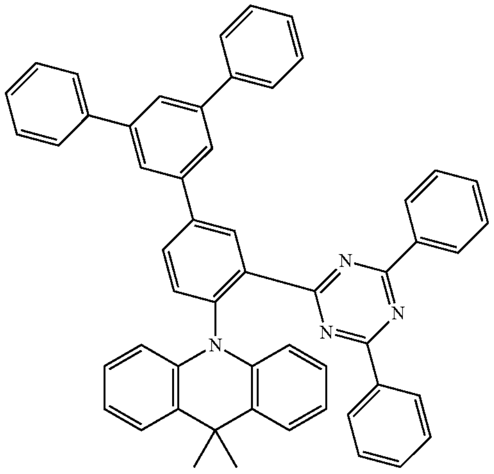
41
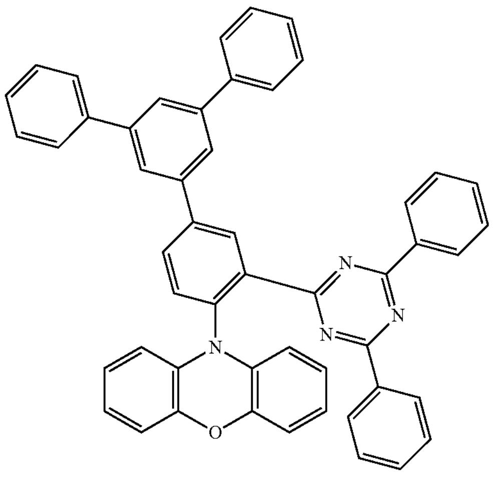
-continued
42
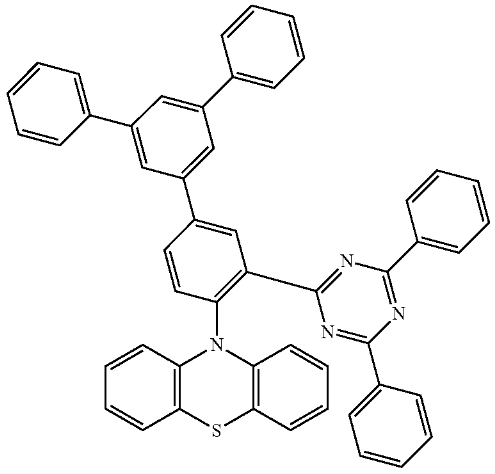
43
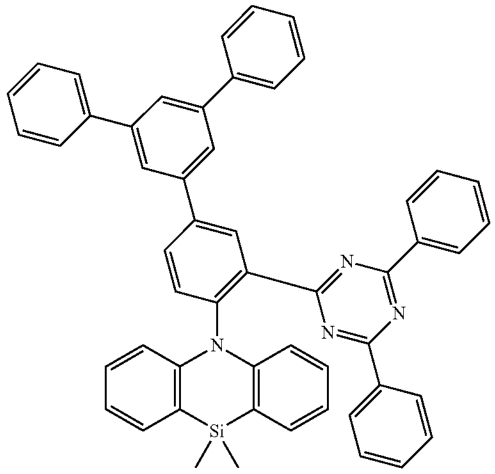
44
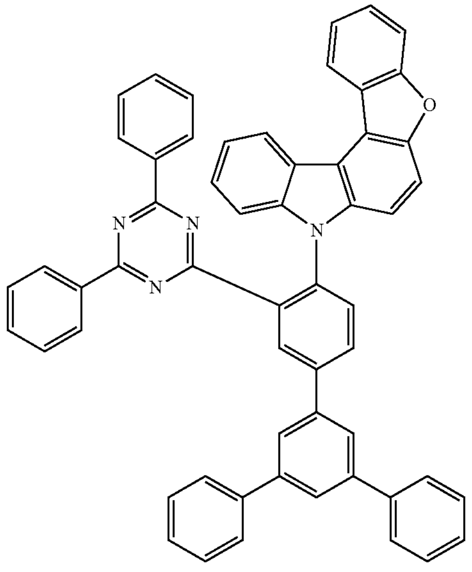

-continued
45
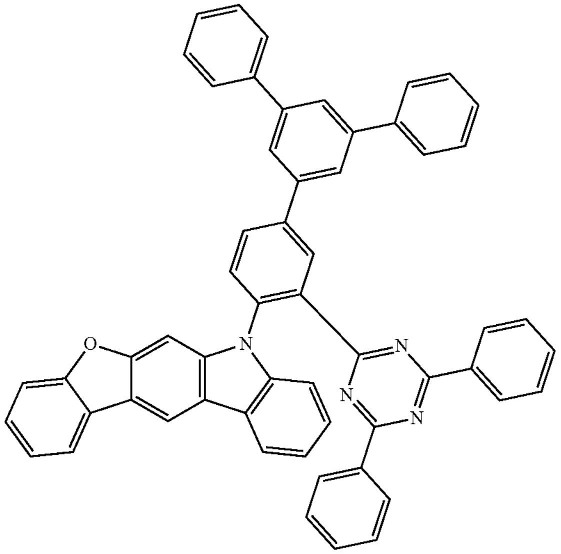
46
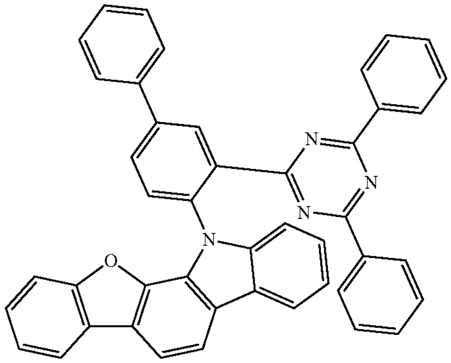
47
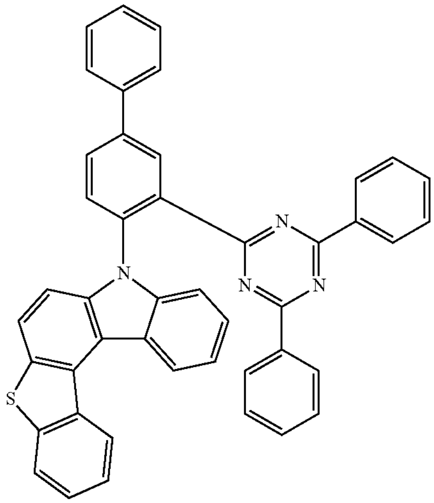
-continued
48
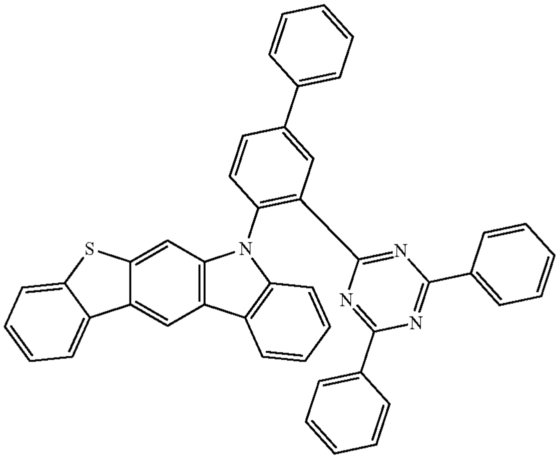
49
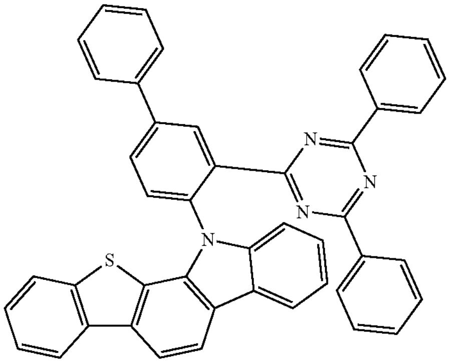
50
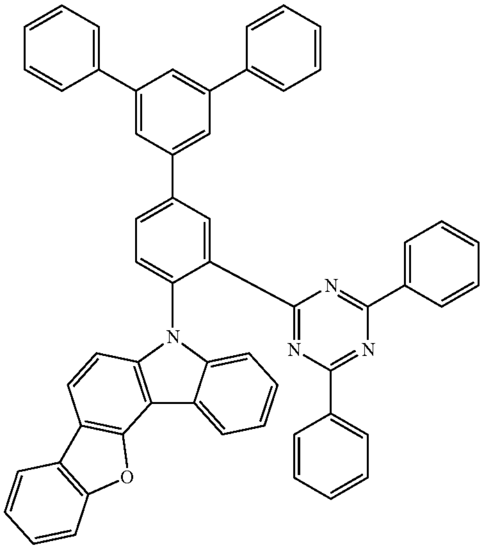

-continued
51
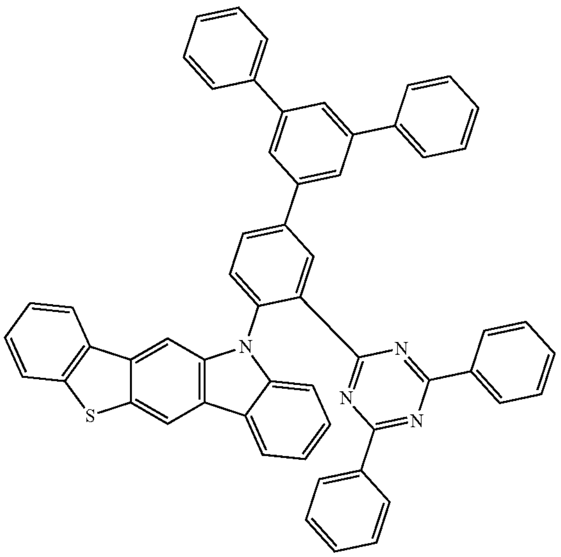
52
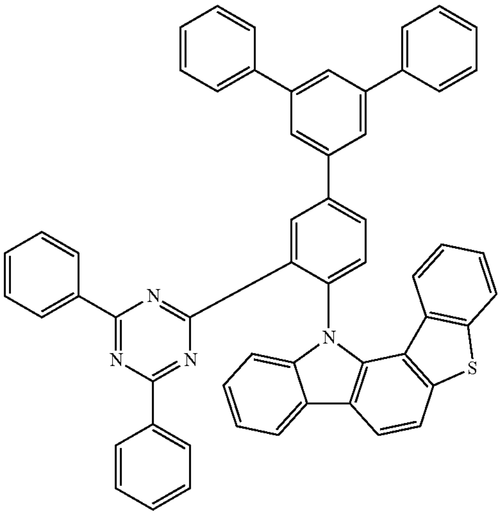
53
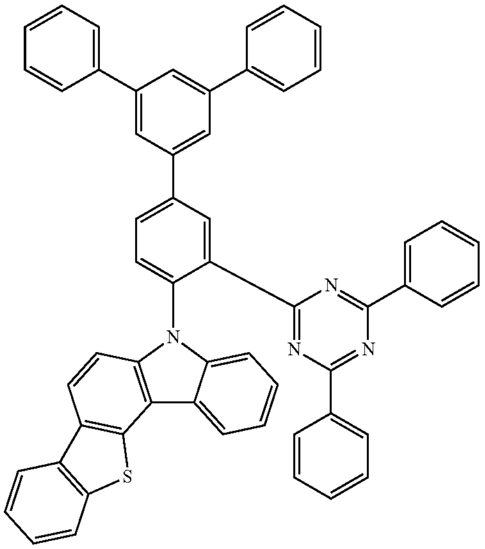
-continued
54
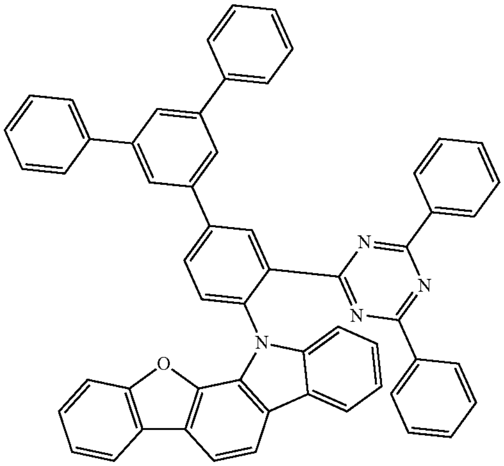
55
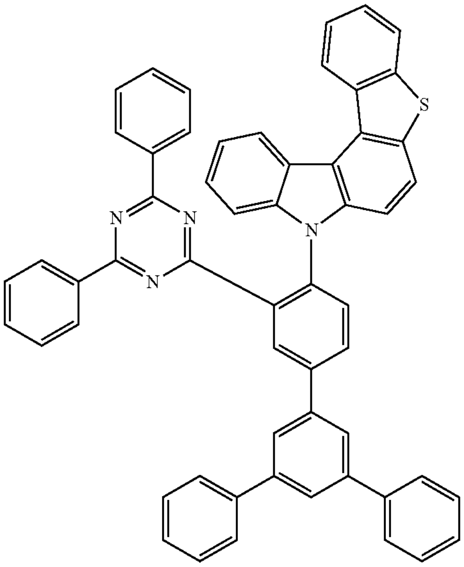
56
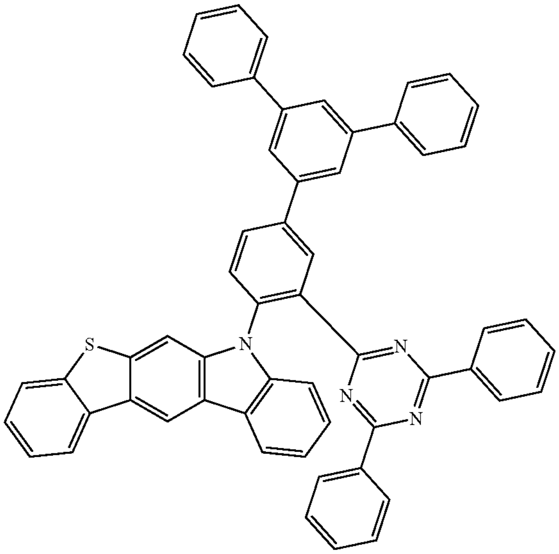

-continued
57
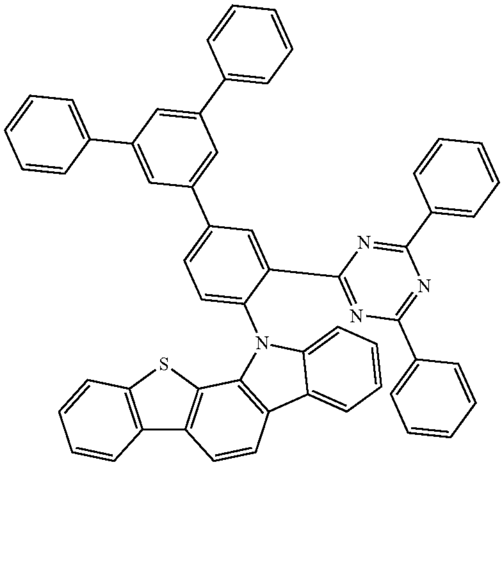
58
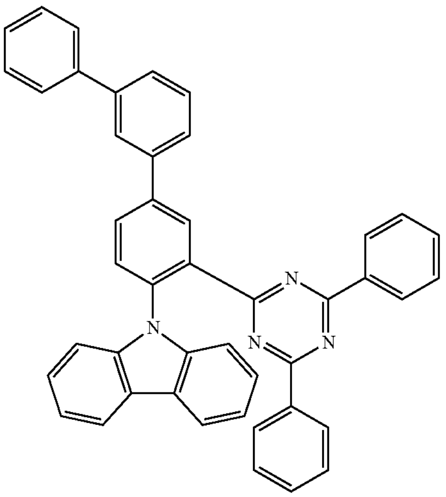
59
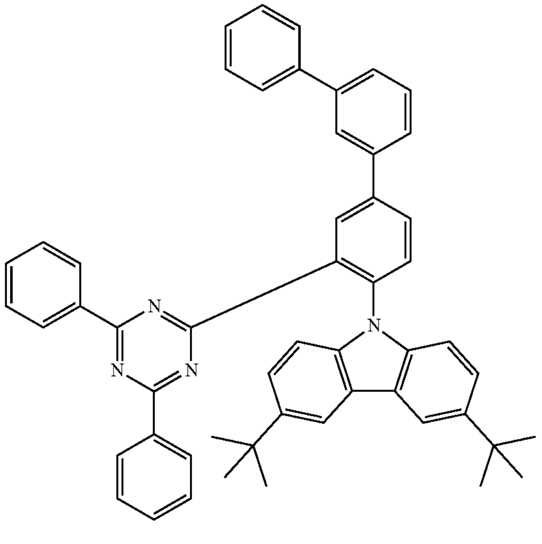
-continued
60
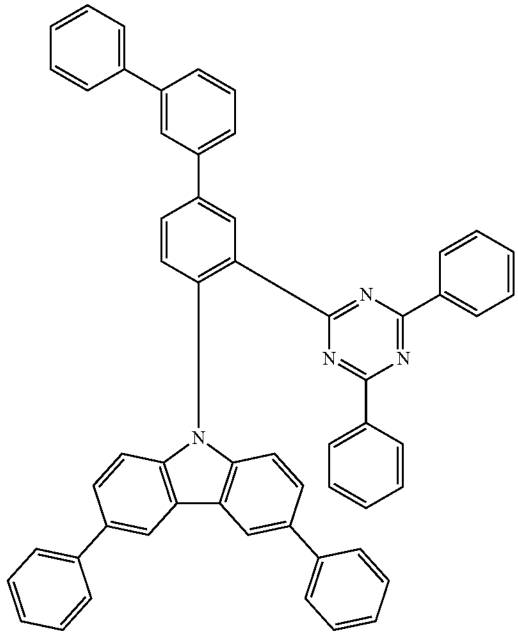
61
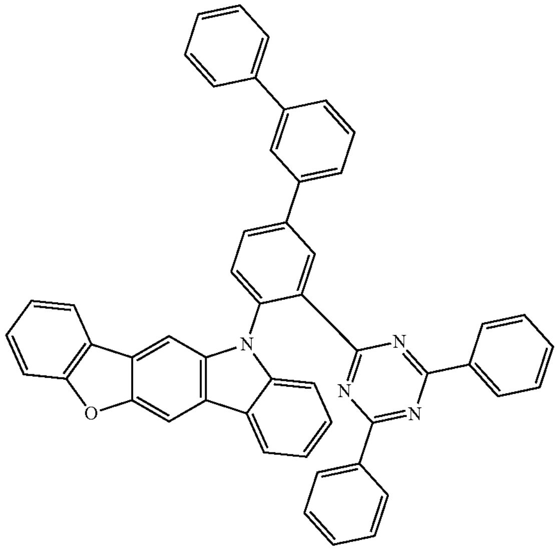

-continued
62
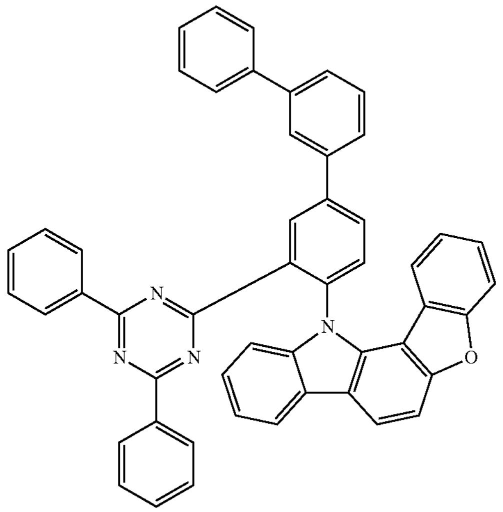
63
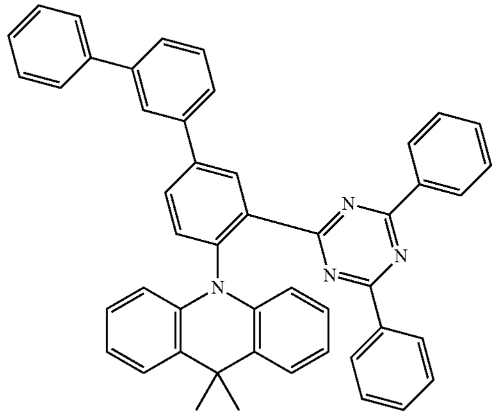
64
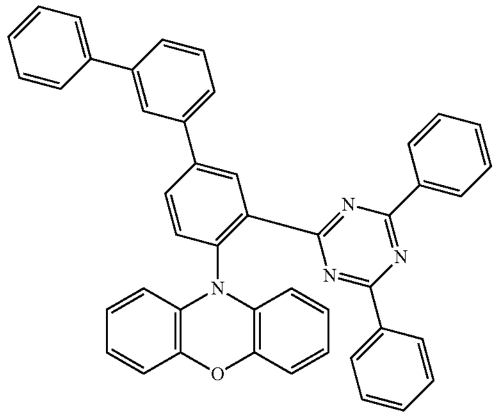
-continued
65
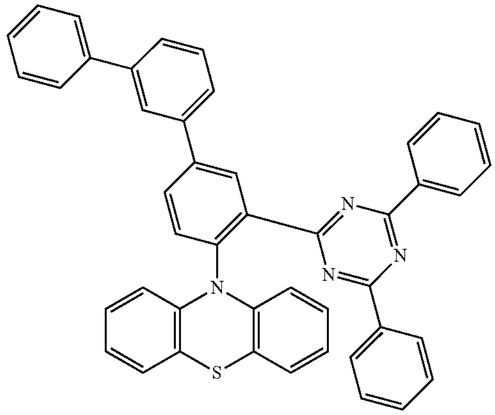
66
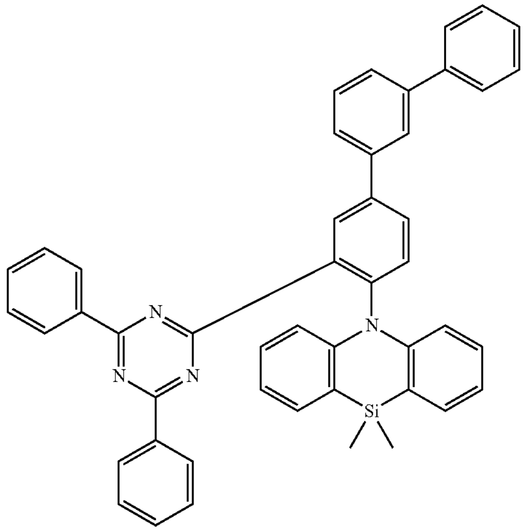
67
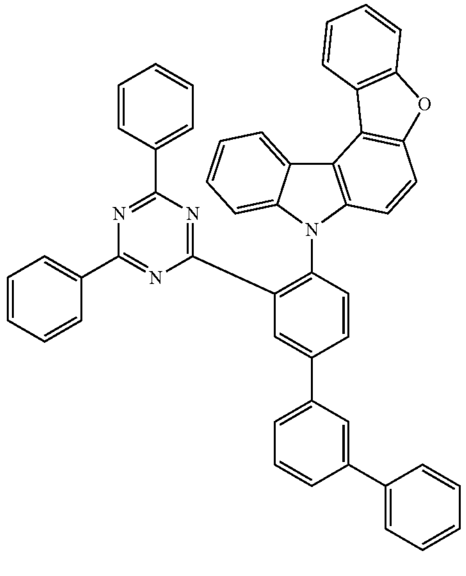

-continued
68
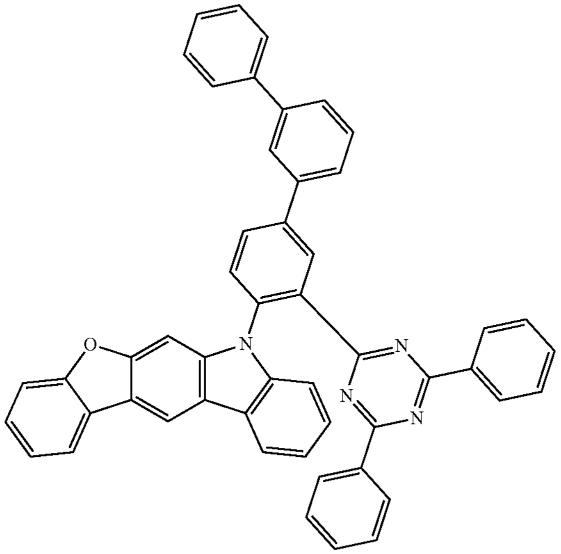
69
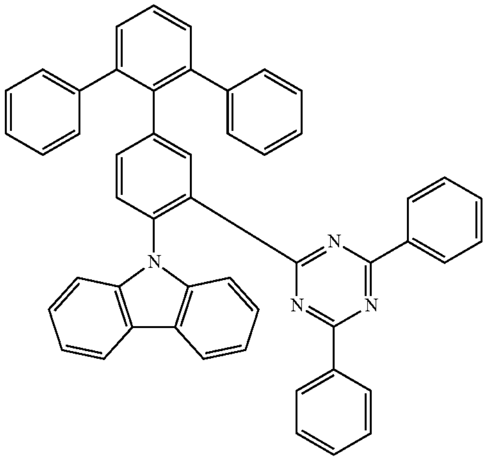
70
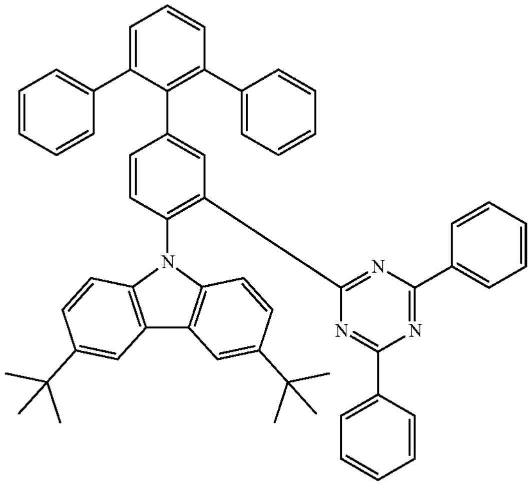
-continued
71
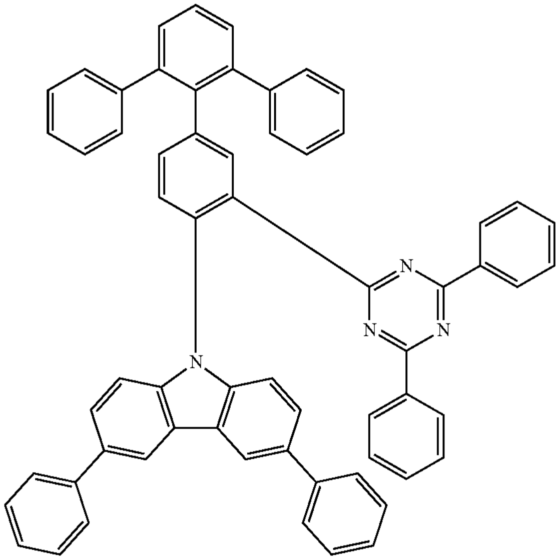
72
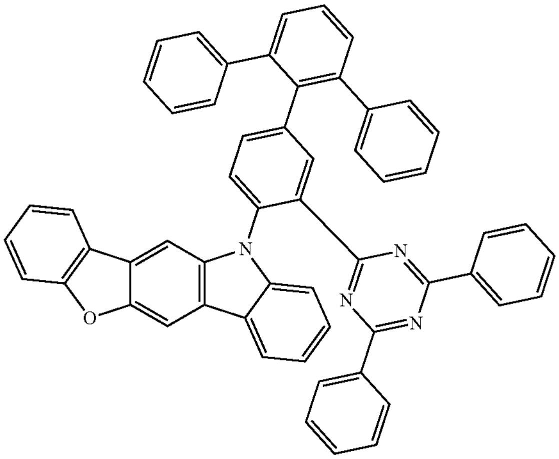
73
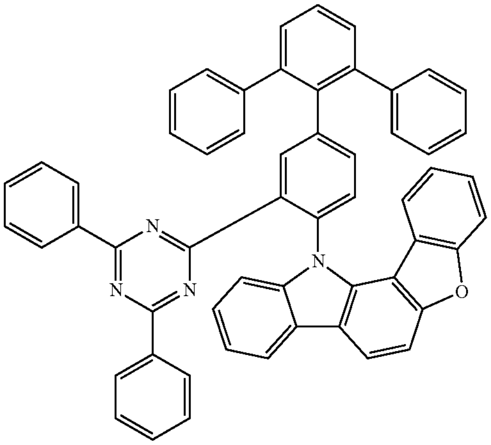

-continued
74
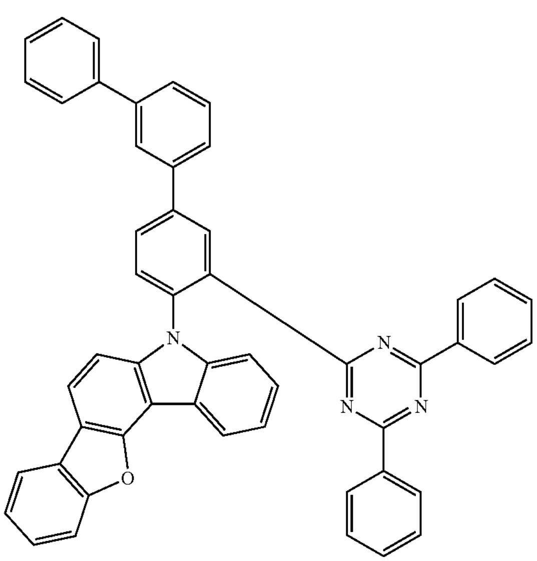
75
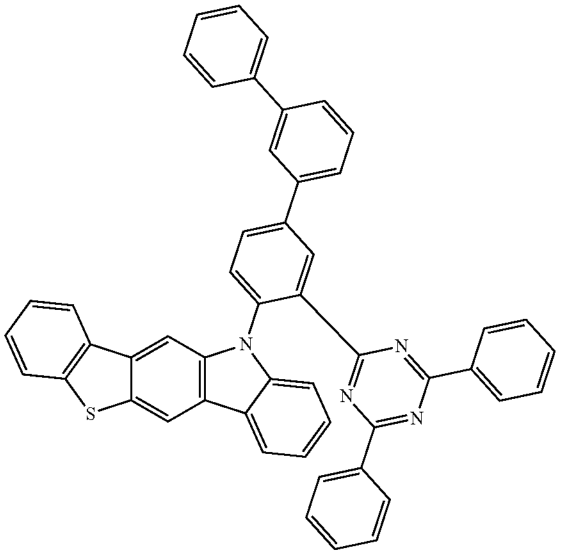
76
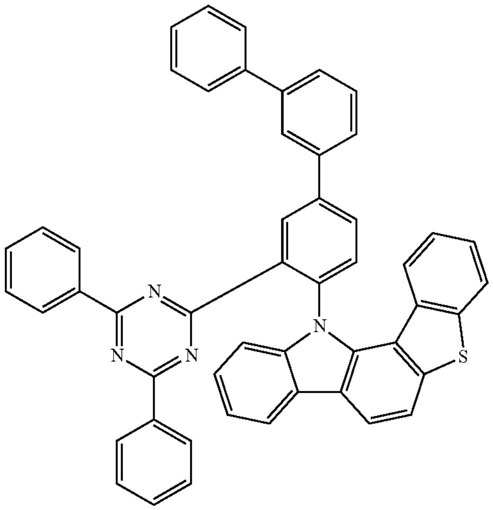
-continued
77
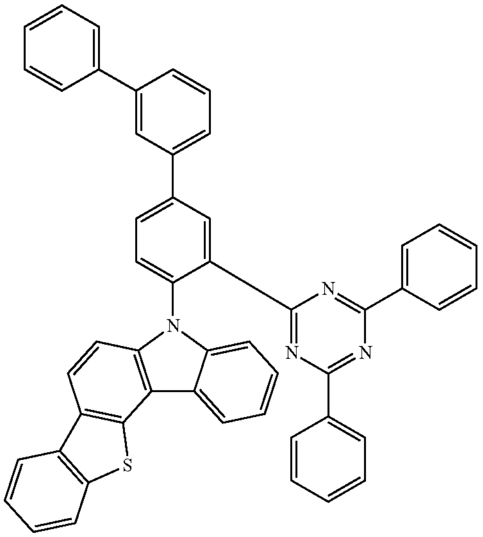
78
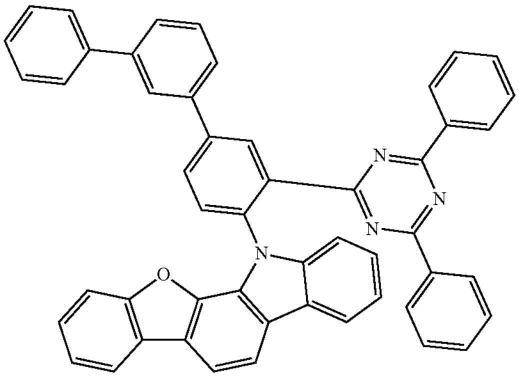
79
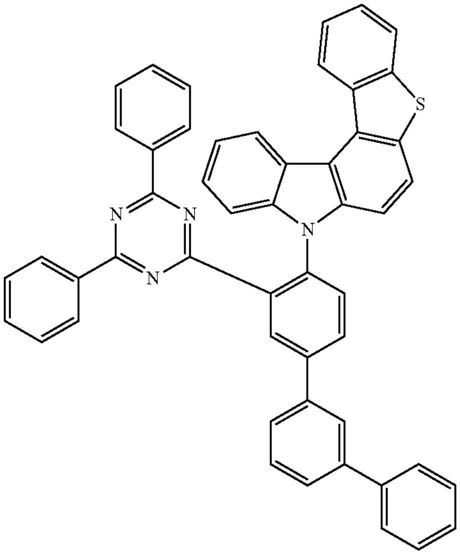

-continued
80
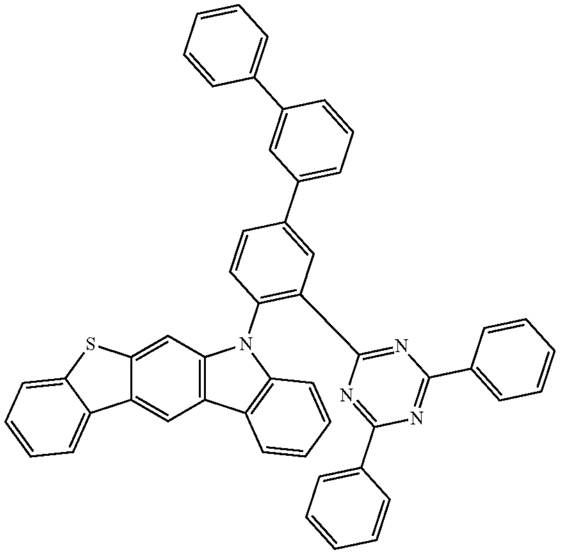
81
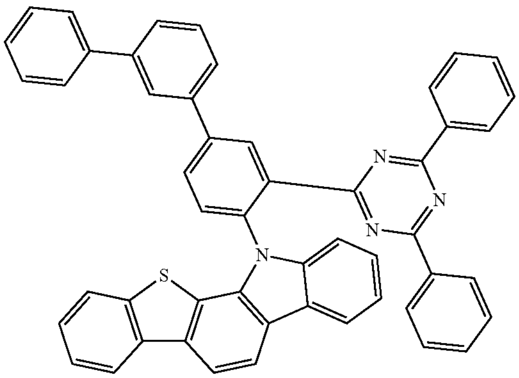
82
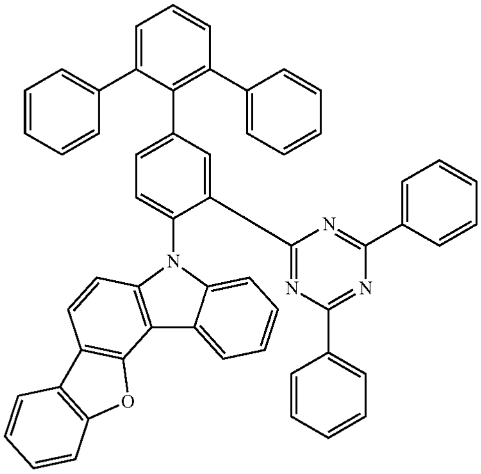
-continued
83
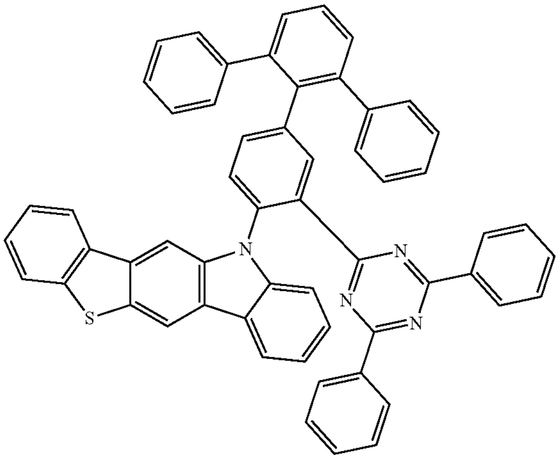
84
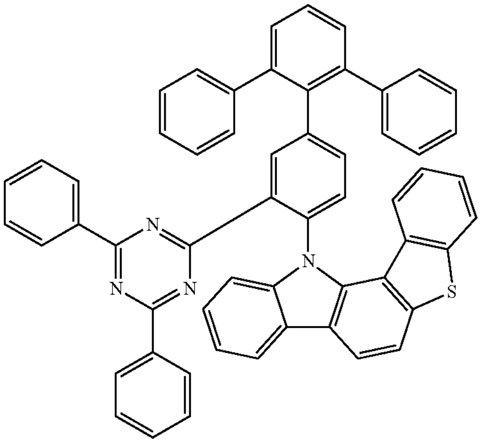
85
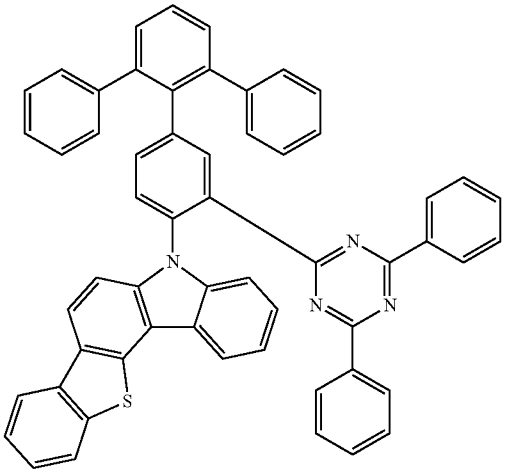

-continued
86
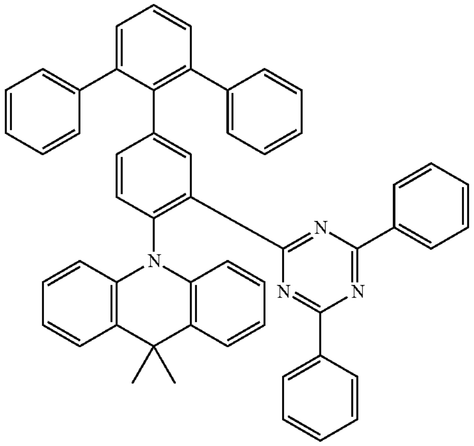
87
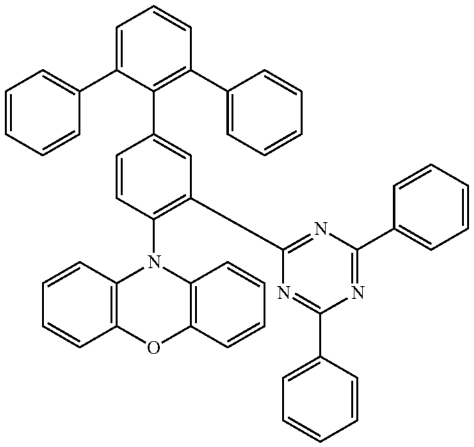
88
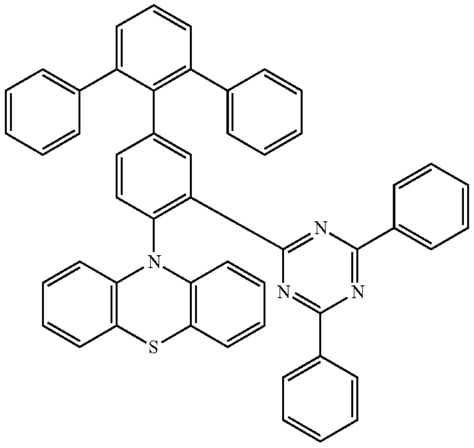
-continued
89
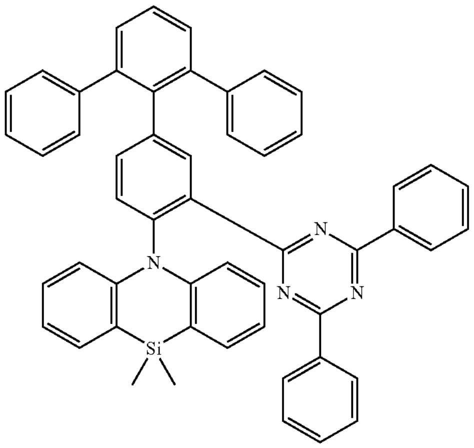
90
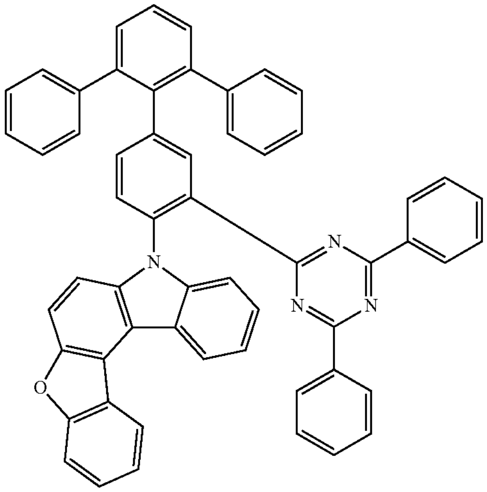
91
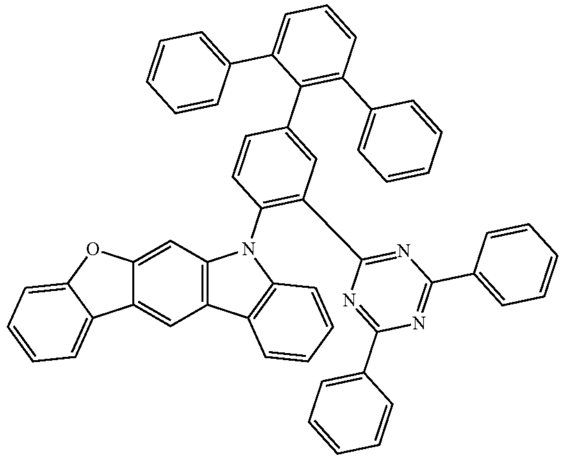

-continued
92
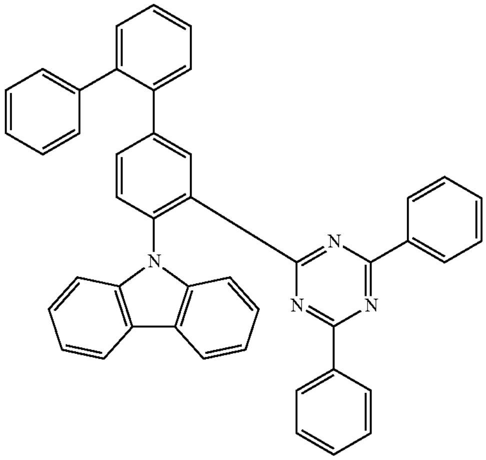
93
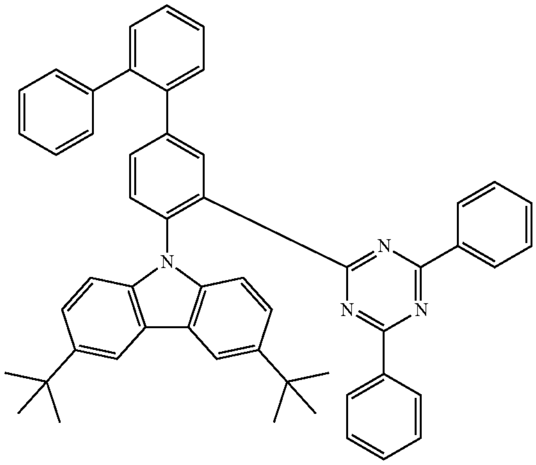
94
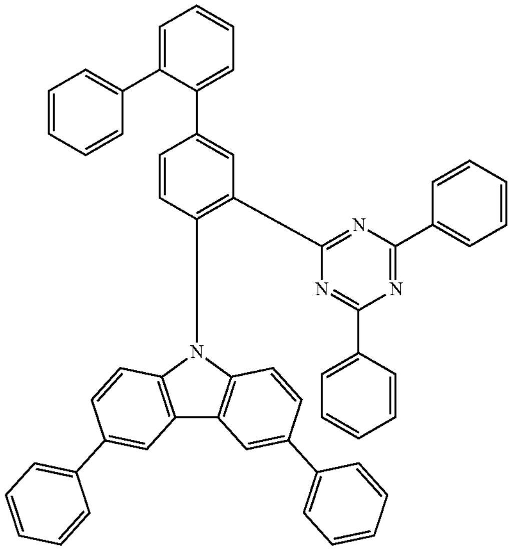
-continued
95
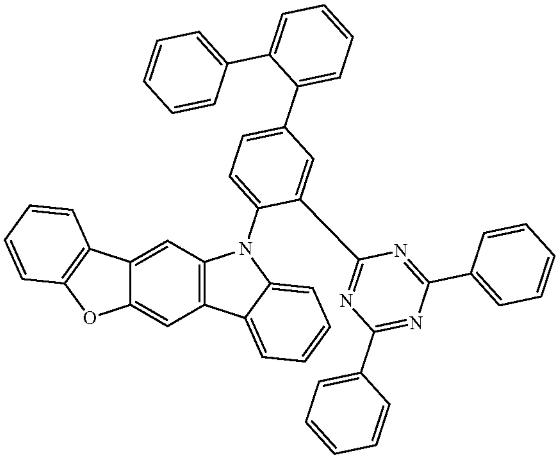
96
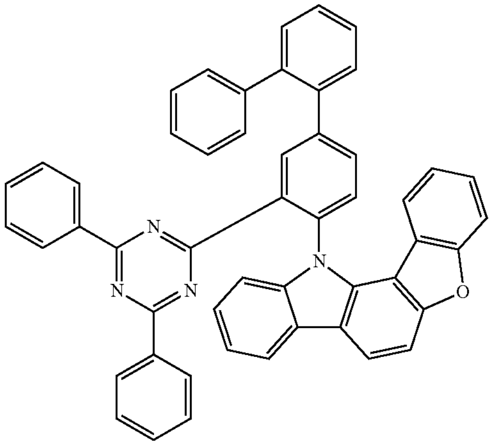
97
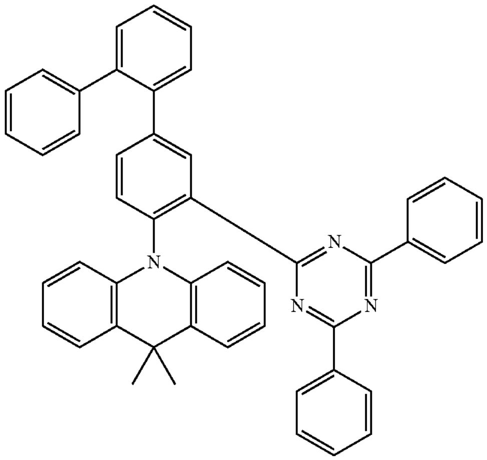

-continued
98
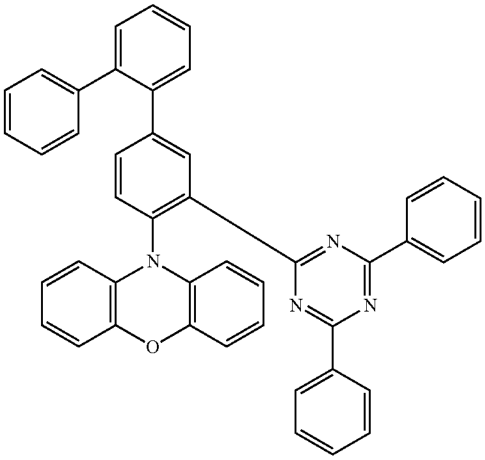
99
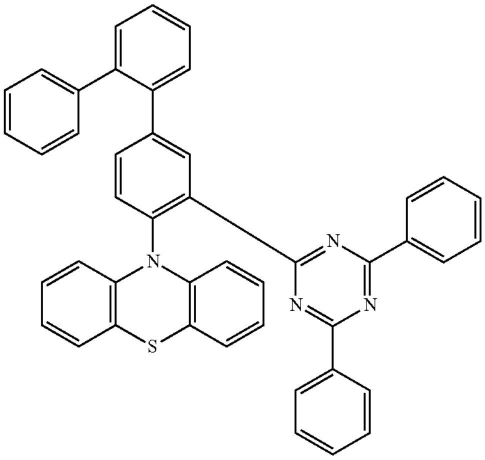
100
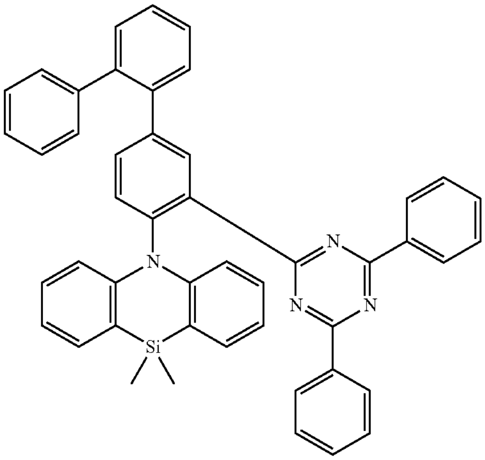
-continued
101
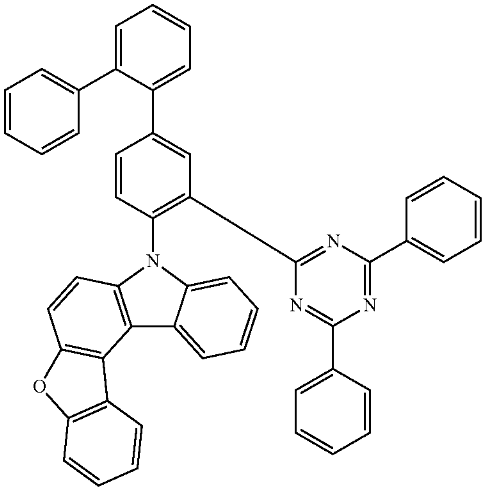
102
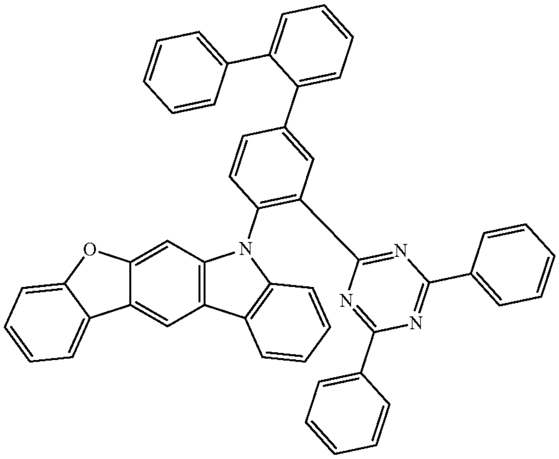
103
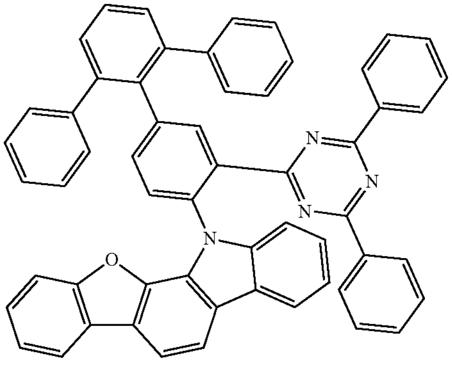

-continued
104
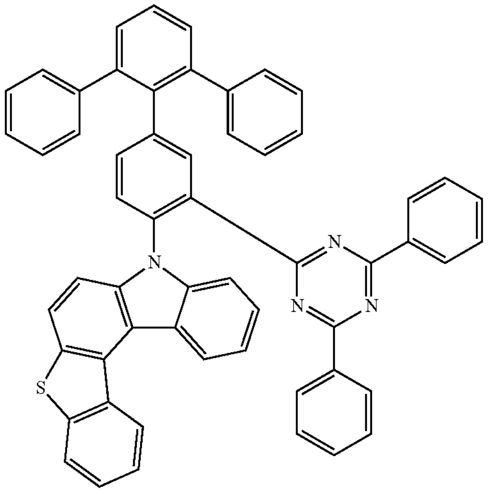
105
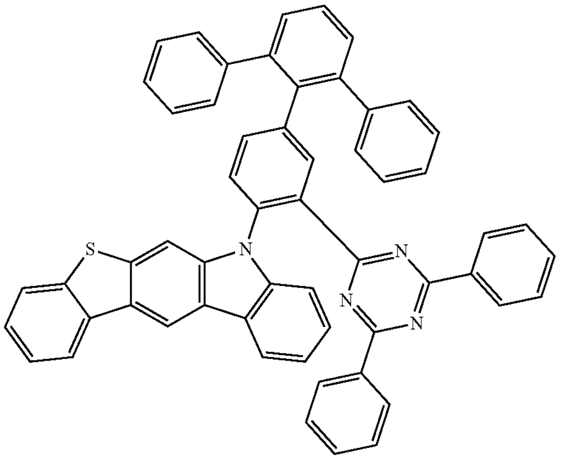
106
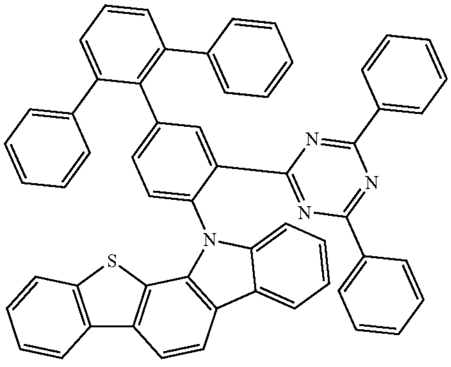
-continued
107
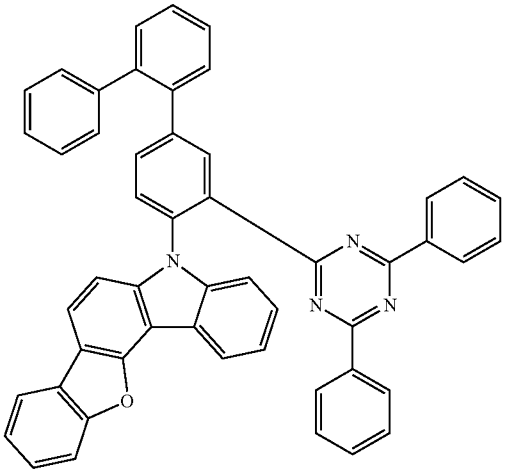
108
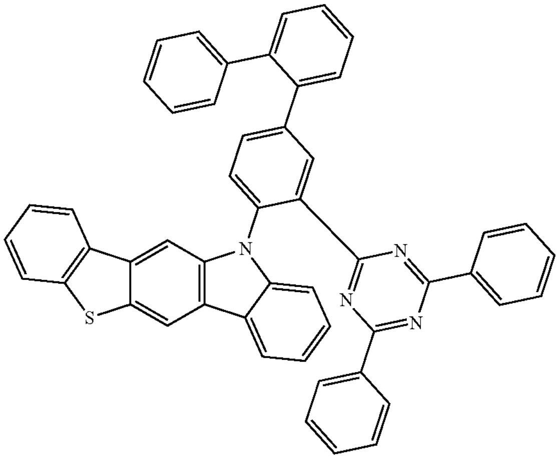
109
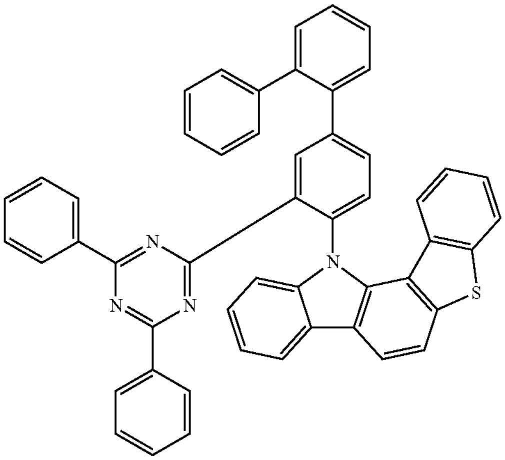

-continued
110
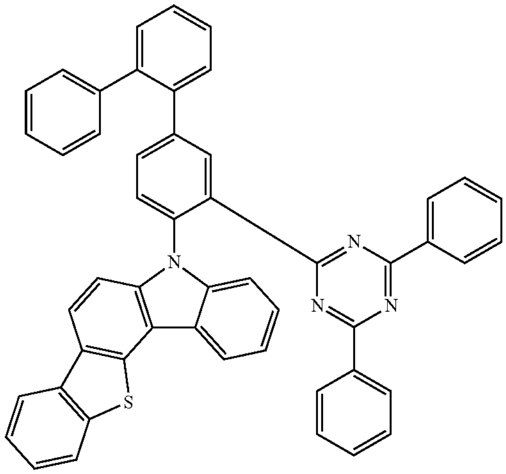
111
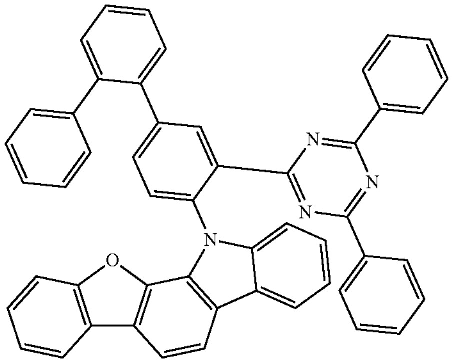
112
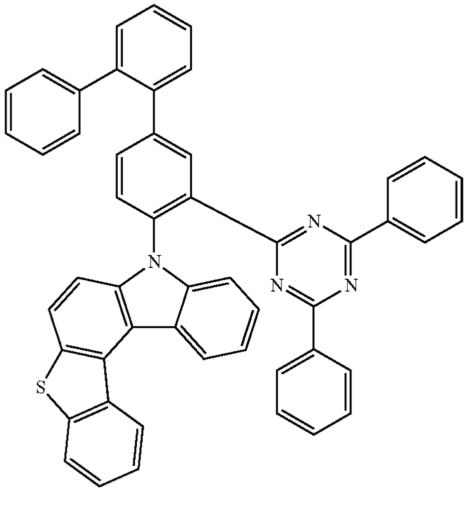
-continued
113
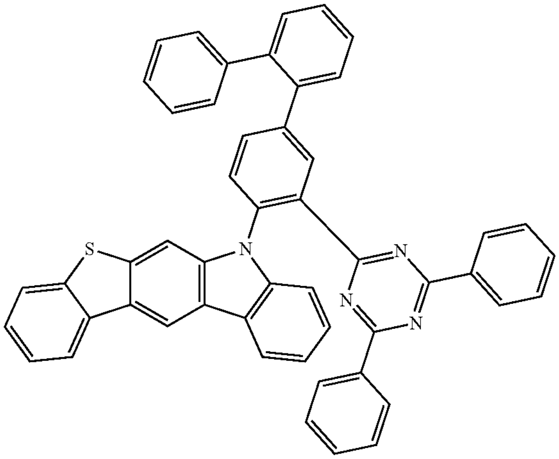
114
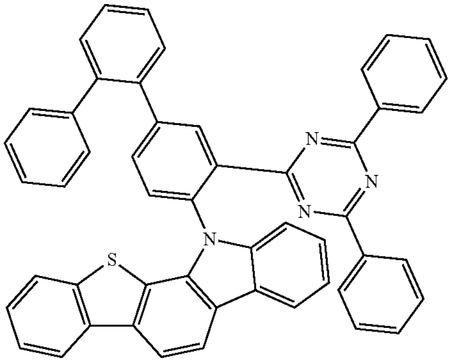
115
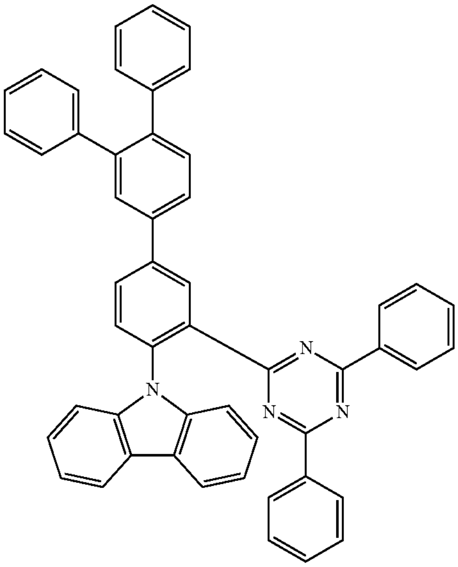

116
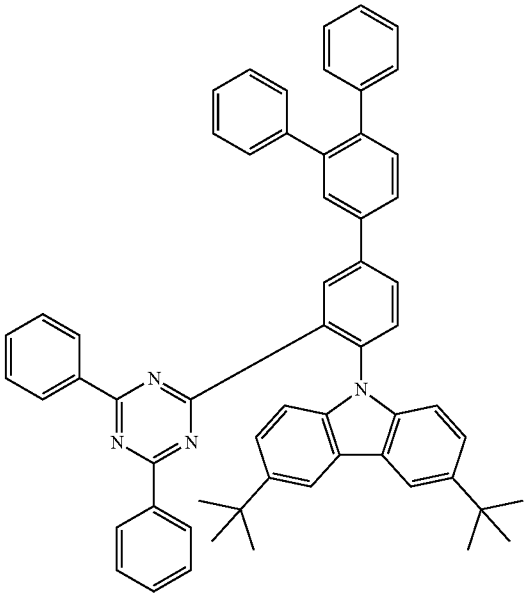
118
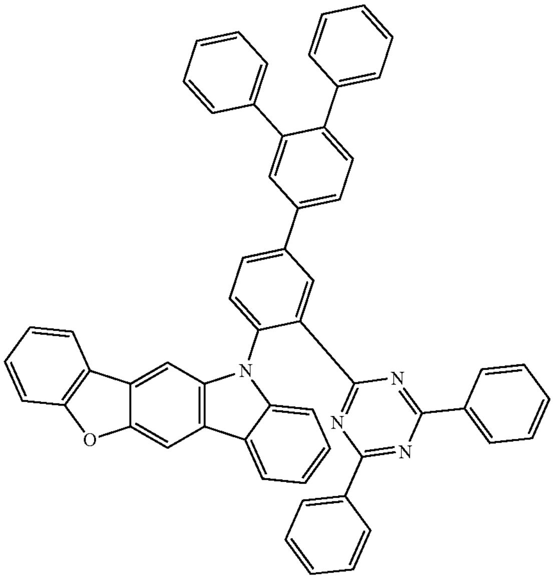
117
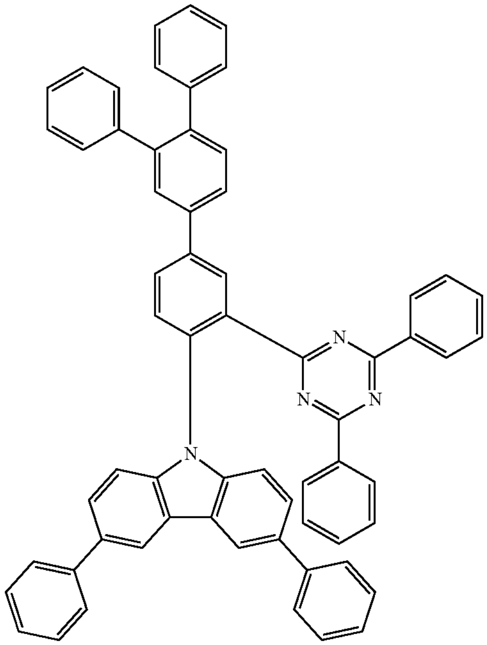
119
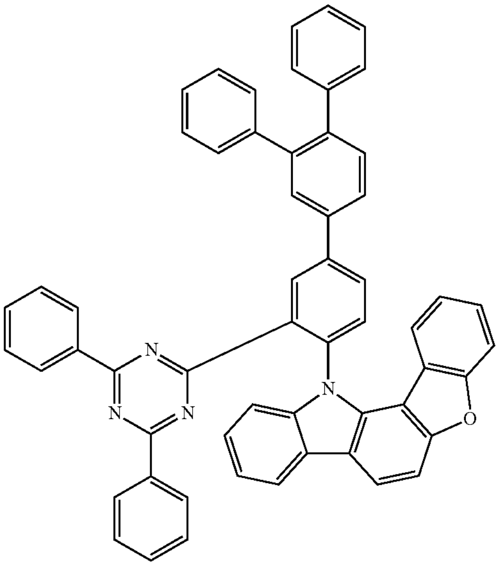

-continued
120
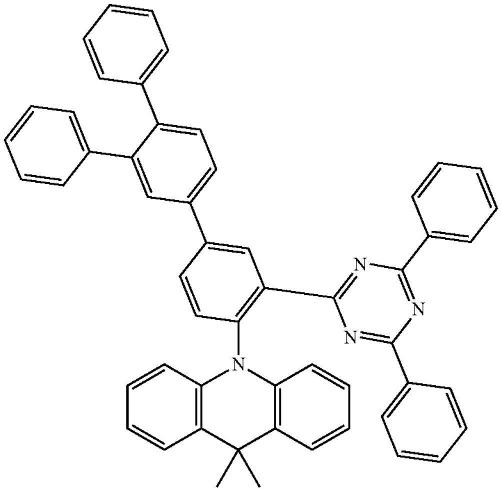
121
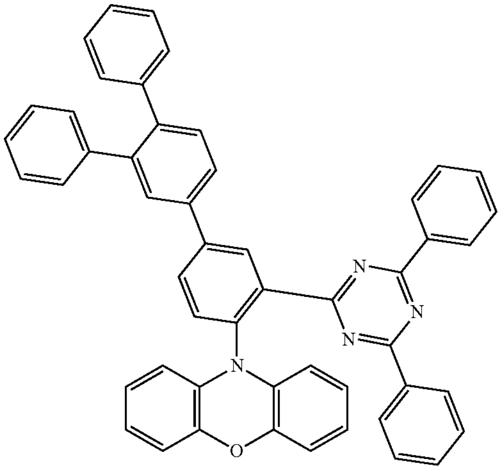
122
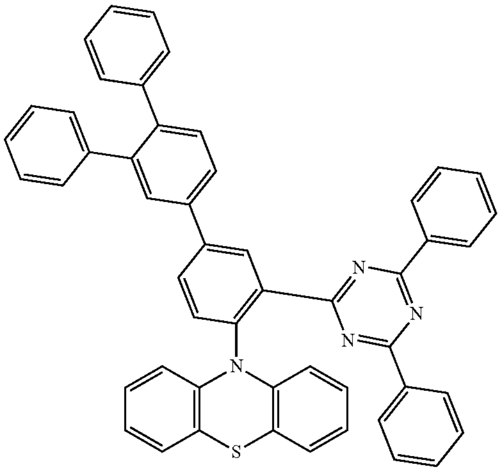
-continued
123
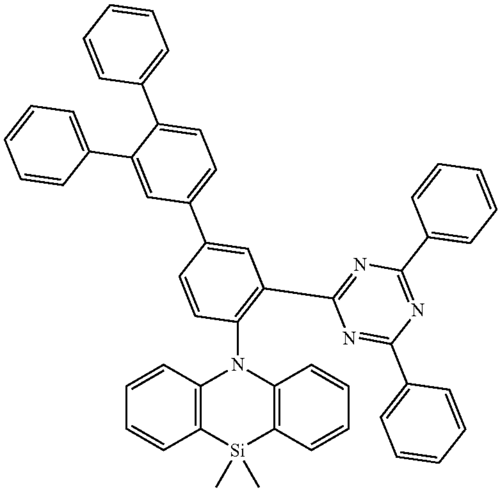
124
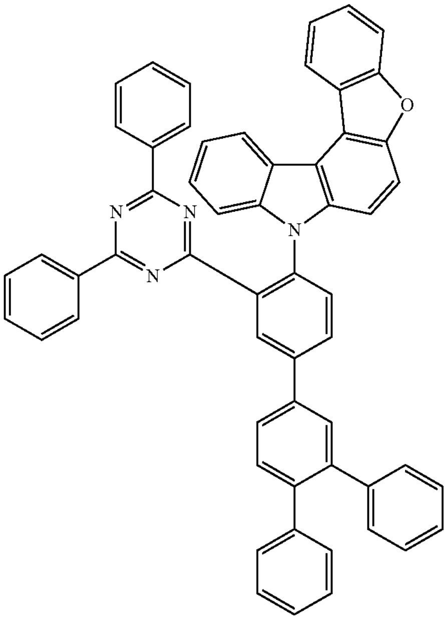

-continued
125
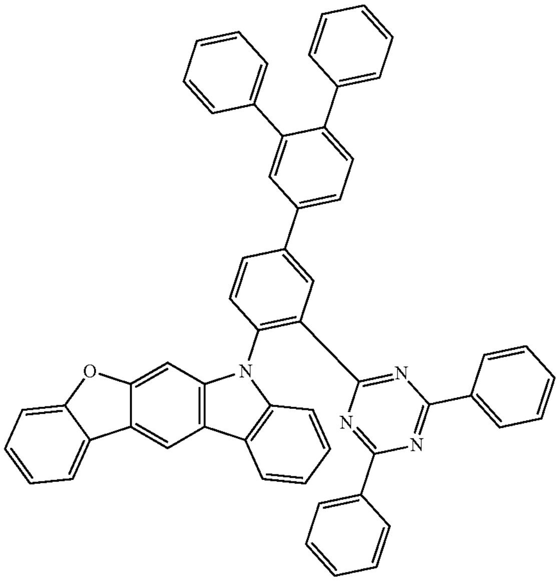
126
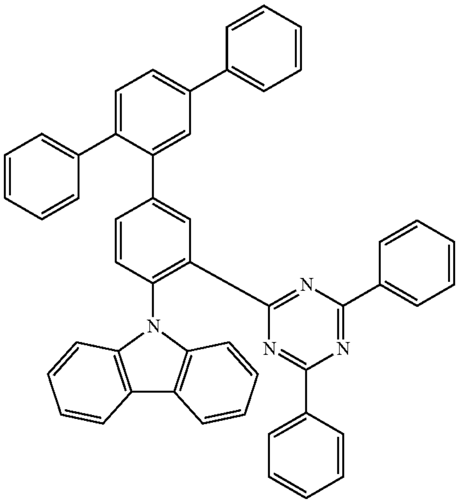
127
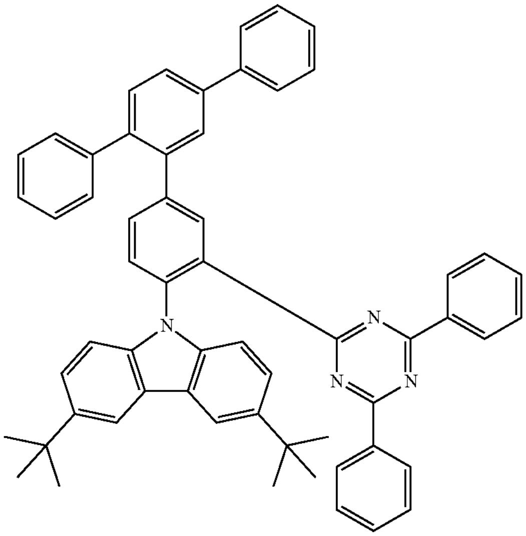
-continued
128
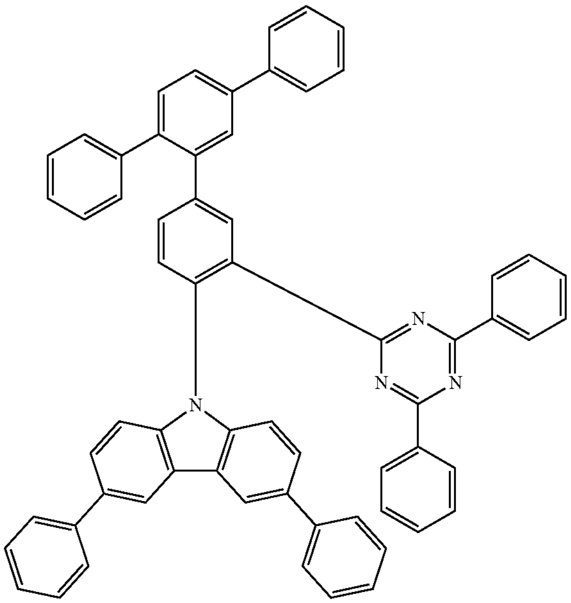
129
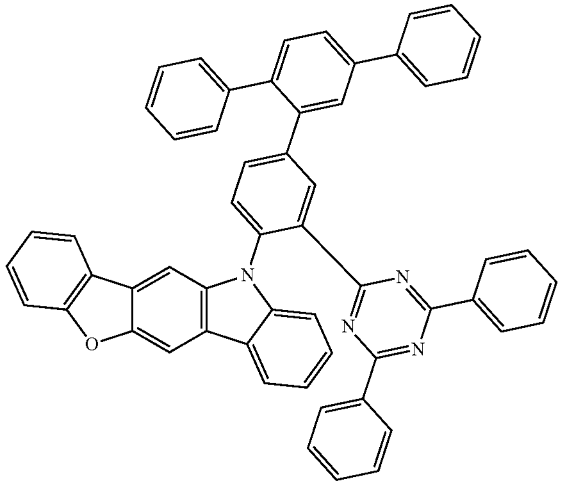
130
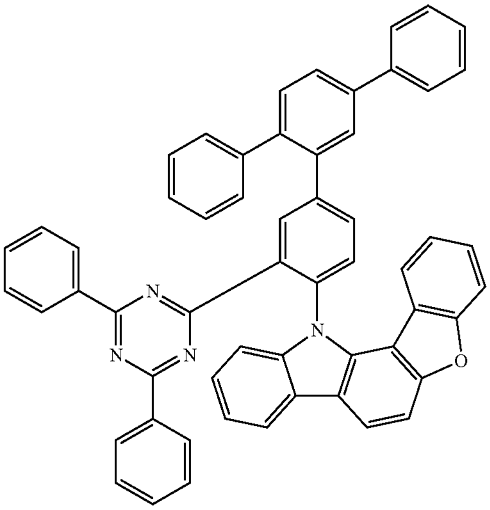

-continued
131
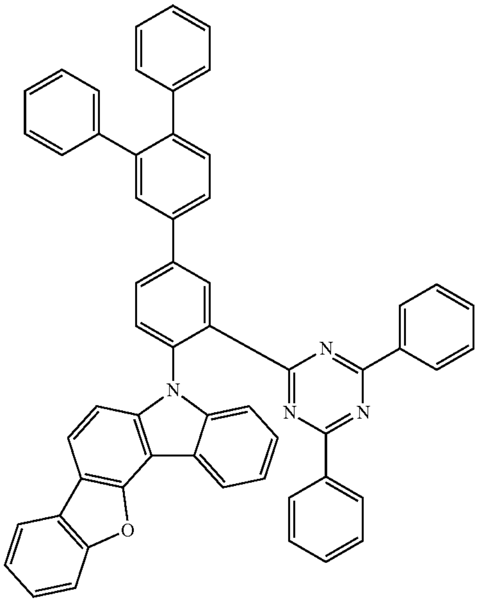
132
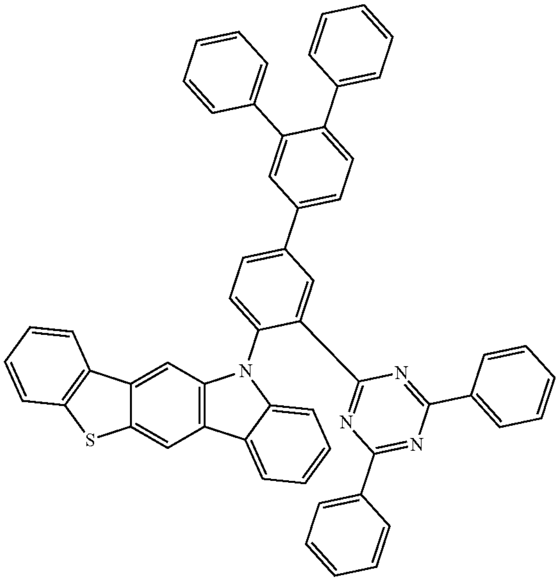
-continued
133
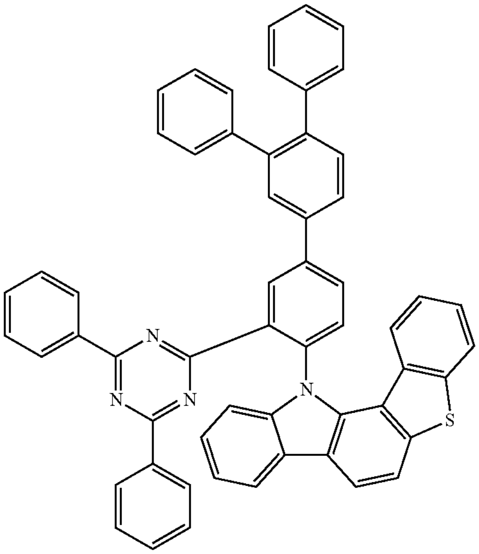
134
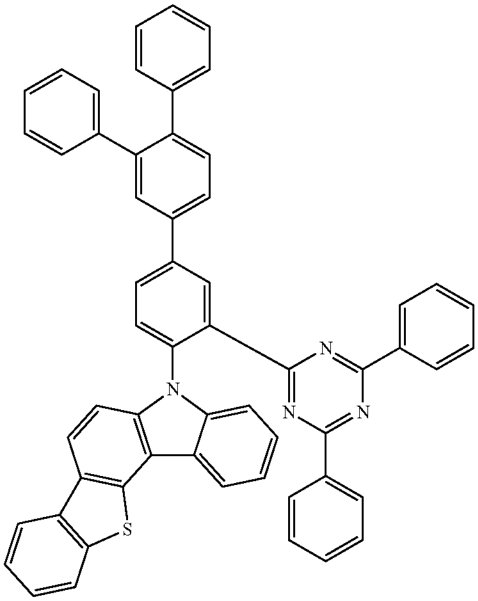
135
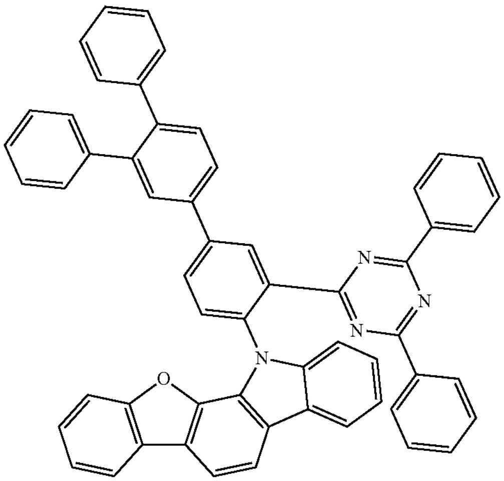

-continued
136
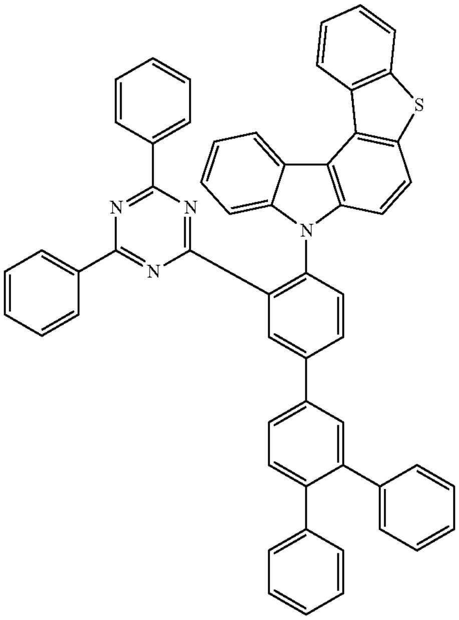
137
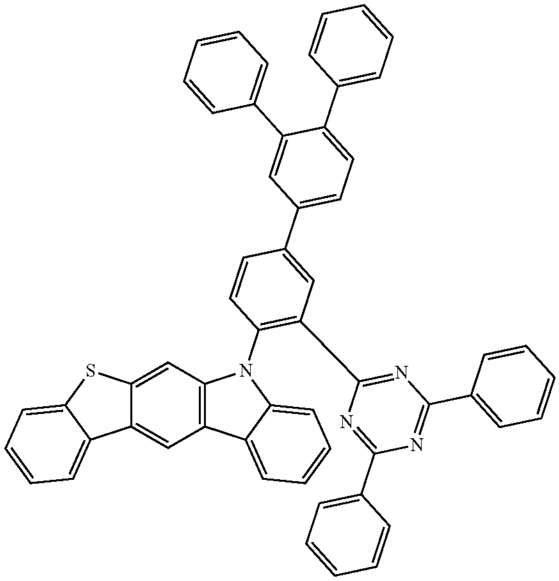
-continued
138
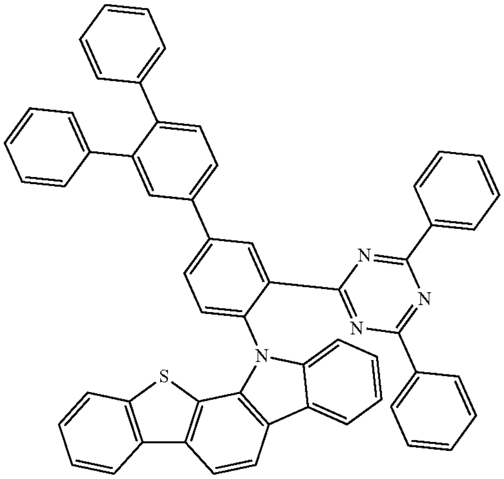
139
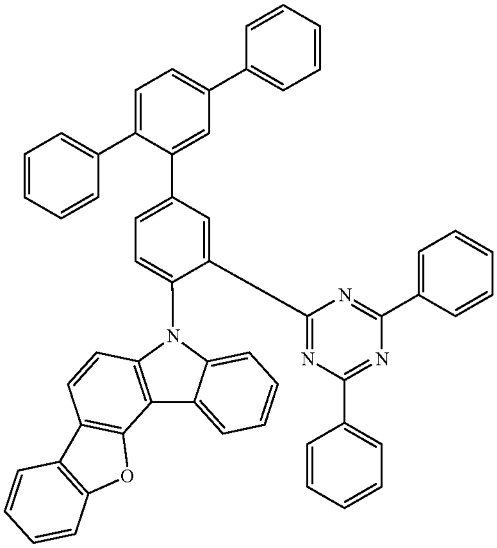
140
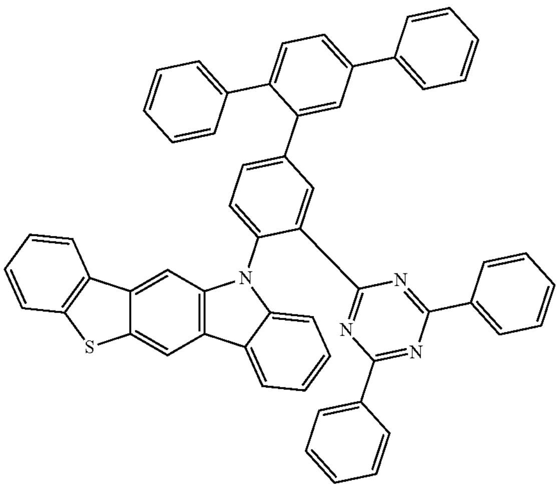

-continued
141
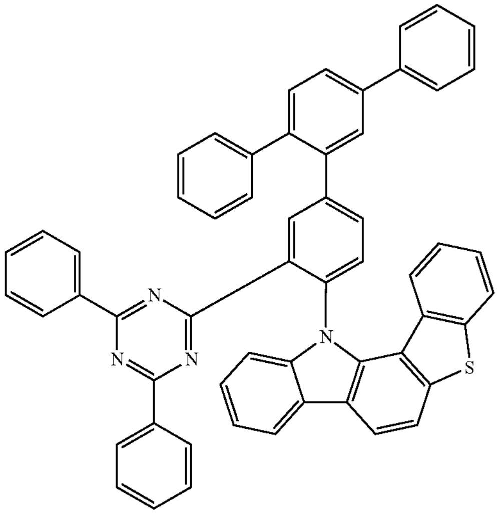
142
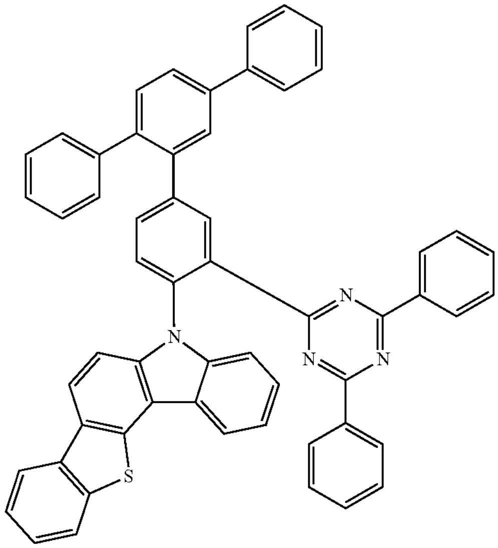
143
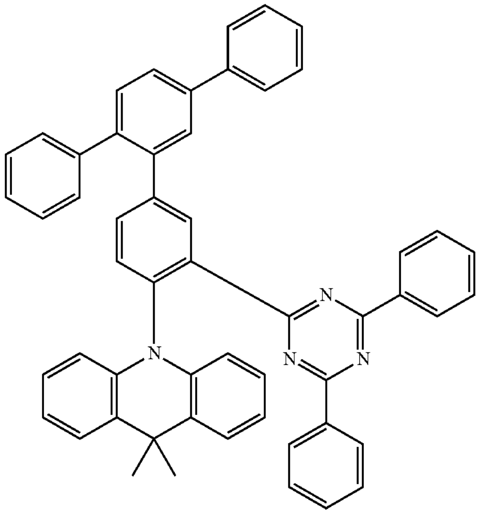
-continued
144
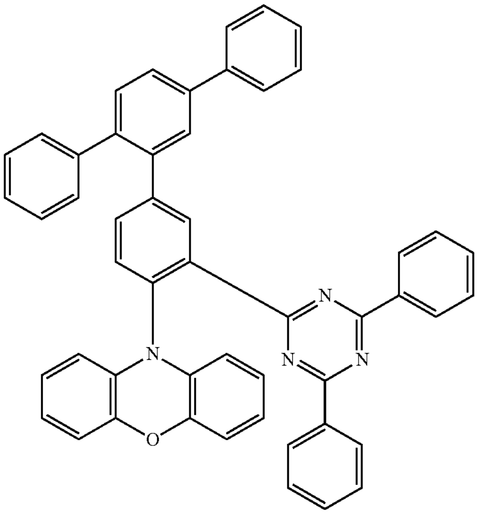
145
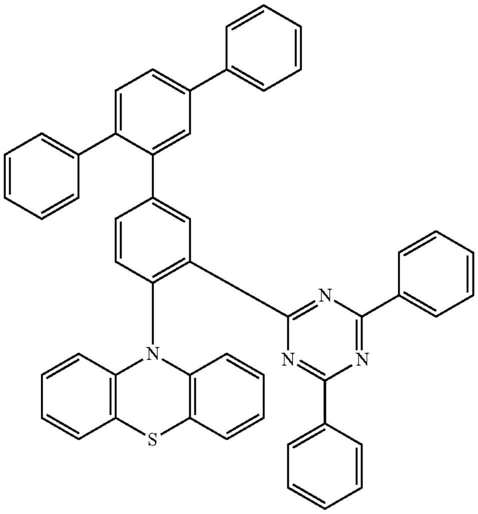
146
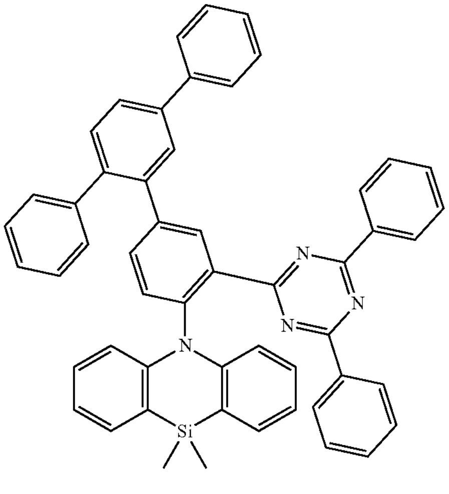

-continued
147
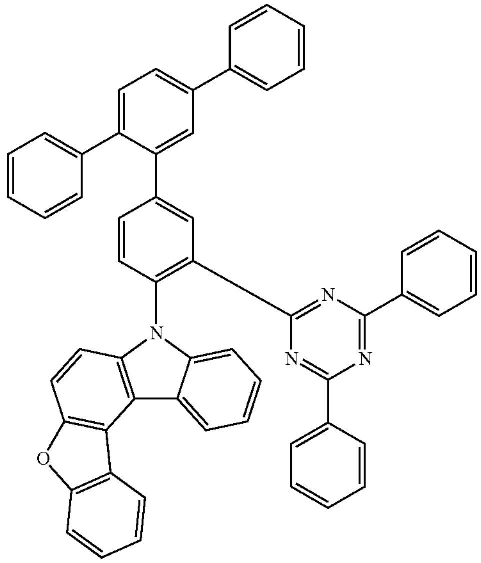
148
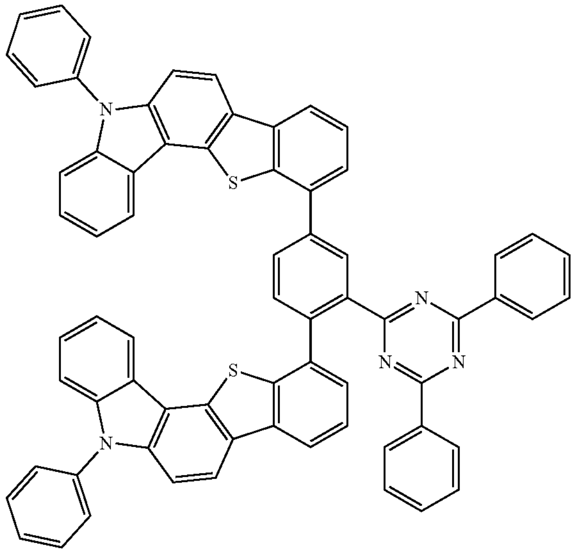
-continued
149
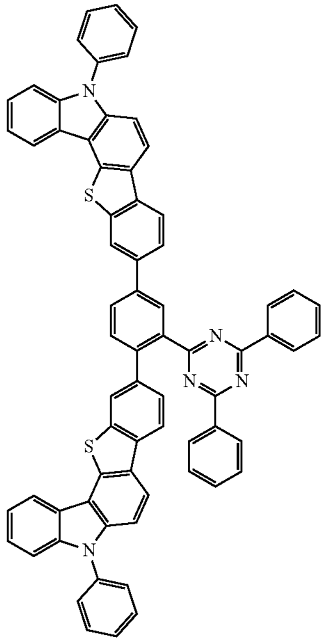
150
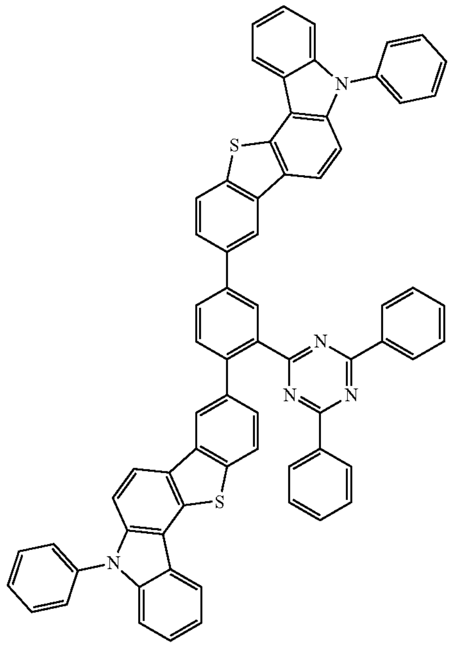

-continued
151
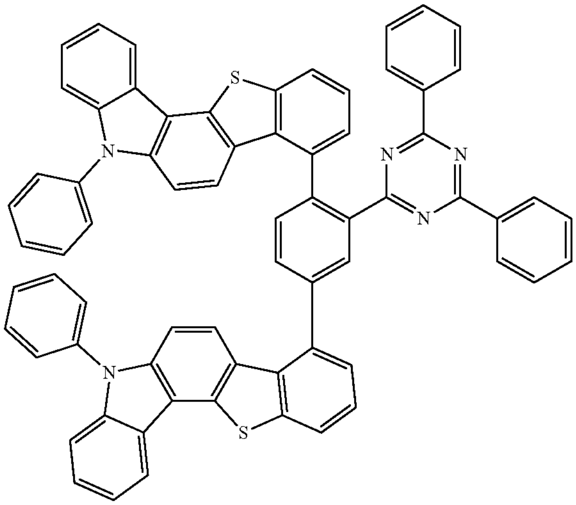
152
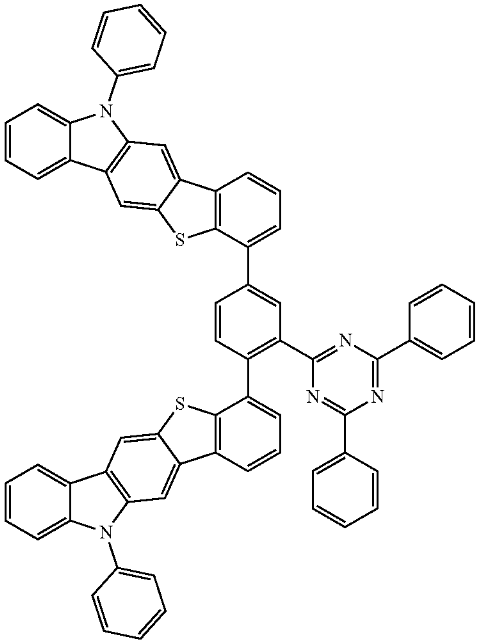
-continued
153
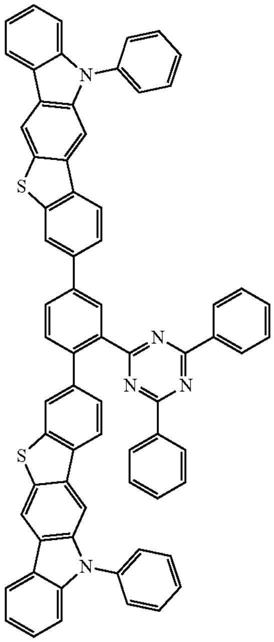
154
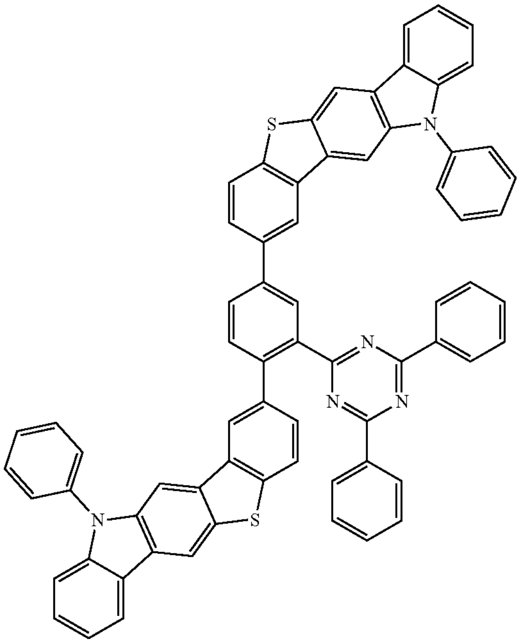

-continued
155
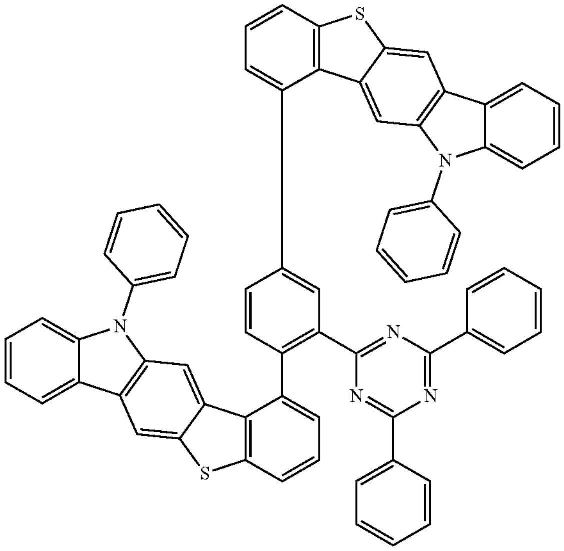
156
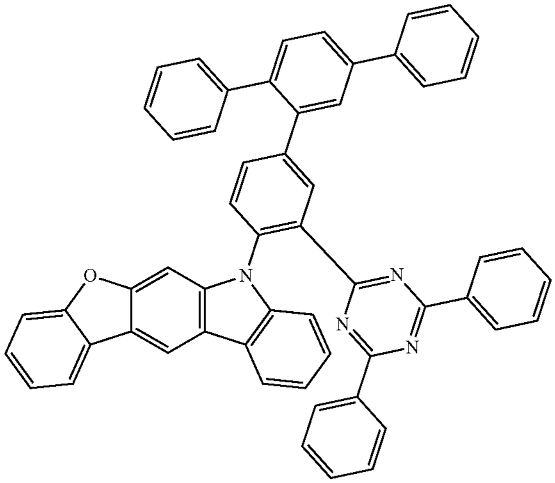
157
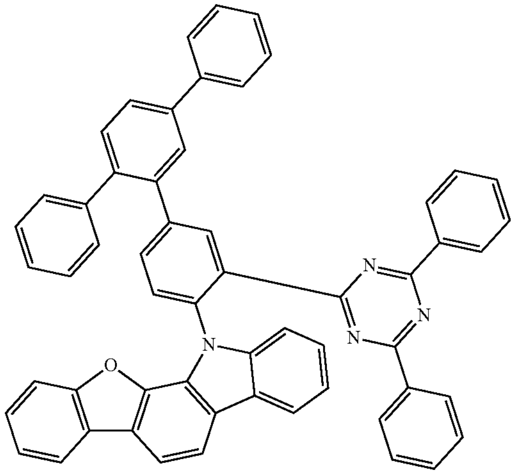
-continued
158
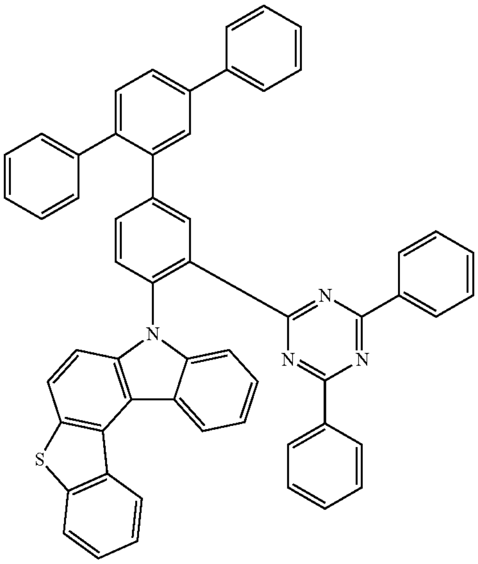
159
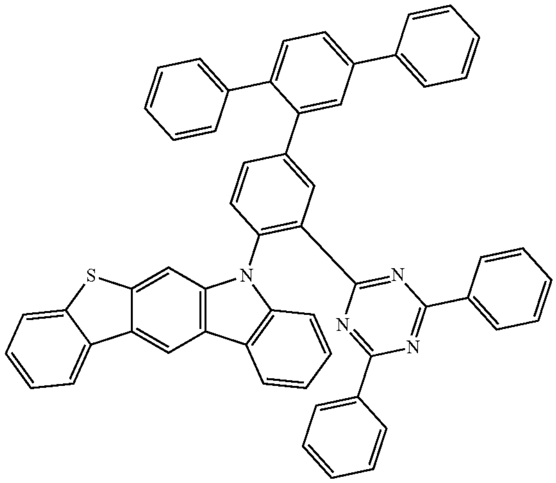
160
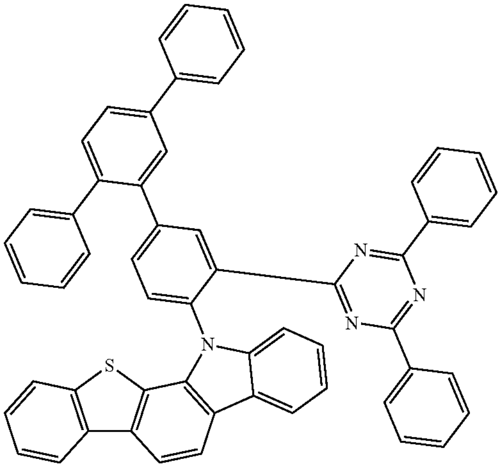

-continued
161
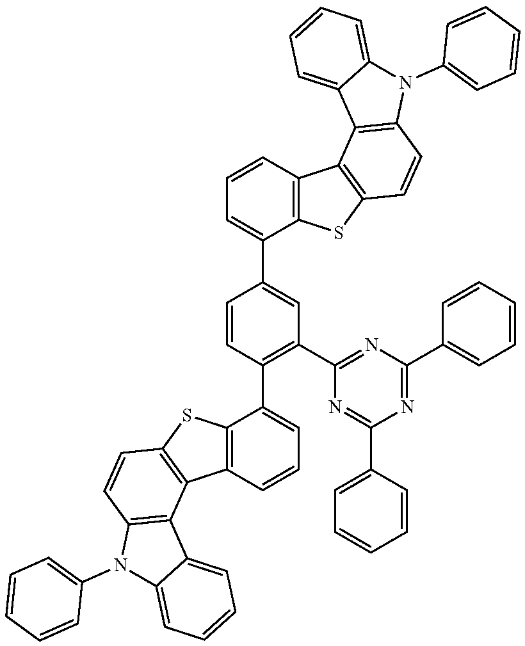
162
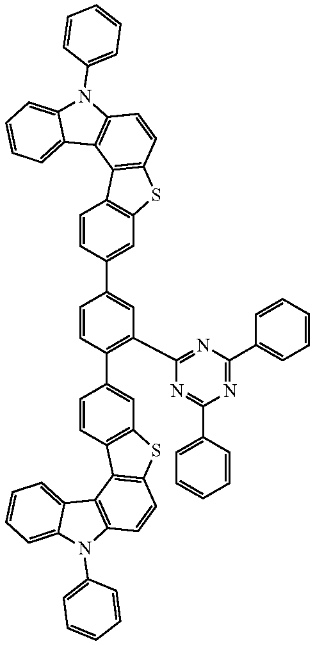
-continued
163
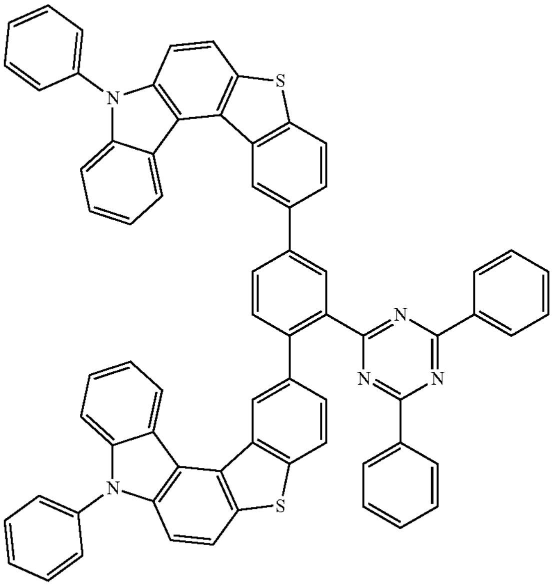
164
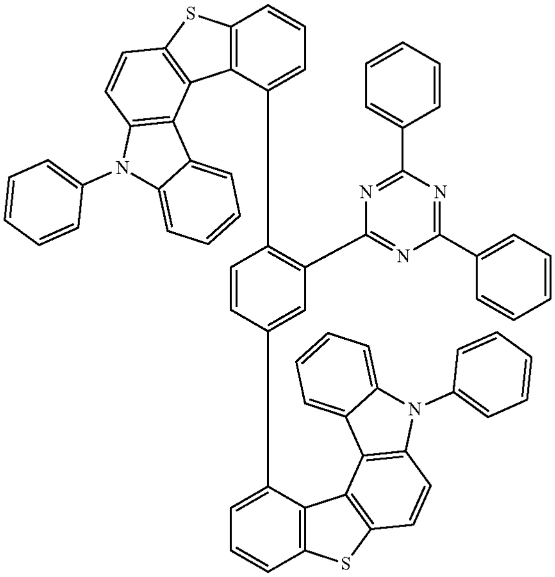

-continued
165
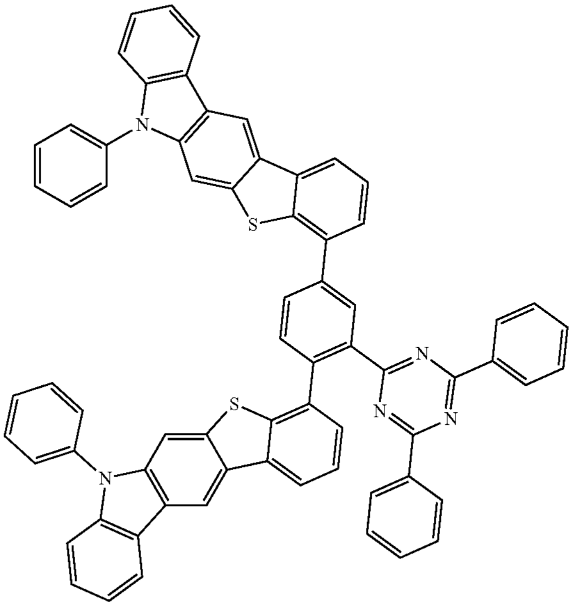
166
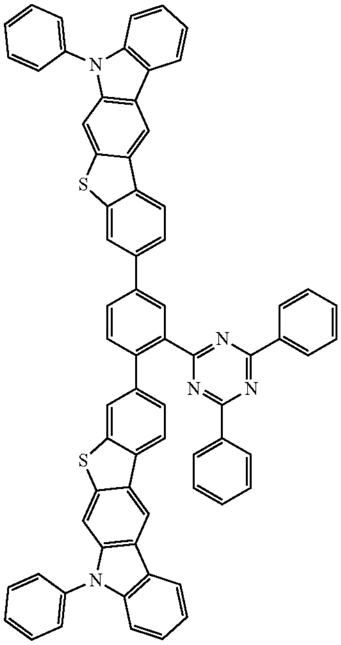
-continued
167
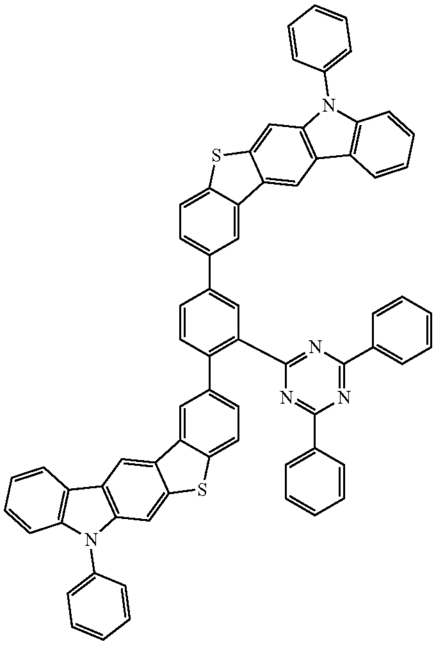
168
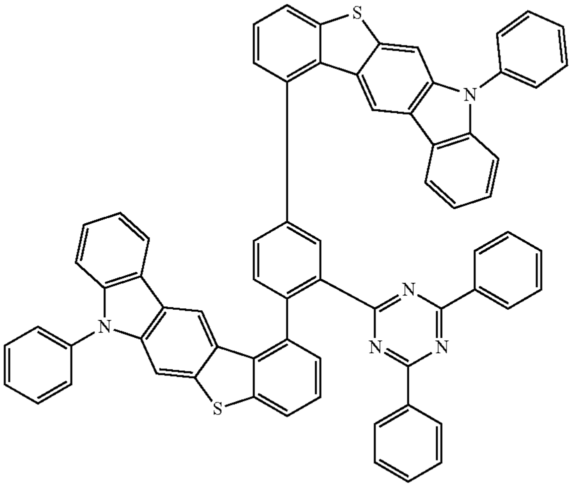

-continued
169
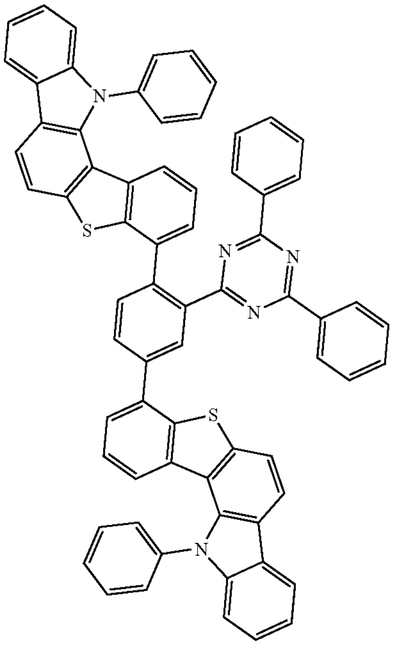
170
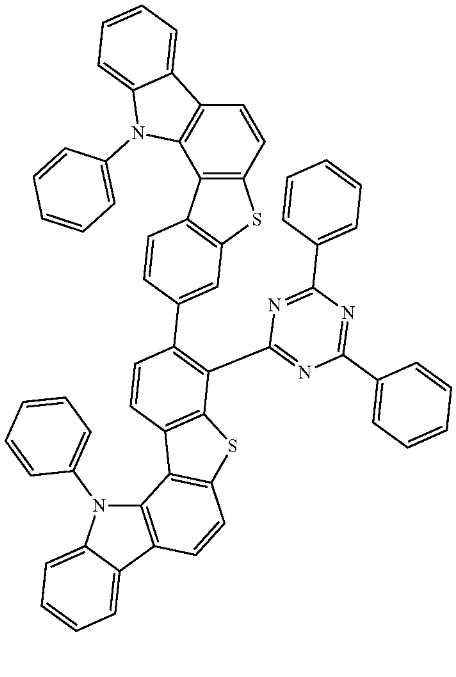
-continued
171
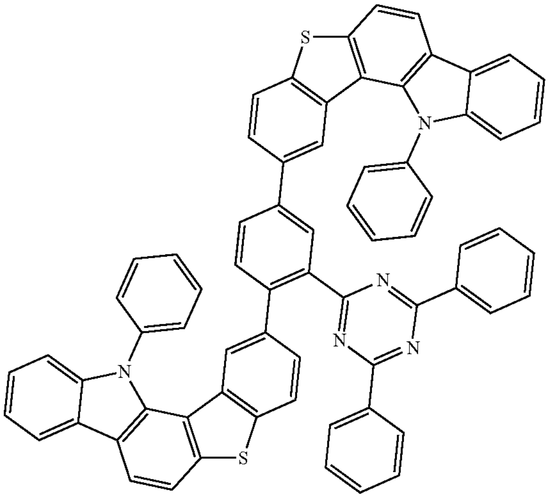
172
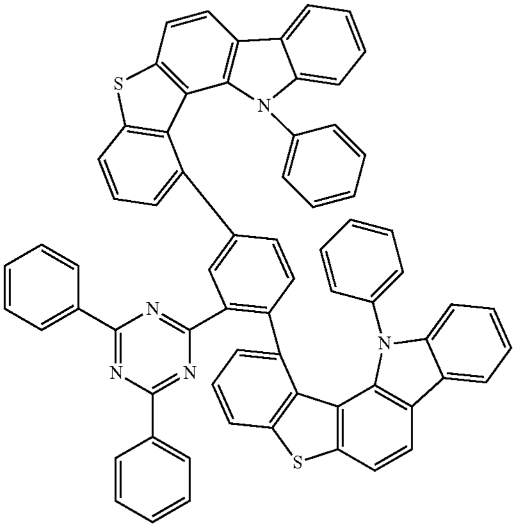
173
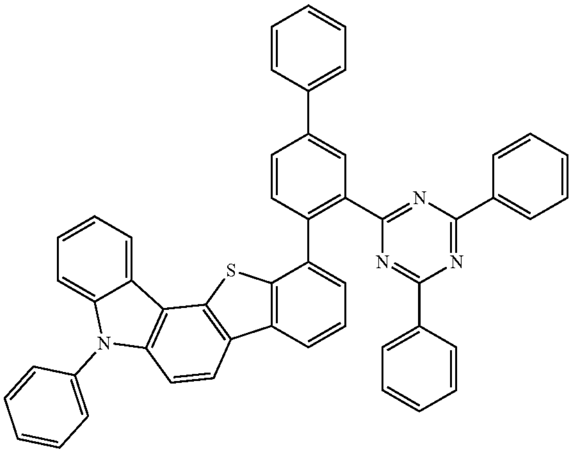

-continued
174
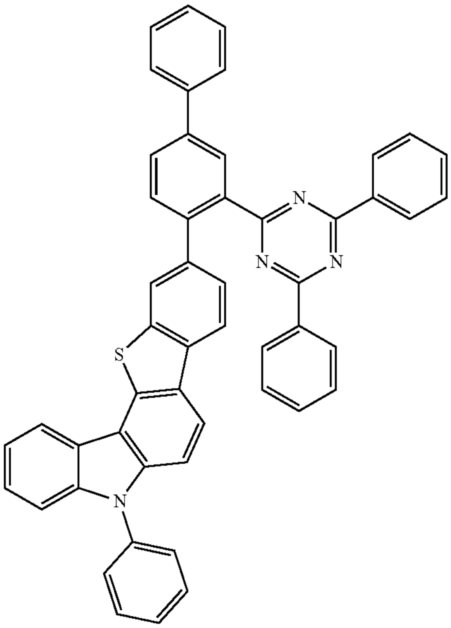
175
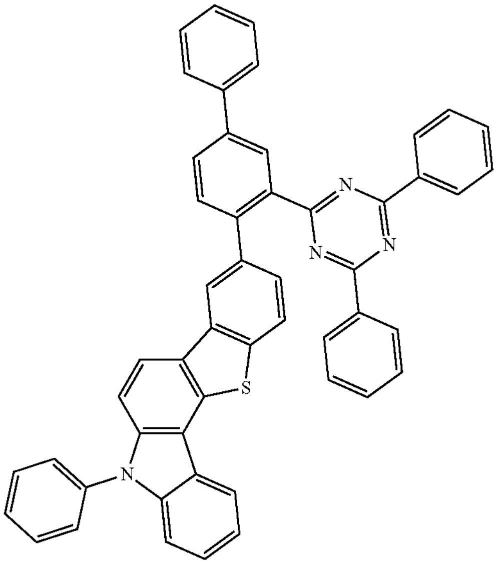
176
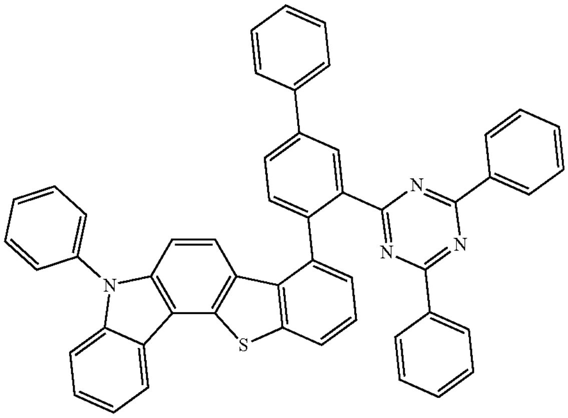
-continued
177
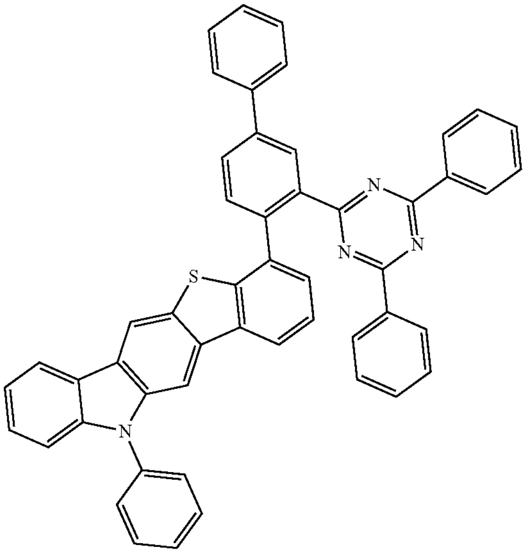
178
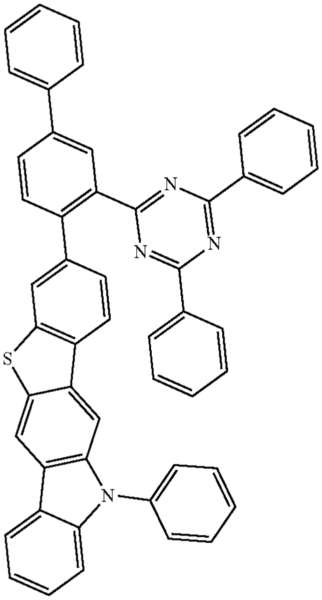

179
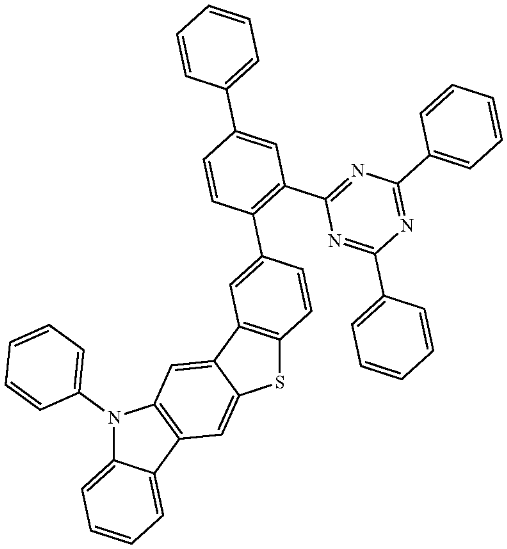
180
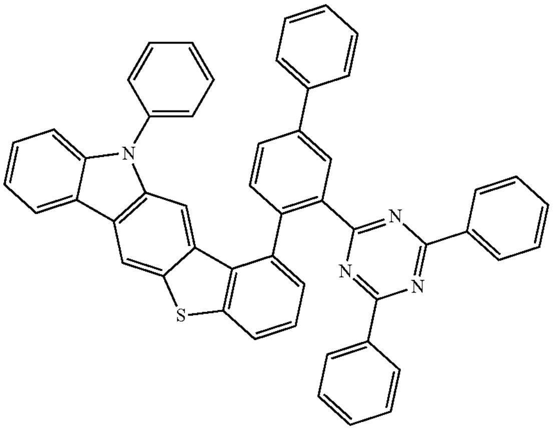
181
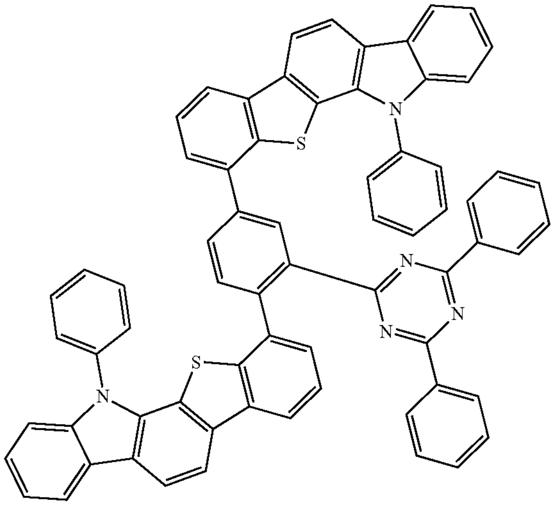
182
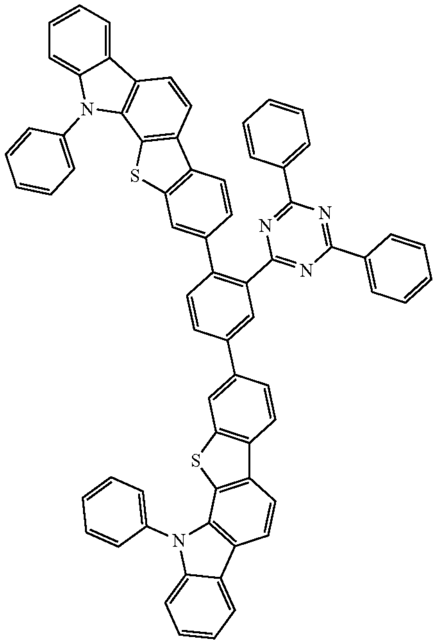
183
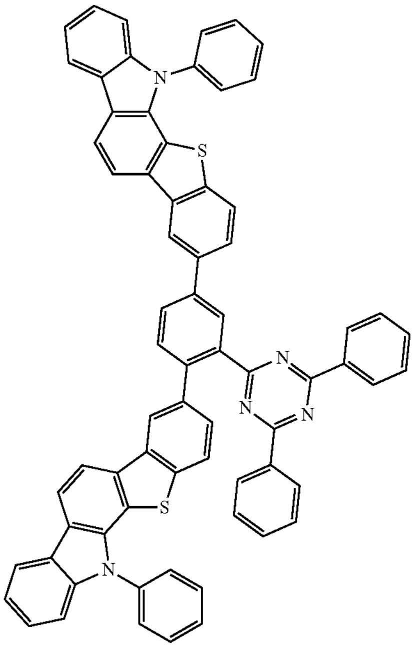

-continued
184
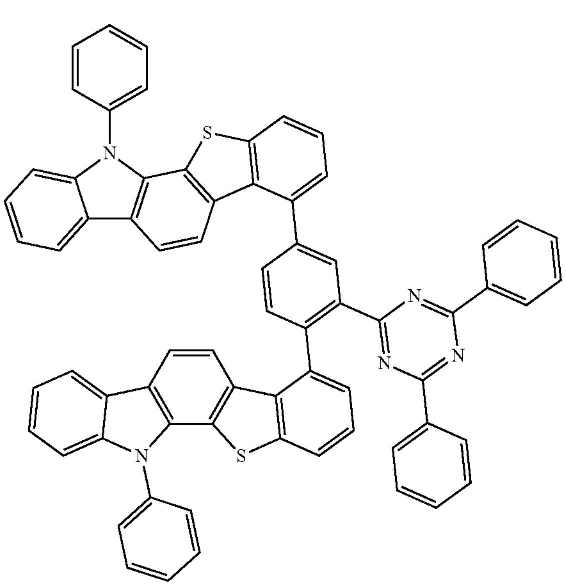
185
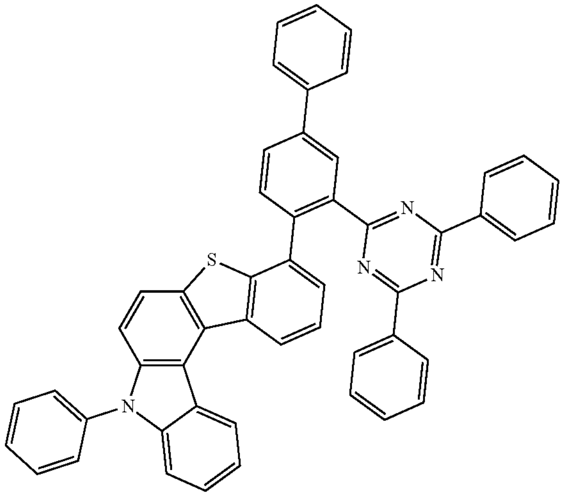
-continued
186
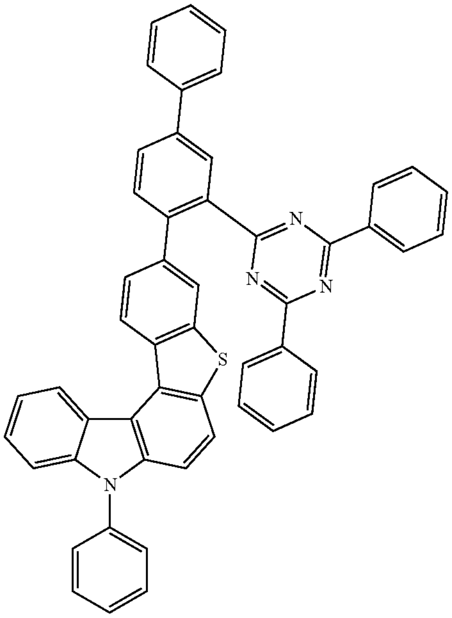
187
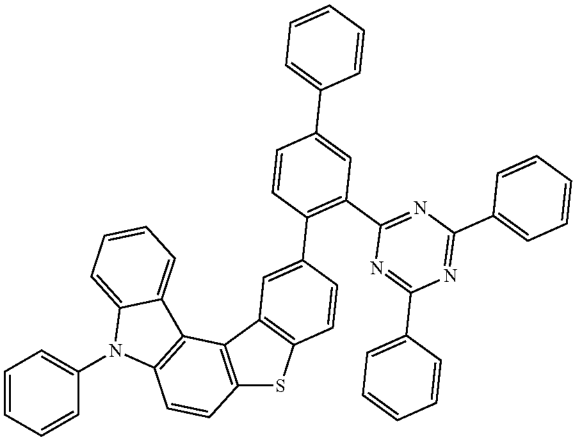
188
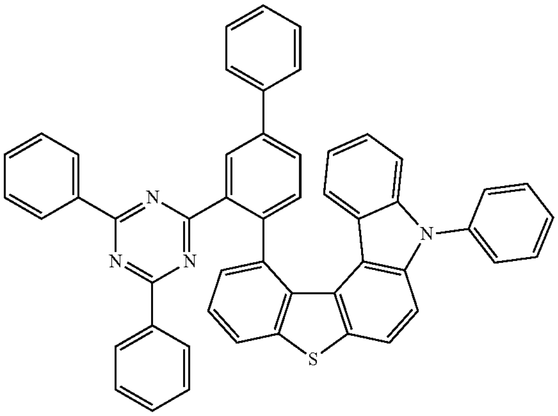

-continued
189
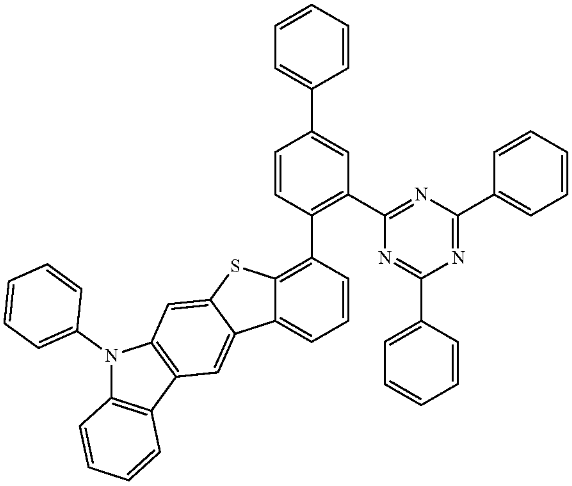
190
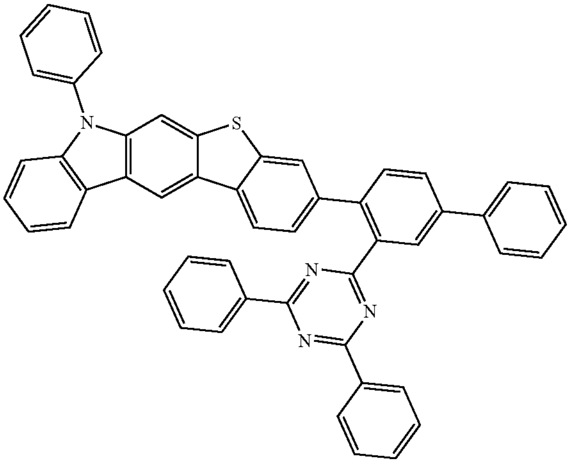
191
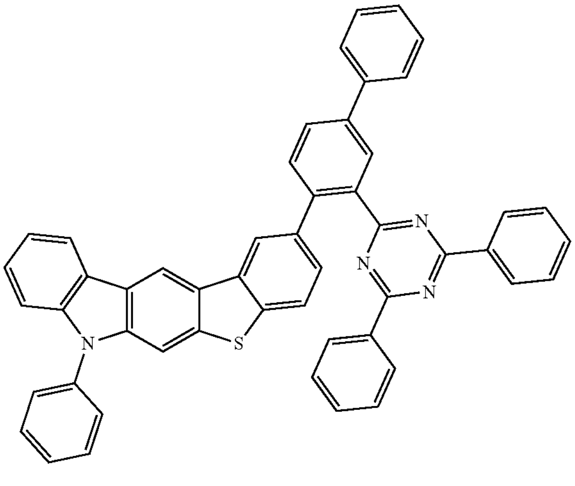
-continued
192
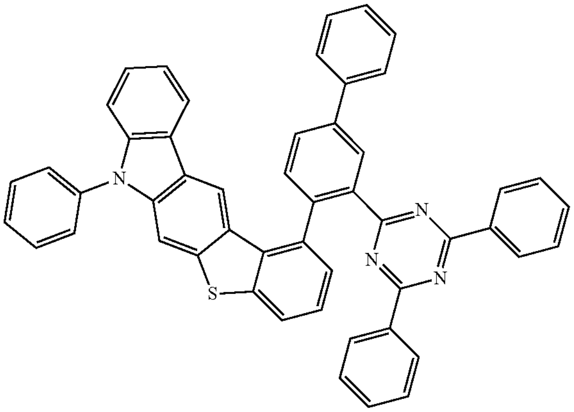
193
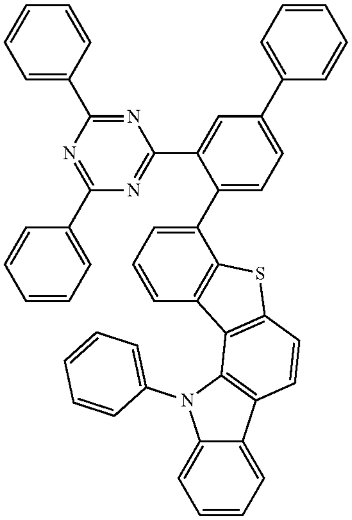
194
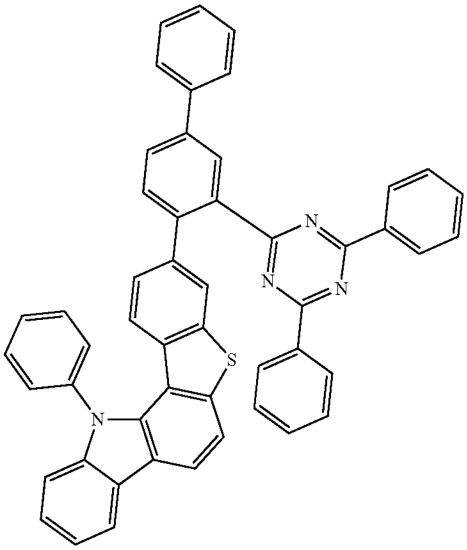

-continued
195
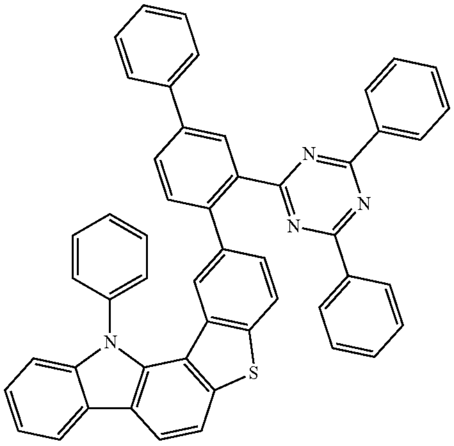
196
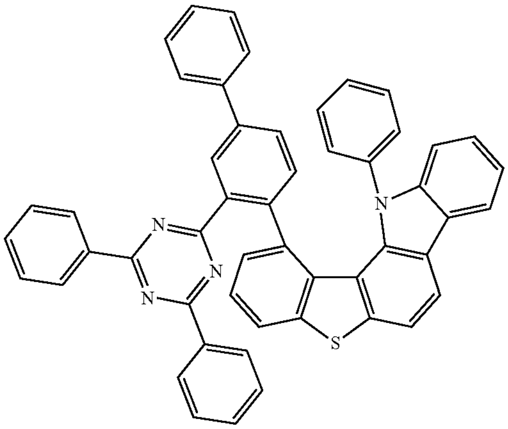
197
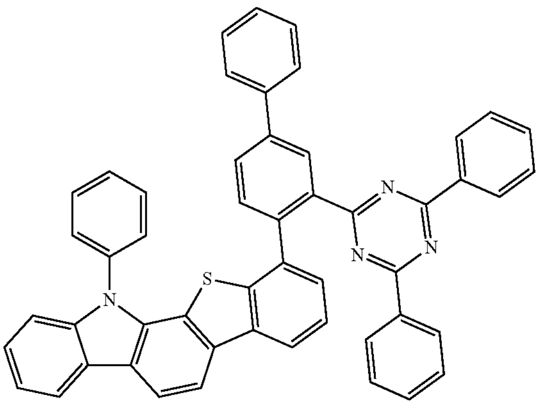
-continued
198
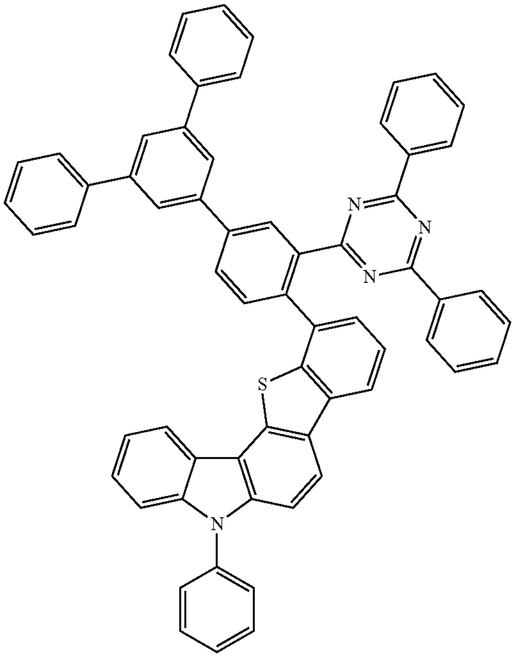
199
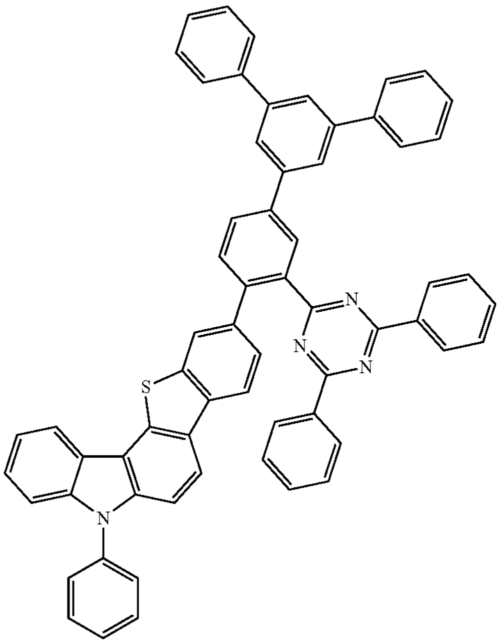

-continued
200
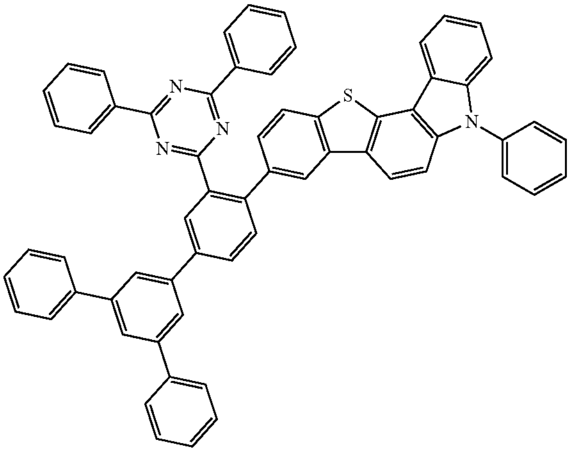
201
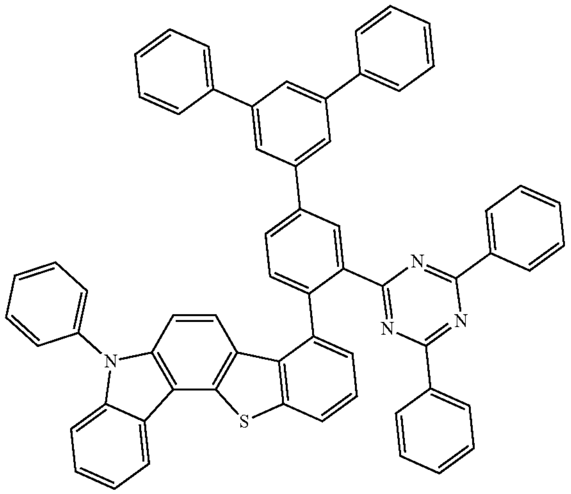
202
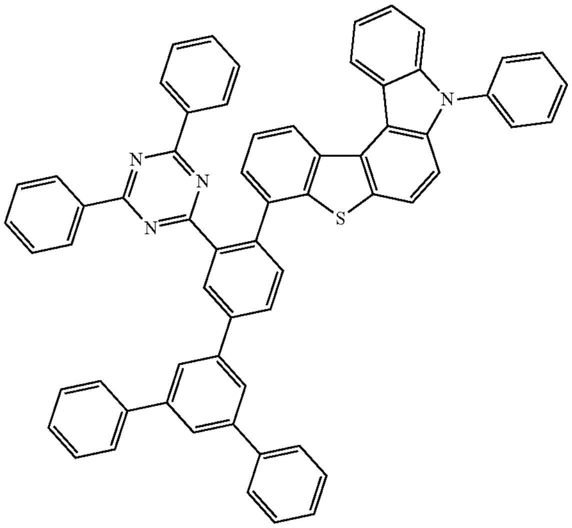
-continued
203
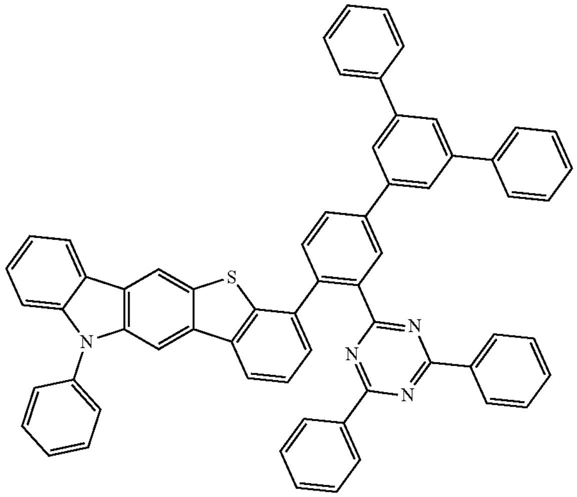
204
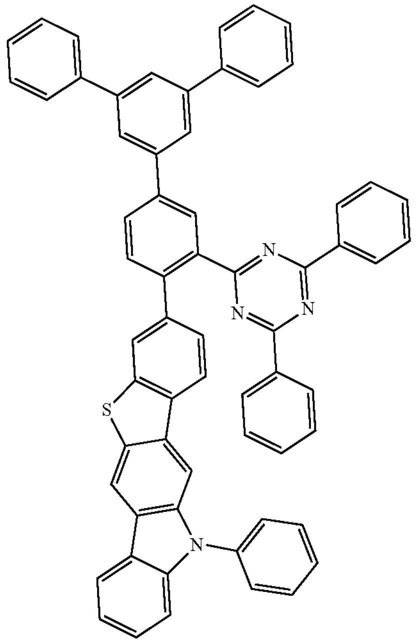

-continued
205
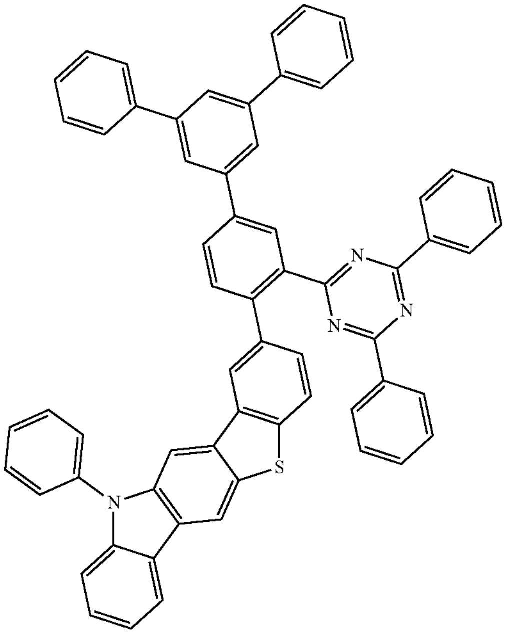
206
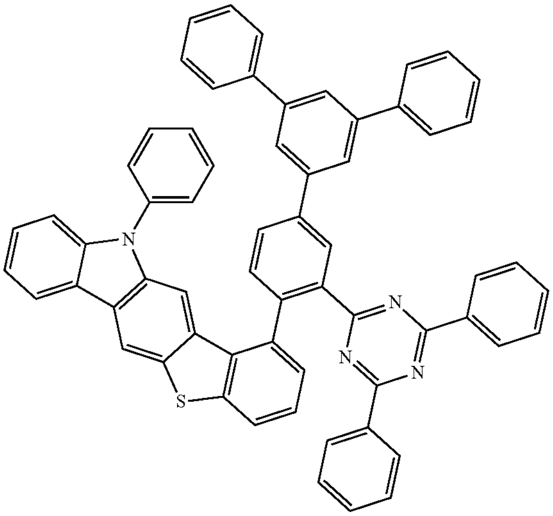
-continued
207
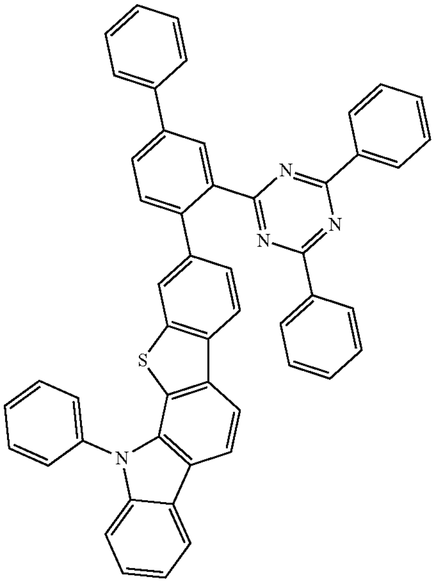
208
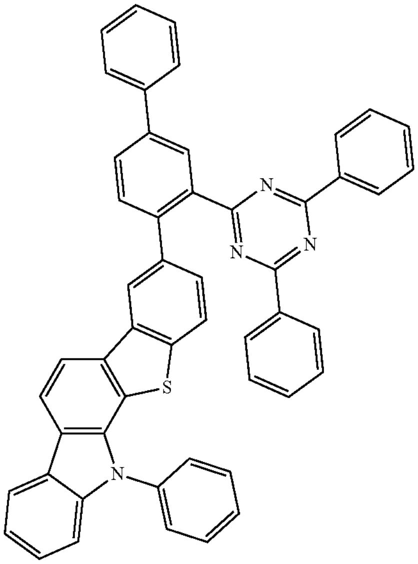
209
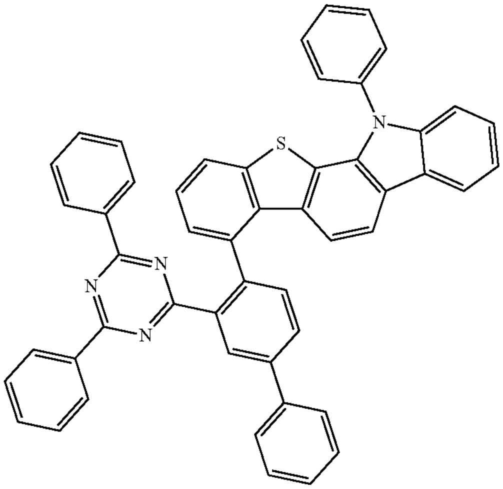

-continued
210
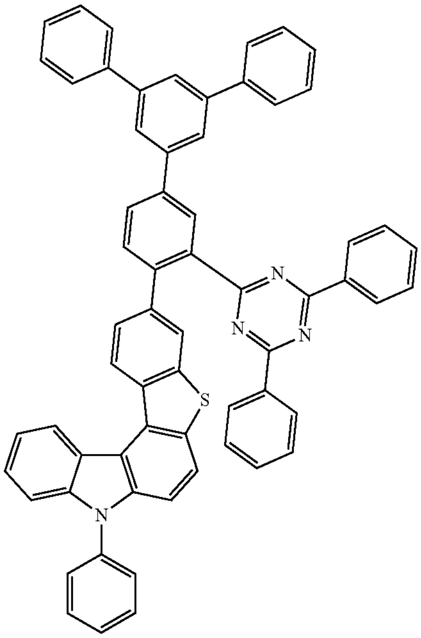
211
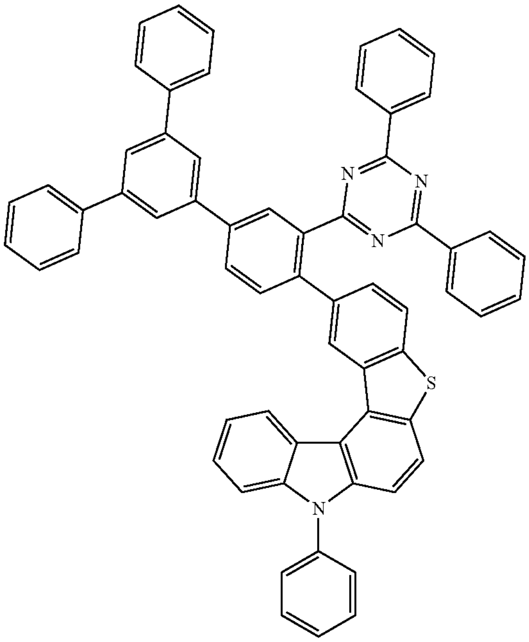
-continued
212
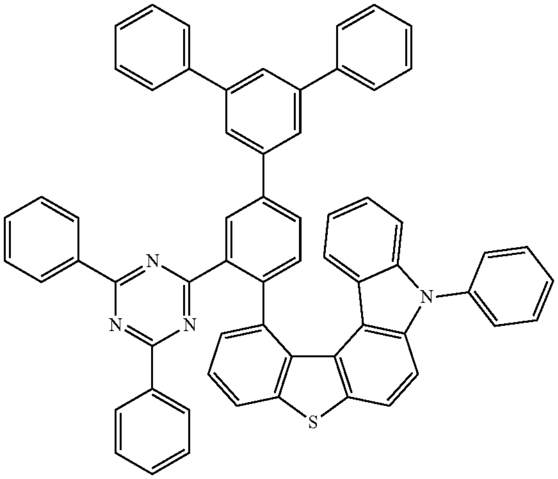
213
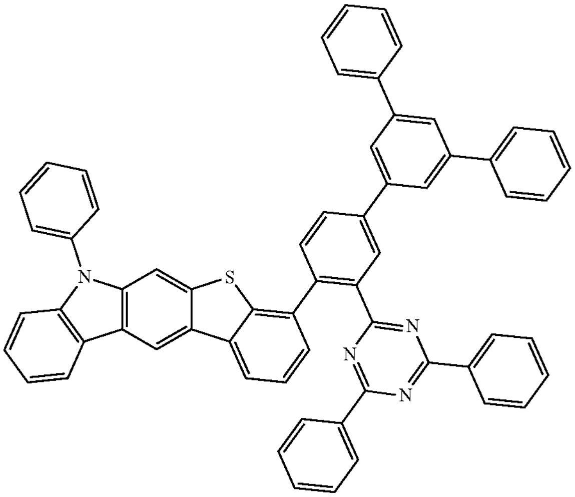
214
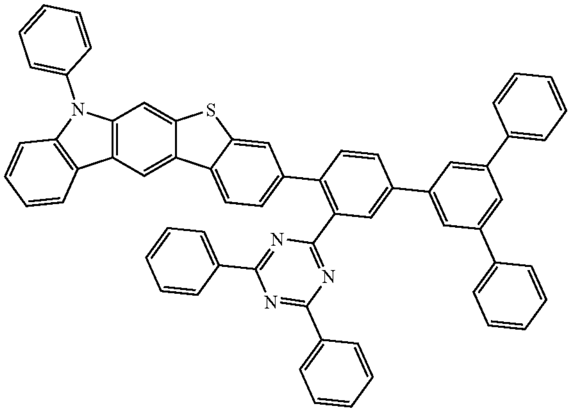

-continued
215
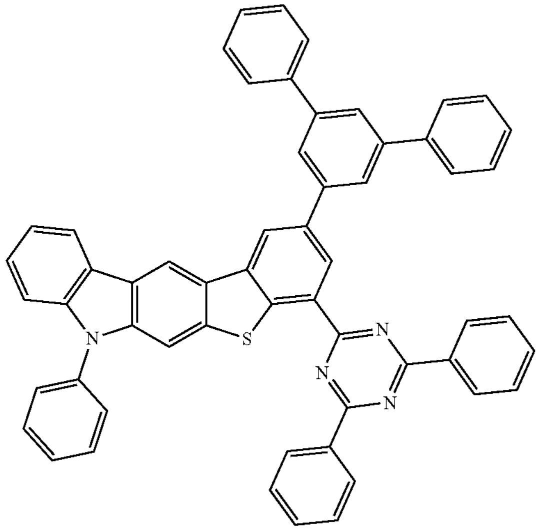
216
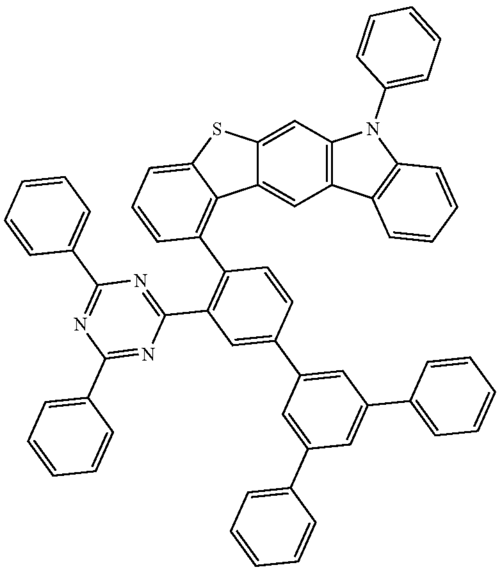
-continued
217
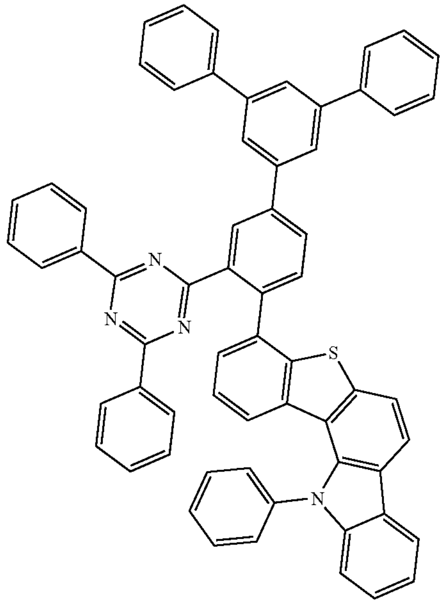
218
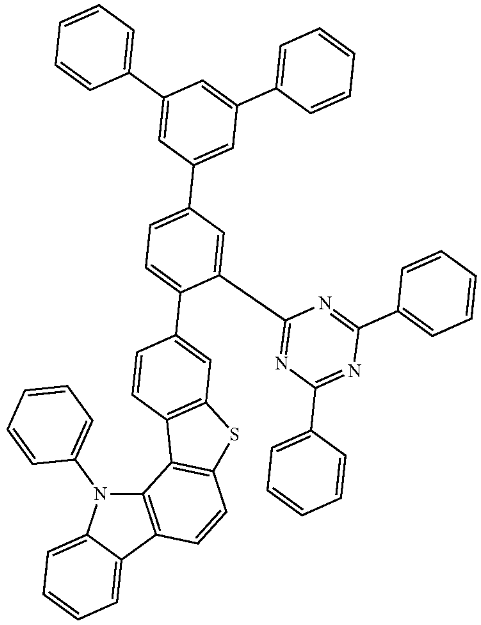

219
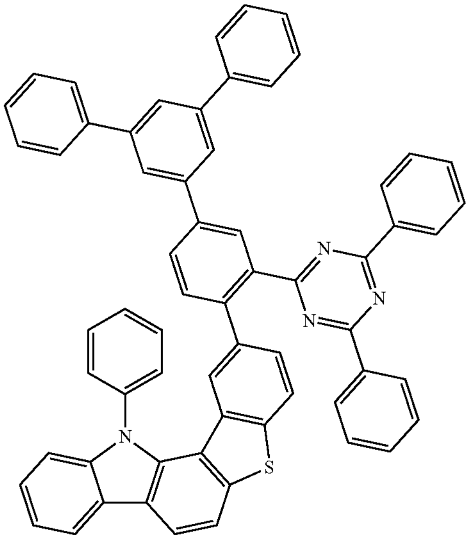
220
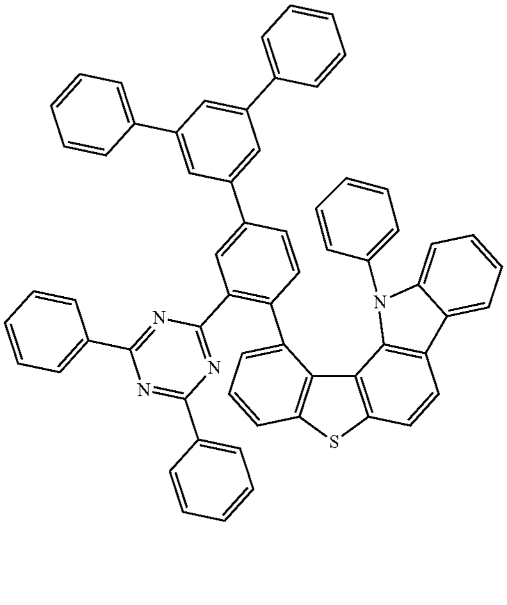
221
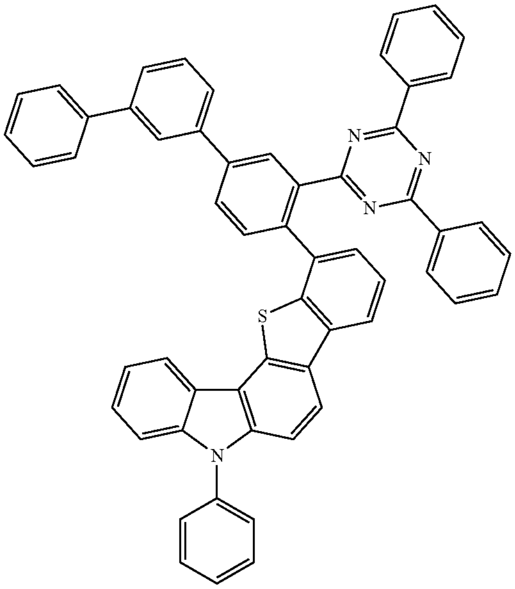
222
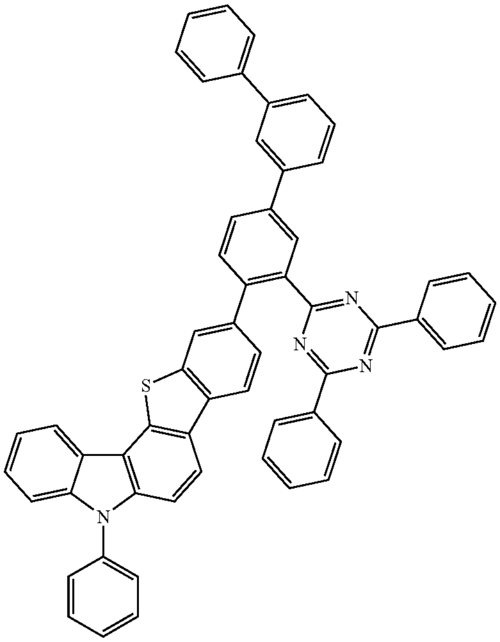

-continued
223
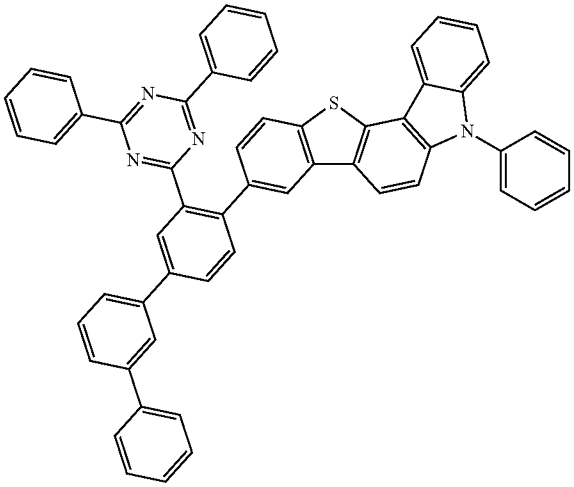
224
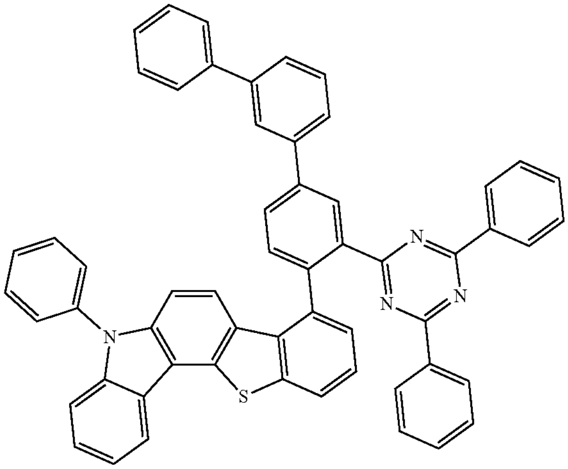
225
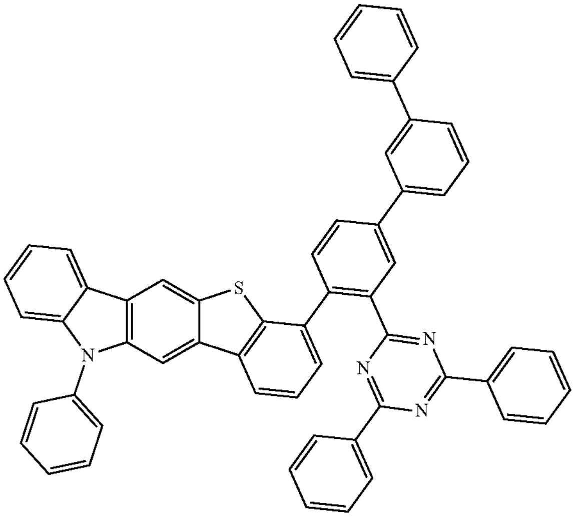
-continued
226
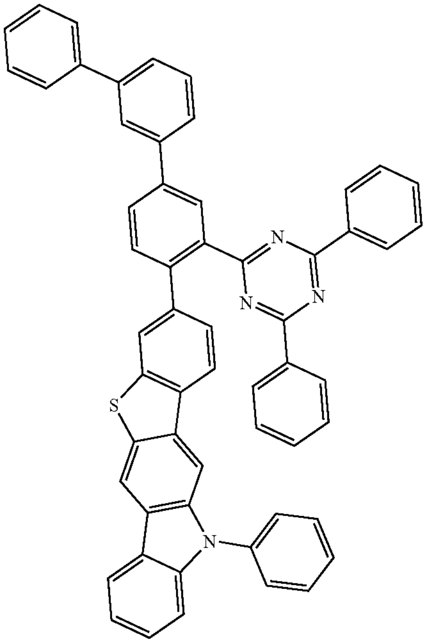
227
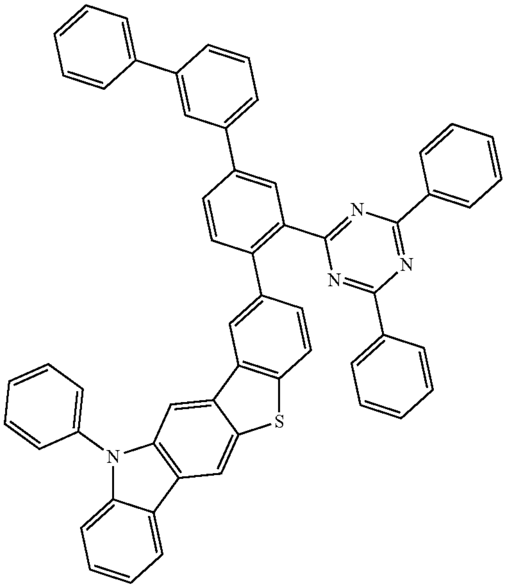

-continued
228
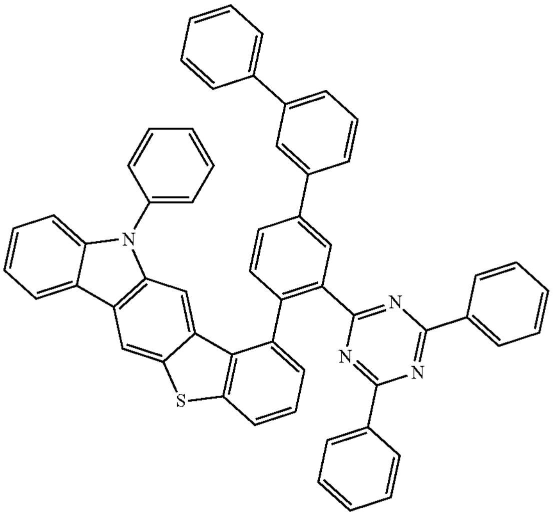
229
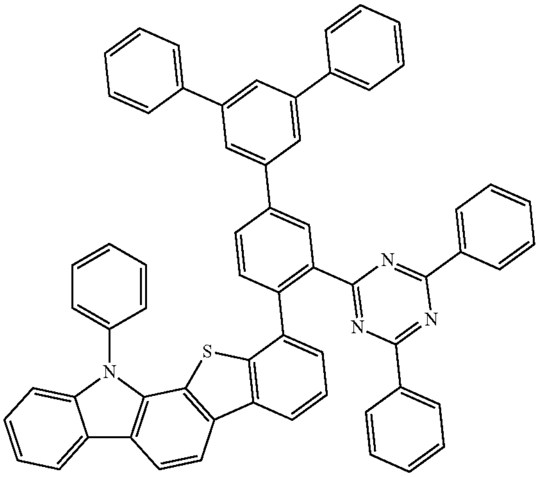
-continued
230
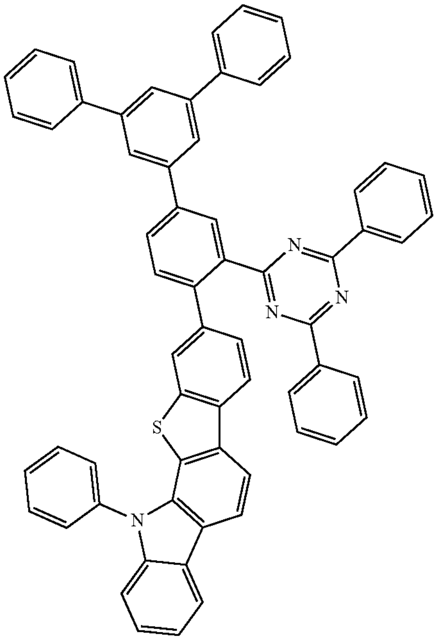
231
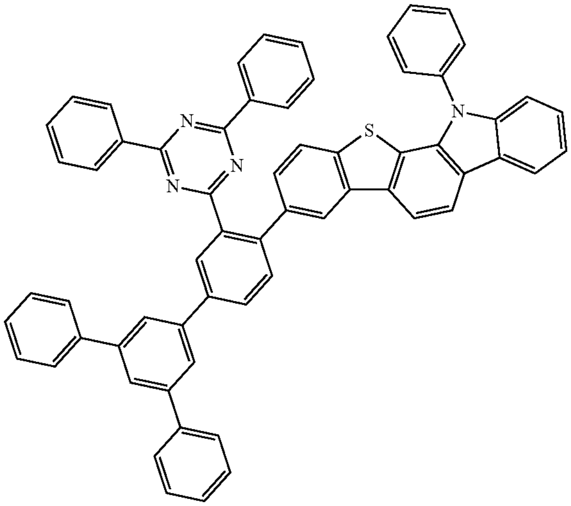

-continued
232
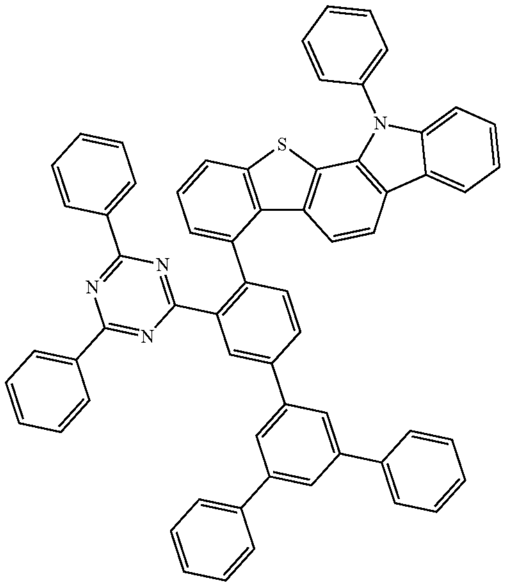
233
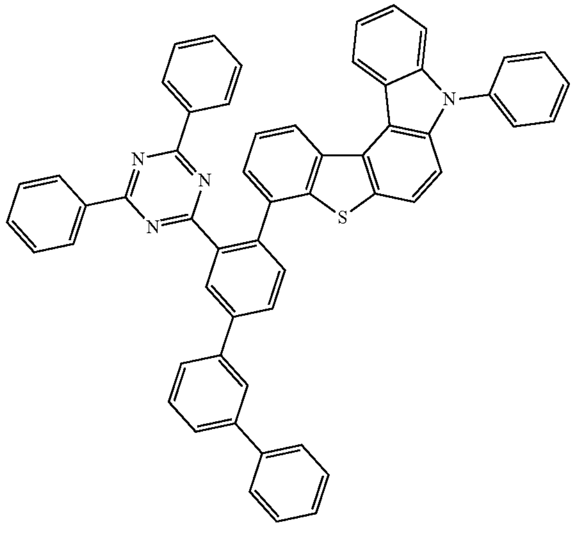
-continued
234
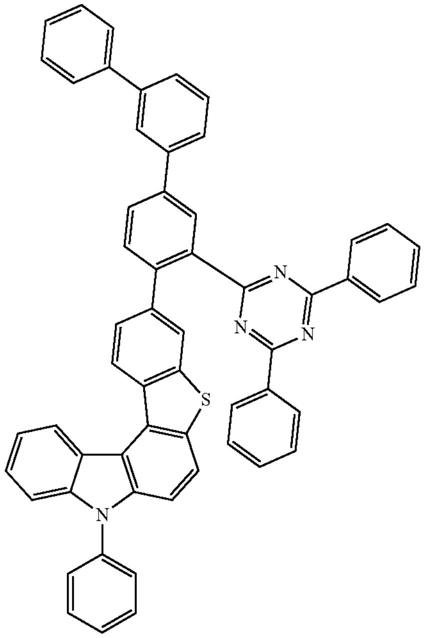
235
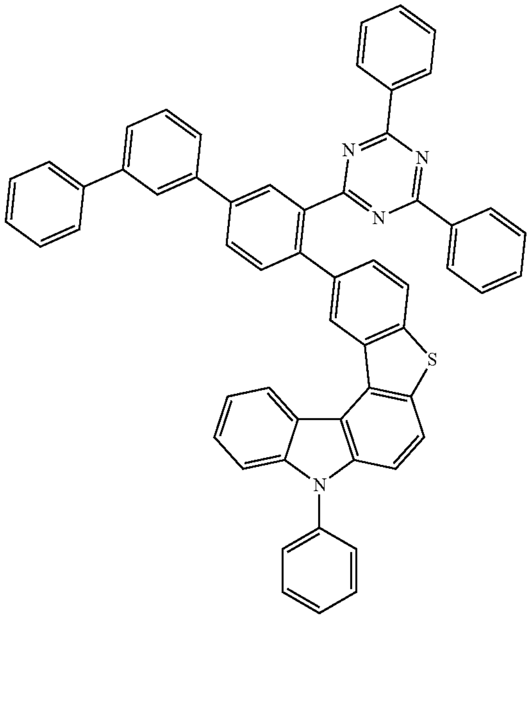

-continued
236
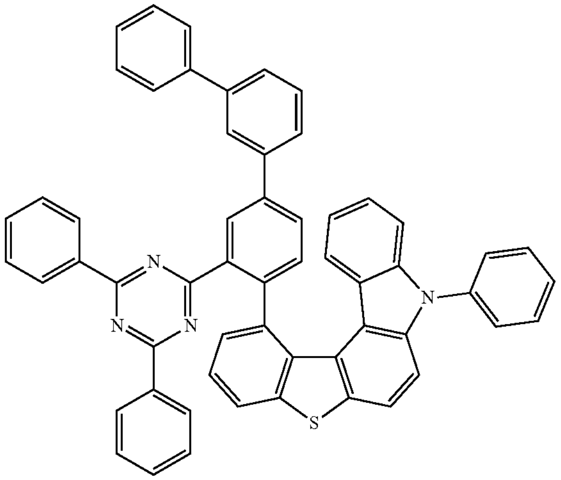
237
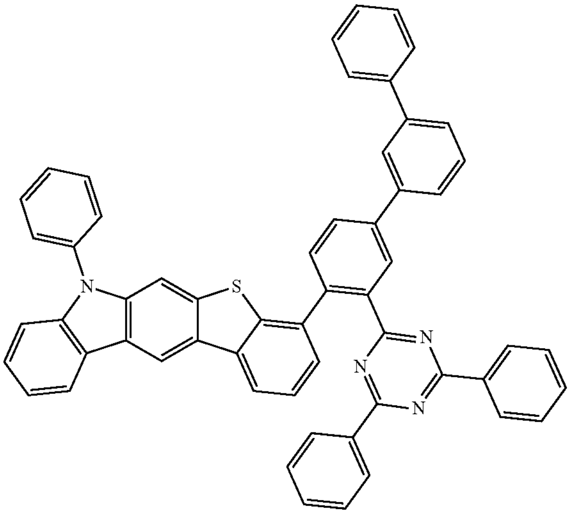
238
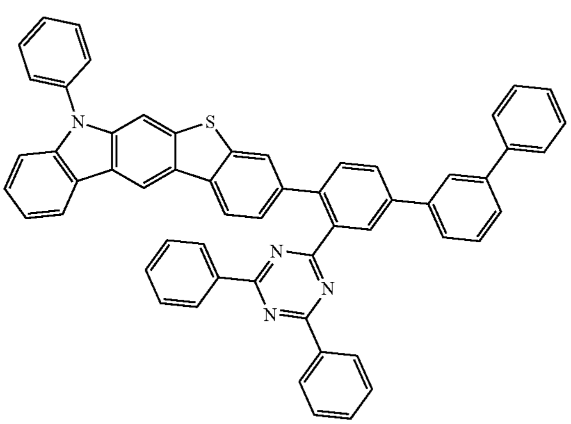
-continued
239
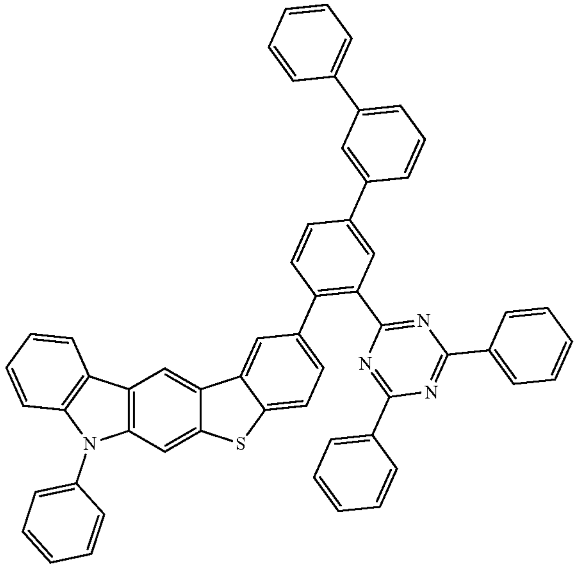
240
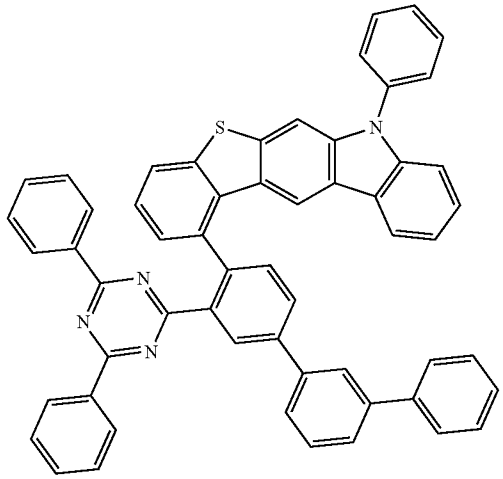
241
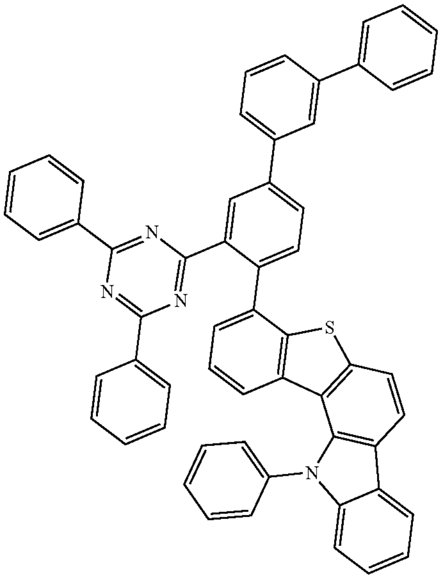

-continued
242
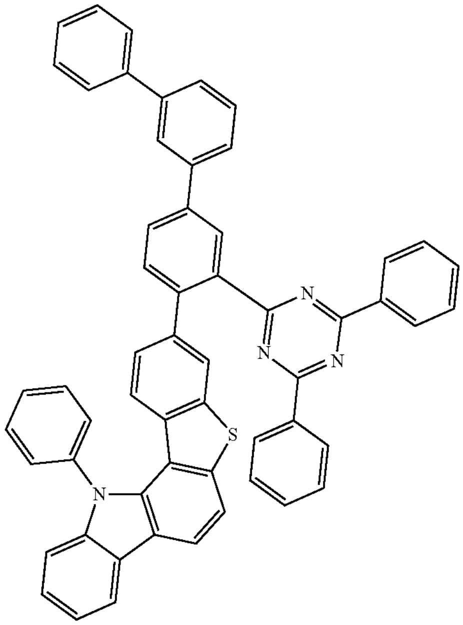
243
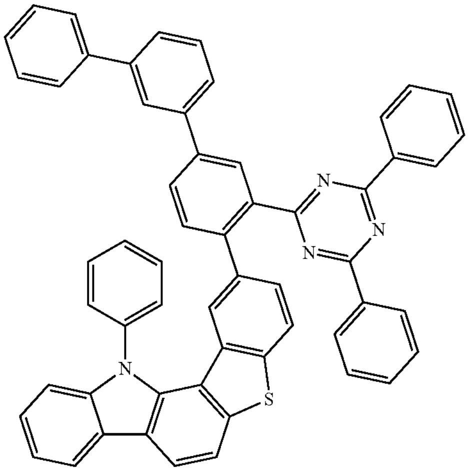
244
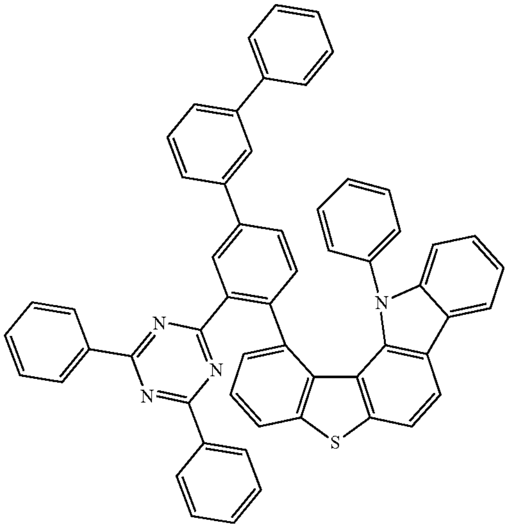
-continued
245
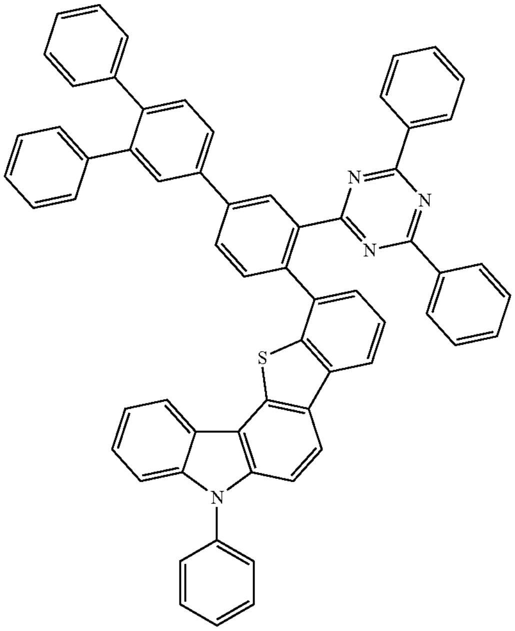
246
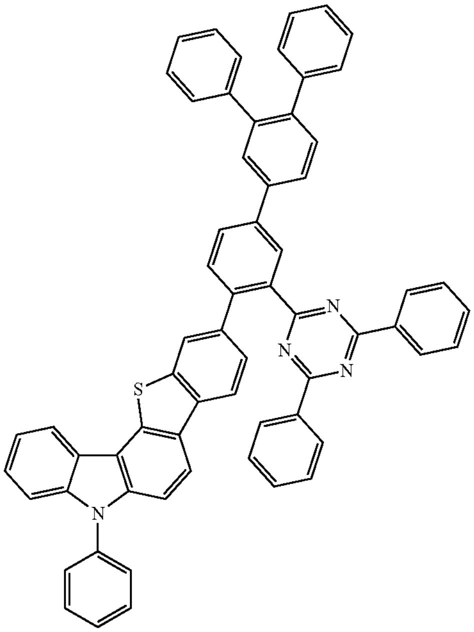

-continued
247
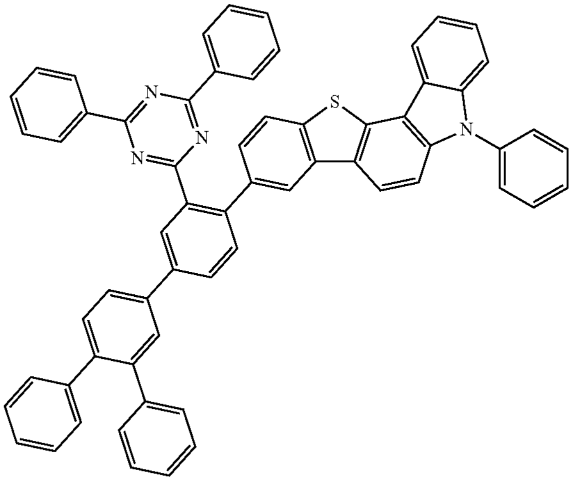
248
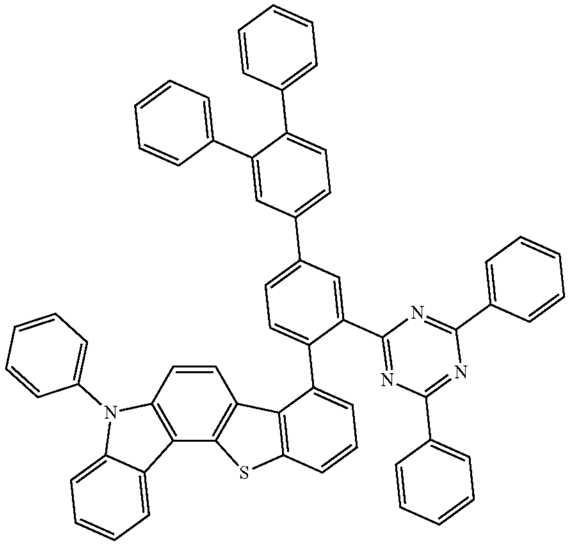
249
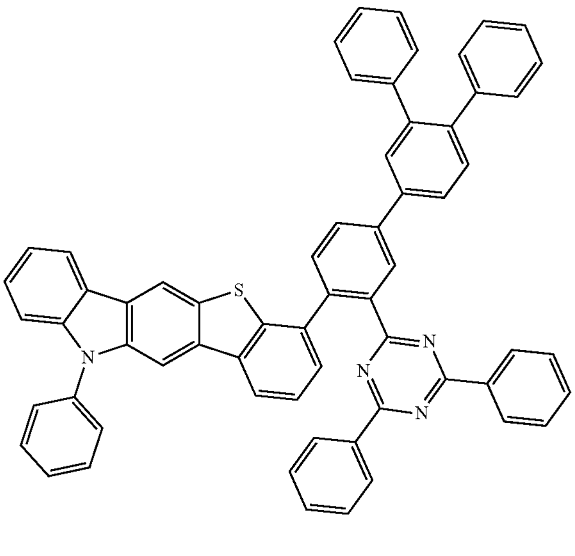
-continued
250
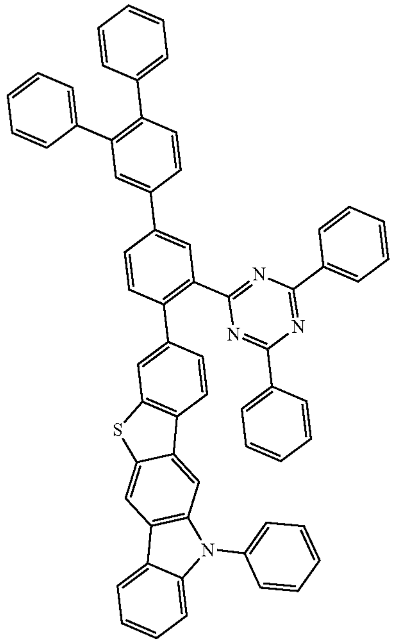
251
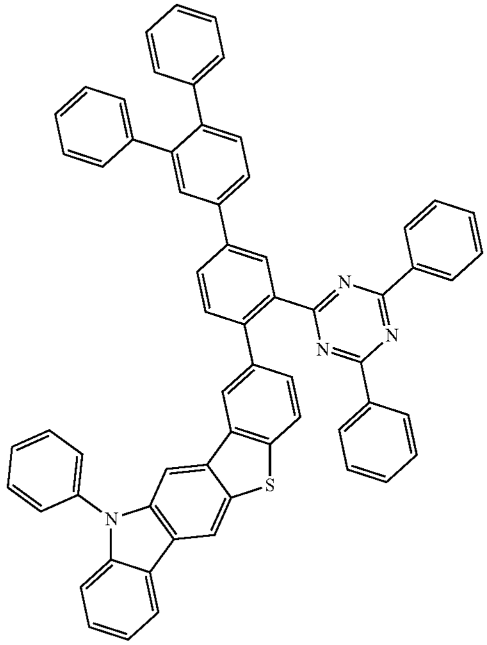

-continued
252
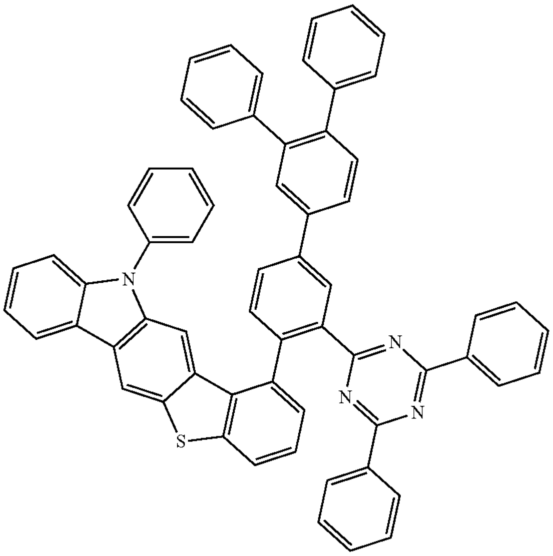
253
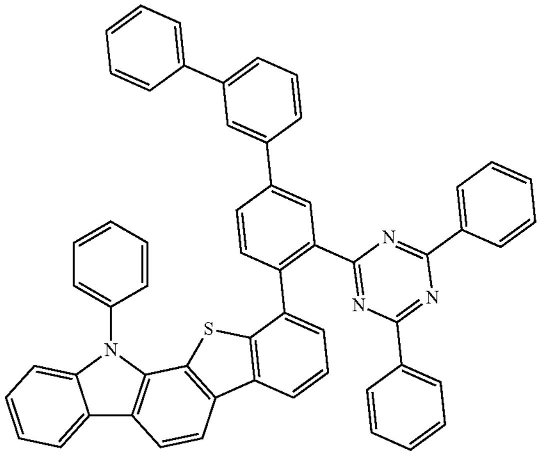
-continued
254
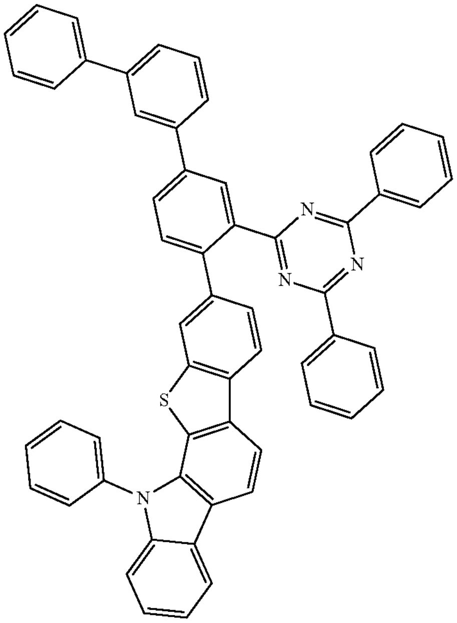
255
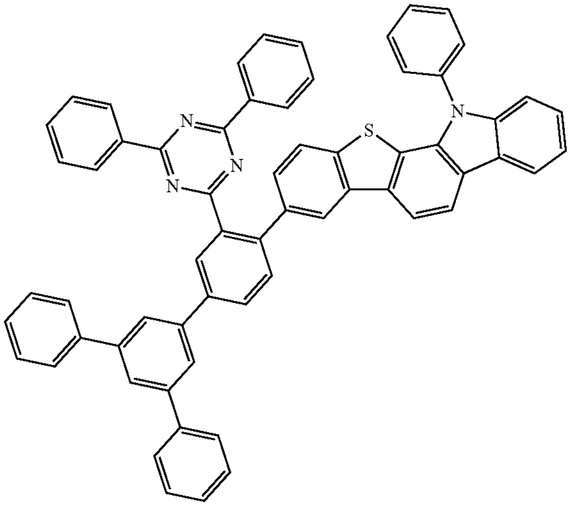

-continued
256
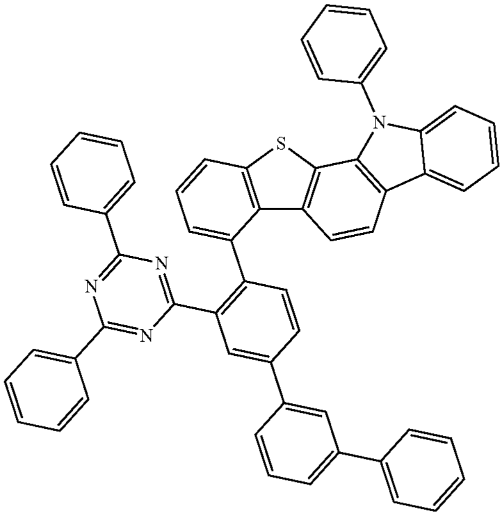
257
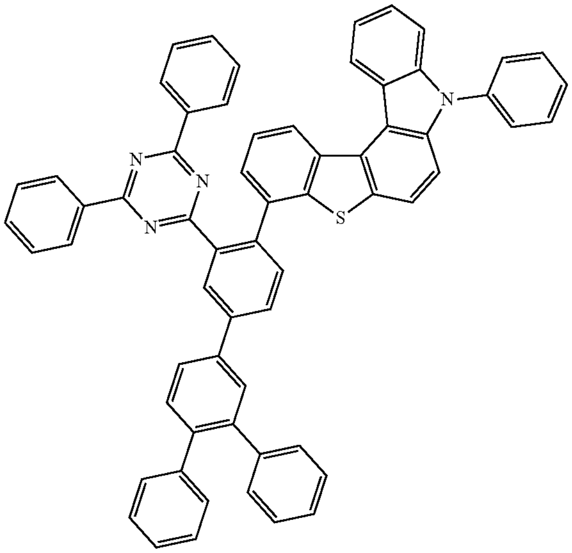
-continued
258
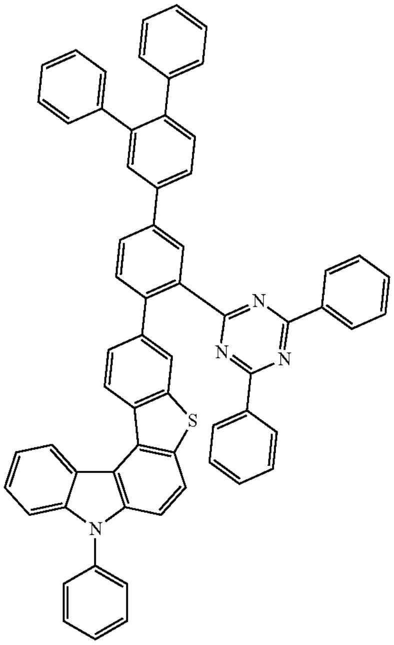
259
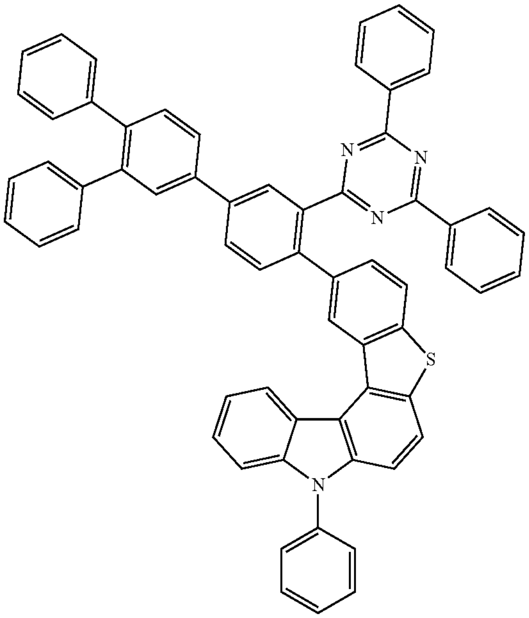

-continued
260
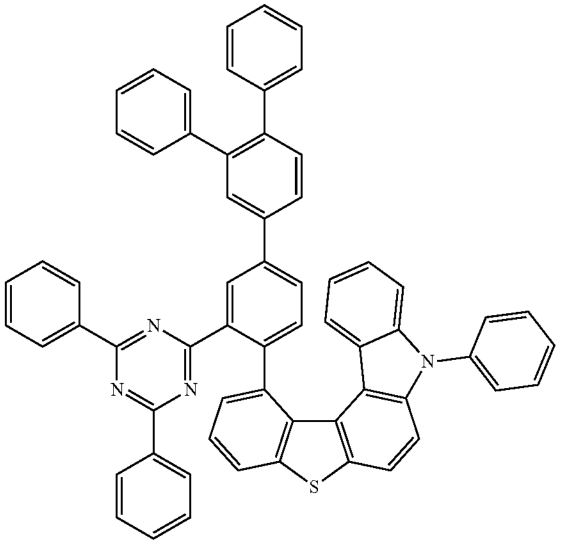
261
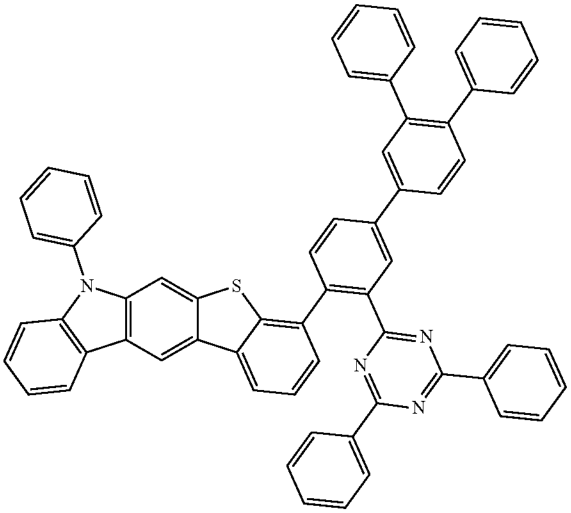
262
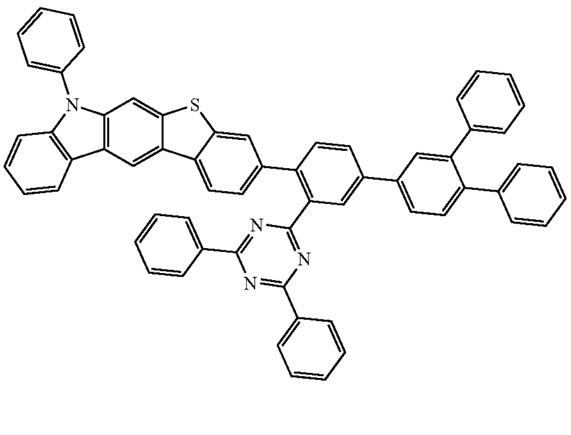
-continued
263
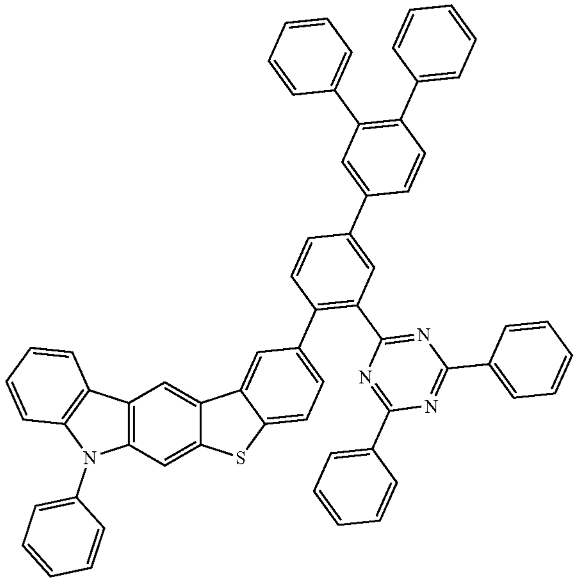
264
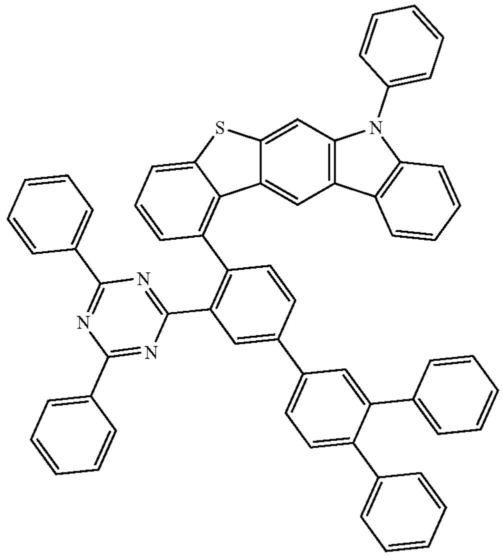

-continued
265
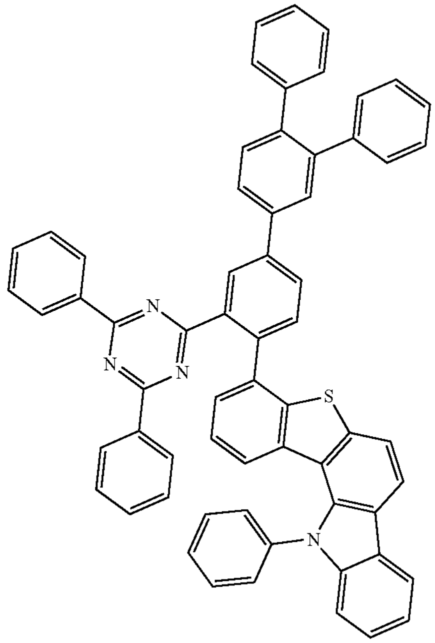
266
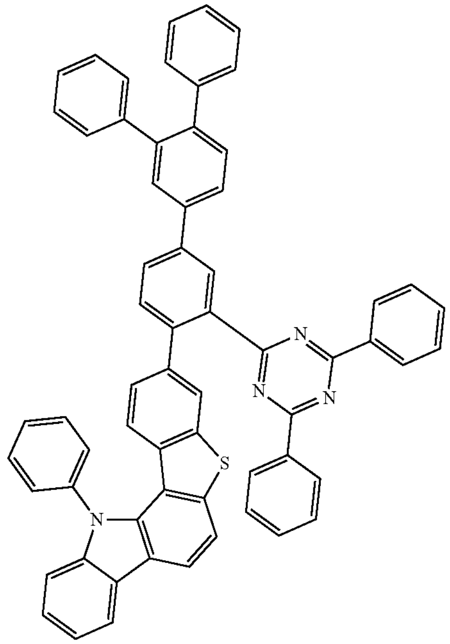
-continued
267
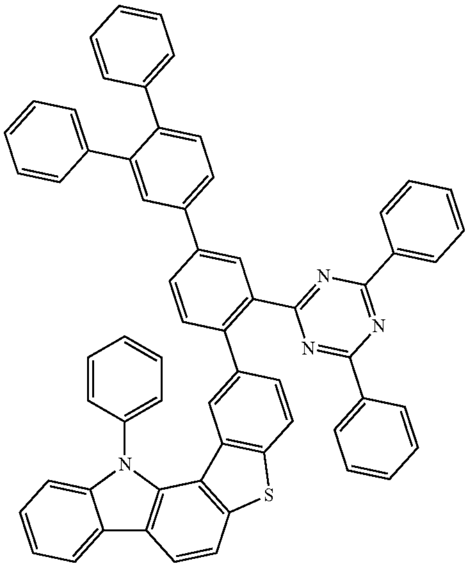
268
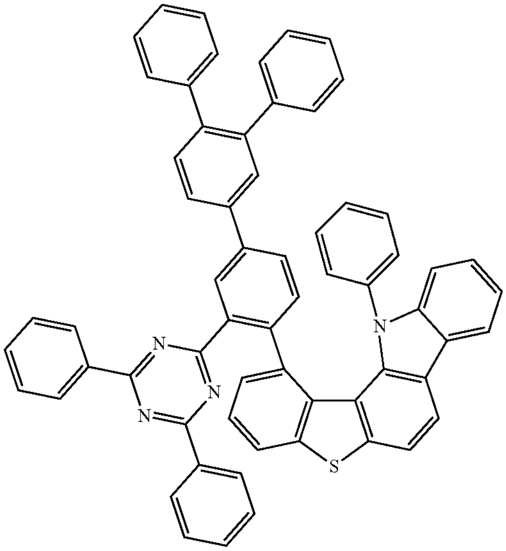

-continued
269
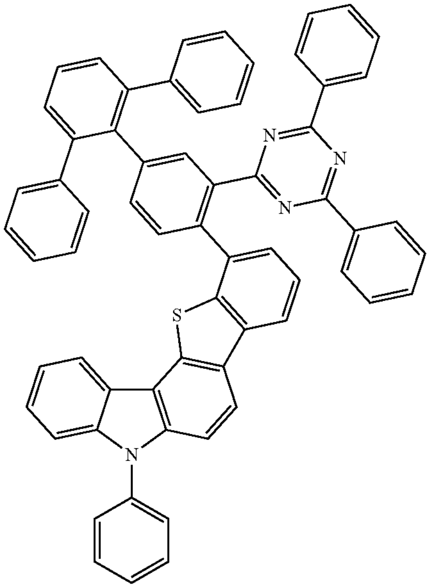
270
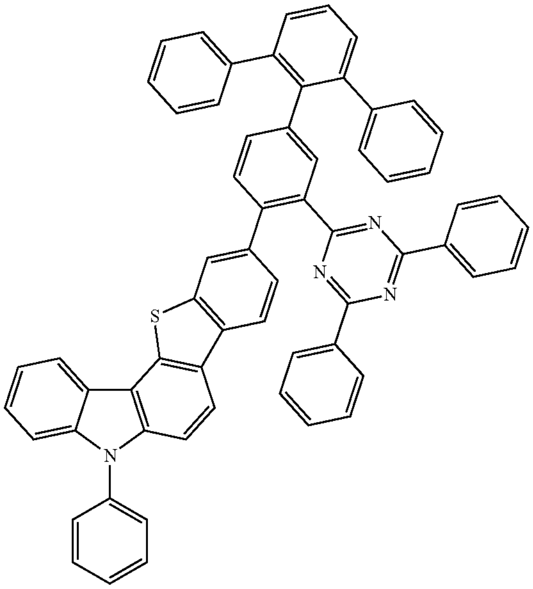
271
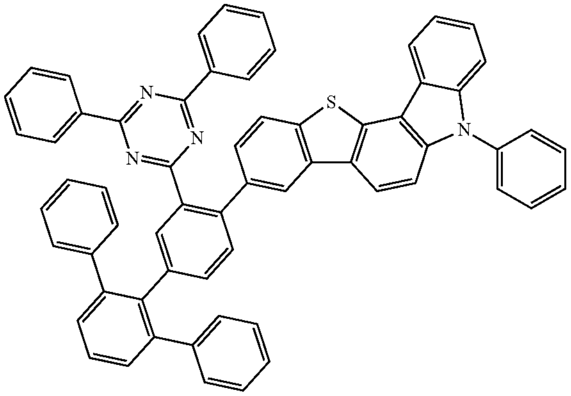
-continued
272
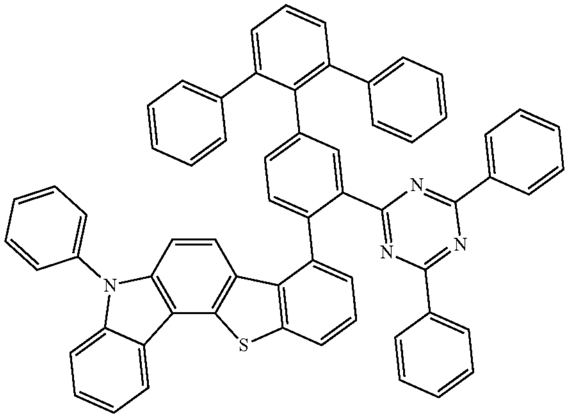
273
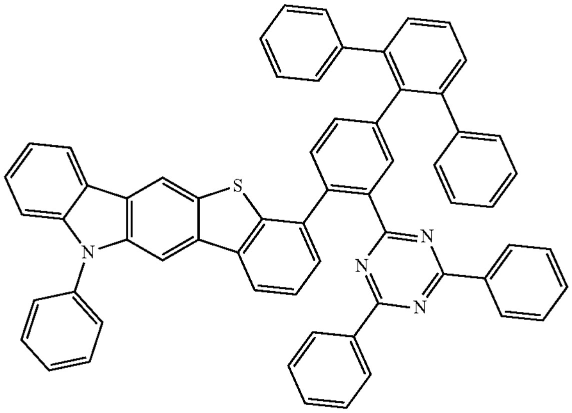
274
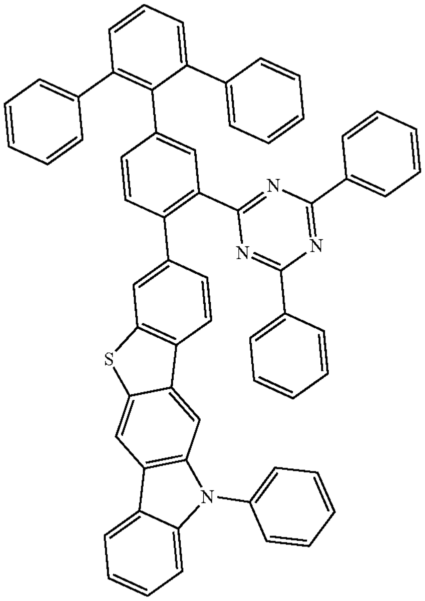

-continued
275
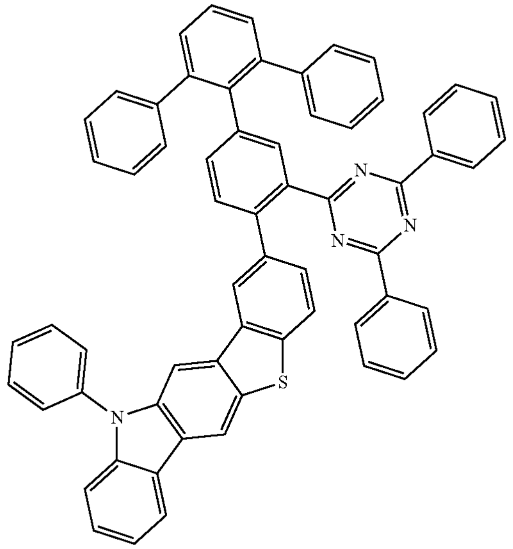
276
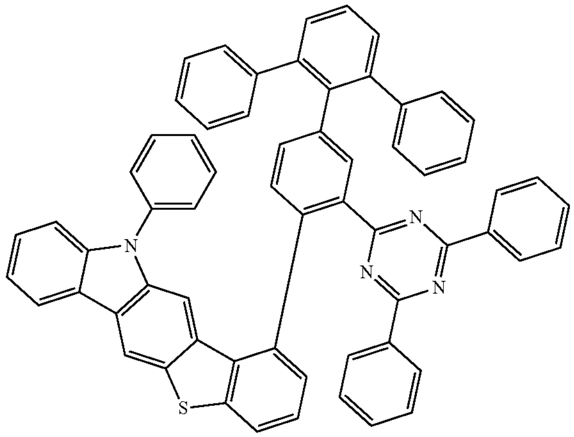
277
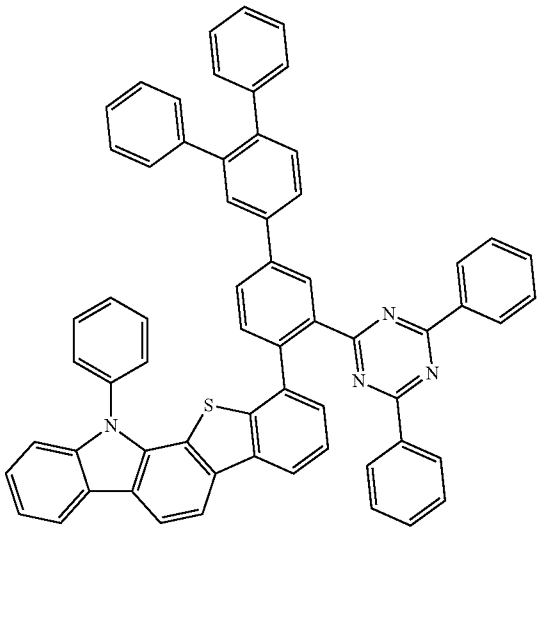
-continued
278
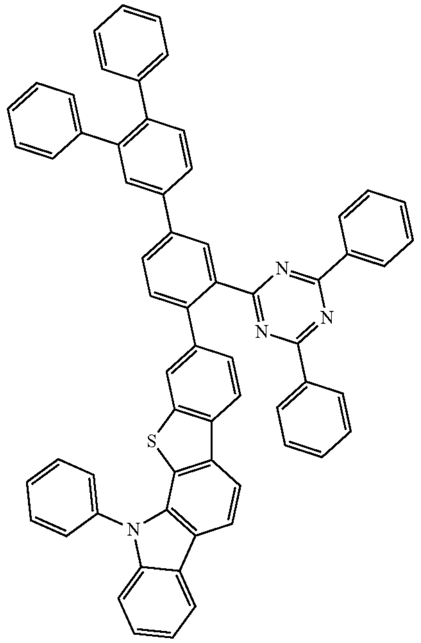
279
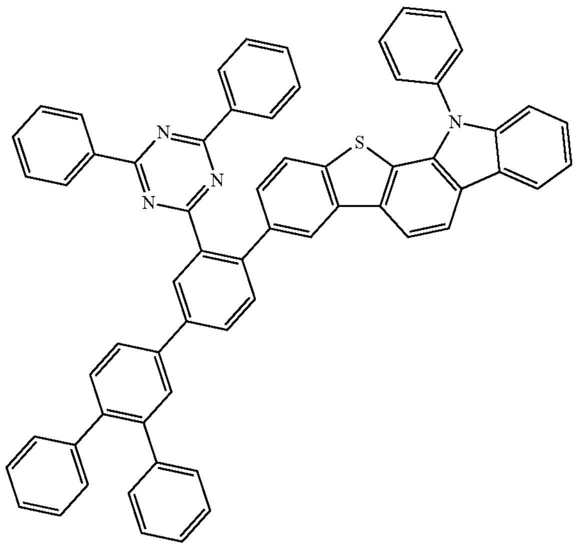

-continued
280
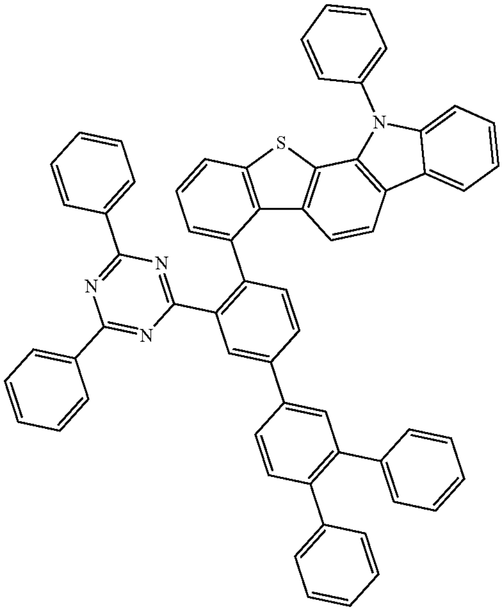
281
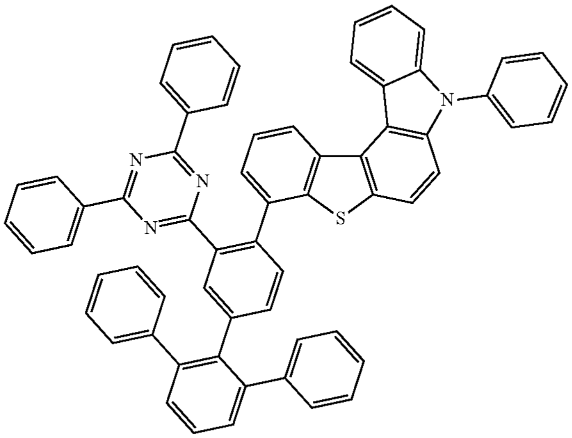
-continued
282
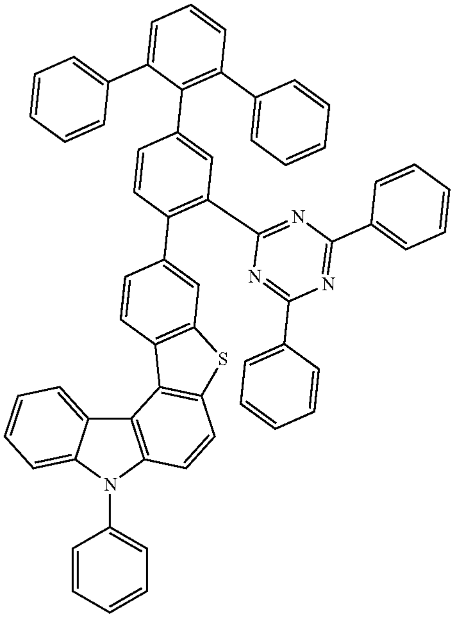
283
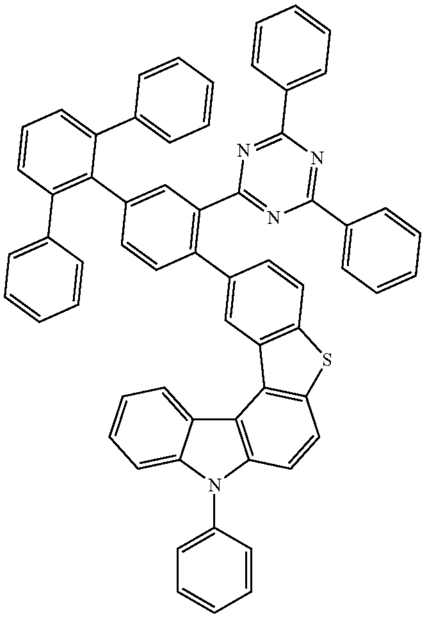

-continued
284
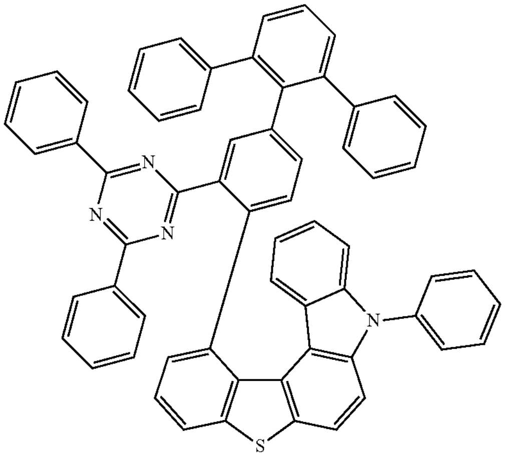
285
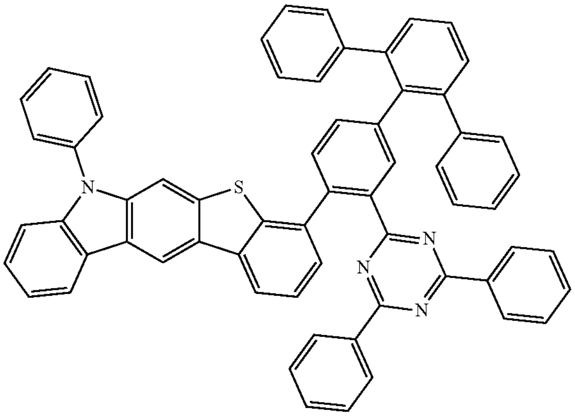
286
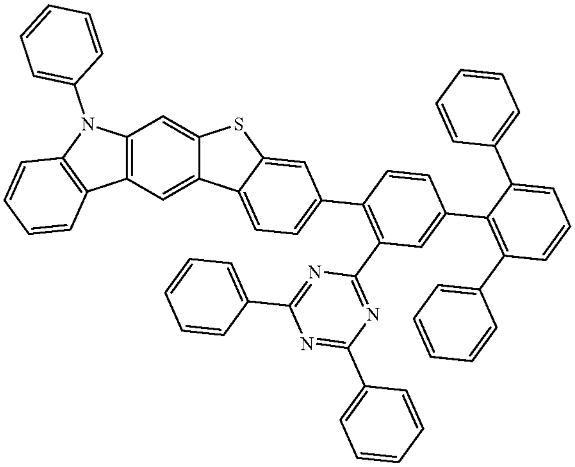
-continued
287
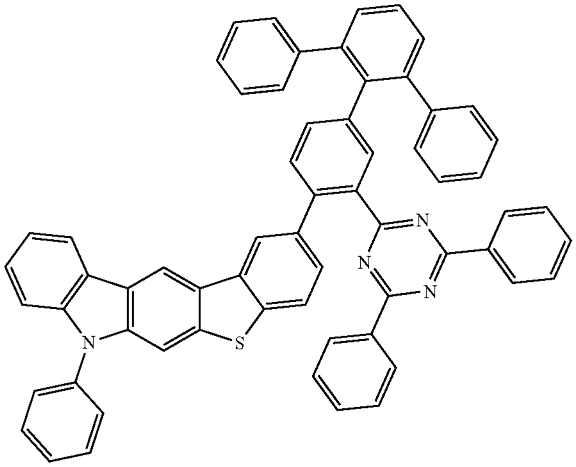
288
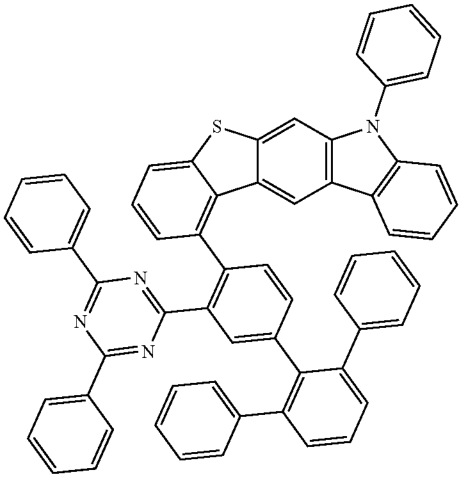
289
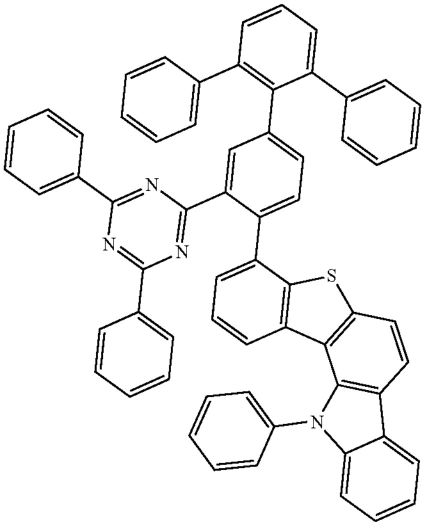

-continued
290
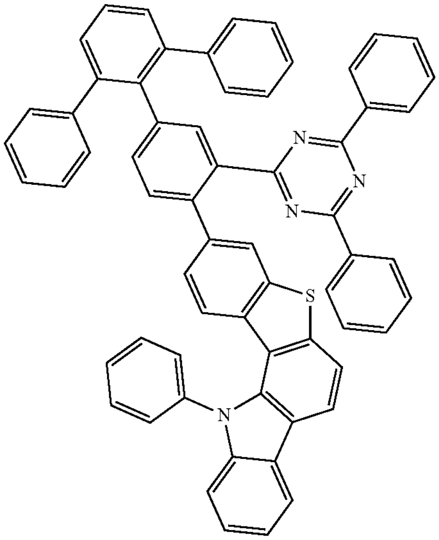
291
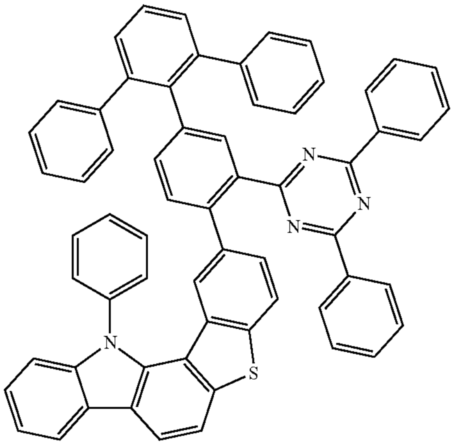
292
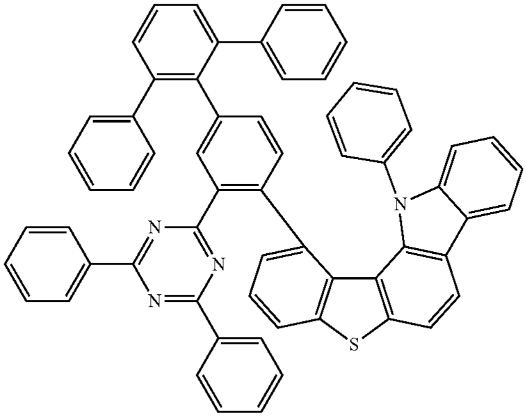
-continued
293
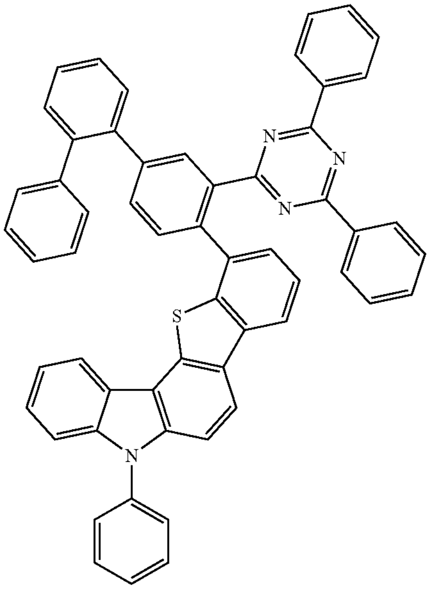
294
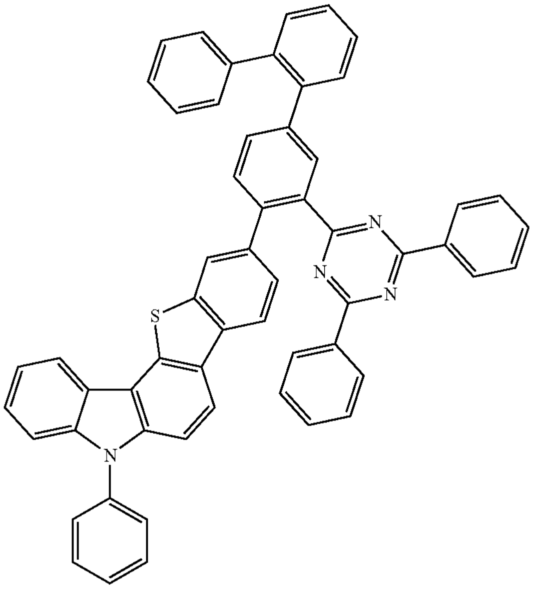
295
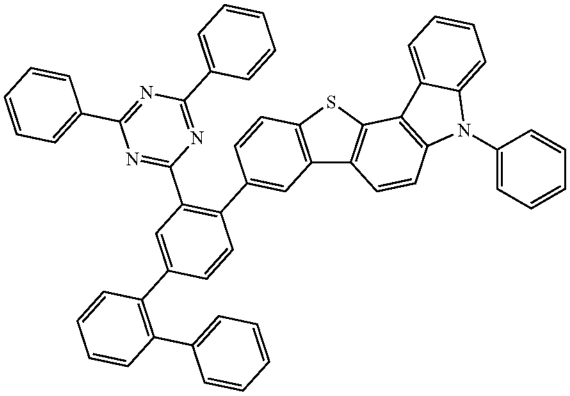

-continued
296
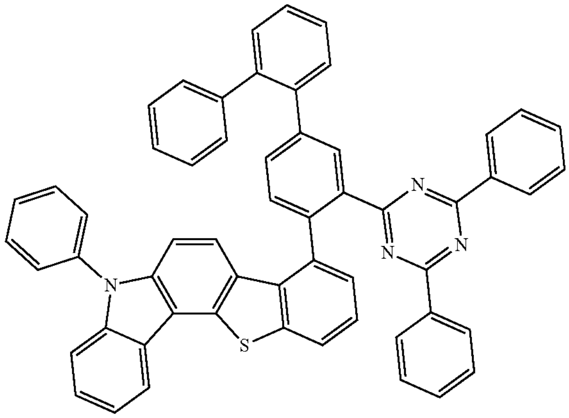
297
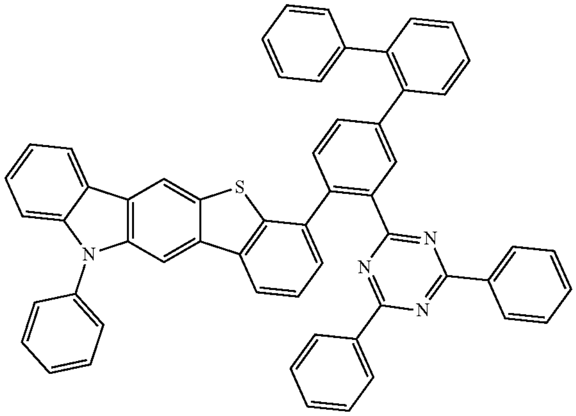
298
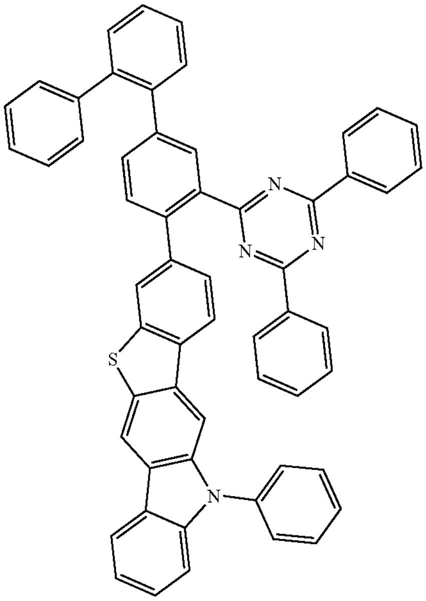
-continued
299
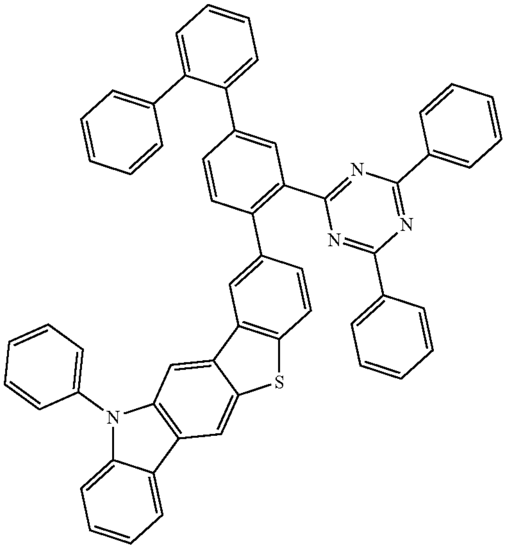
300
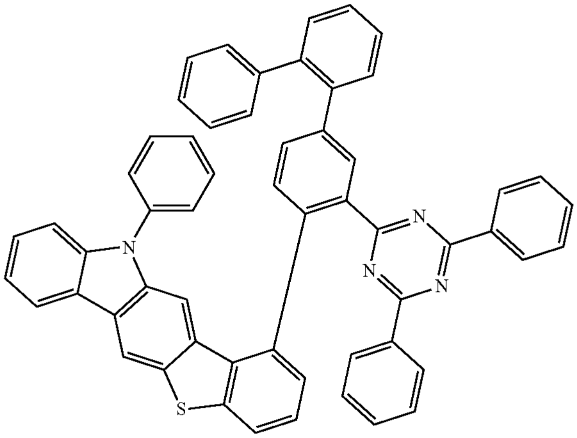
301
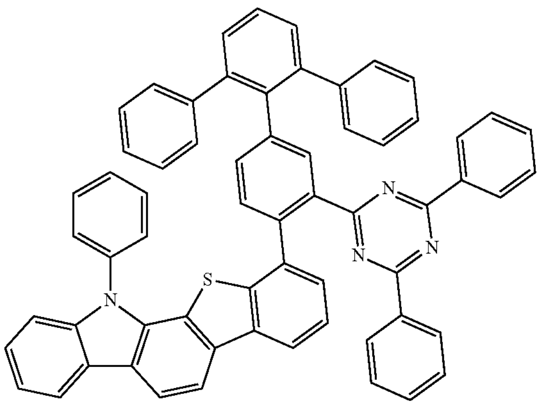

-continued
302
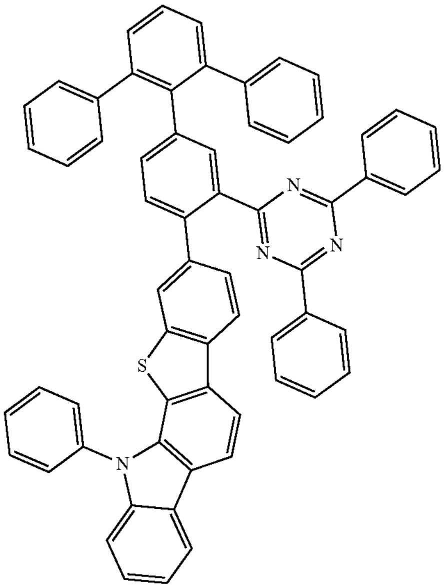
303
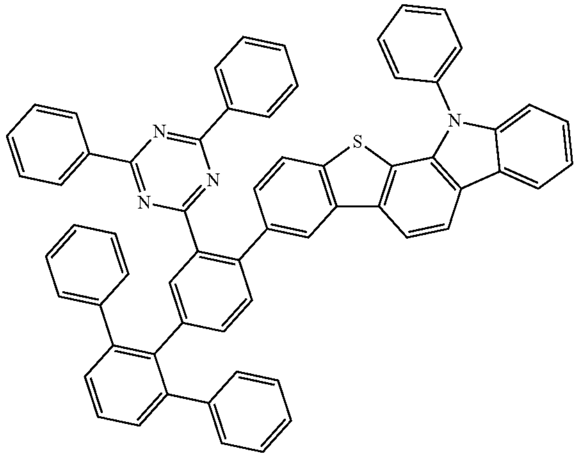
304
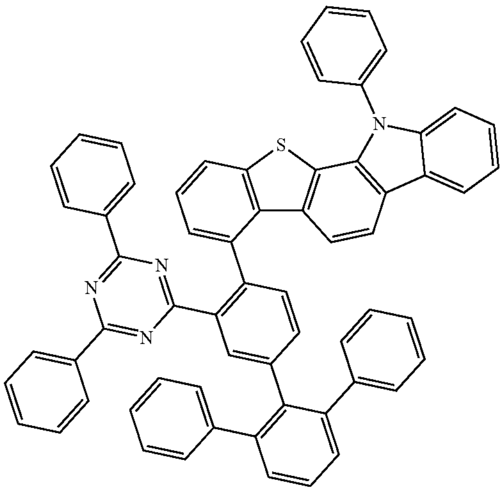
-continued
305
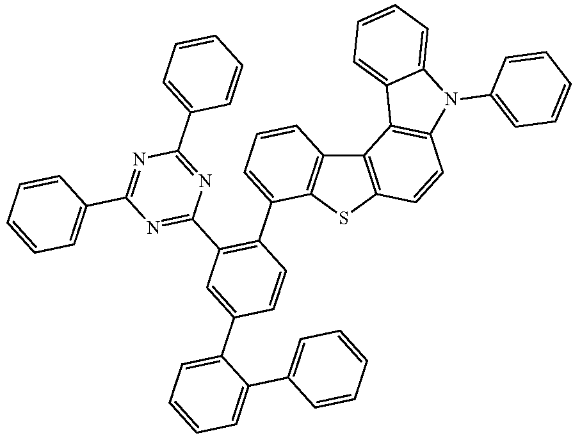
306
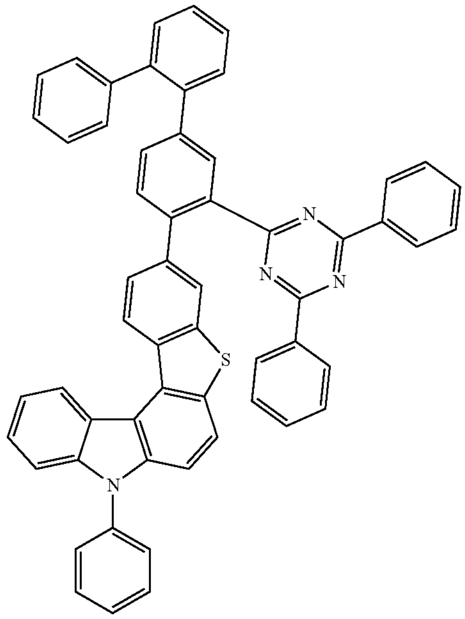

-continued
307
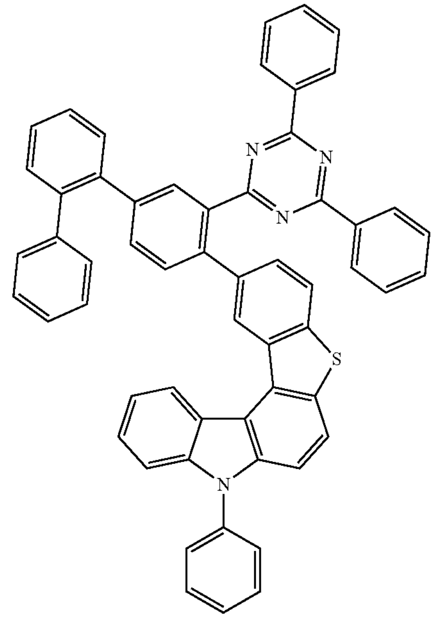
308
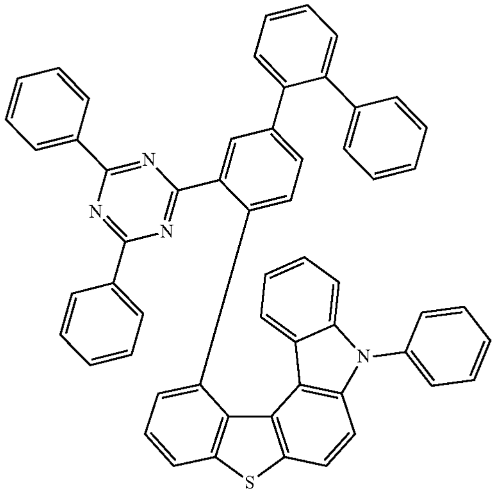
309
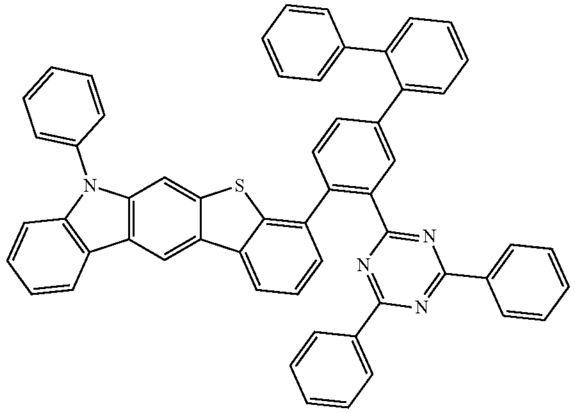
-continued
310
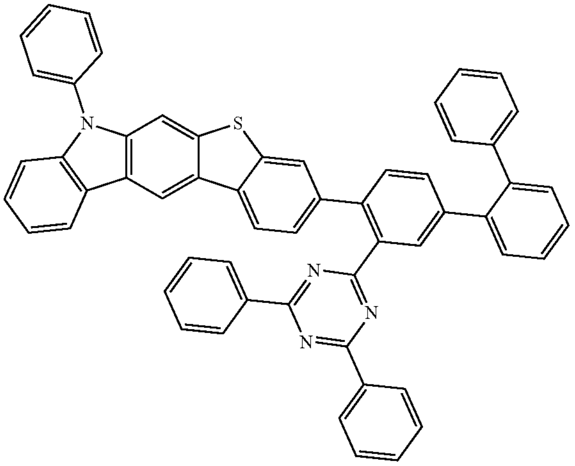
311
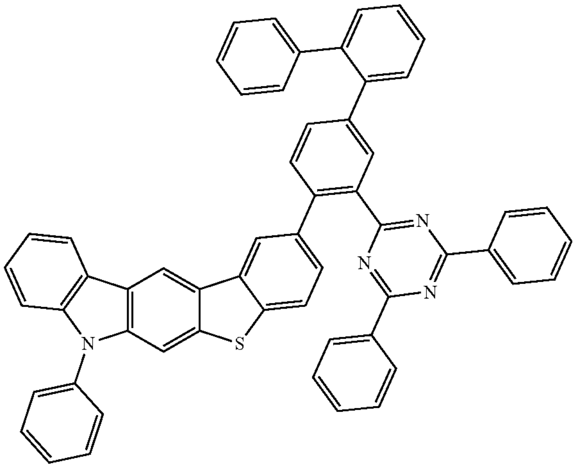
312
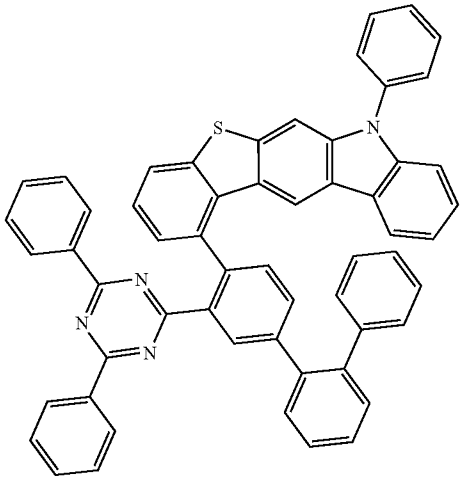

-continued
313
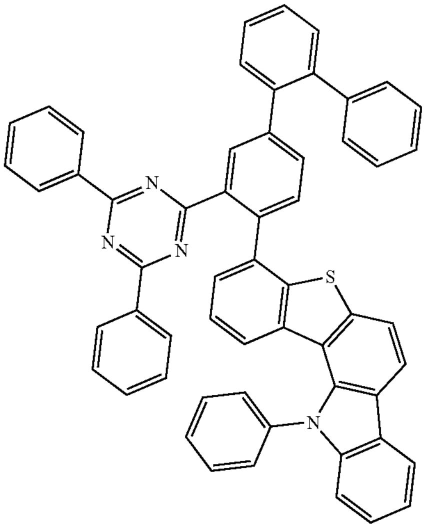
314
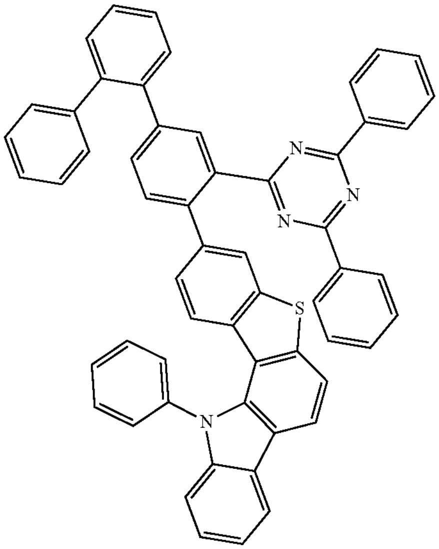
315
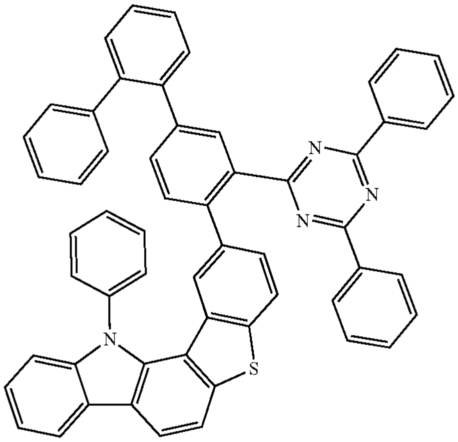
-continued
316
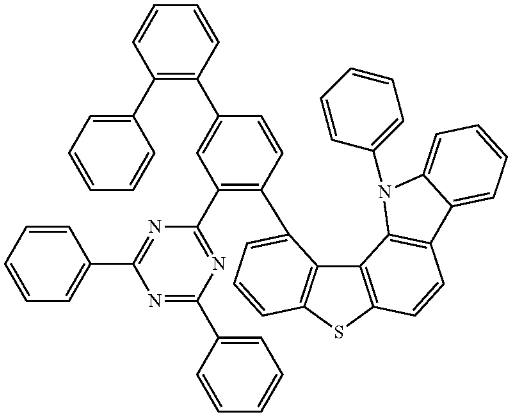
317
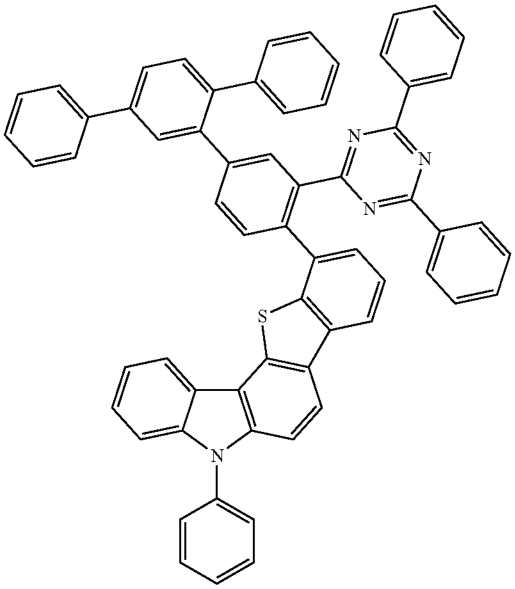

-continued
318
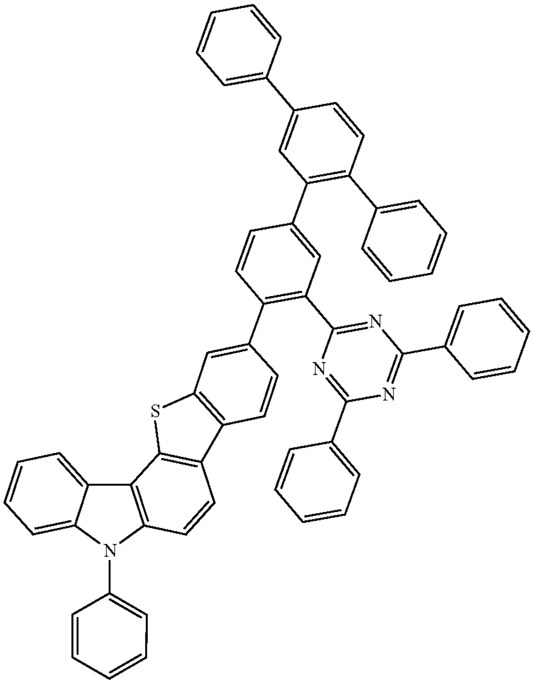
319
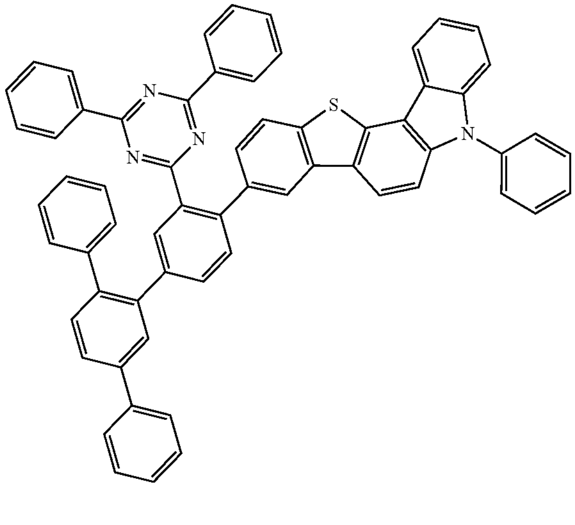
-continued
320
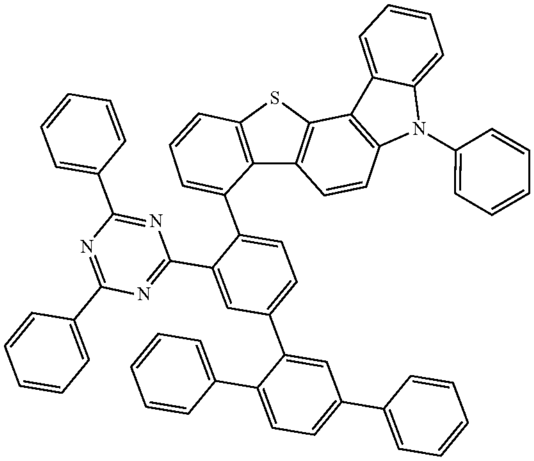
321
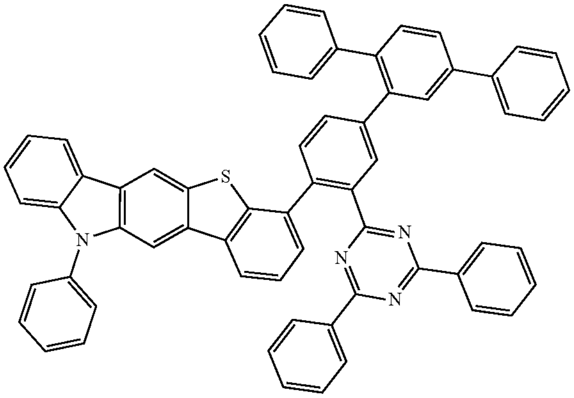
322
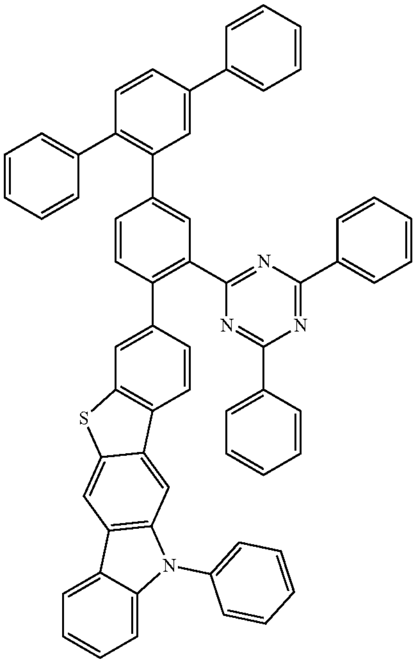

323
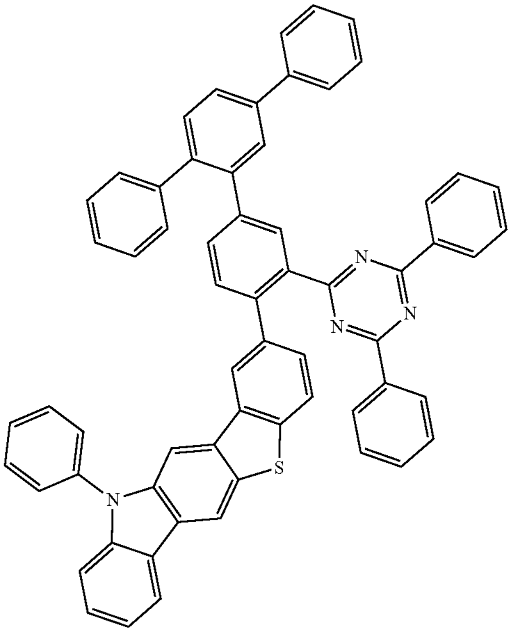
324
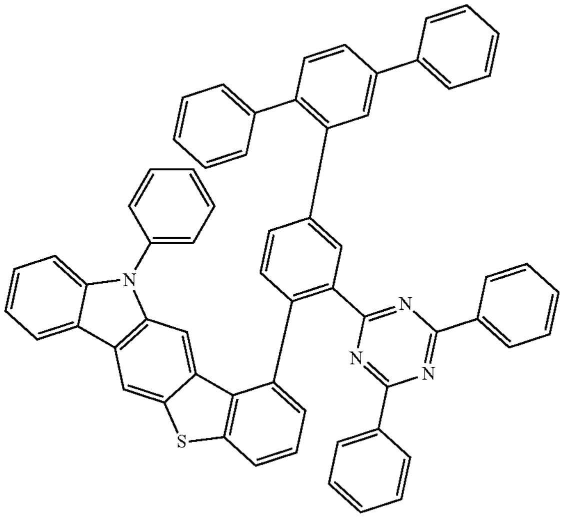
325
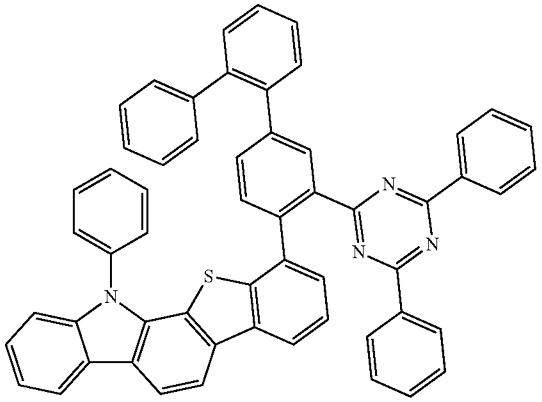
326
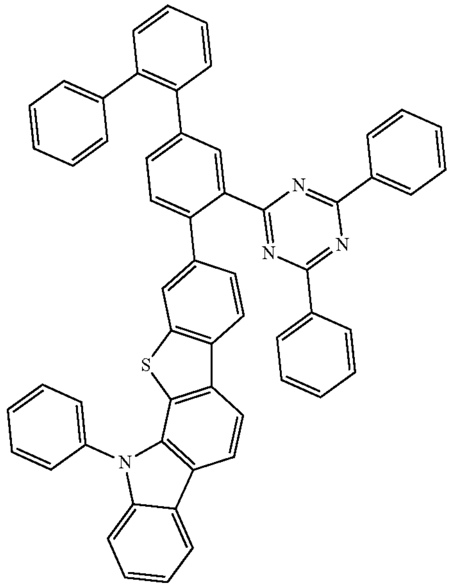
327
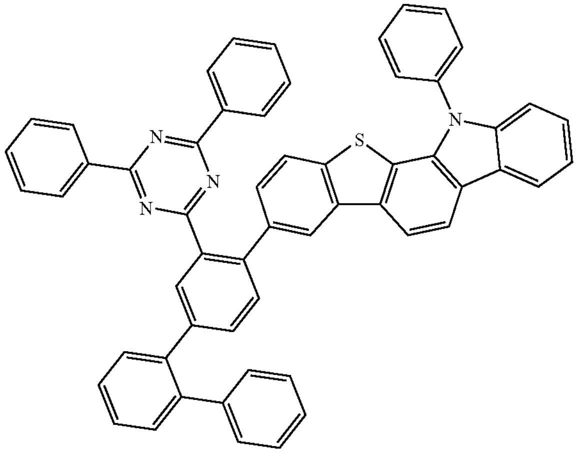
328
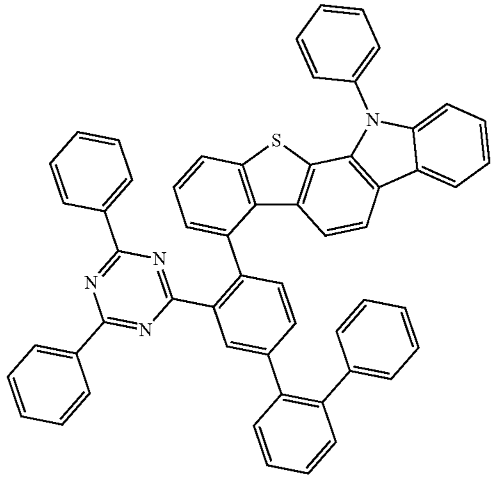

-continued
329
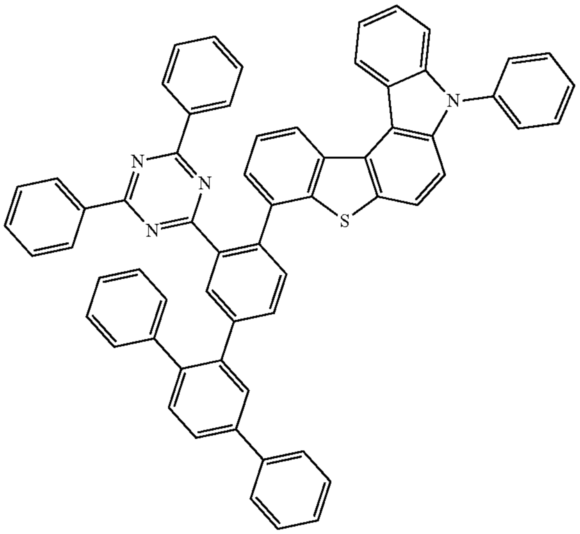
330
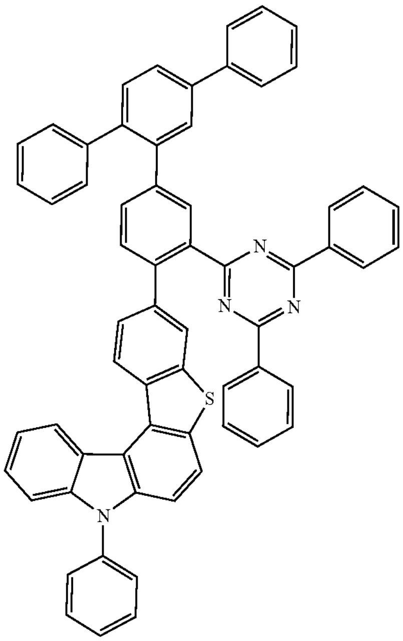
-continued
331
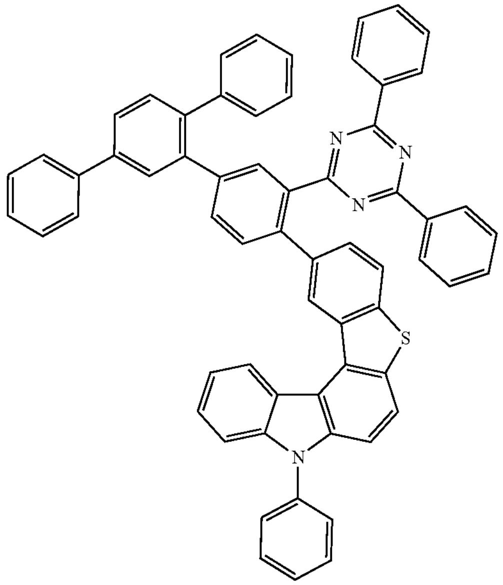
332
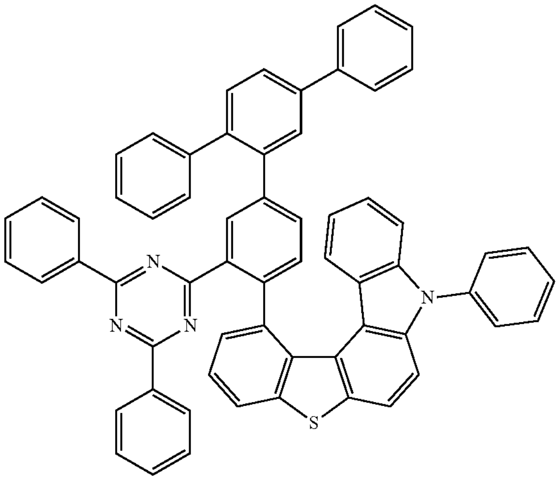
333
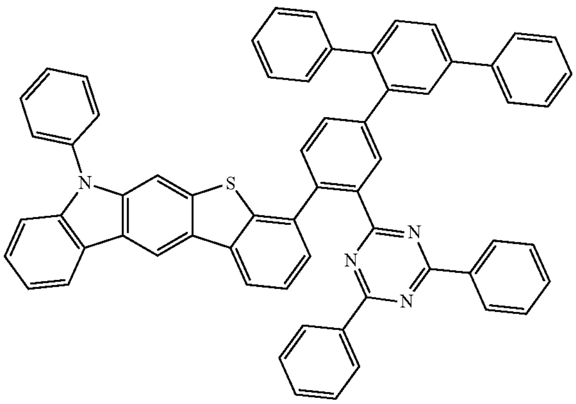

-continued
334
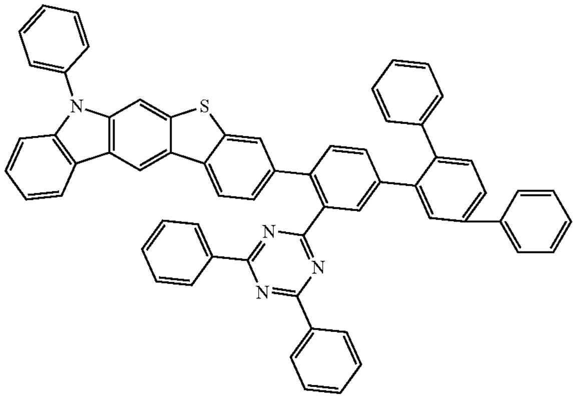
335
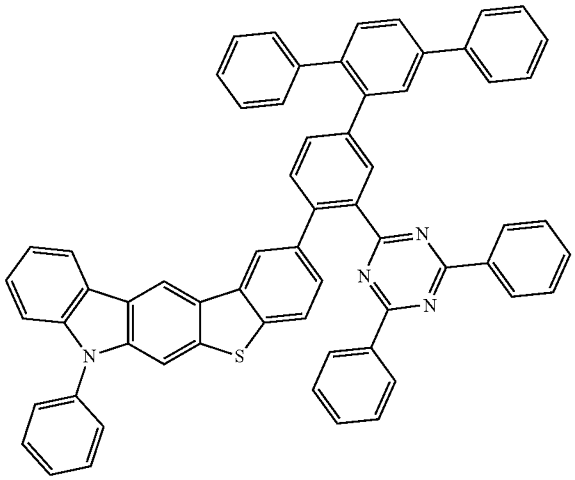
336
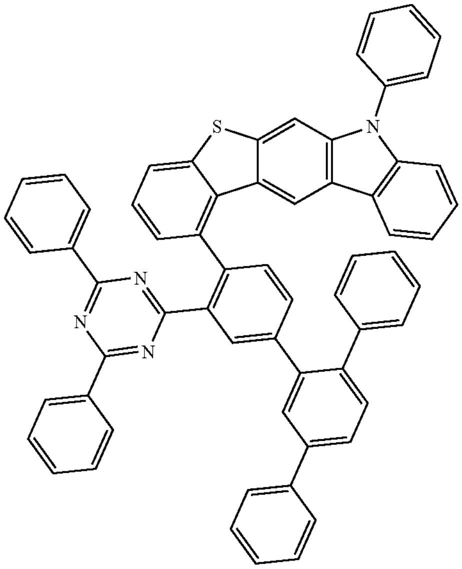
-continued
337
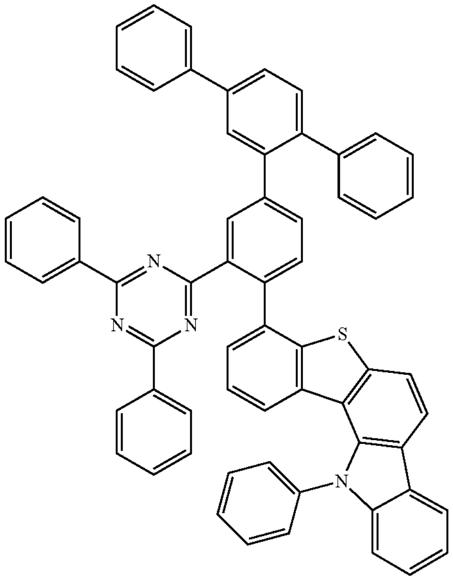
338
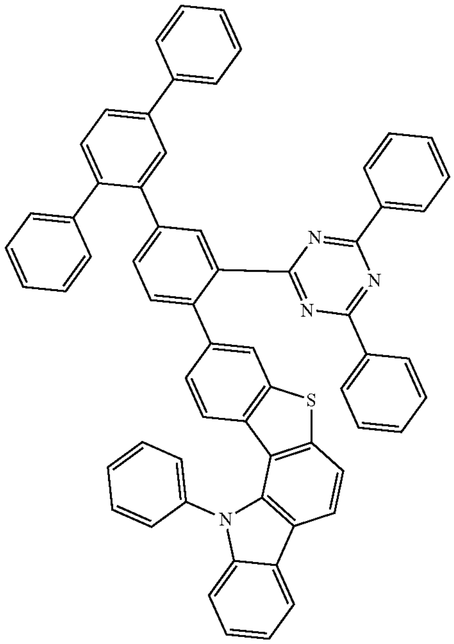

-continued
339
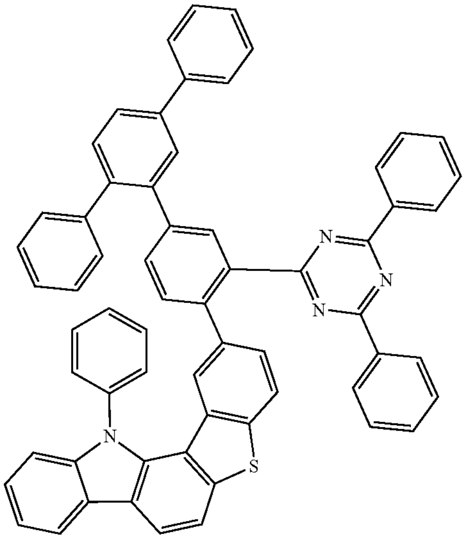
340
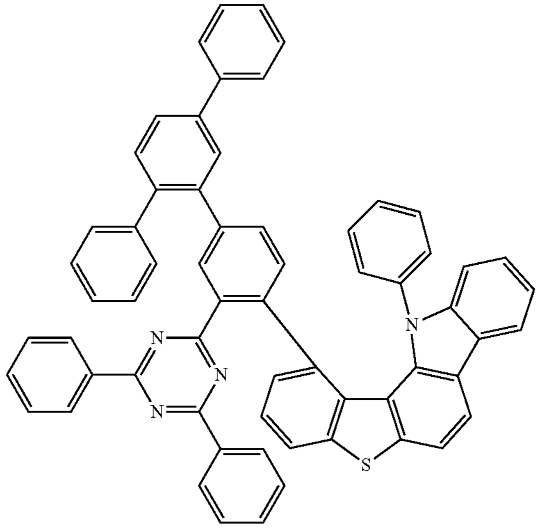
341
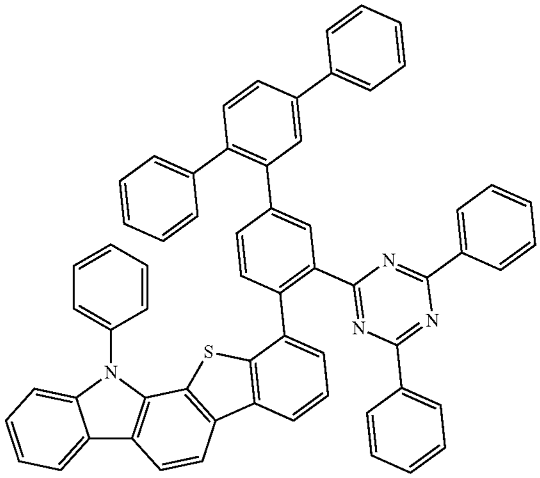
-continued
342
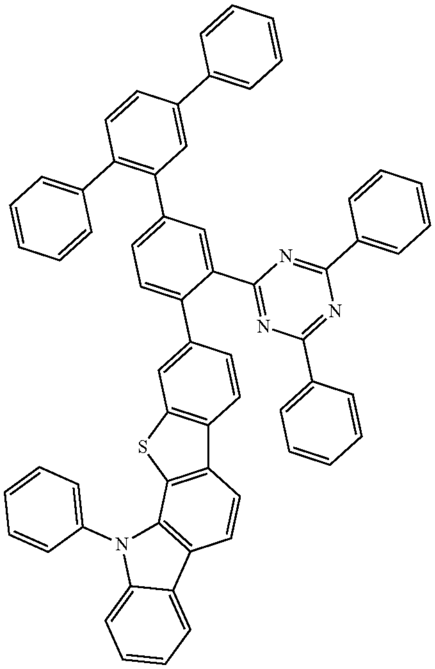
343
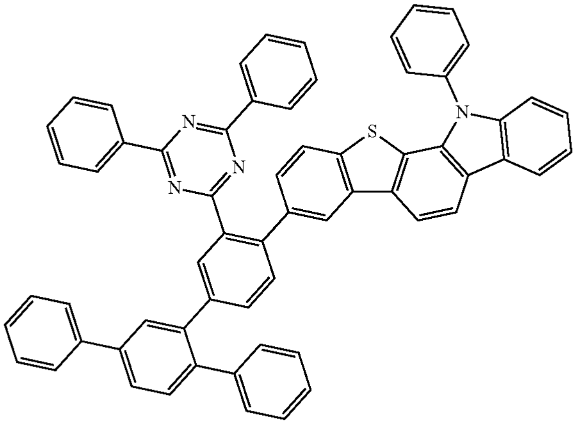

-continued
344
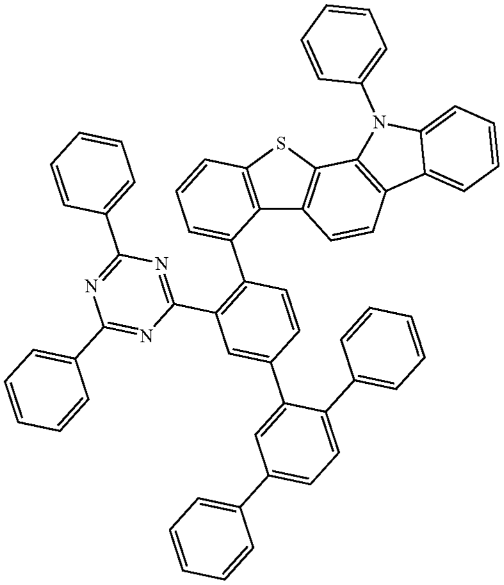
345
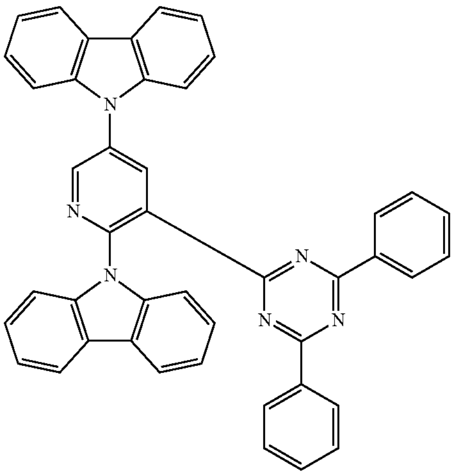
346
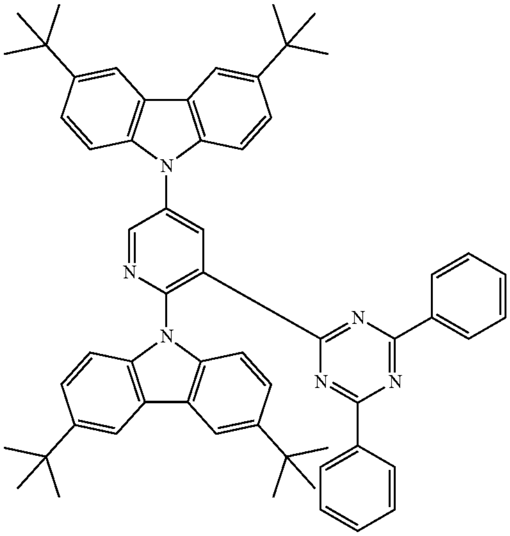
-continued
347
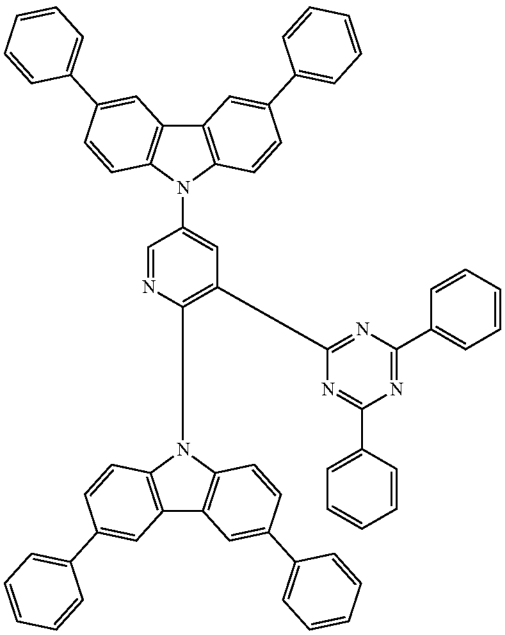
348
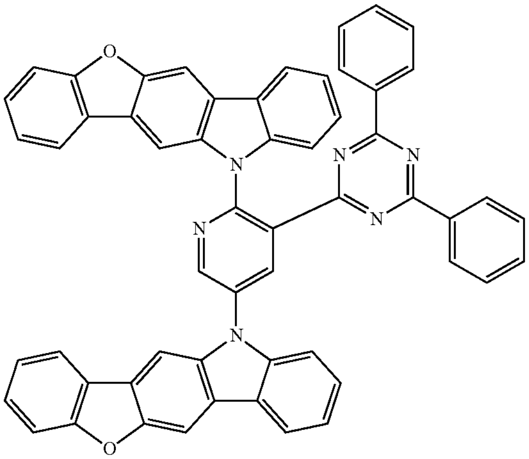
349
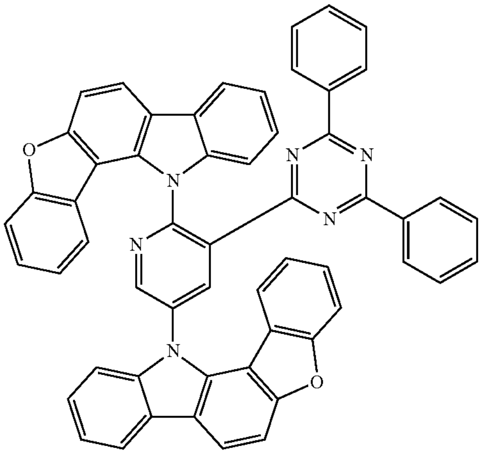

-continued
350
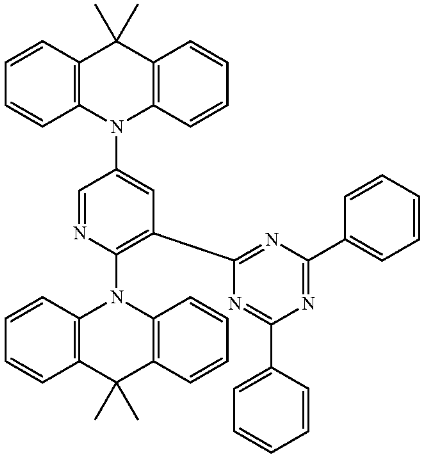
351
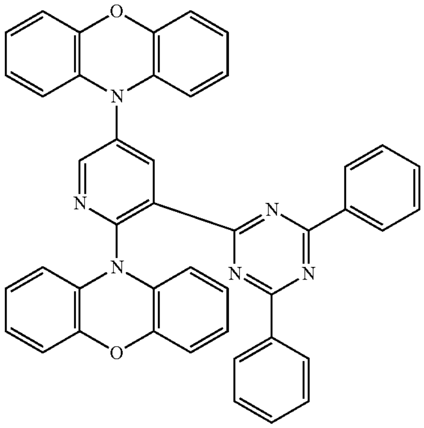
352
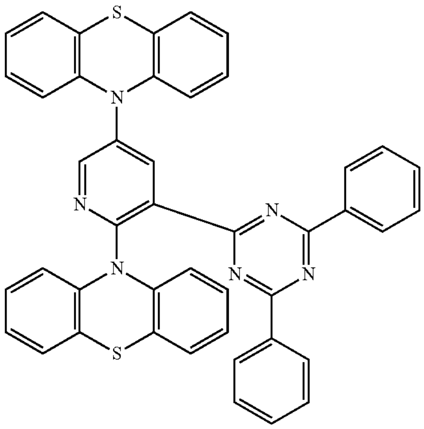
-continued
353
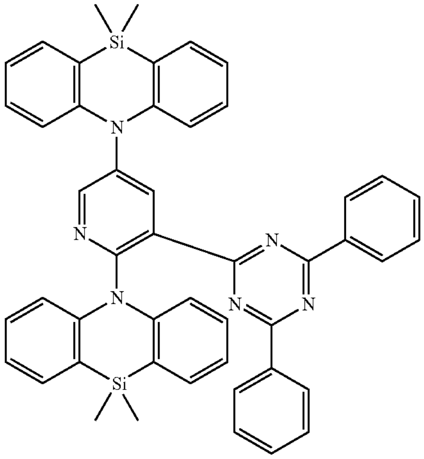
354
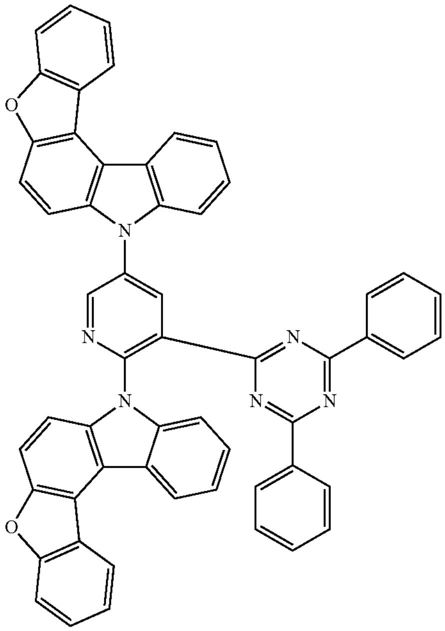
355
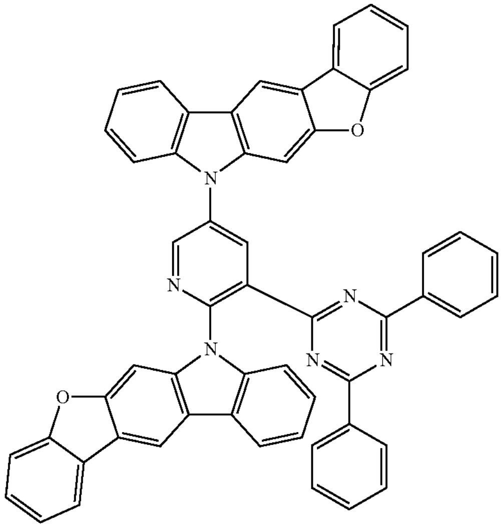

-continued
356
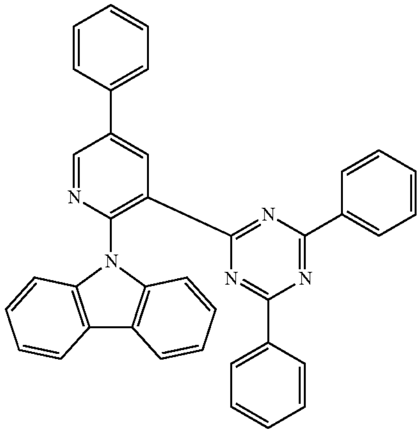
357
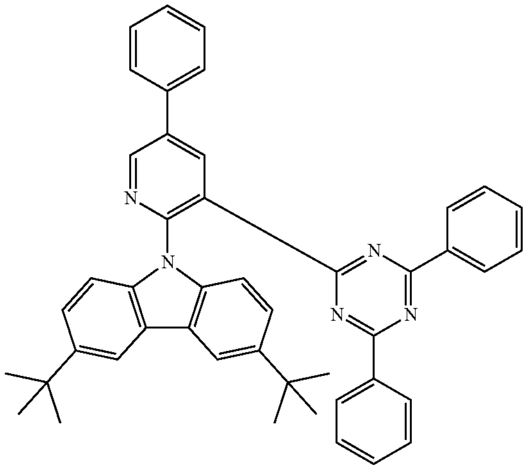
358
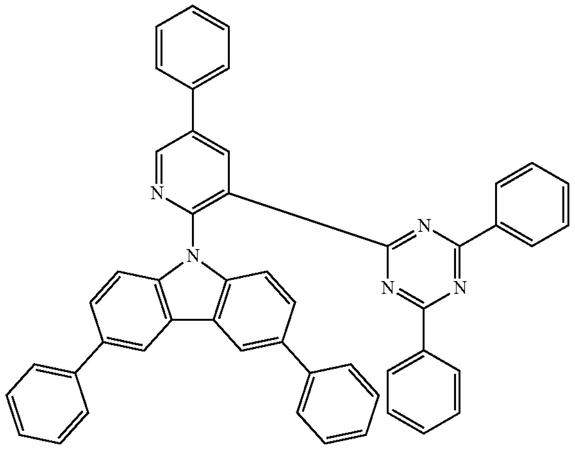
-continued
359
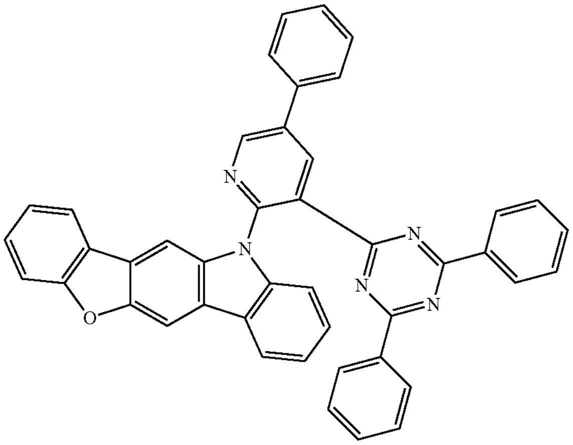
360
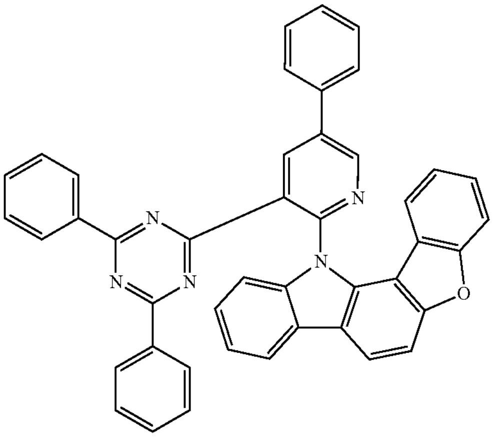
361
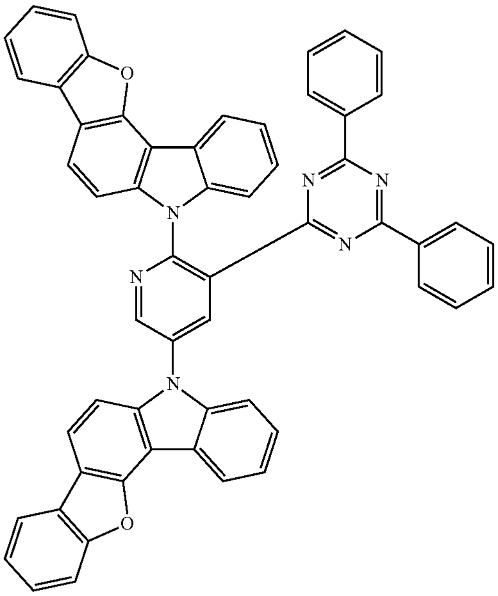

-continued
362
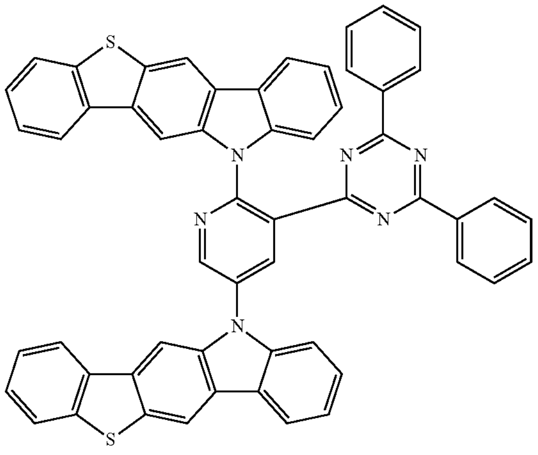
363
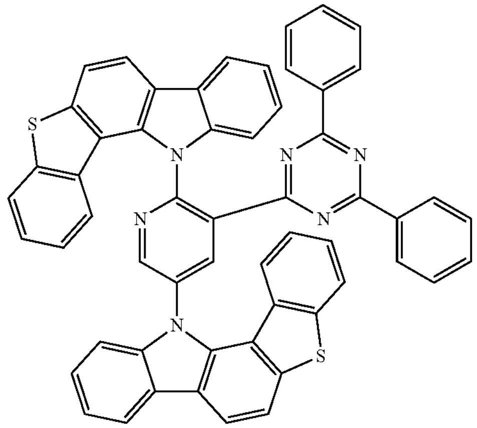
364
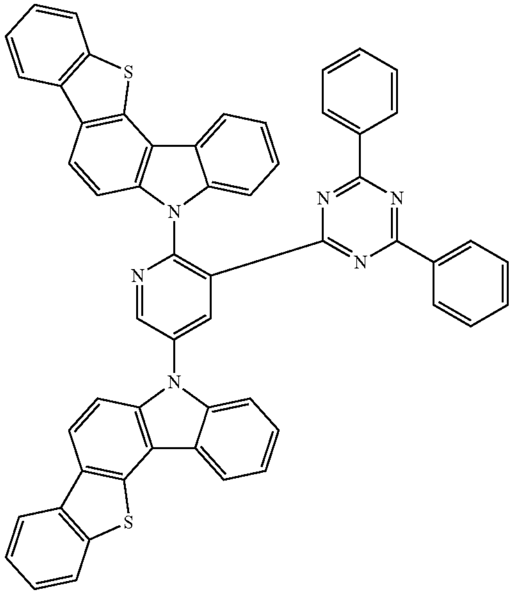
-continued
365
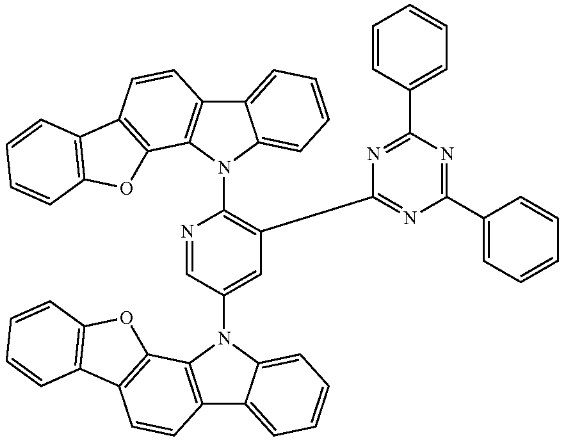
366
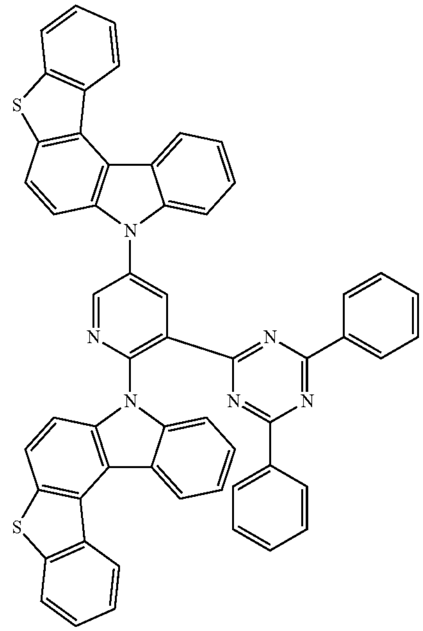
367
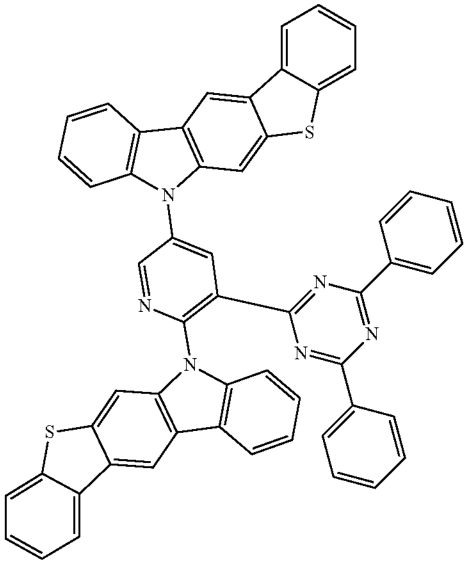

-continued
368
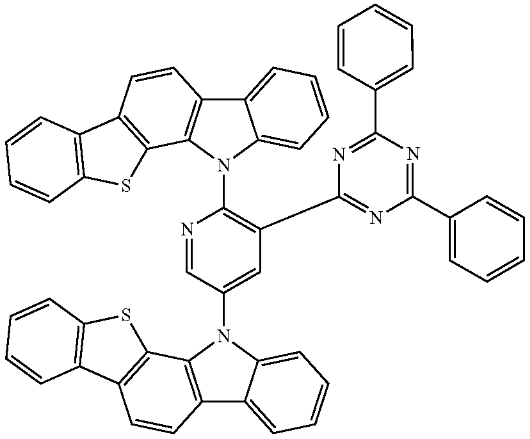
369
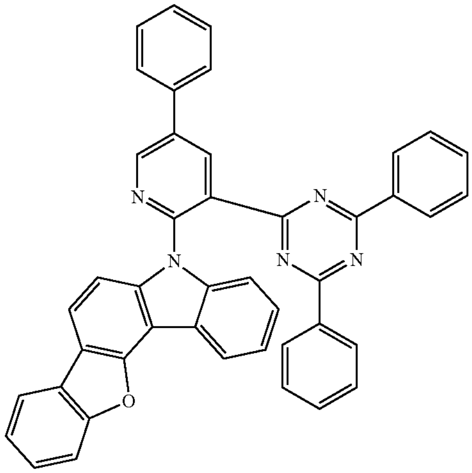
370
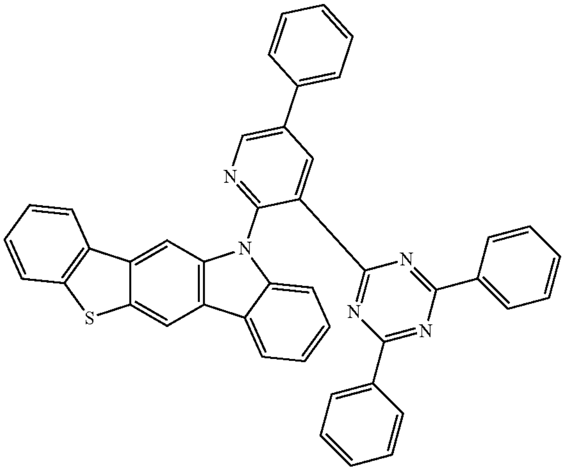
-continued
371
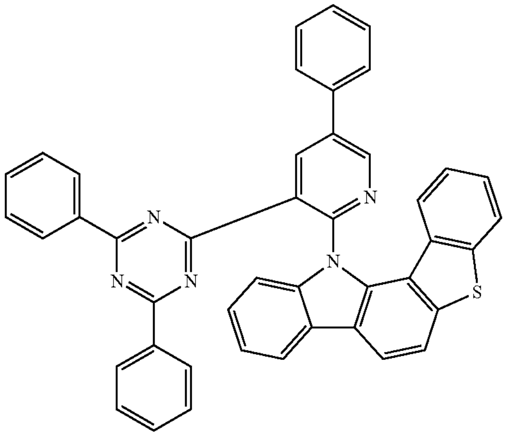
372
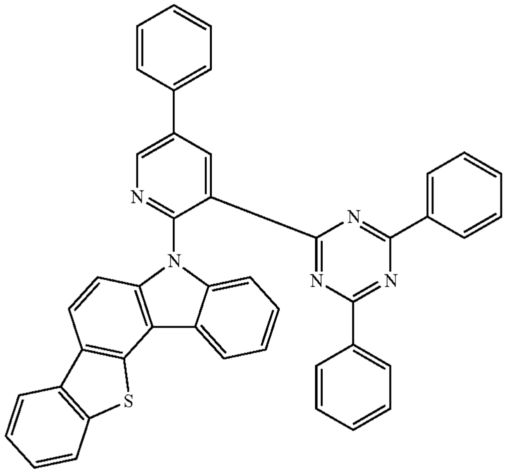
373
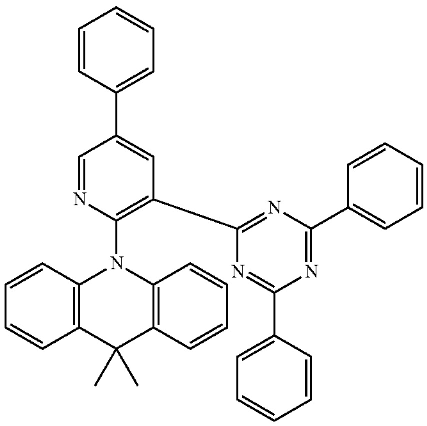

-continued
374
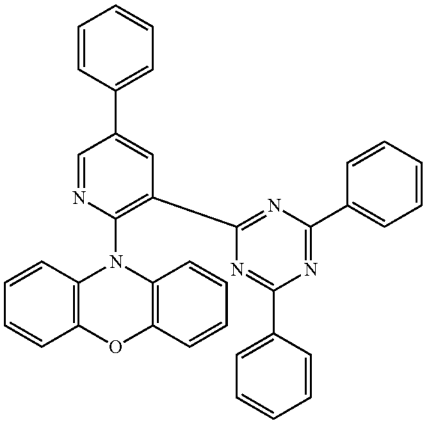
375
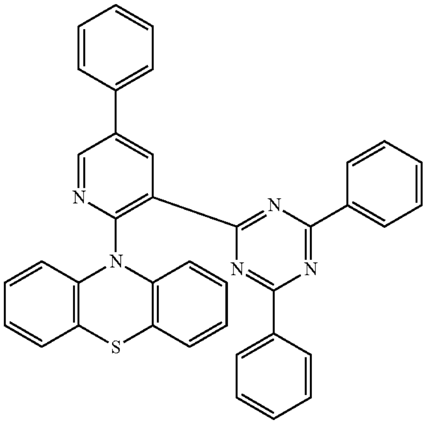
376
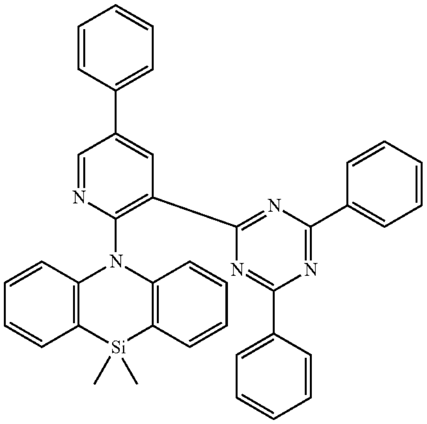
-continued
377
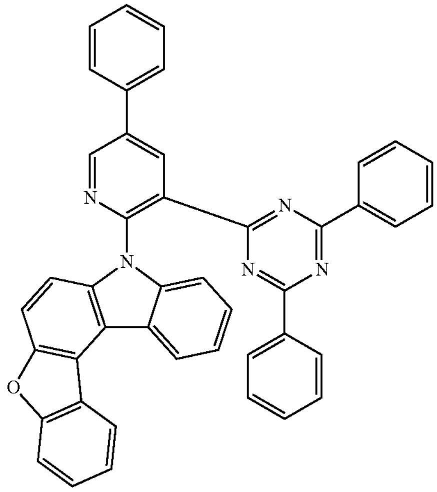
378
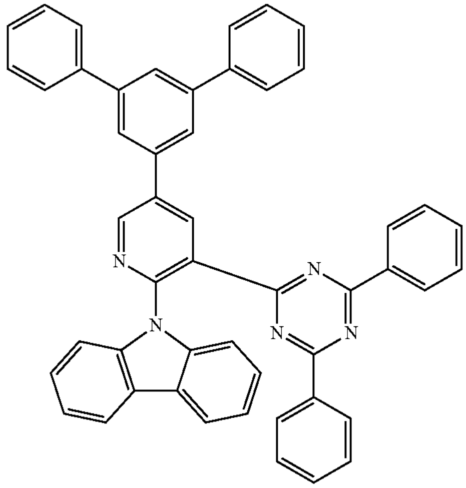
379
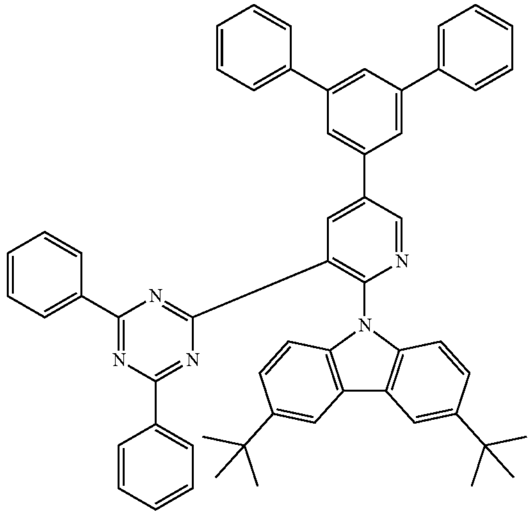

-continued
380
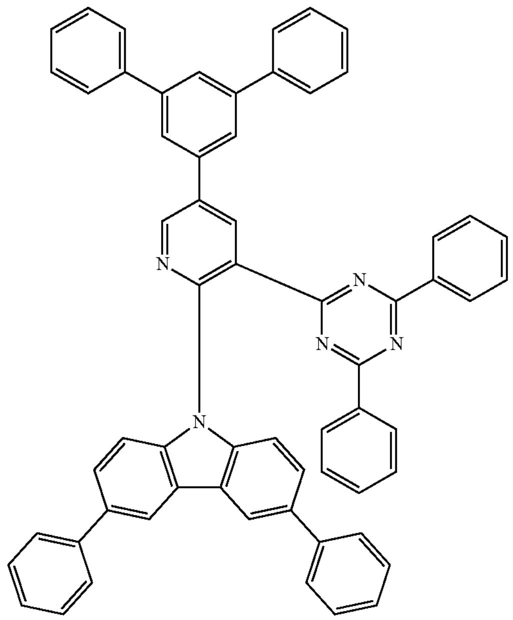
381
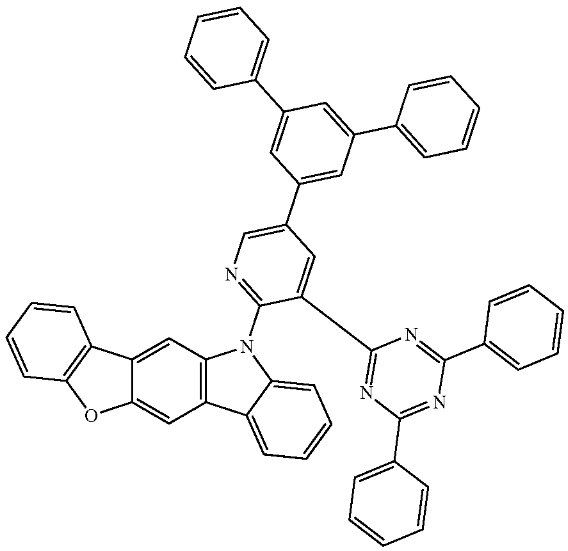
-continued
382
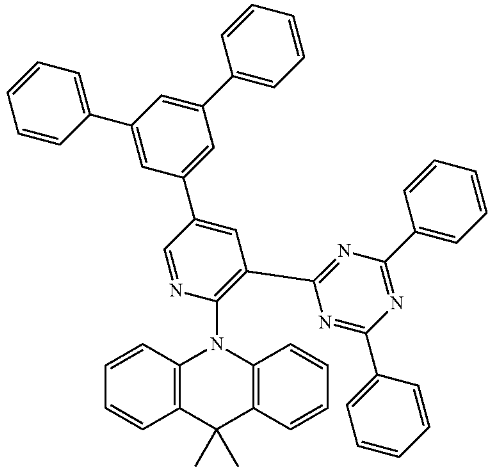
383
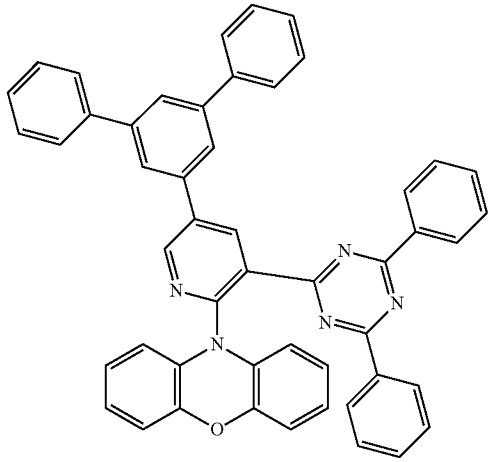
384
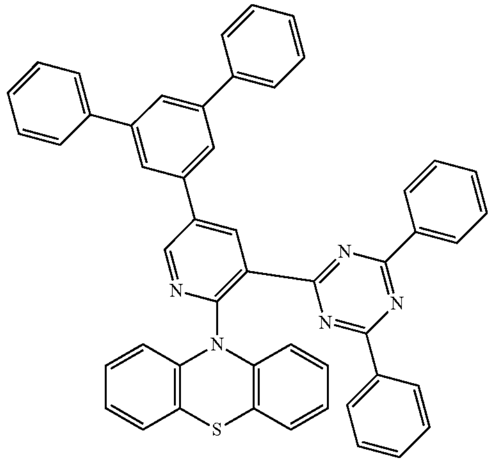

385
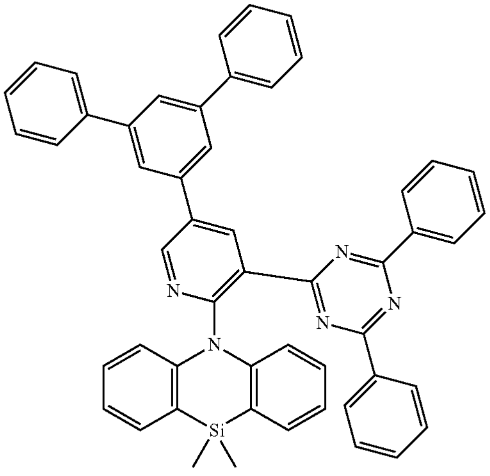
386
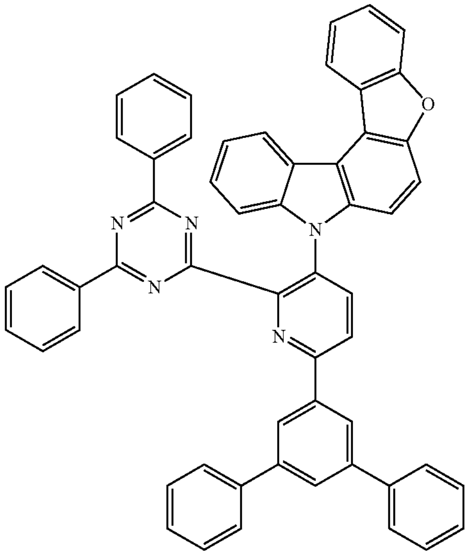
387
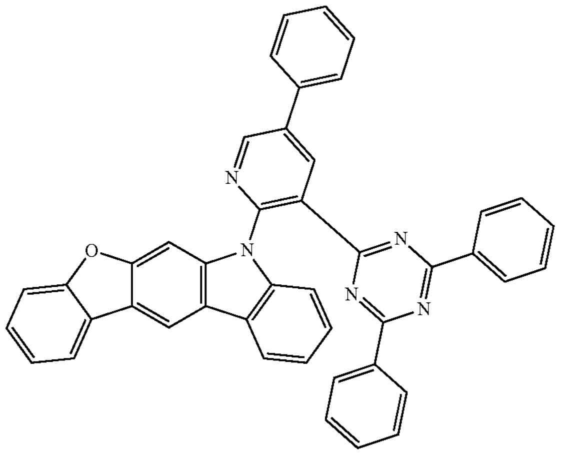
388
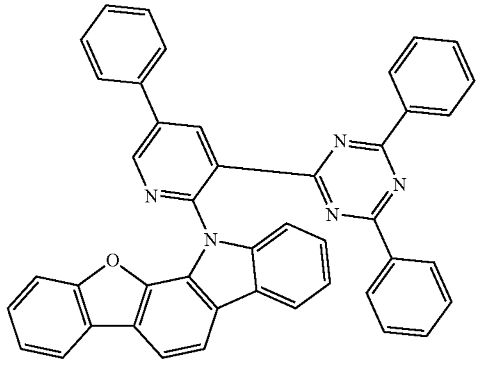
389
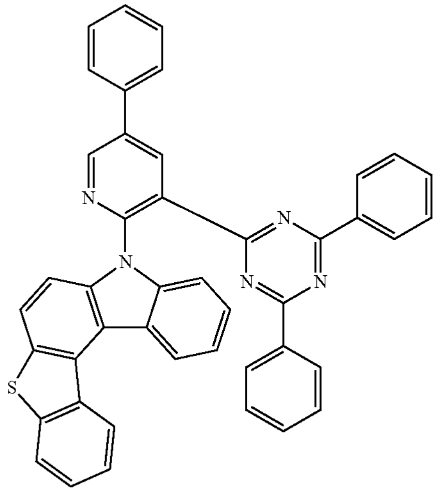
390
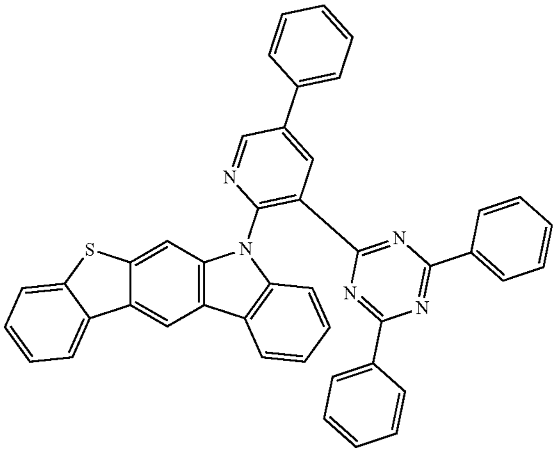

-continued
391
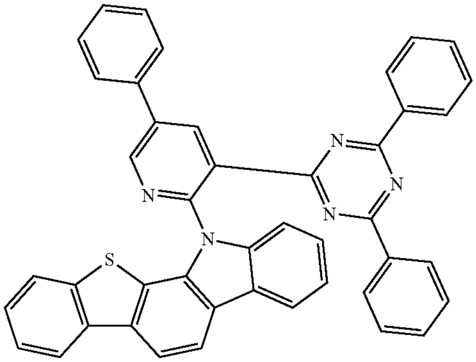
392
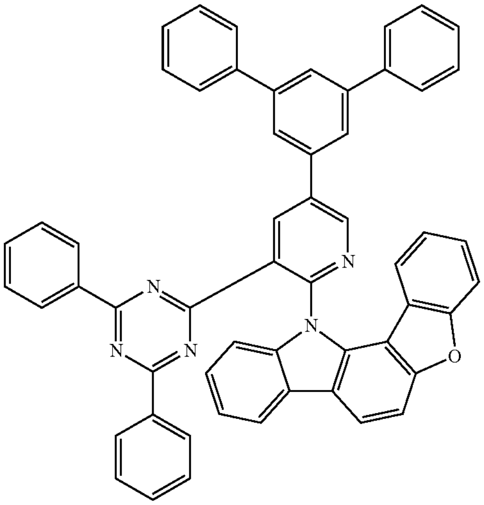
393
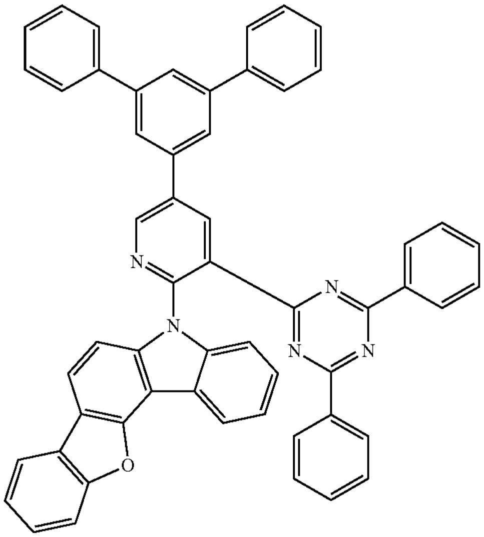
-continued
394
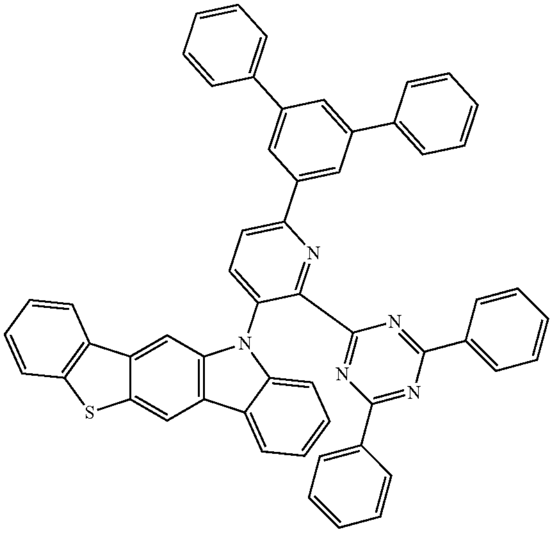
395
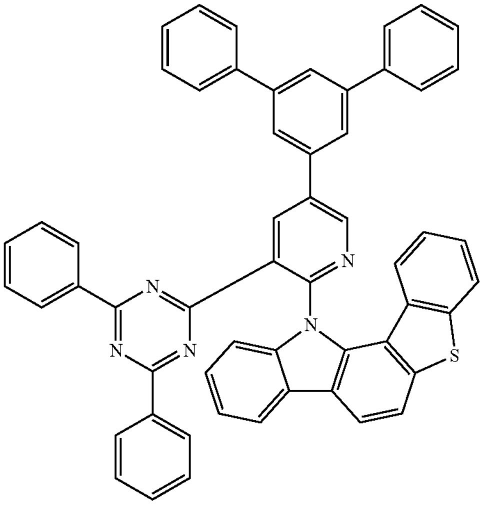
396
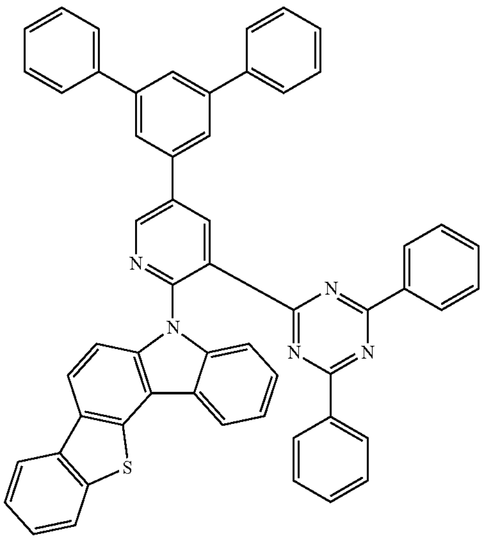

-continued
397
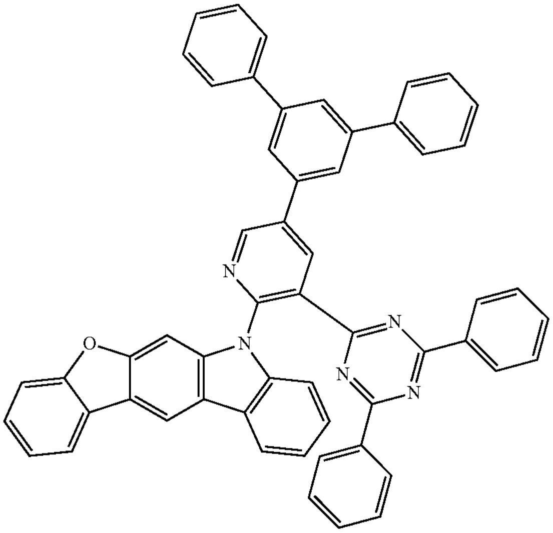
398
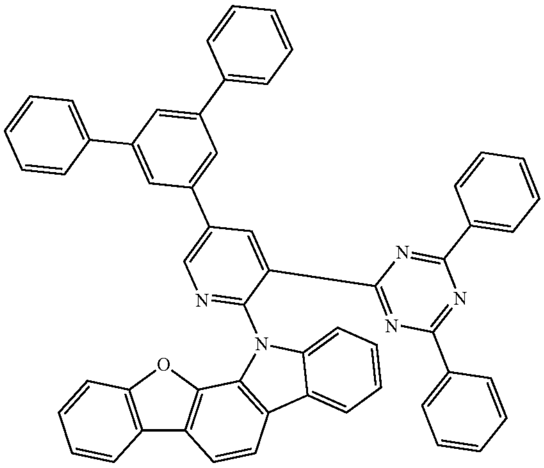
399
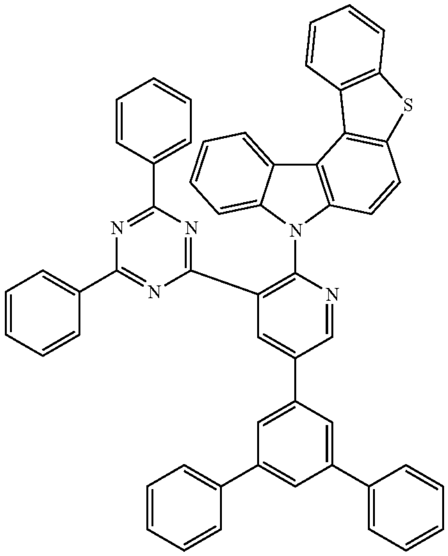
-continued
400
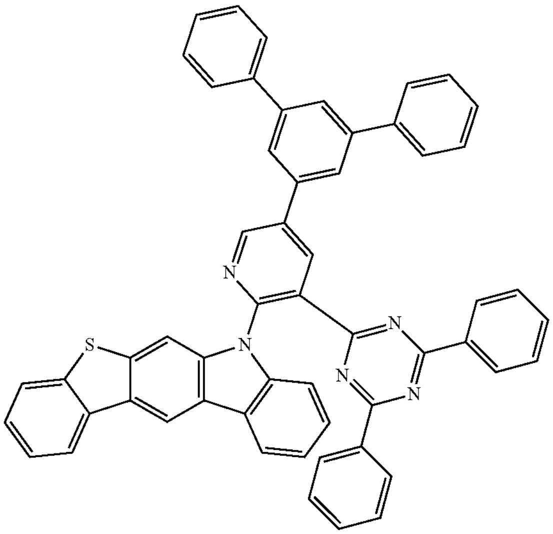
401
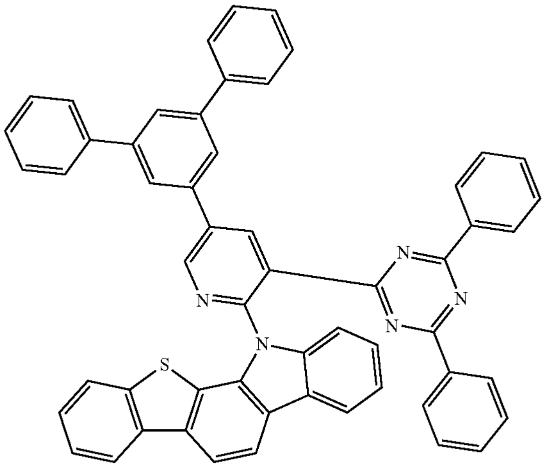
402
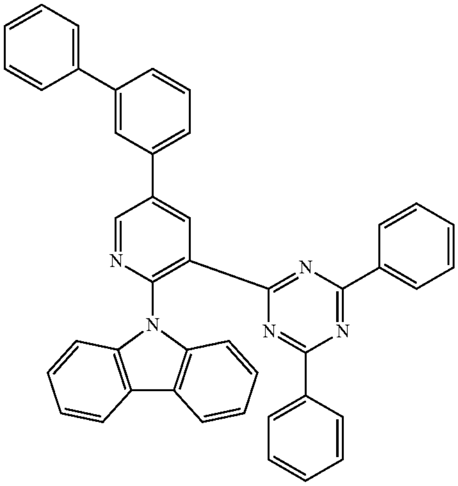

-continued
403
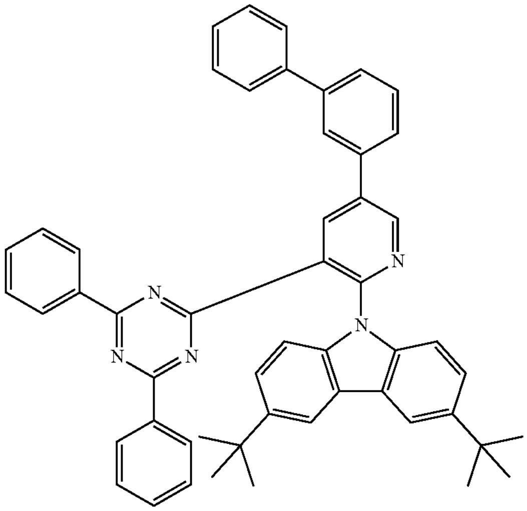
404
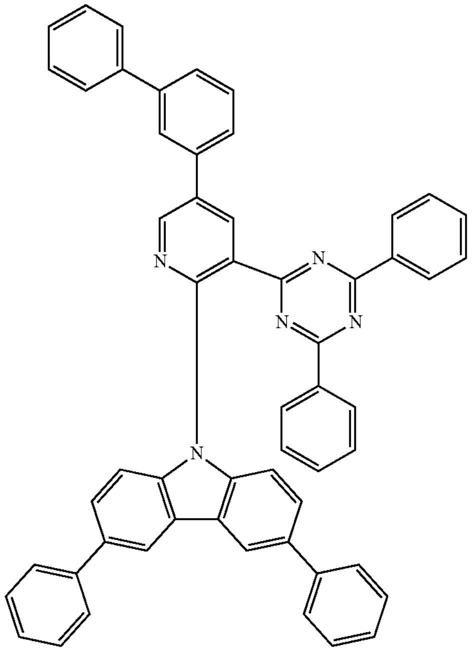
-continued
405
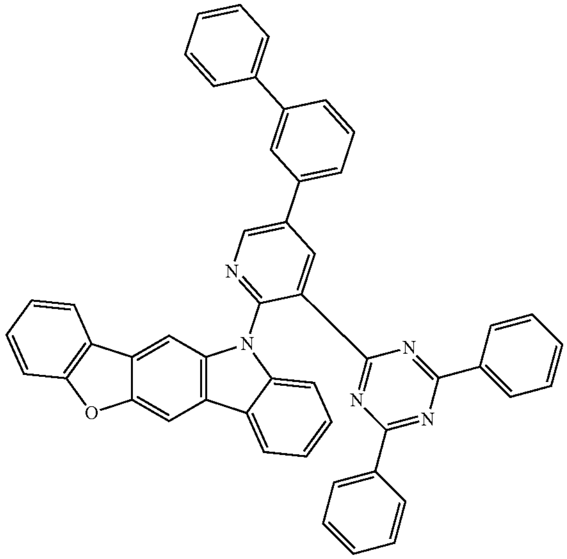
406
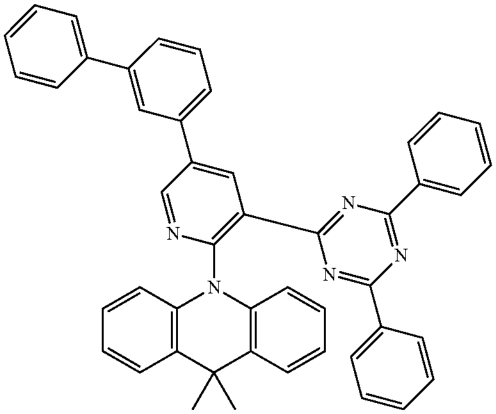
407
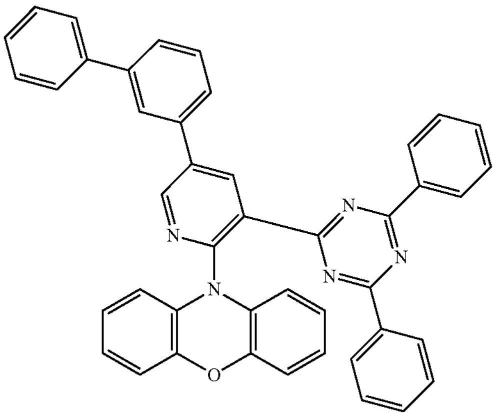

-continued
408
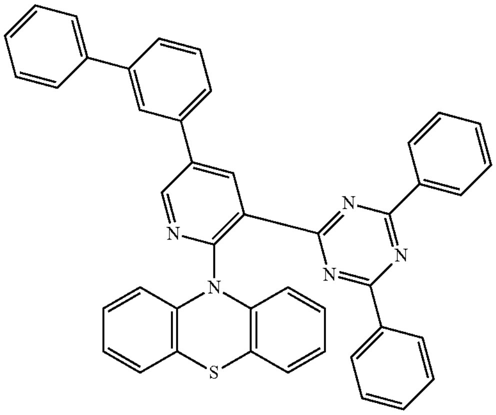
409
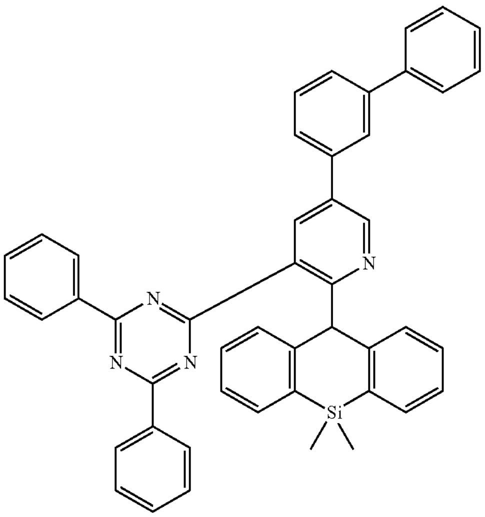
410
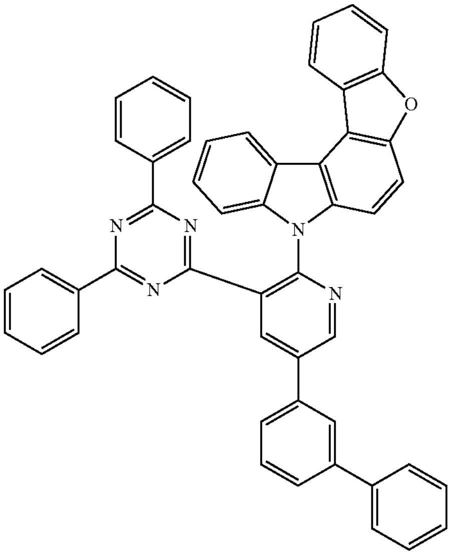
-continued
411
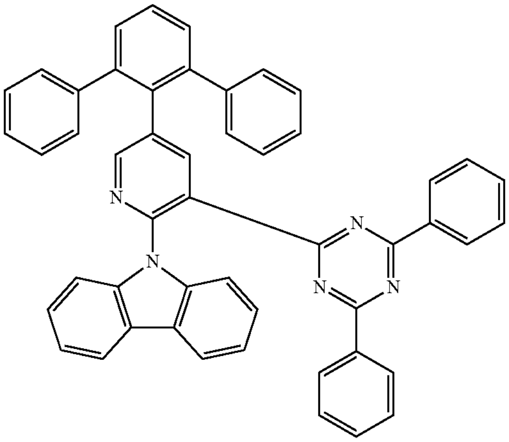
412
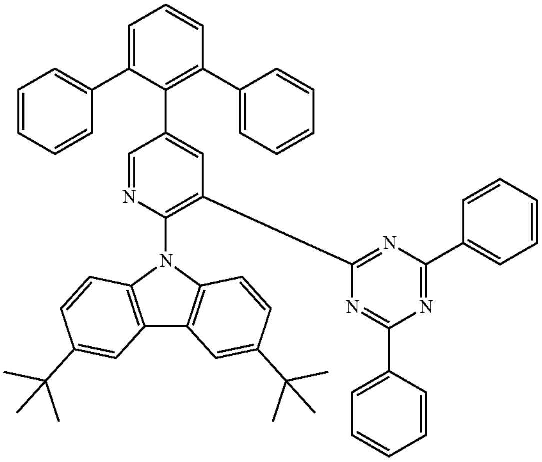
413
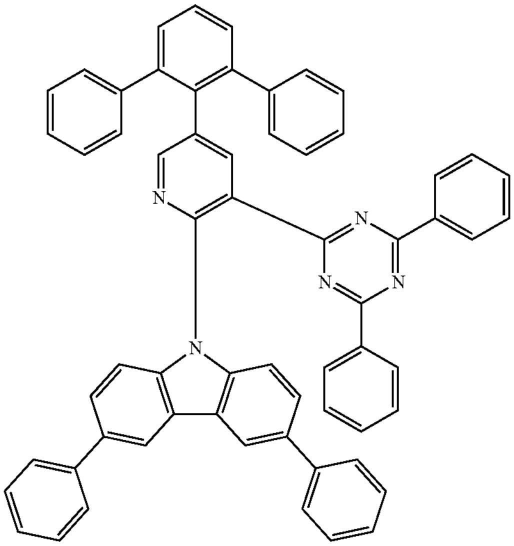

-continued
414
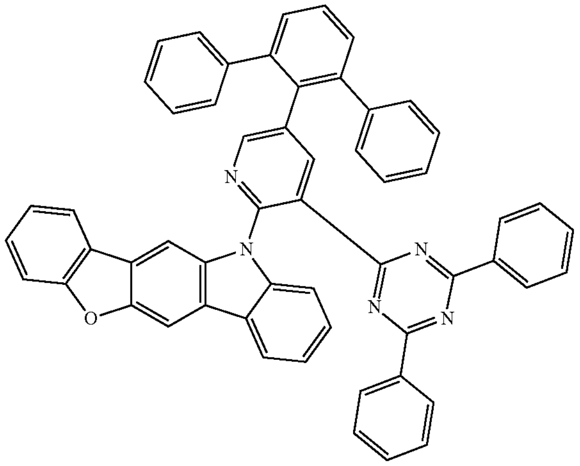
415
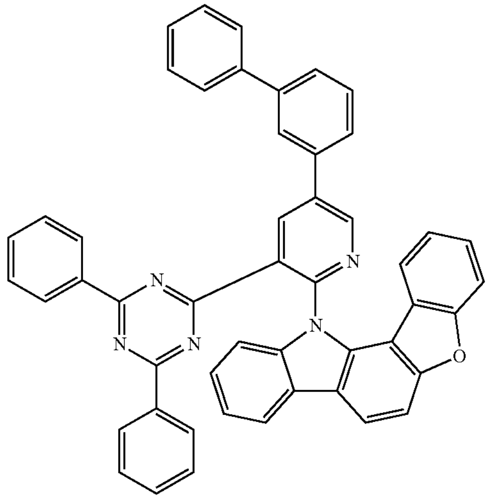
416
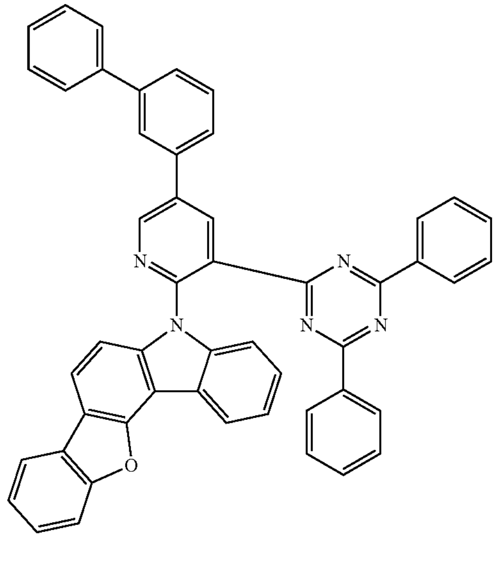
-continued
417
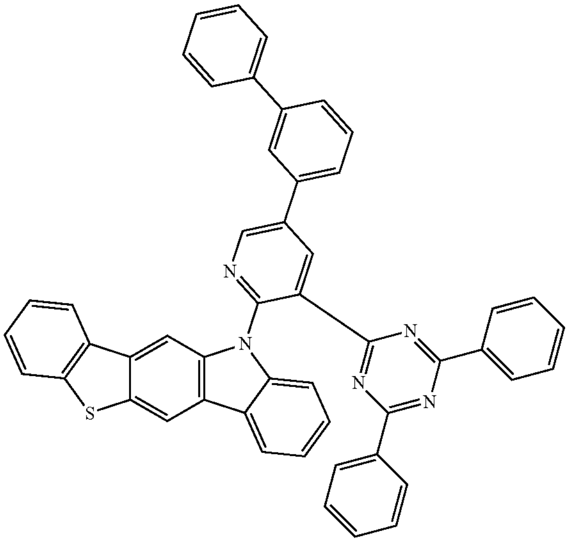
418
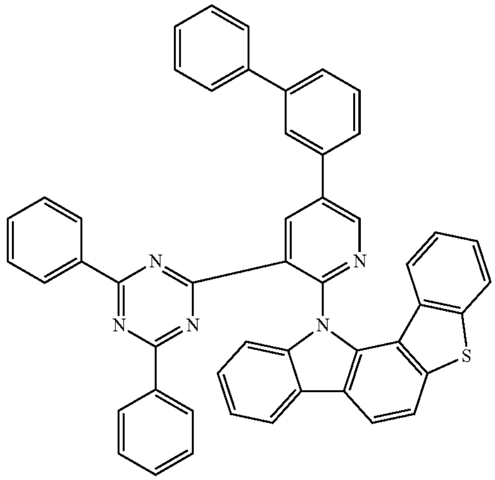
419
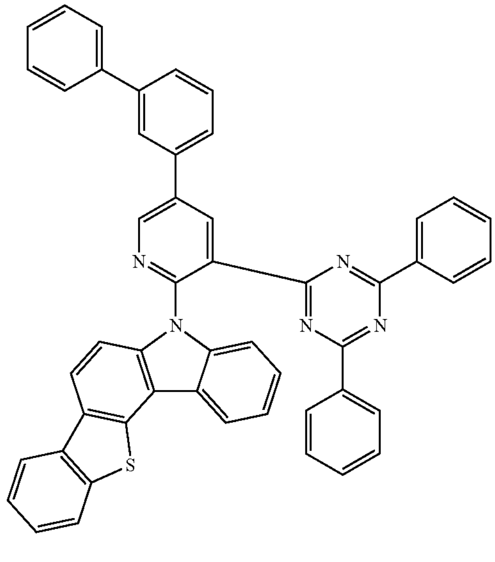

420
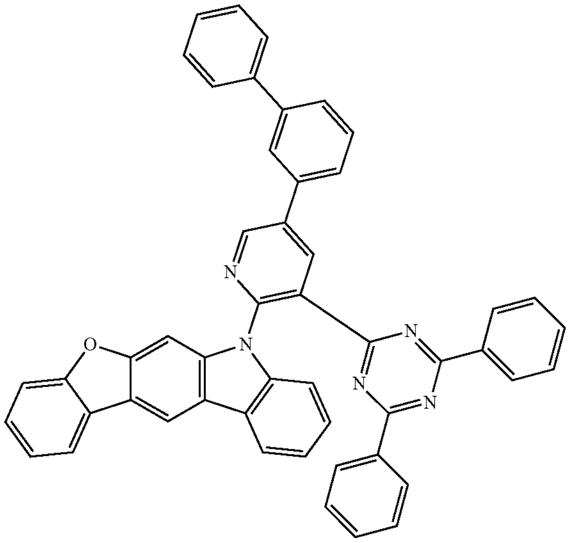
421
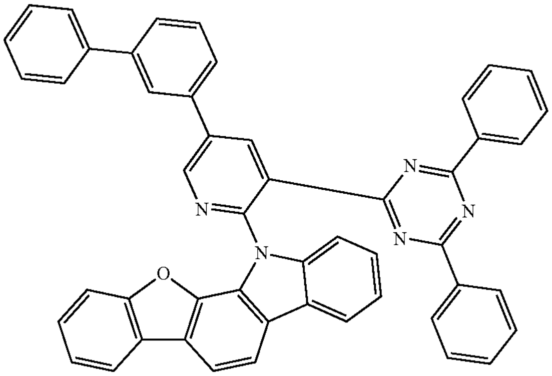
423
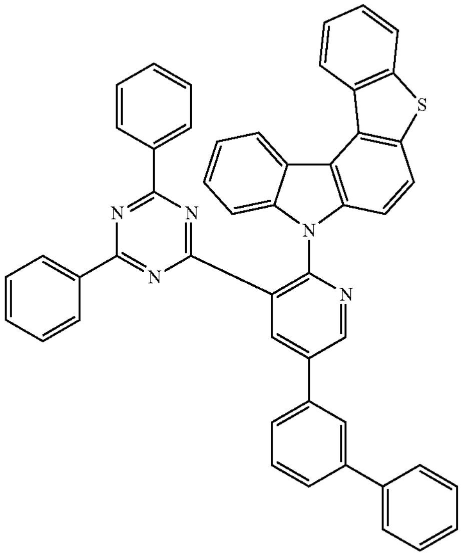
424
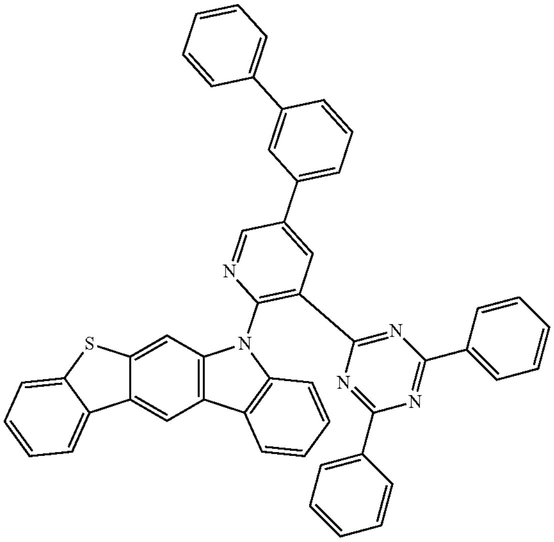
425
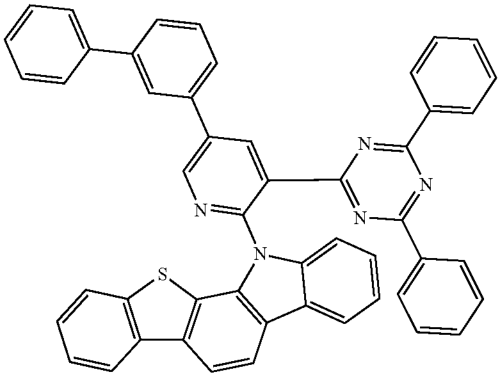
426
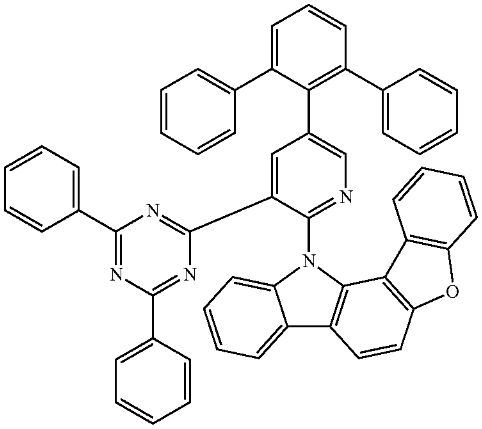

-continued
427
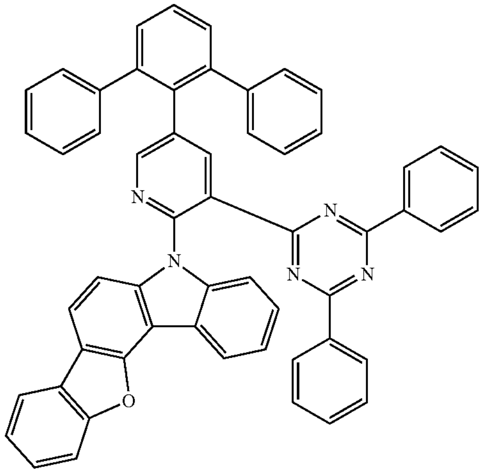
428
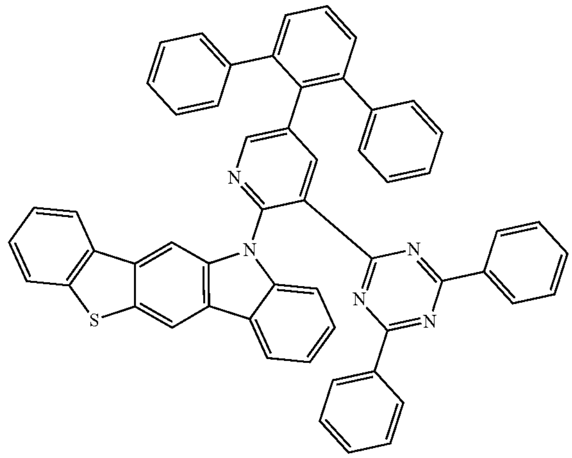
429
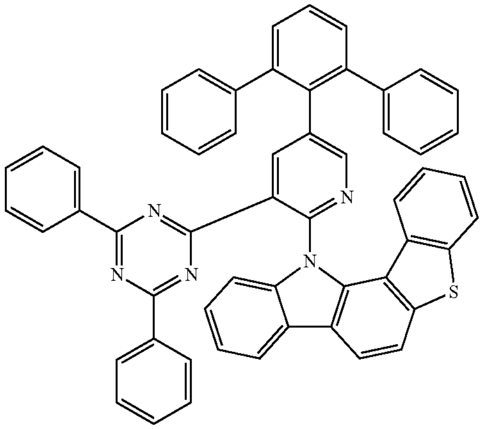
-continued
430
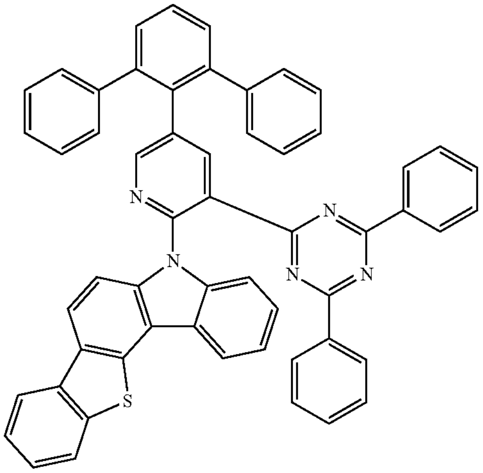
431
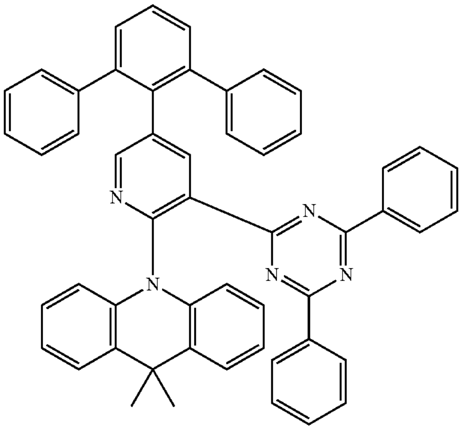
432
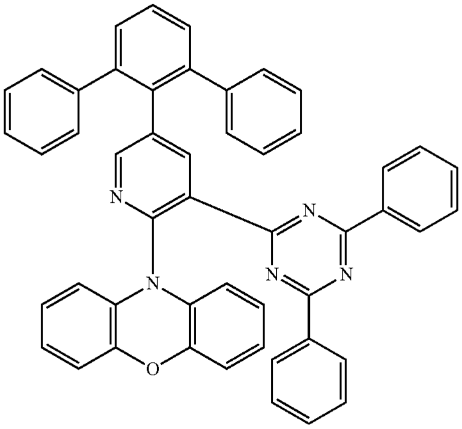

-continued
433
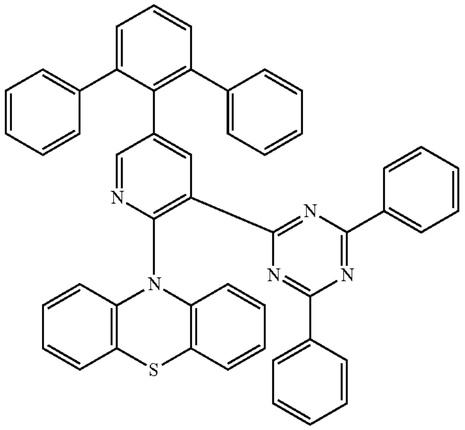
434
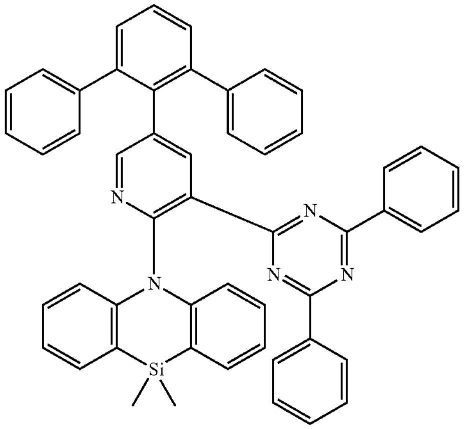
435
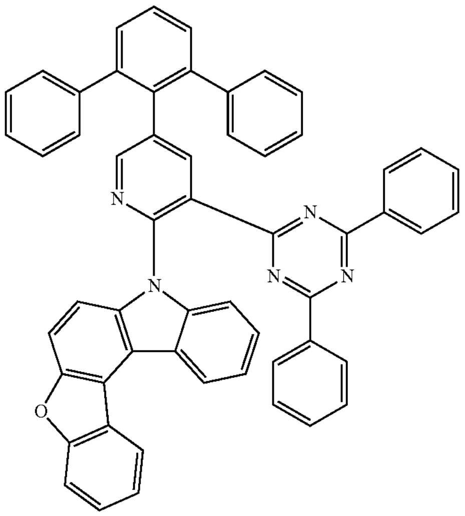
-continued
436
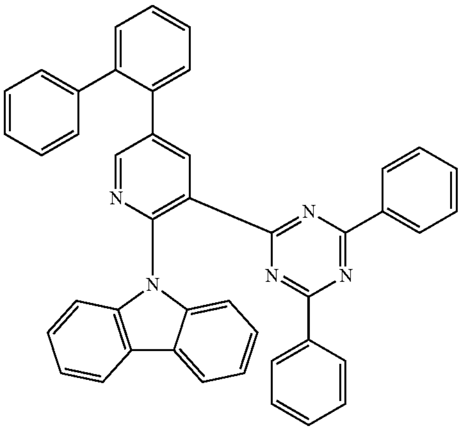
437
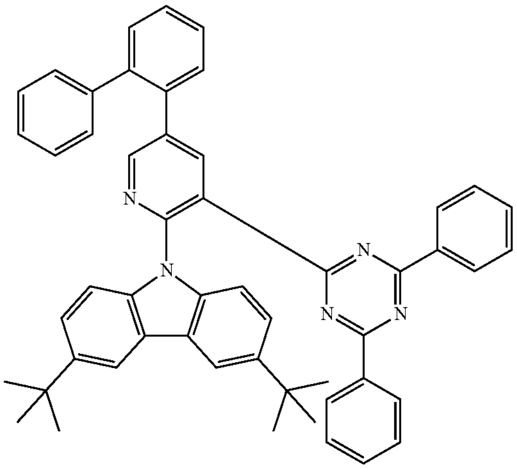
438
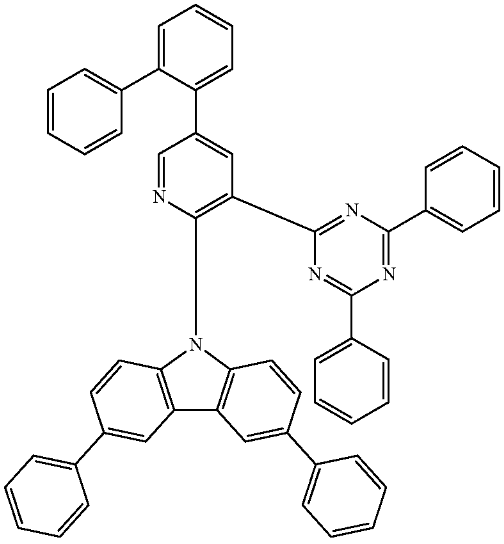

-continued
439
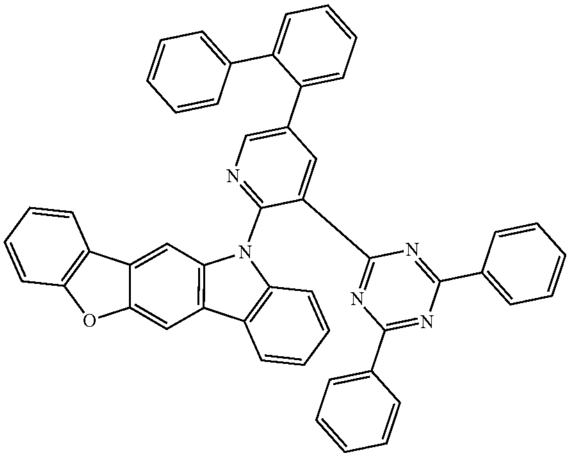
440
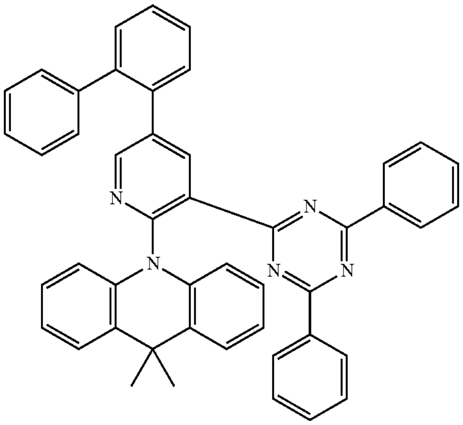
441
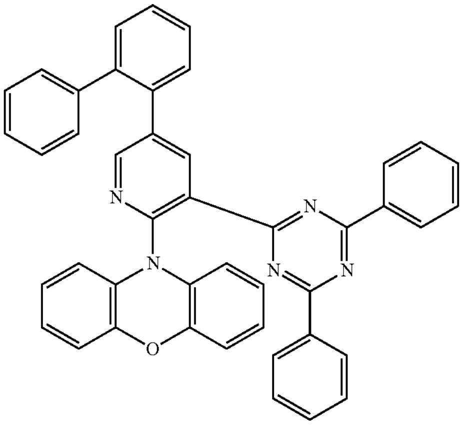
-continued
442
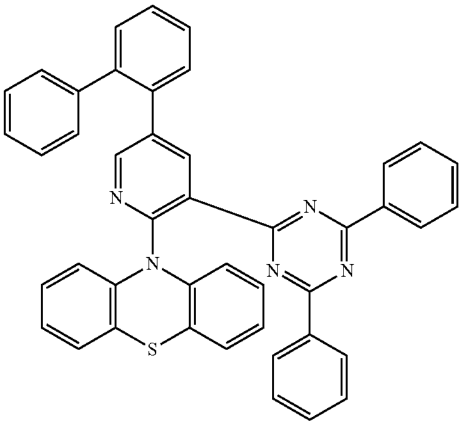
443
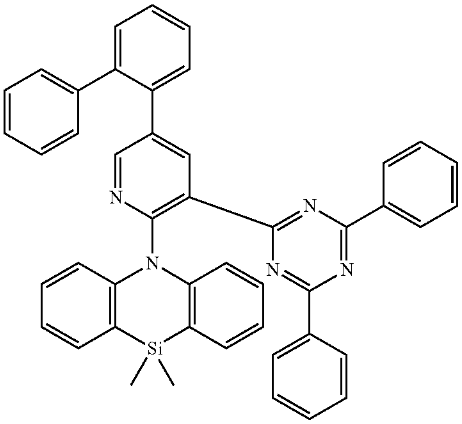
444
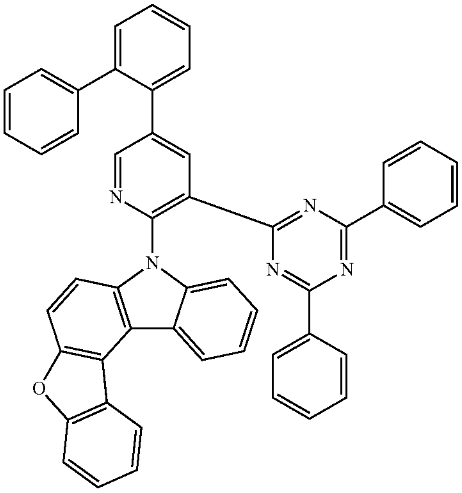

-continued
445
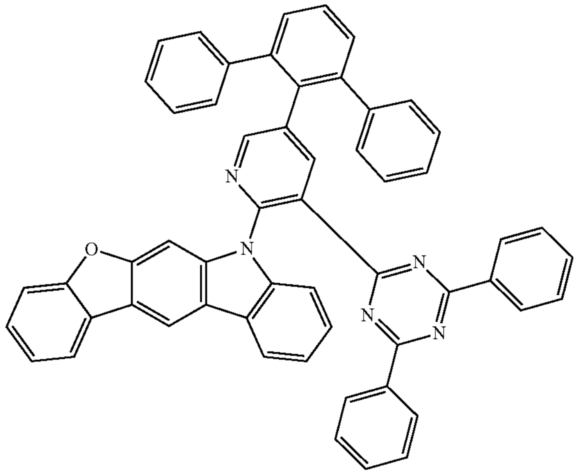
446
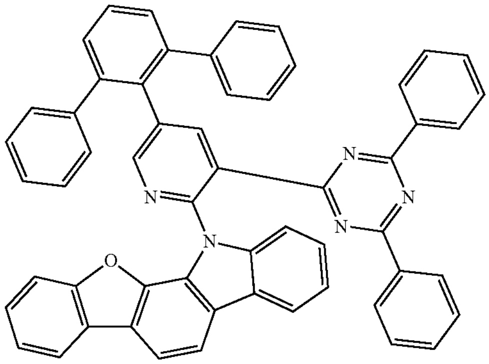
447
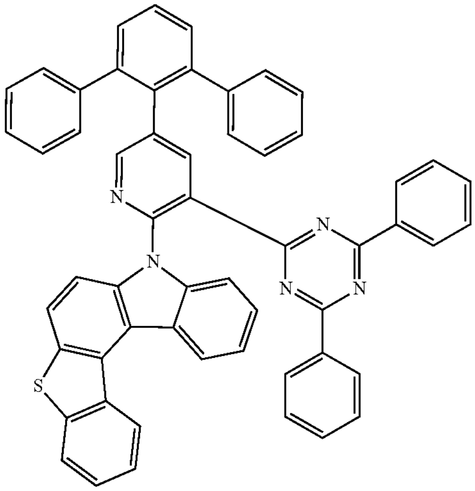
-continued
448
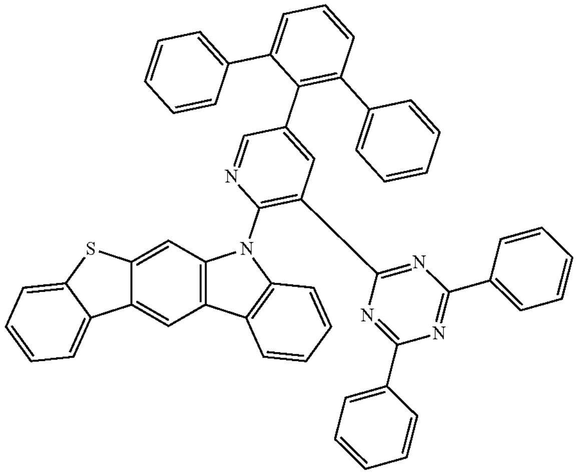
449
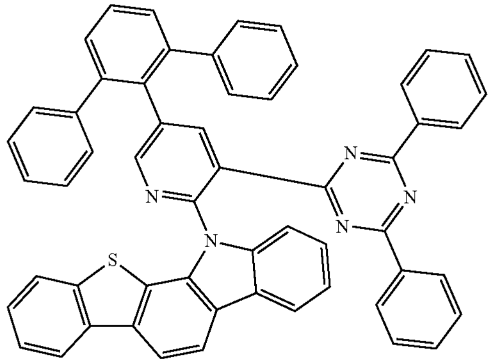
450
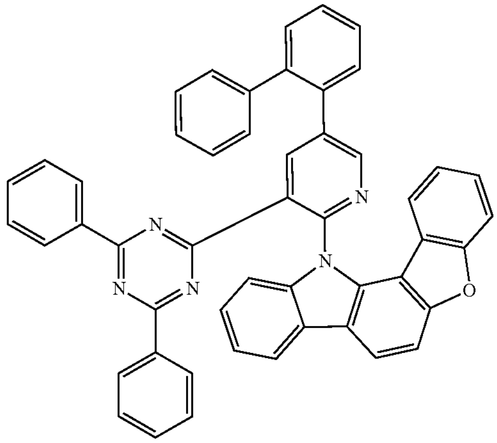

-continued
451
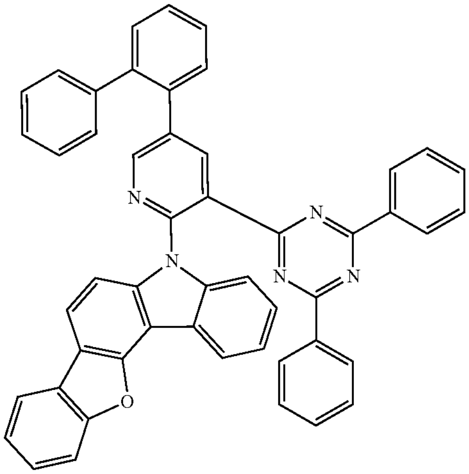
452
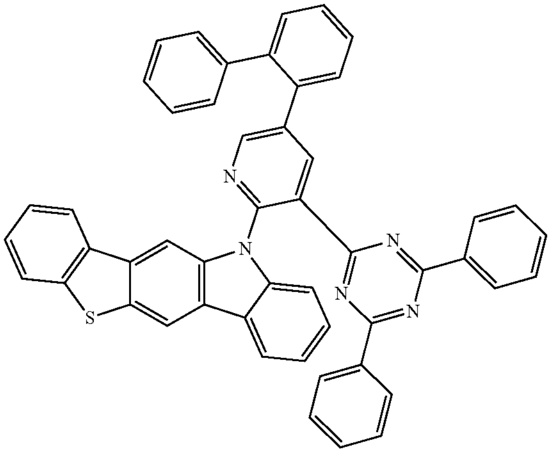
453
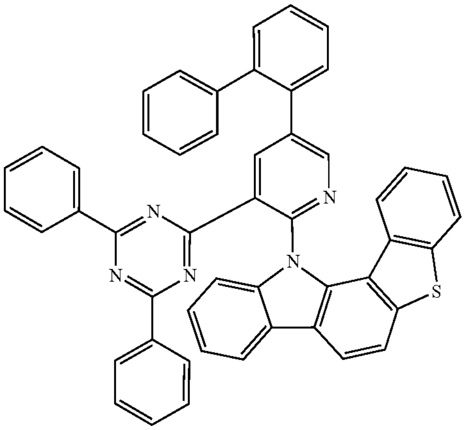
-continued
454
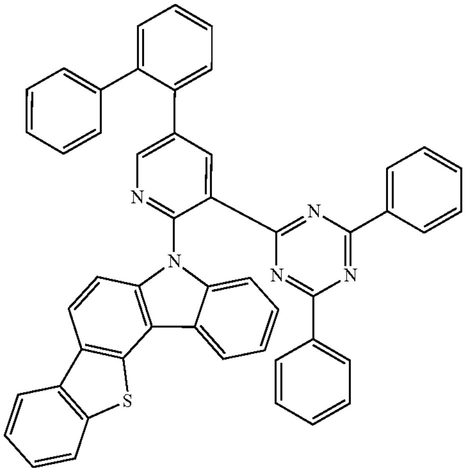
455
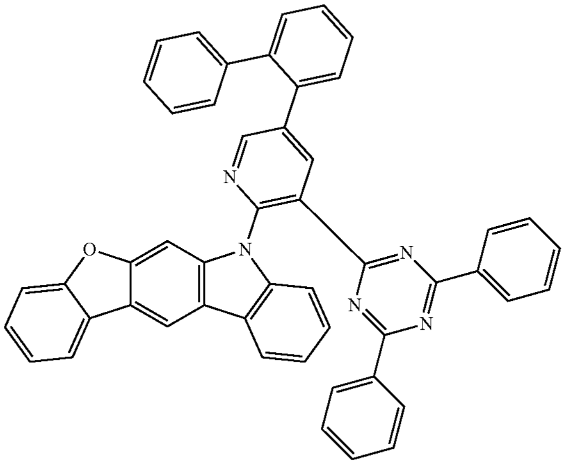
456
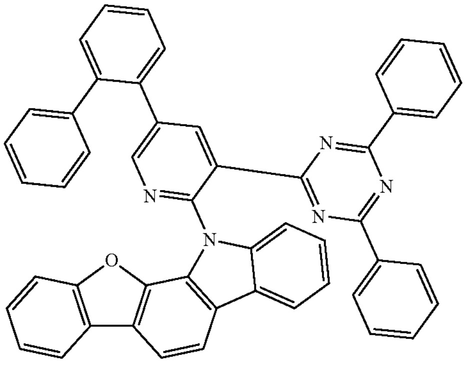

-continued
457
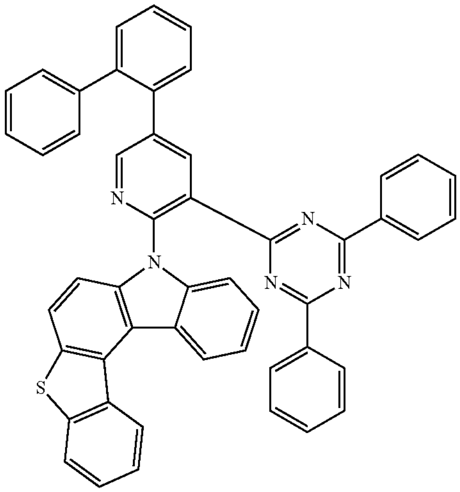
458
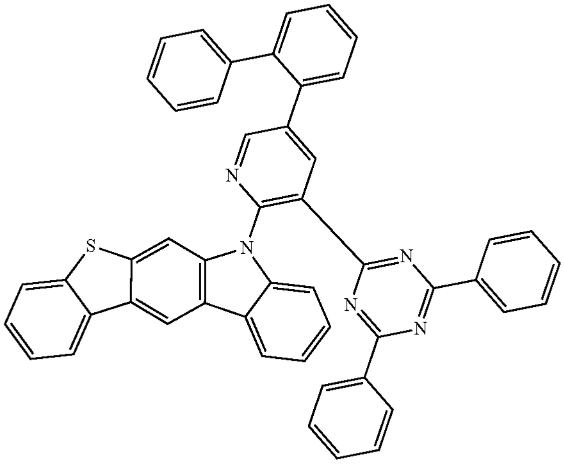
459
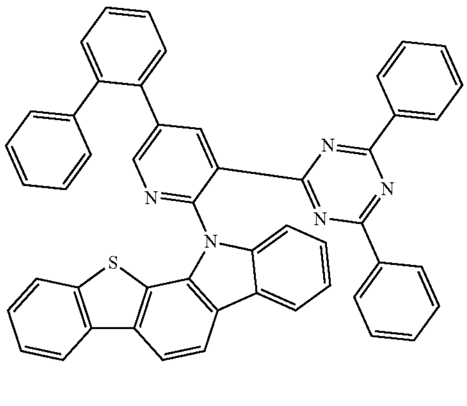
-continued
460
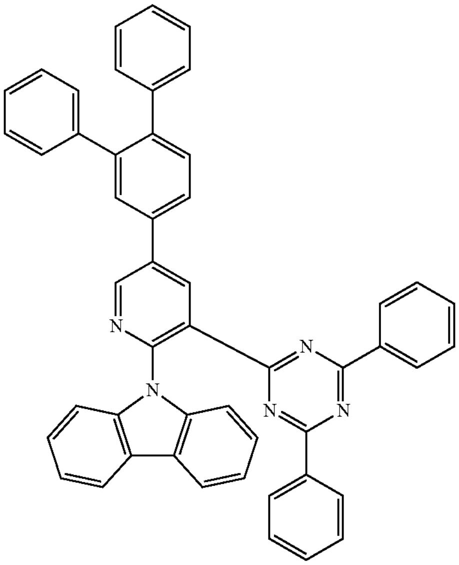
461
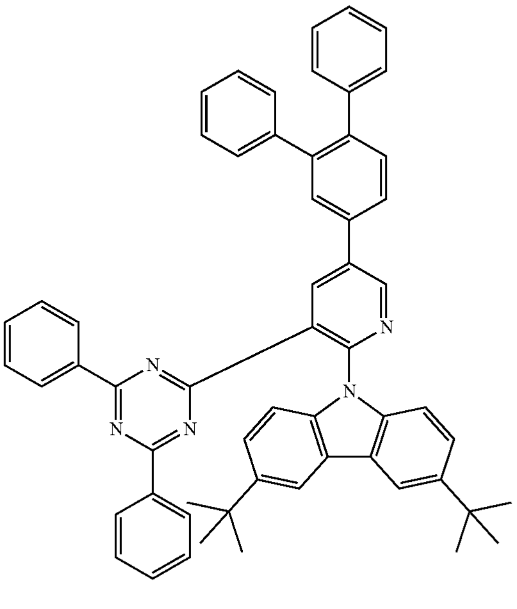

-continued
462
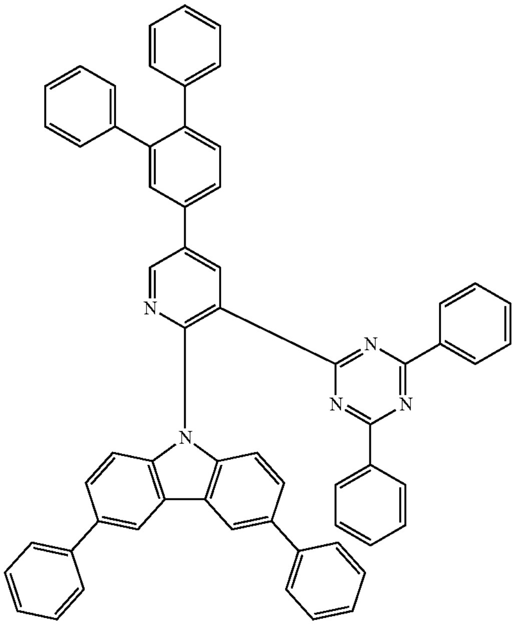
463
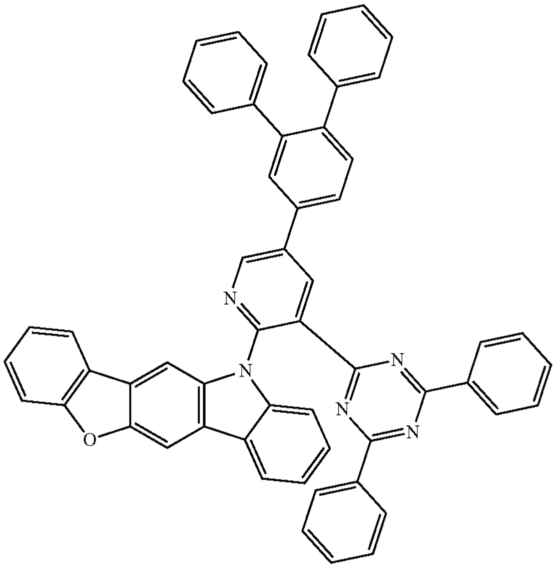
-continued
464
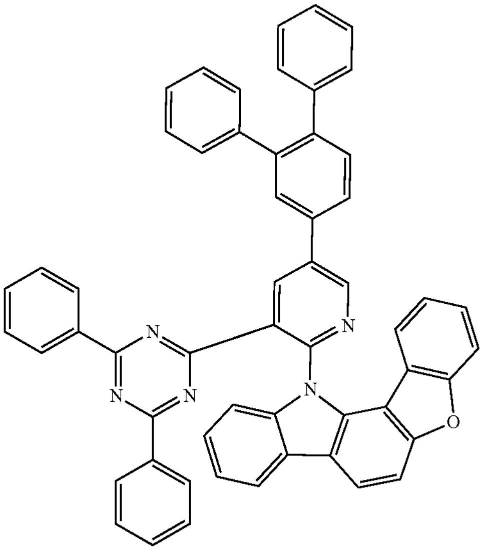
465
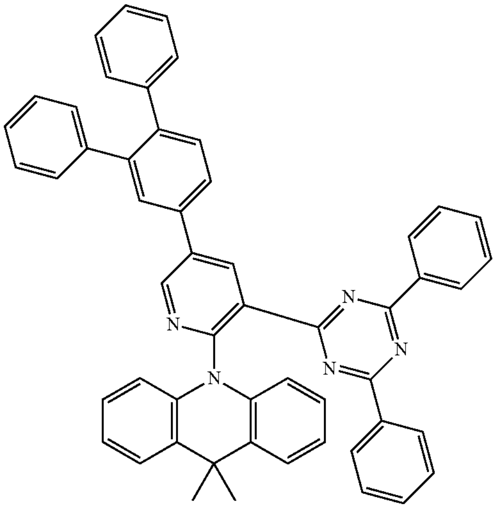
466
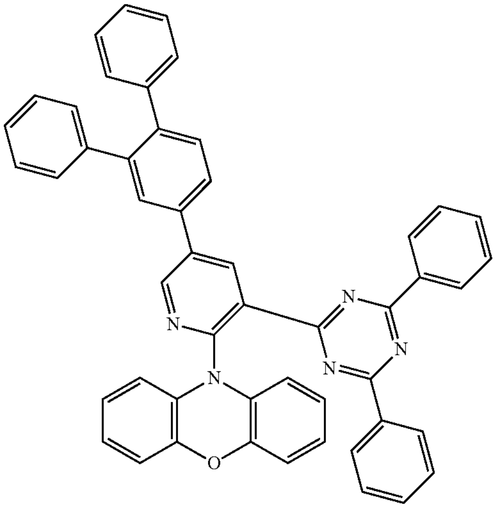

-continued
467
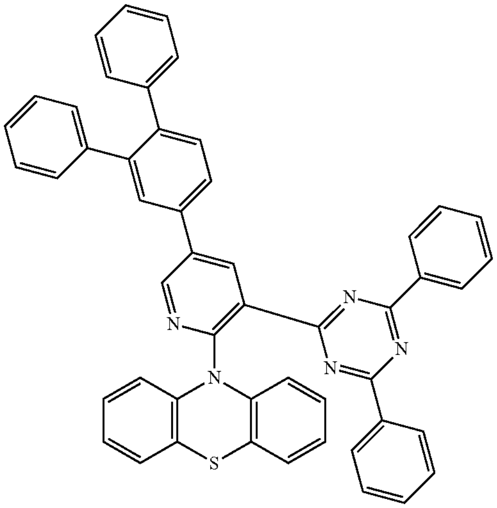
468
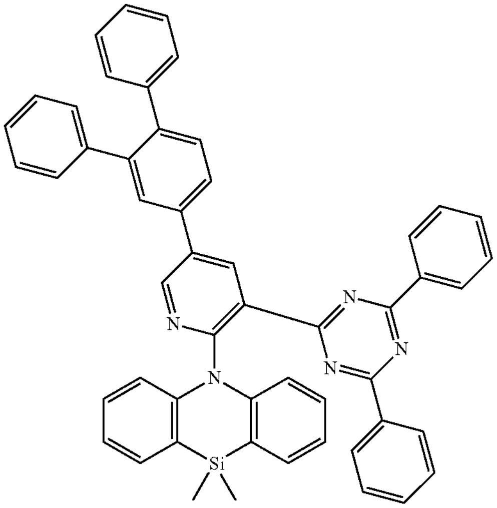
-continued
469
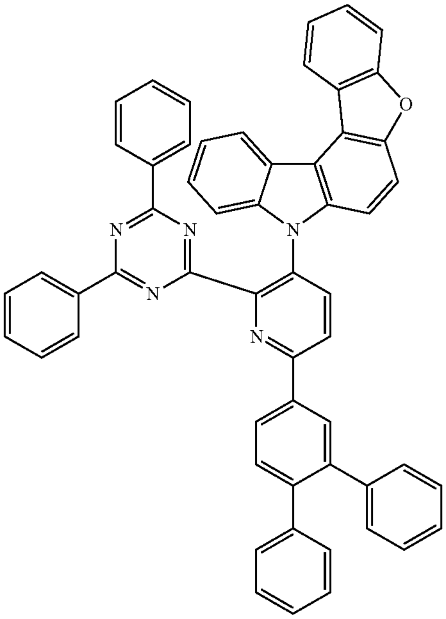
470
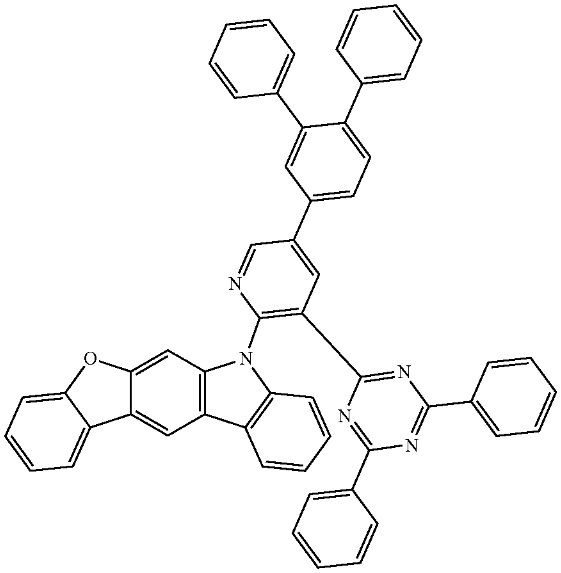

471
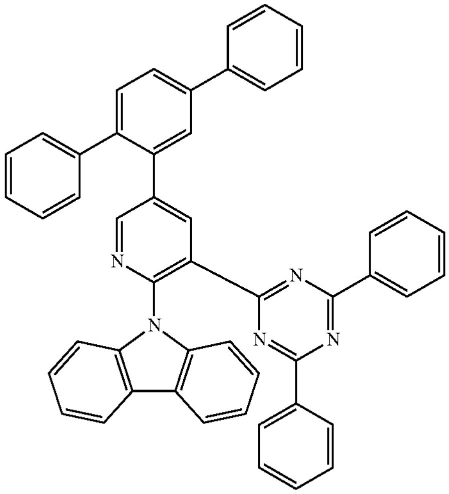
472
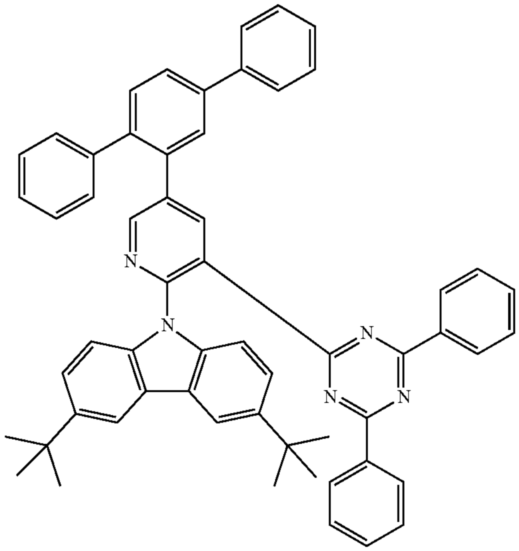
473
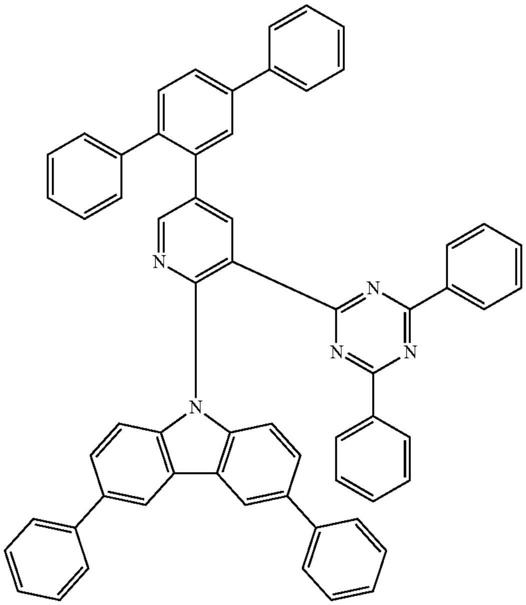
474
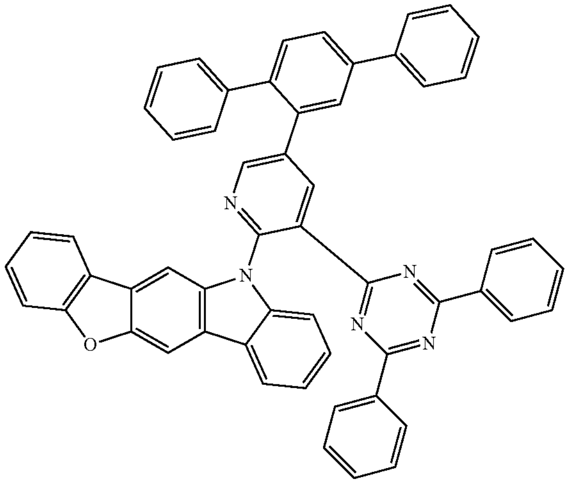
475
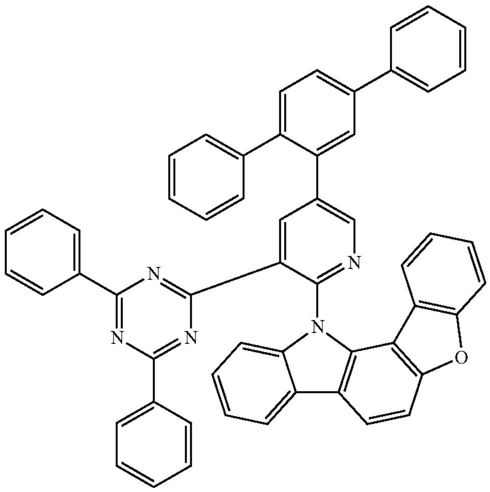

-continued
476
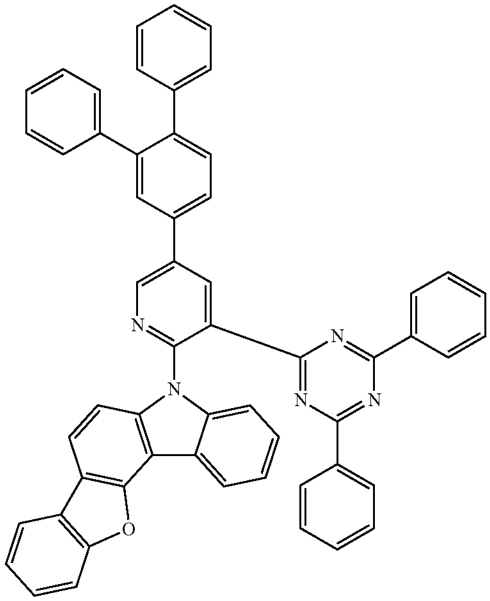
477
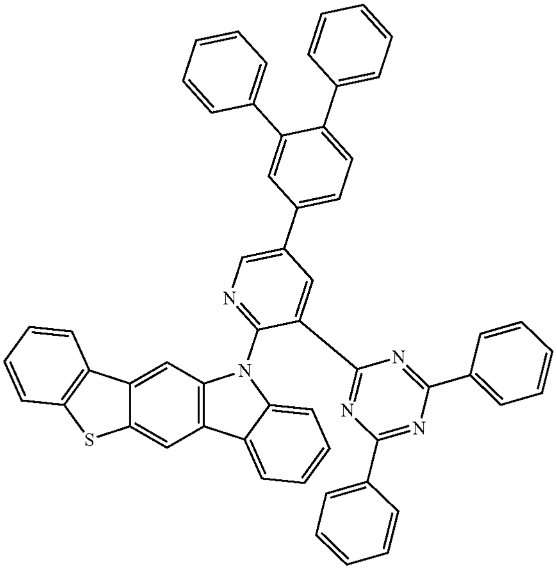
-continued
478
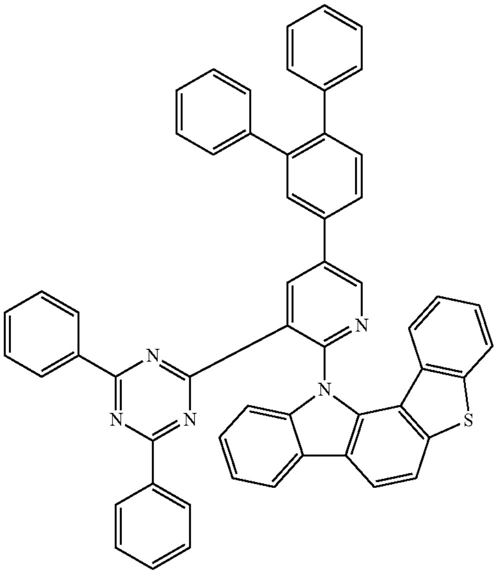
479
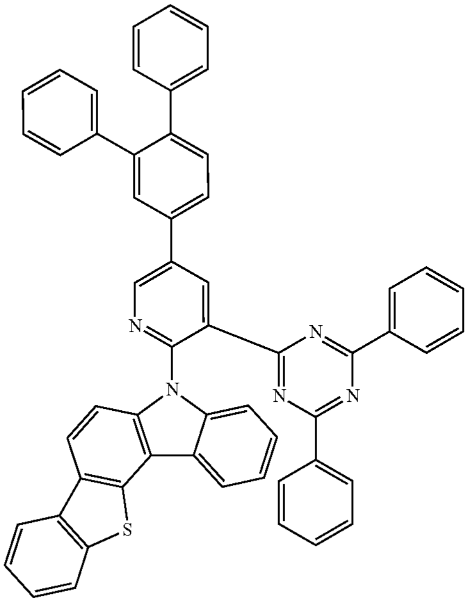

-continued
480
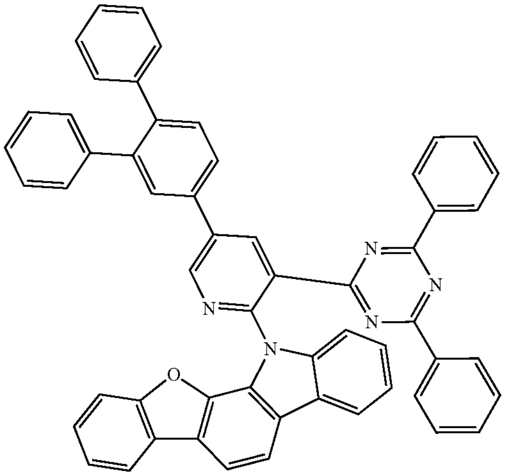
481
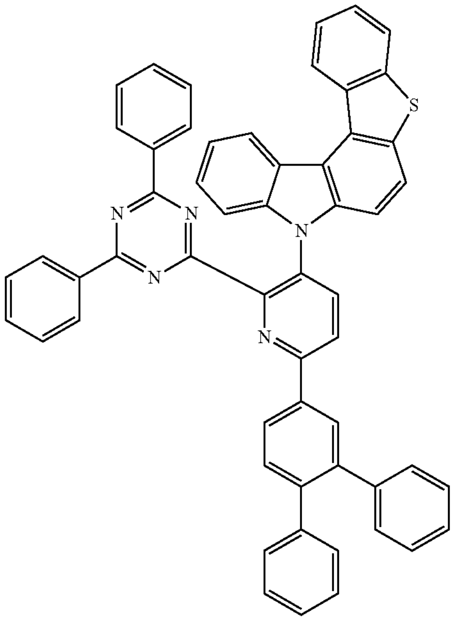
-continued
482
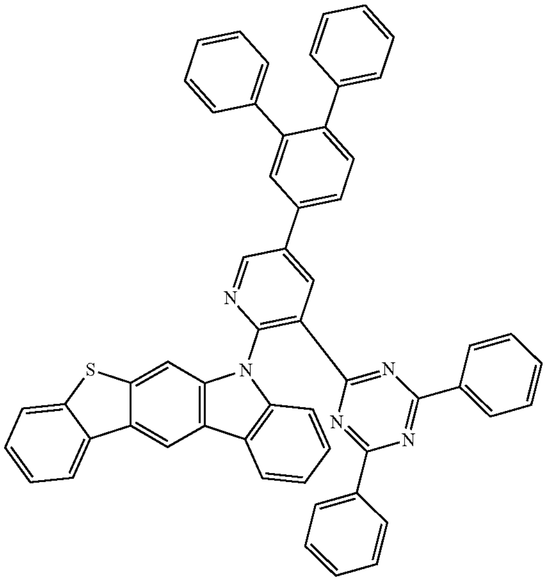
483
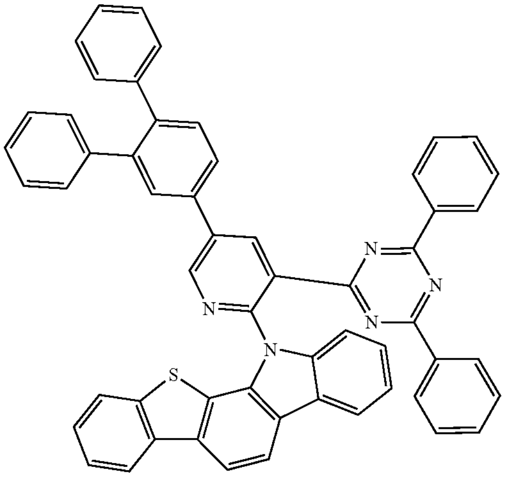
484
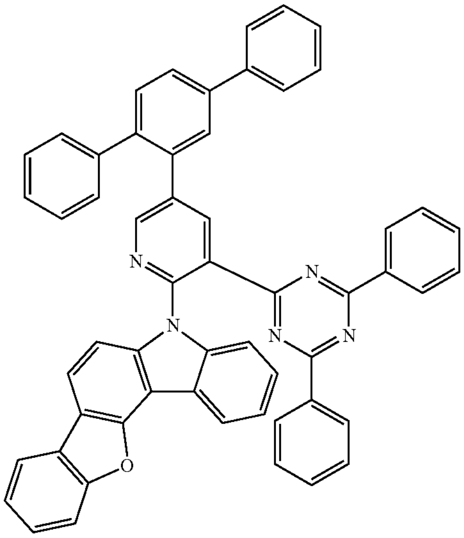

-continued
485
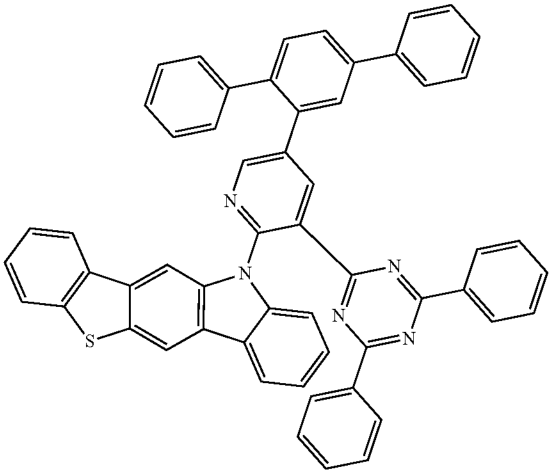
486
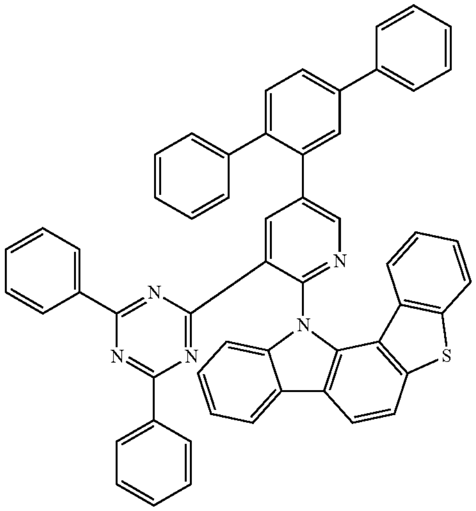
487
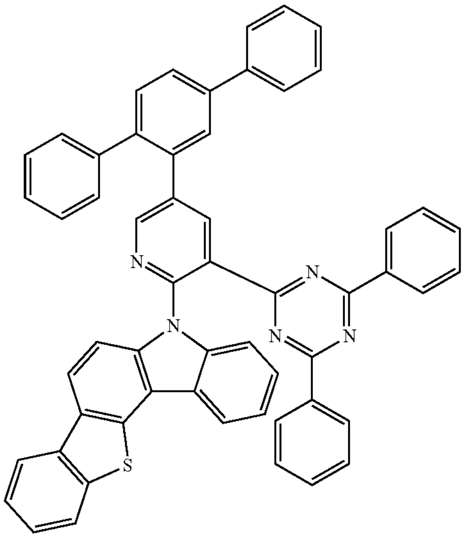
-continued
488
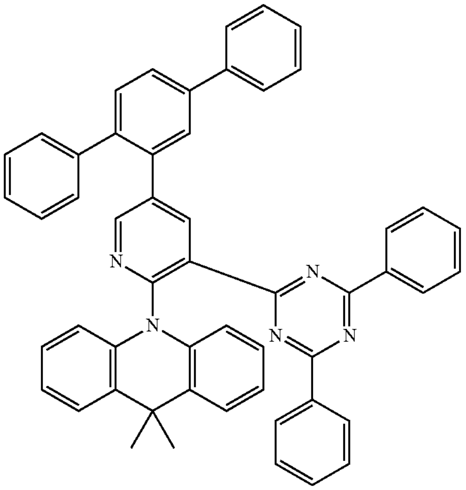
489
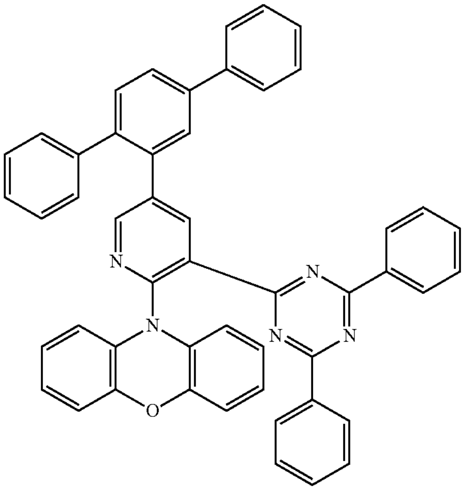
490
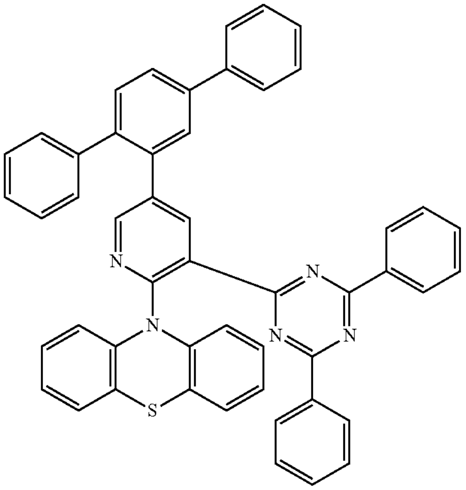

-continued
491
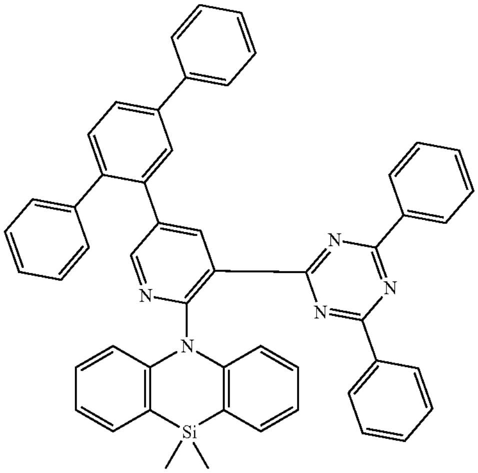
492
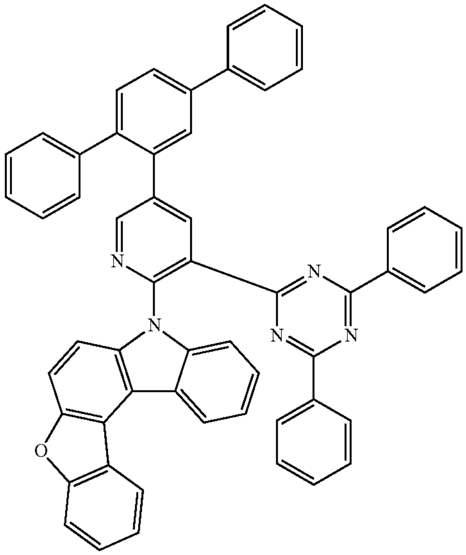
493
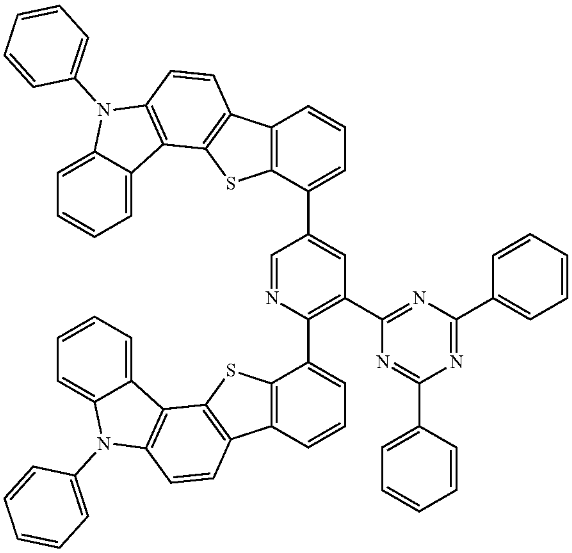
-continued
494
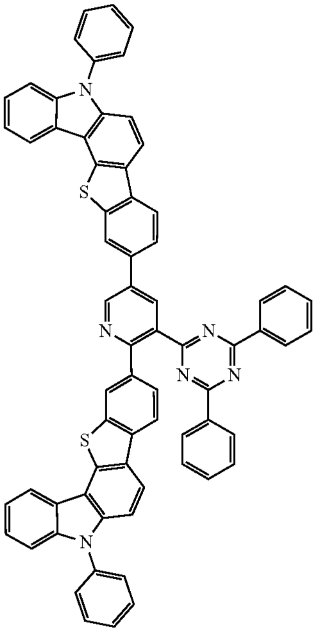
495
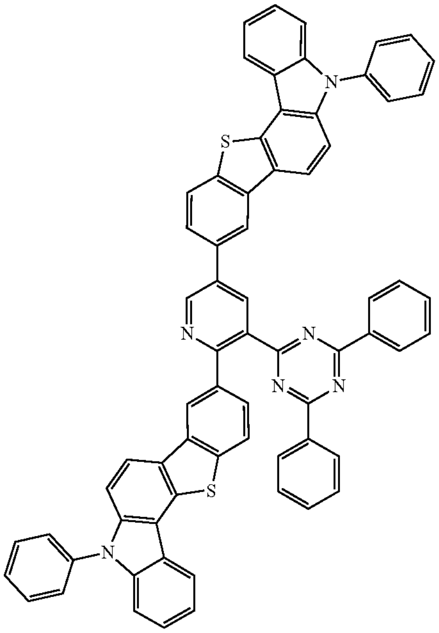

-continued
496
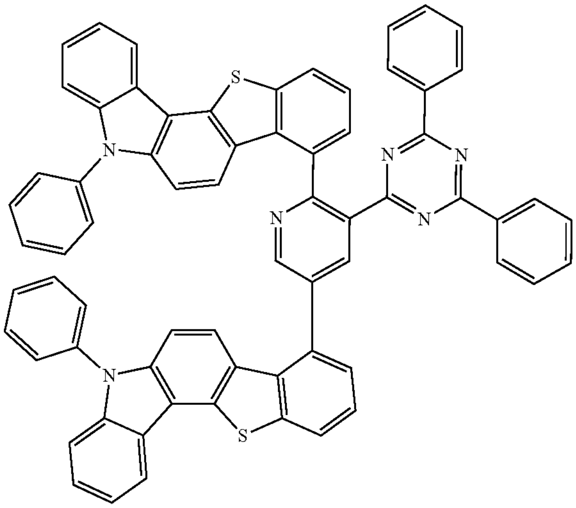
-continued
498
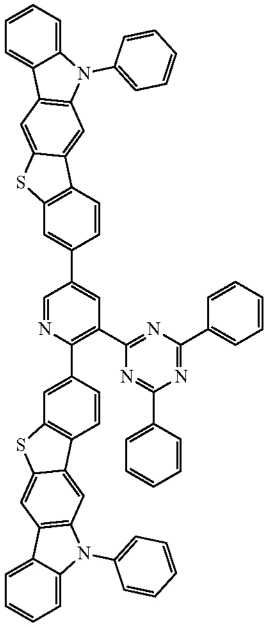
497
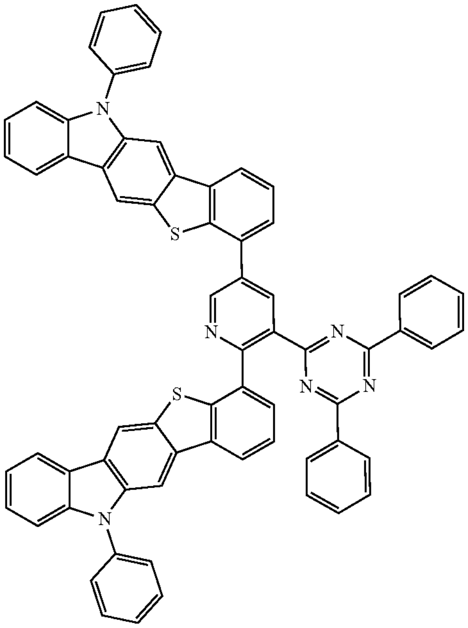
499
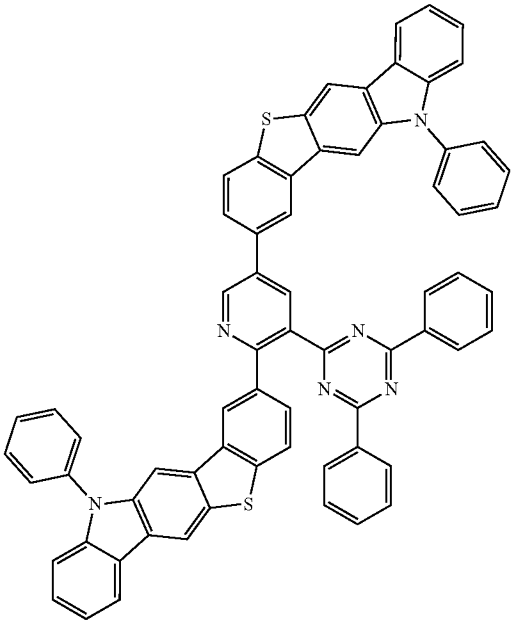

-continued
500
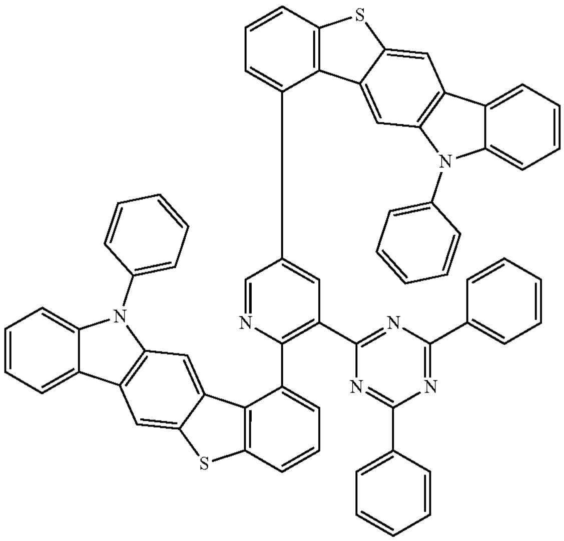
501
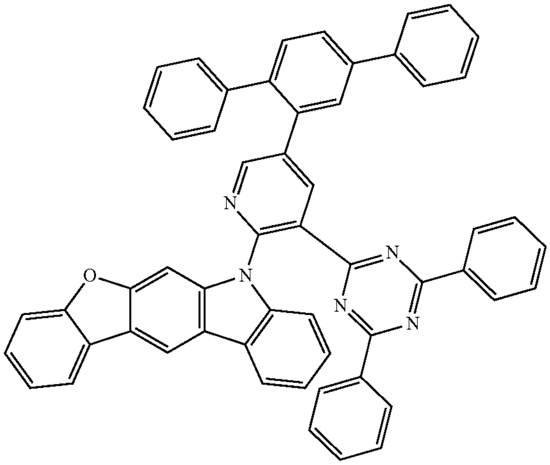
502
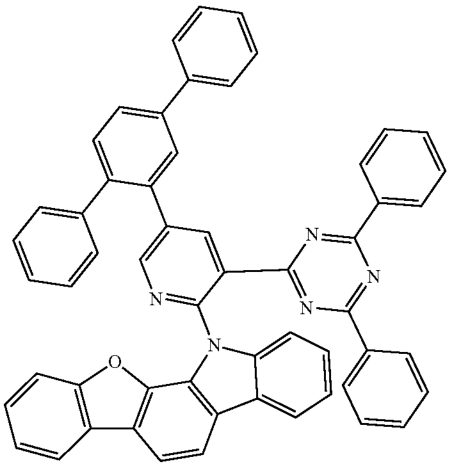
-continued
503
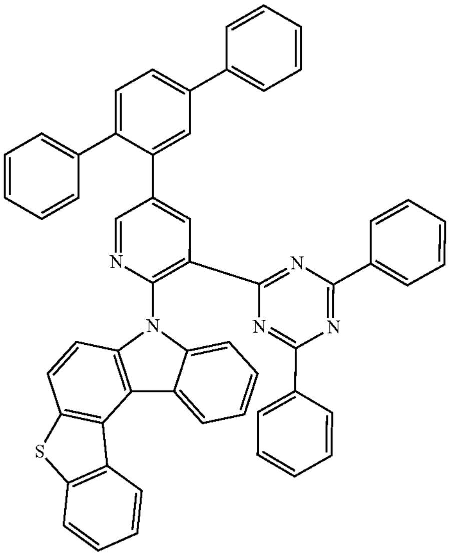
504
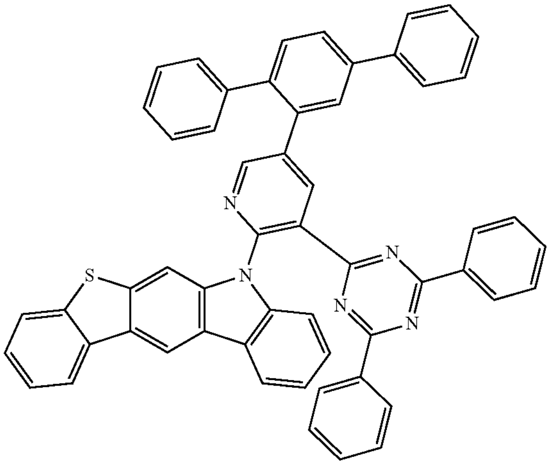
505
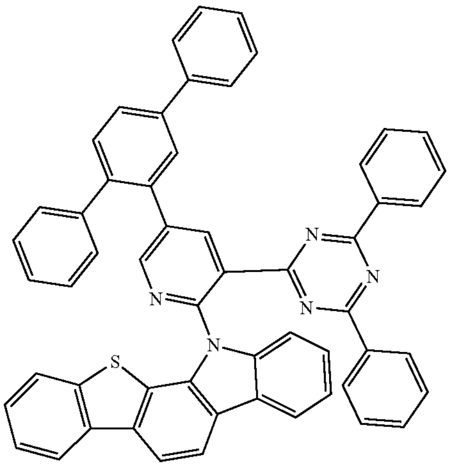

-continued
506
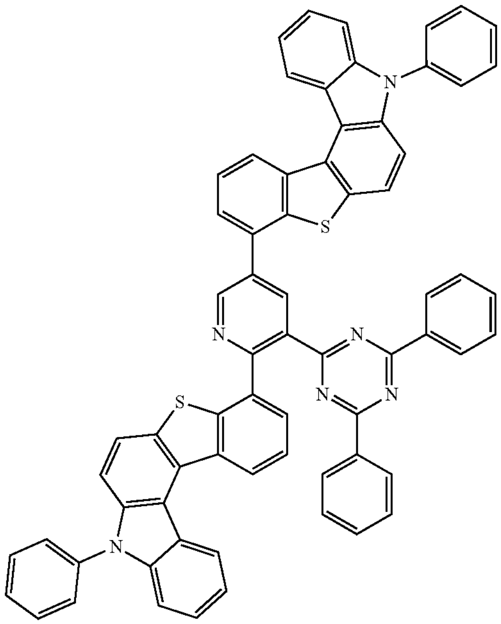
507
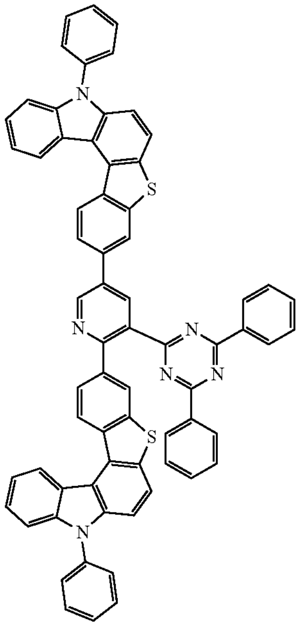
-continued
508
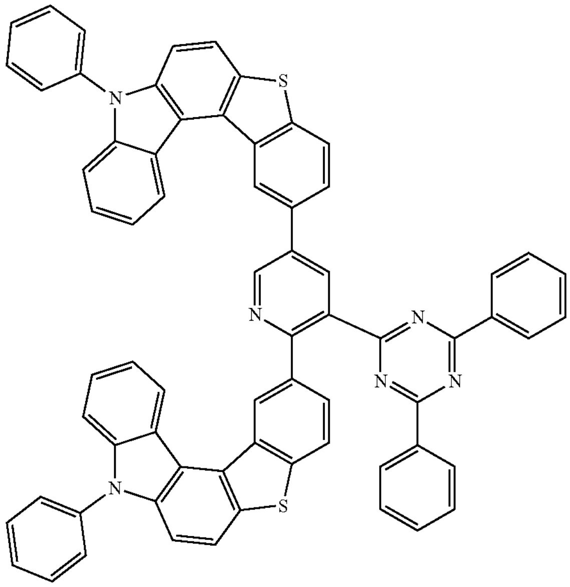
509
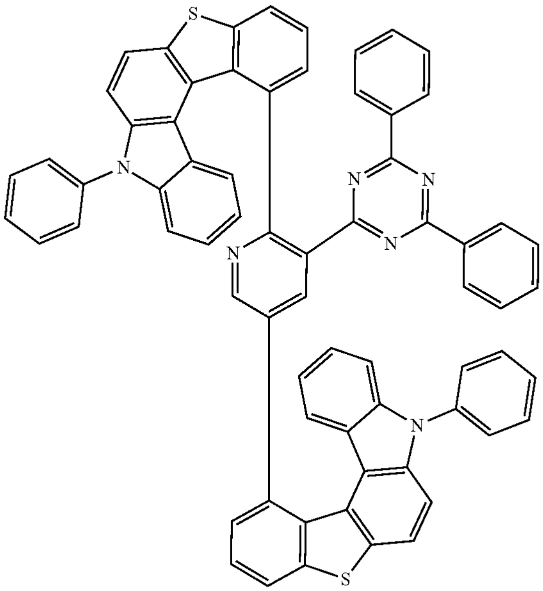

-continued
510
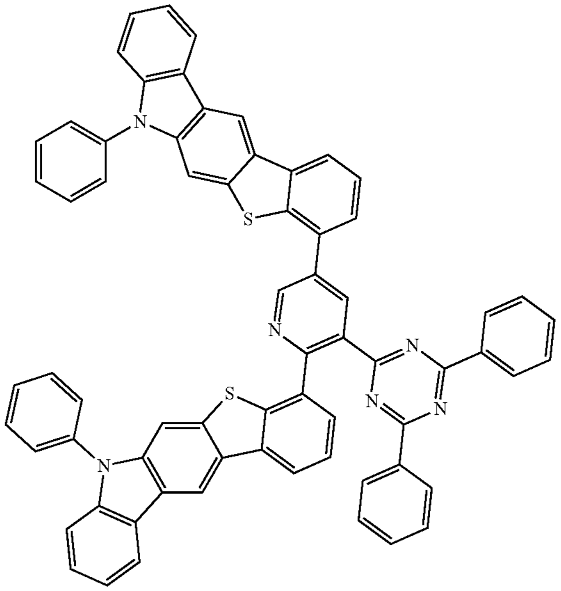
511
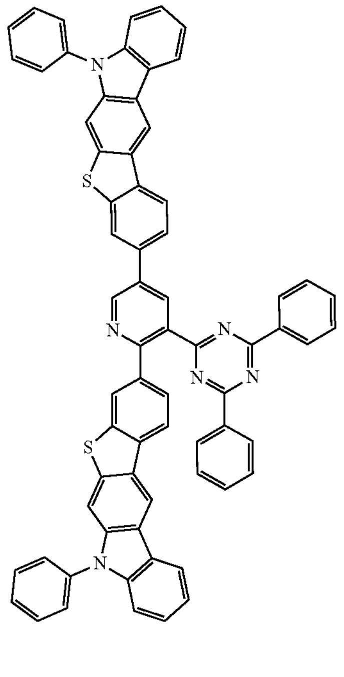
-continued
512
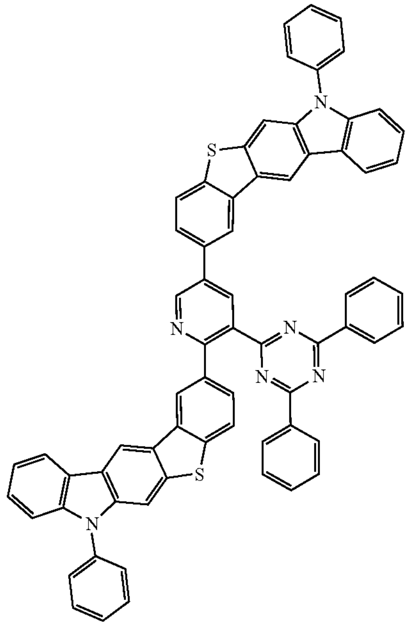
513
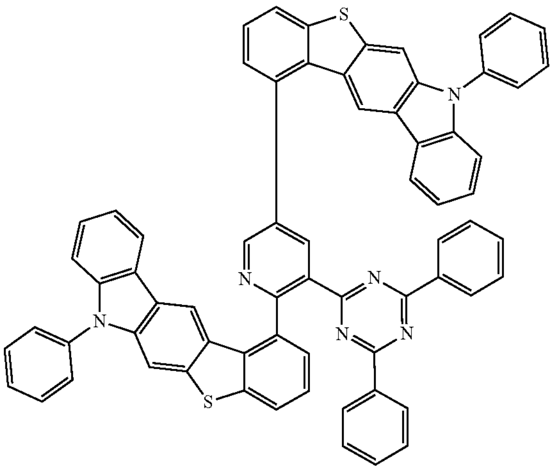

-continued
514
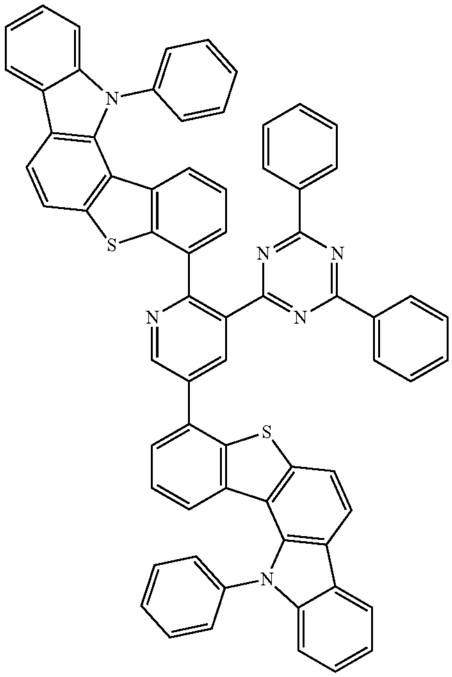
515
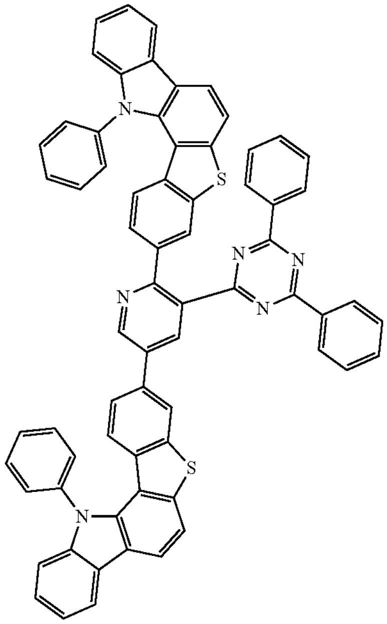
-continued
516
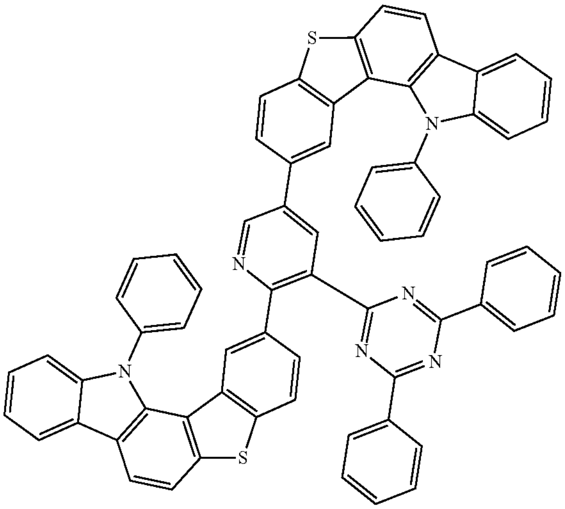
517
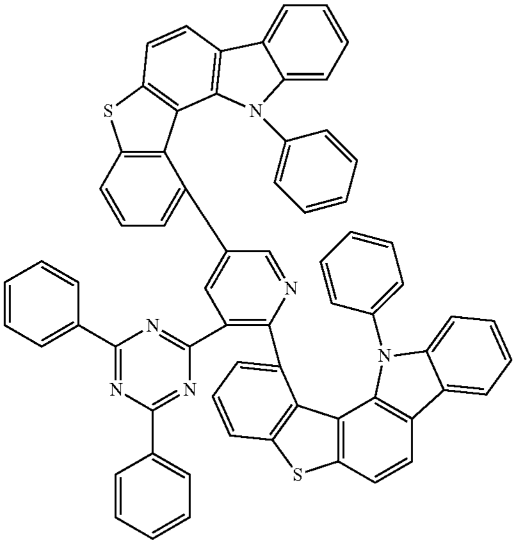
518
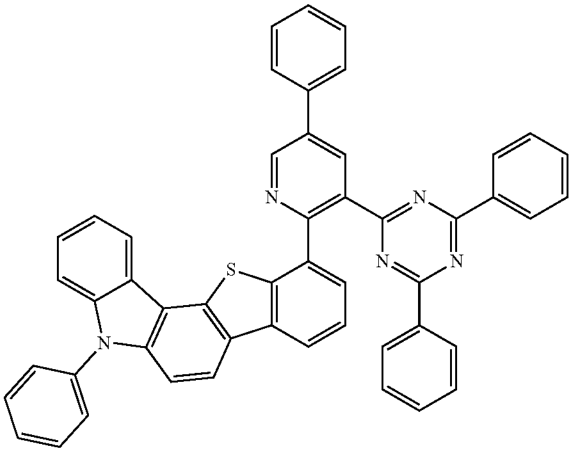

-continued
519
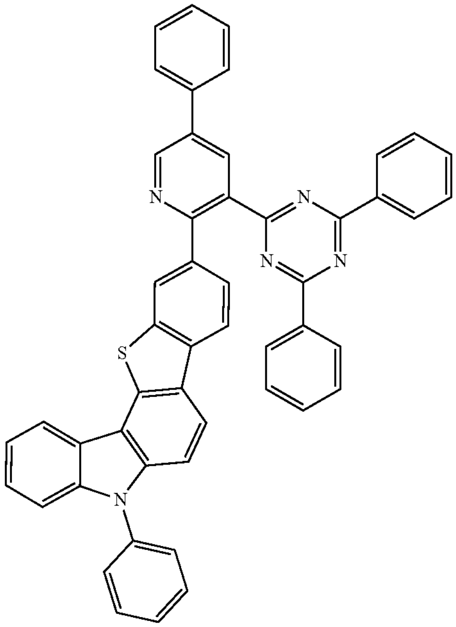
520
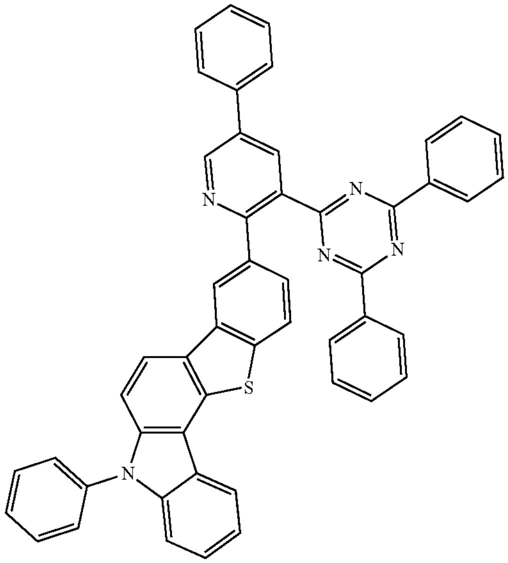
521
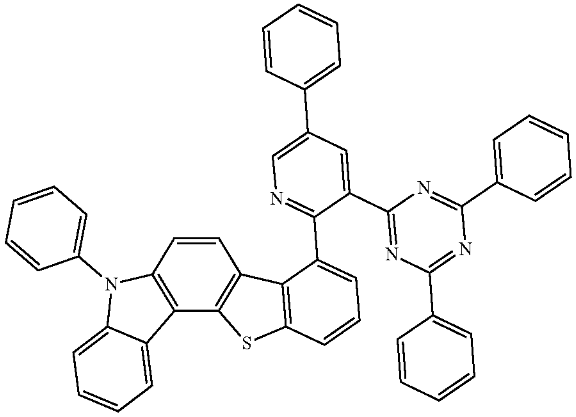
-continued
522
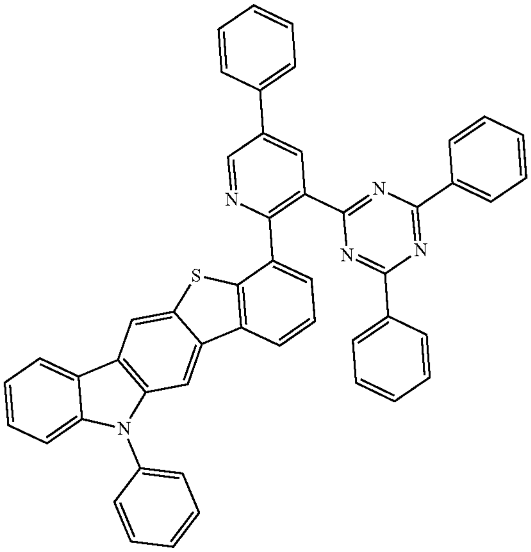
523
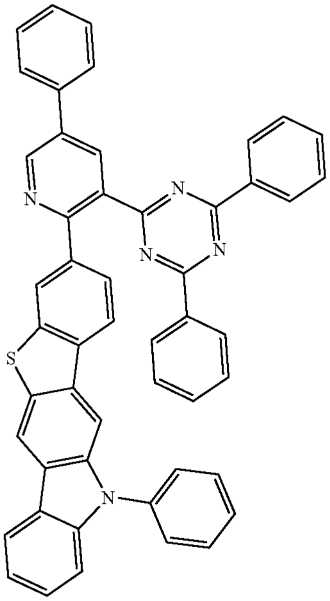

-continued
524
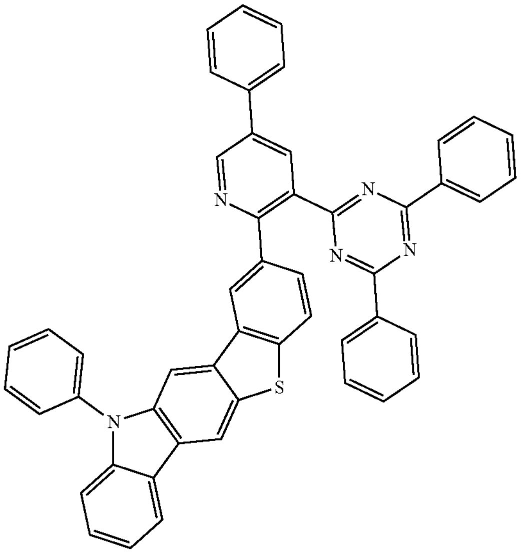
525
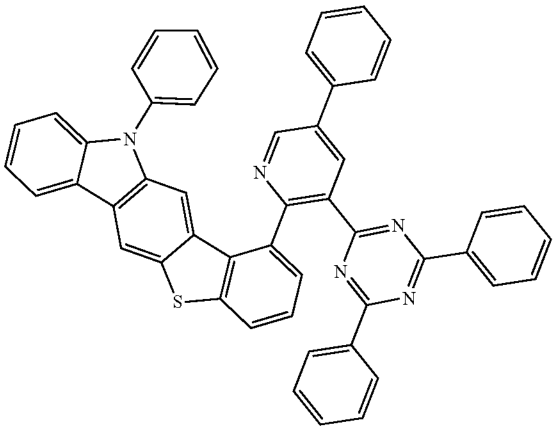
526
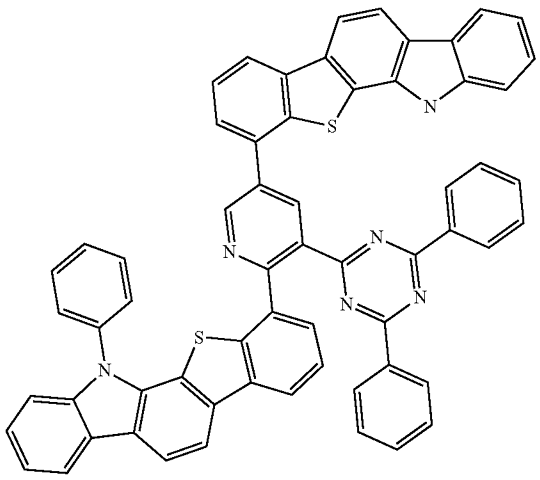
-continued
527
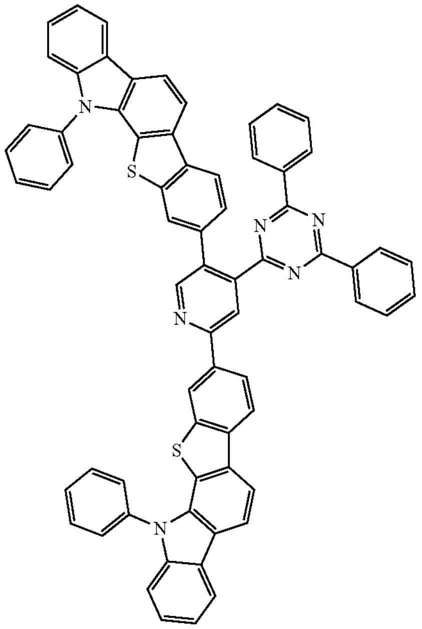
528
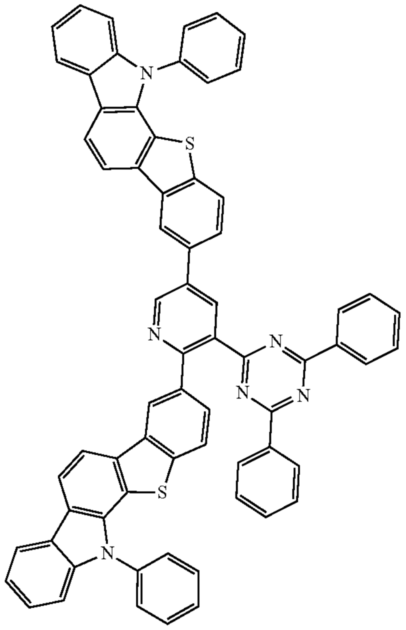

-continued
529
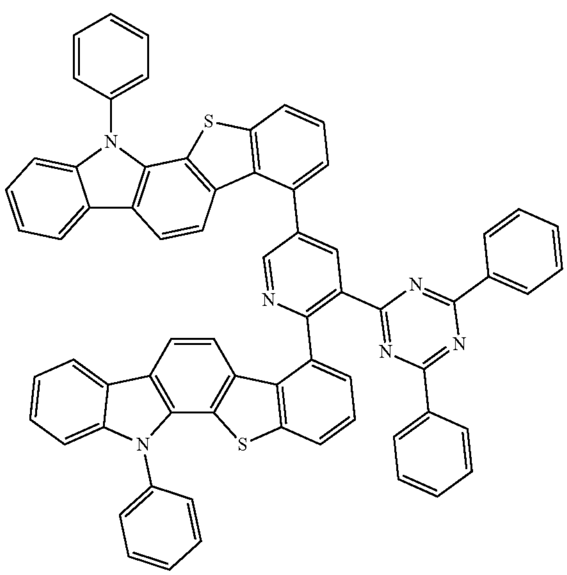
530
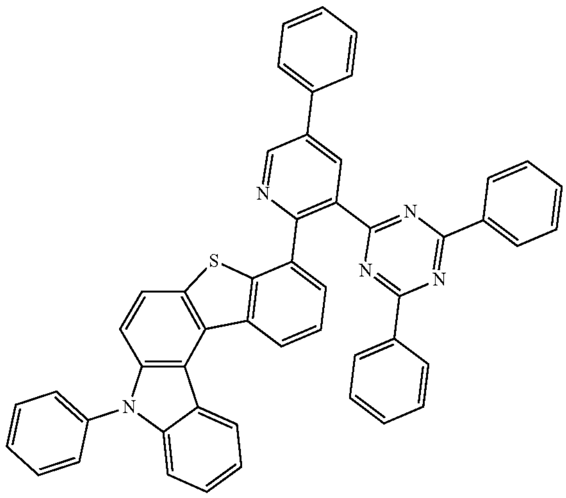
-continued
531
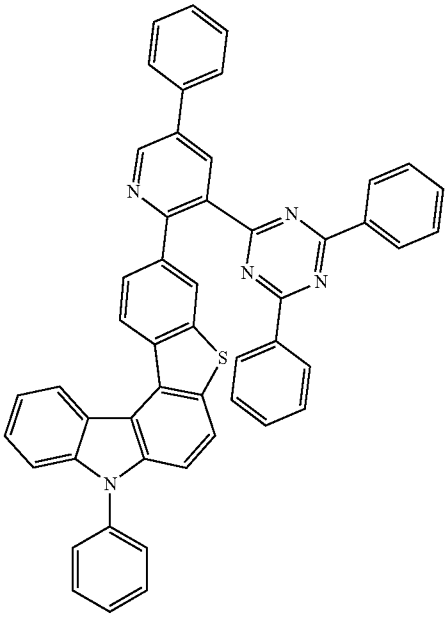
532
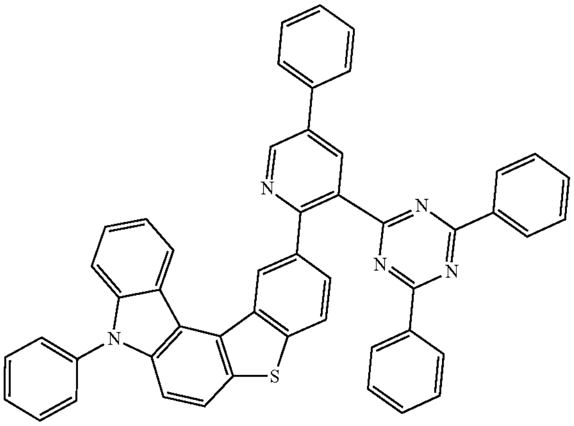
533
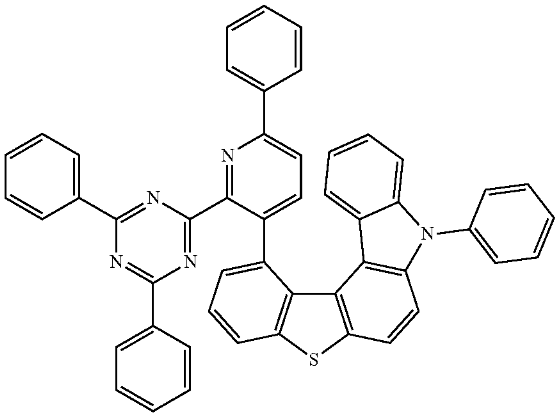

-continued
534
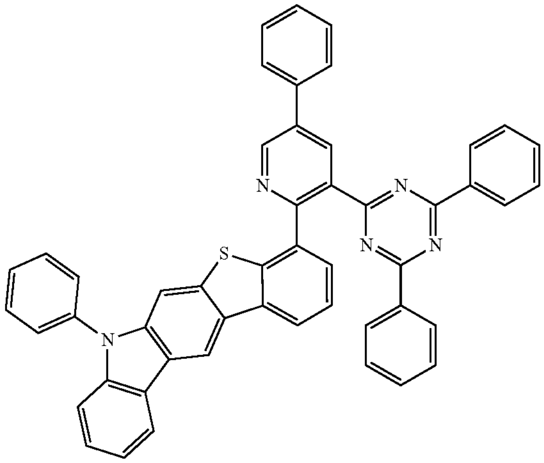
535
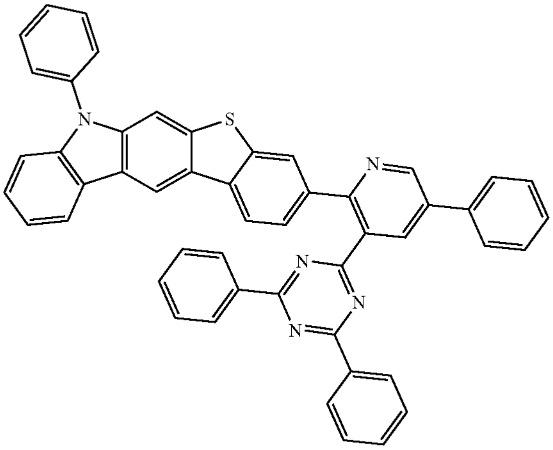
536
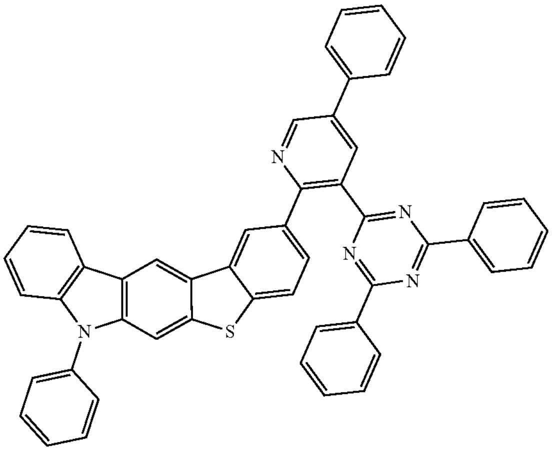
537
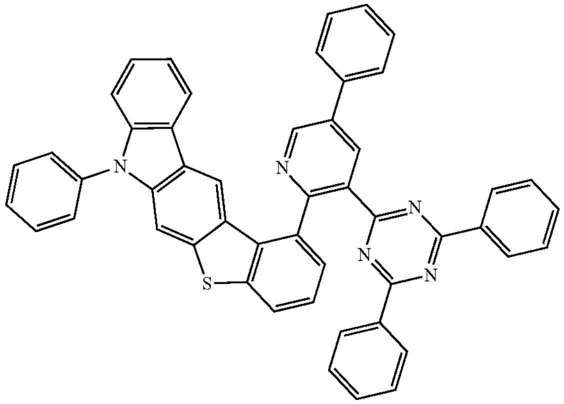
538
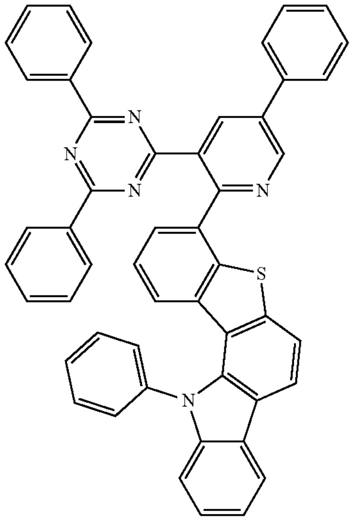
539
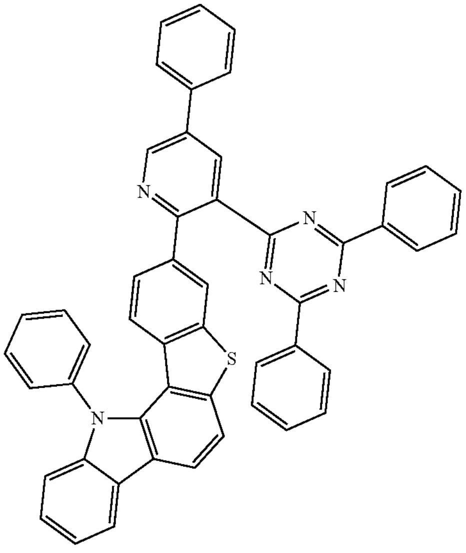

-continued
540
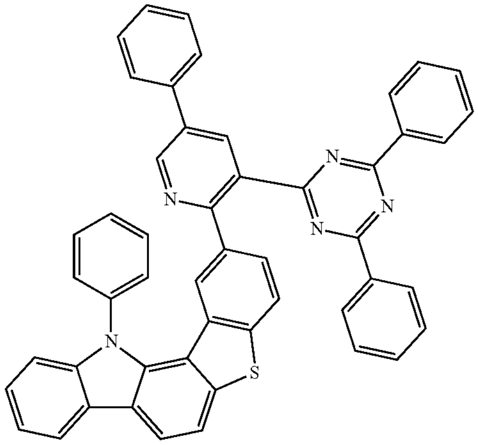
541
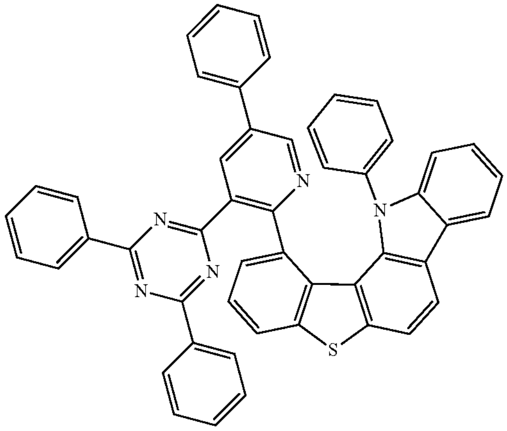
542
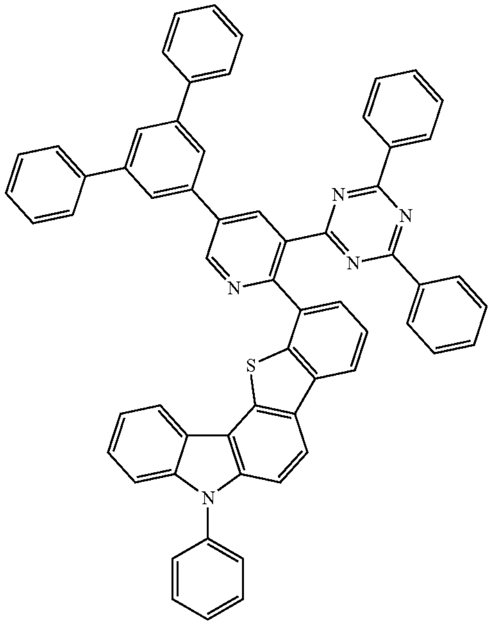
-continued
543
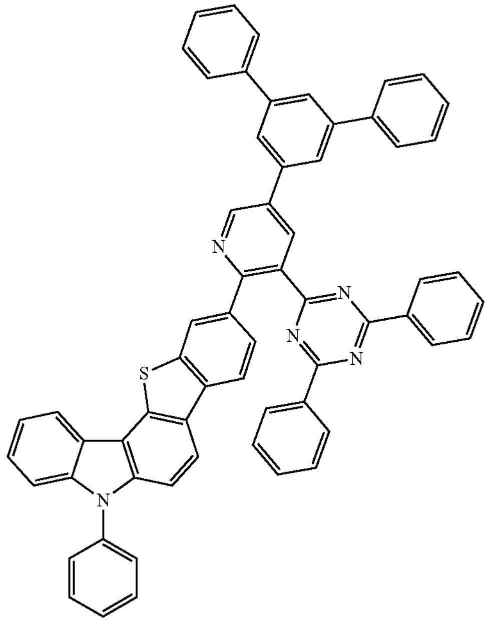
544
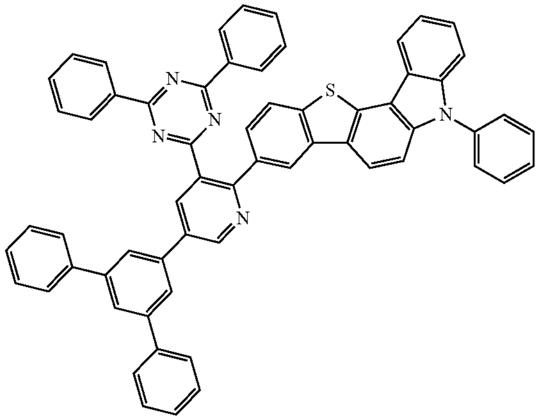
545
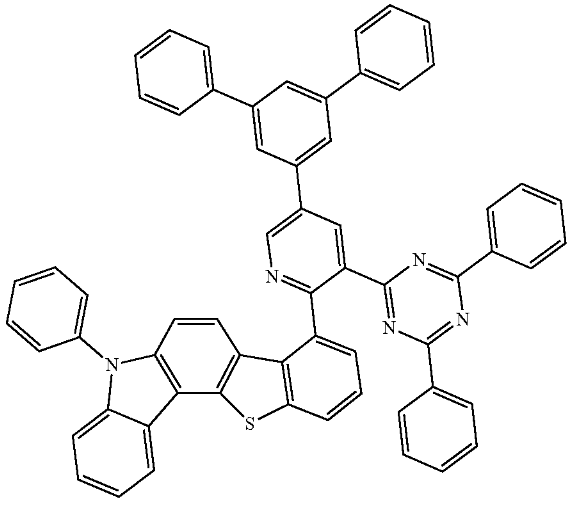

546
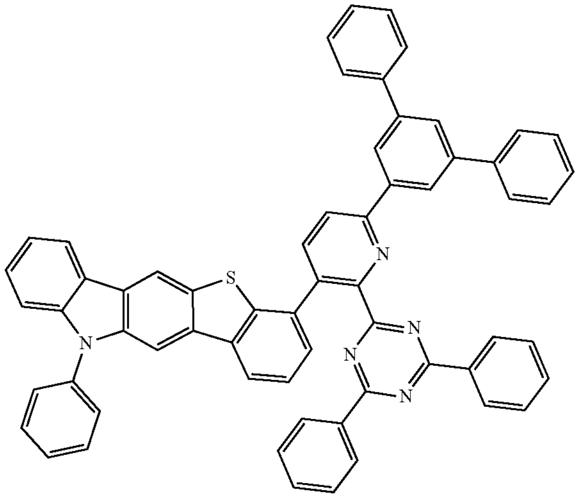
547
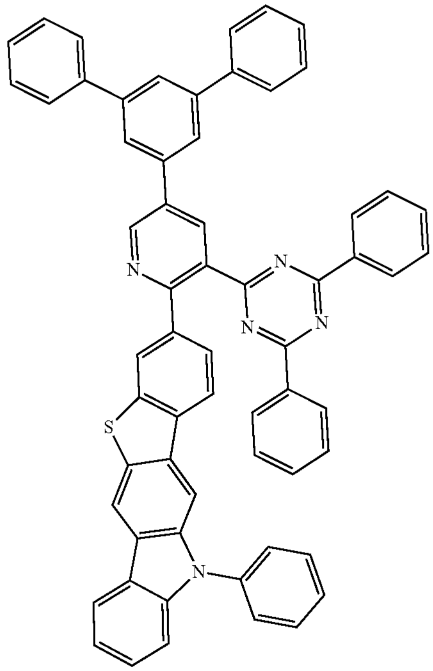
548
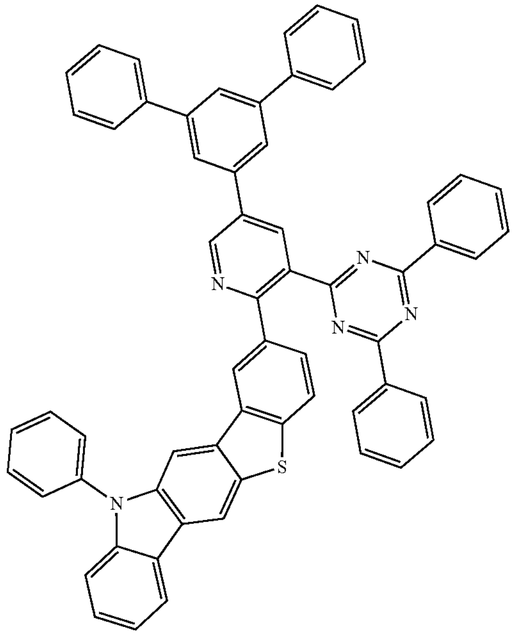
549
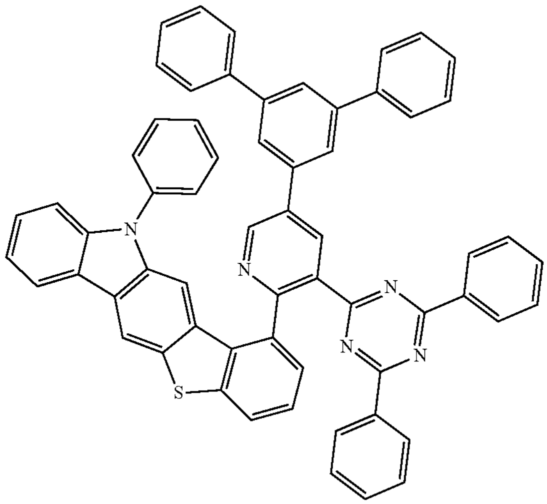
550
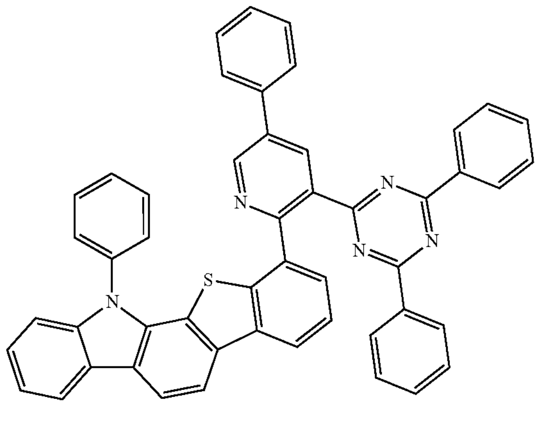

-continued
551
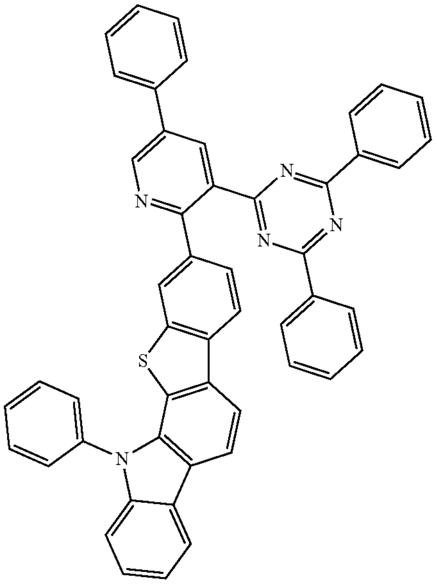
552
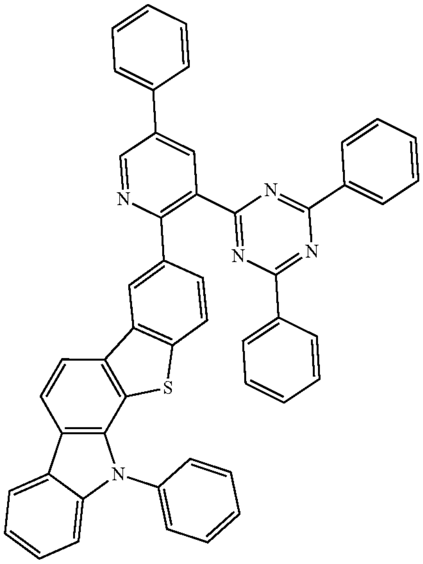
553
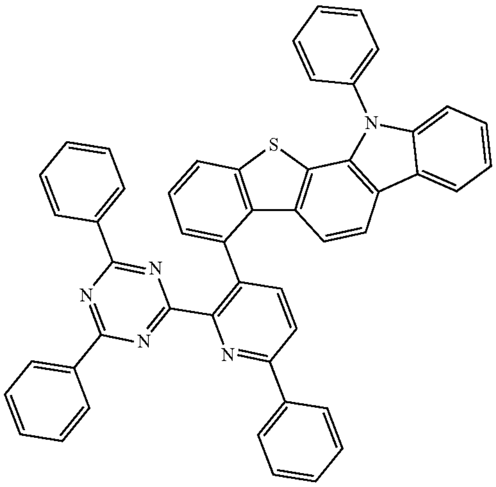
-continued
554
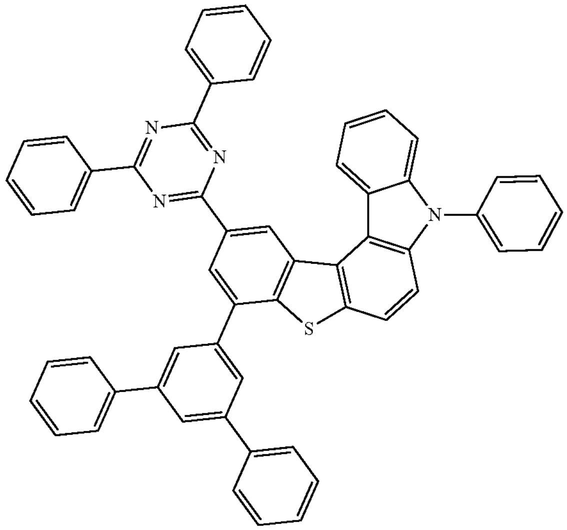
555
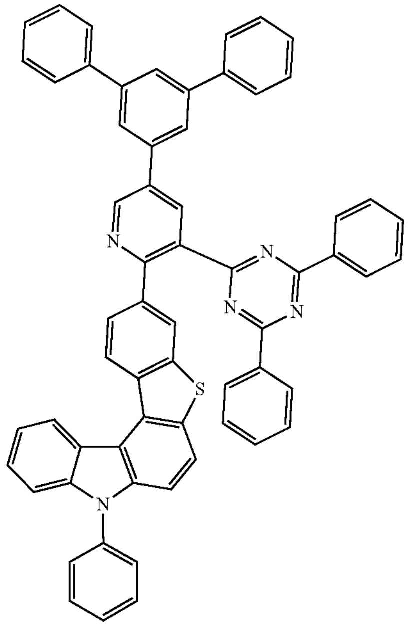

556
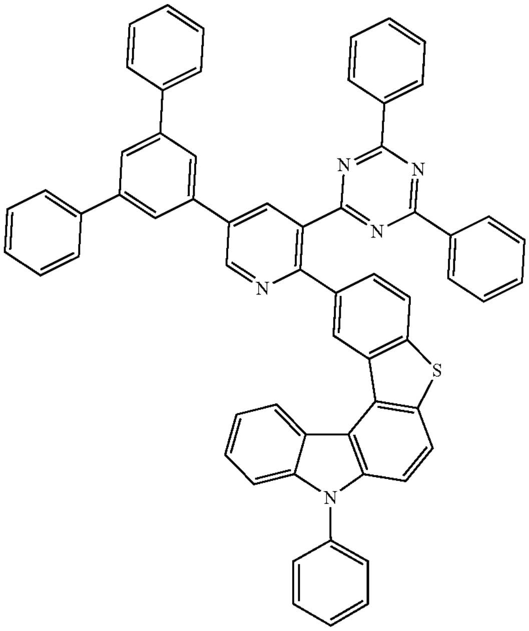
557
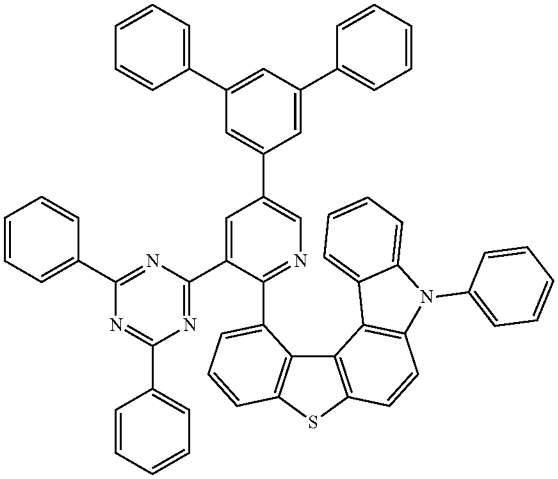
558
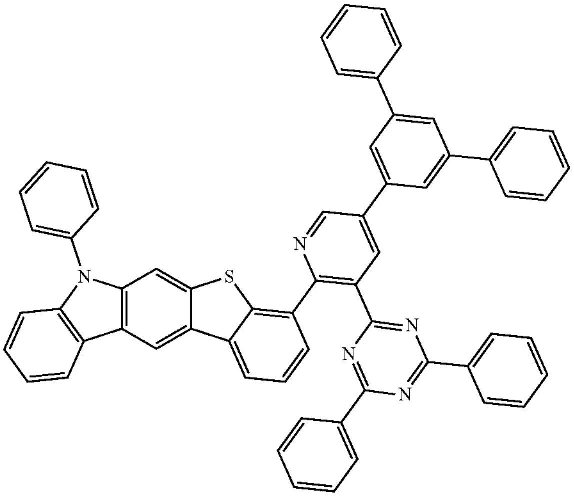
559
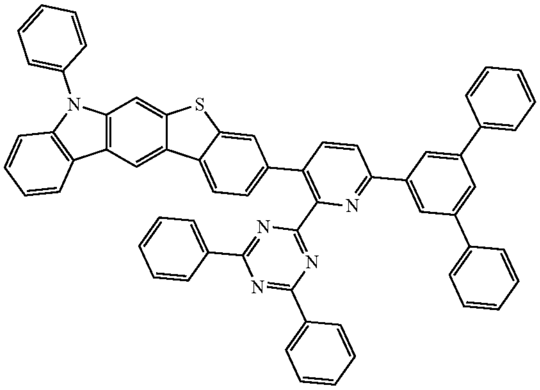
560
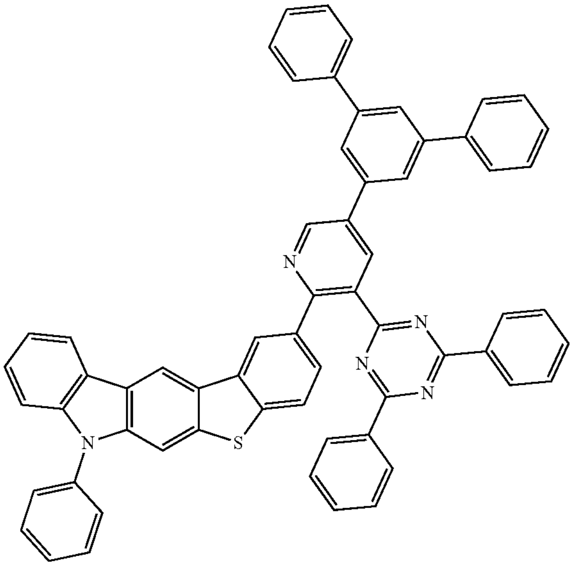

-continued
561
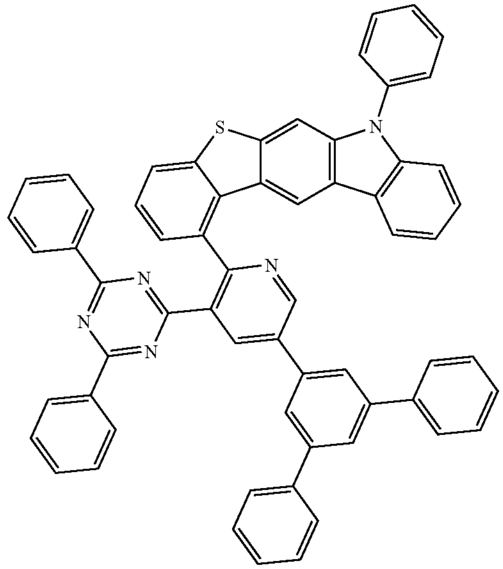
562
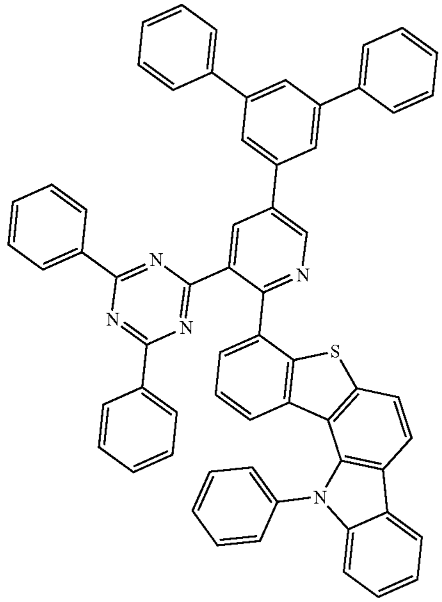
-continued
563
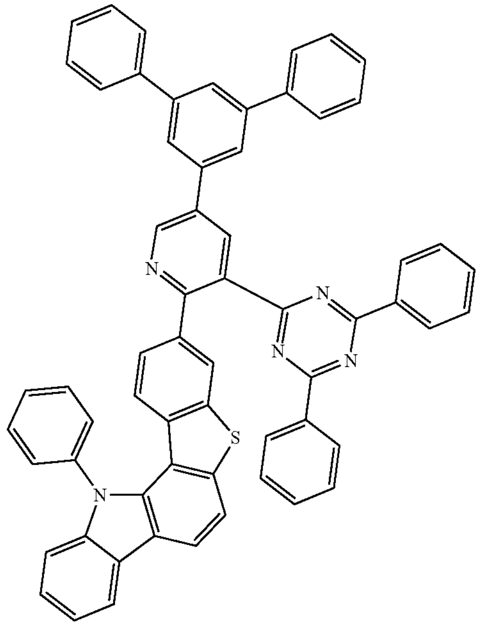
564
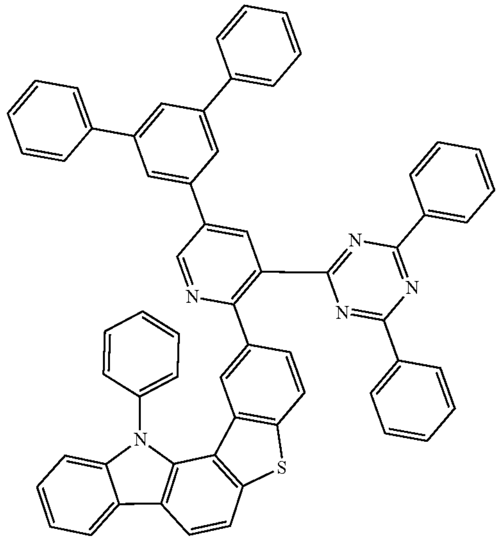

-continued
565
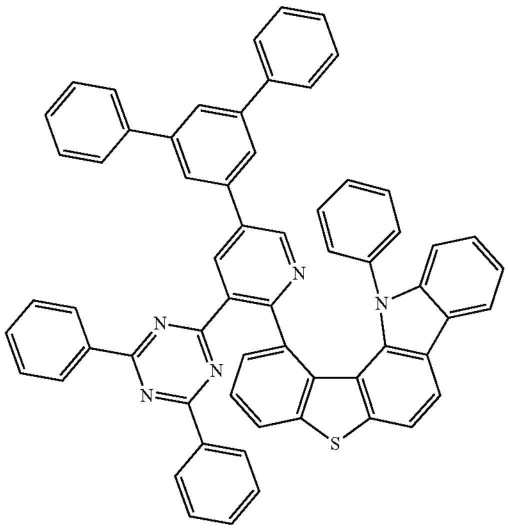
566
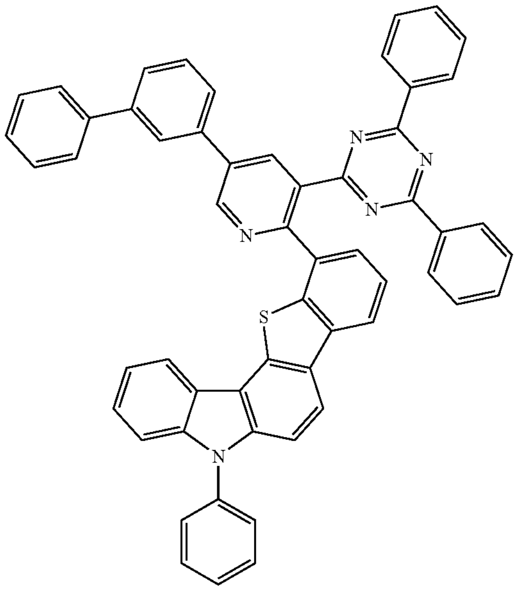
-continued
567
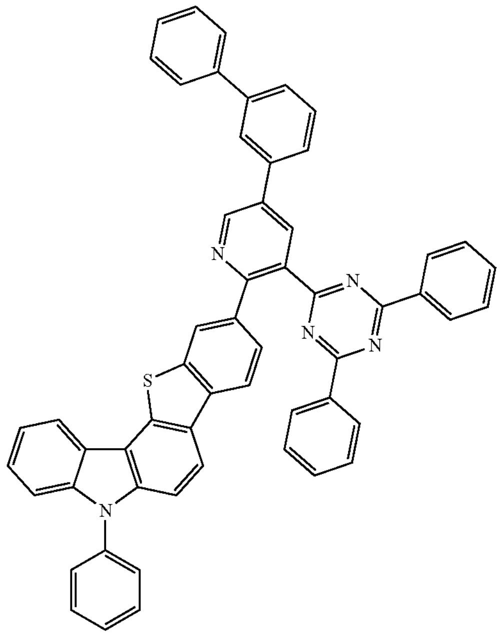
568
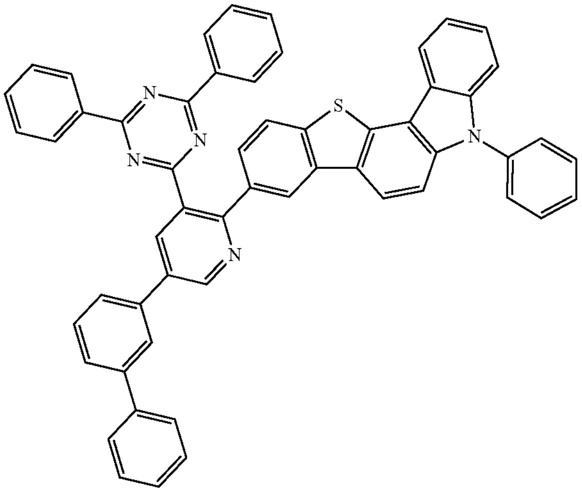
569
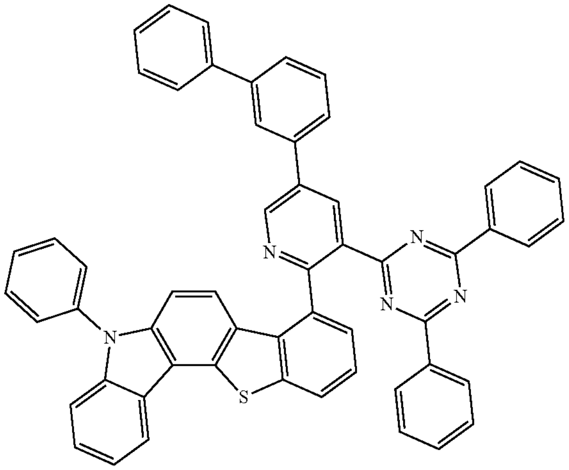

-continued
570
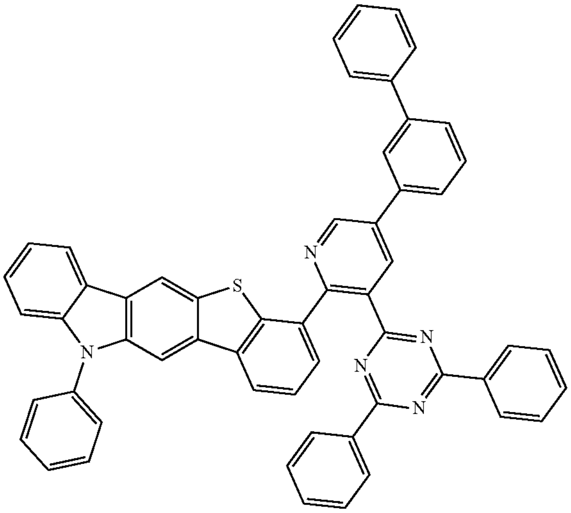
571
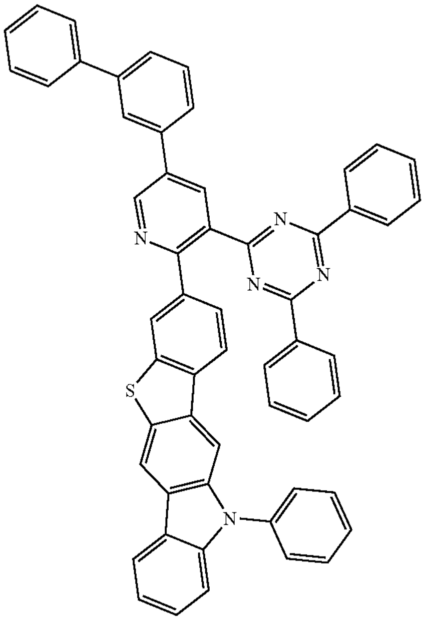
-continued
572
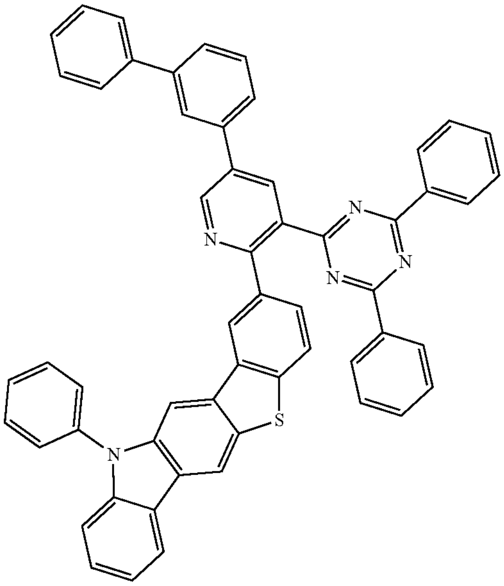
573
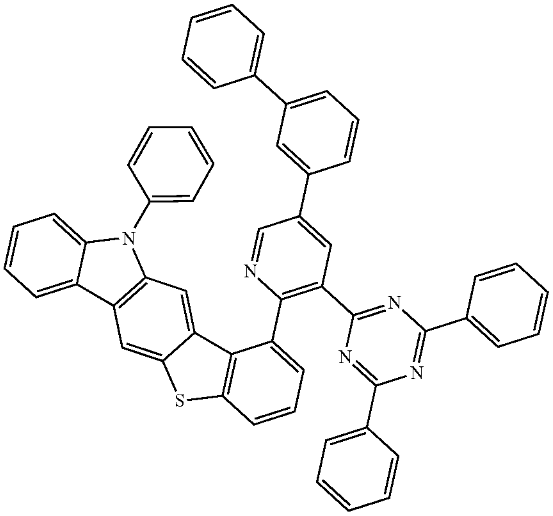
574
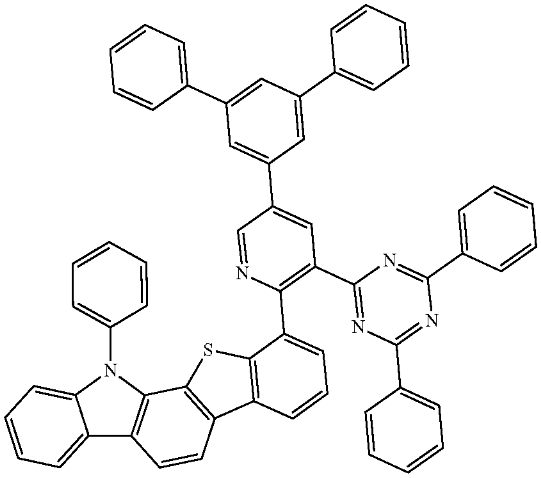

575
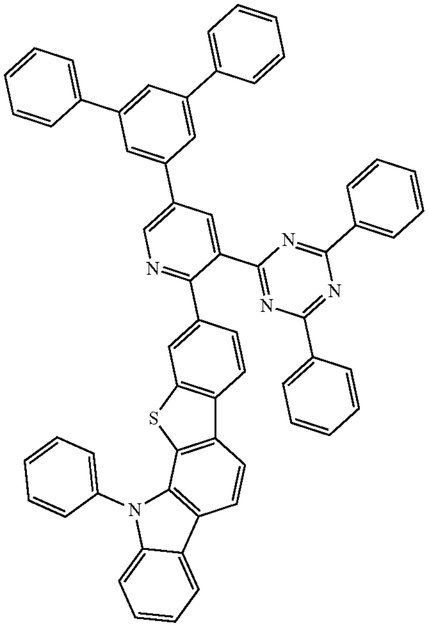
577
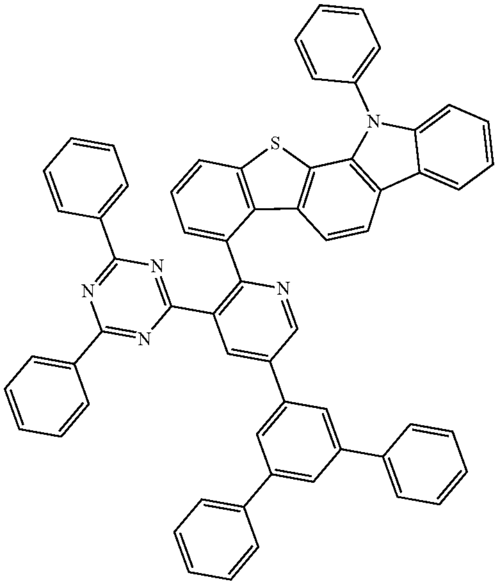
576
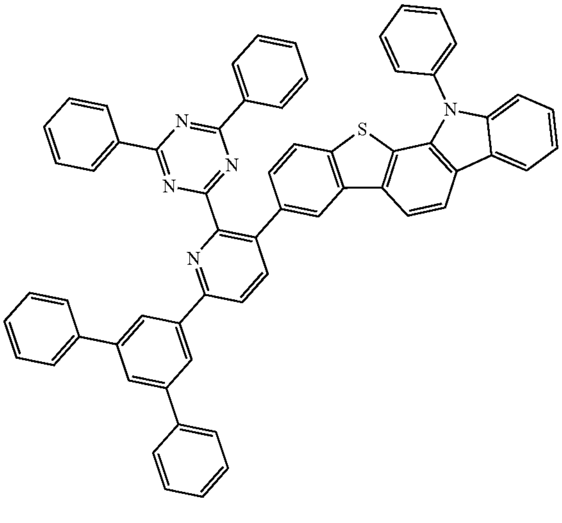
578
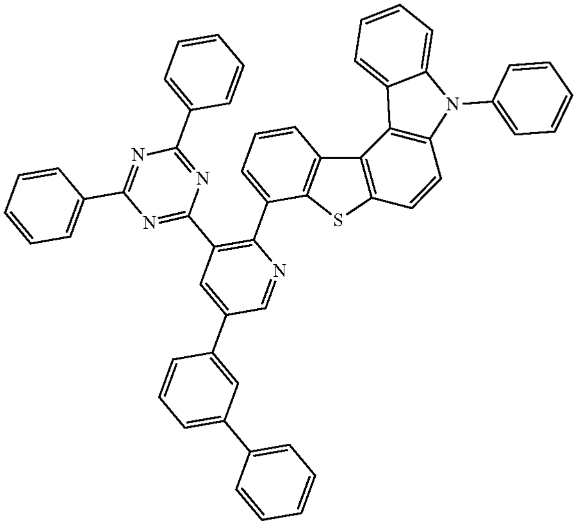

-continued
579
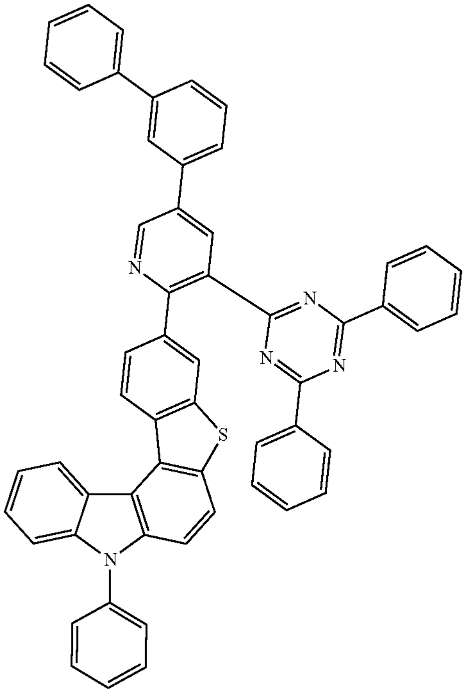
580
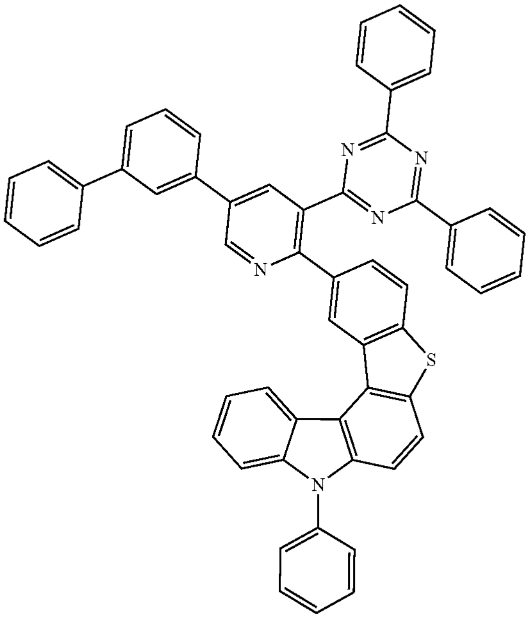
-continued
581
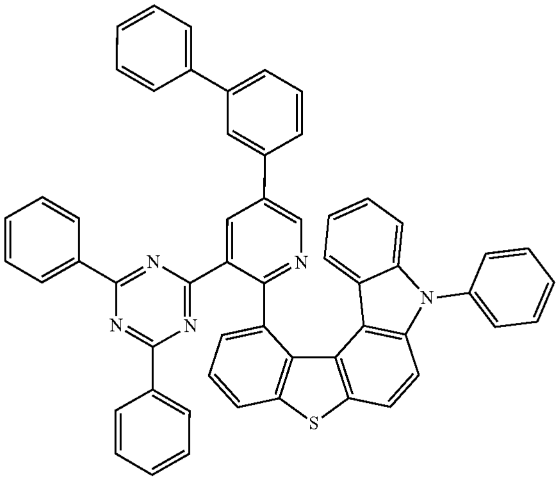
582
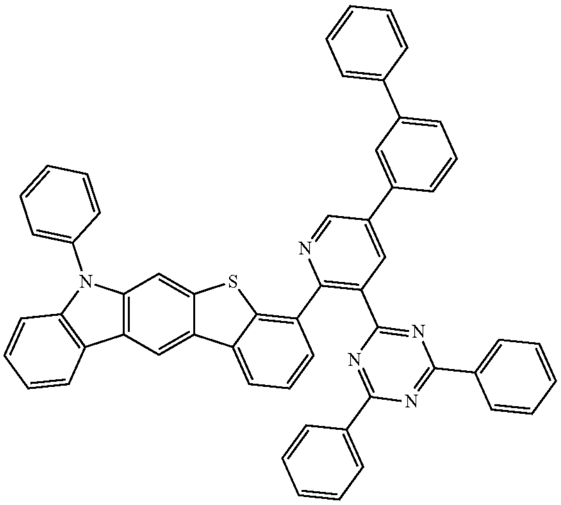
583
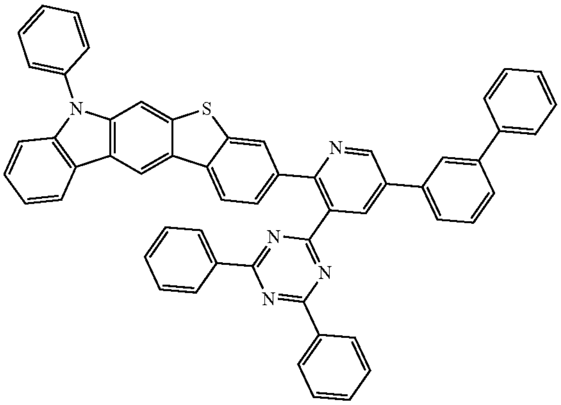

-continued
584
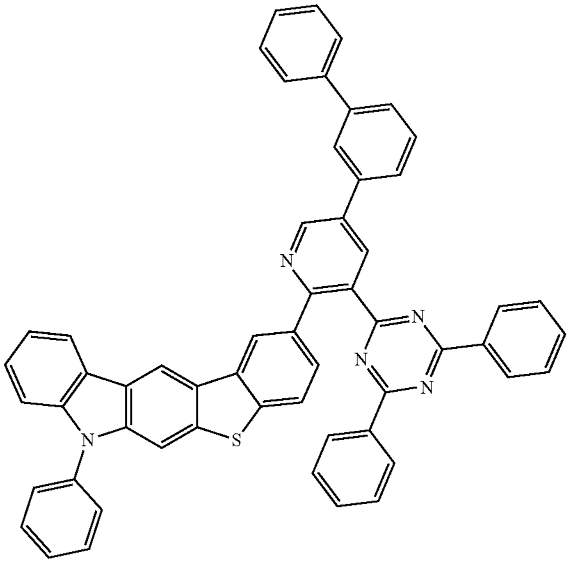
585
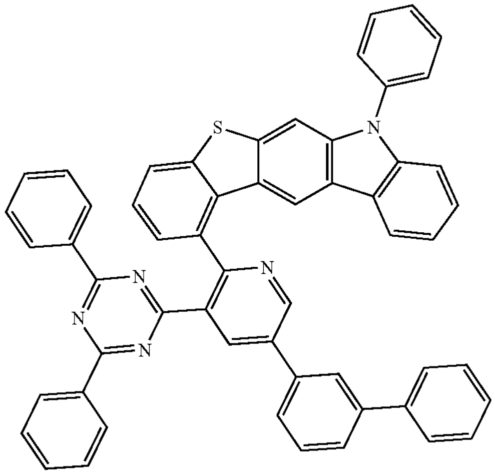
586
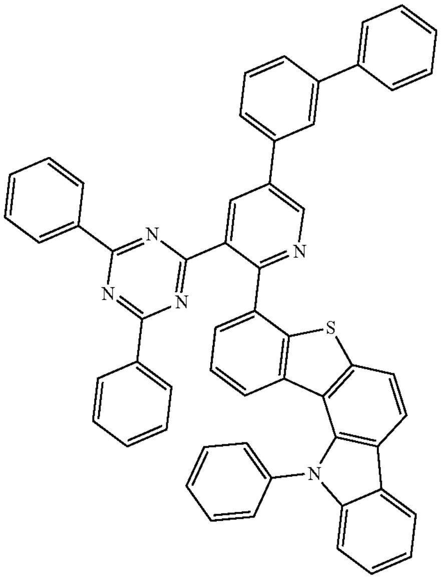
-continued
587
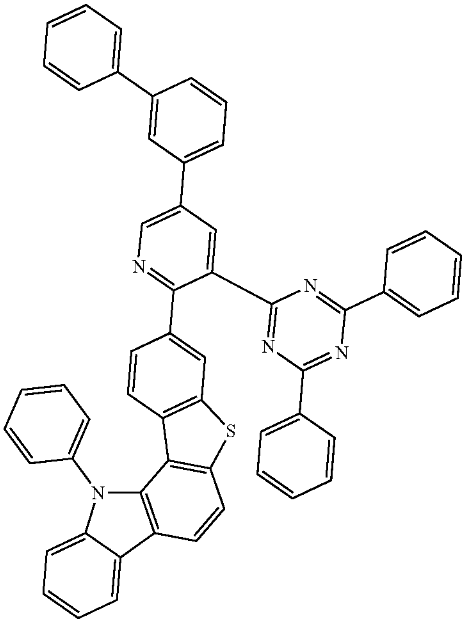
588
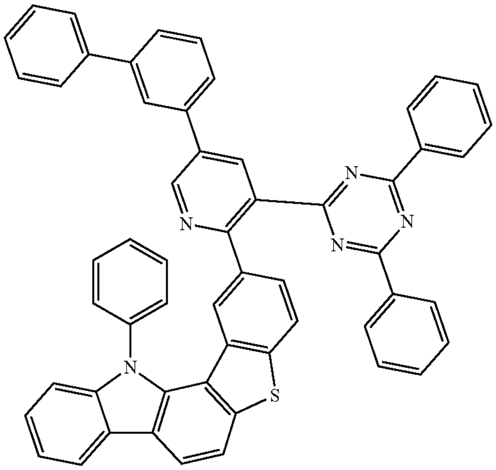

-continued
589
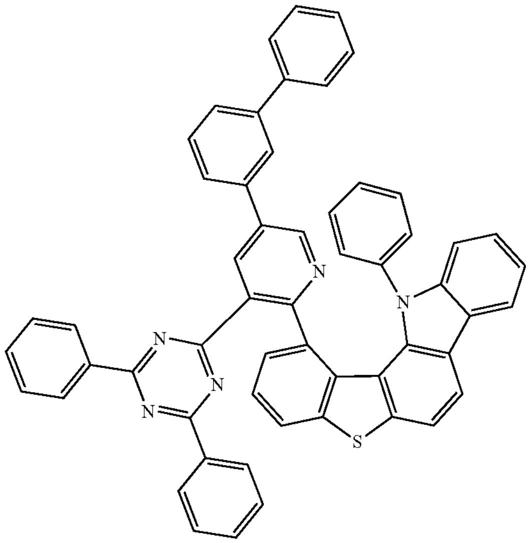
590
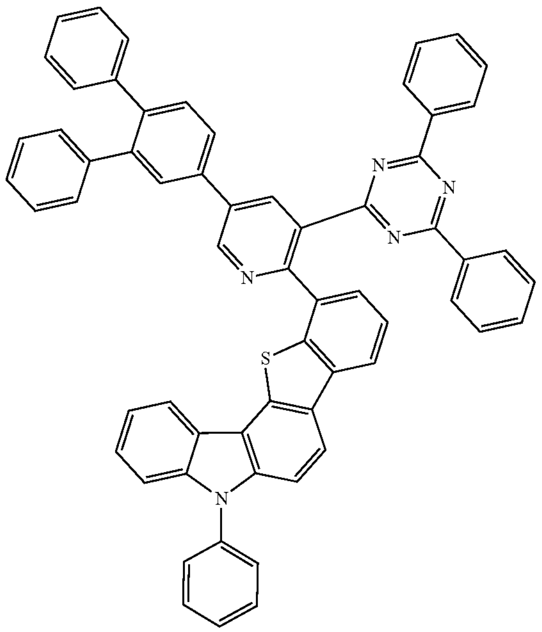
-continued
591
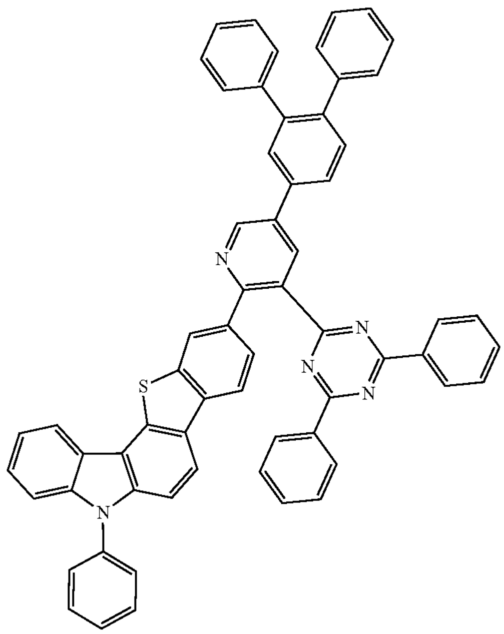
592
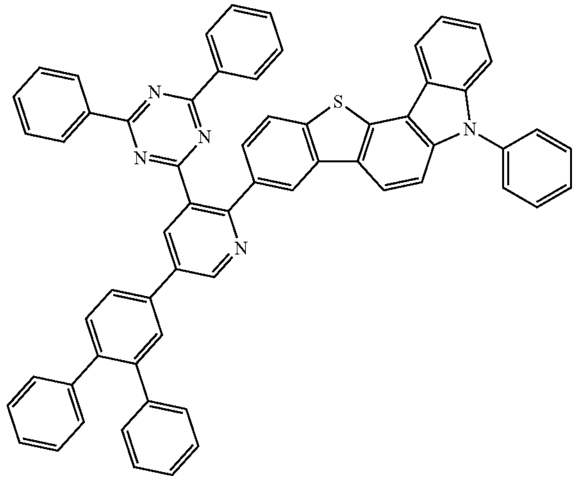

593
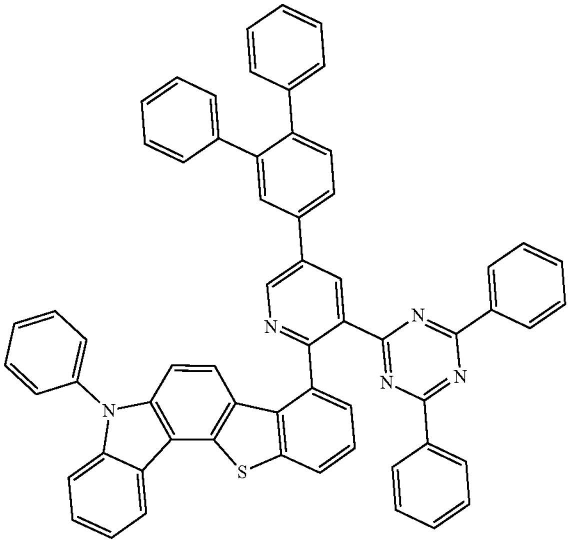
594
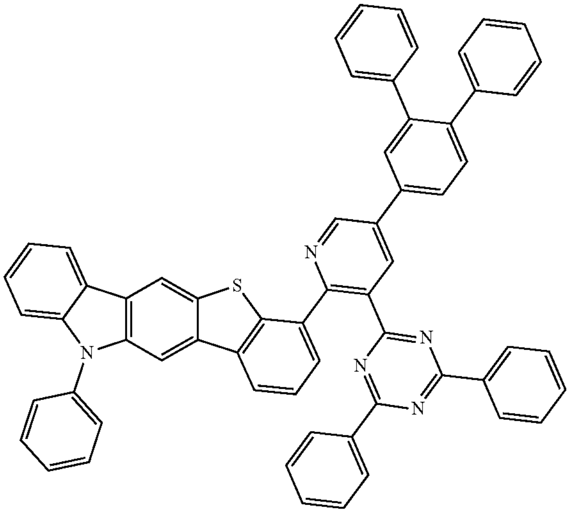
595
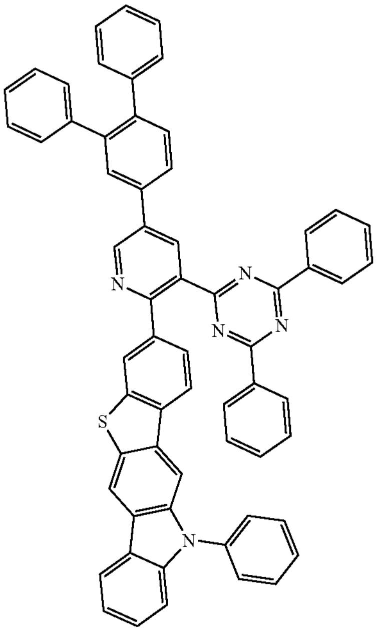
596
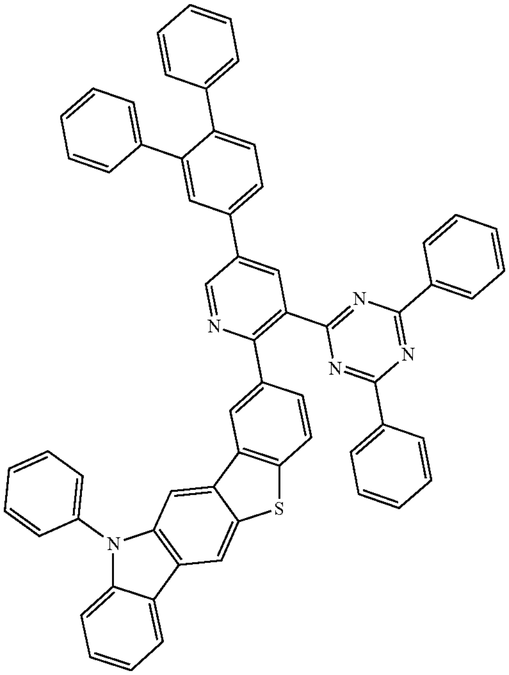

-continued
597
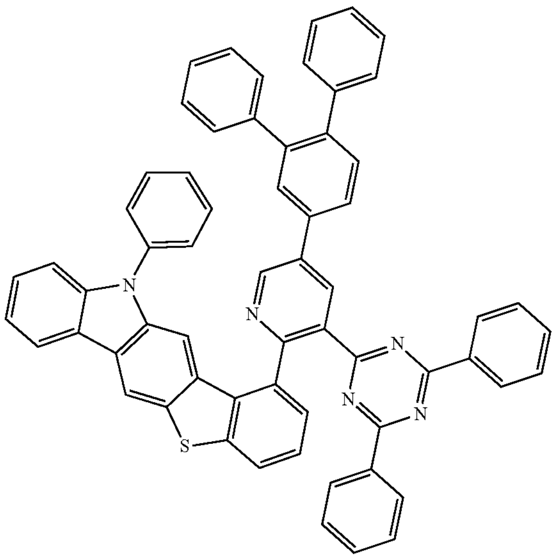
598
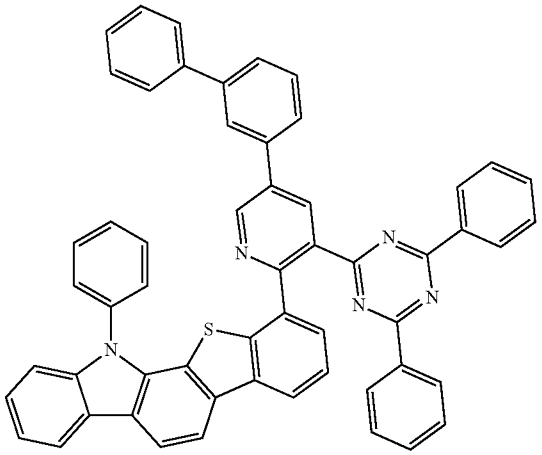
-continued
599
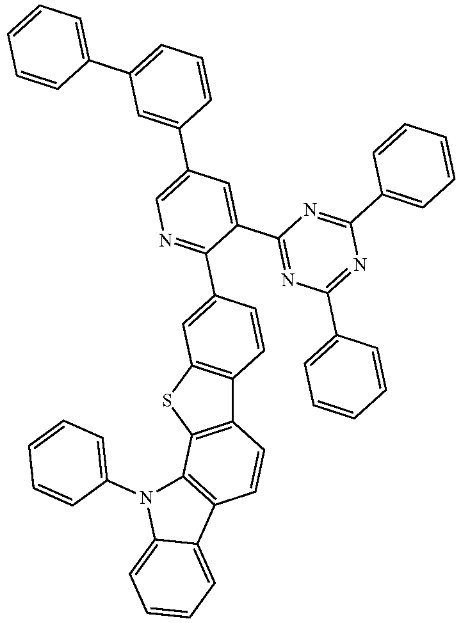
600
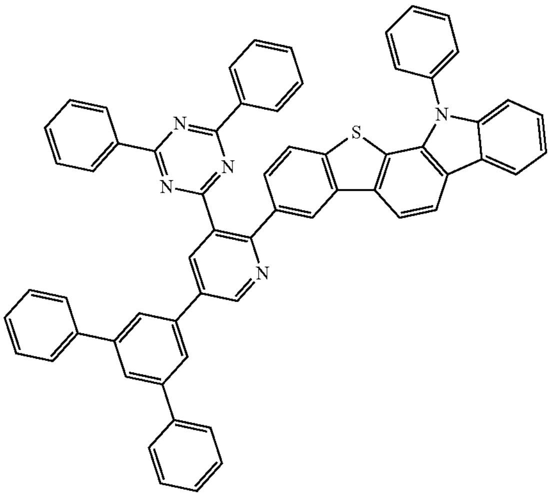

-continued
601
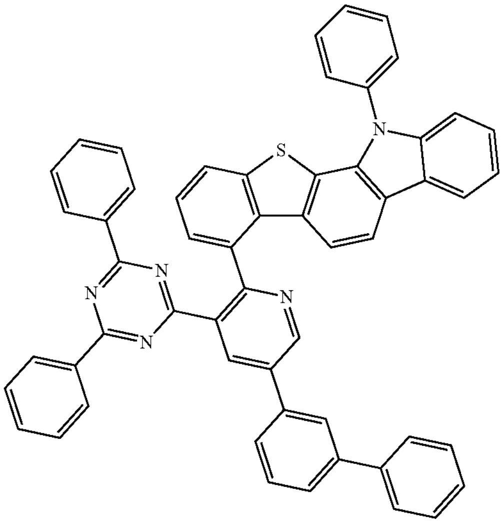
602
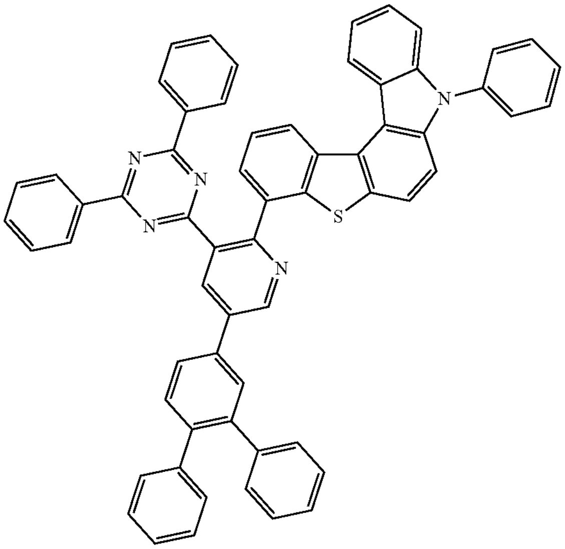
-continued
603
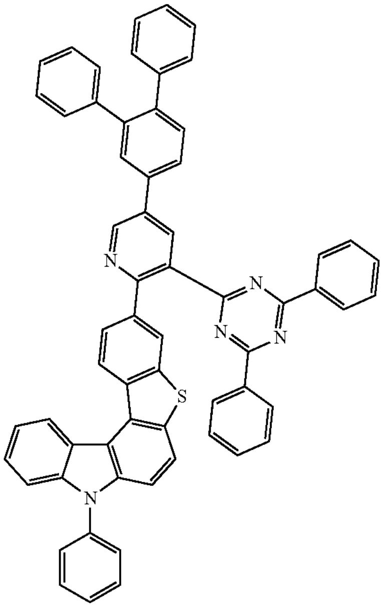
604
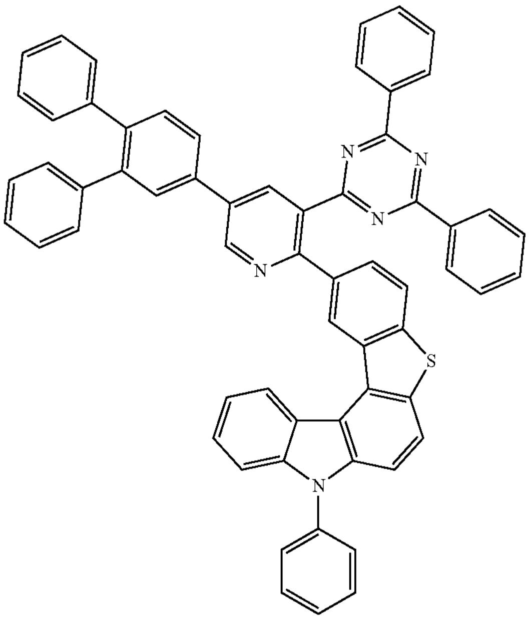

-continued
605
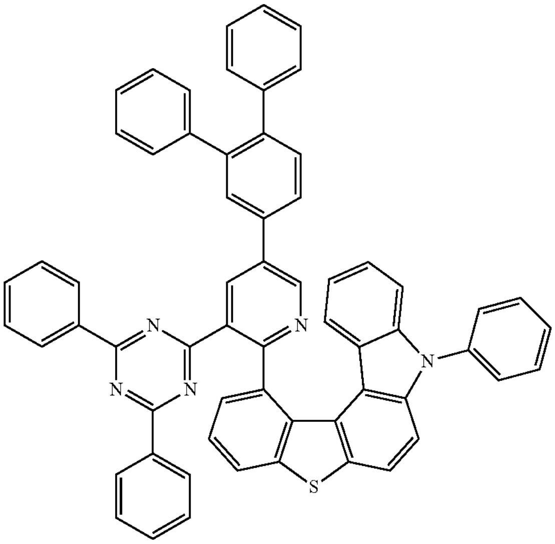
606
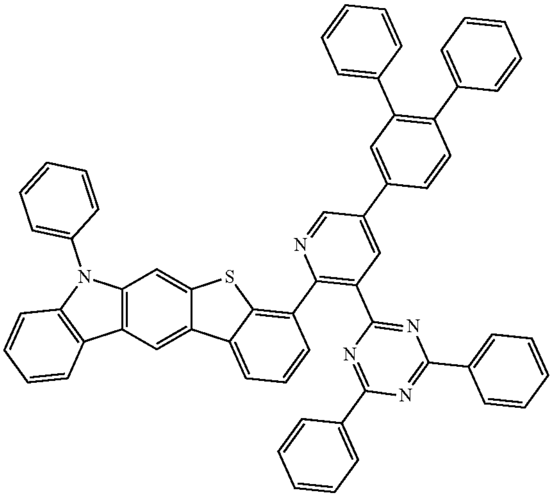
607
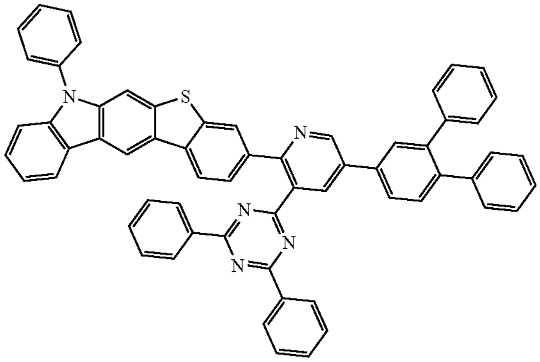
-continued
608
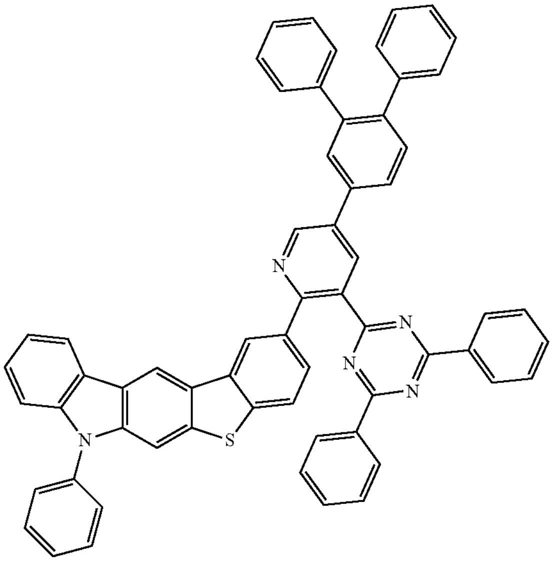
609
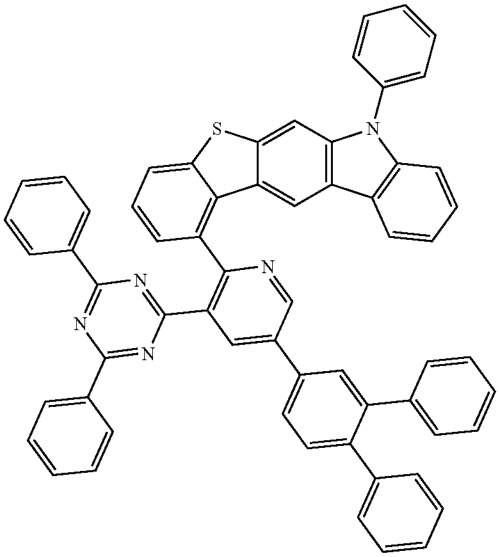

610
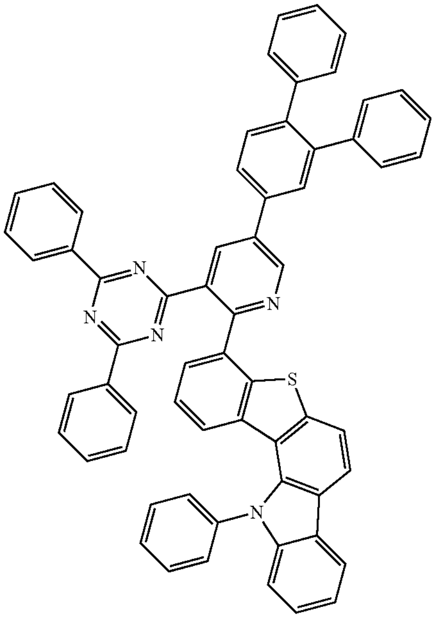
611
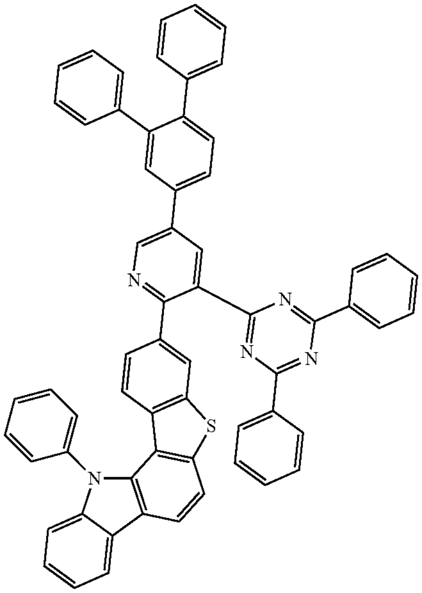
612
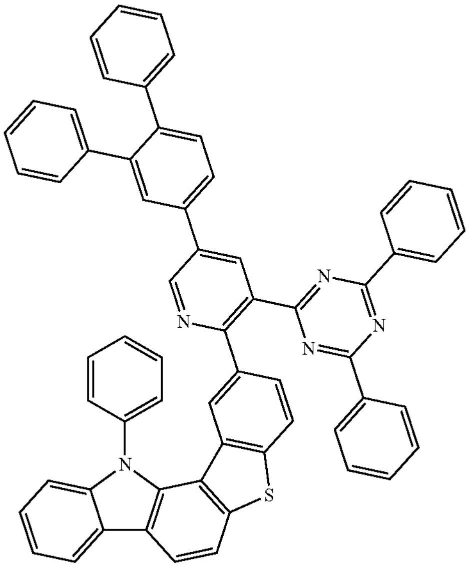
613
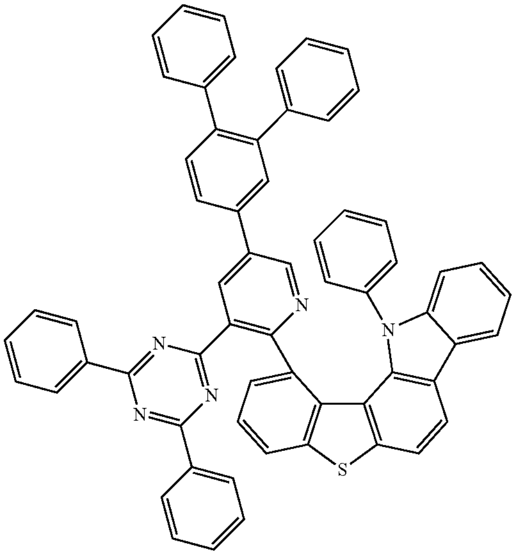

-continued
614
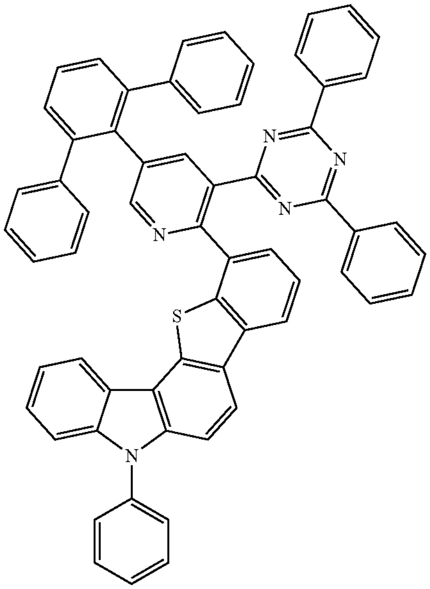
615
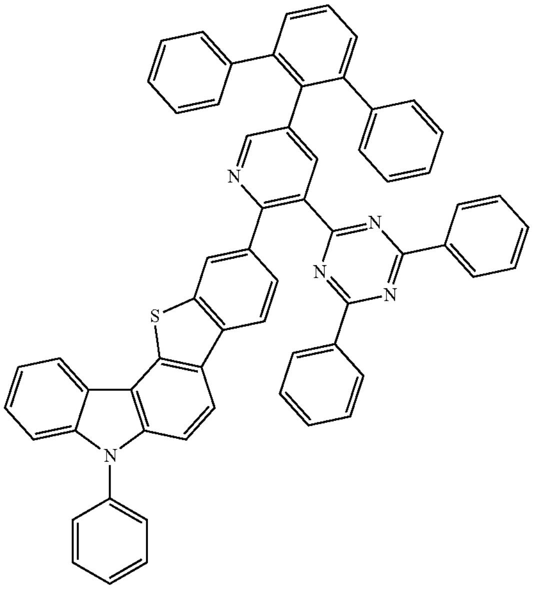
616
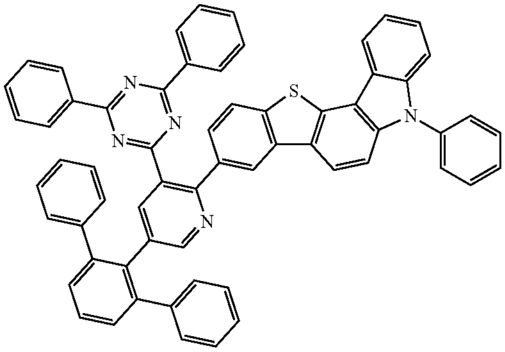
-continued
617
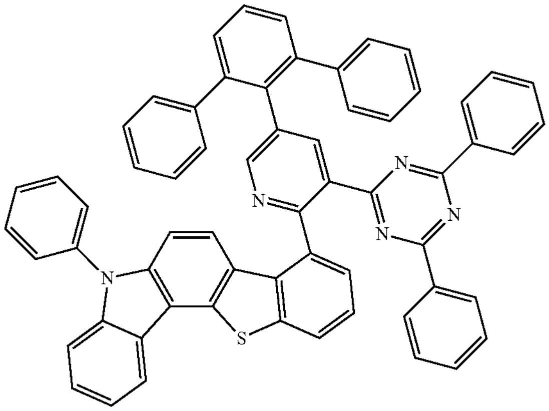
618
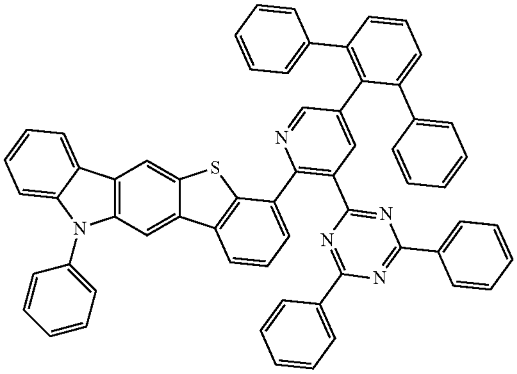
619
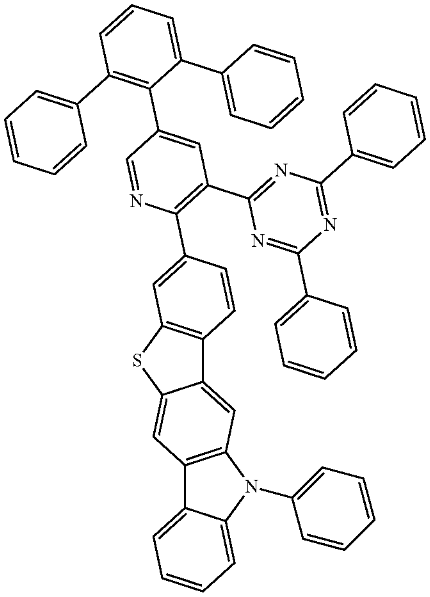

-continued
620
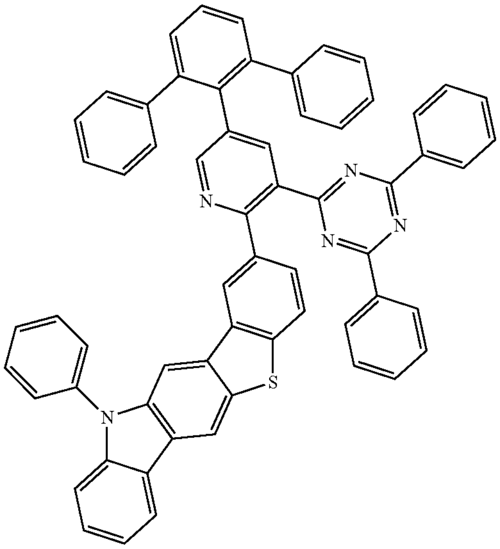
621
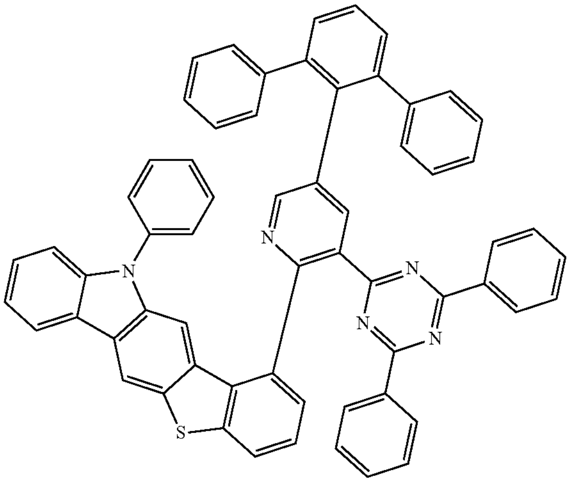
622
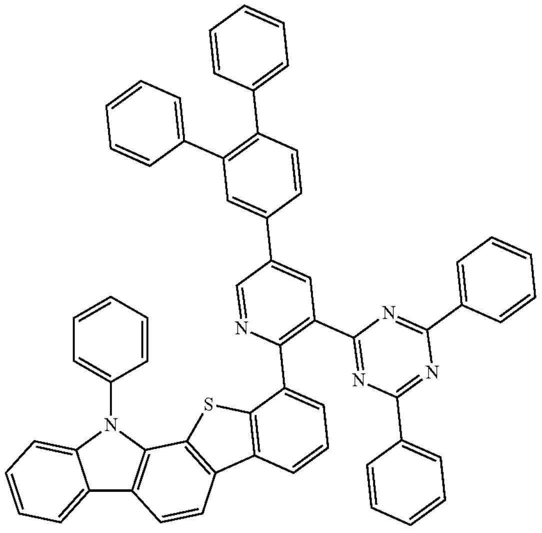
-continued
623
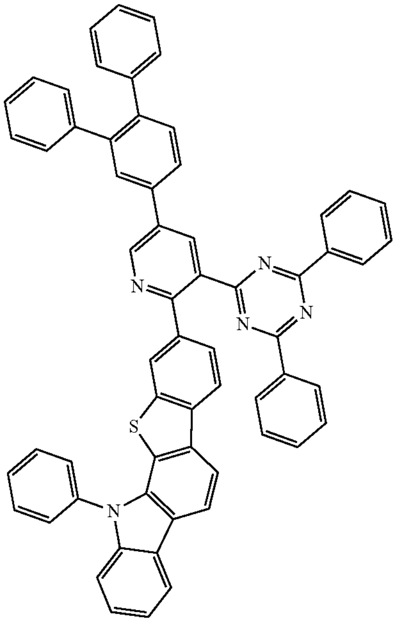
624
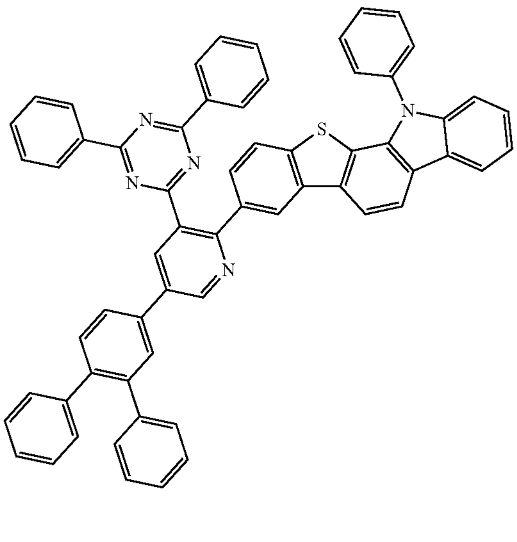

-continued
625
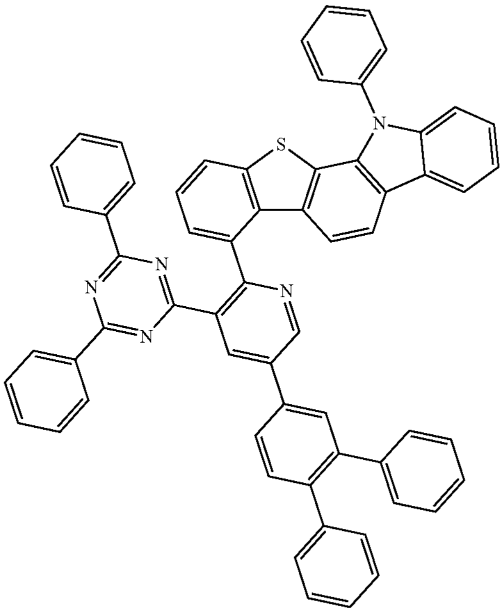
626
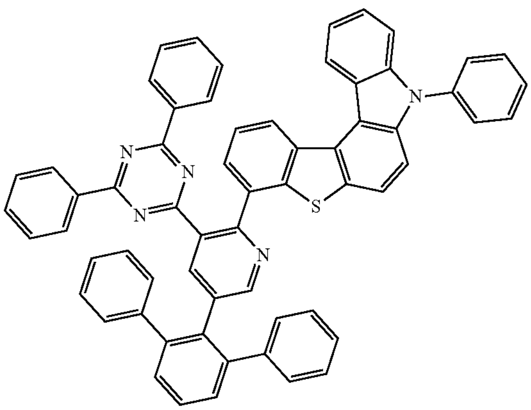
-continued
627
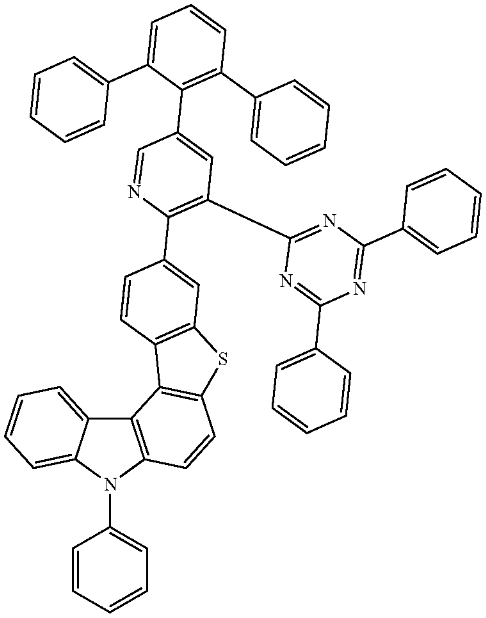
628
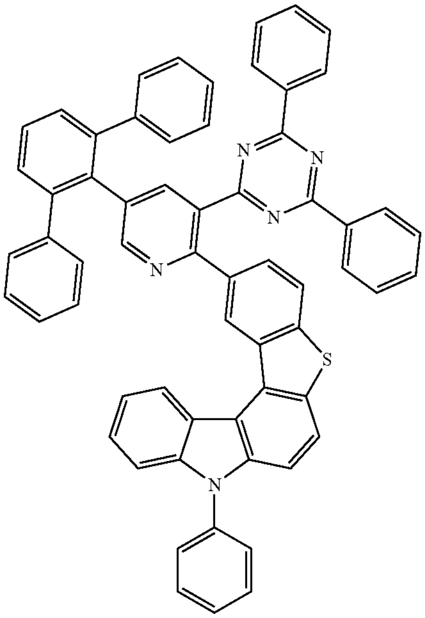

629
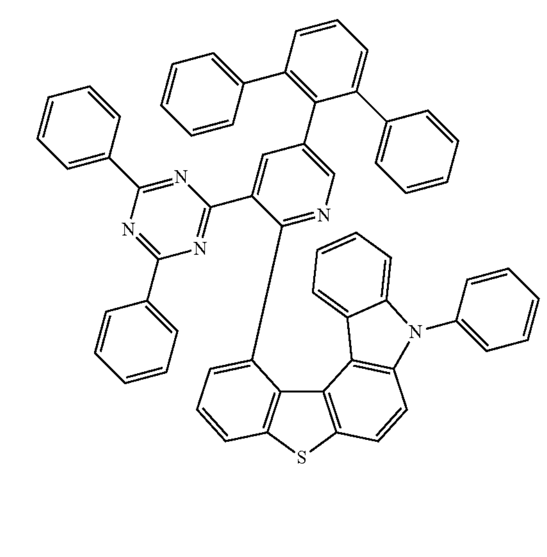
630
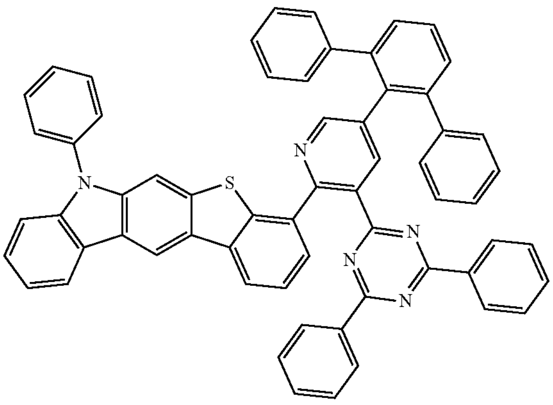
631
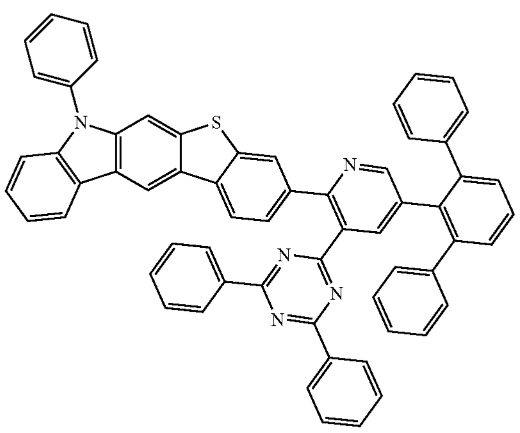
632
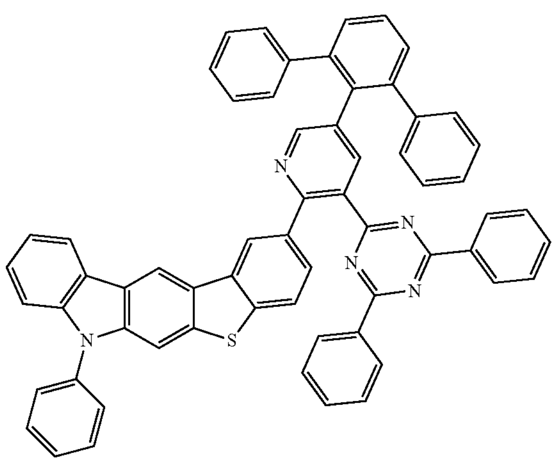
633
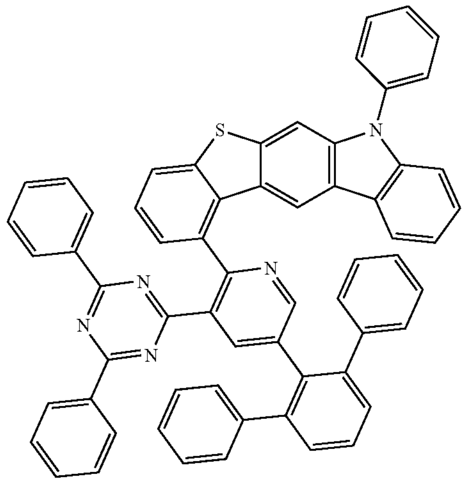
634
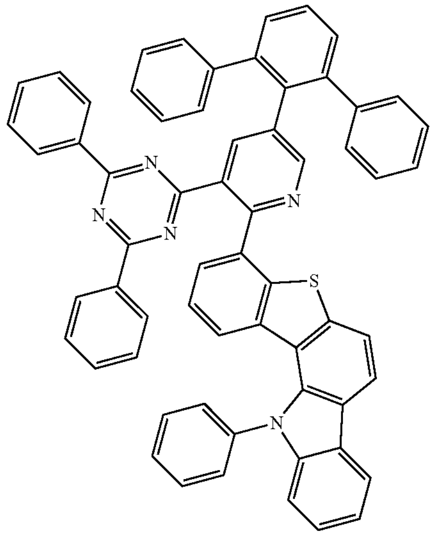

-continued
635
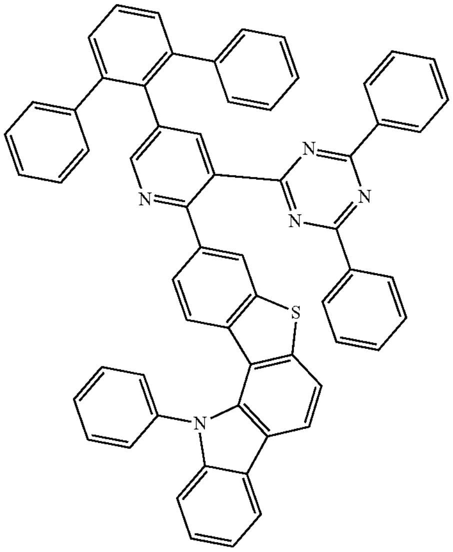
636
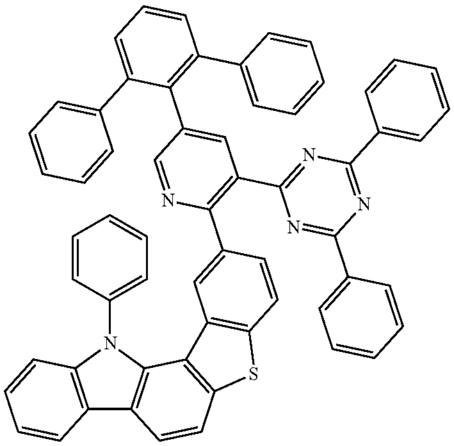
637
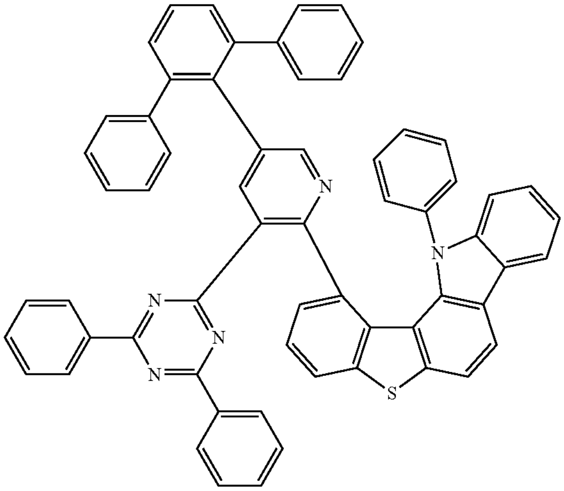
-continued
638
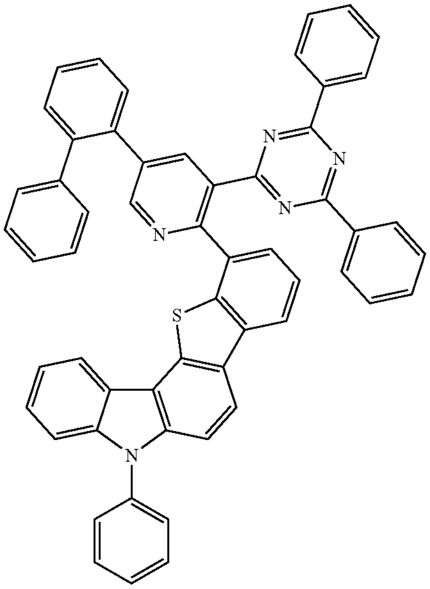
639
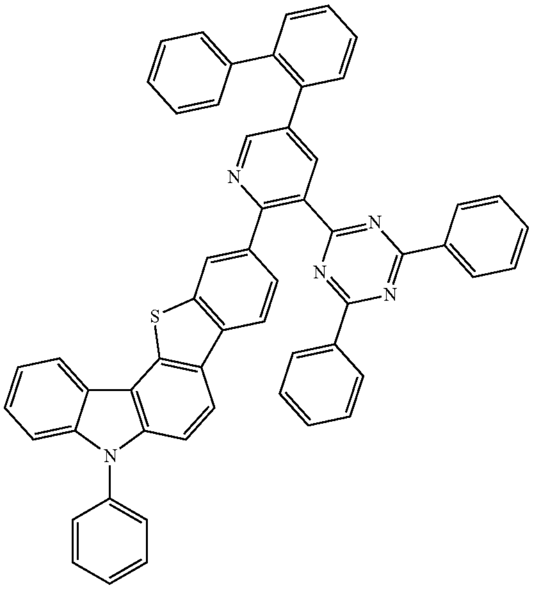
640
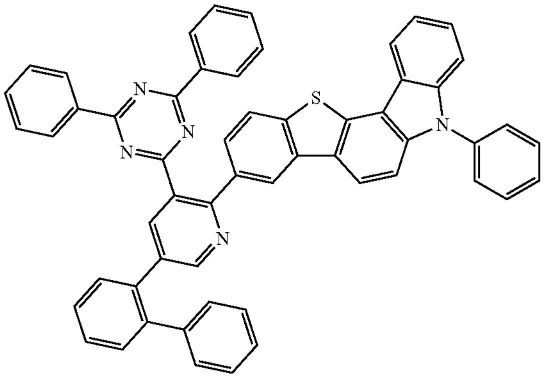

-continued
641
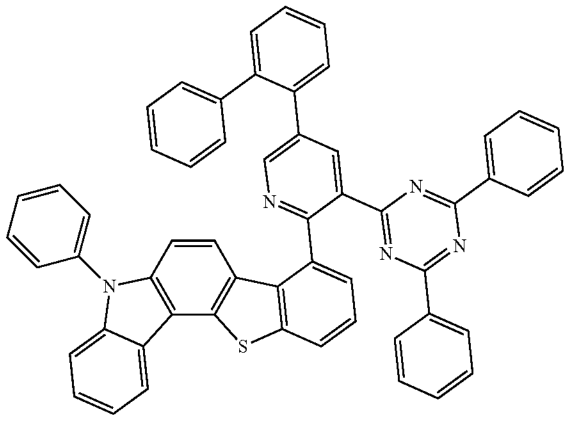
642
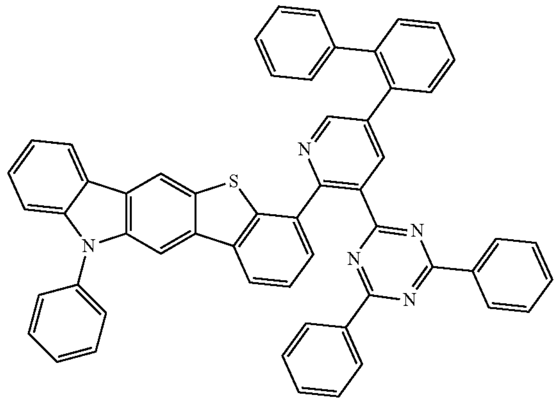
643
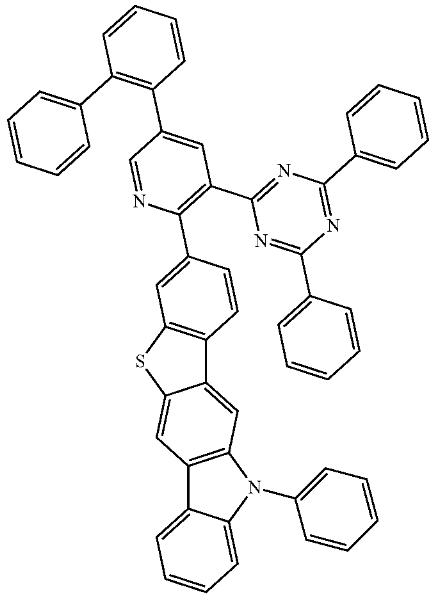
-continued
644
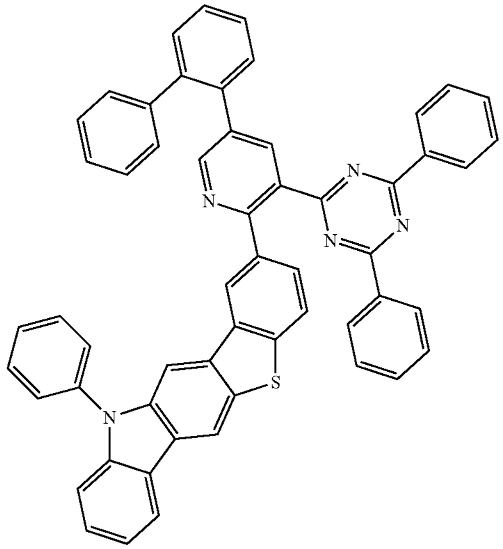
645
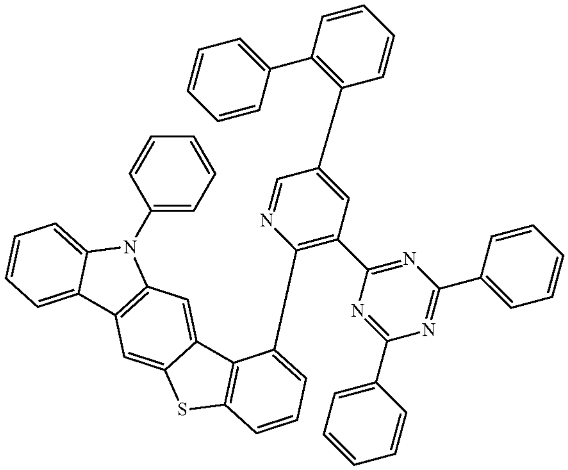
646
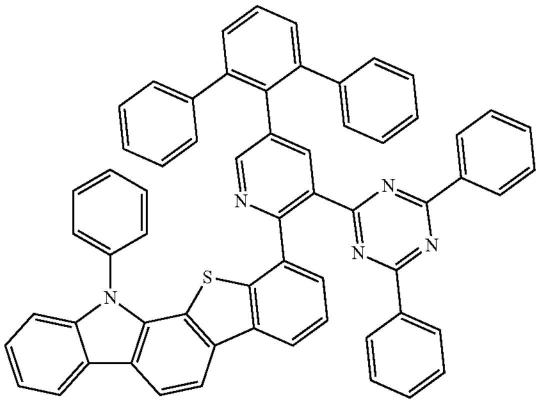

-continued
647
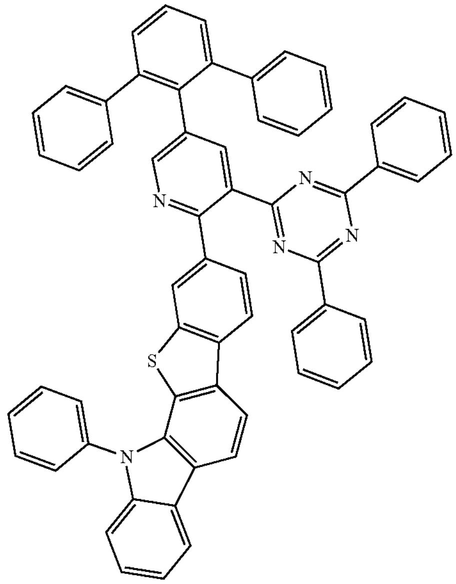
648
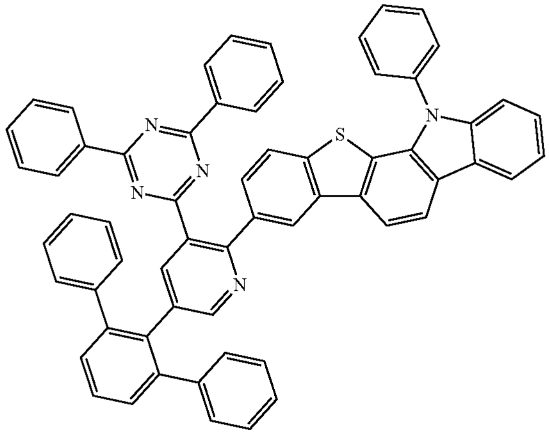
649
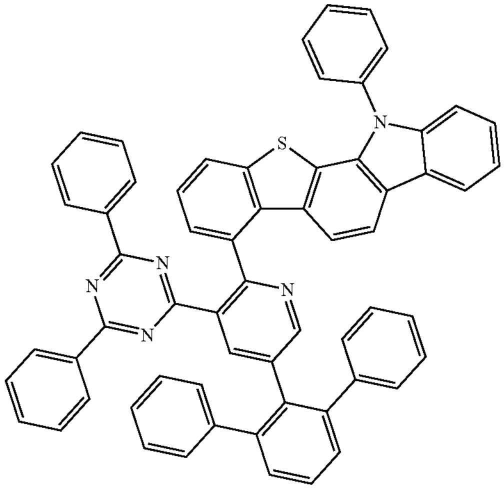
-continued
650
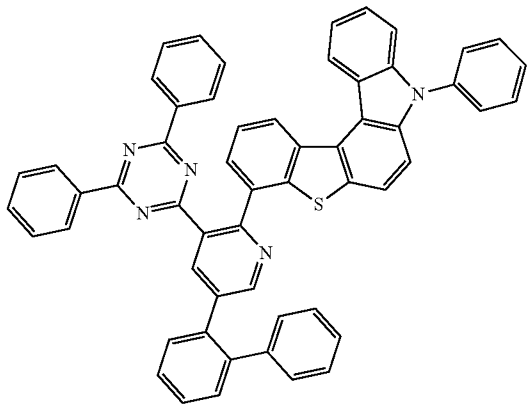
651
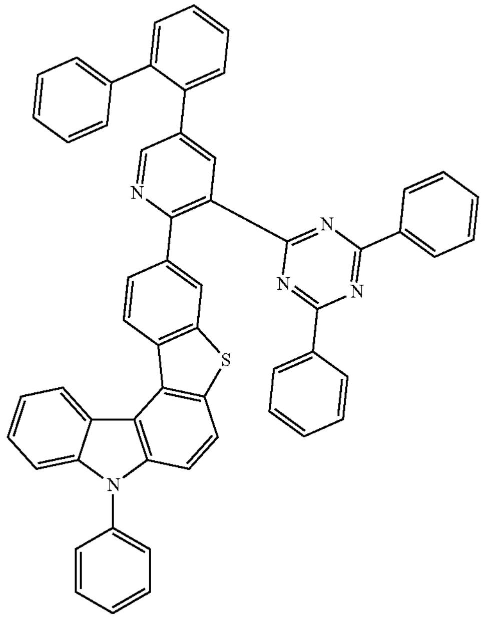
652
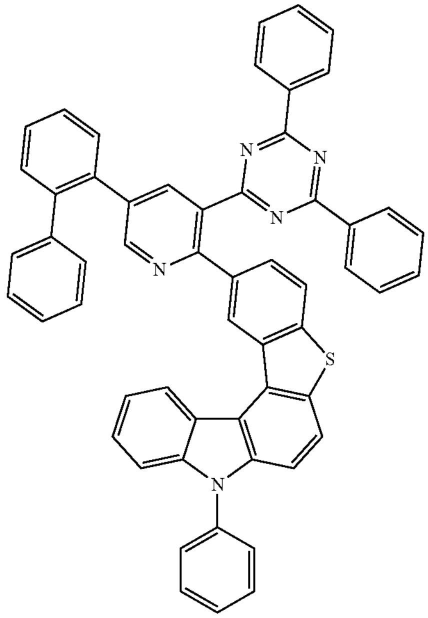

-continued
653
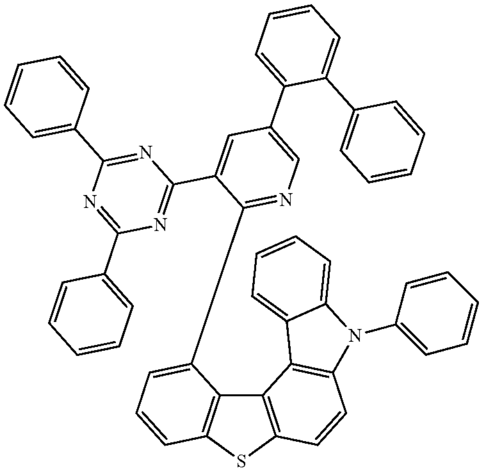
654
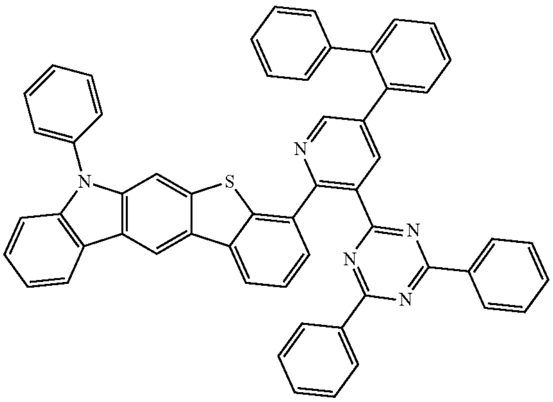
655
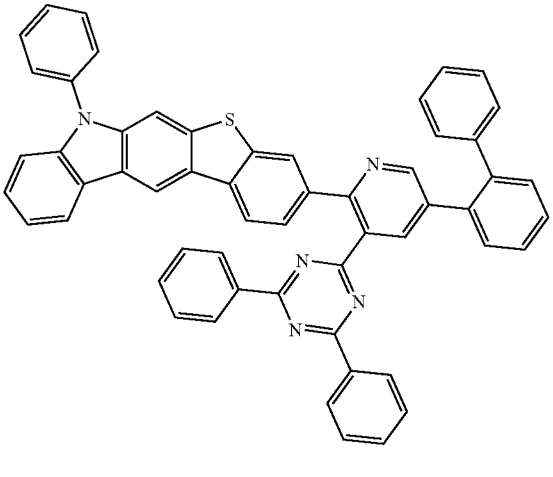
-continued
656
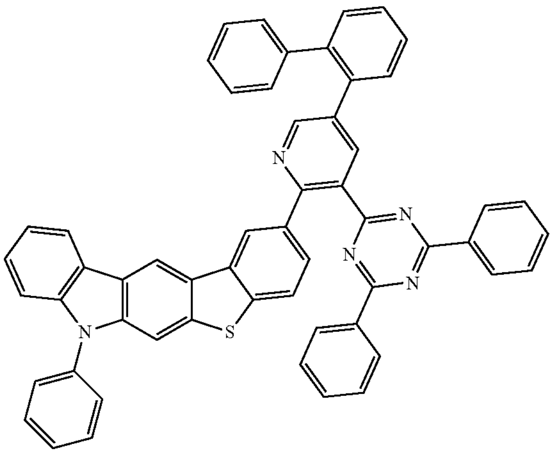
657
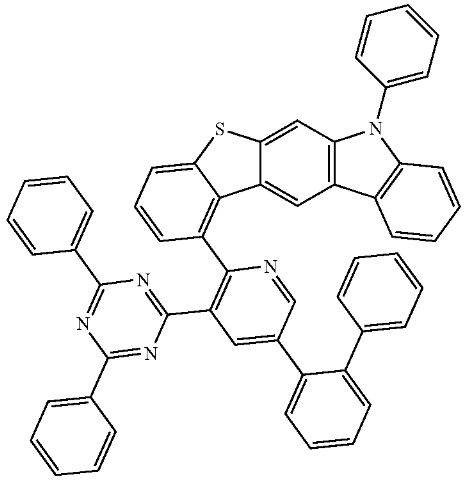
658
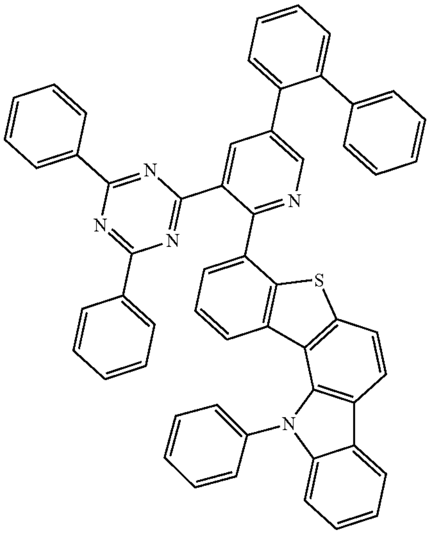

-continued
659
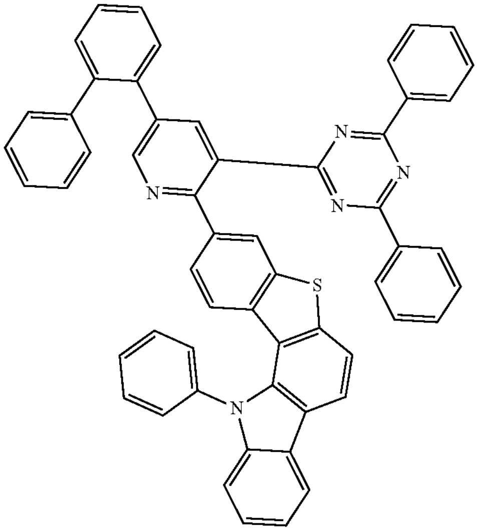
660
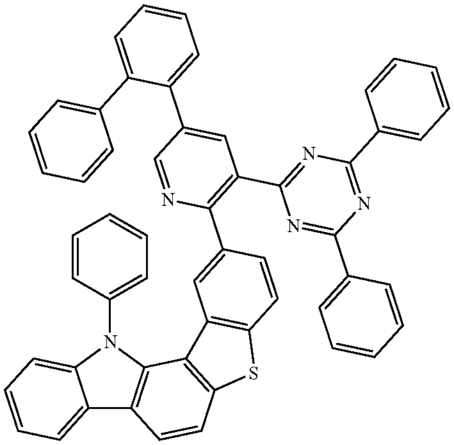
661
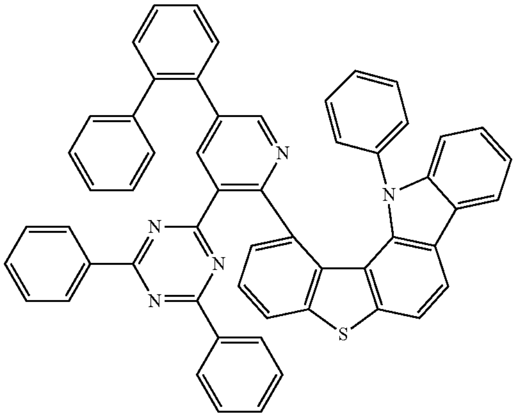
-continued
662
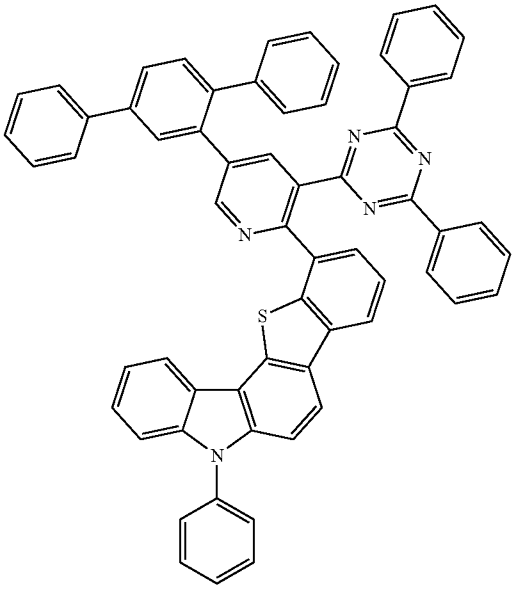
663
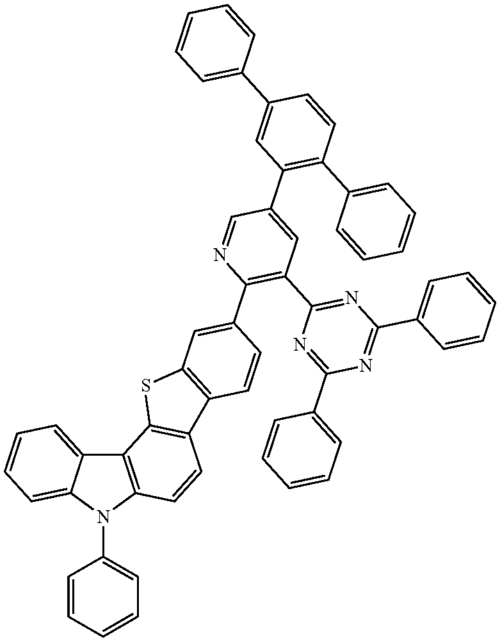

-continued
664
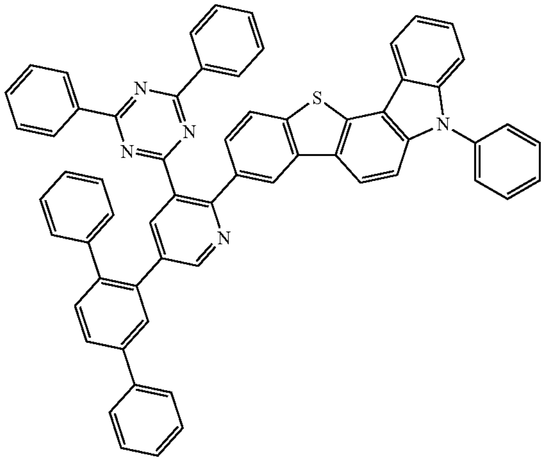
665
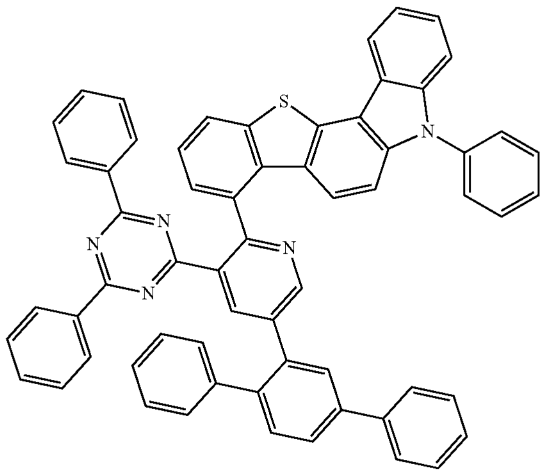
666
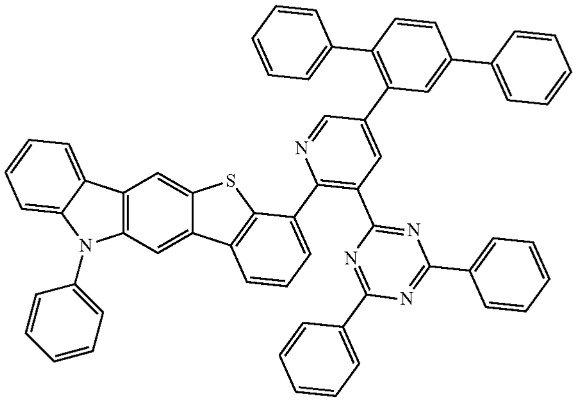
-continued
667
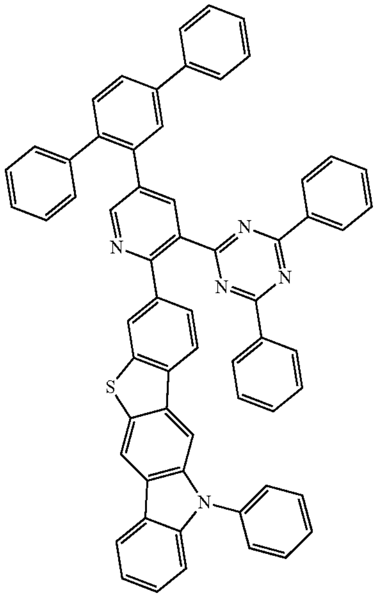
668
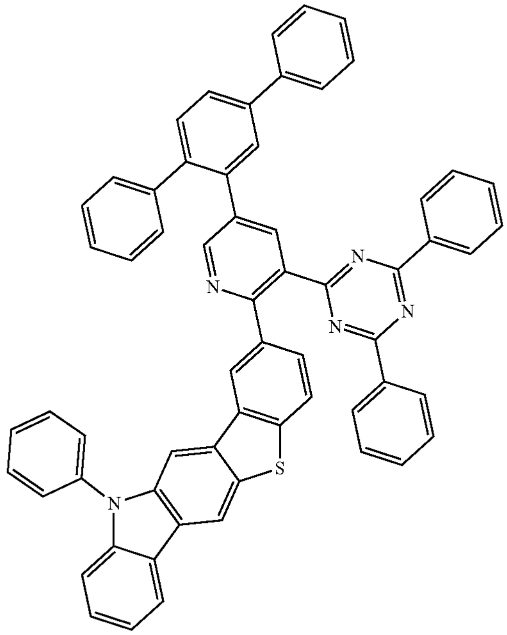

-continued
669
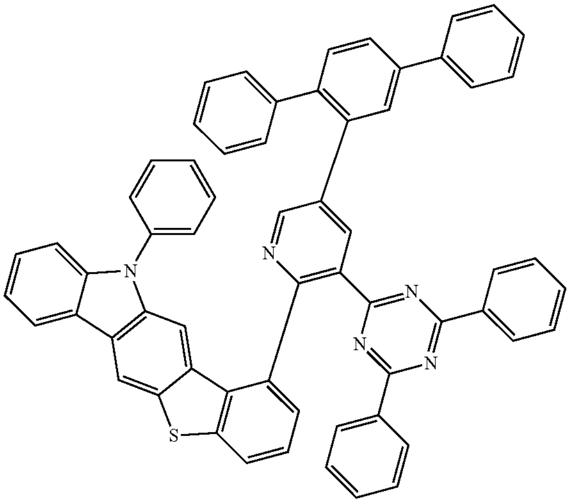
670
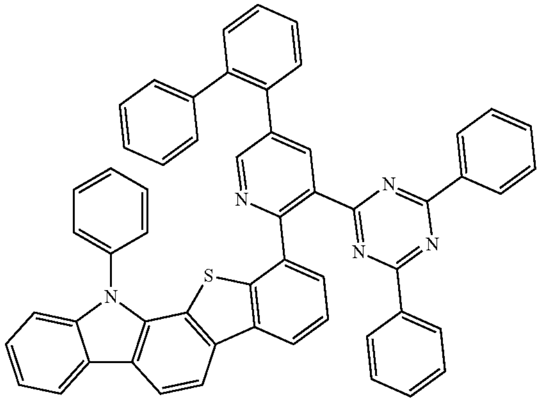
671
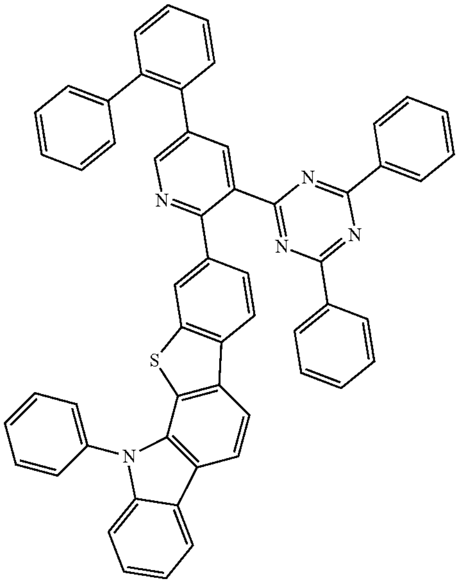
-continued
672
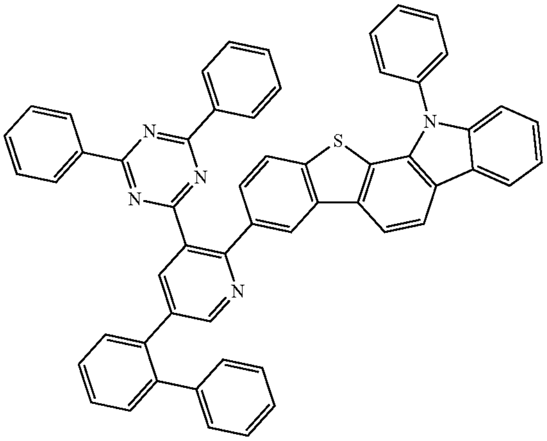
673
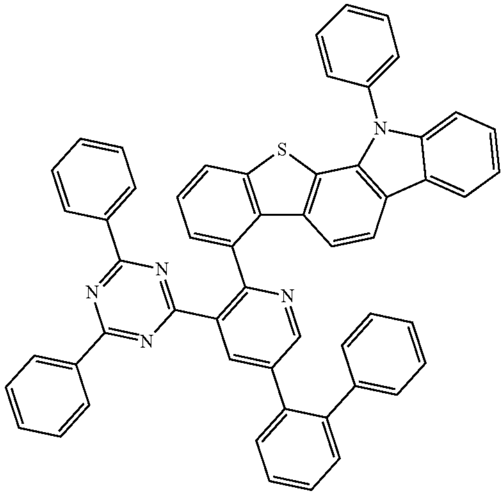
674
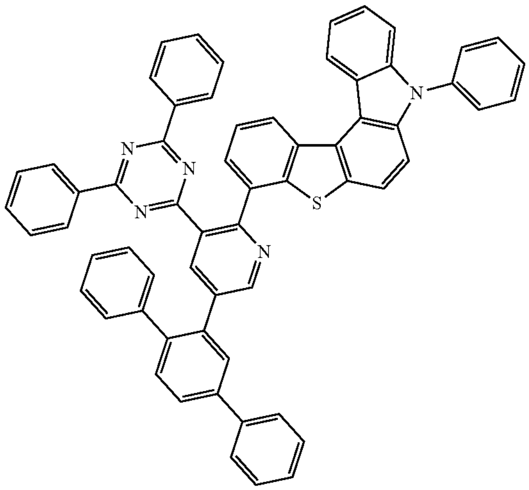

-continued
675
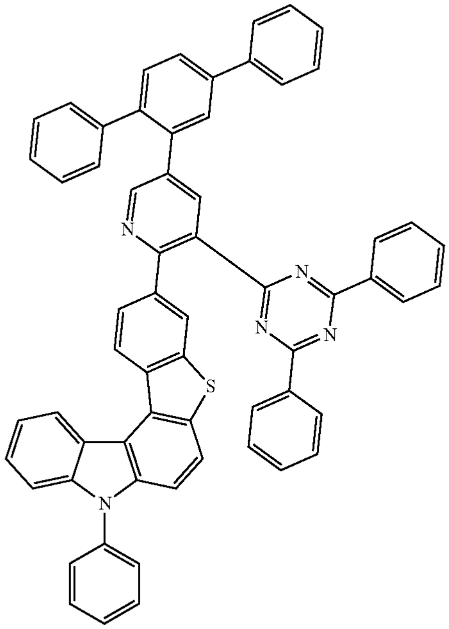
676
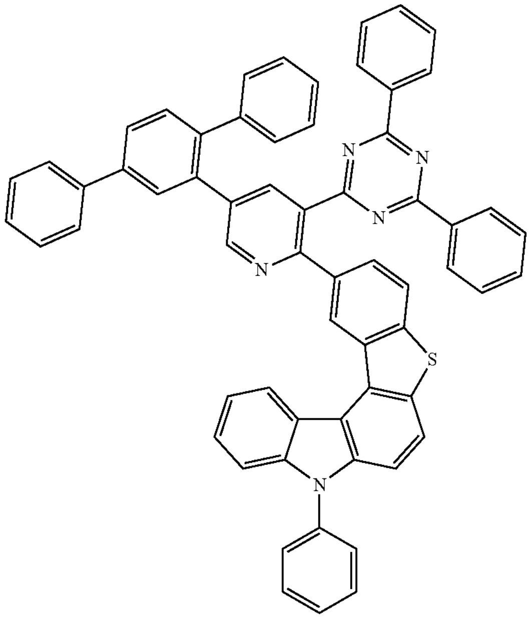
-continued
677
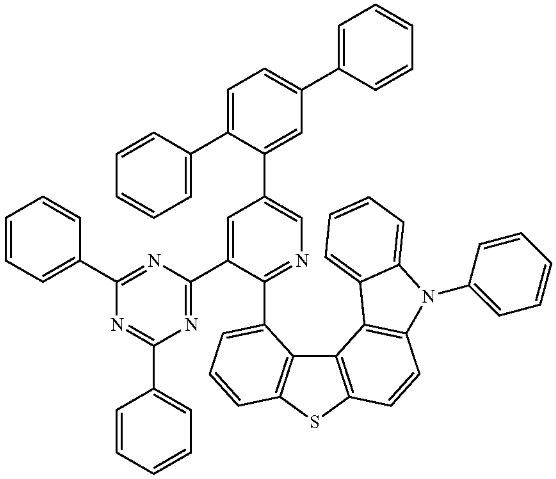
678
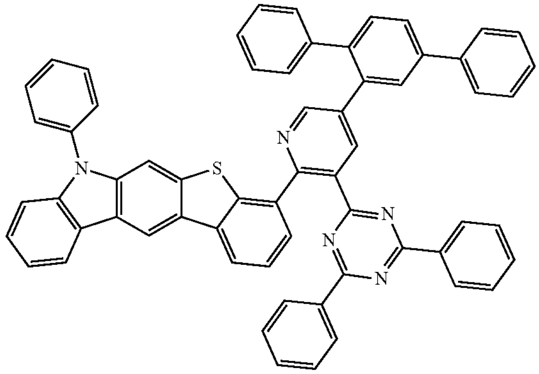
679
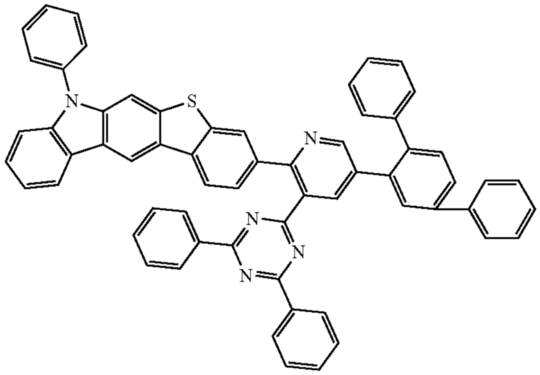

-continued
680
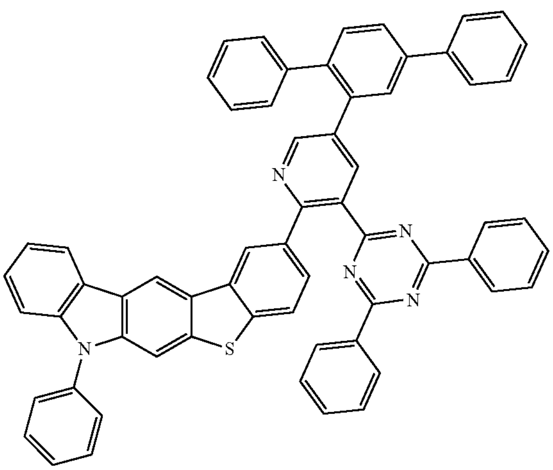
681
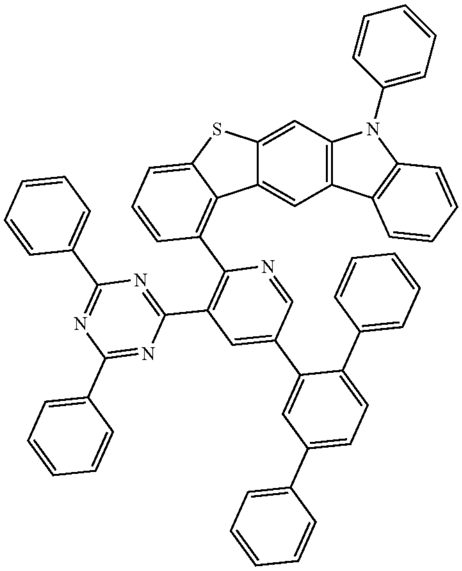
682
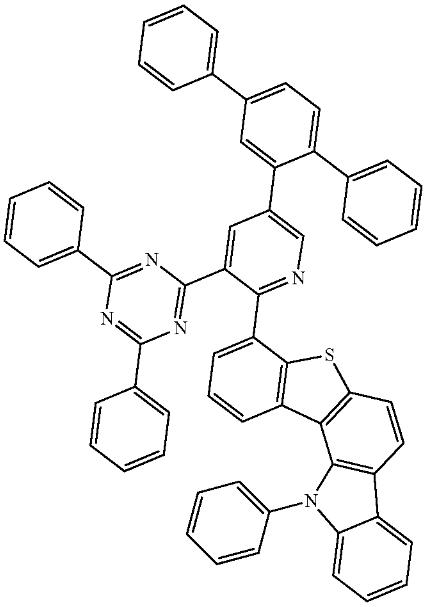
-continued
683
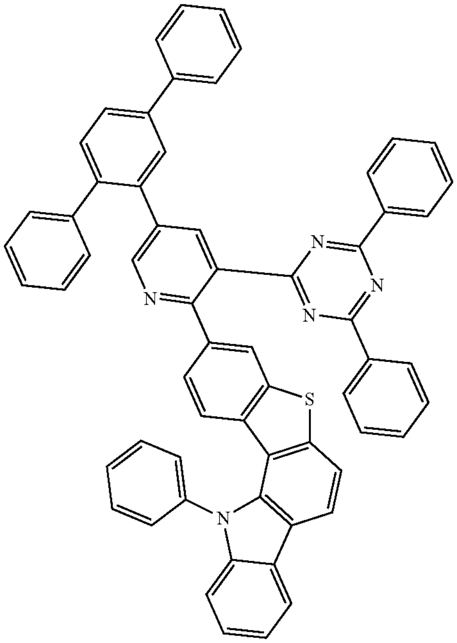
684
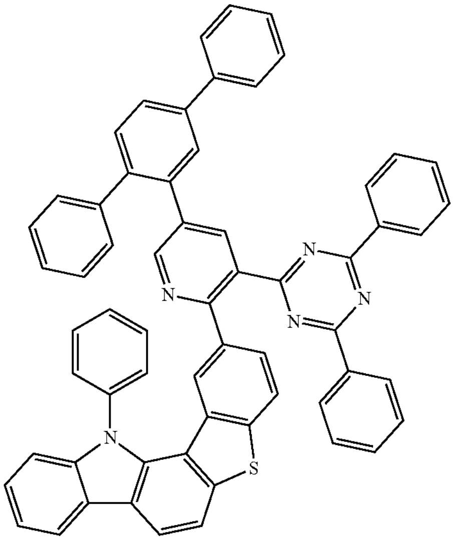

685
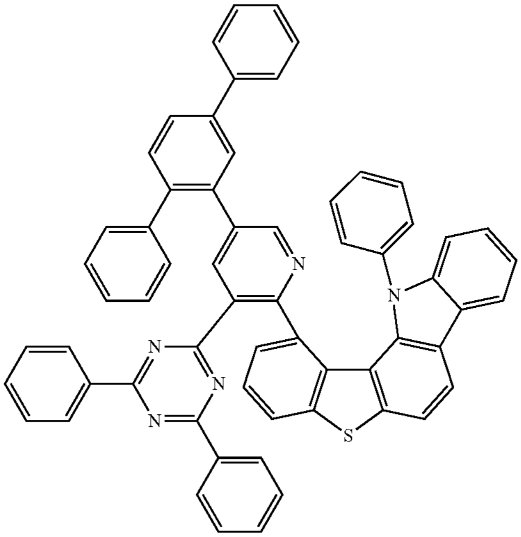
686
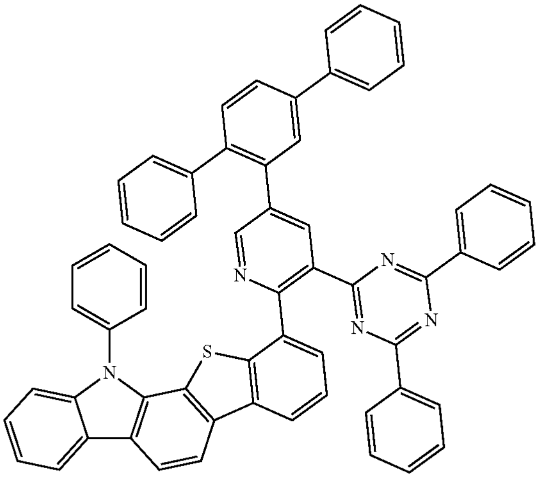
687
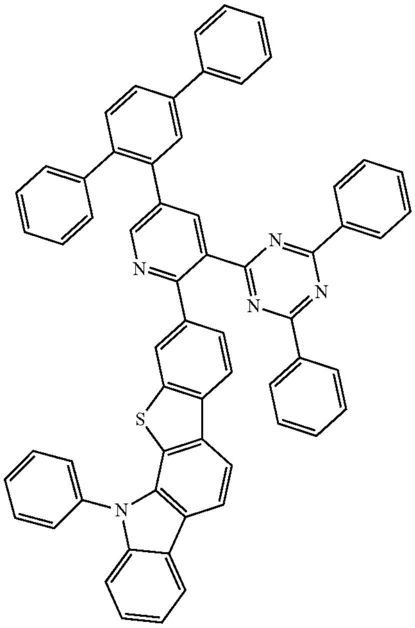
688
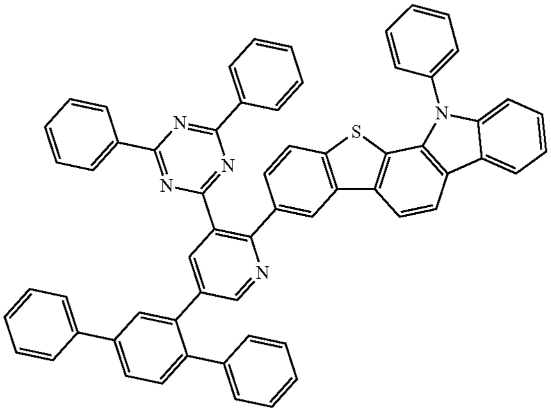

-continued
689
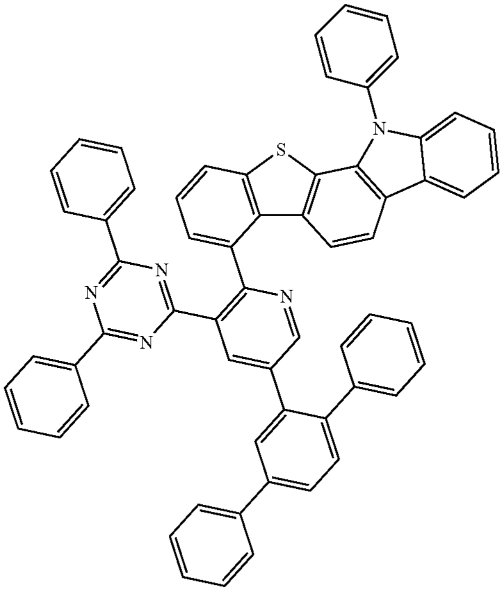
690
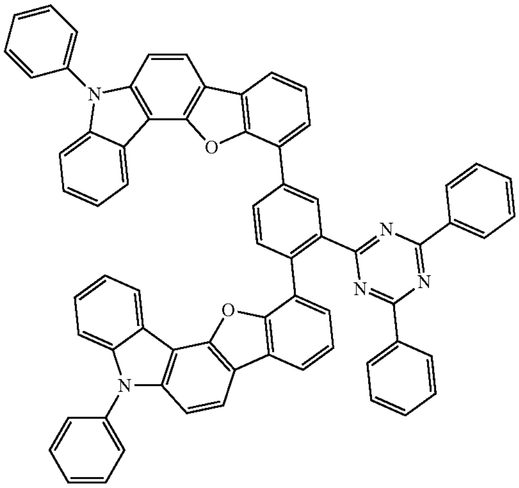
-continued
691
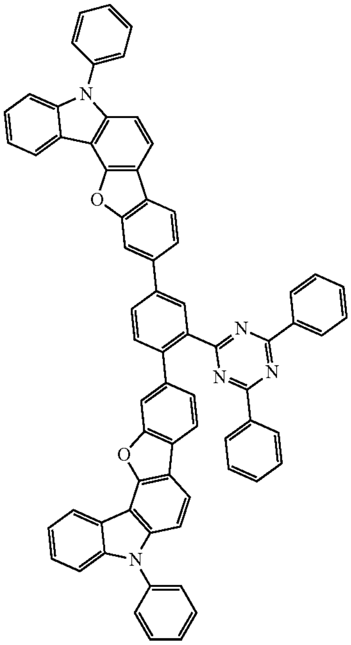
692
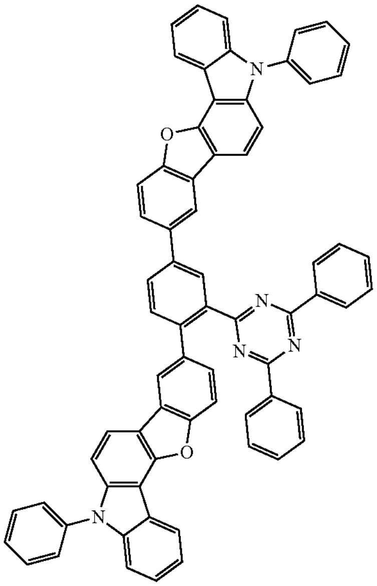

-continued
693
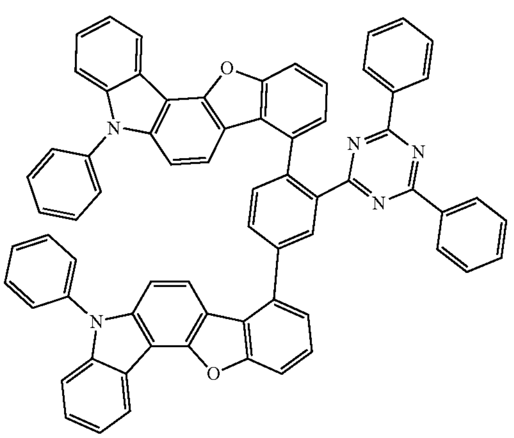
694
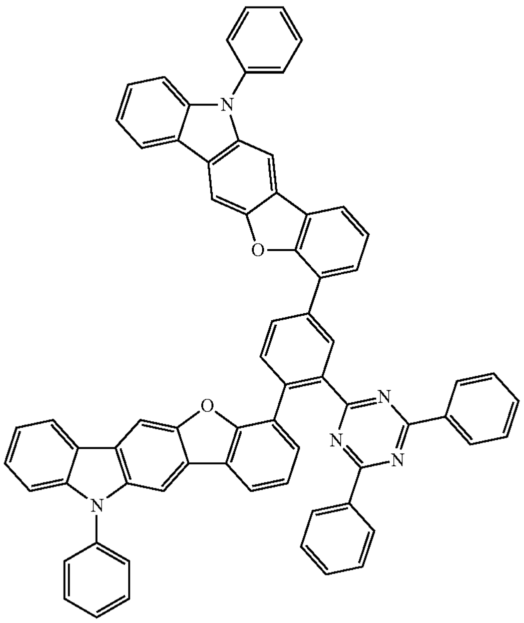
-continued
695
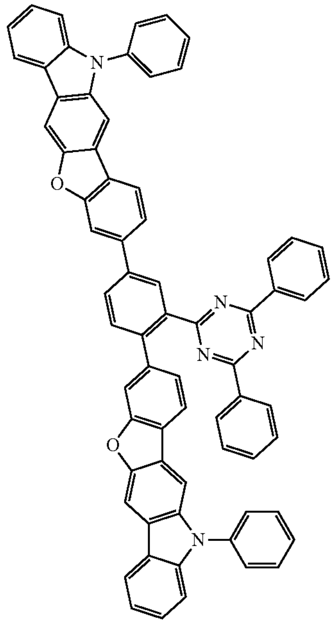
696
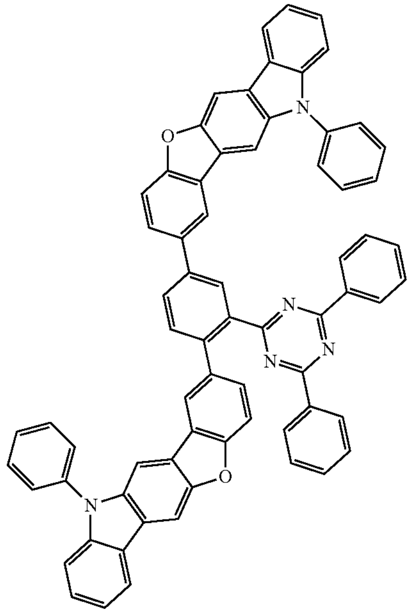

-continued
697
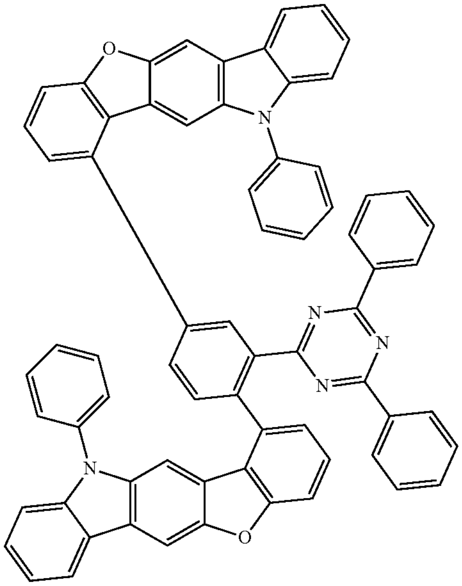
699
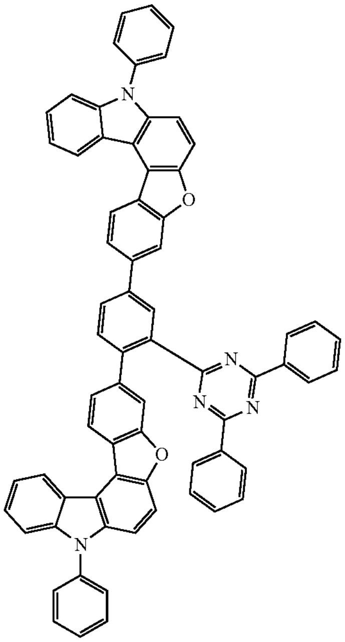
698
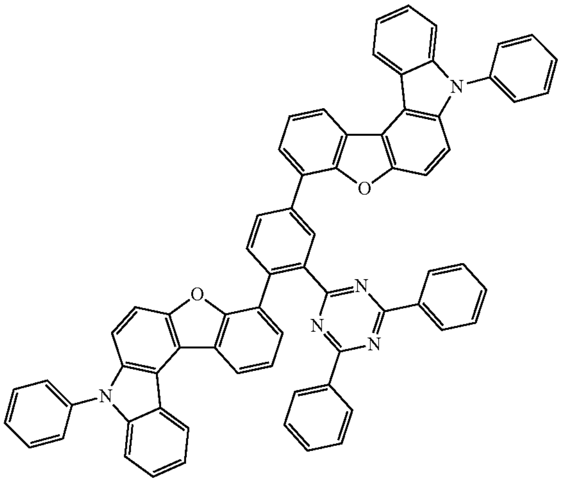
700
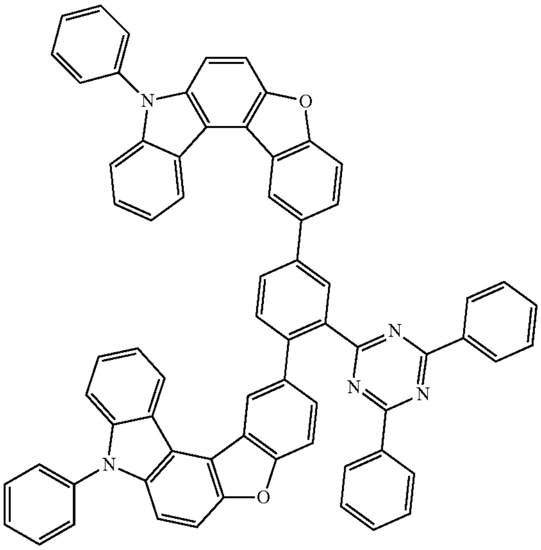

-continued
701
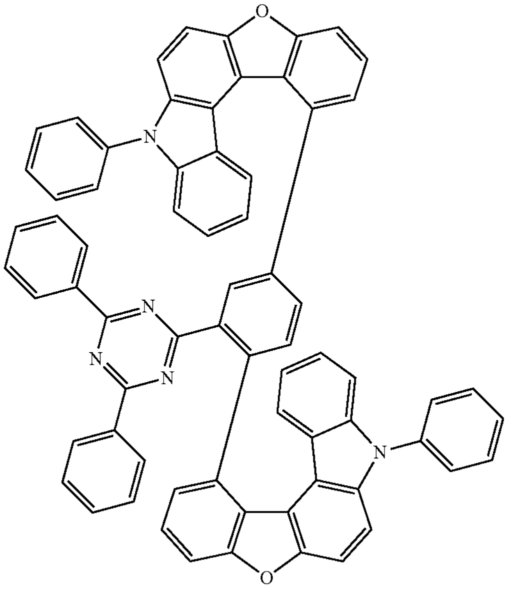
702
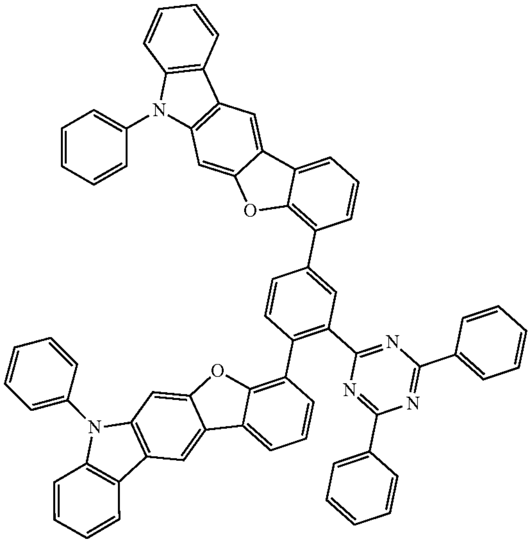
-continued
703
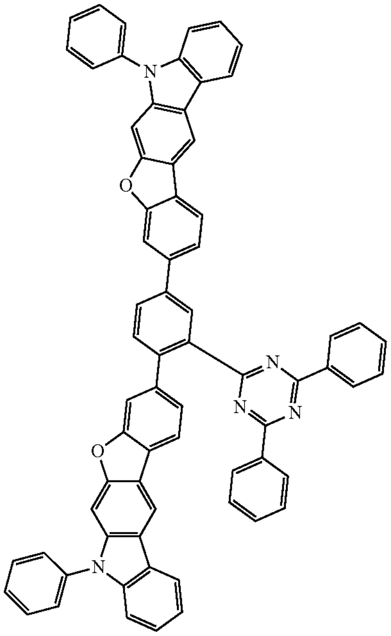
704
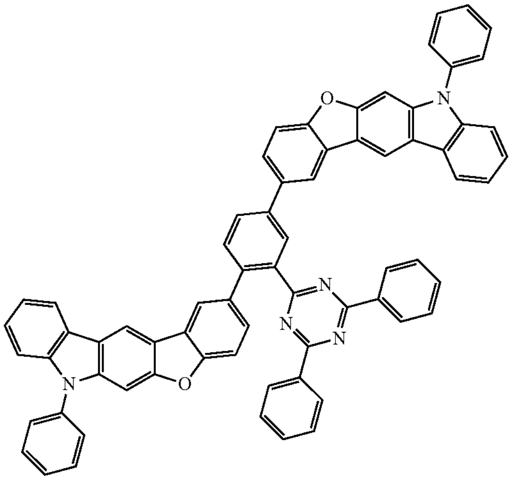

-continued
705
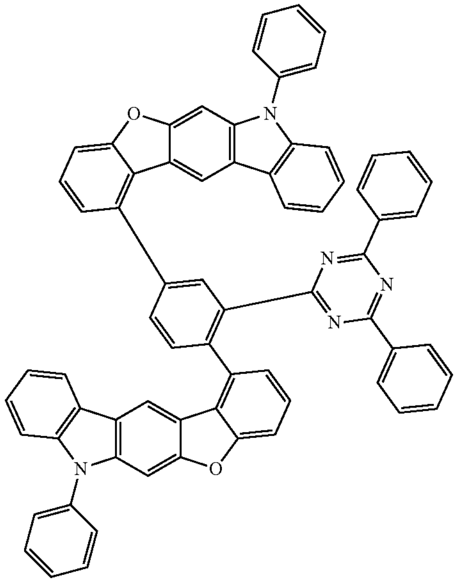
706
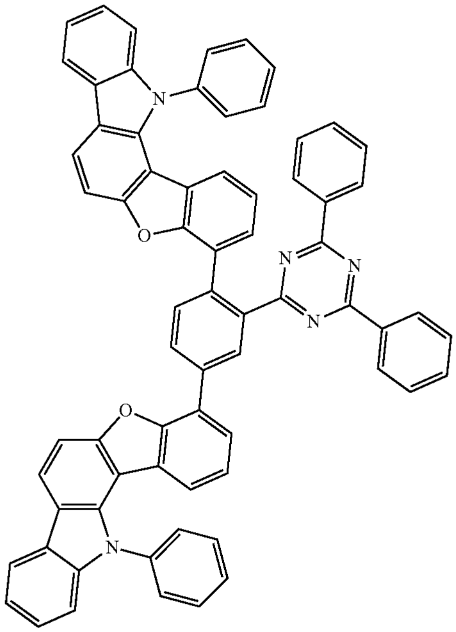
-continued
707
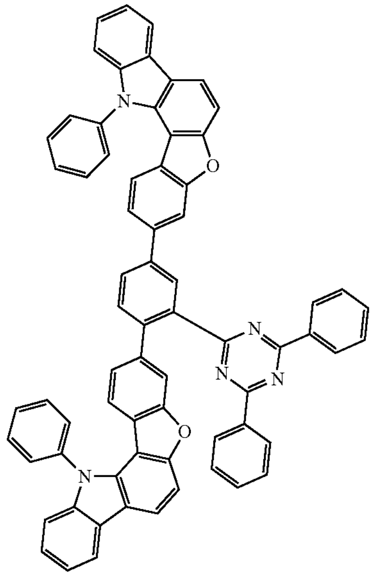
708
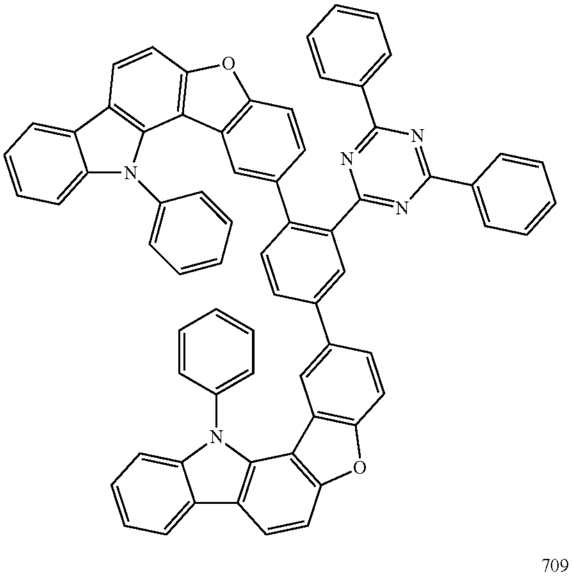
709
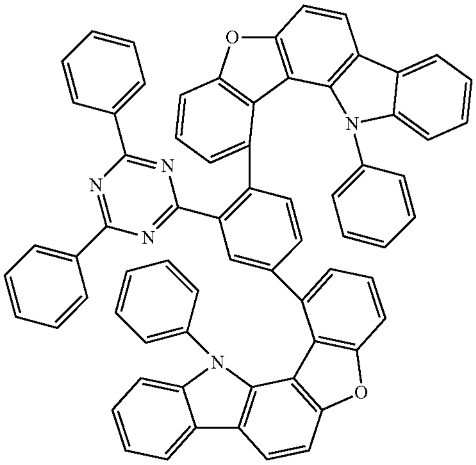

-continued
710
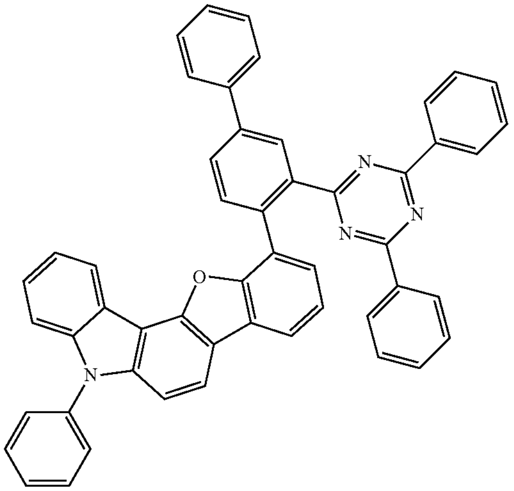
711
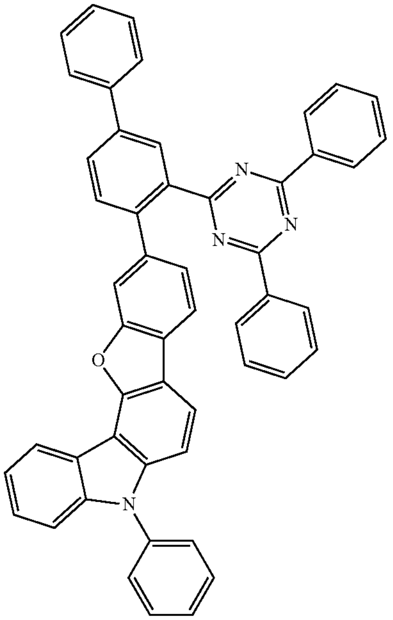
-continued
712
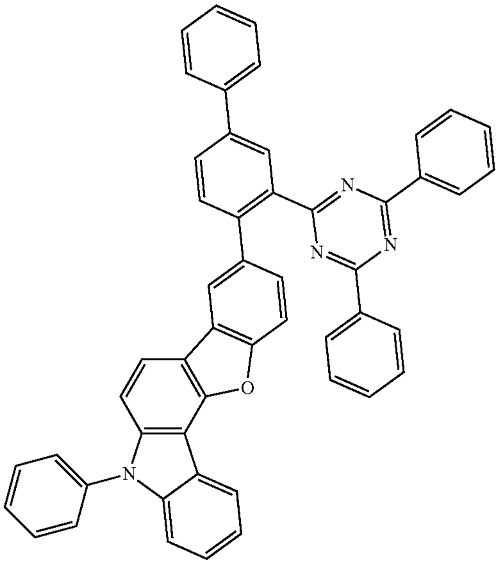
713
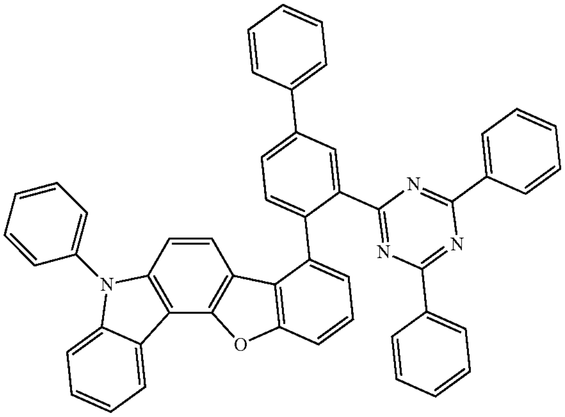
714
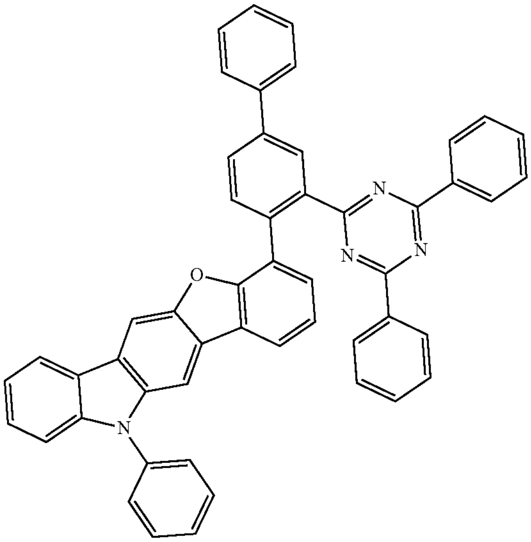

-continued
715
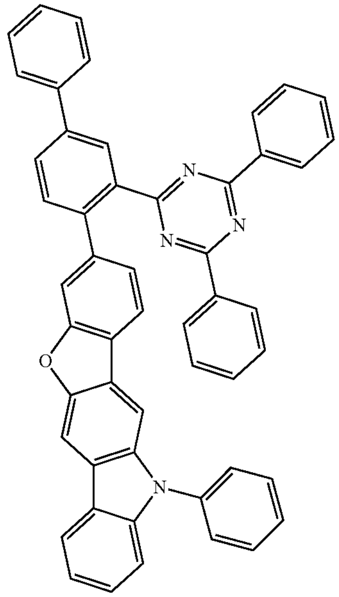
716
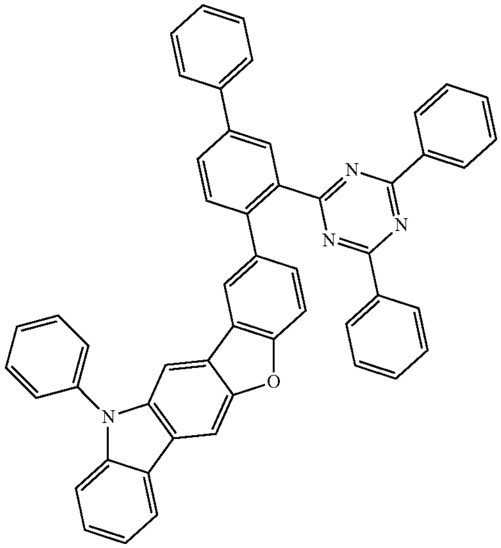
717
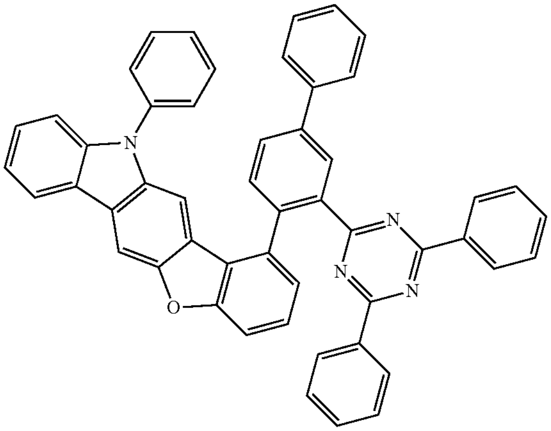
-continued
718
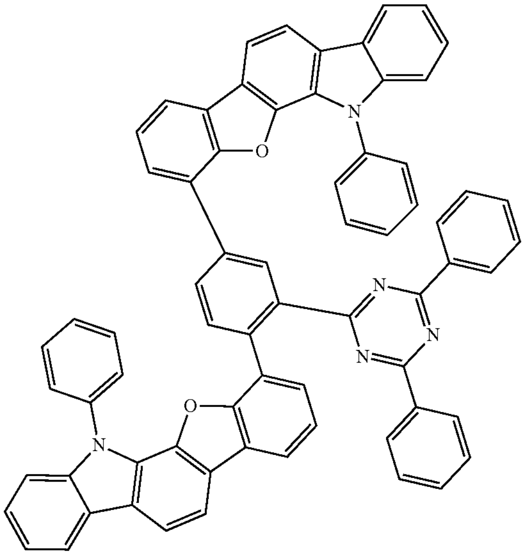
719
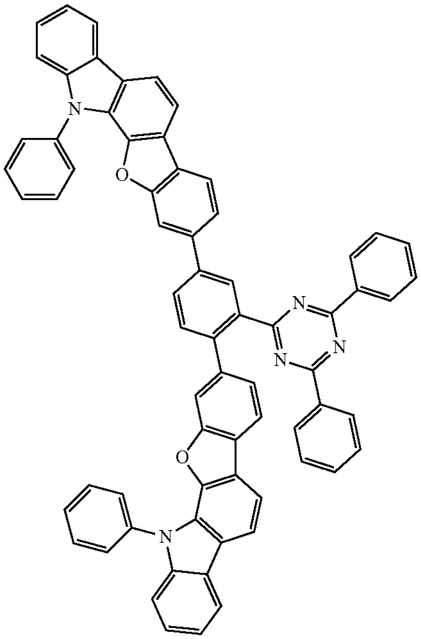

-continued
720
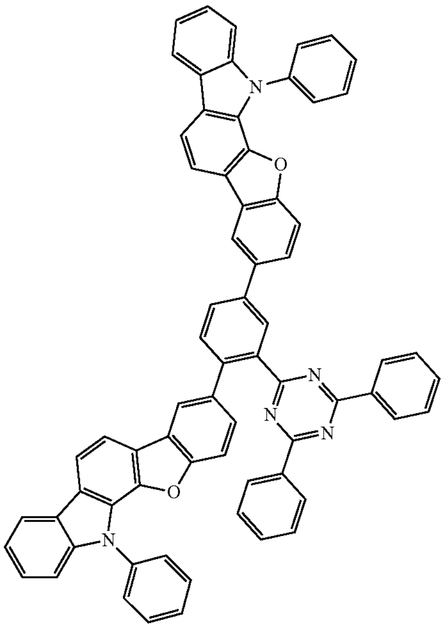
721
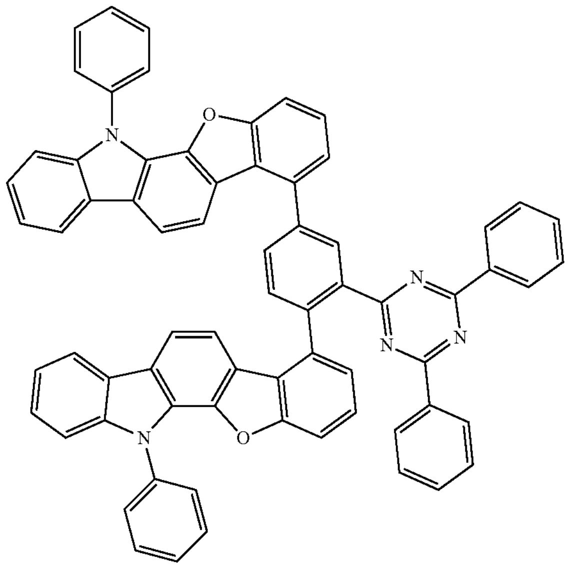
-continued
722
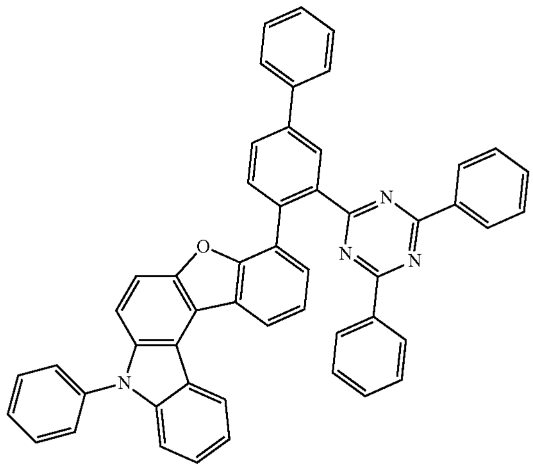
723
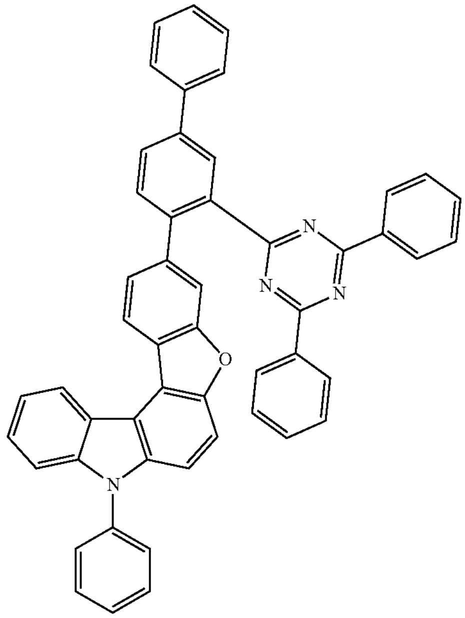
724
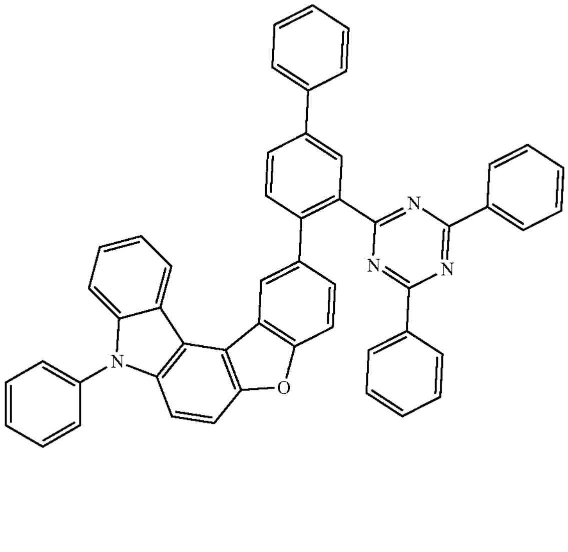

-continued
725
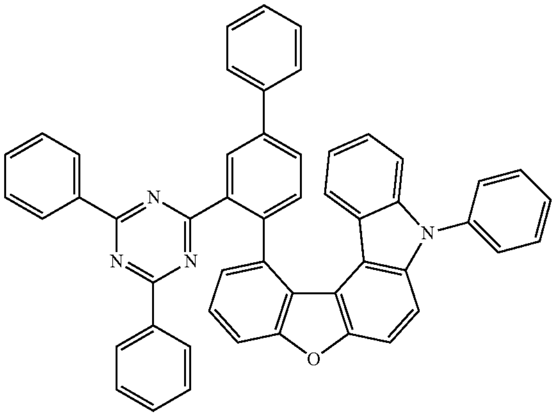
726
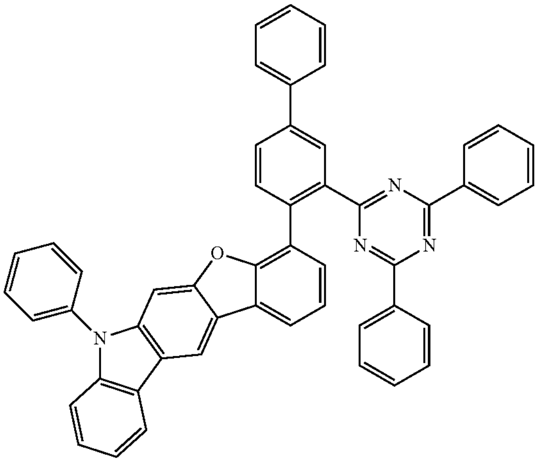
727
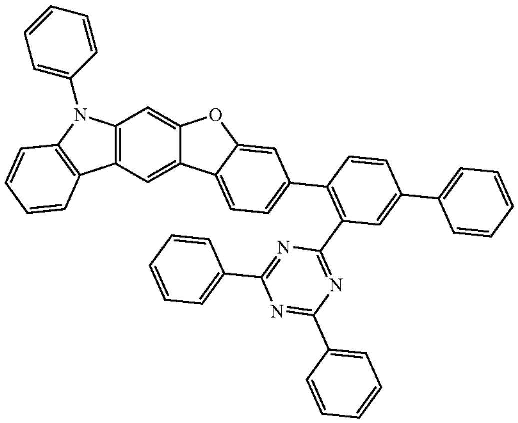
-continued
728
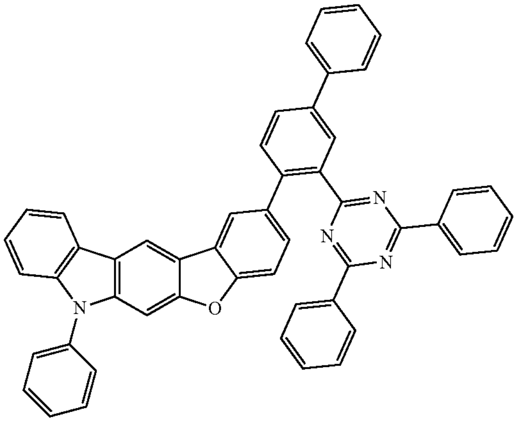
729
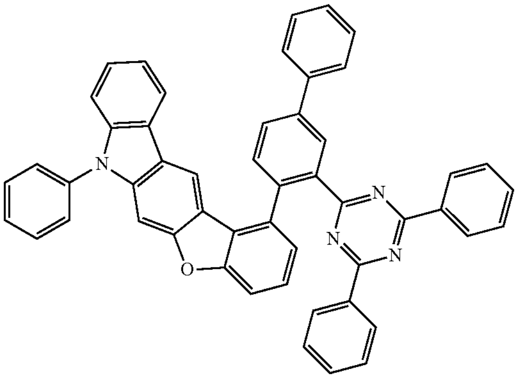
730
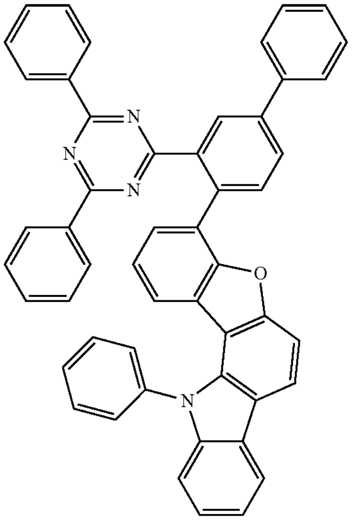

731
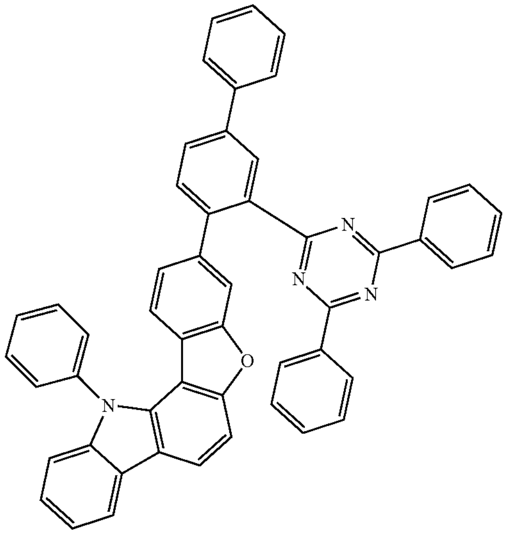
732
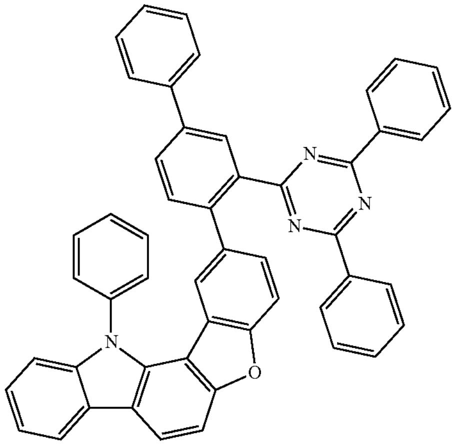
733
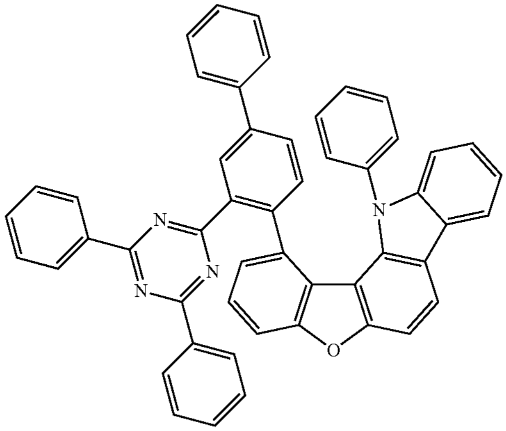
734
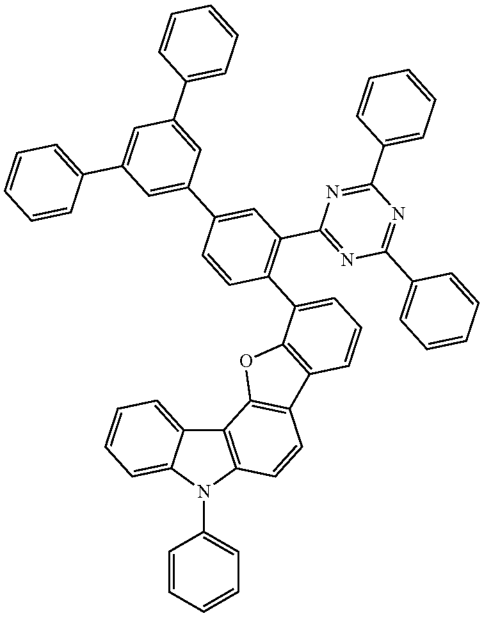
735
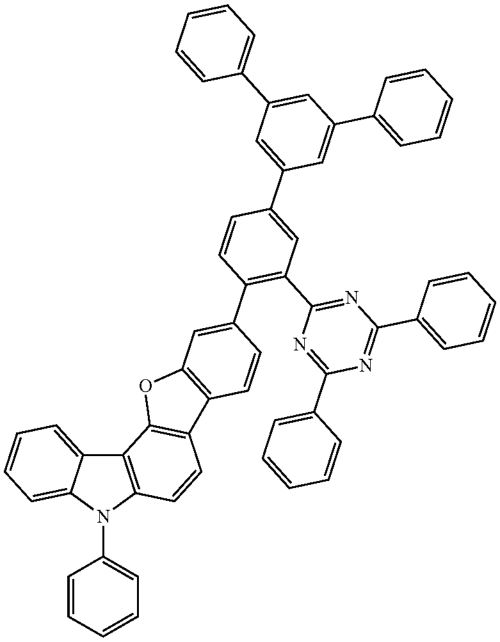

-continued
736
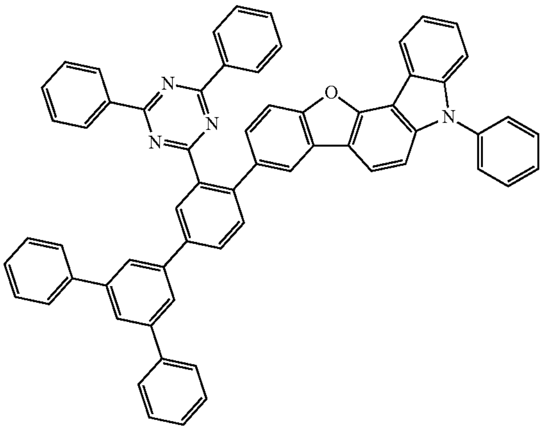
737
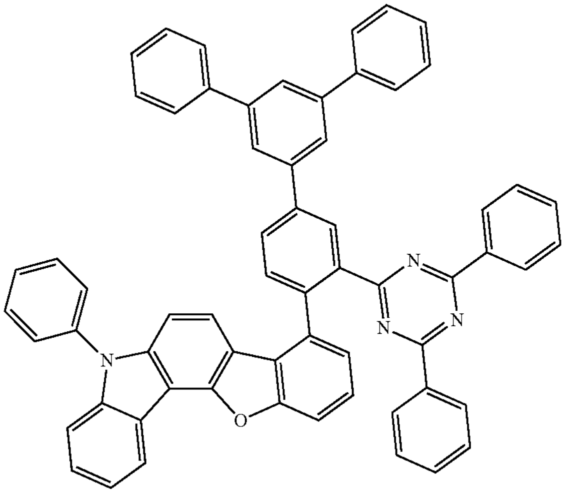
738
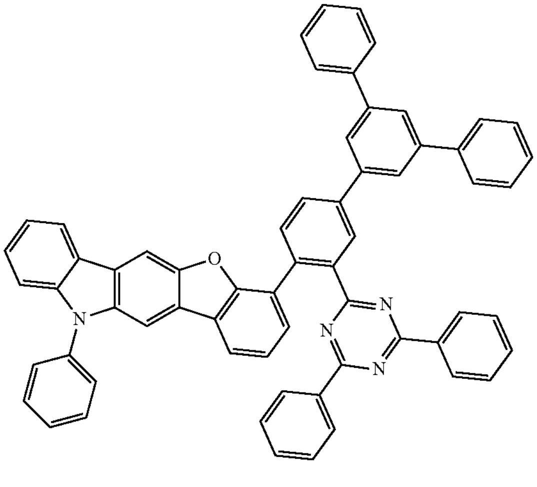
-continued
739
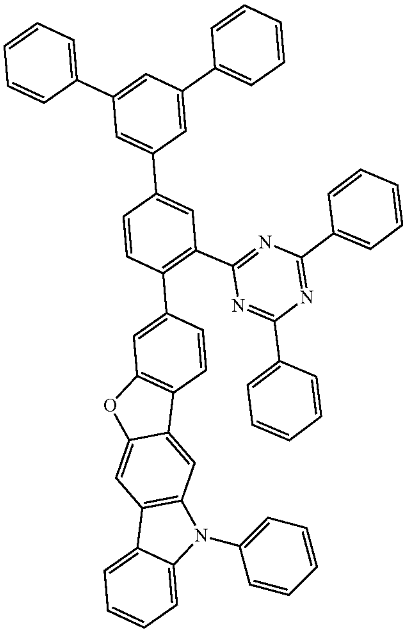
740
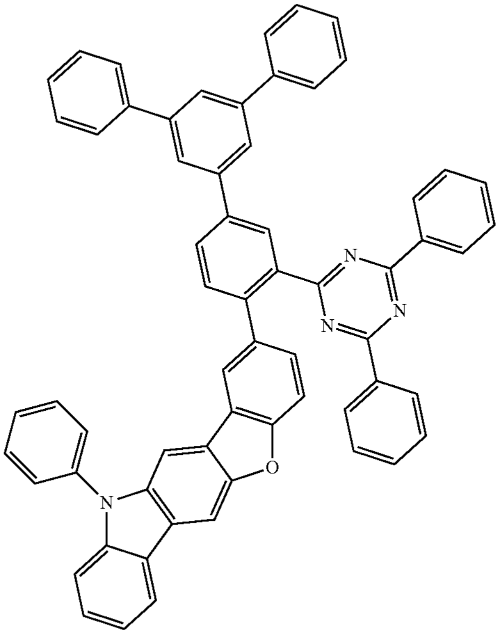

-continued
741
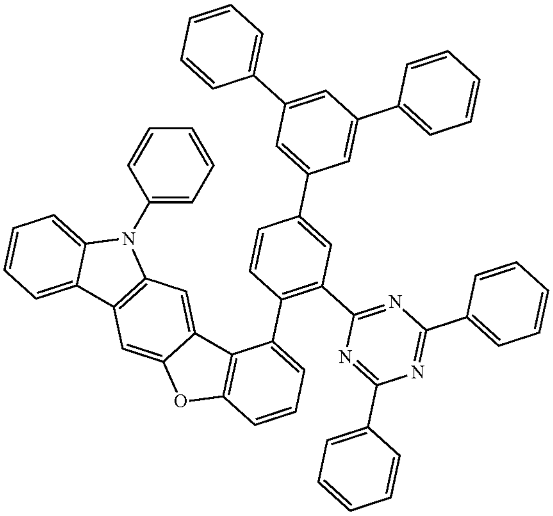
742
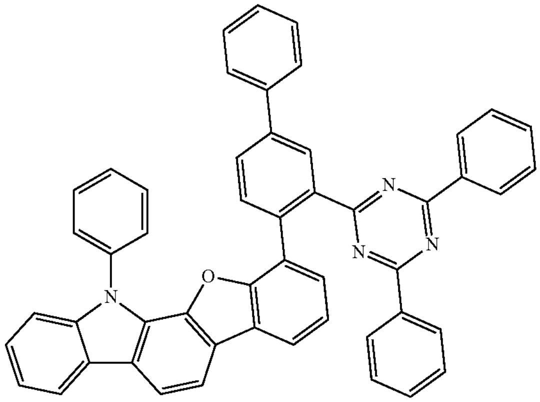
743
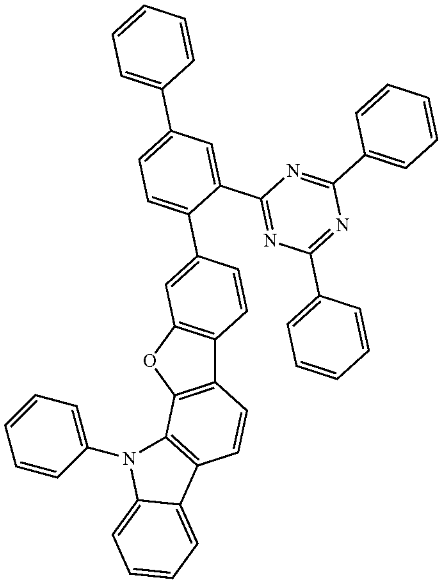
-continued
744
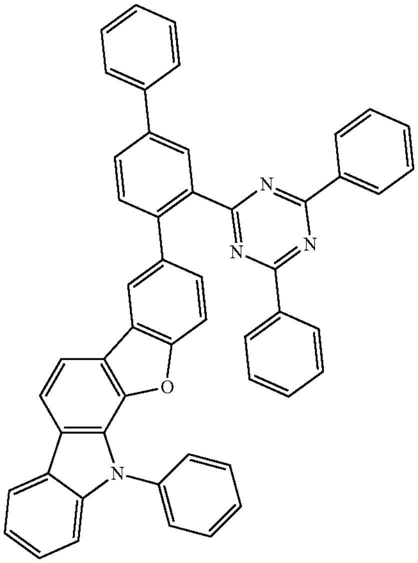
745
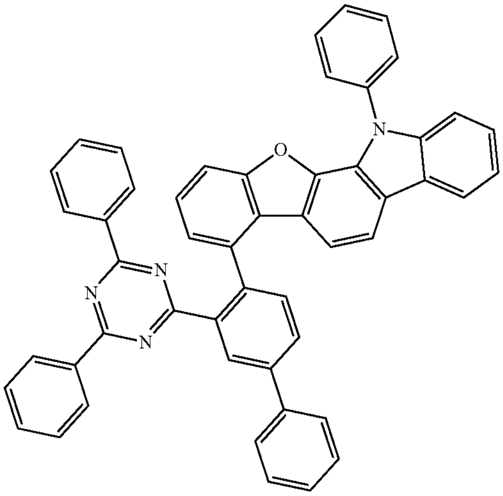
746
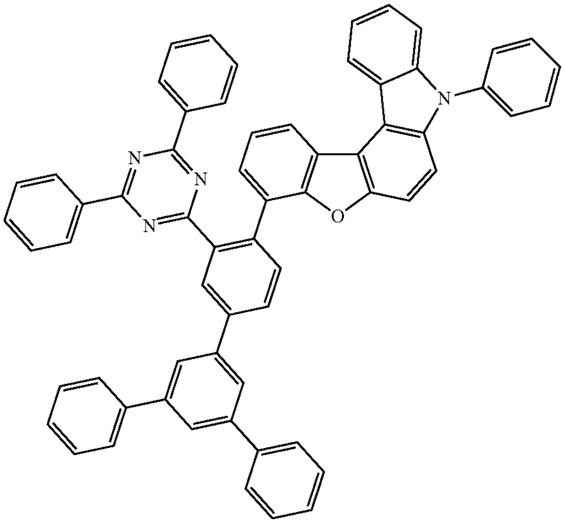

-continued
747
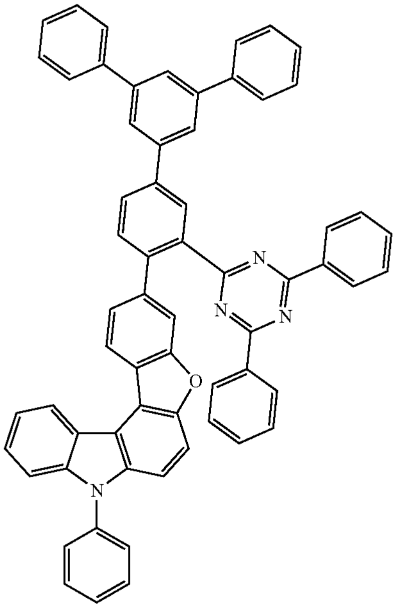
748
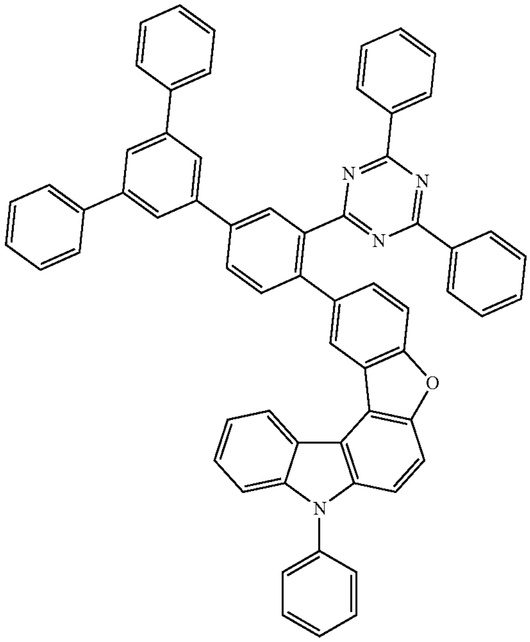
-continued
749
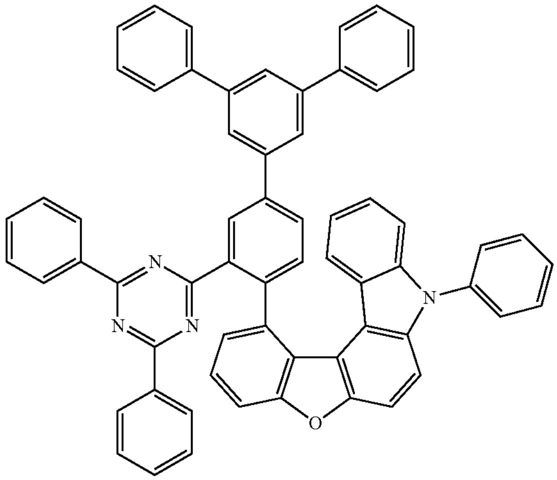
750
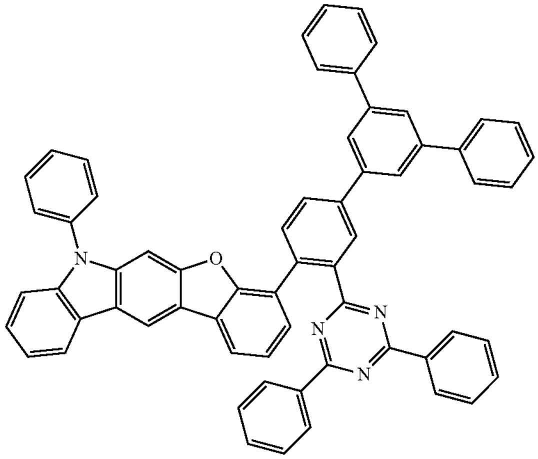
751
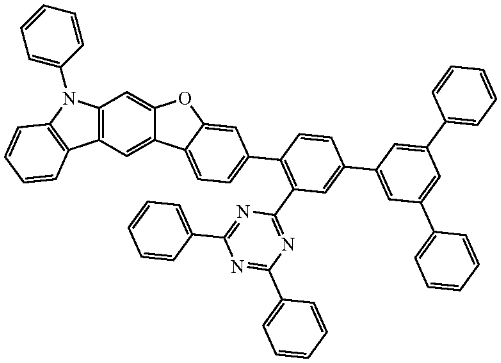

-continued
752
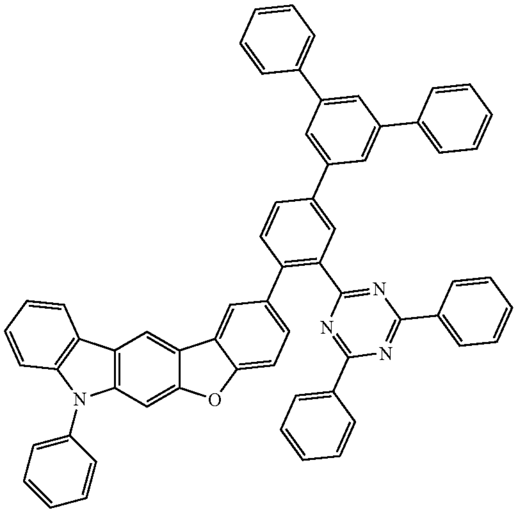
753
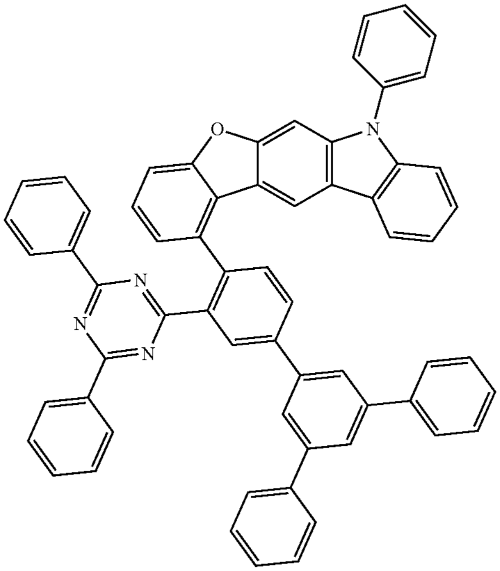
-continued
754
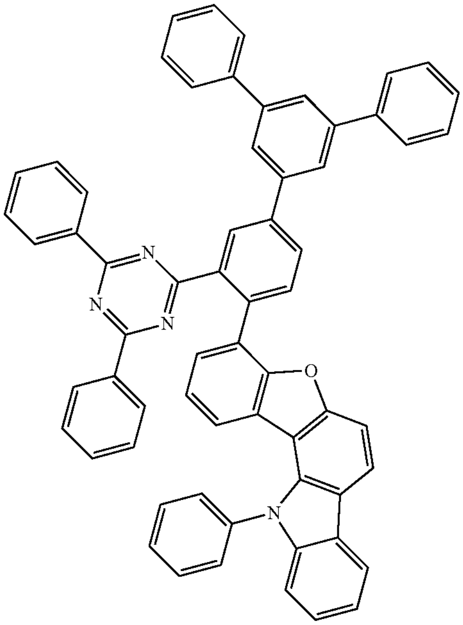
755
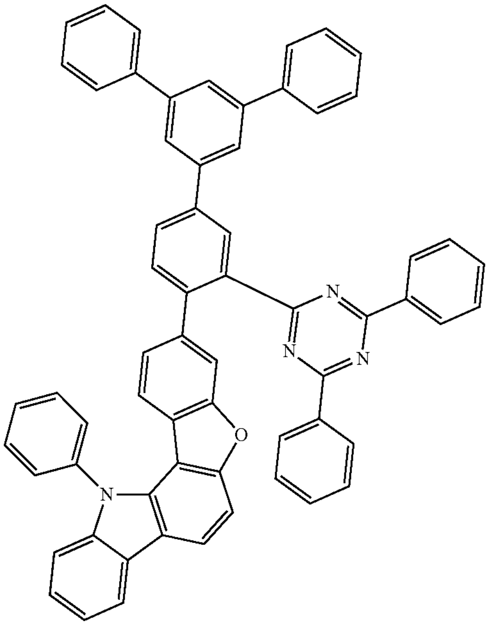

-continued
756
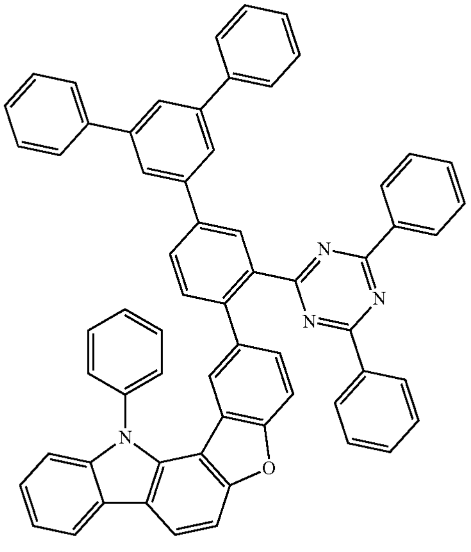
757
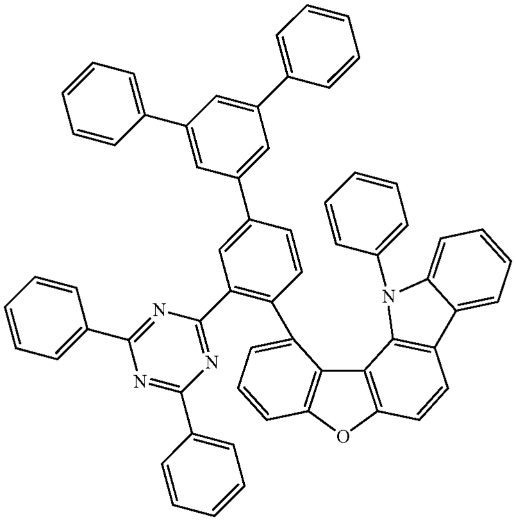
-continued
758
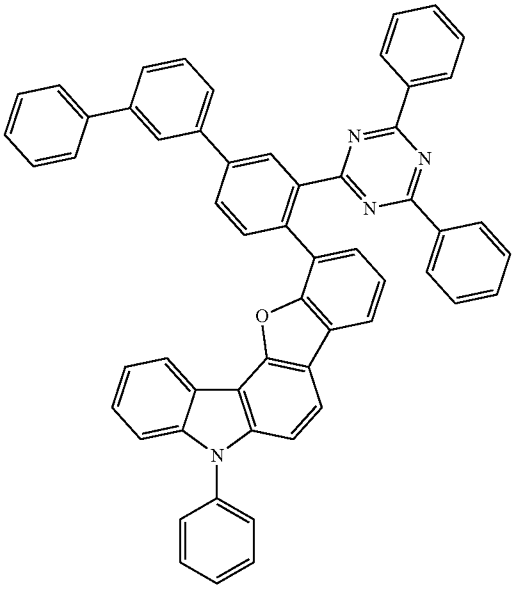
759
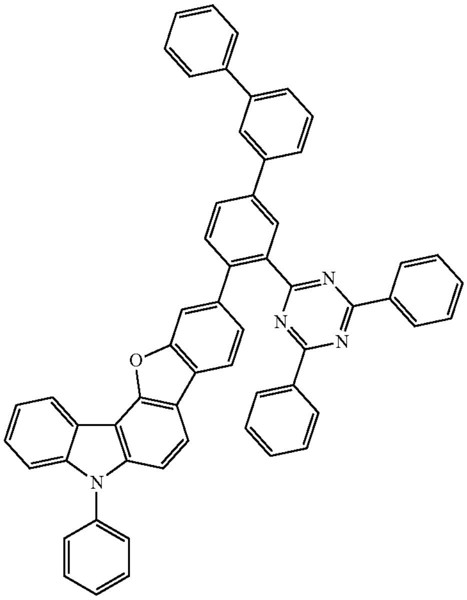

-continued
760
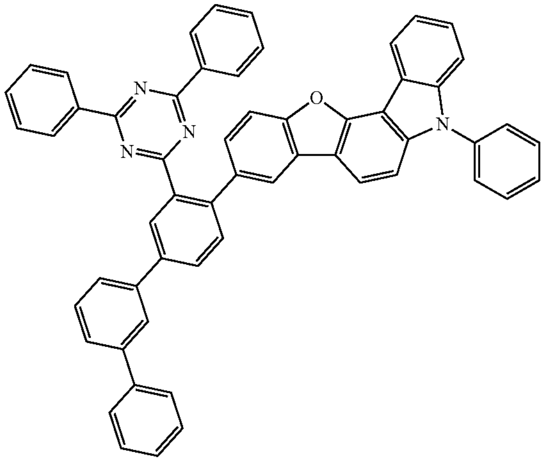
761
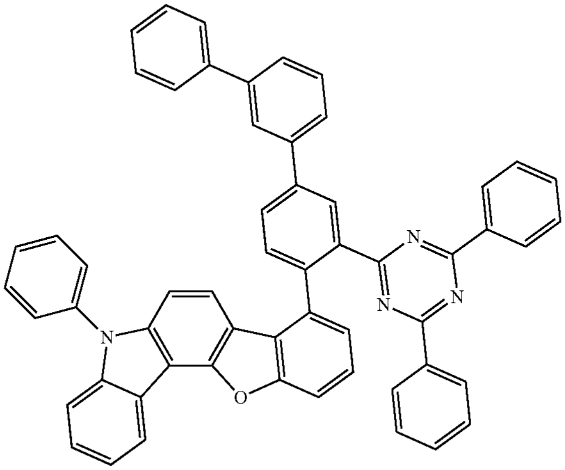
762
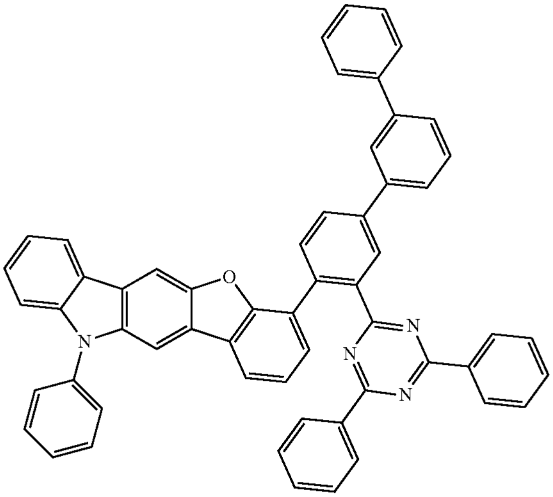
-continued
763
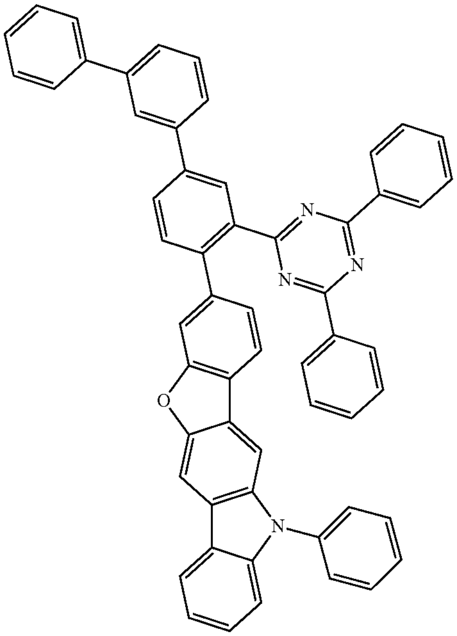
764
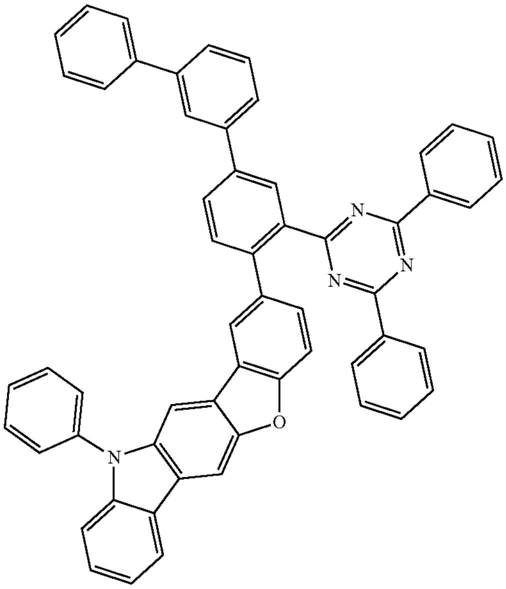

-continued
765
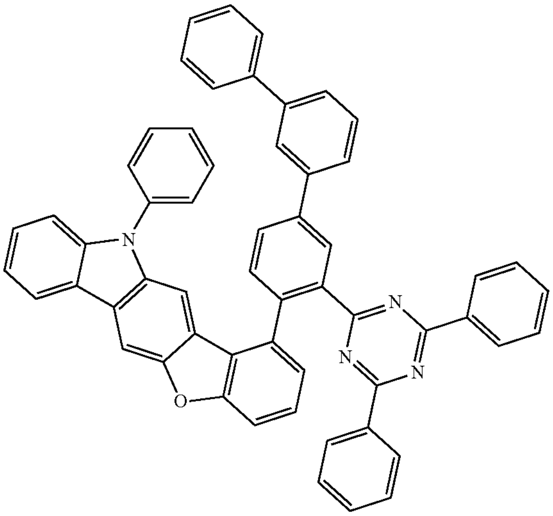
766
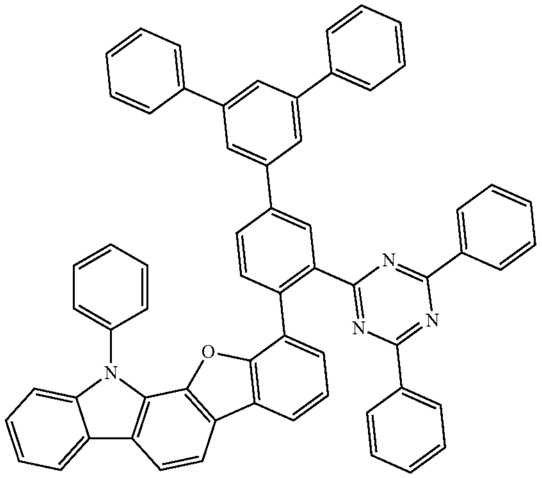
767
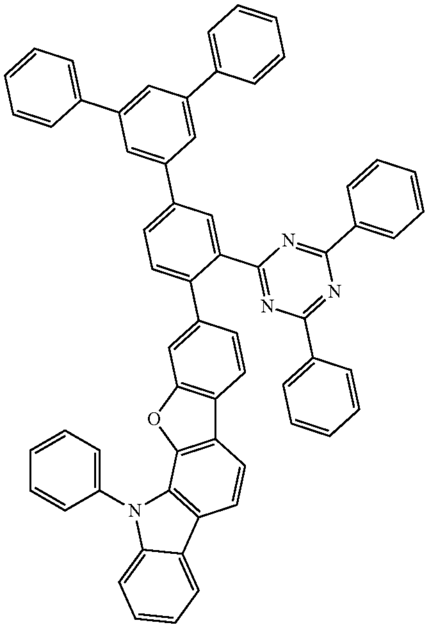
-continued
768
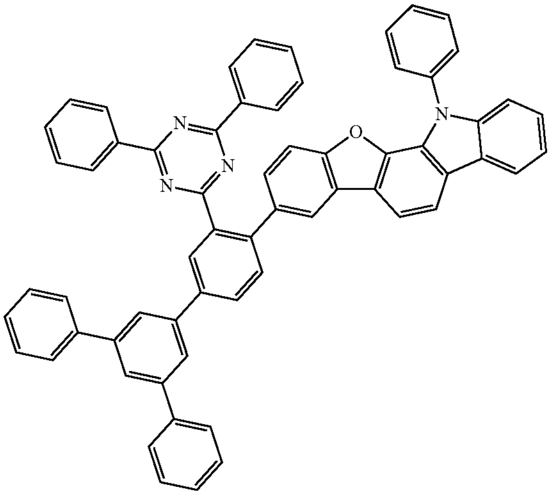
769
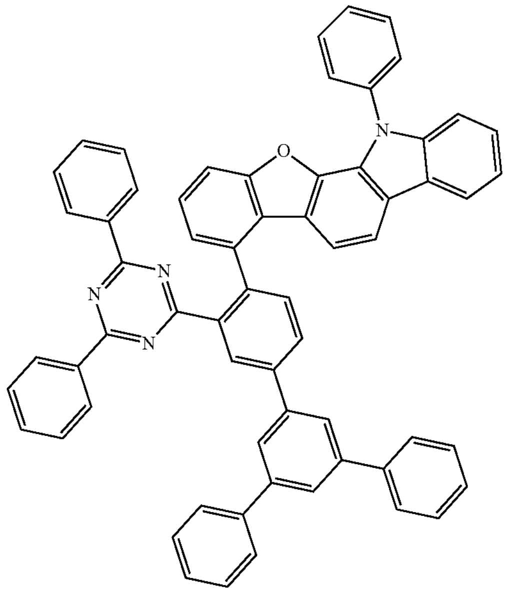
770
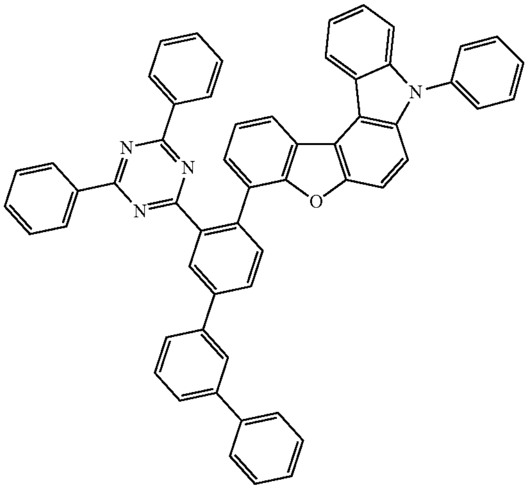

-continued
771
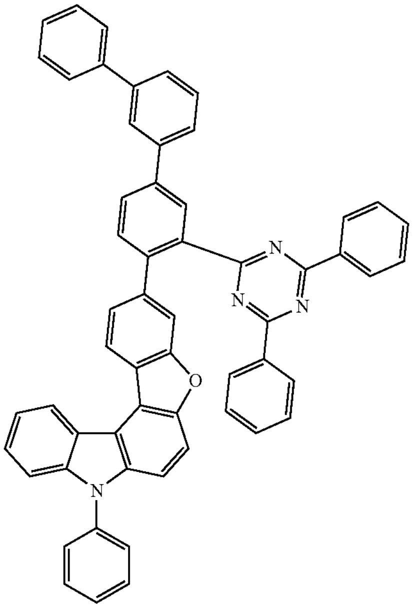
772
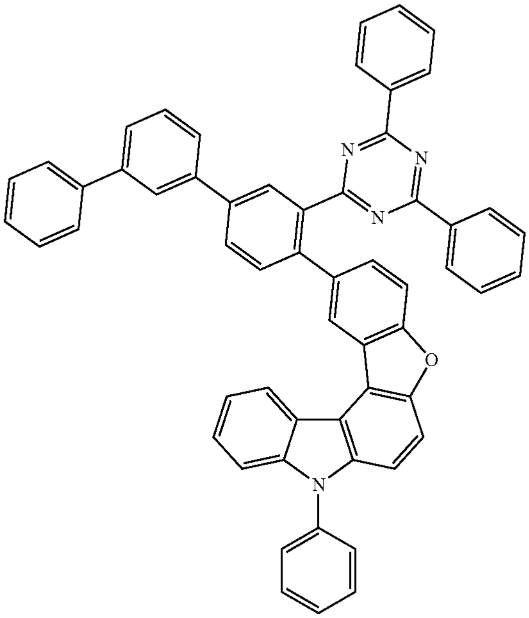
-continued
773
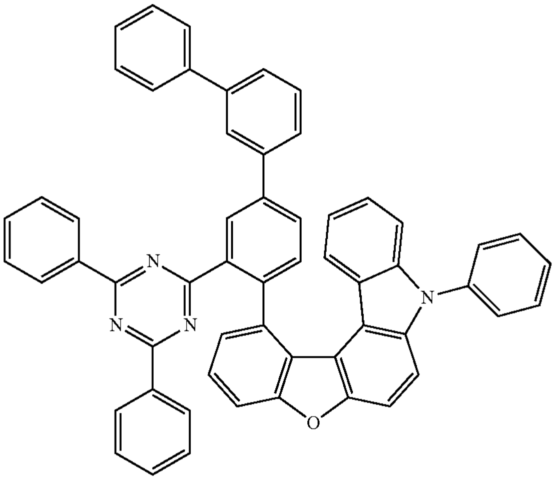
774
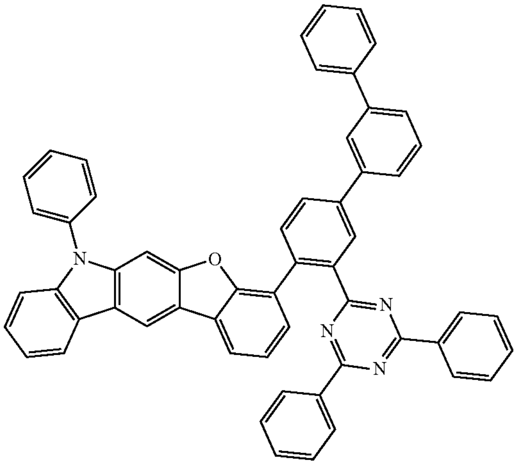
775
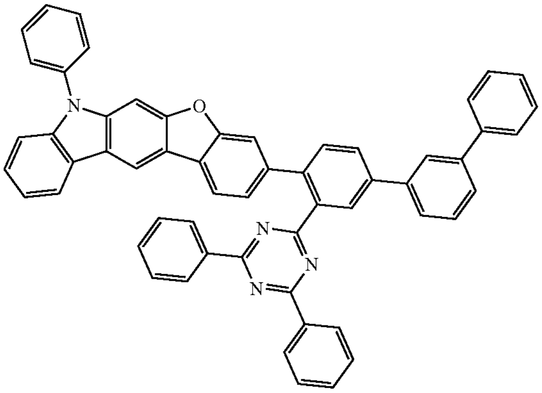

-continued
776
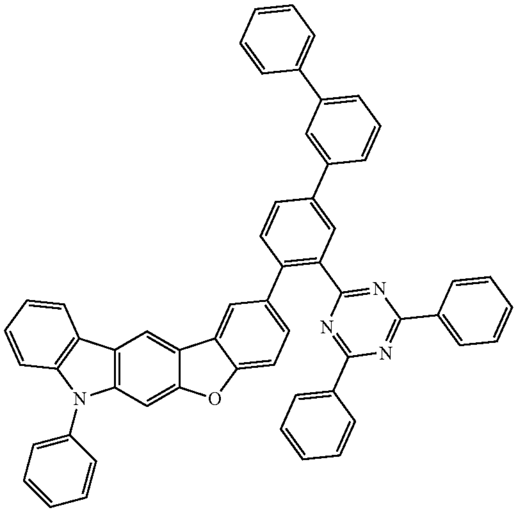
777
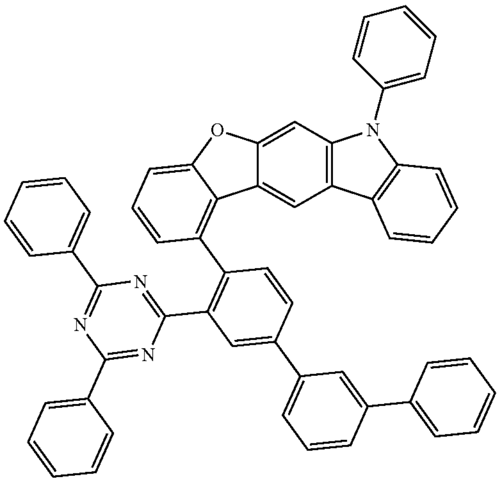
778
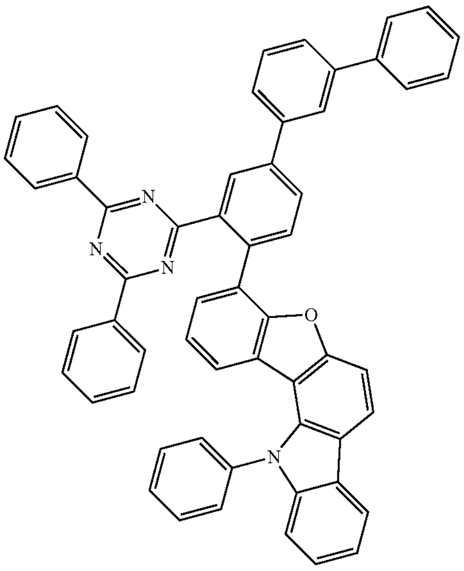
-continued
779
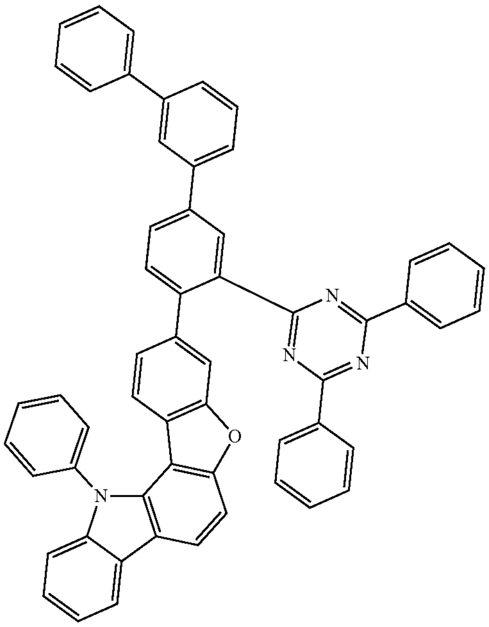
780
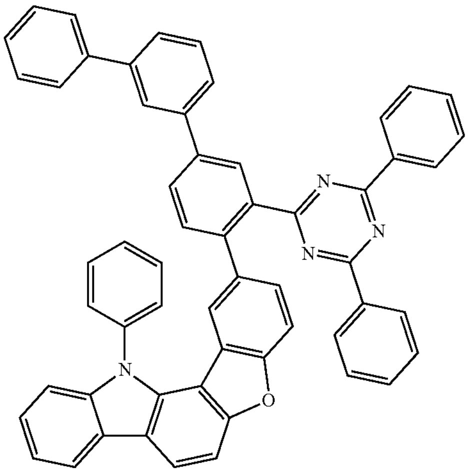
781
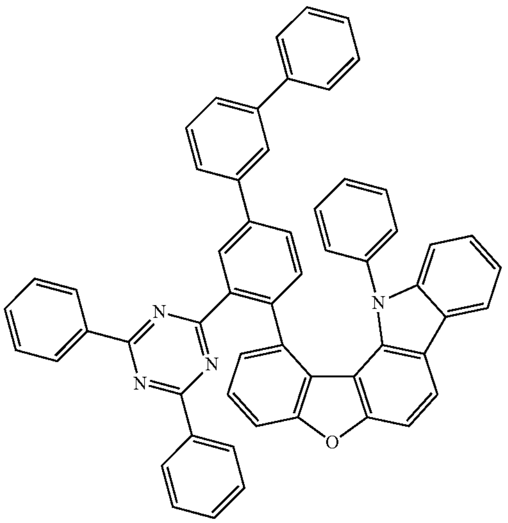

-continued
782
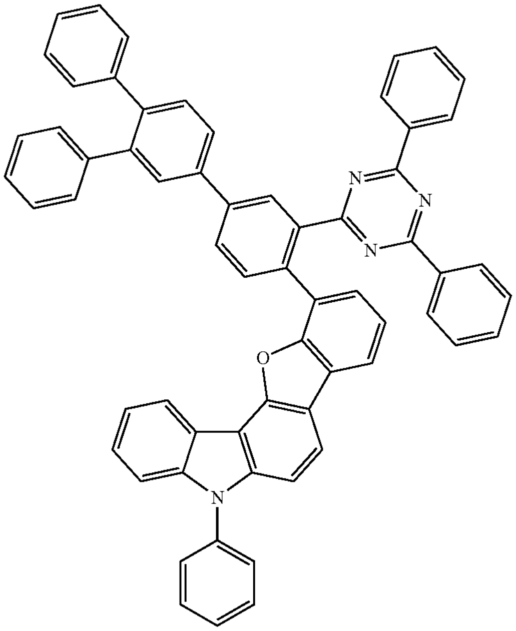
783
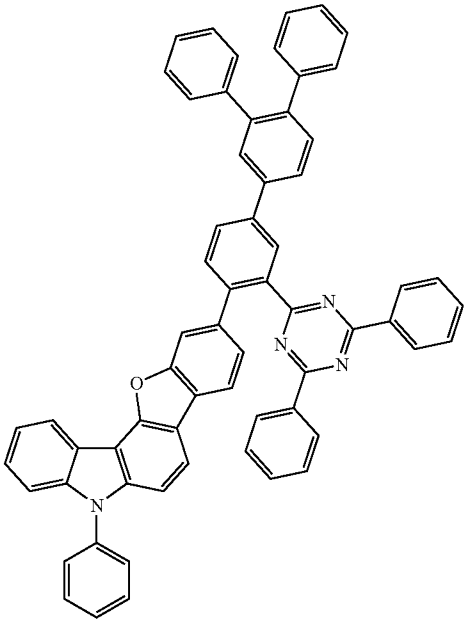
-continued
784
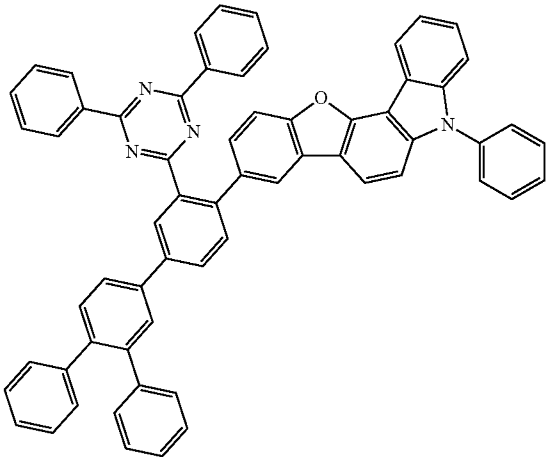
785
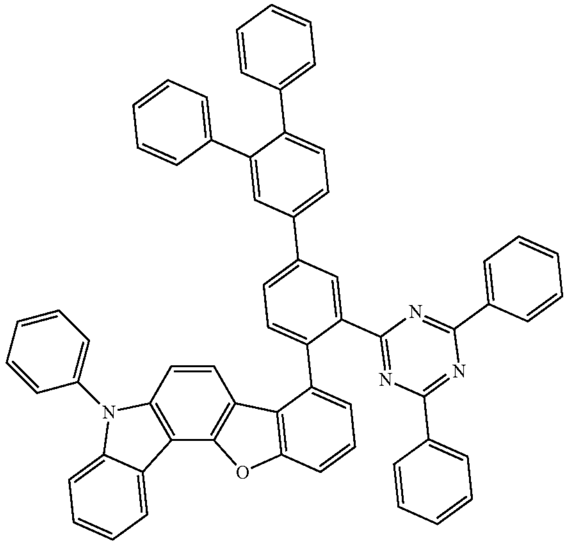
786
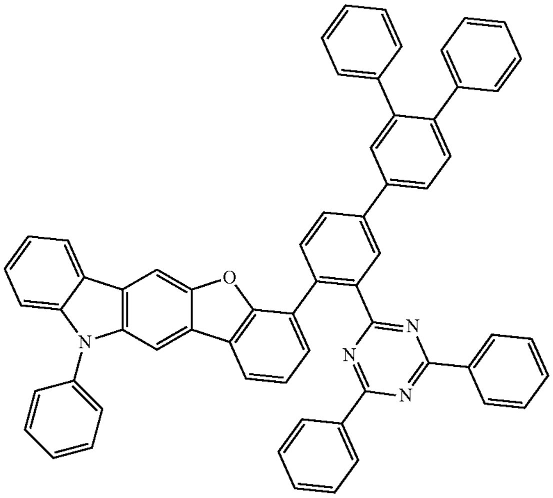

-continued
787
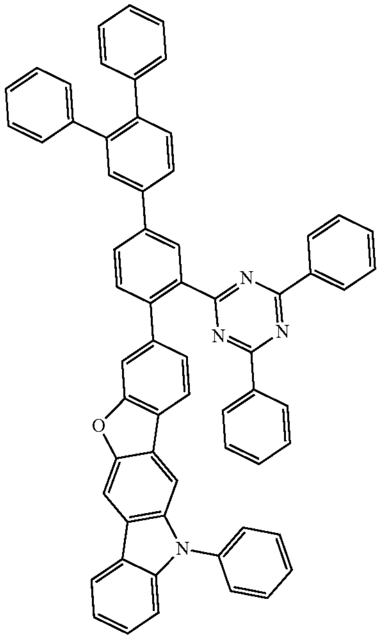
788
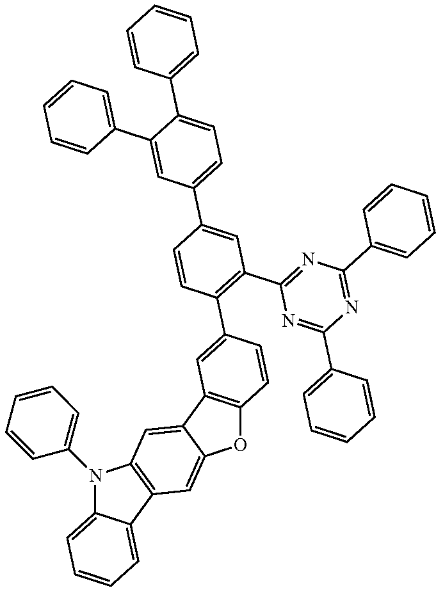
-continued
789
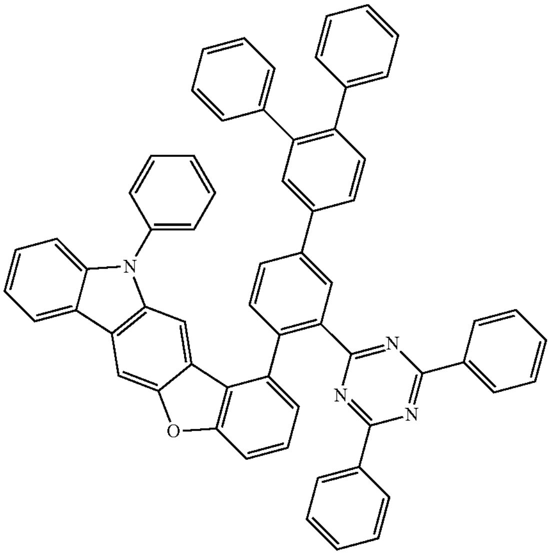
790
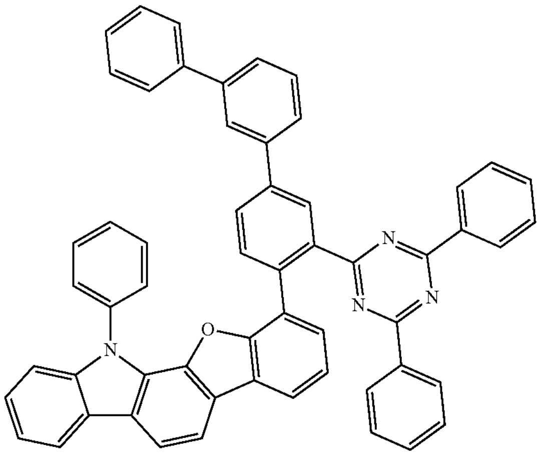

-continued
791
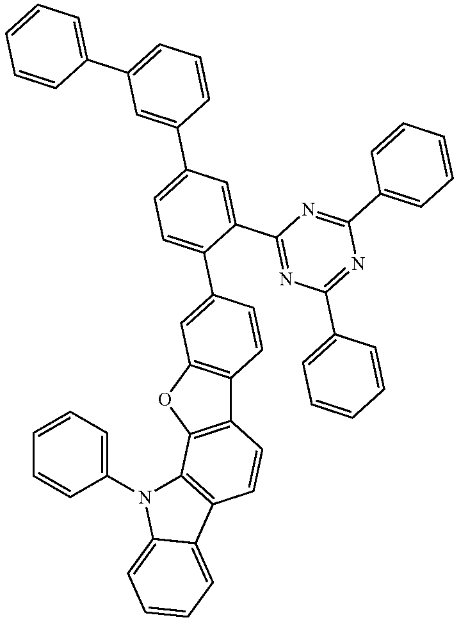
792
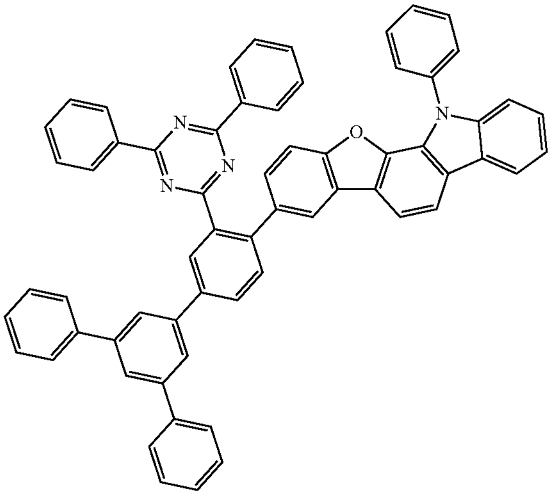
-continued
793
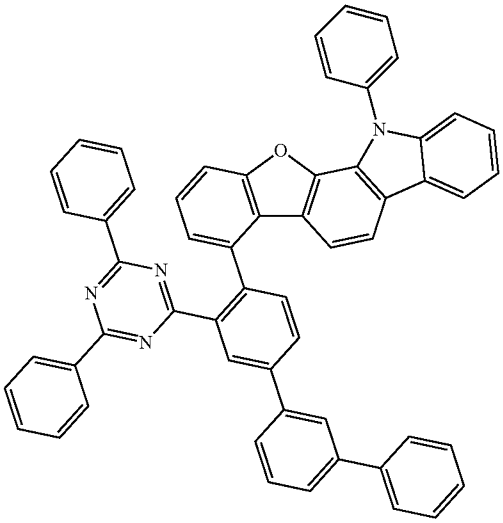
794
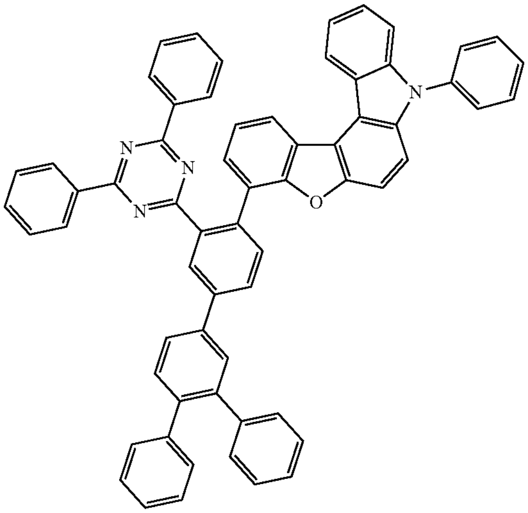

-continued
795
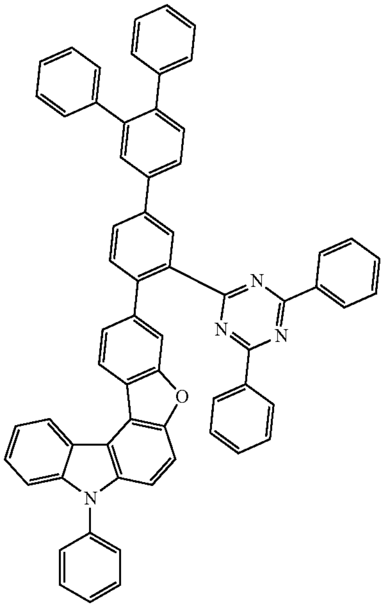
796
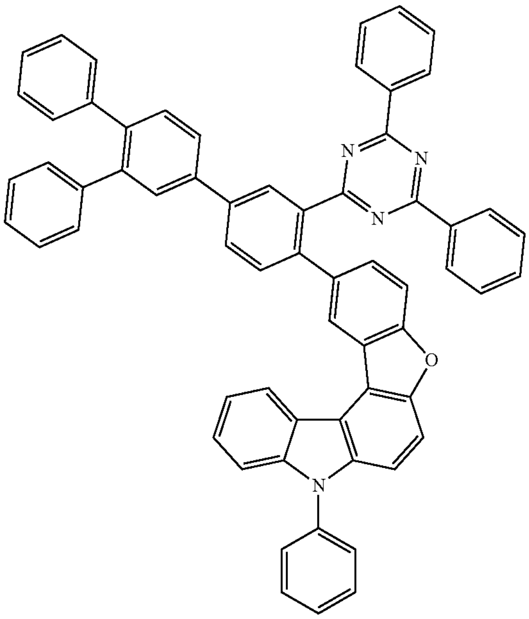
-continued
797
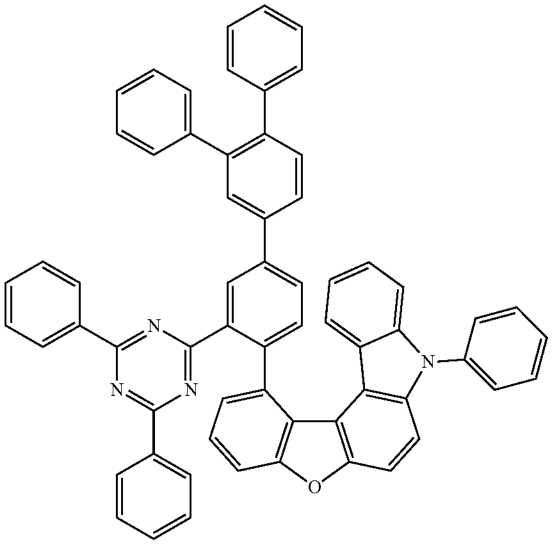
798
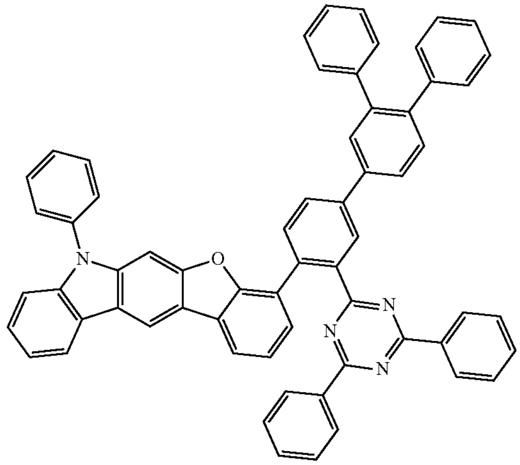
799
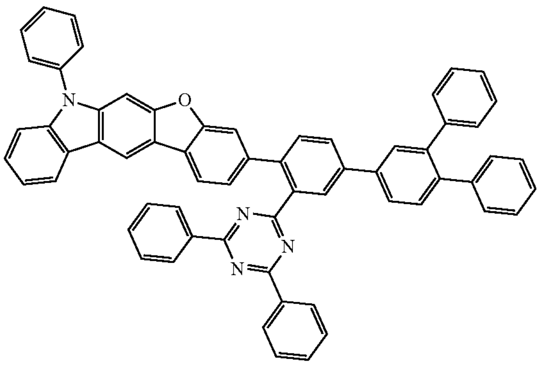

800
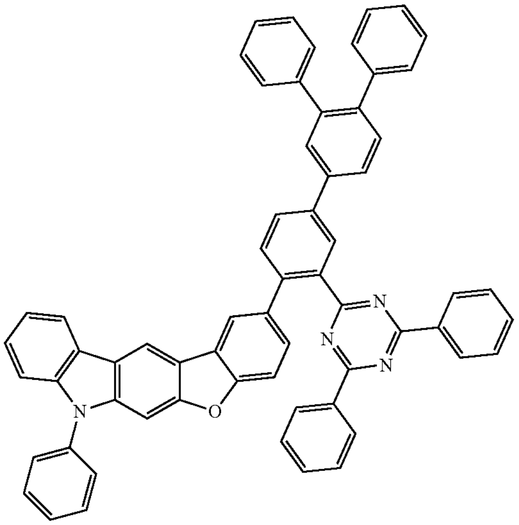
801
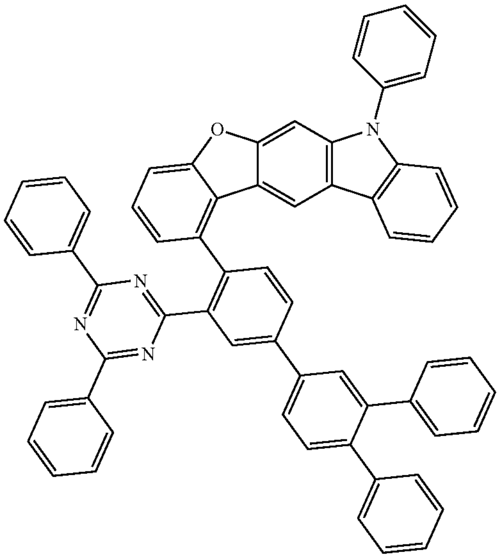
802
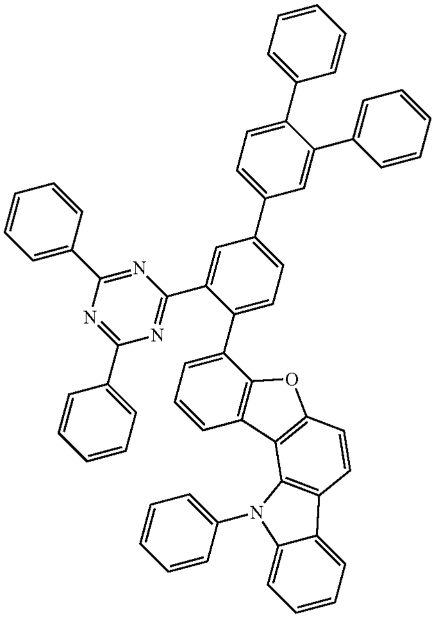
803
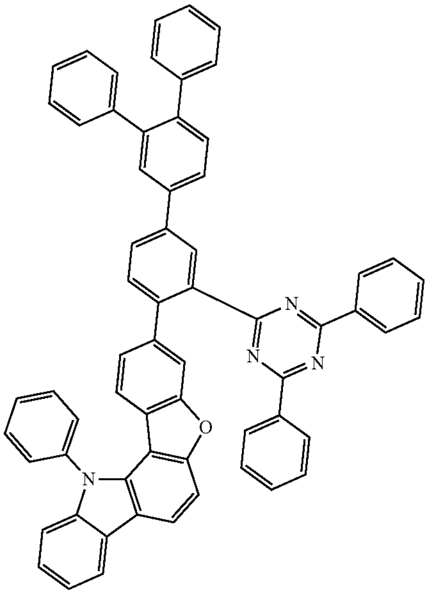

-continued
804
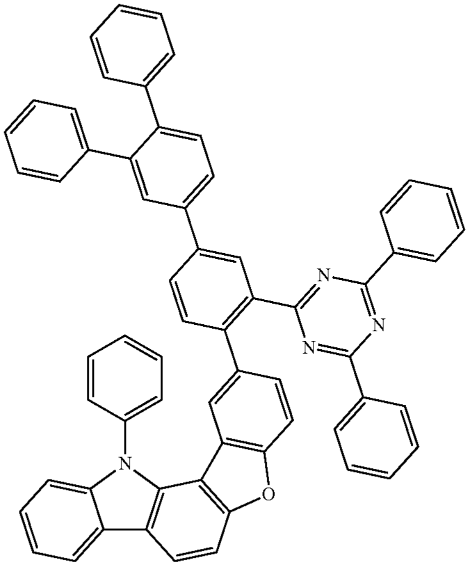
805
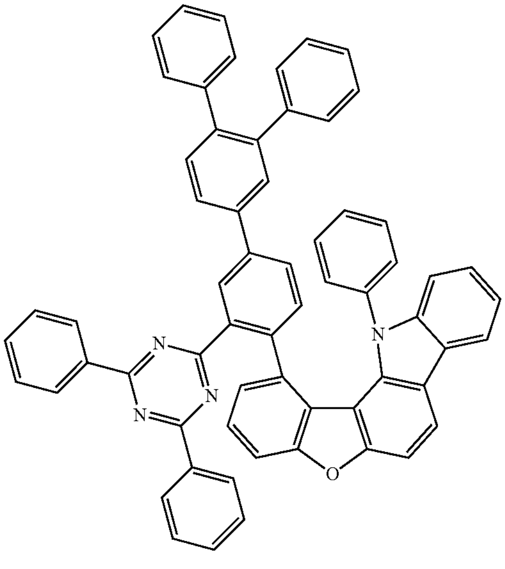
-continued
806
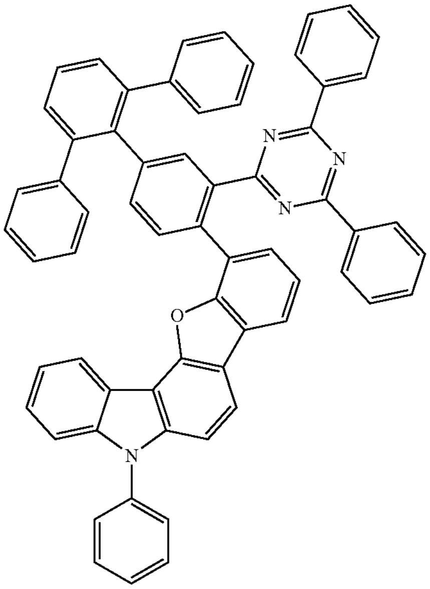
807
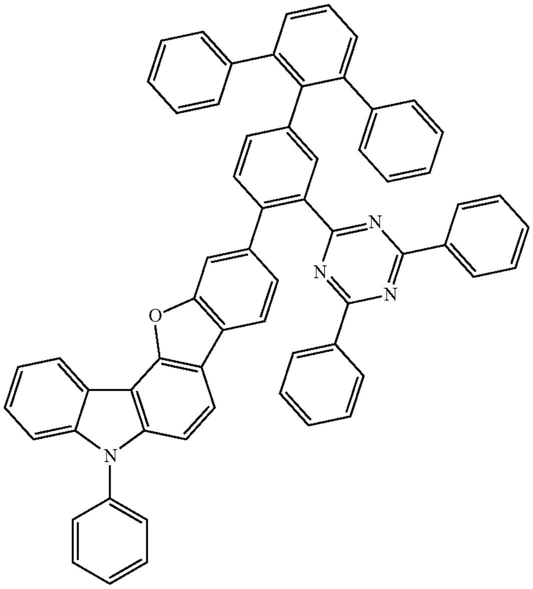
808
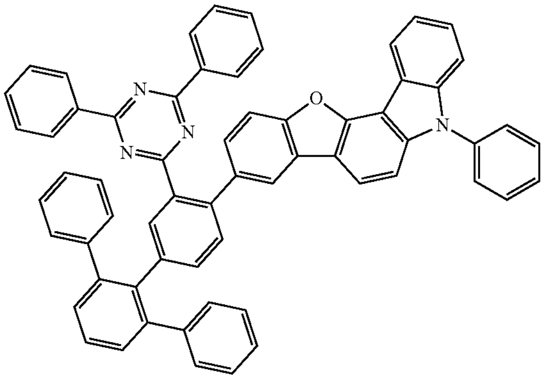

-continued
809
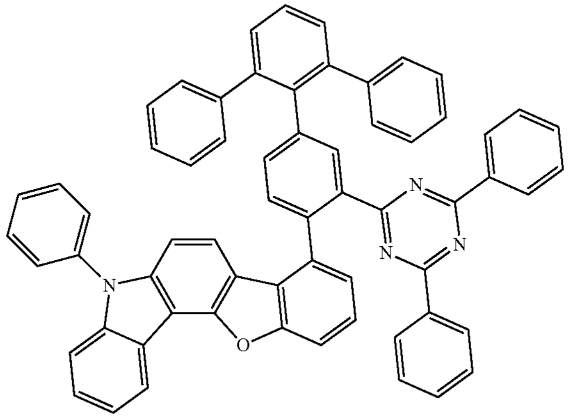
810
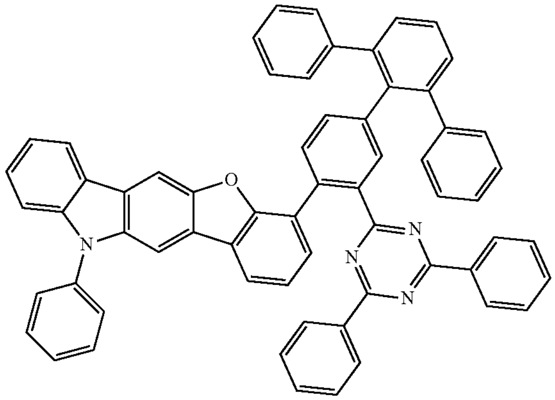
811
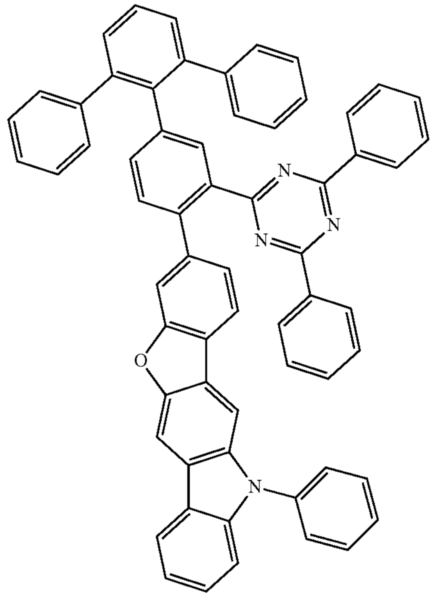
-continued
812
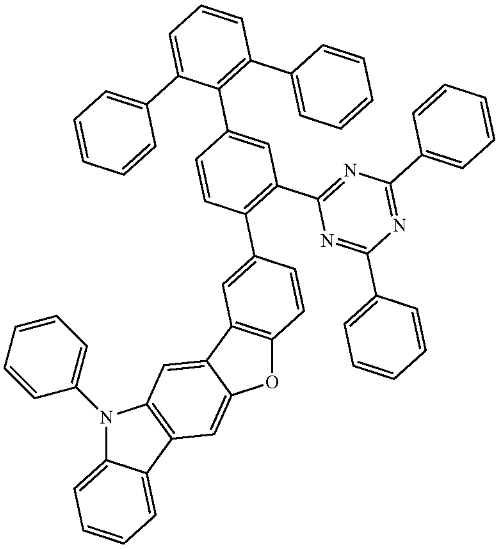
813
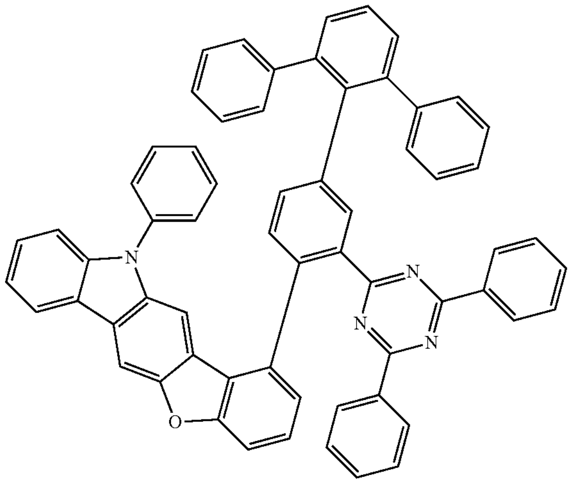
814
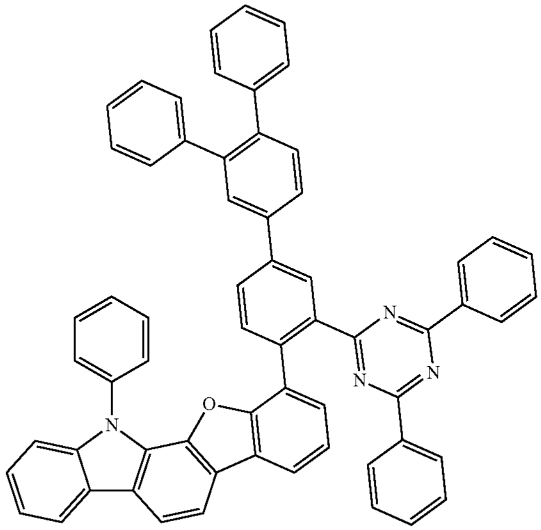

-continued
815
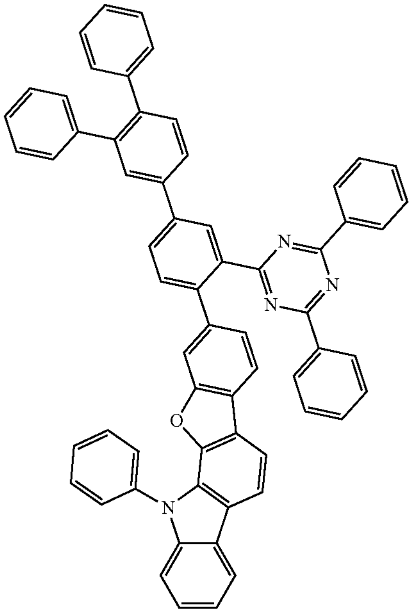
816
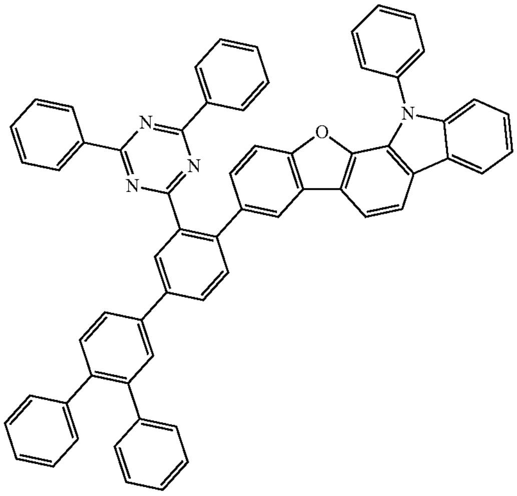
-continued
817
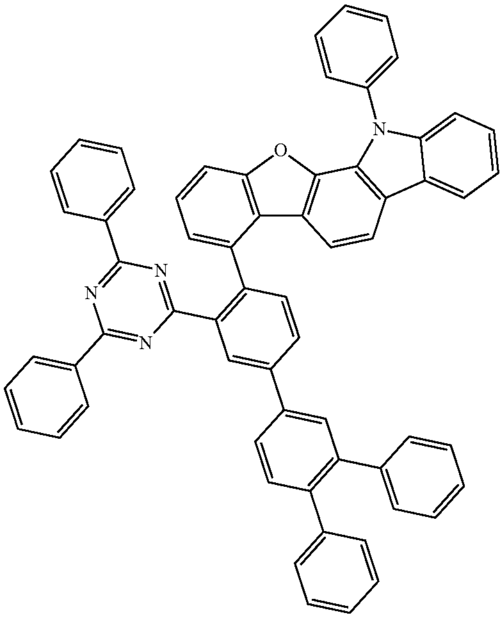
818
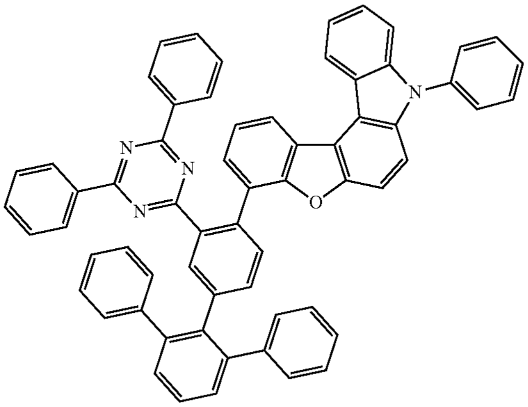

-continued
819
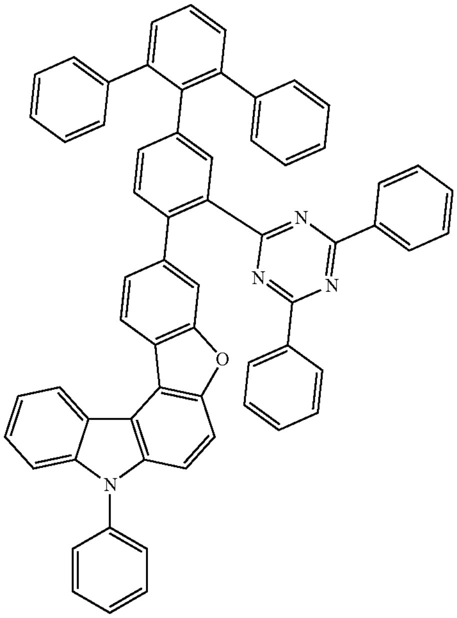
820
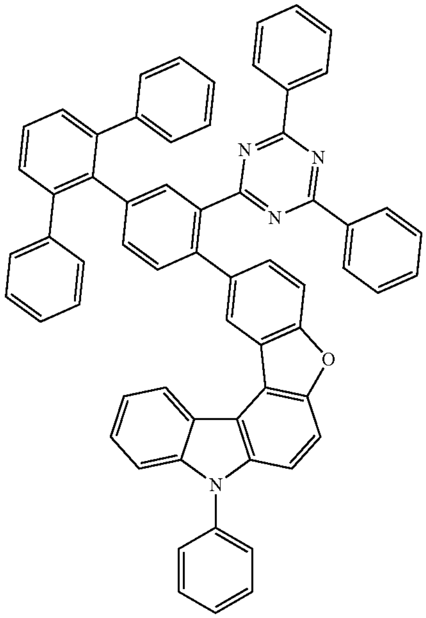
-continued
821
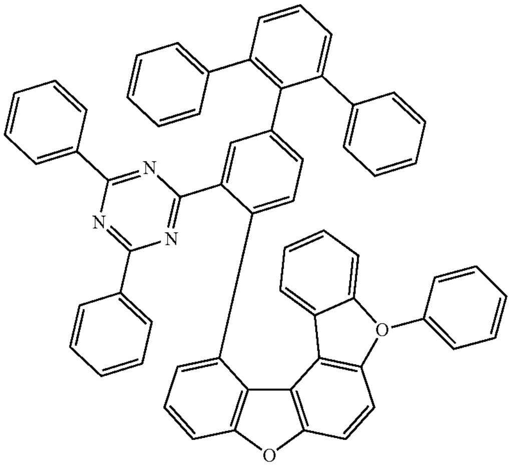
822
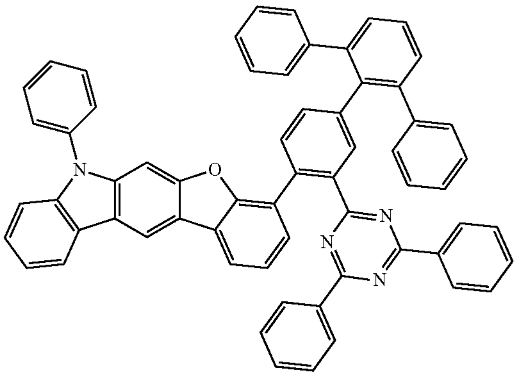
823
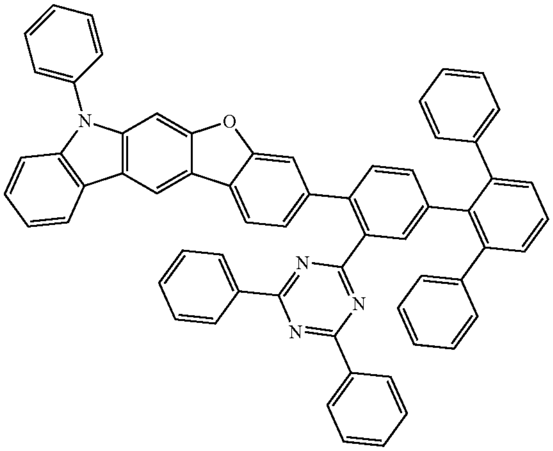

-continued
824
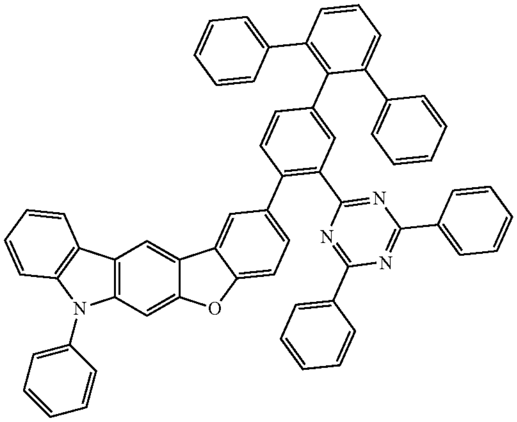
825
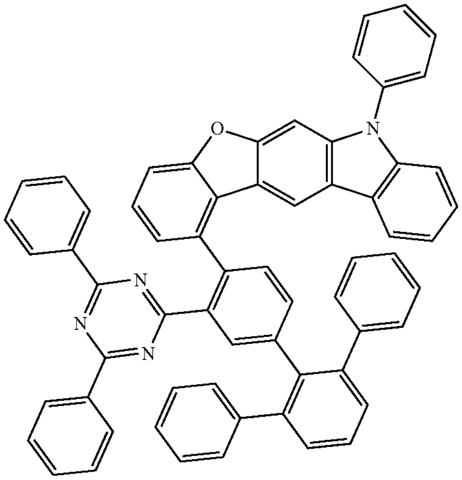
826
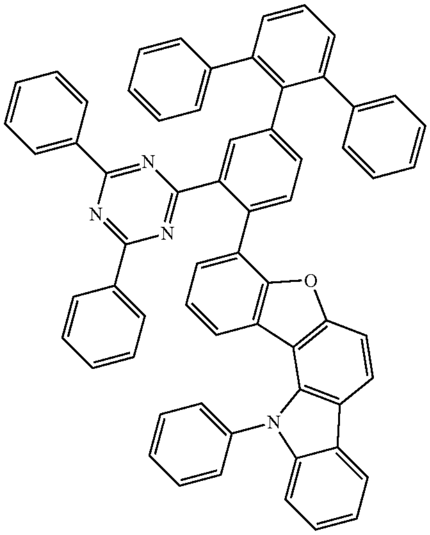
-continued
827
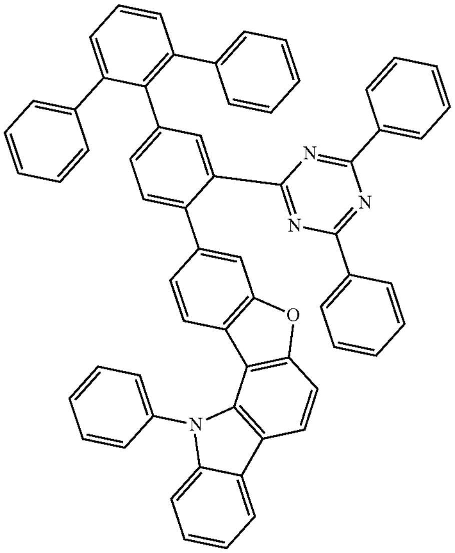
828
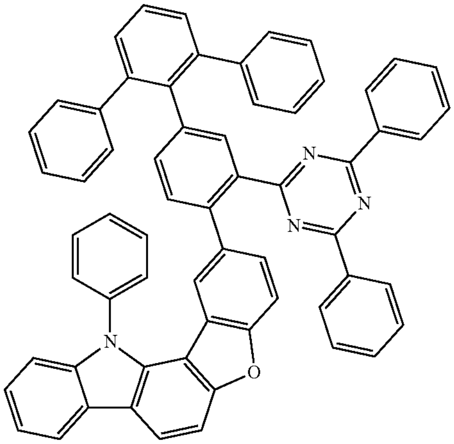
829
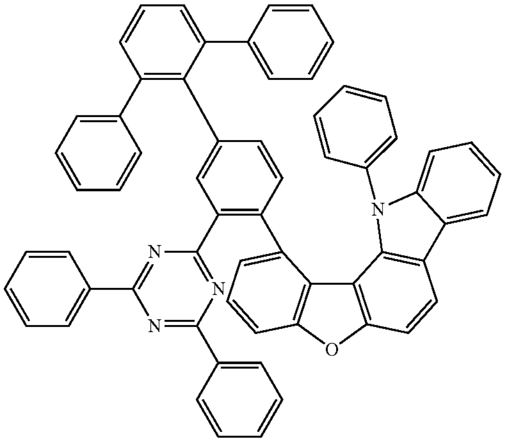

-continued
830
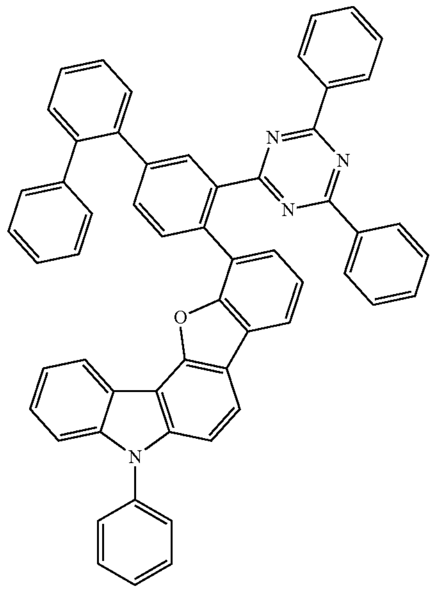
831
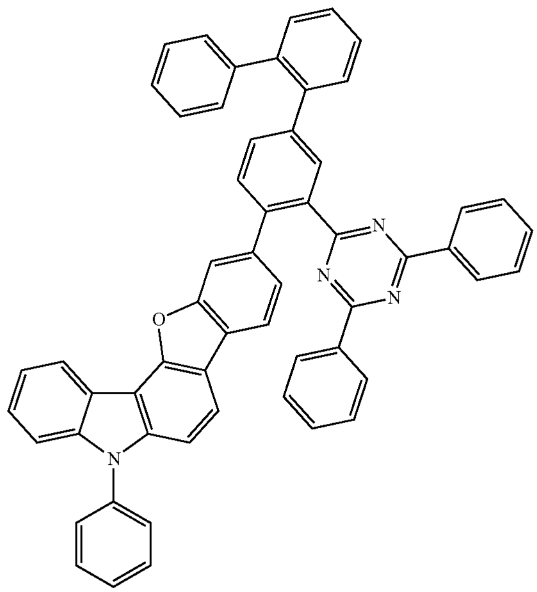
832
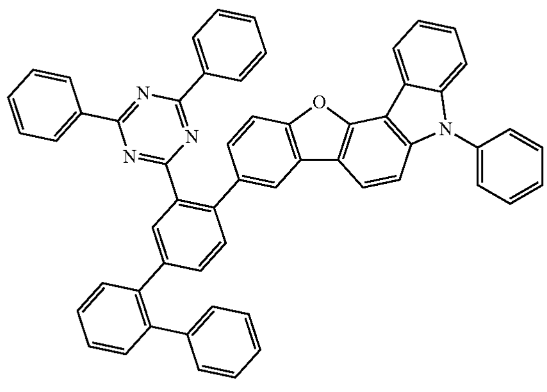
-continued
833
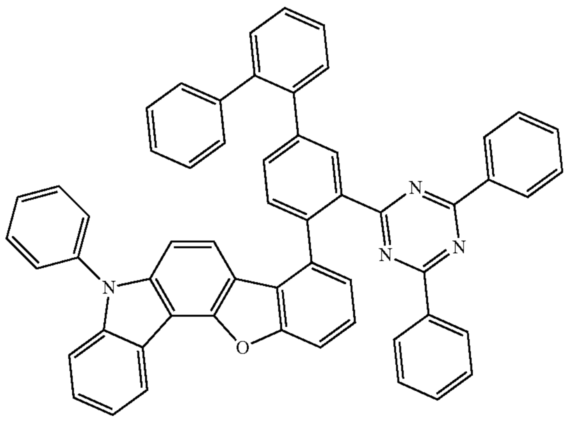
834
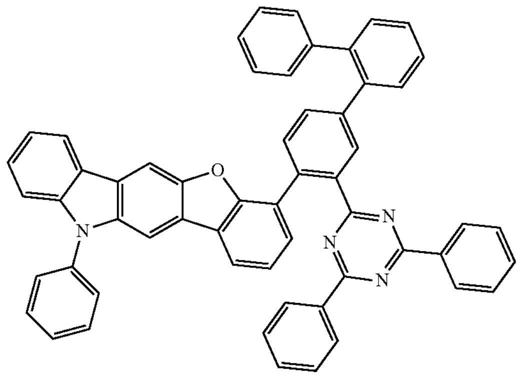
835
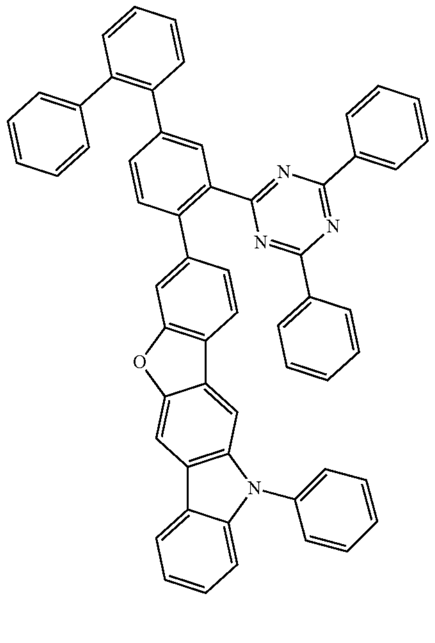

-continued
836
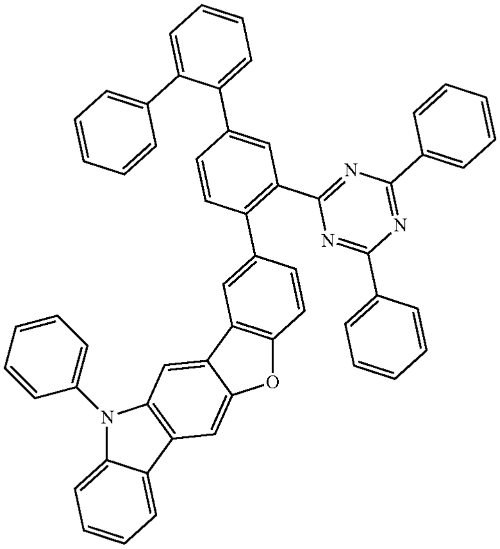
837
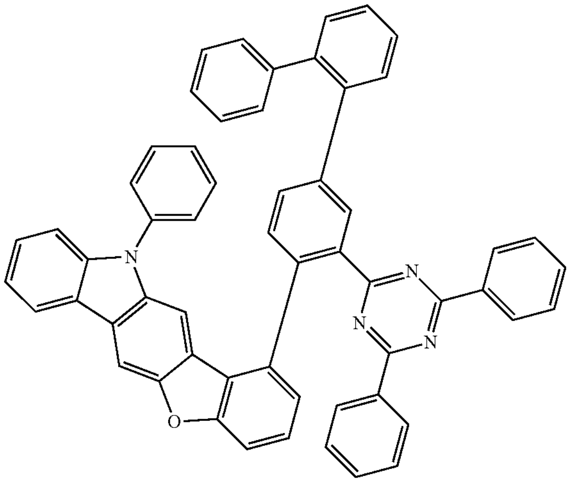
838
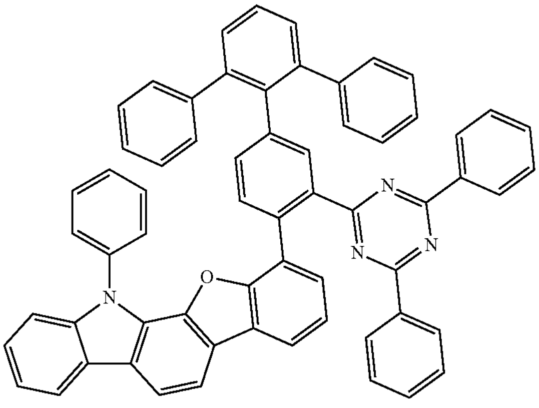
-continued
839
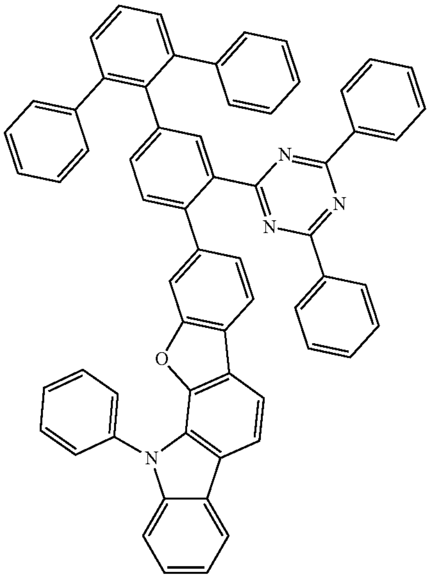
840
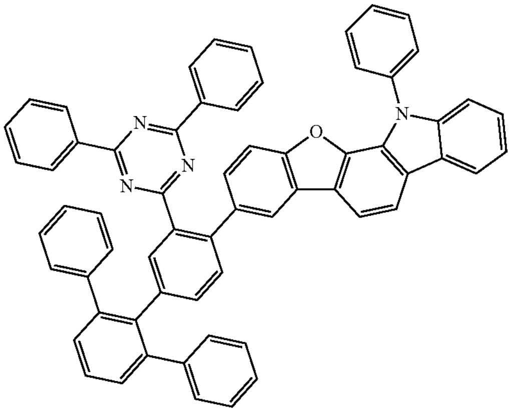
841
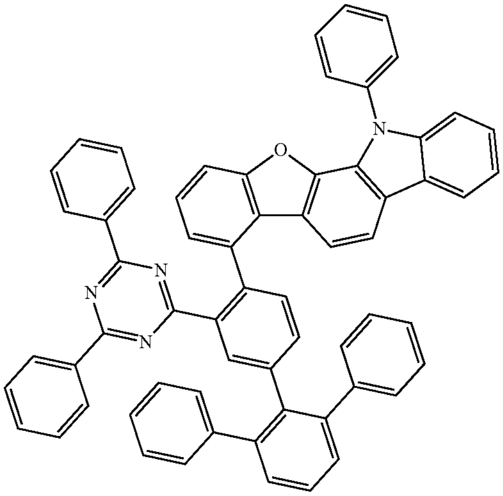

-continued
842
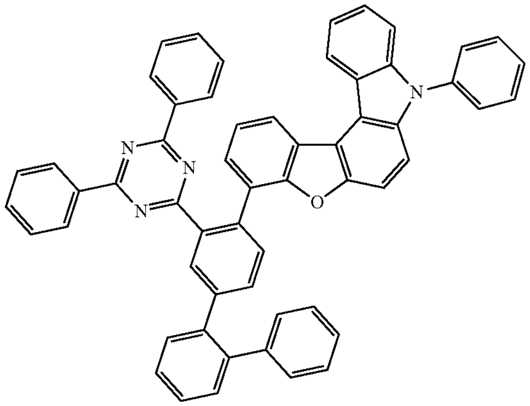
843
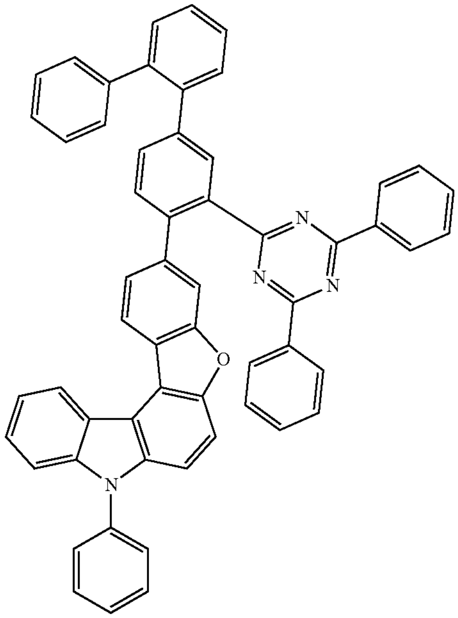
844
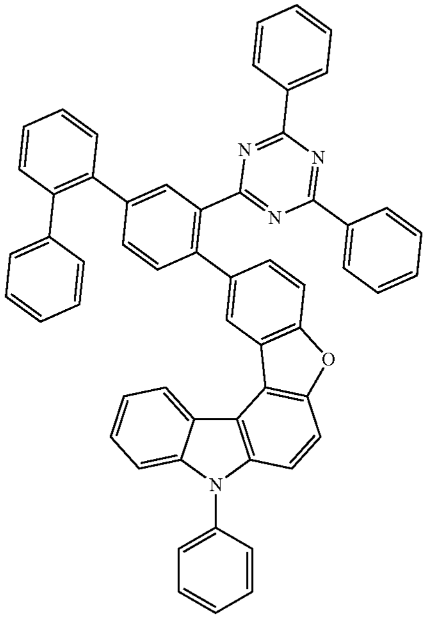
-continued
845
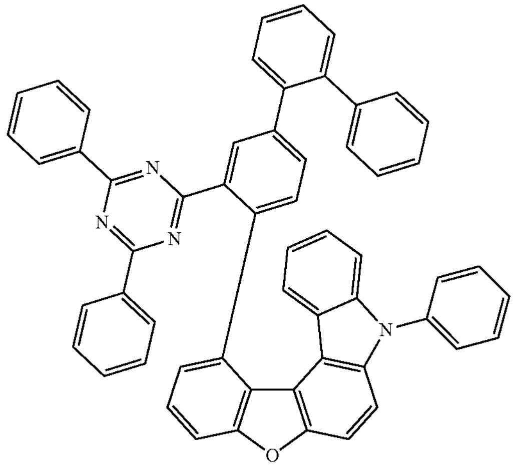
846
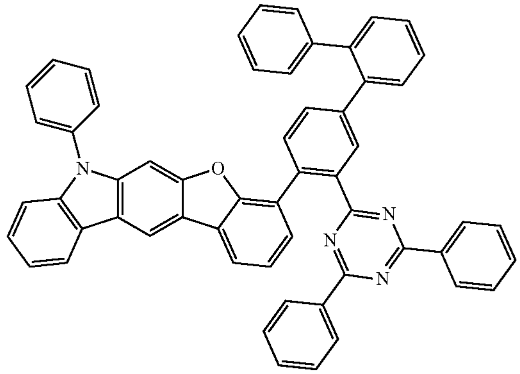
847
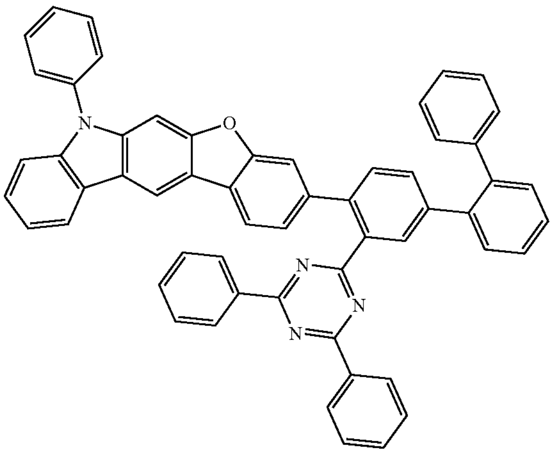

-continued
848
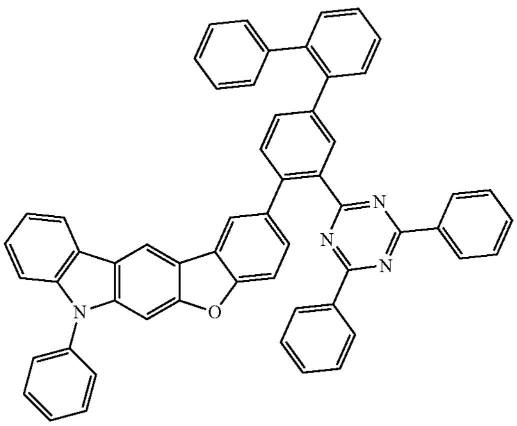
849
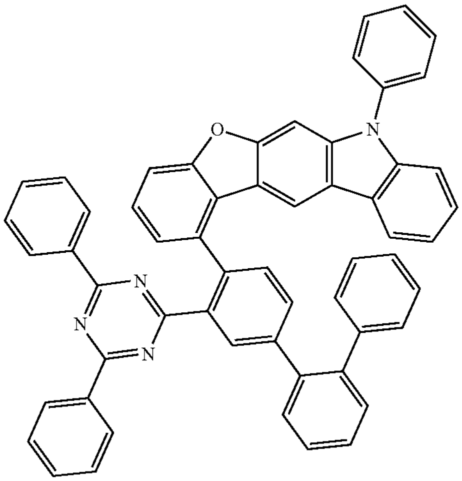
850
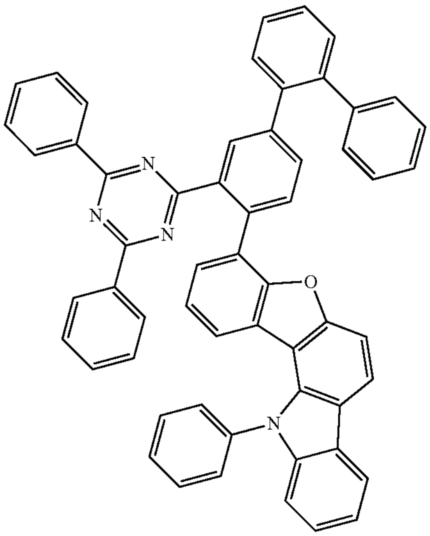
-continued
851
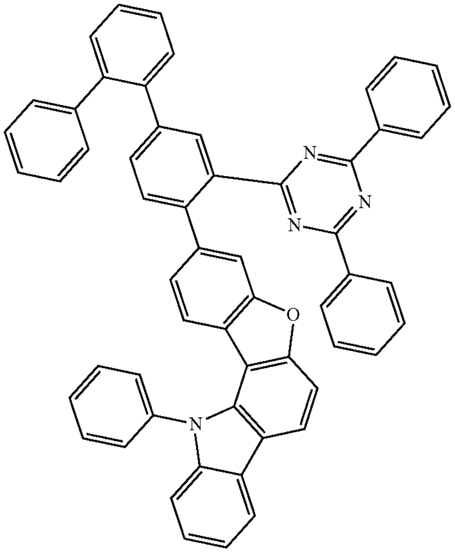
852
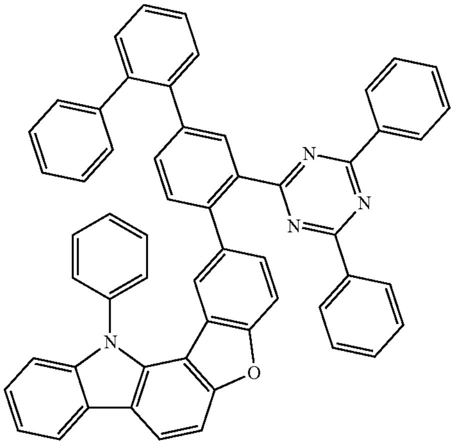
853
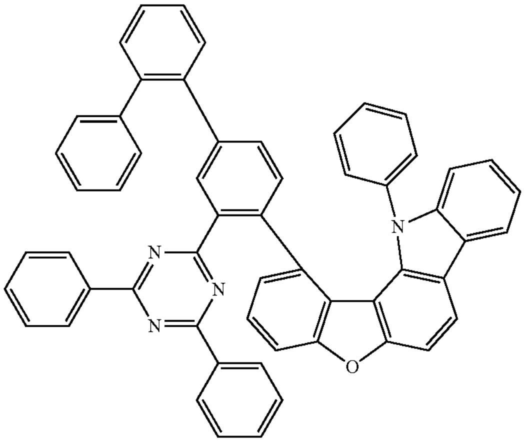

-continued
854
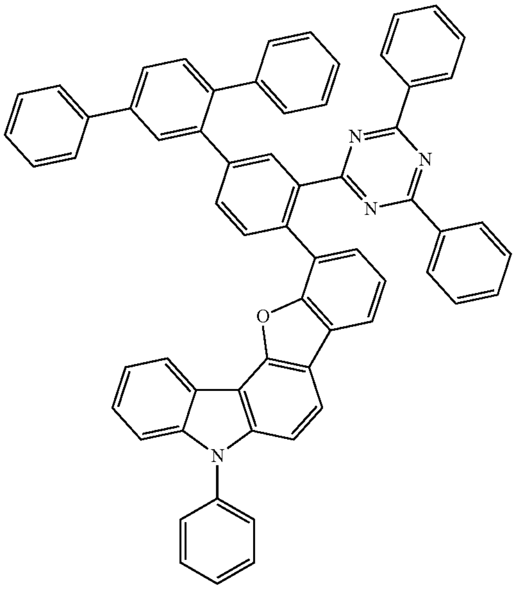
855
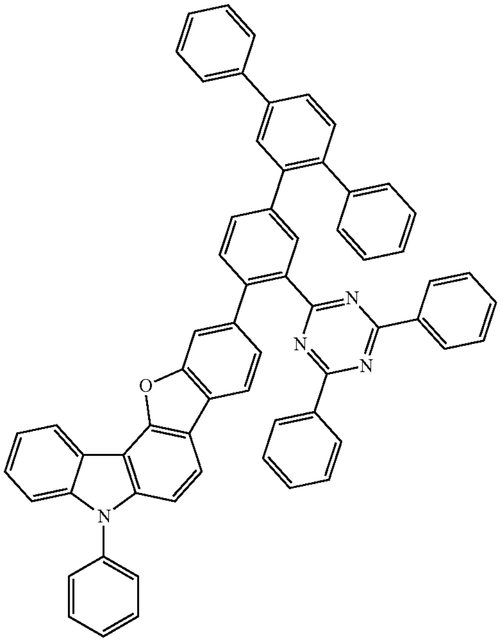
-continued
856
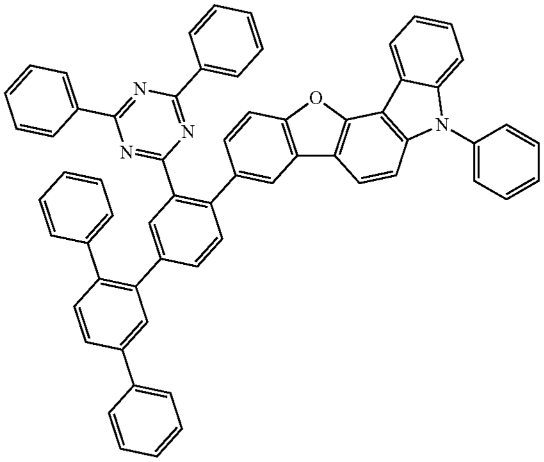
857
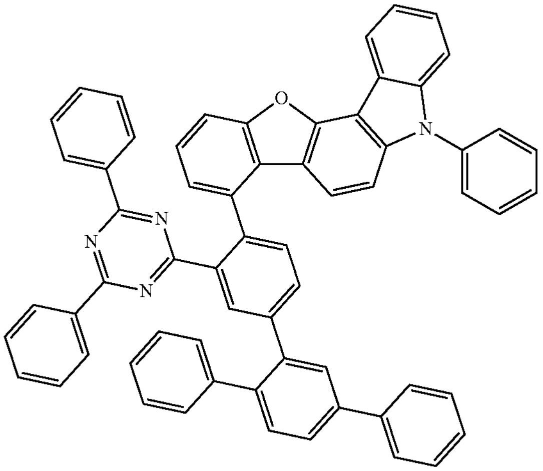
858
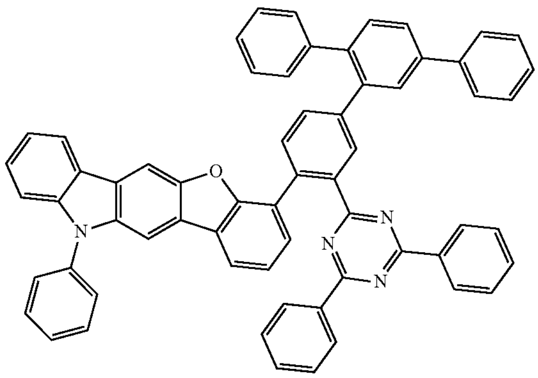

-continued
859
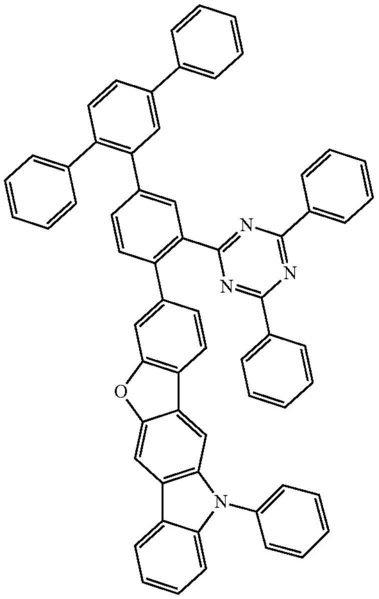
860
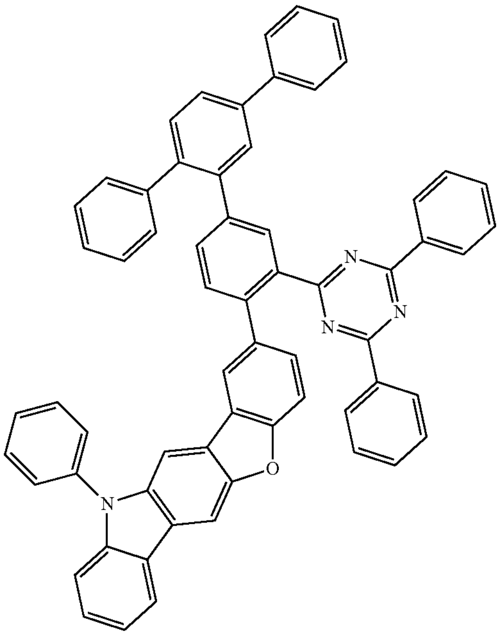
-continued
861
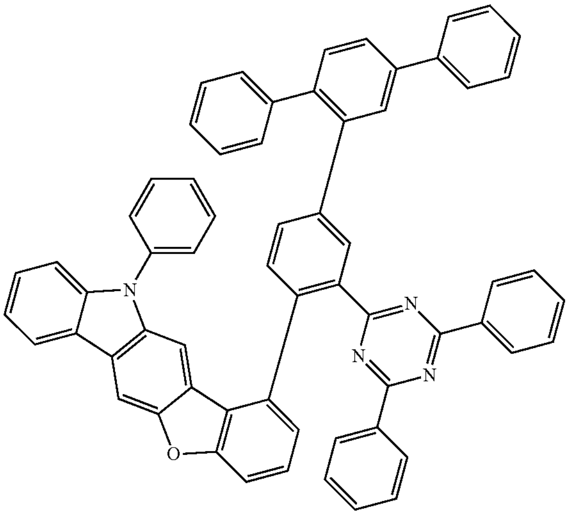
862
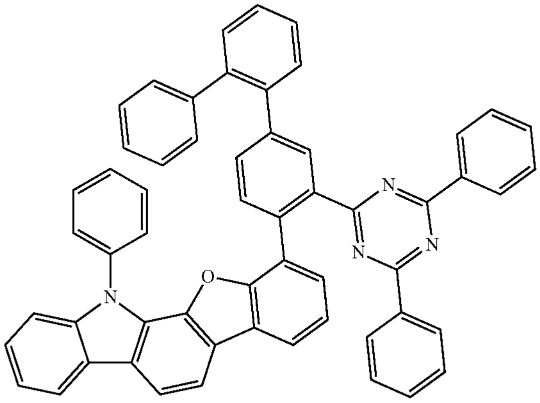
863
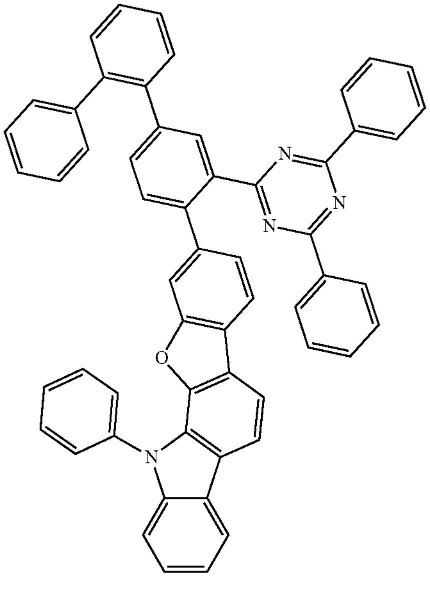

864
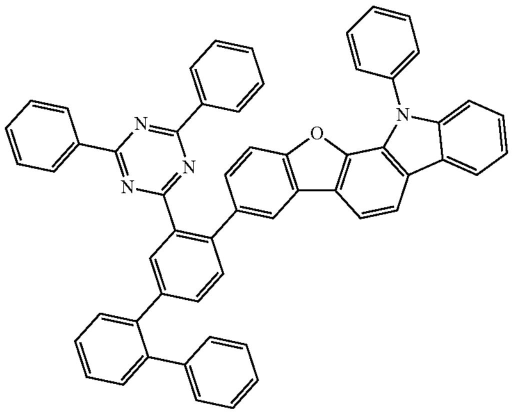
865
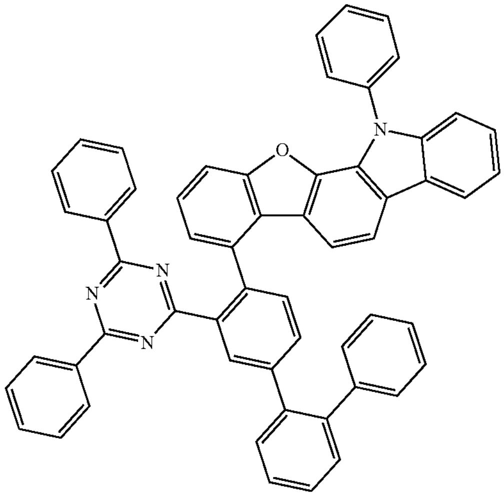
866
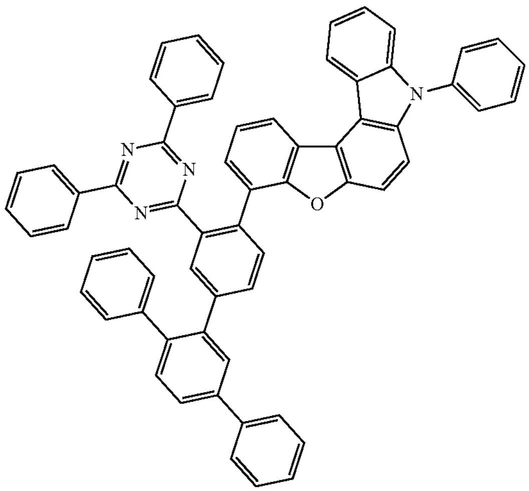
867
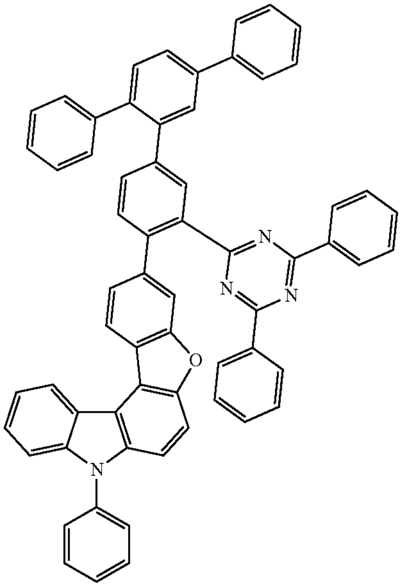
868
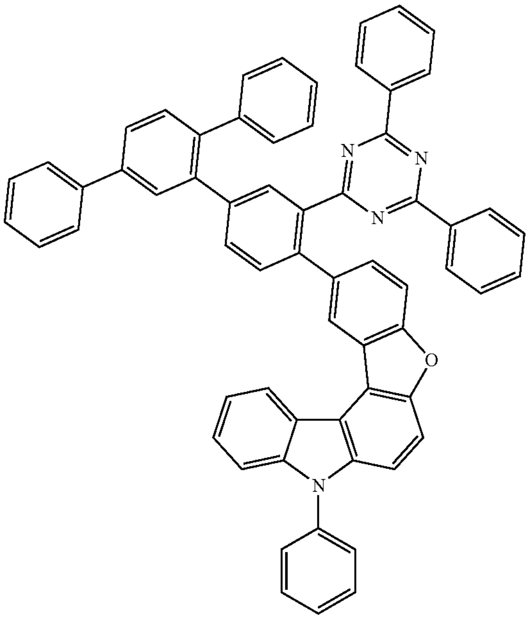

-continued
869
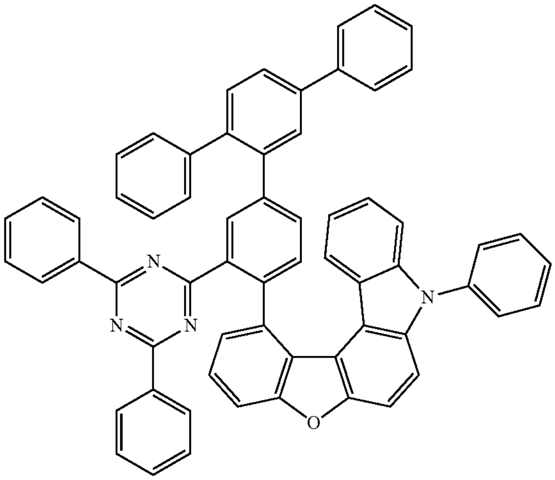
870
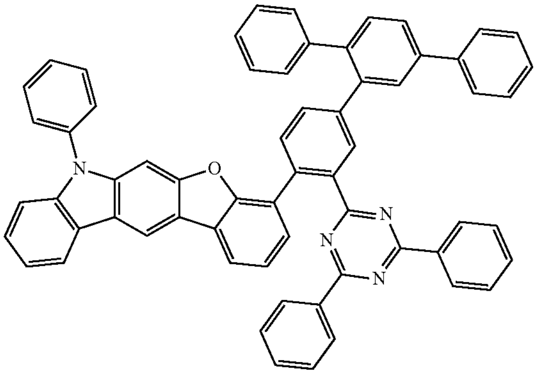
871
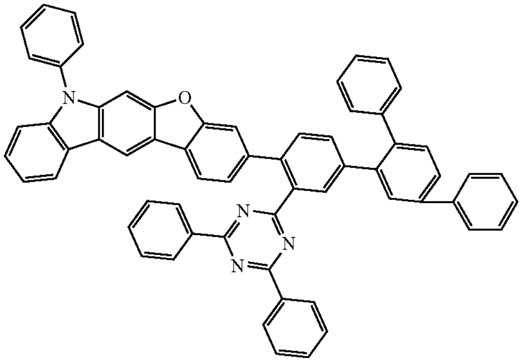
-continued
872
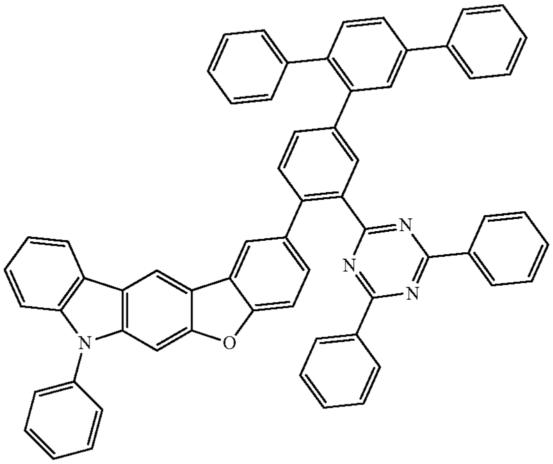
873
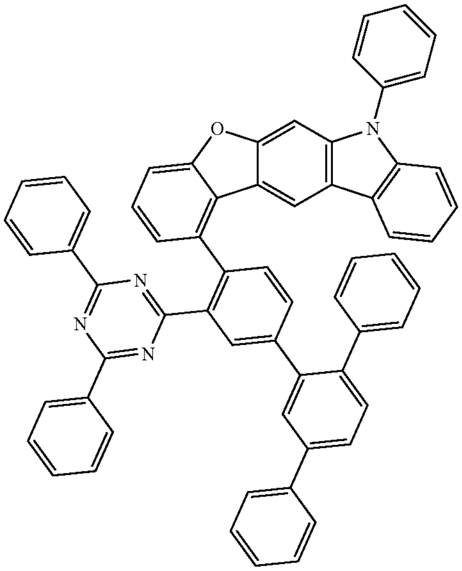

-continued
874
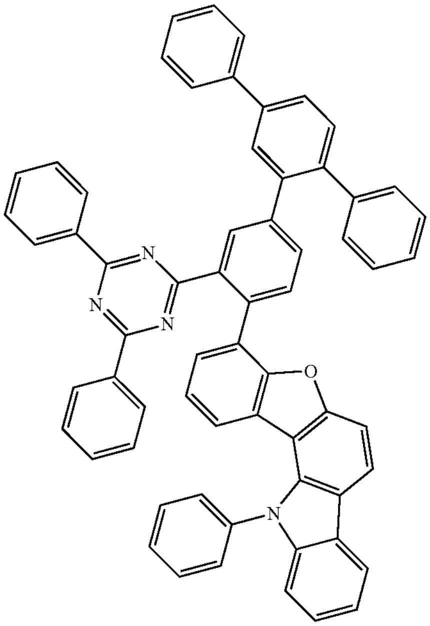
875
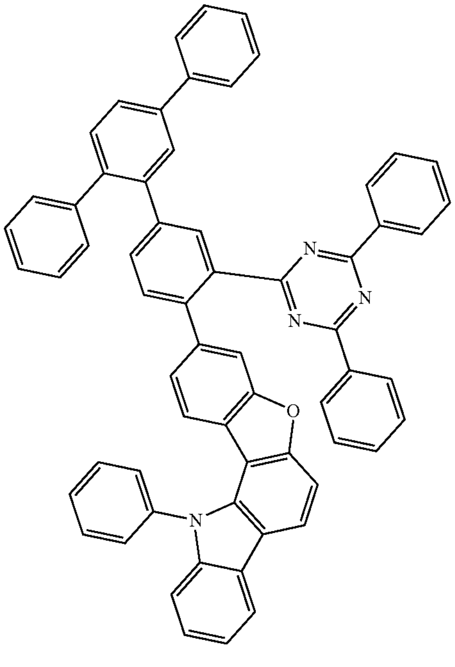
-continued
876
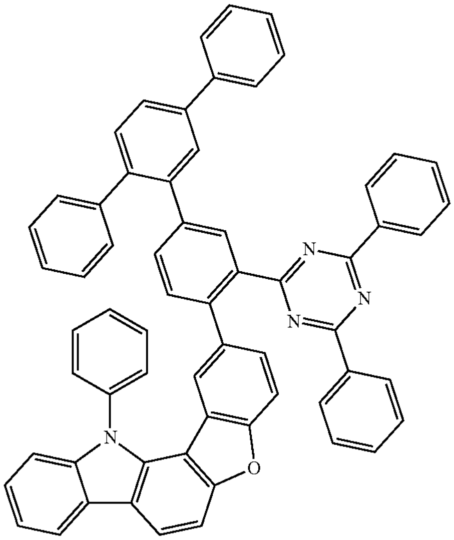
877
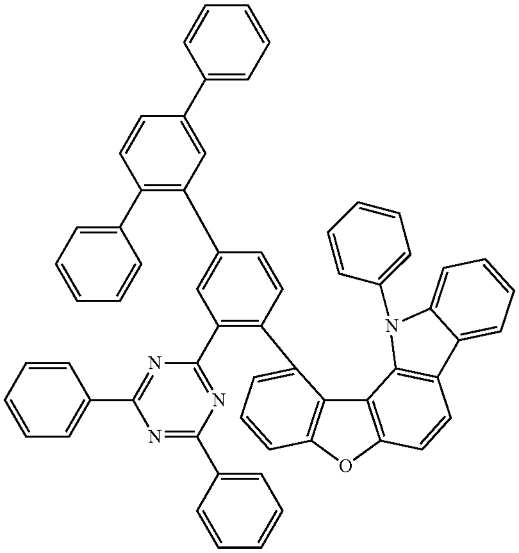
878
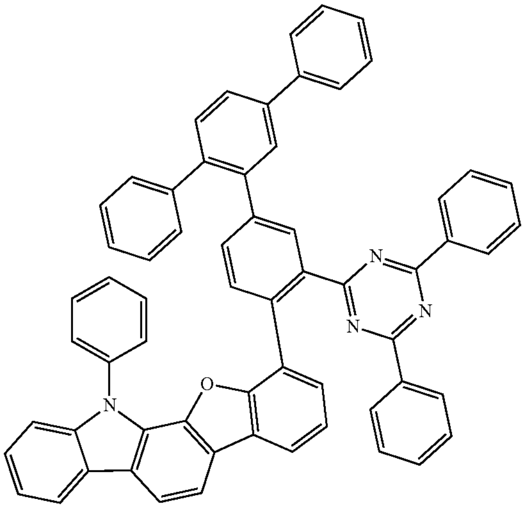

-continued
879
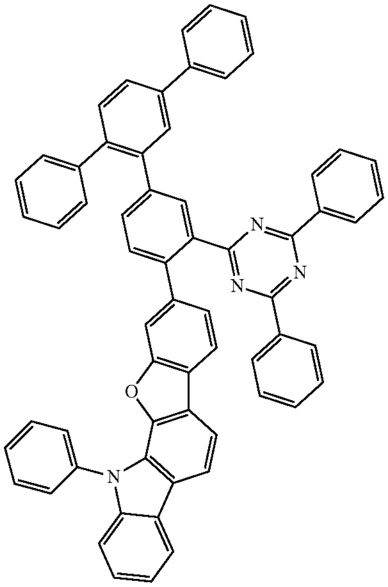
880
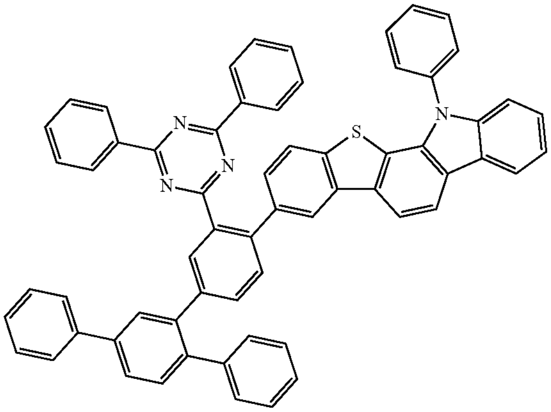
881
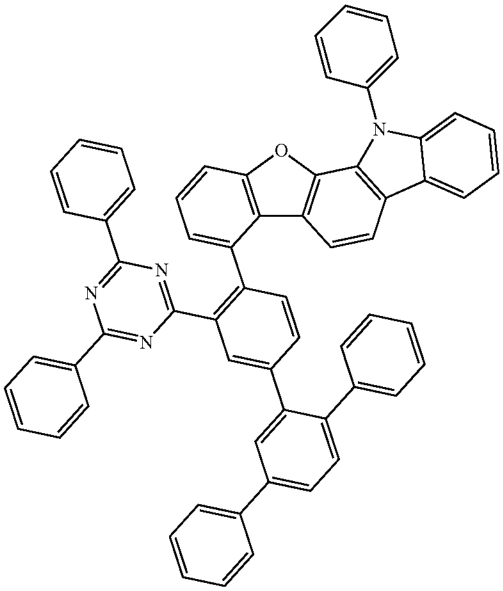
-continued
882
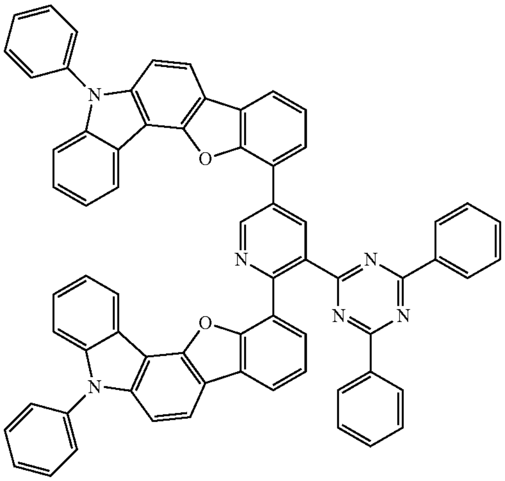
883
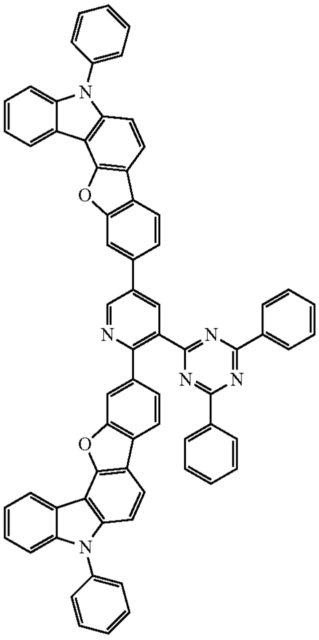

-continued
884
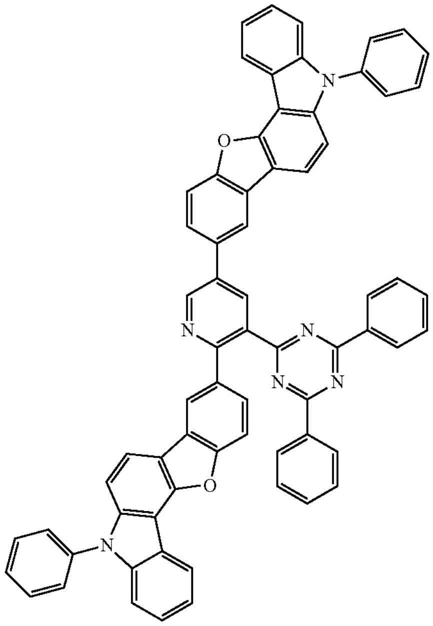
885
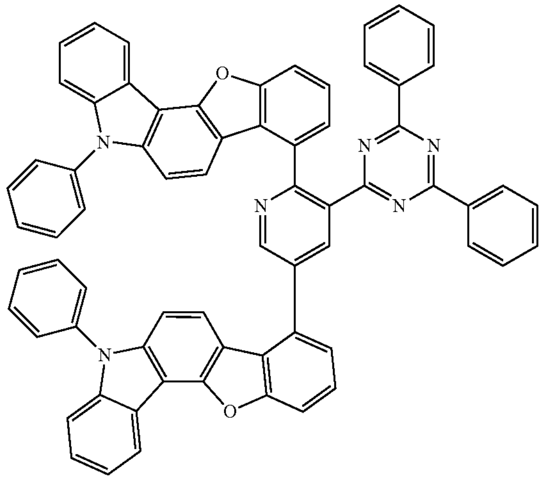
-continued
886
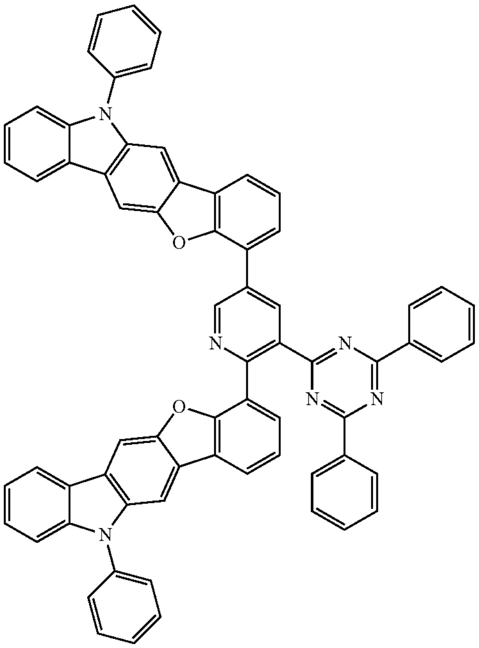
887
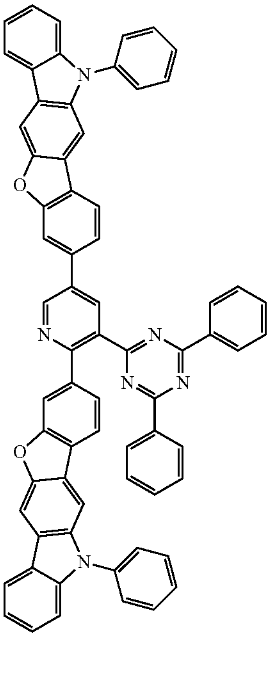

-continued
888
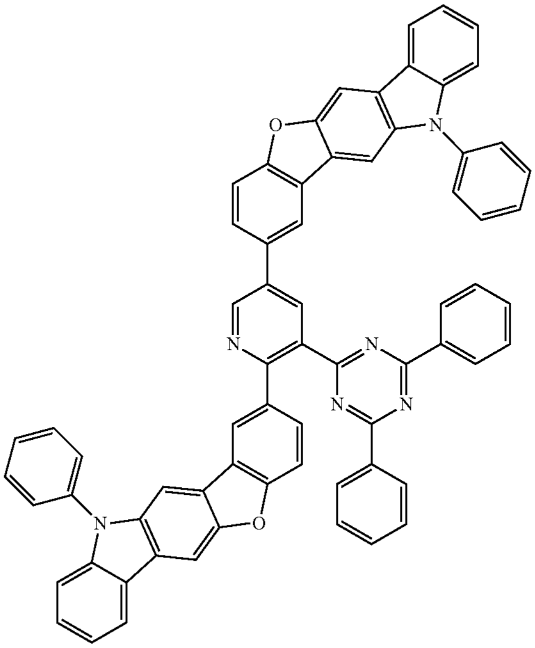
889
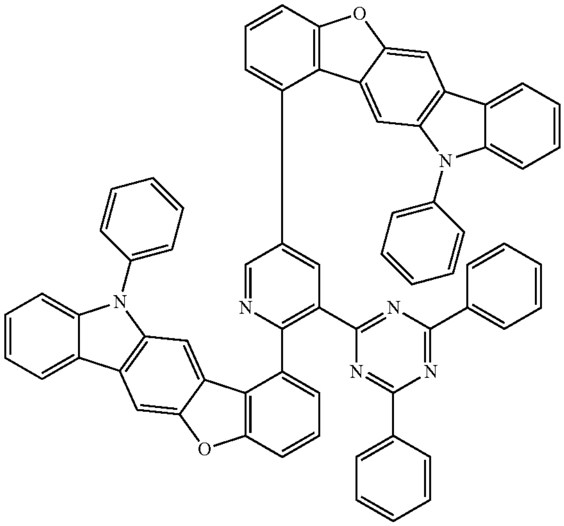
-continued
890
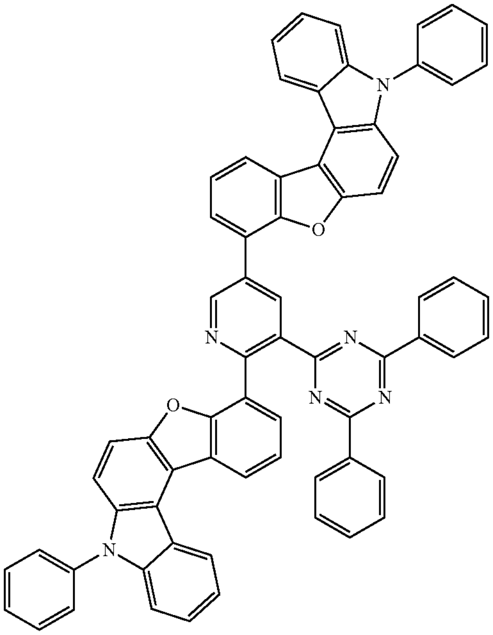
891
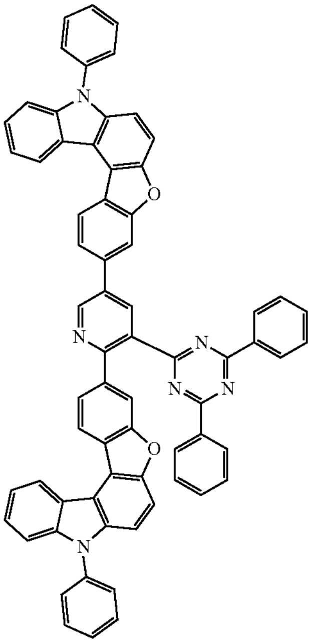

-continued
892
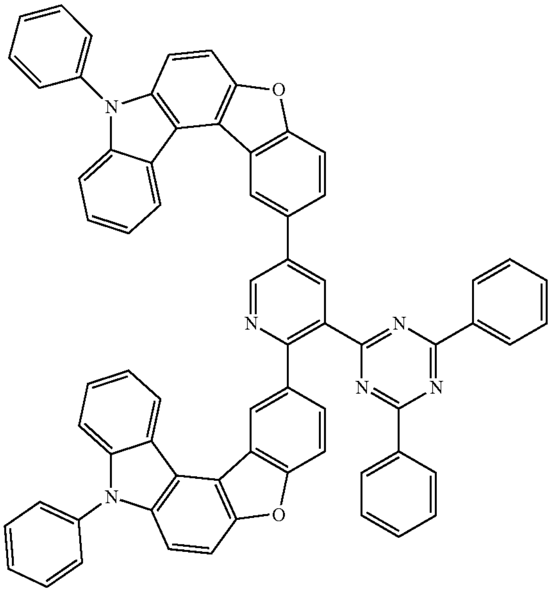
893
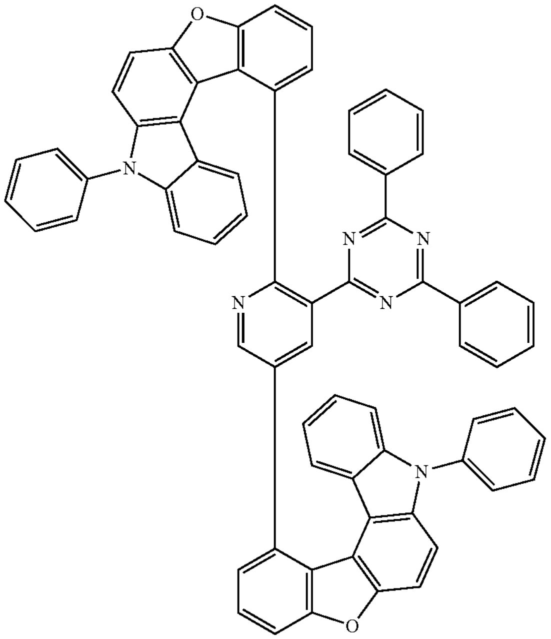
-continued
894
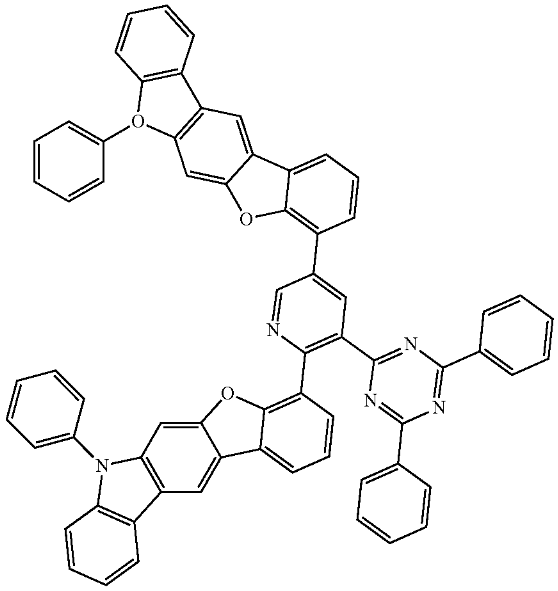
895
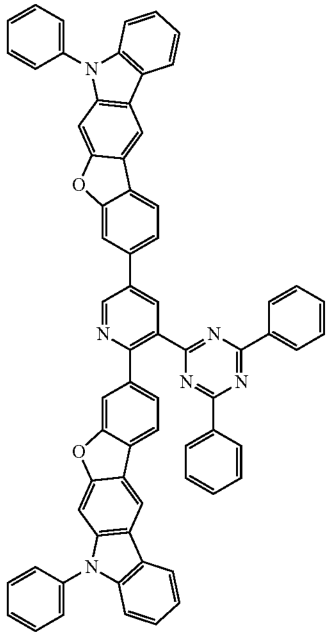

-continued
896
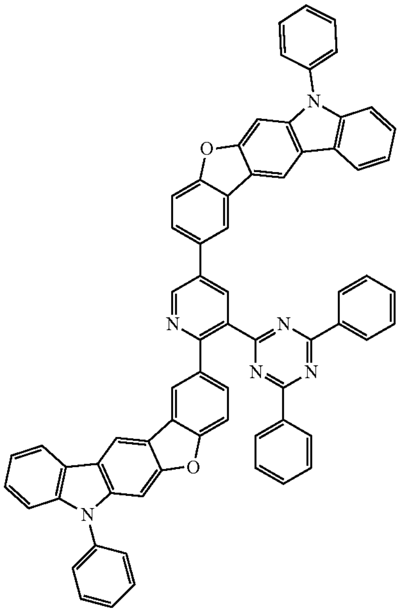
898
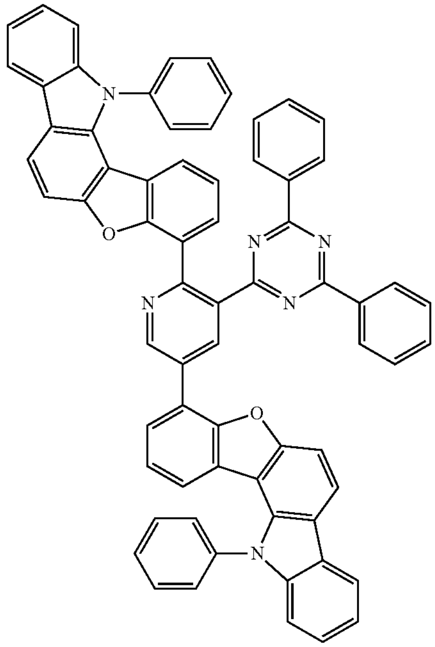
897
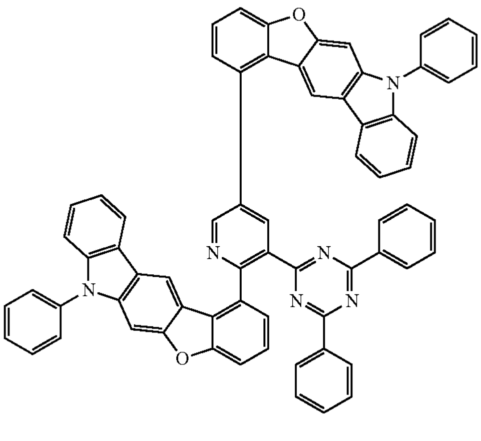
899
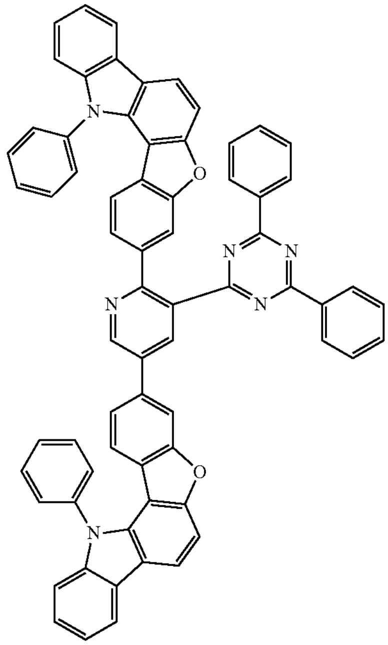

-continued
900
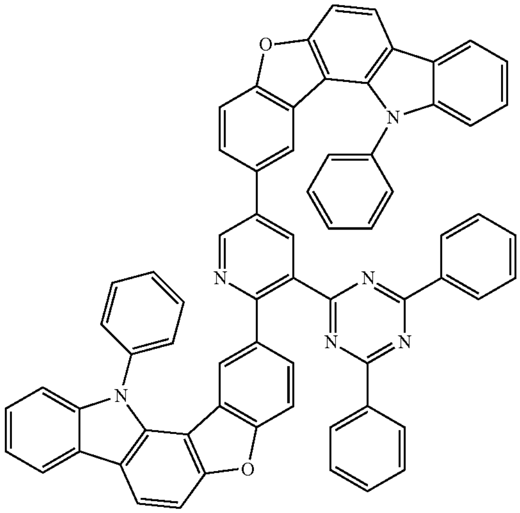
901
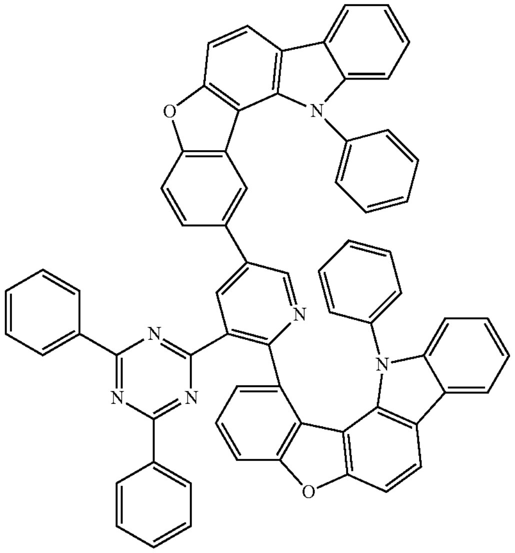
902
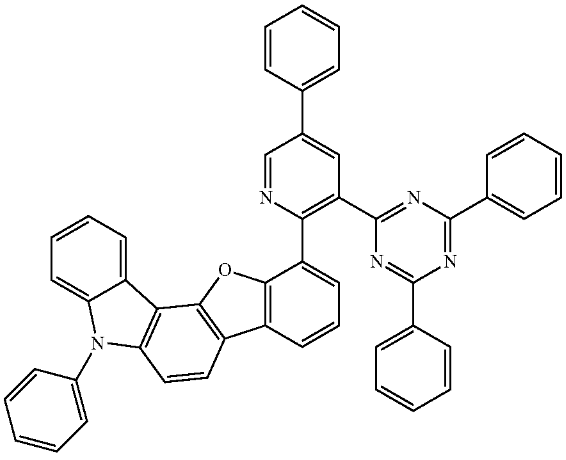
-continued
903
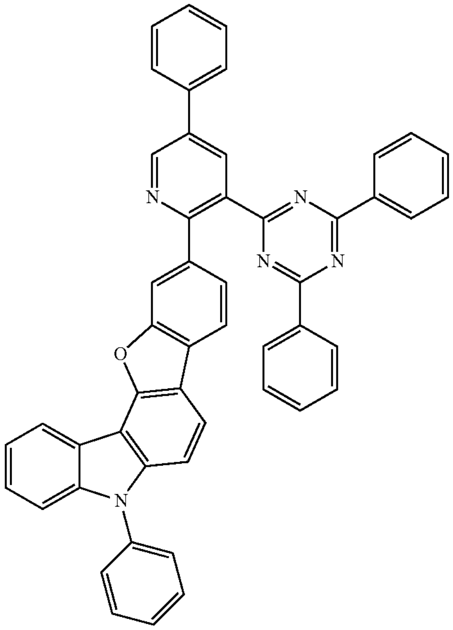
904
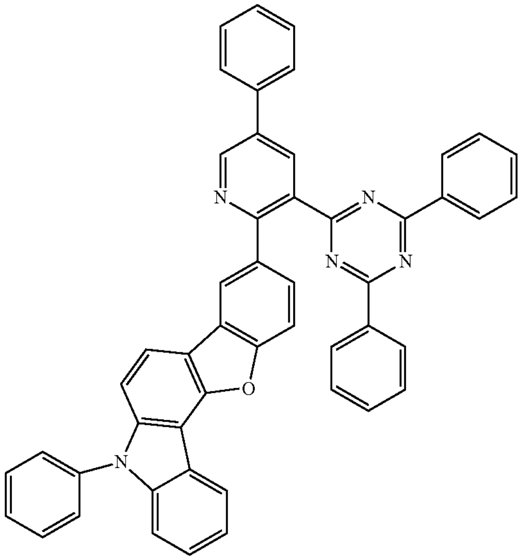
905
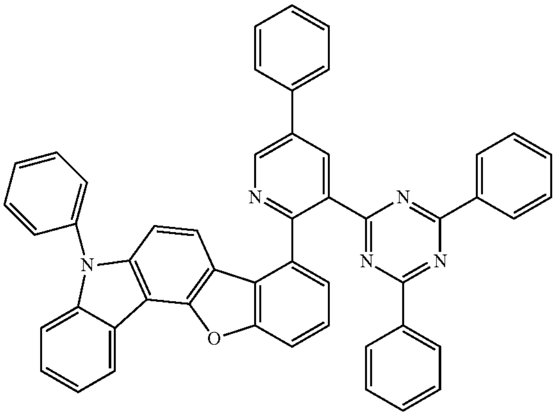

-continued
906
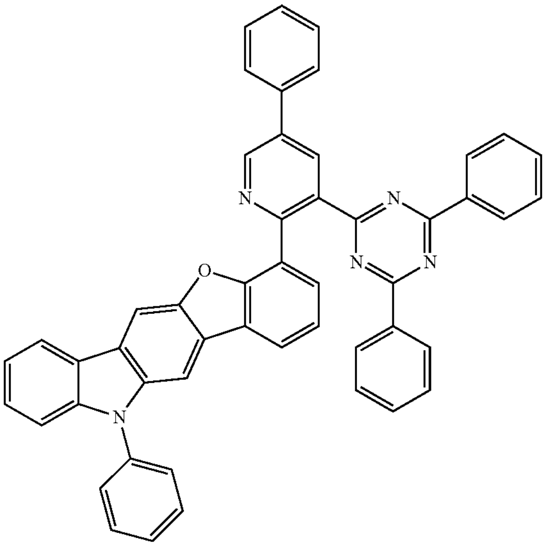
907
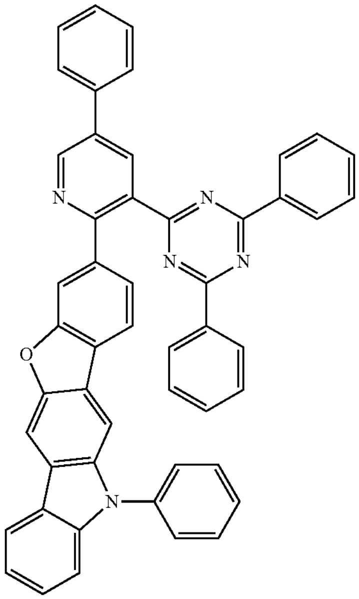
-continued
908
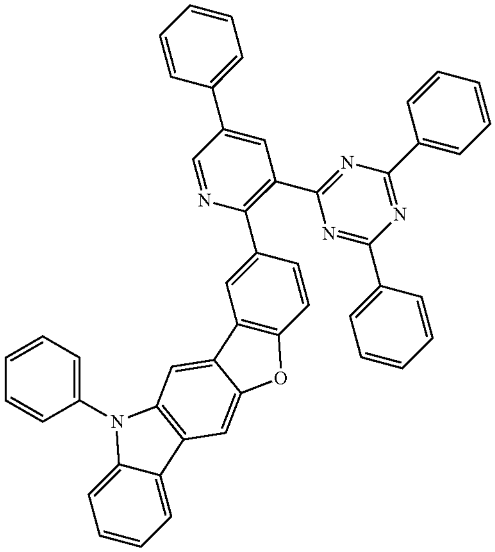
909
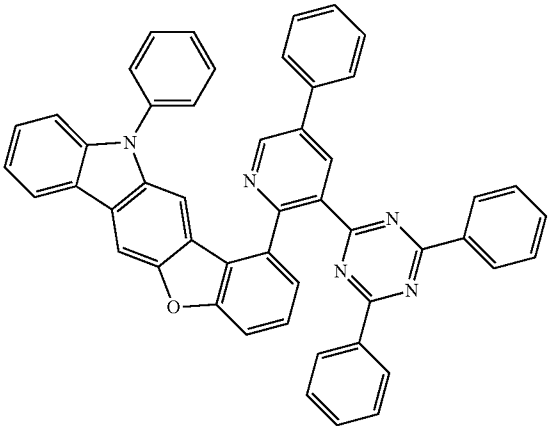
910
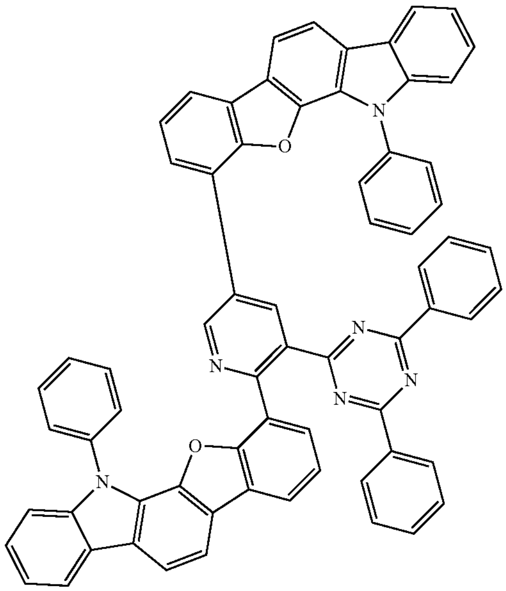

-continued
911
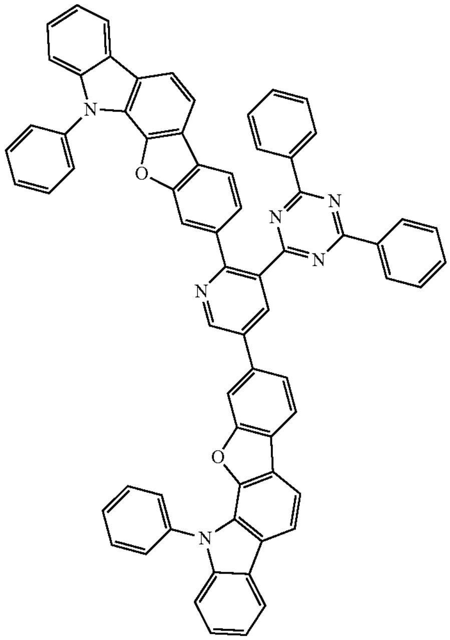
912
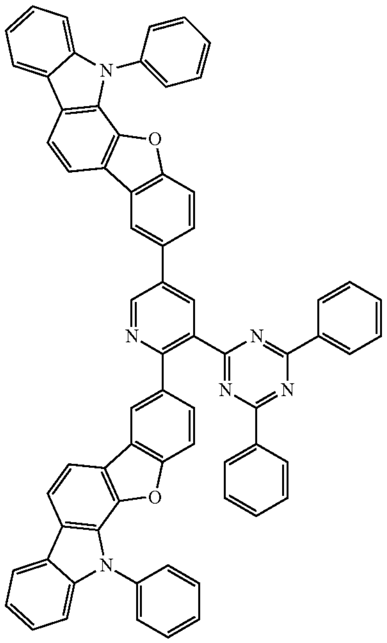
-continued
913
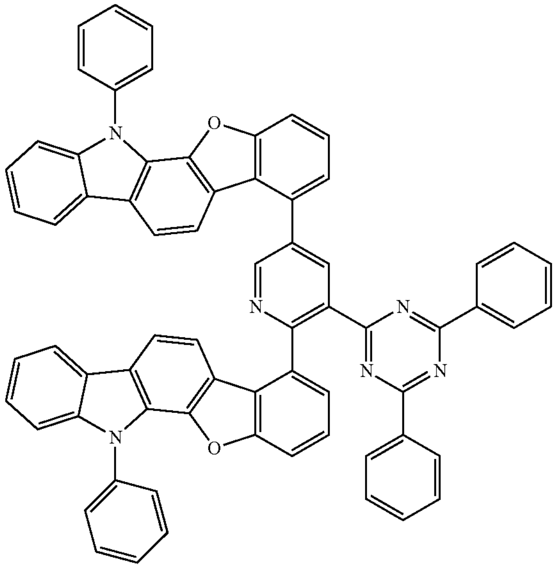
914
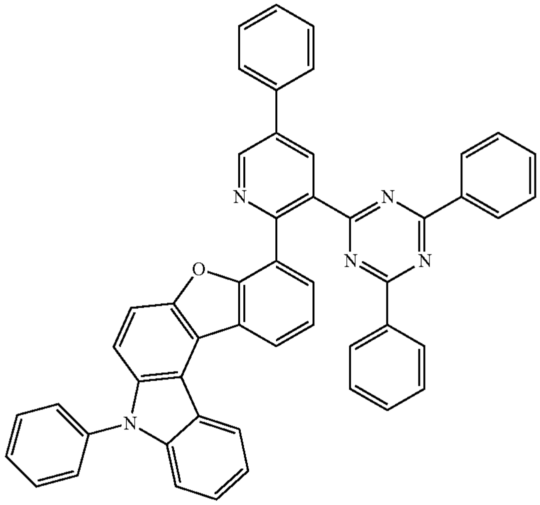

-continued
915
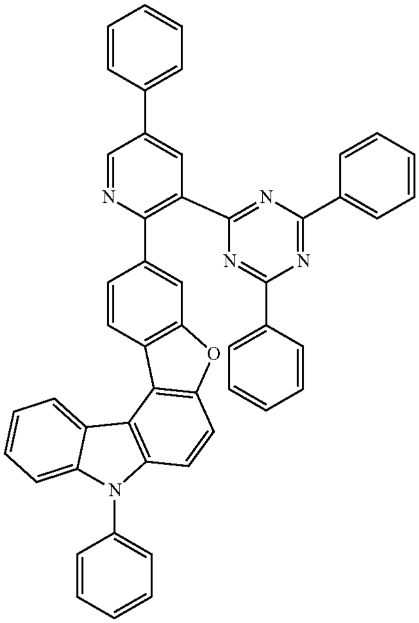
916
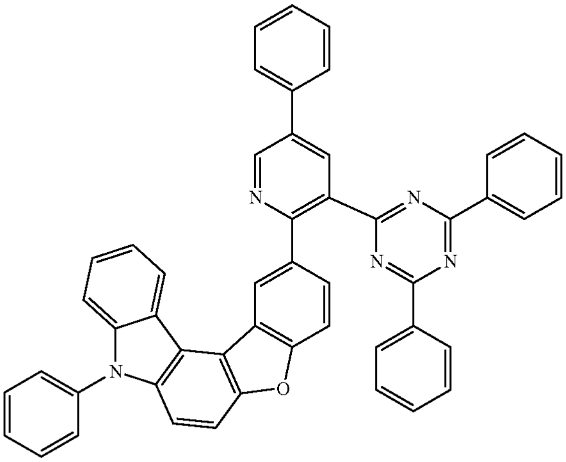
917
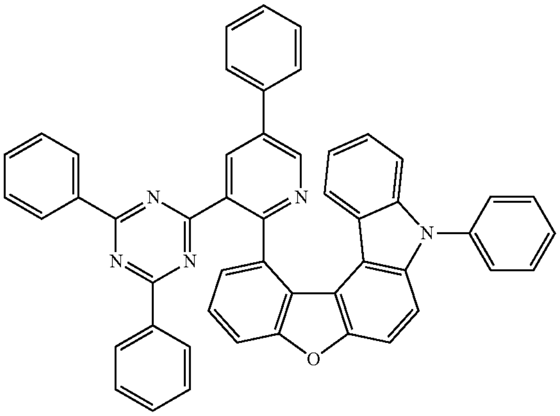
-continued
918
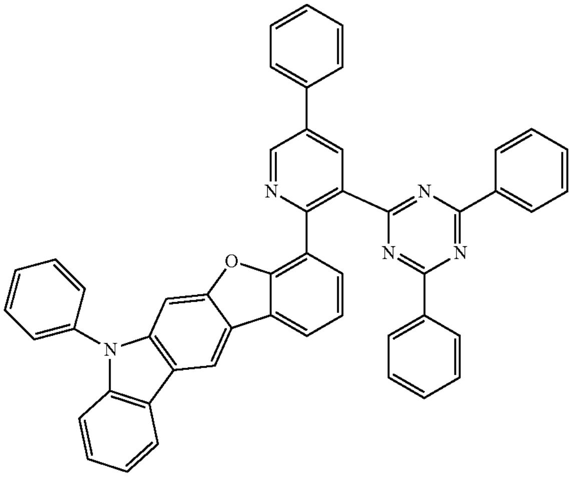
919
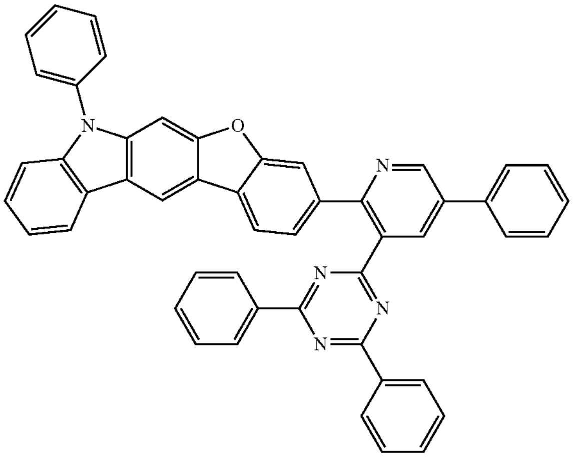
920
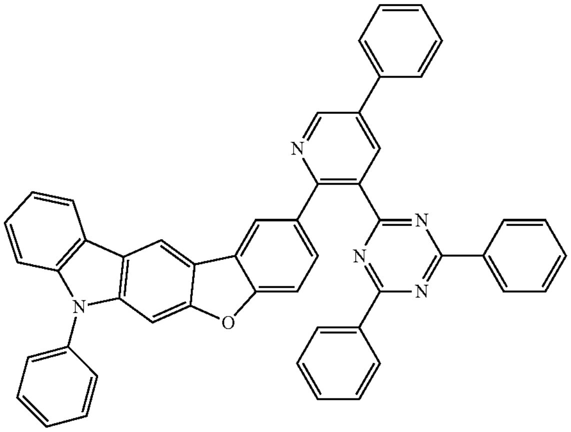

921
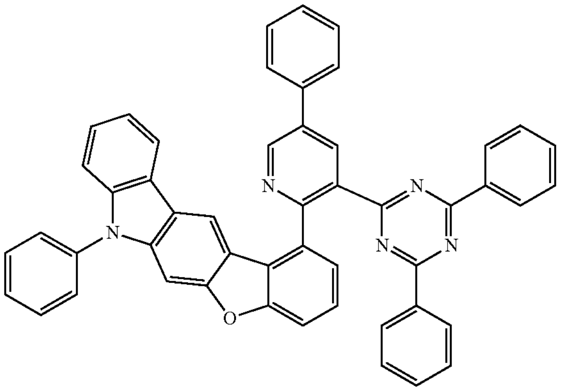
922
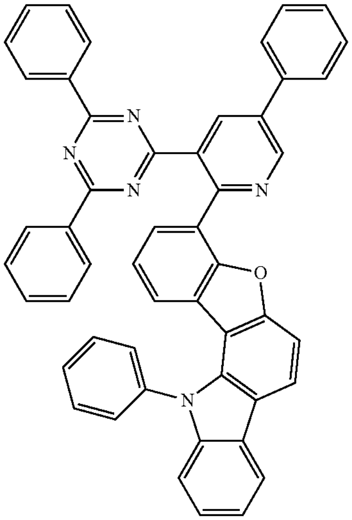
923
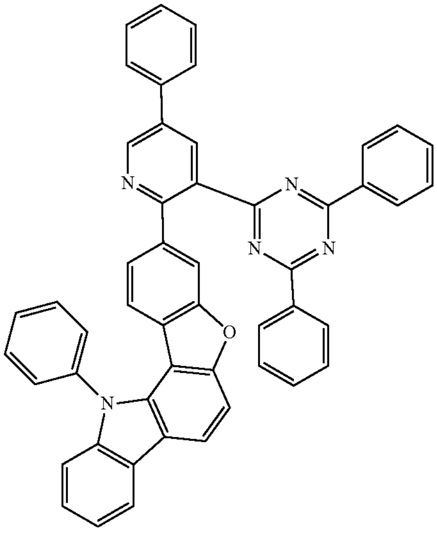
924
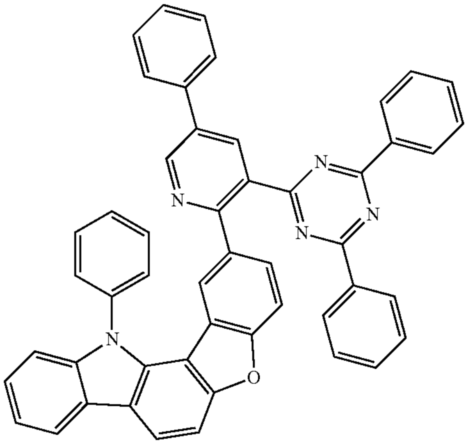
925
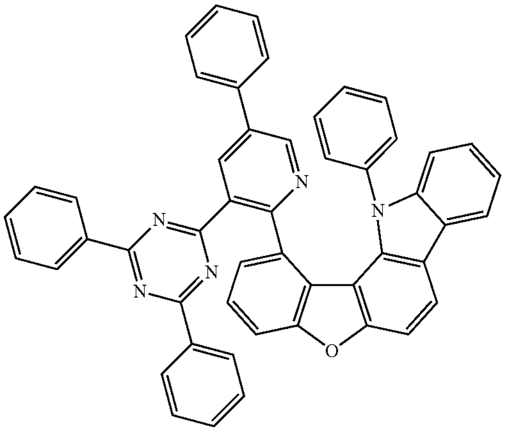
926
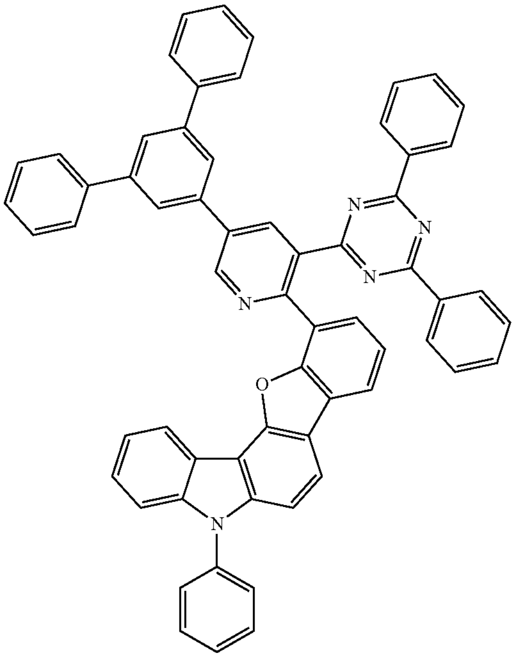

-continued
927
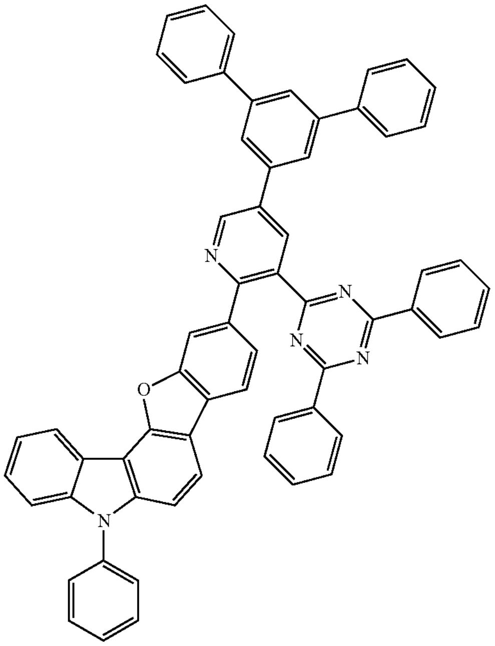
928
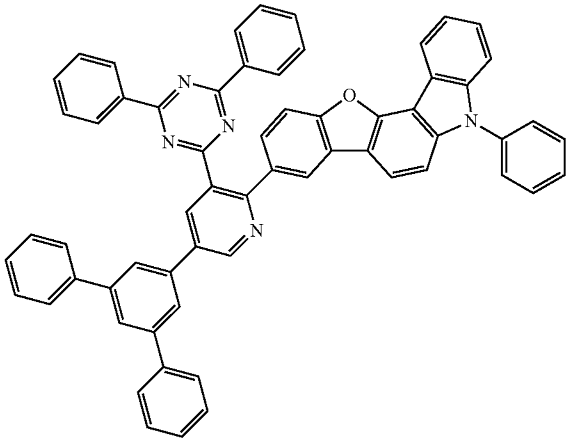
929
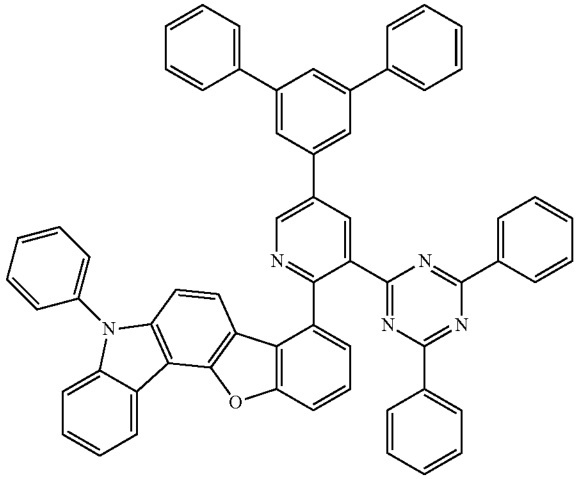
-continued
930
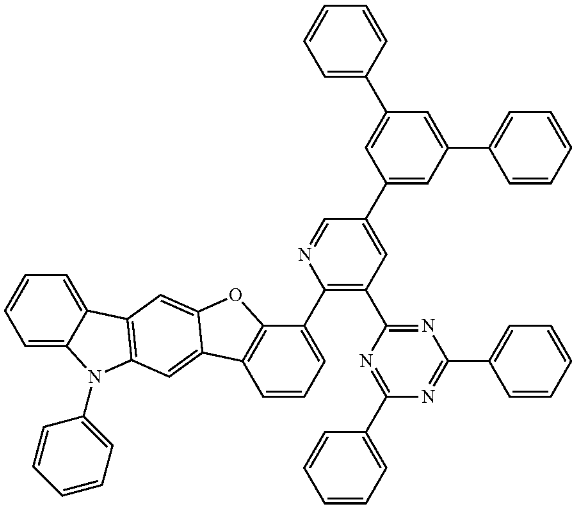
931
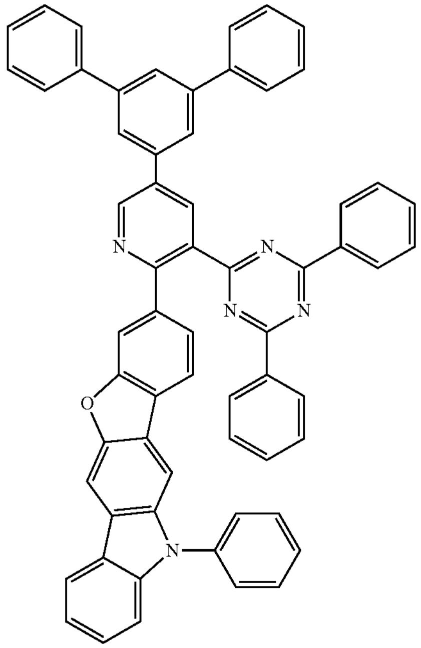

-continued
932
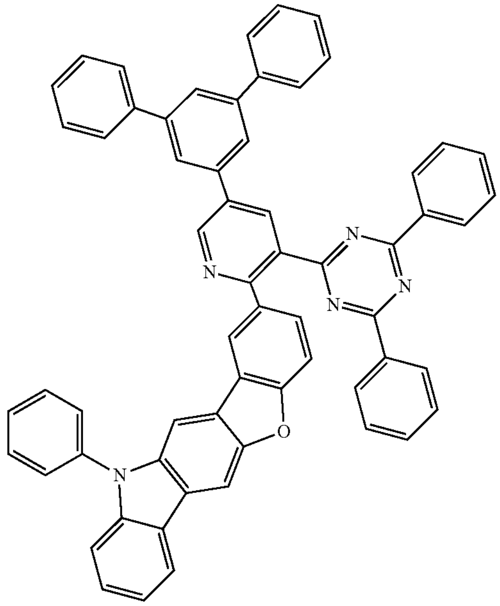
933
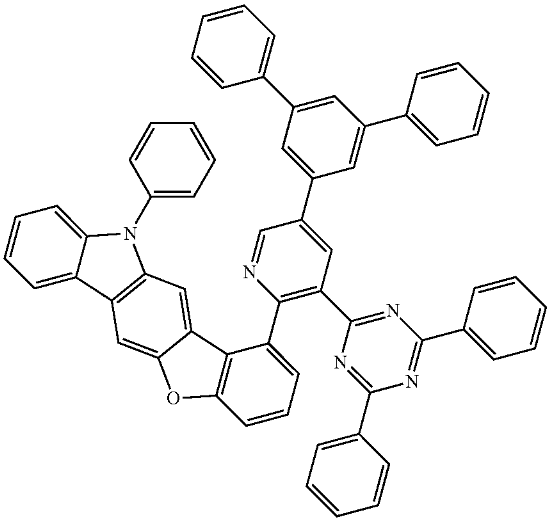
934
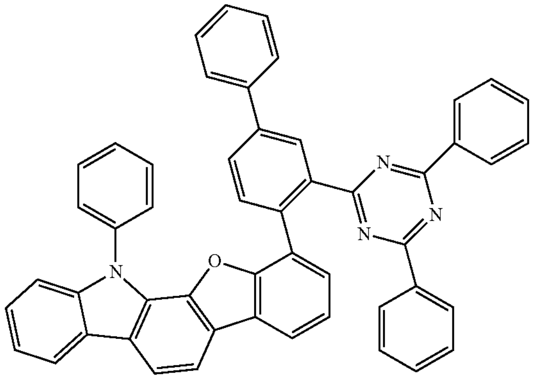
-continued
935
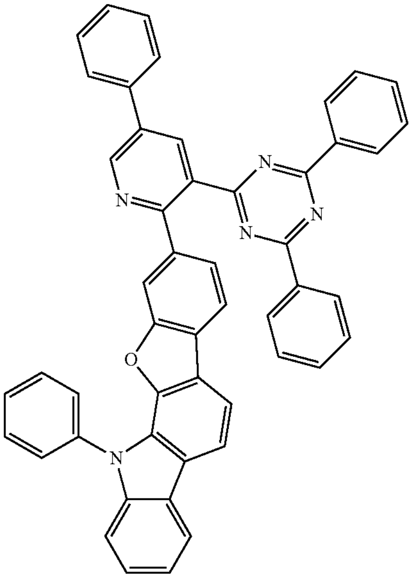
936
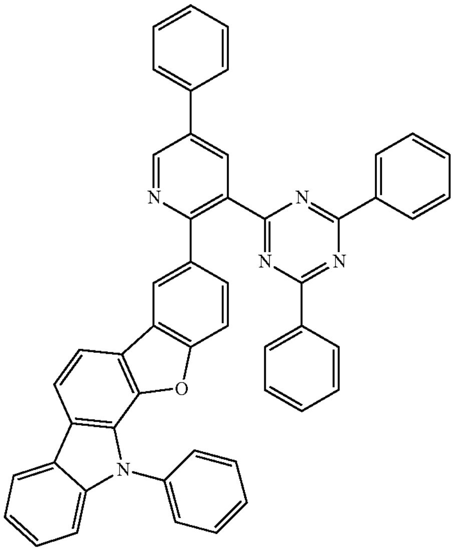
937
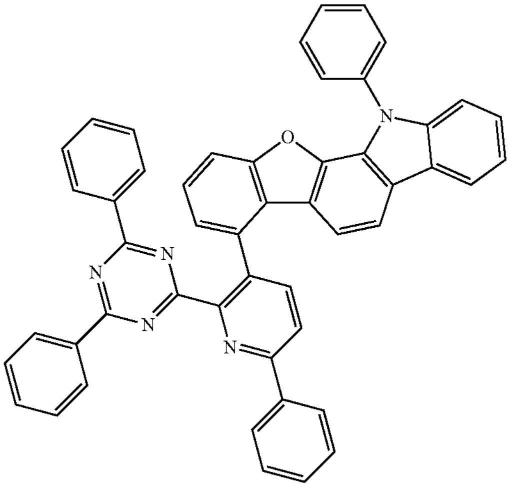

-continued
938
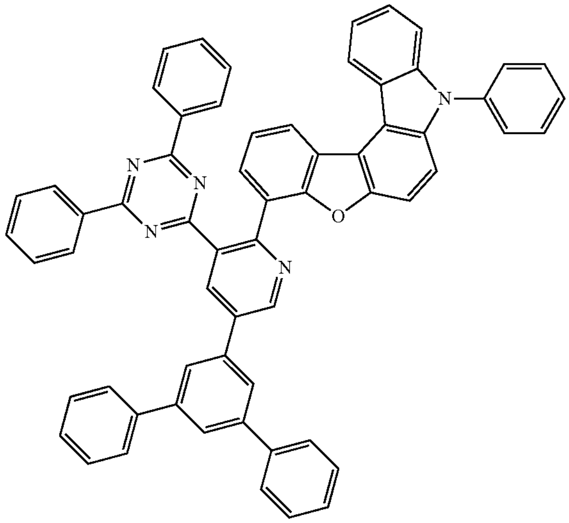
939
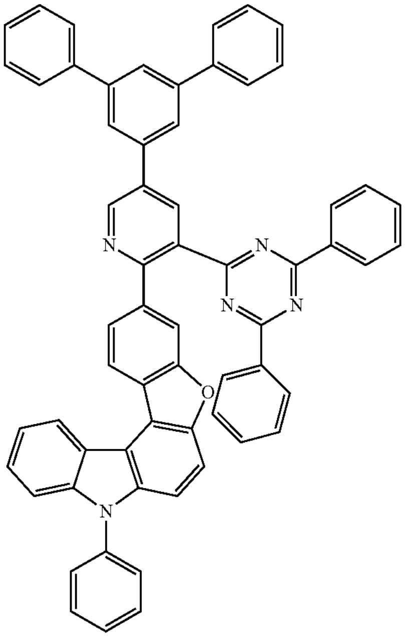
-continued
940
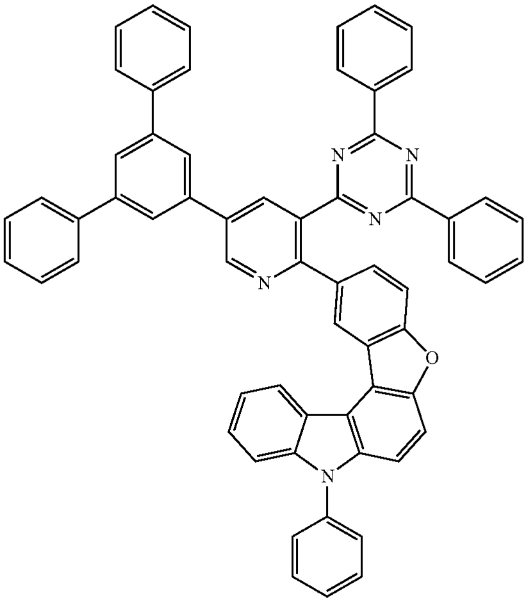
941
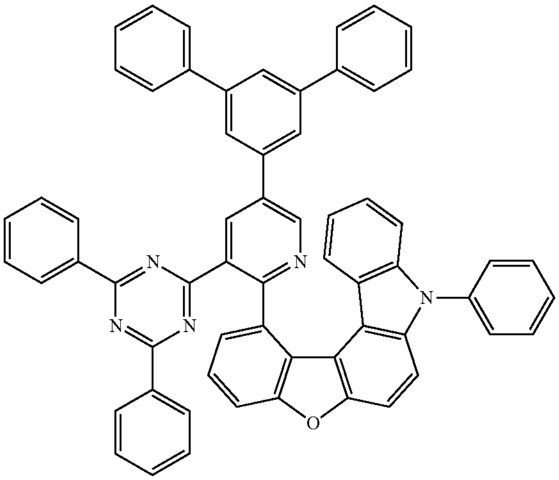
942
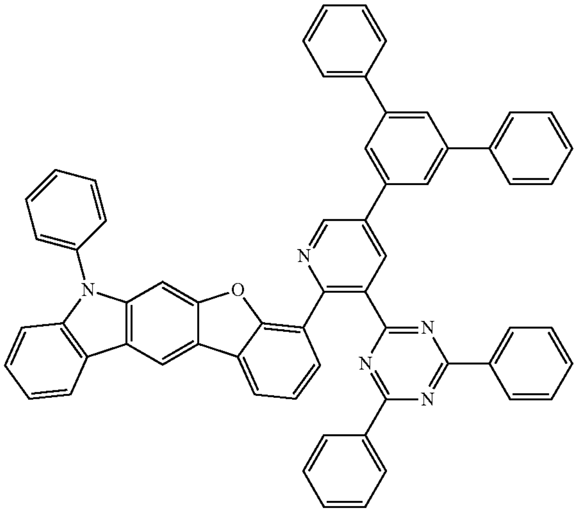

943
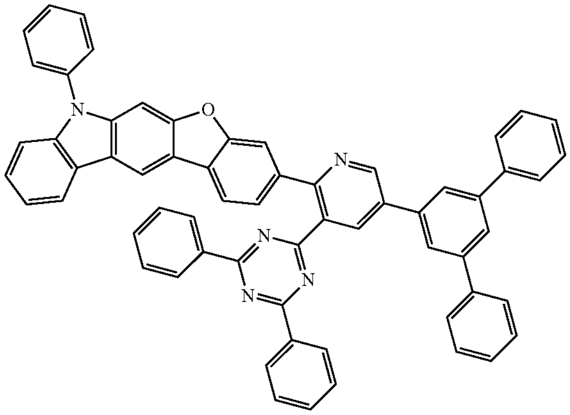
944
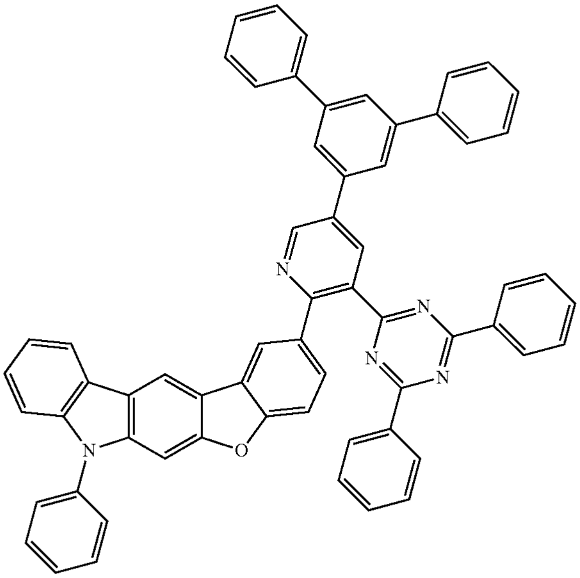
945
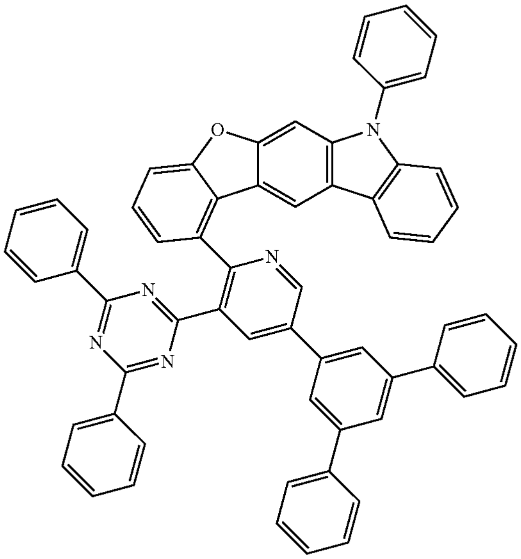
946
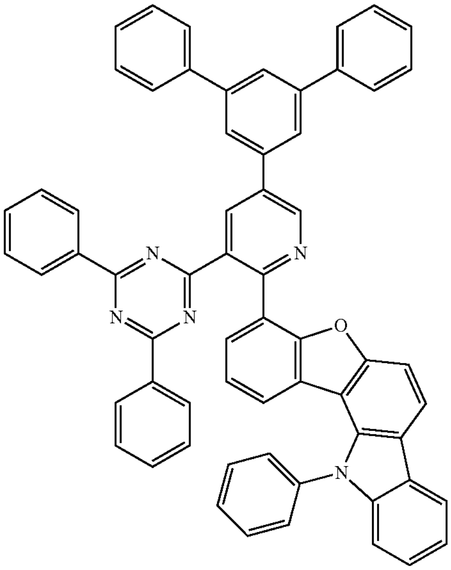
947
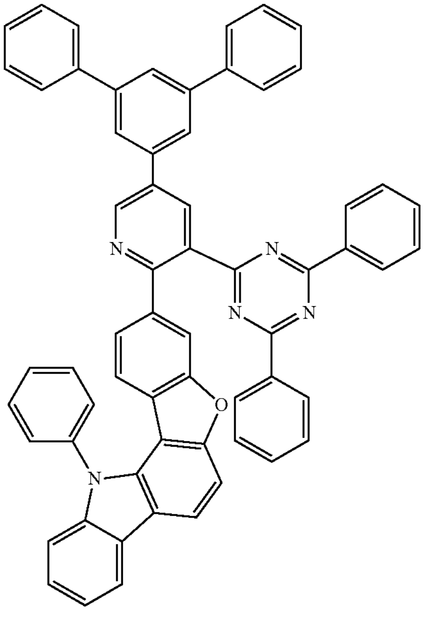

-continued
948
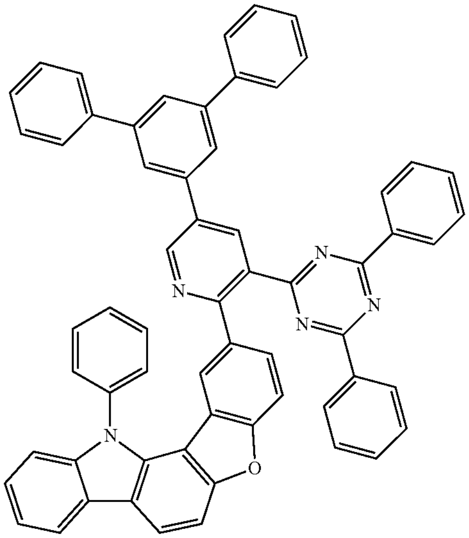
949
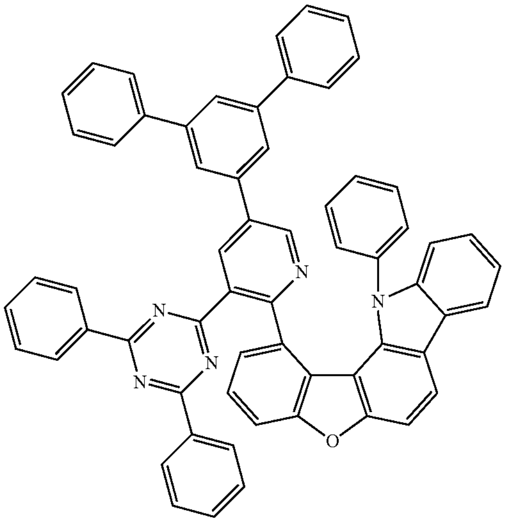
-continued
950
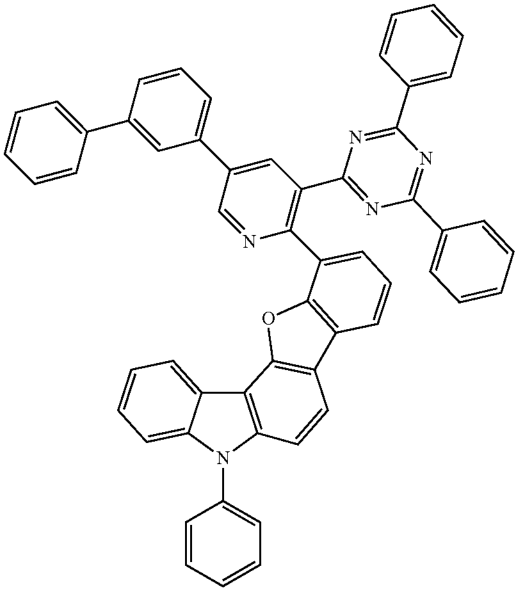
951
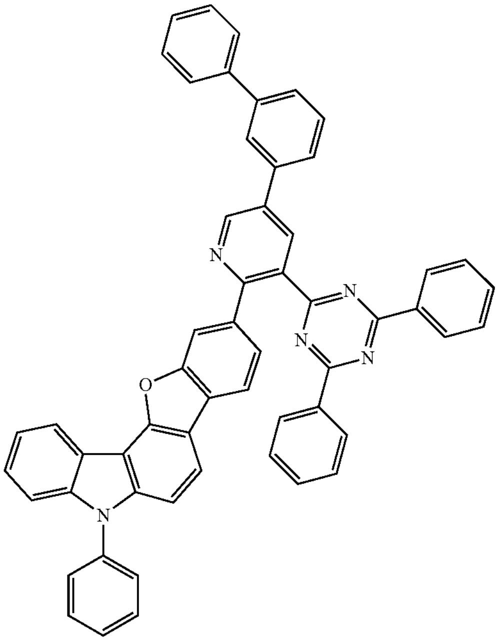

-continued
952
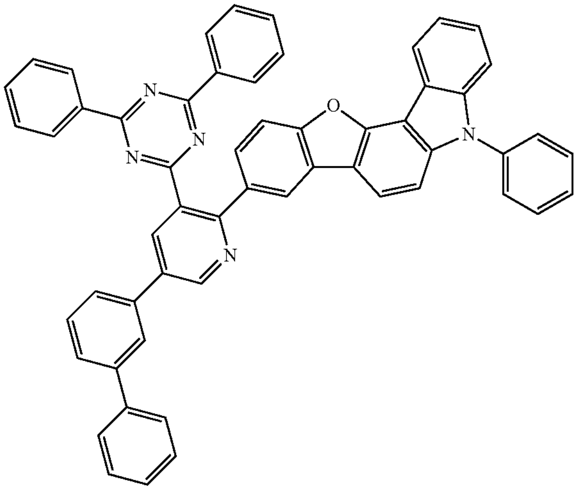
953
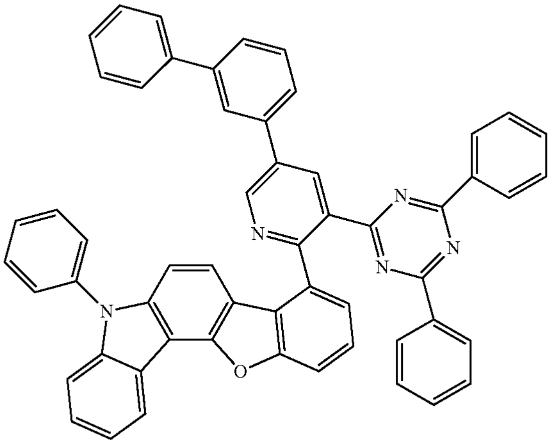
954
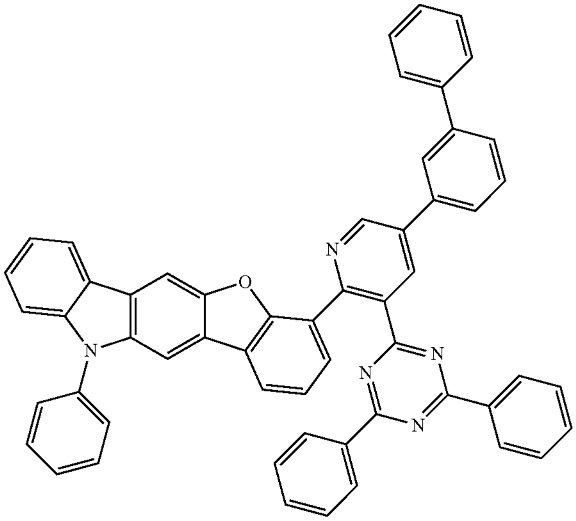
-continued
955
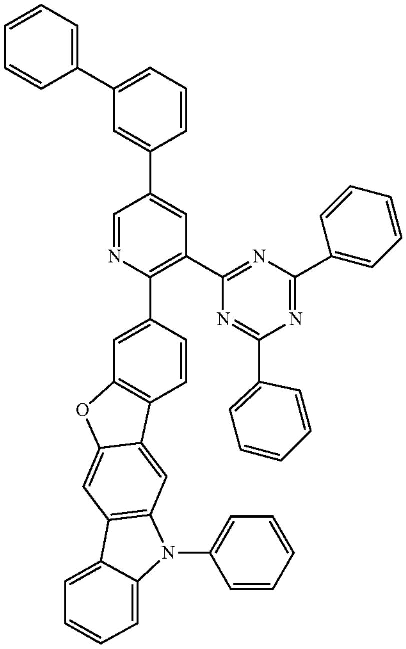
956
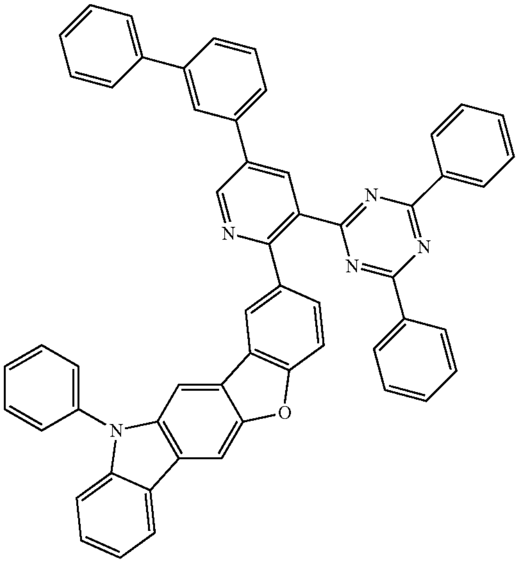

-continued
957
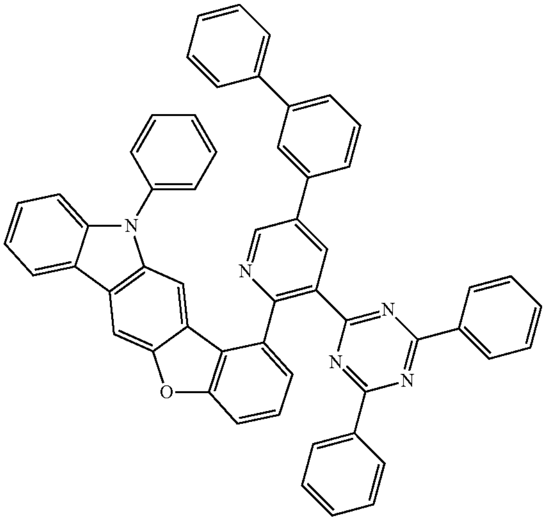
958
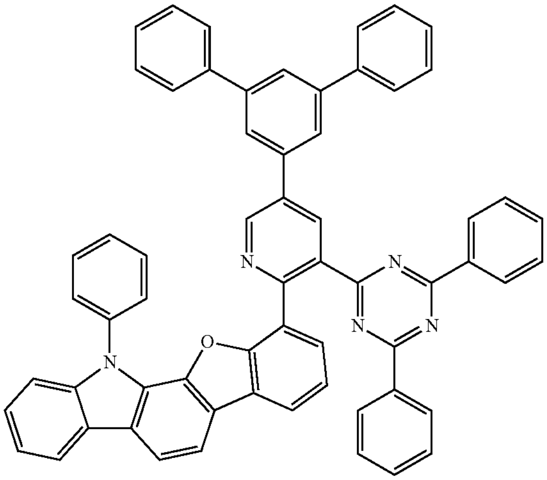
-continued
959
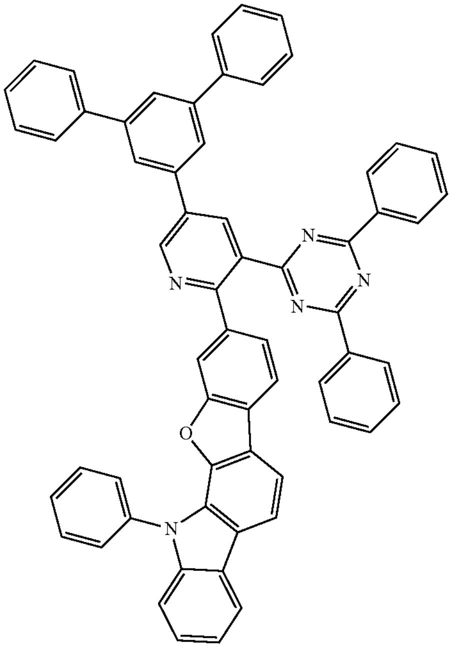
960
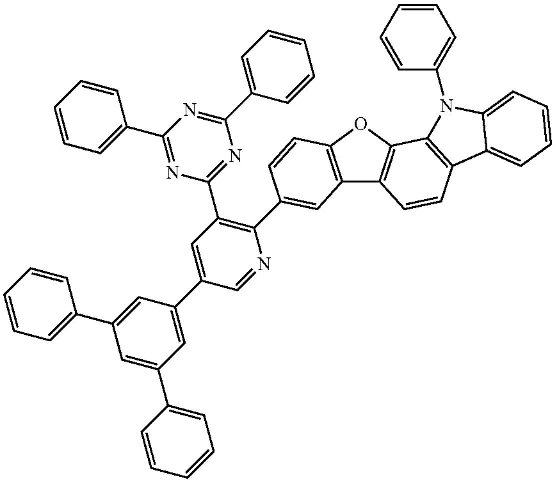

-continued
961
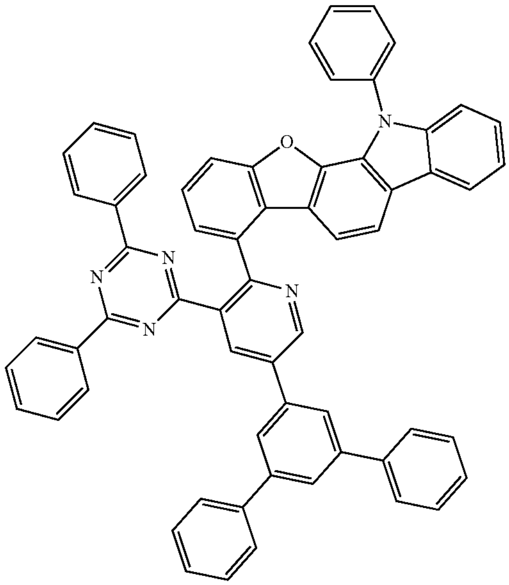
962
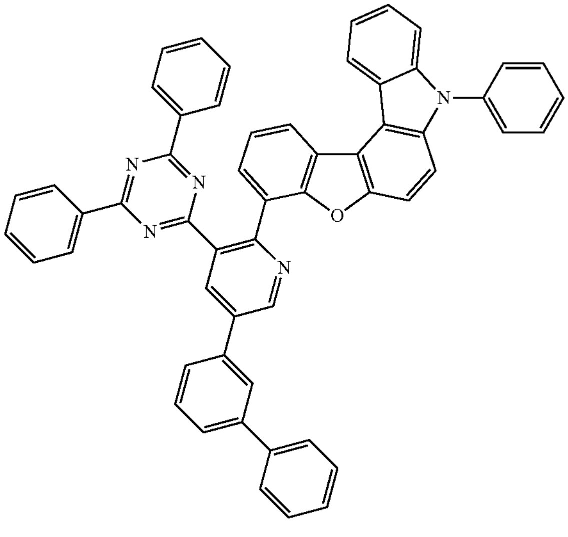
-continued
963
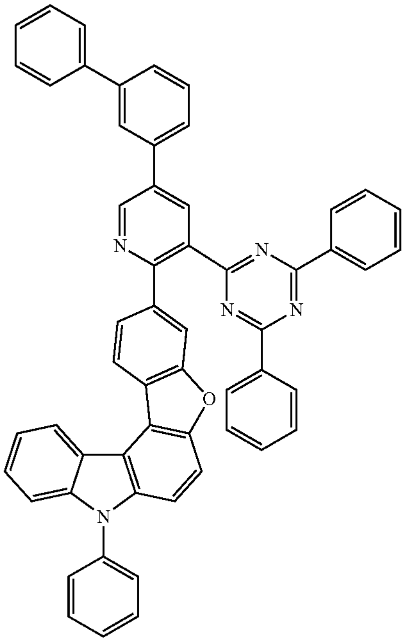
964
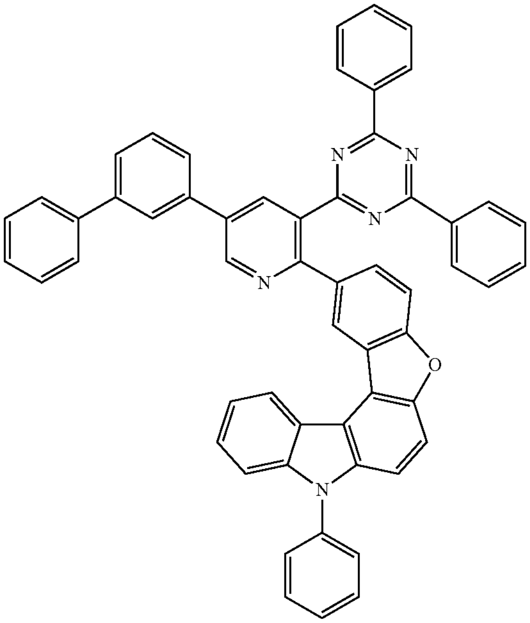

-continued
965
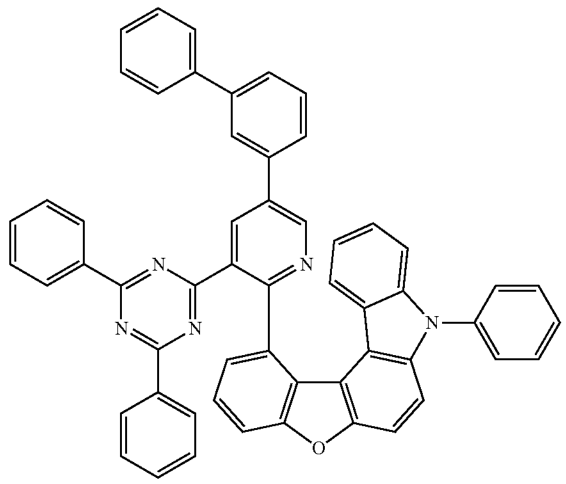
966
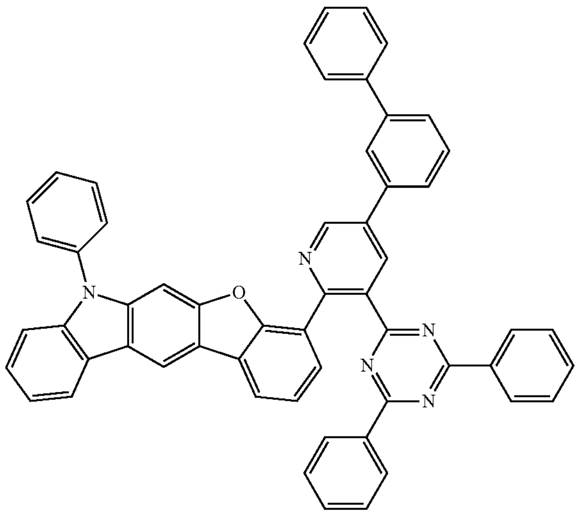
967
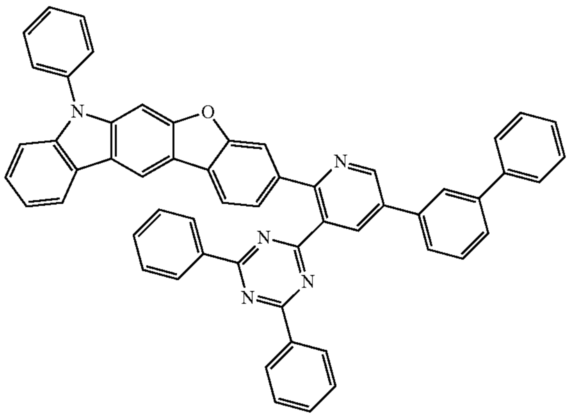
-continued
968
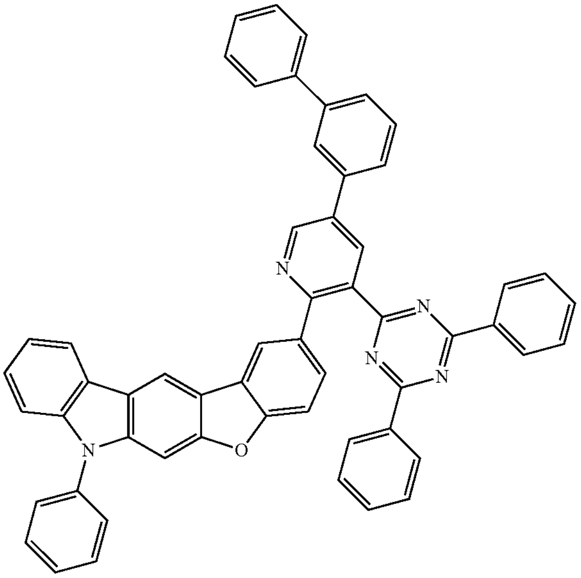
969
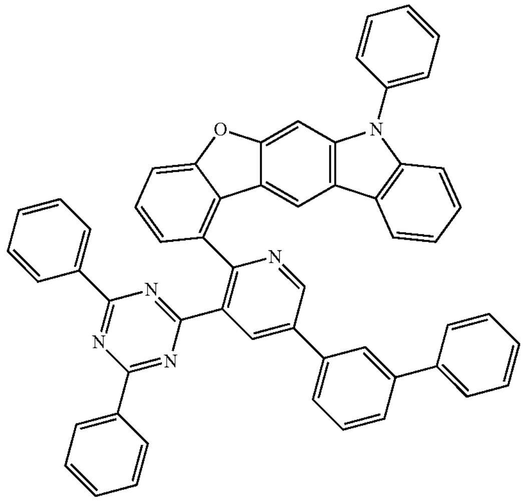

-continued
970
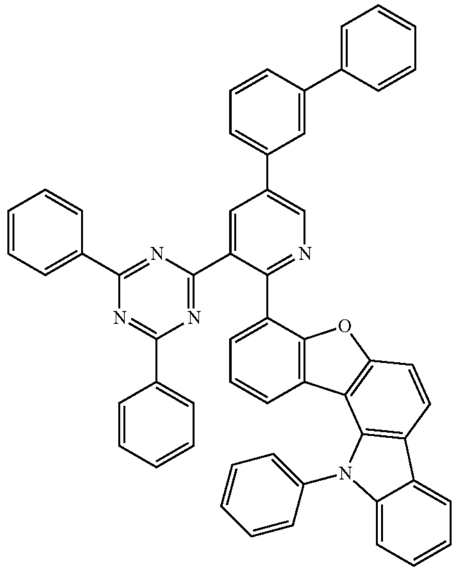
971
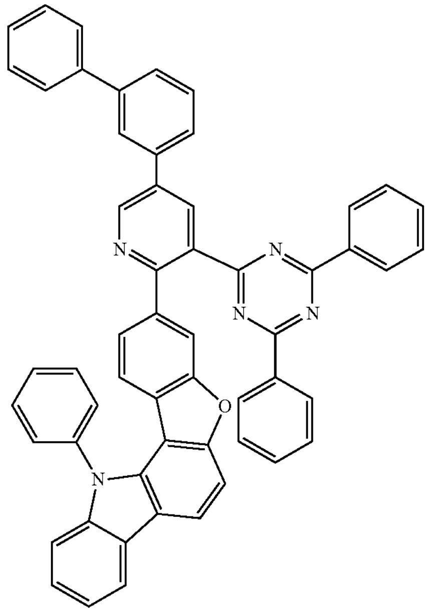
972
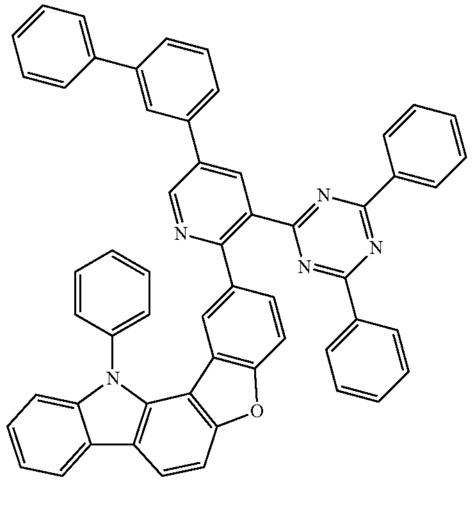
-continued
973
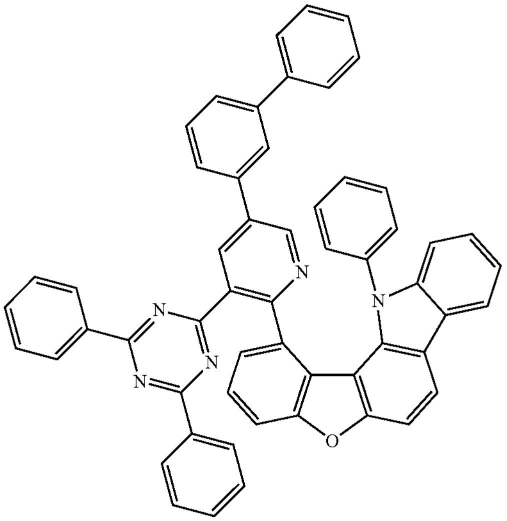
974
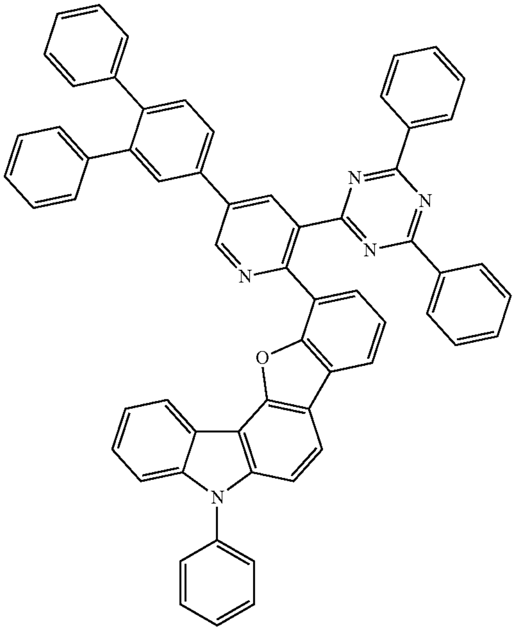

-continued
975
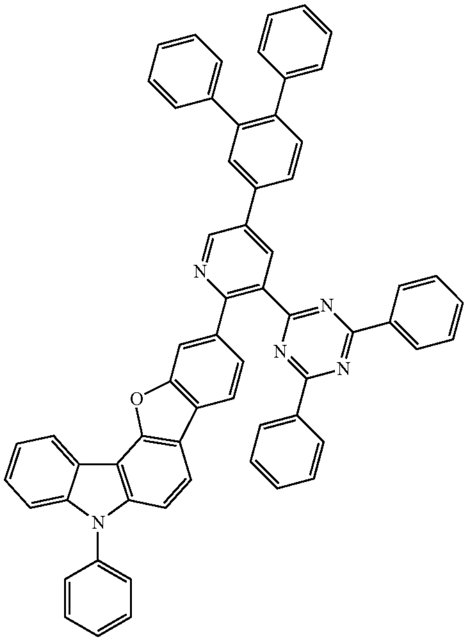
976
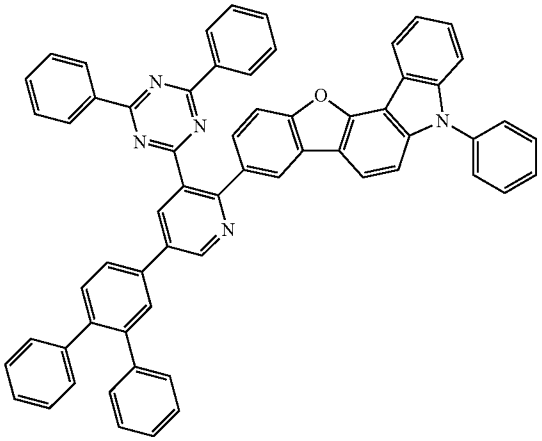
977
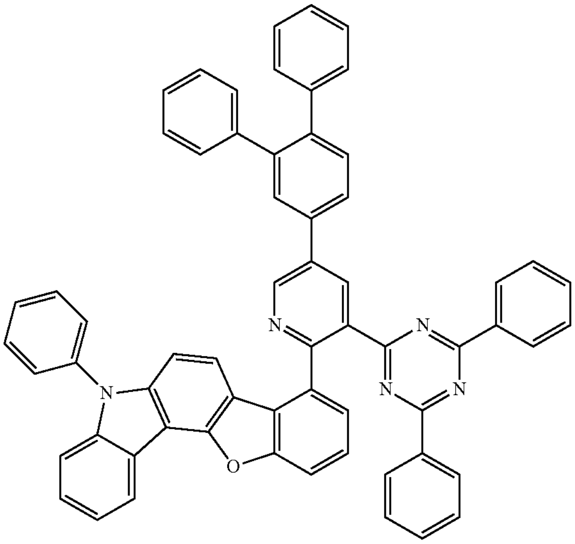
-continued
978
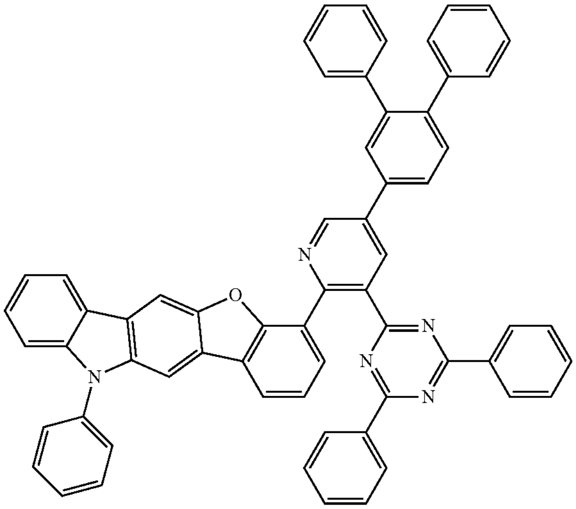
979
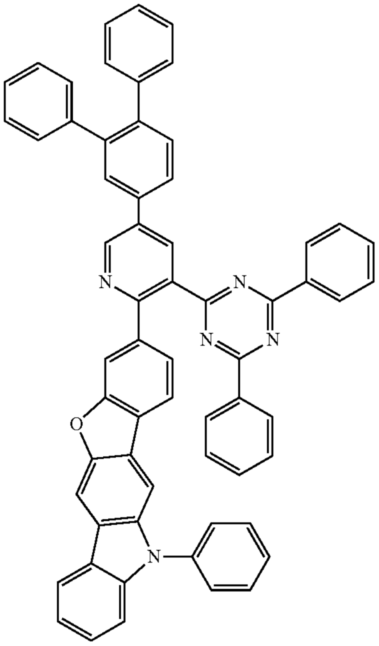

-continued
980
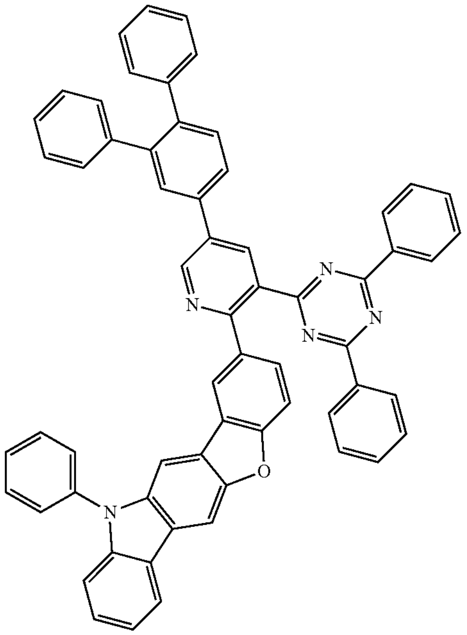
981
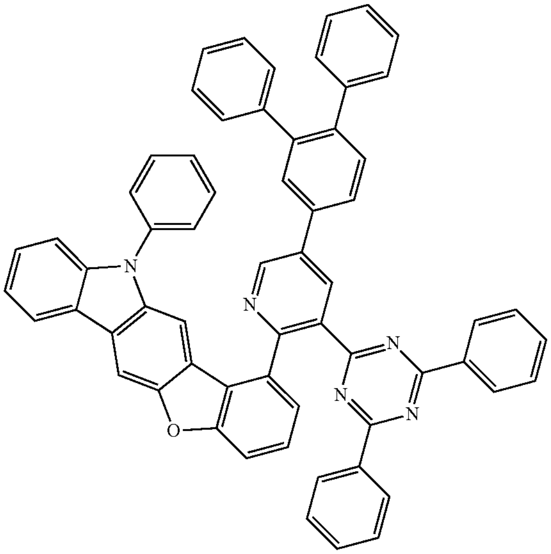
982
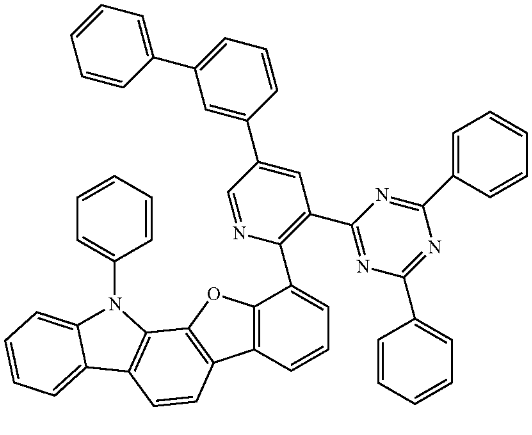
-continued
983
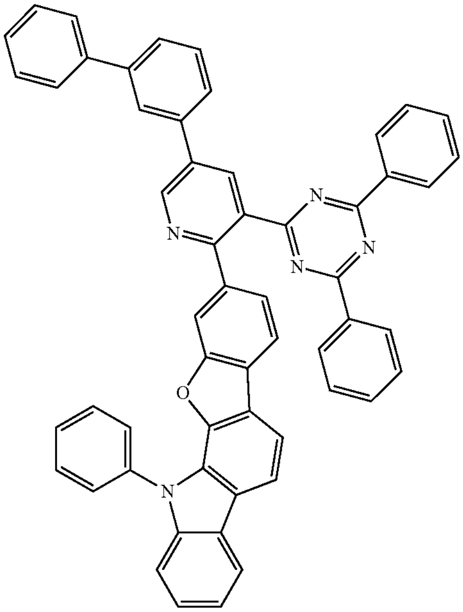
984
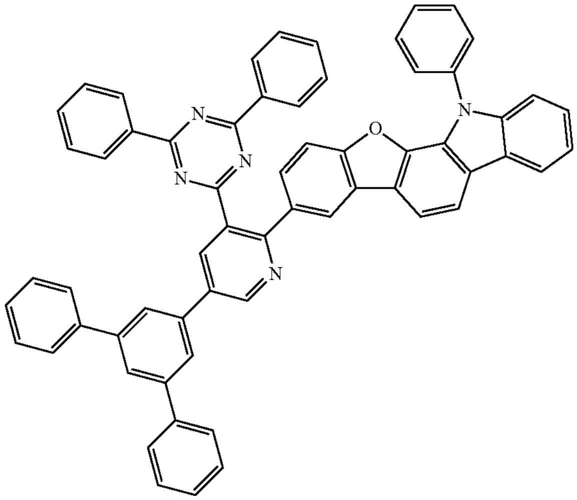
985
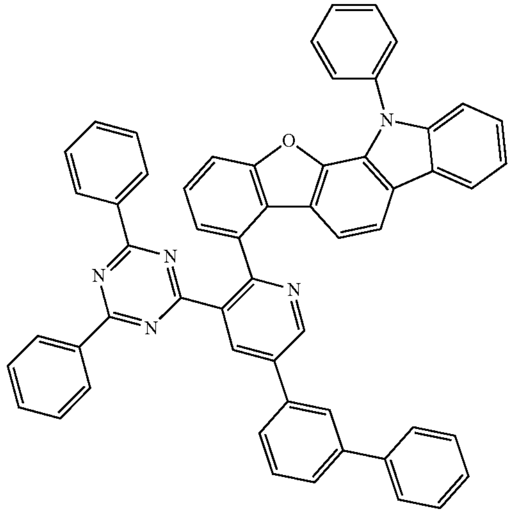

-continued
986
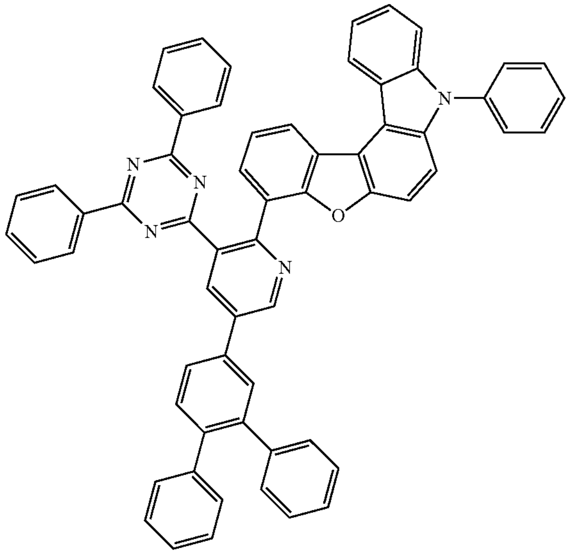
987
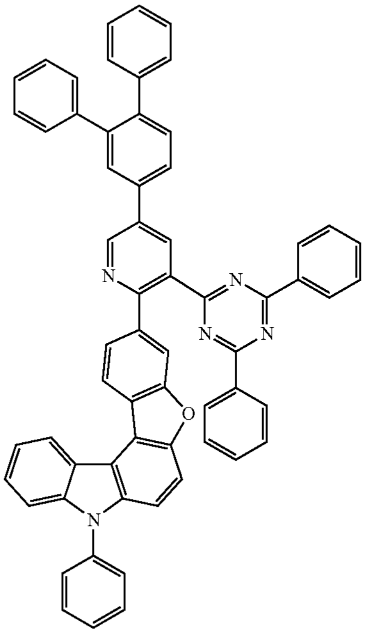
-continued
988
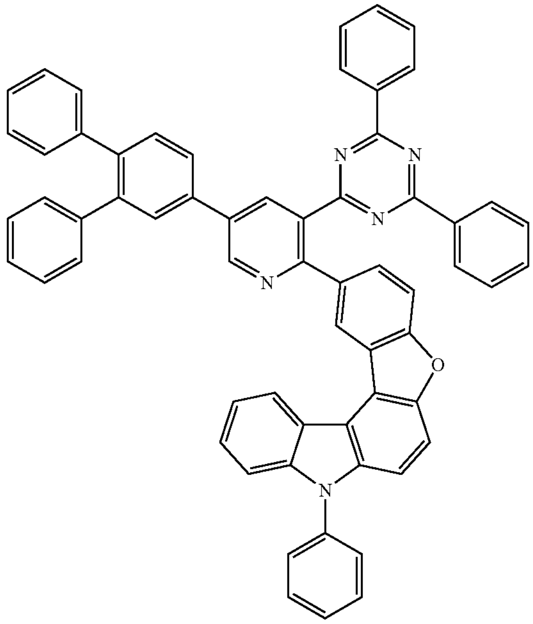
989
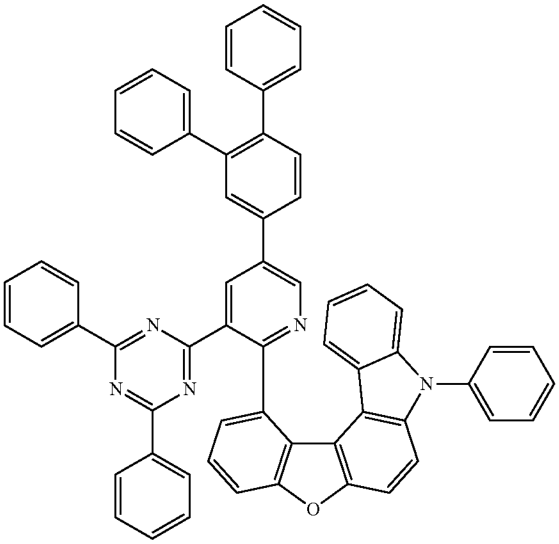

-continued
990
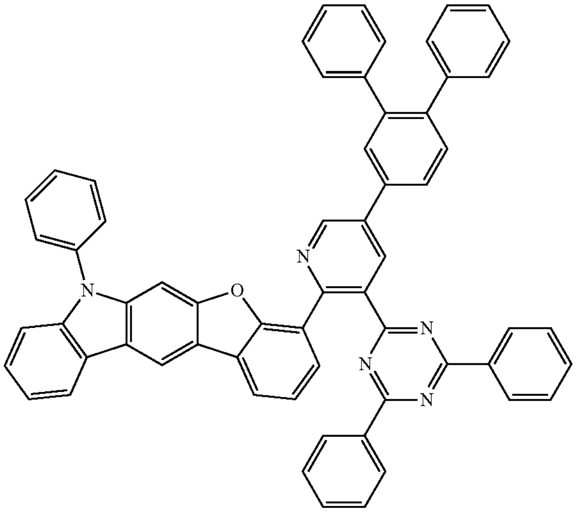
991
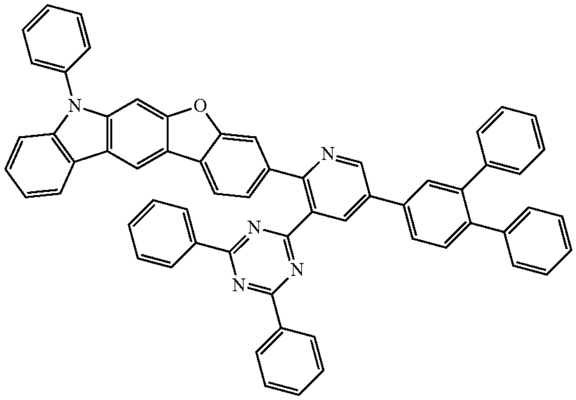
992
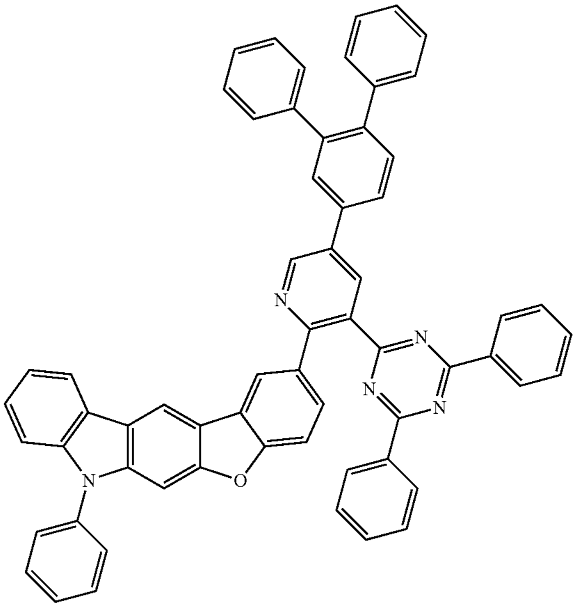
-continued
993
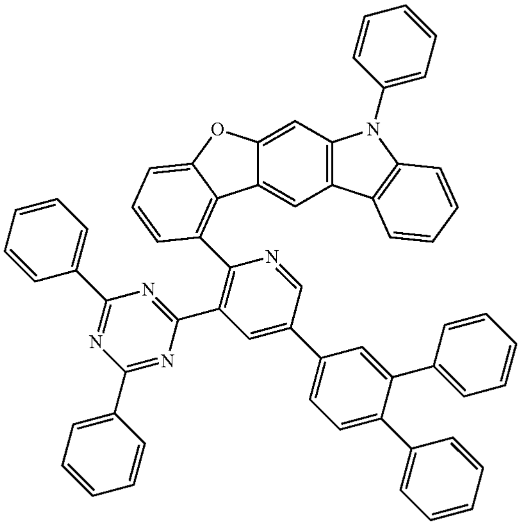
994
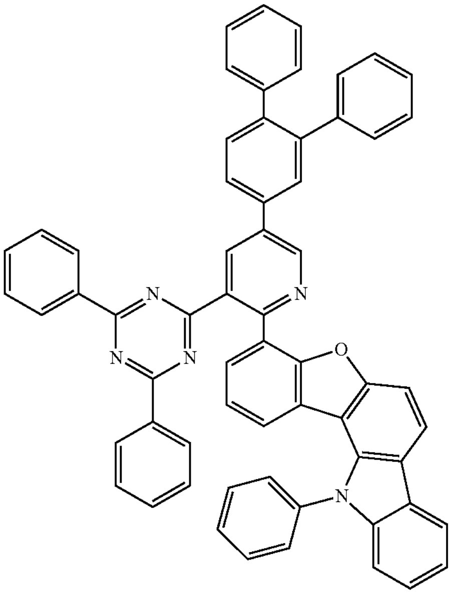

-continued
995
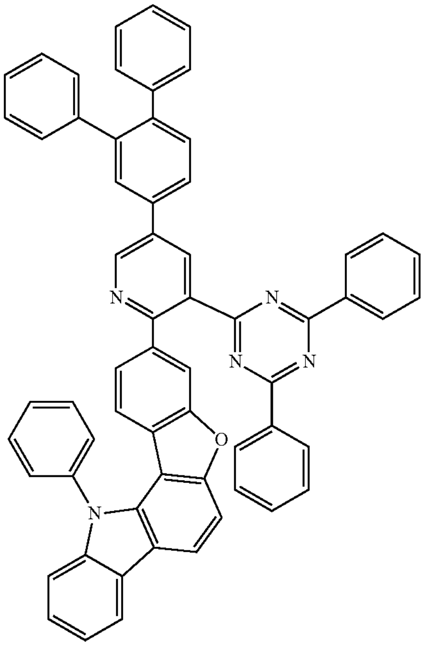
996
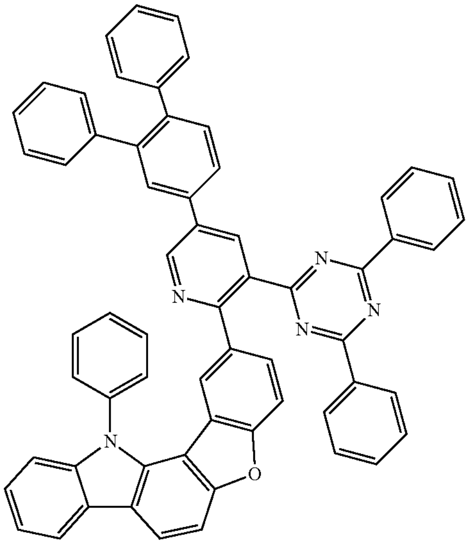
-continued
997
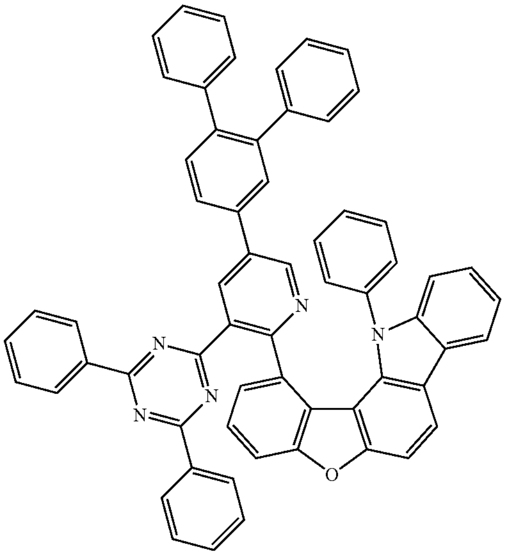
998
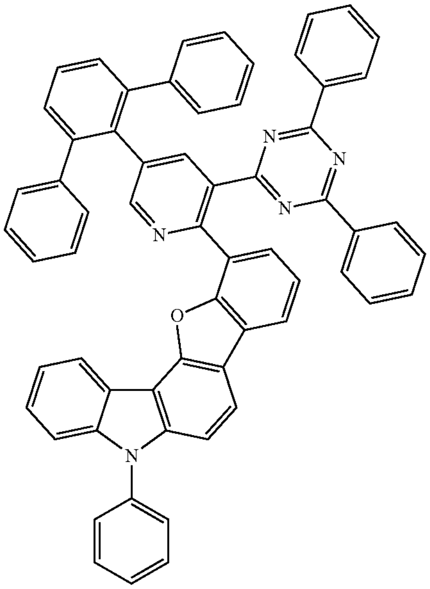

-continued
999
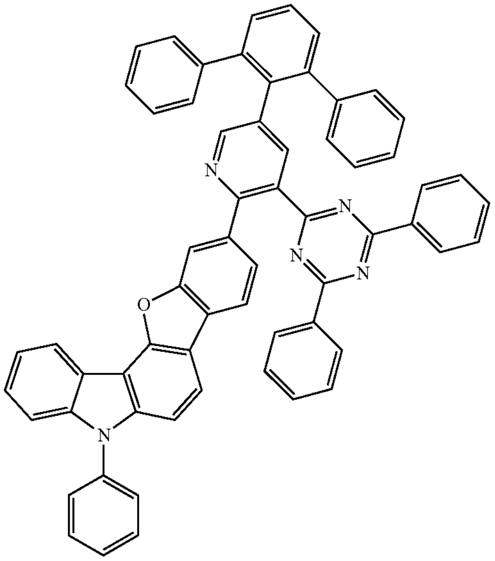
1000
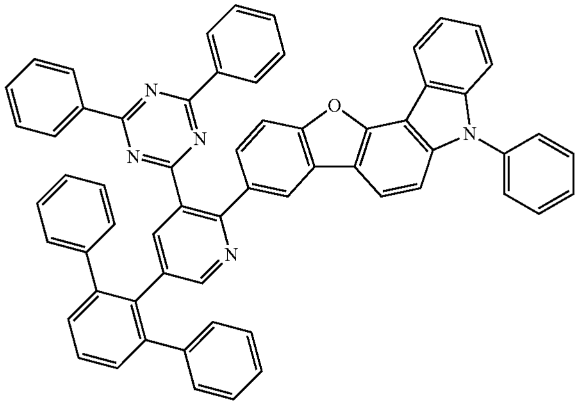
1001
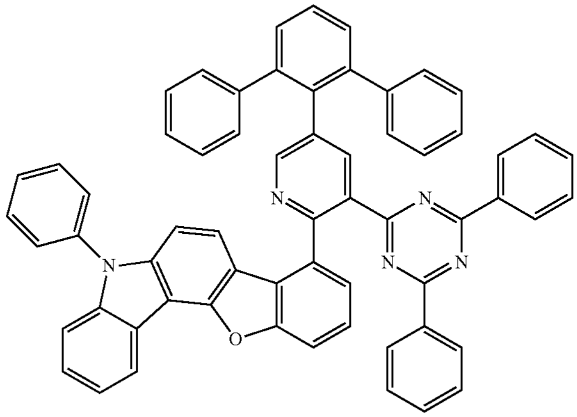
-continued
1002
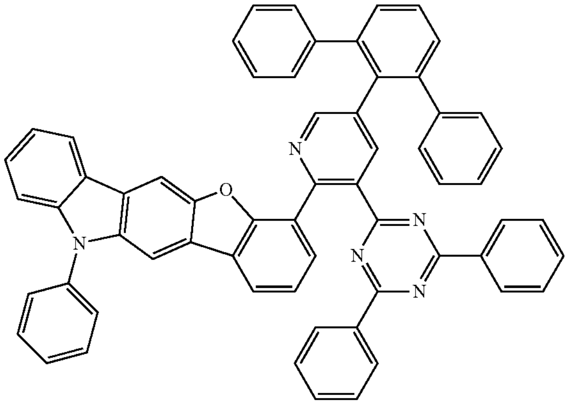
1003
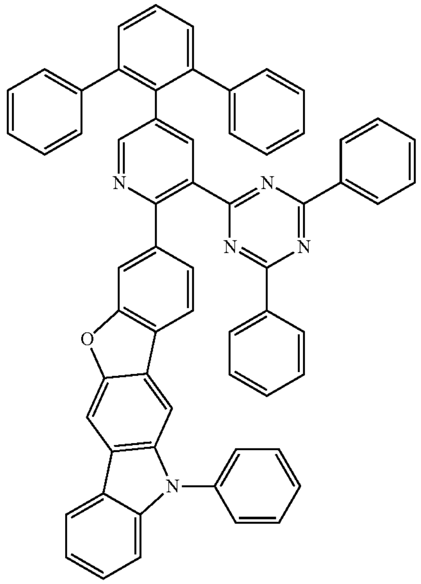
1004
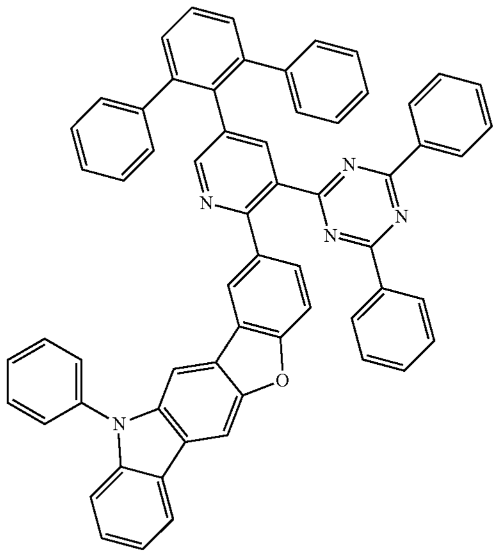

-continued
1005
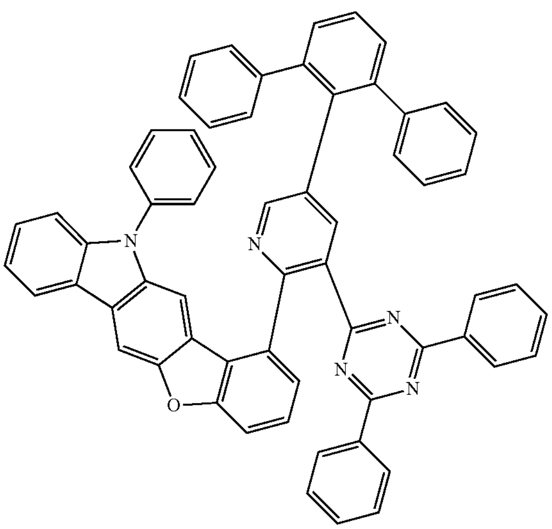
1006
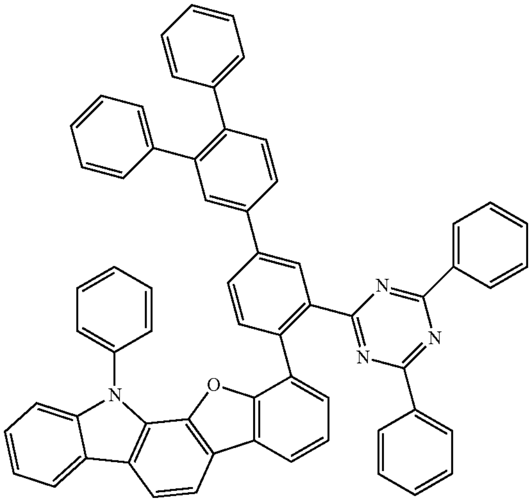
-continued
1007
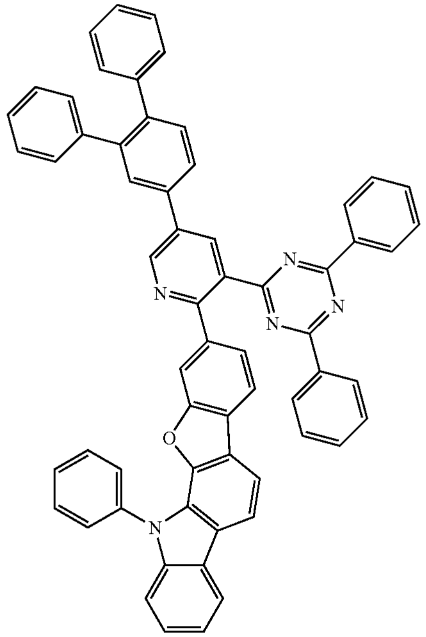
1008
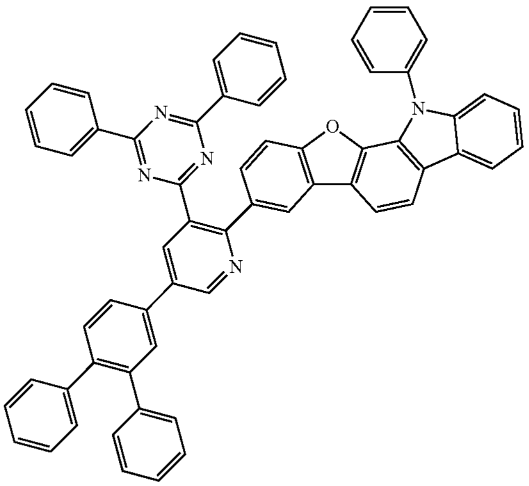

-continued
1009
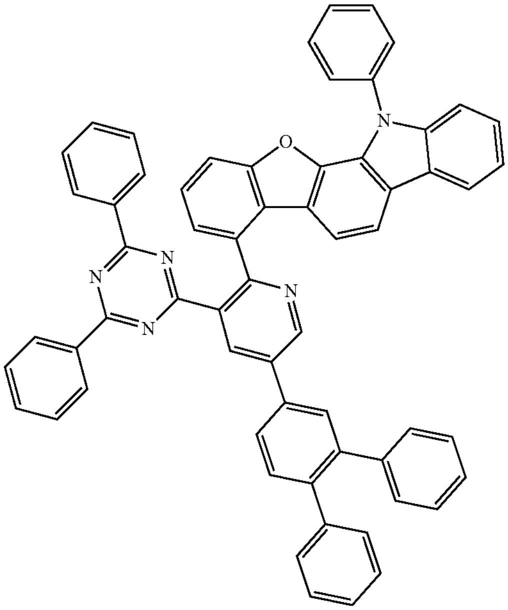
1010
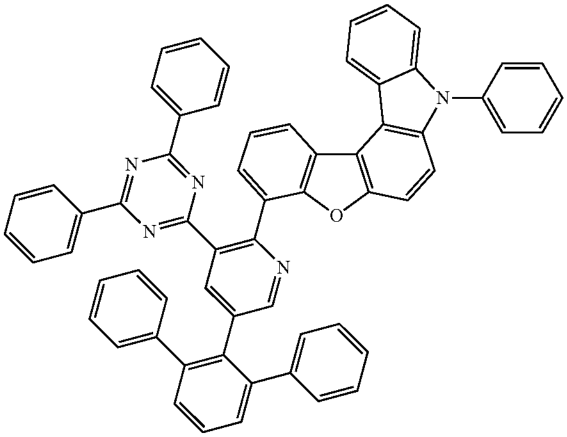
-continued
1011
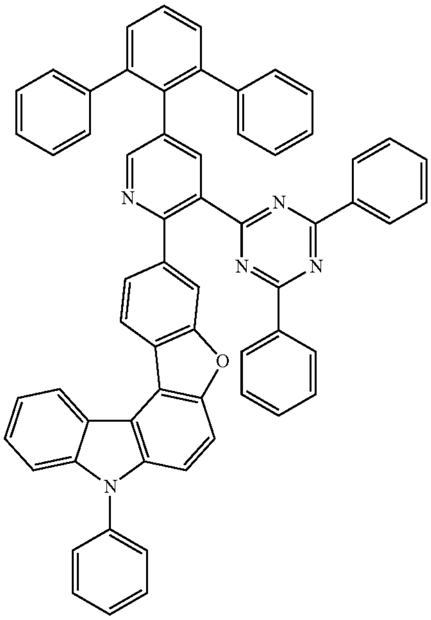
1012
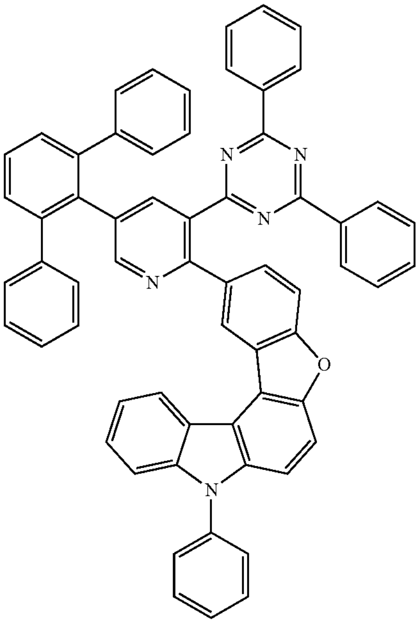

-continued
1013
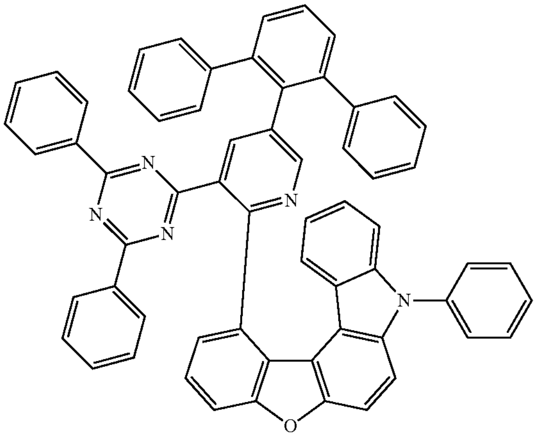
1014
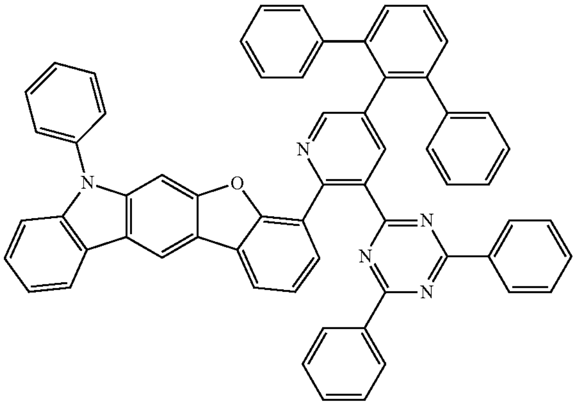
1015
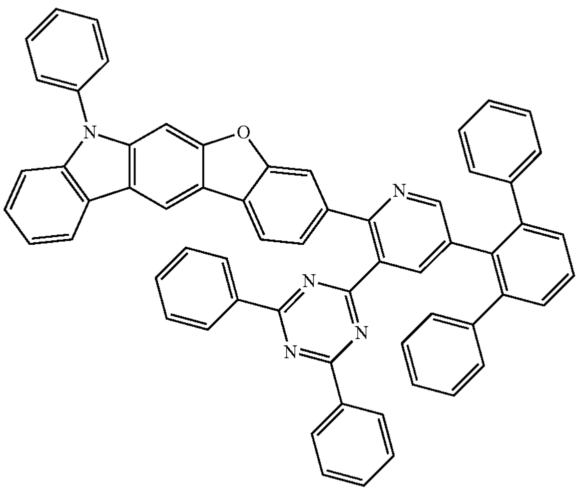
-continued
1016
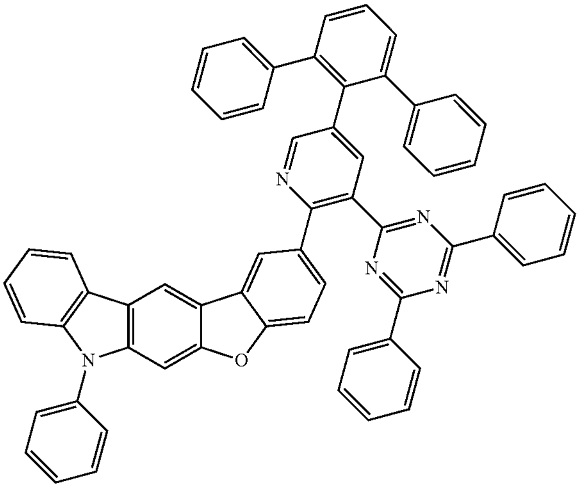
1017
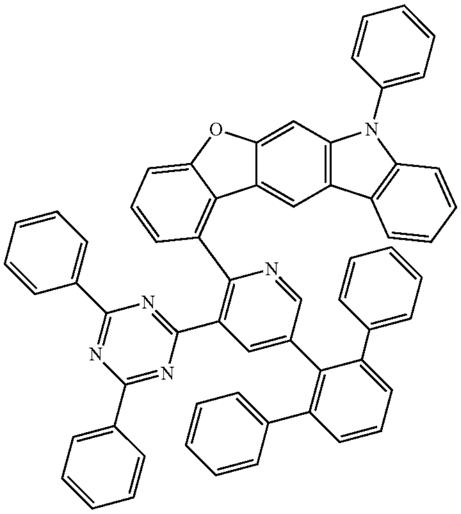
1018
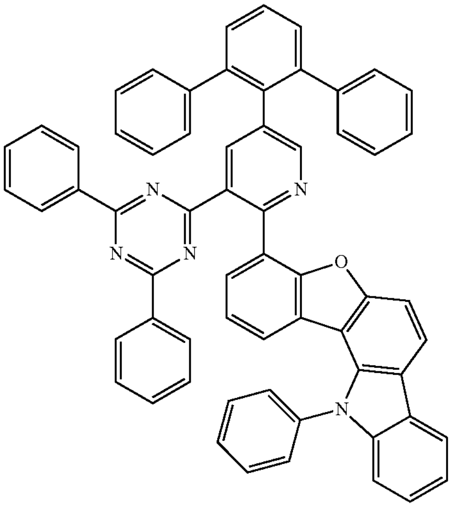

-continued
1019
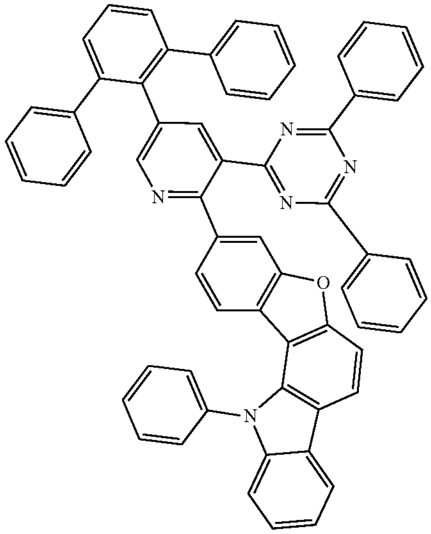
1020
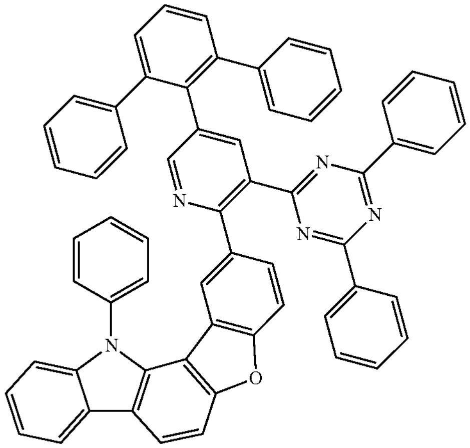
1021
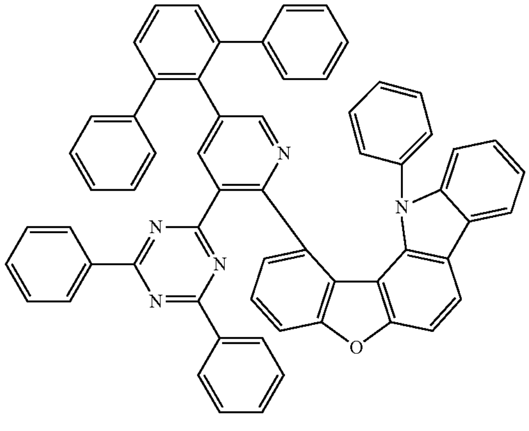
-continued
1022
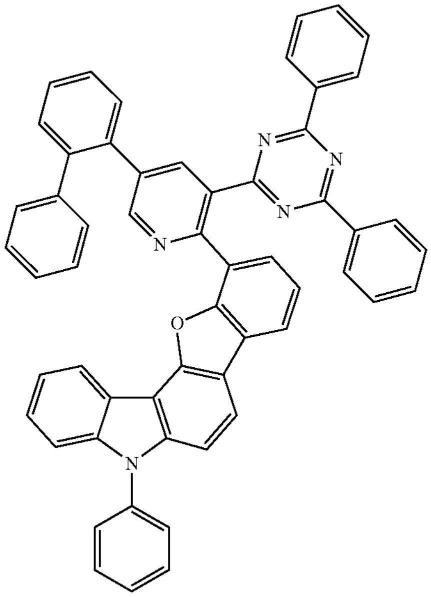
1023
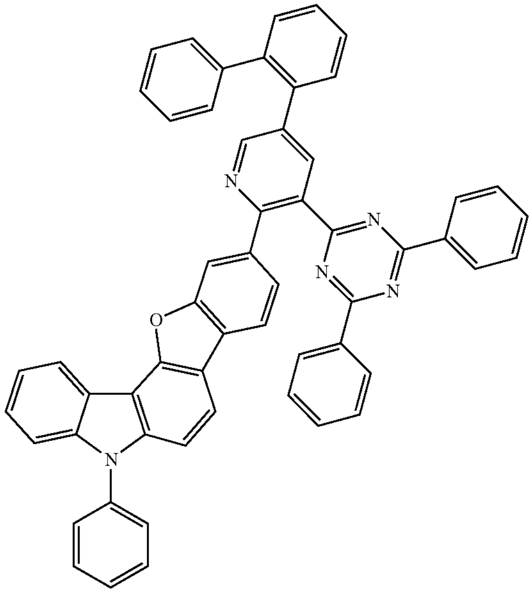
1024
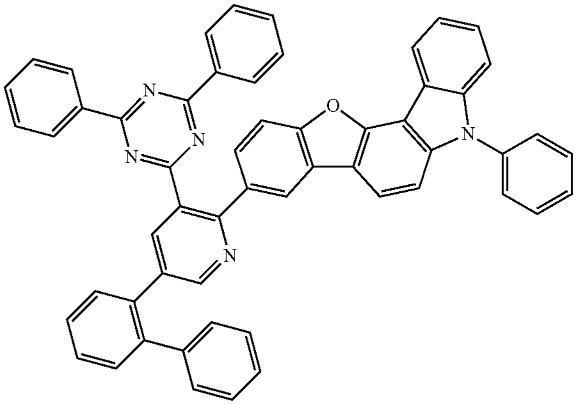

-continued
1025
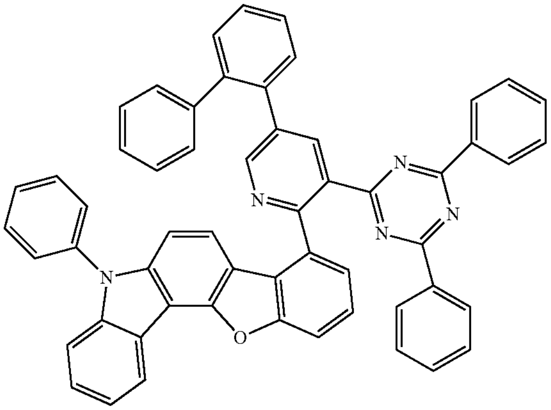
1026
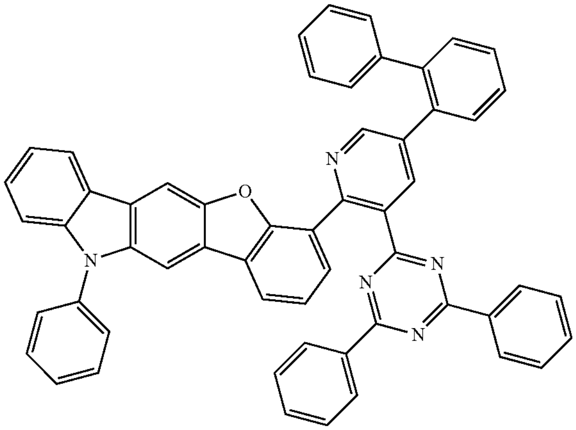
1027
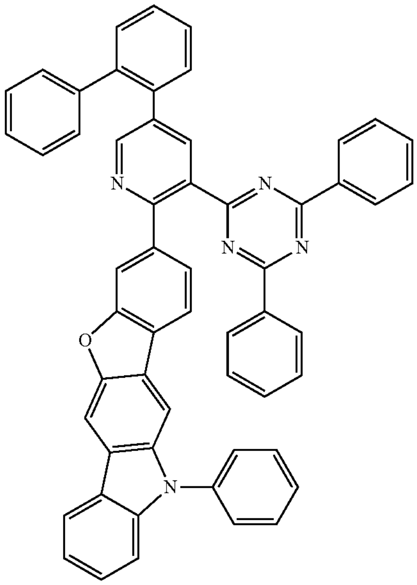
-continued
1028
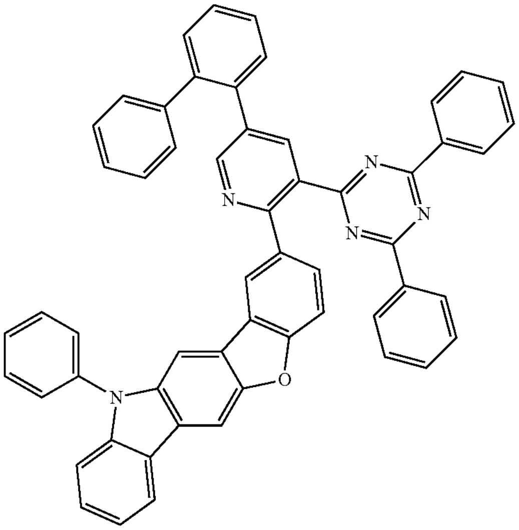
1029
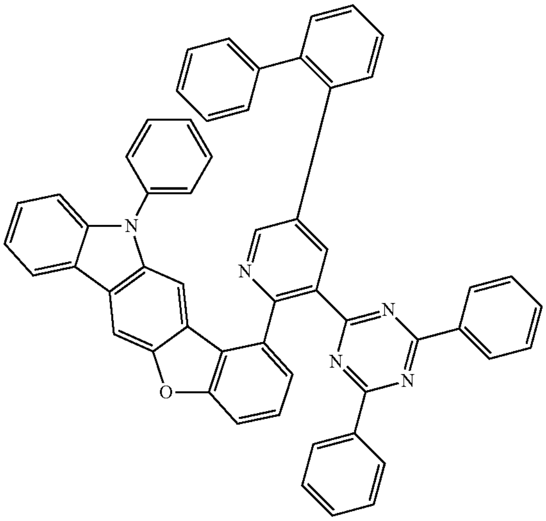
1030
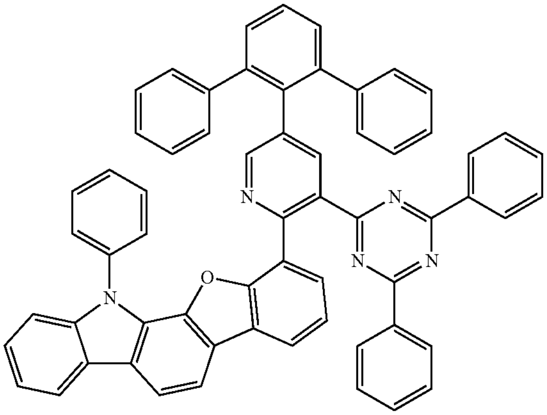

-continued
1031
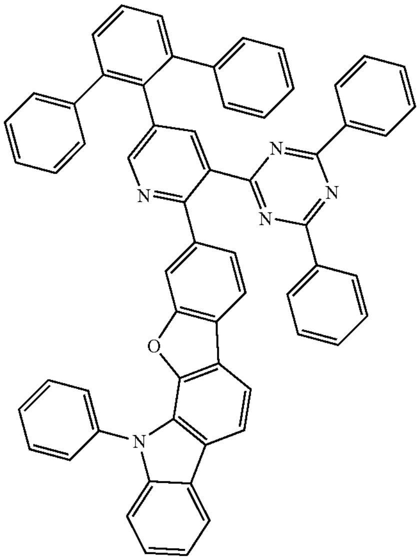
1032
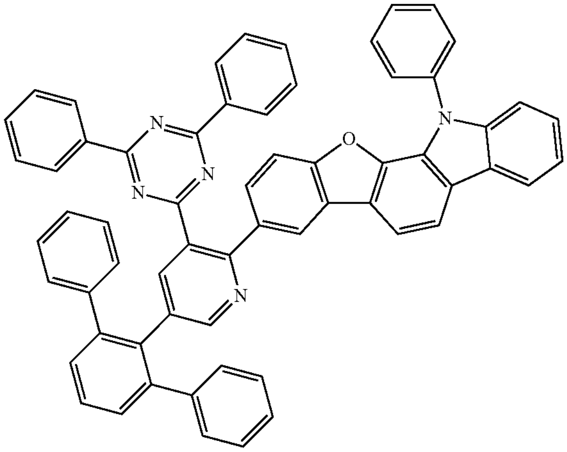
1033
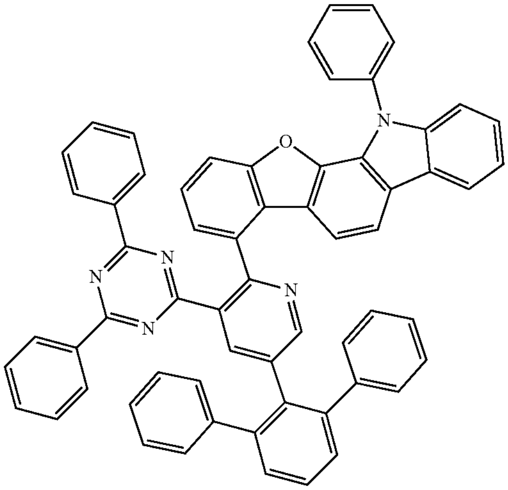
-continued
1034
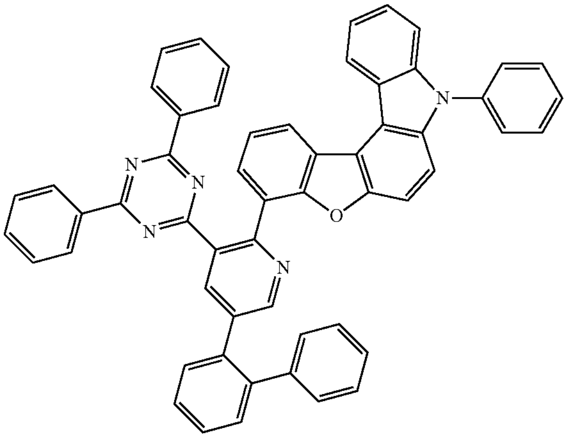
1035
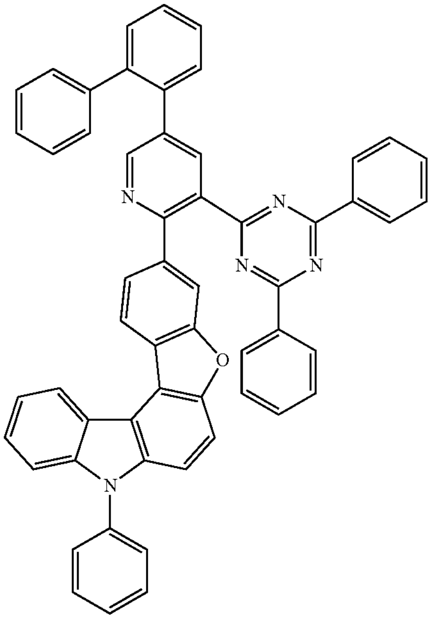

-continued
1036
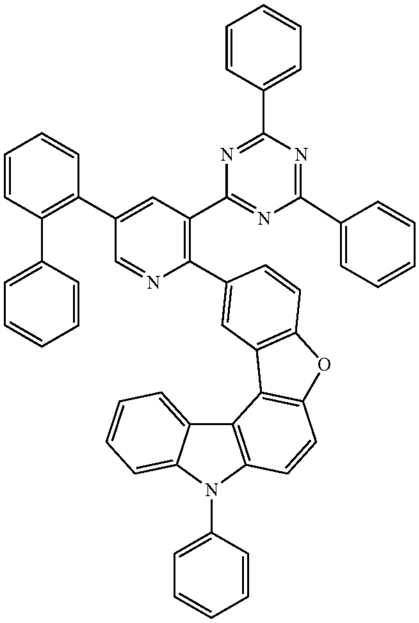
1037
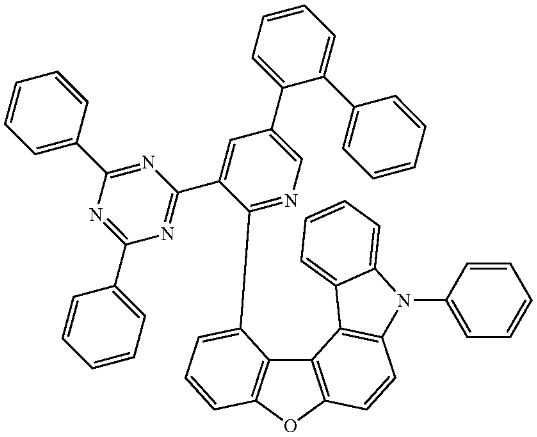
1038
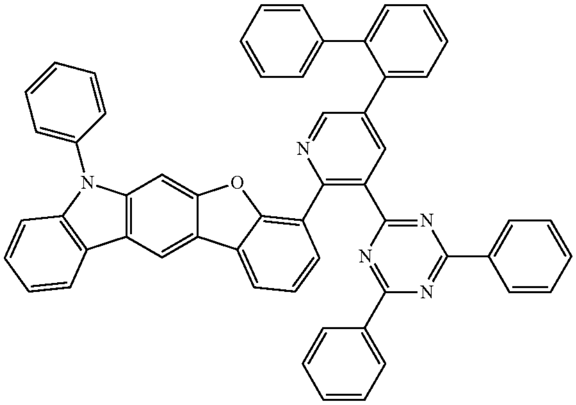
-continued
1039
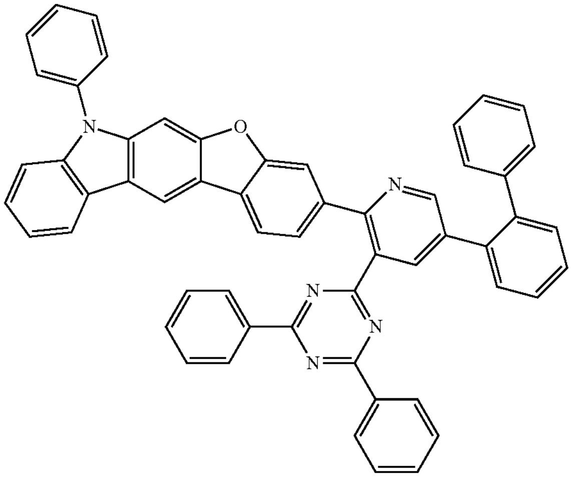
1040
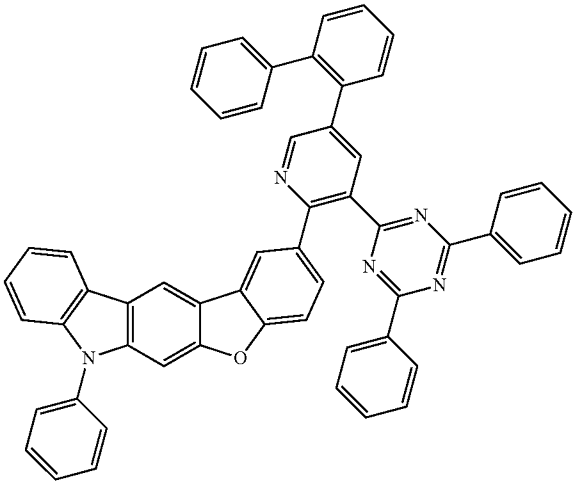
1041
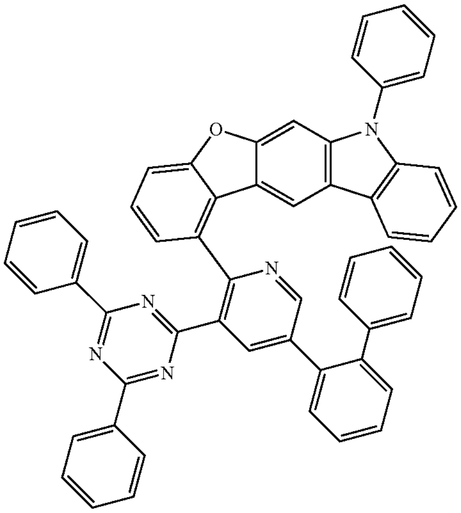

-continued
1042
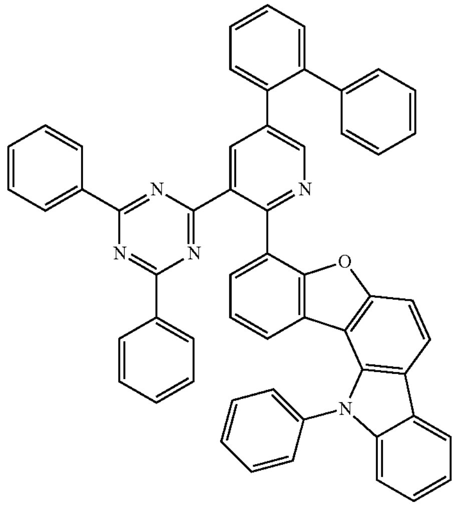
1043
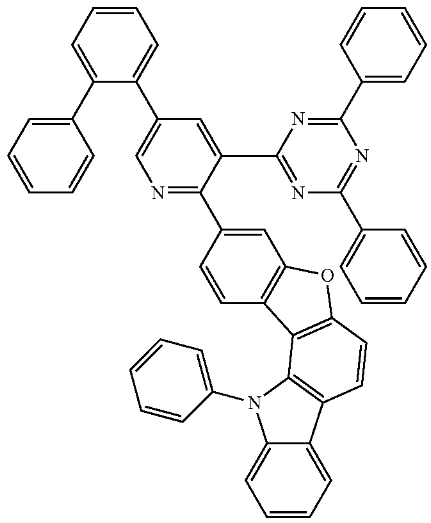
1044
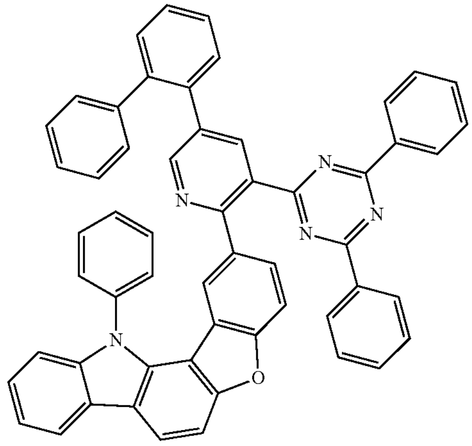
-continued
1045
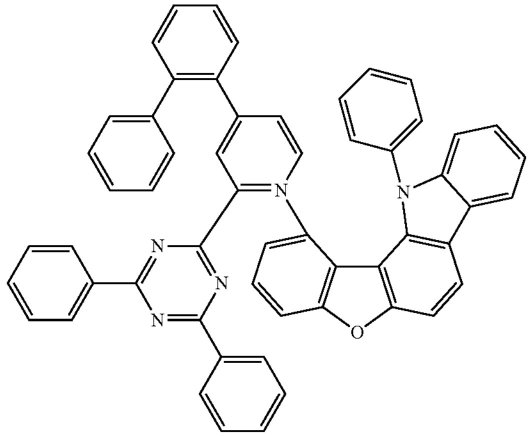
1046
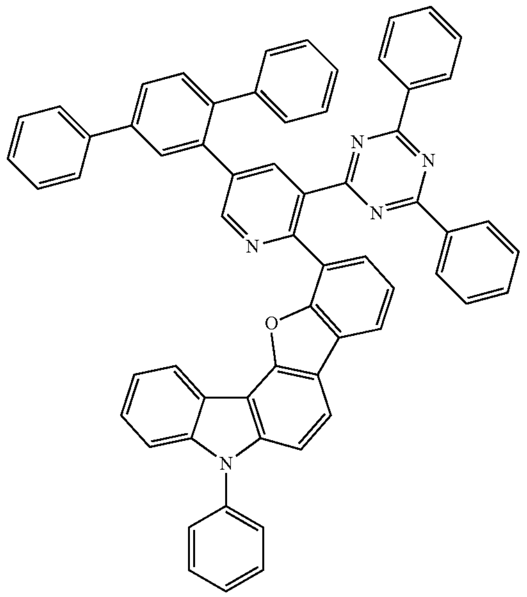

-continued
1047
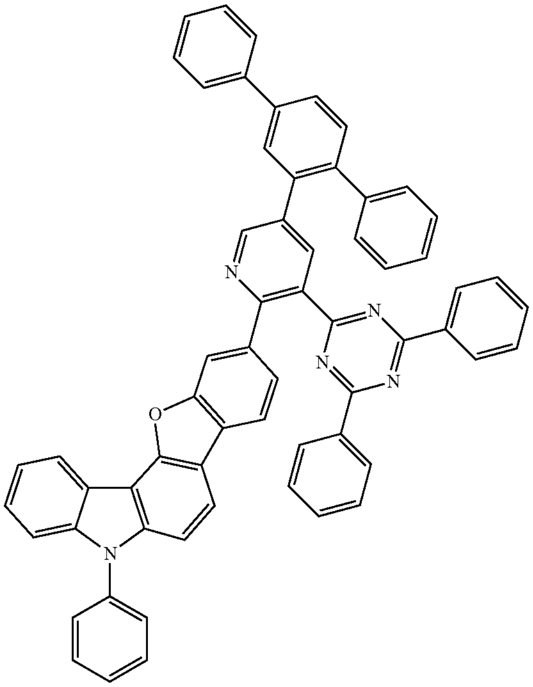
1048
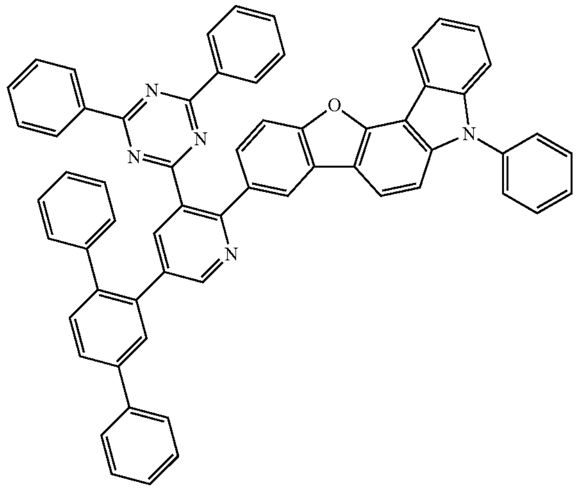
-continued
1049
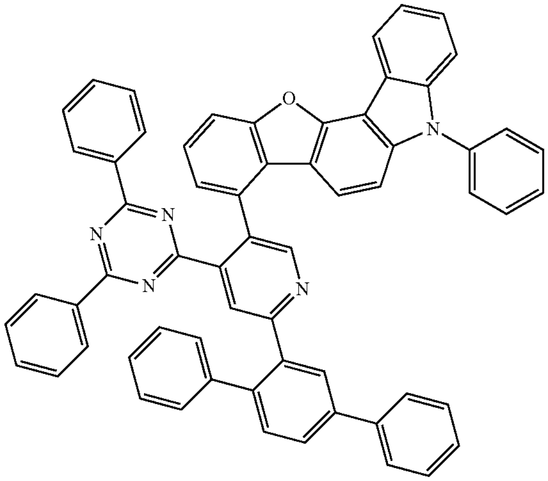
1050
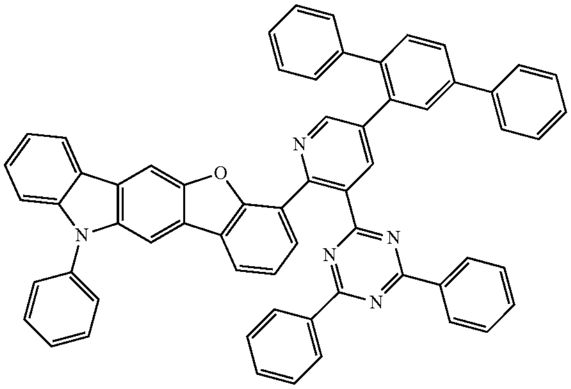
1051
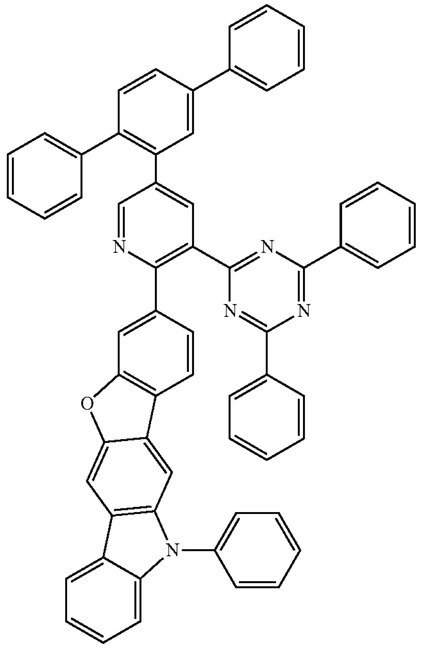

-continued
1052
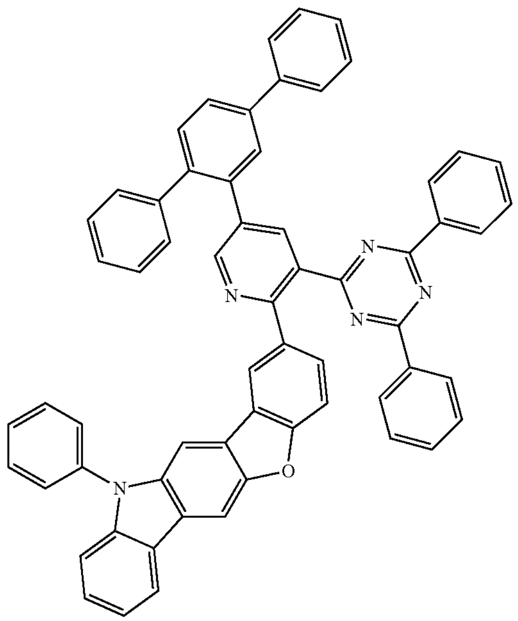
1053
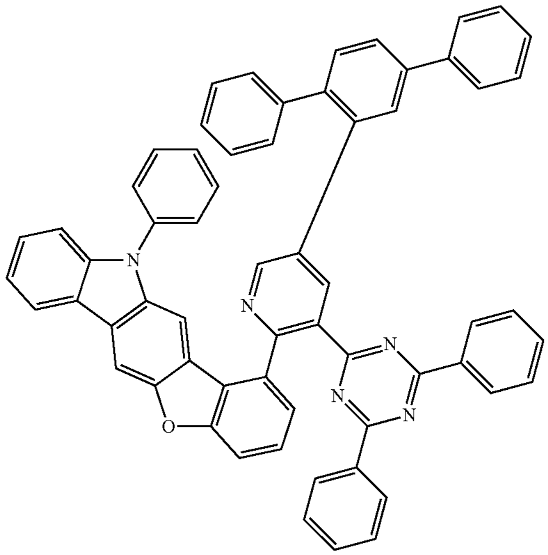
1054
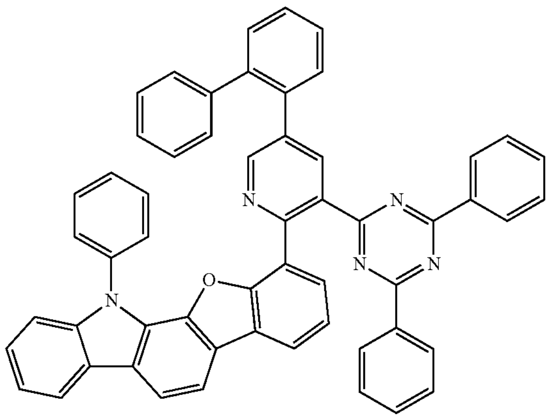
-continued
1055
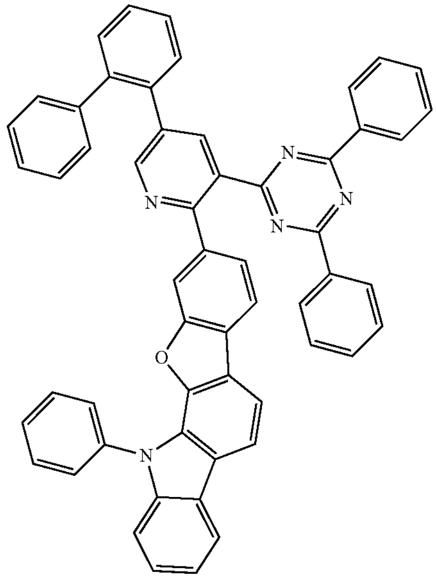
1056
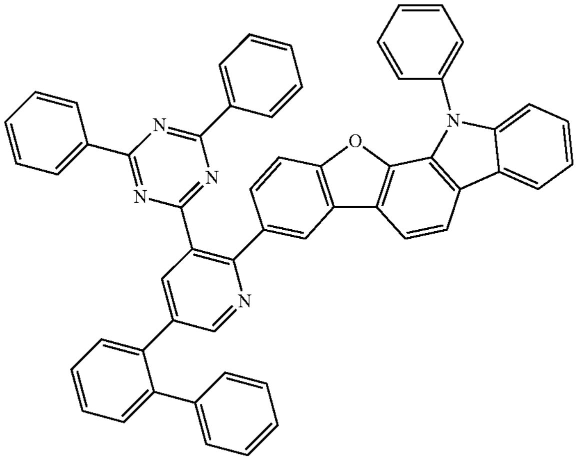
1057
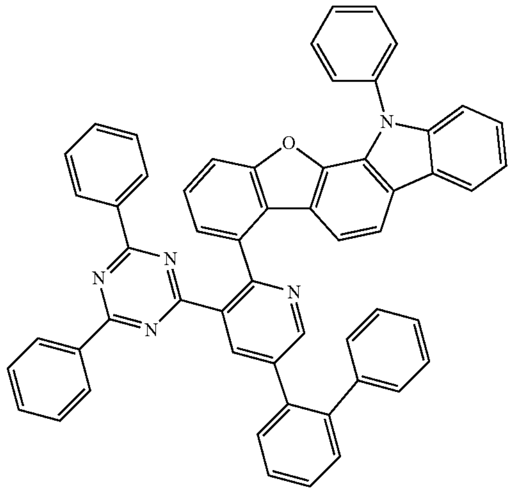

-continued
1058
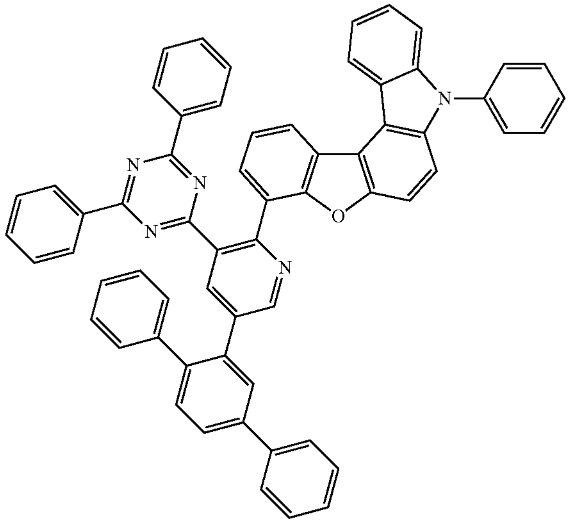
1059
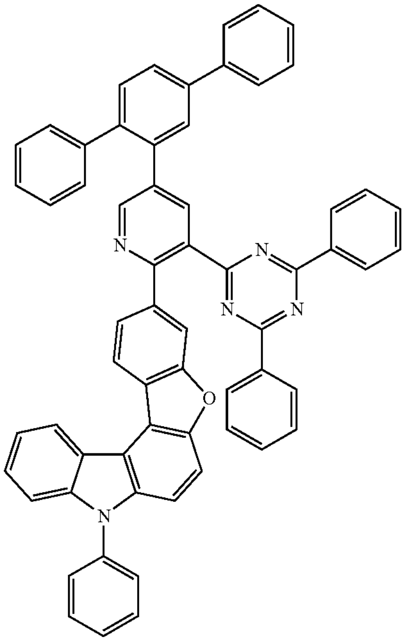
-continued
1060
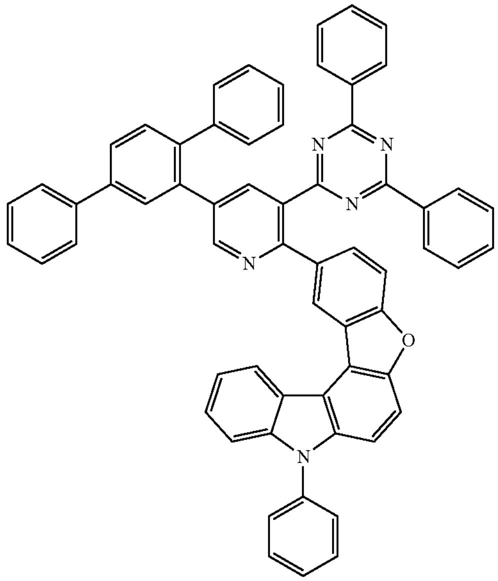
1061
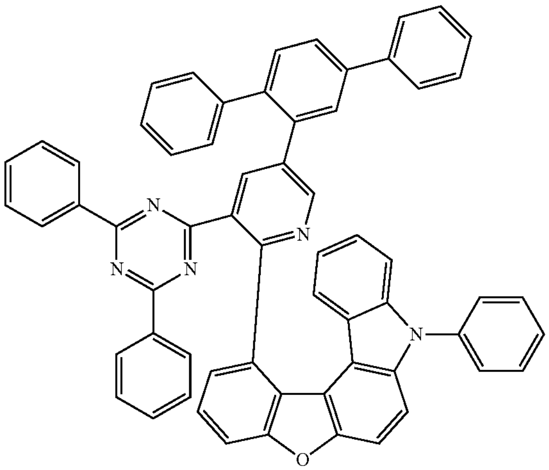
1062
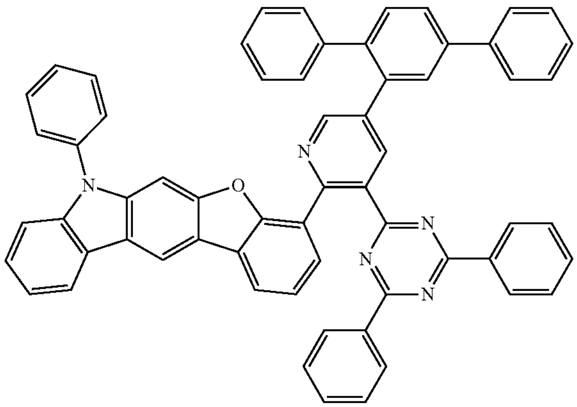

-continued
1063
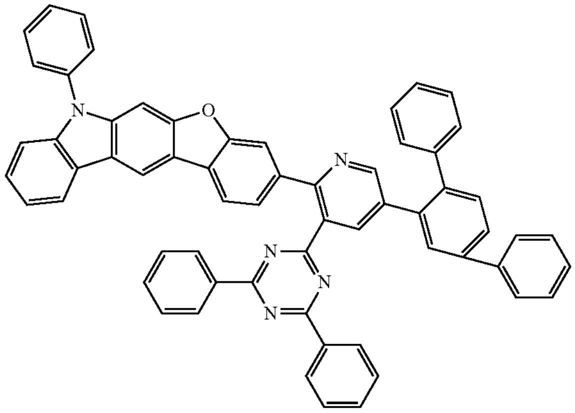
1064
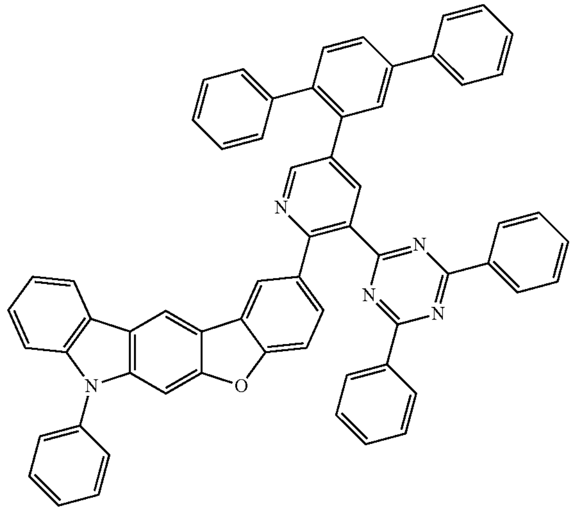
1065
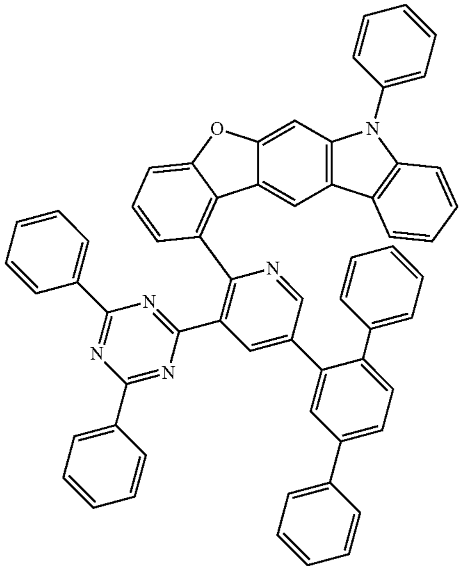
-continued
1066
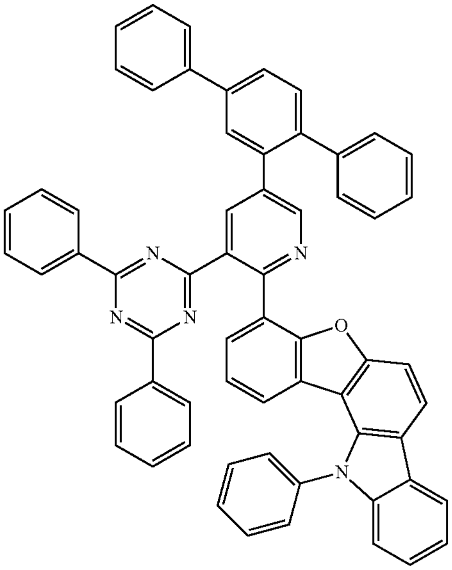
1067
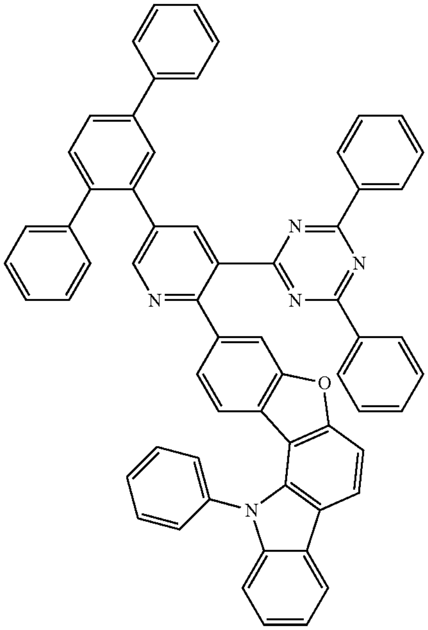

-continued
1068
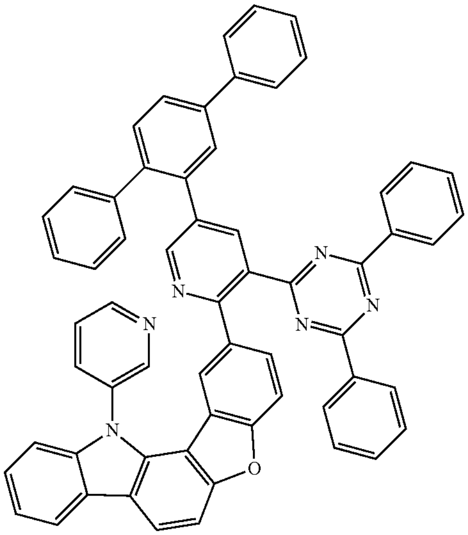
1069
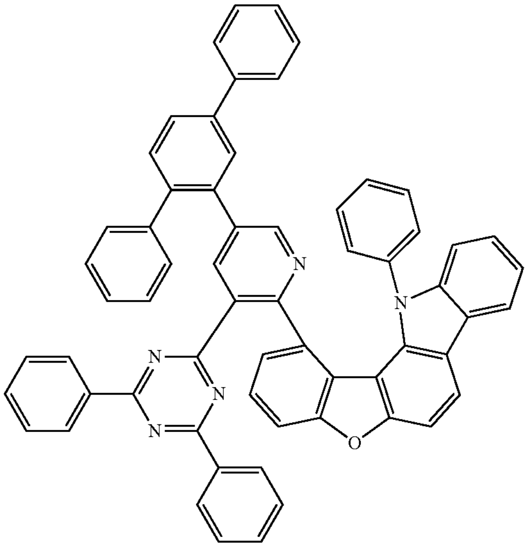
1070
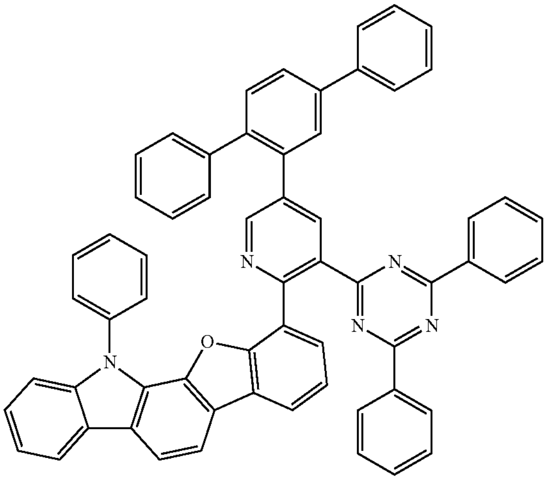
-continued
1071
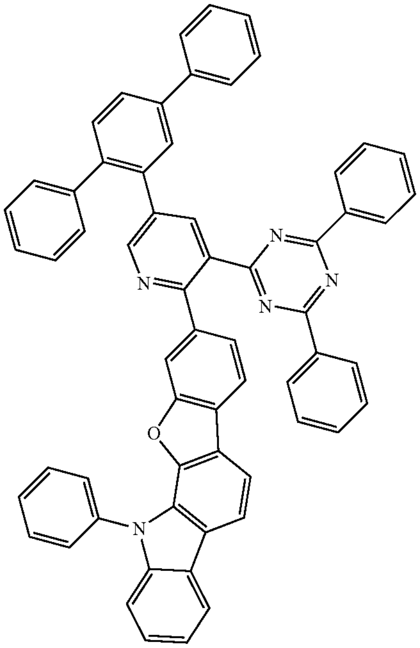
1072
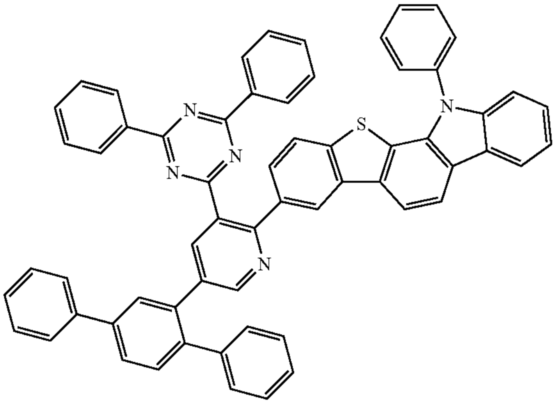

-continued
1073
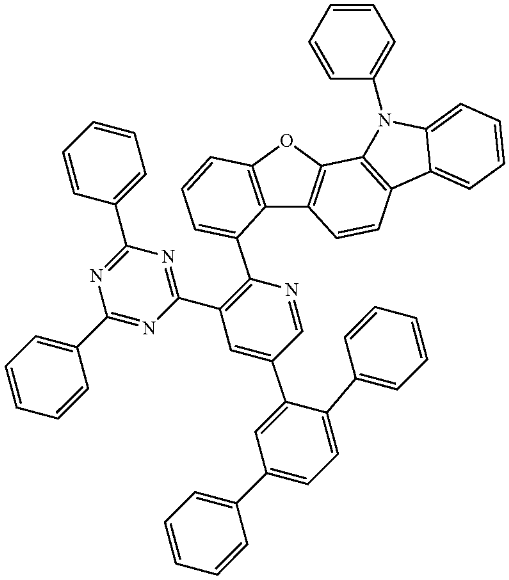
1074
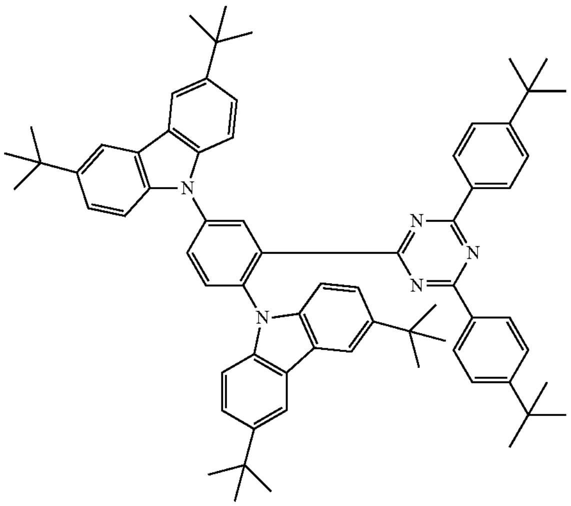
-continued
1075
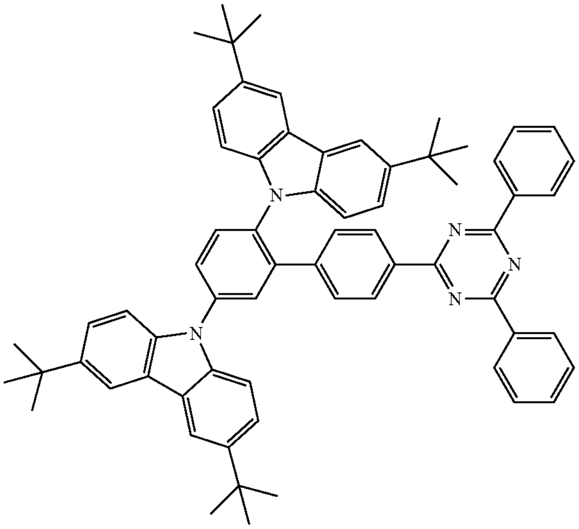
1076
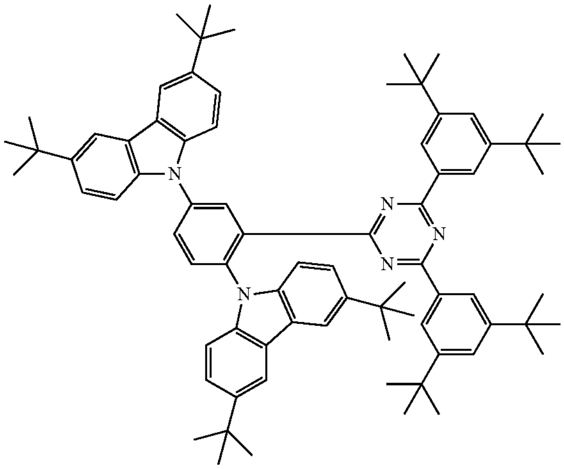
1077
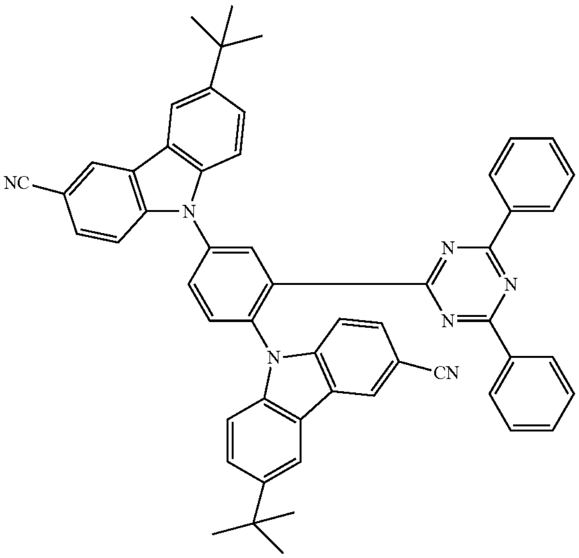

-continued

1078

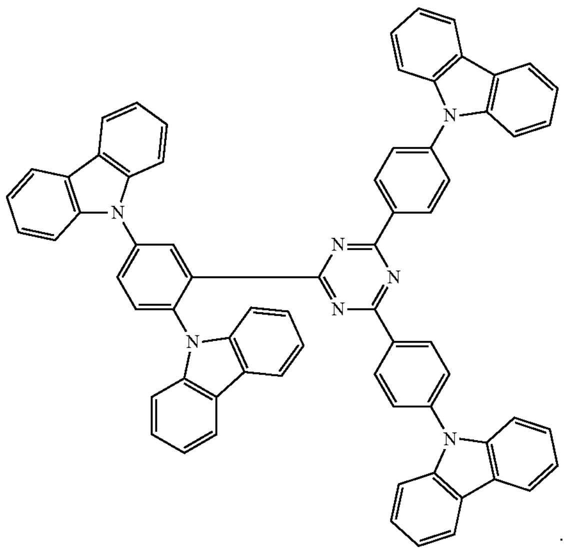

$Ar_1$ and $Ar_2$ in Formula 1 are located at "para" positions each other as can be confirmed in Formula 1. Therefore, an overlap density of the highest occupied molecular orbital (HOMO)-lowest unoccupied molecular orbital (LUMO) in a molecule of the heterocyclic compound represented by Formula 1 increases, and a value of an oscillator strength (f) increases. As a result, the luminescence efficiency of an electronic device, for example, an organic light-emitting device, which includes the heterocyclic compound, may be improved.

Also, in Formula 1, $X_1$ may be N or $C(R_1)$, $X_2$ may be N or $C(R_2)$, $X_3$ may be N or $C(R_3)$, $R_1$ to $R_3$ may each independently be hydrogen, deuterium, a $C_1$-$C_{20}$ alkyl group, a $C_1$-$C_{20}$ alkyl group substituted with at least one deuterium, a $C_1$-$C_{20}$ alkoxy group, a $C_1$-$C_{20}$ alkoxy group substituted with at least one deuterium, or $—Si(Q_{101})(Q_{102})(Q_{103})$. That is, in Formula 1, $R_1$ to $R_3$ may each be a non-cyclic group. Therefore, since the heterocyclic compound represented by Formula 1 may have a relatively low deposition temperature, an electronic device, for example, an organic light-emitting device, which includes the heterocyclic compound, may have excellent lifespan characteristics.

Furthermore, in Formula 1, $X_{11}$ to $X_{13}$ may each independently be N or C(CN). Therefore, since the heterocyclic compound represented by Formula 1 has a relatively small decay time (Tau), an electronic device, for example, an organic light-emitting device, which includes the heterocyclic compound, may have excellent lifespan characteristics.

The heterocyclic compound represented by Formula 1 may have a singlet energy level (expressed in electron volts, eV) in a range of about 2.5 eV to about 3.0 eV.

Also, a difference (being an absolute value) between a singlet energy level (eV) of the heterocyclic compound and a triplet energy level (eV) of the heterocyclic compound may be in a range of about 0 eV to about 0.5 eV. Therefore, the heterocyclic compound represented by Formula 1 may emit delayed fluorescence having high efficiency and/or high luminance.

When a difference between a singlet energy level (eV) of the heterocyclic compound represented by Formula 1 and a triplet energy level (eV) of the heterocyclic compound represented by Formula 1 is within this range, up-conversion from a triplet state to a singlet state is effectively performed, and the heterocyclic compound may emit delayed fluorescence having high efficiency.

The singlet energy level and the triplet energy level are evaluated by using a density functional theory (DFT) method (for example, a DFT method of Gaussian program) structurally optimized at a level of B3LYP/6-31G(d,p).

Synthesis methods of the heterocyclic compound represented by Formula 1 may be recognized by those of ordinary skill in the art by referring to Synthesis Examples.

Another aspect of the present disclosure may provide an organic light-emitting device including: a first electrode; a second electrode; and an organic layer disposed between the first electrode and the second electrode, wherein the organic layer includes an emission layer, and wherein the organic layer includes at least one heterocyclic compound represented by Formula 1.

For example, the emission layer may include the heterocyclic compound represented by Formula 1. The emission layer including the heterocyclic compound may be an emission layer according to a first embodiment or a second embodiment.

First Embodiment

The heterocyclic compound represented by Formula 1, which is included in the emission layer, may emit fluorescence (for example, thermally activated delayed fluorescence).

For example, the emission layer may consist of the heterocyclic compound represented by Formula 1.

In an embodiment, the emission layer may include a host and a dopant. The dopant may include the heterocyclic compound represented by Formula 1. An amount of the host may be larger than an amount of the dopant. The host and the dopant may be different from each other.

The heterocyclic compound included in the emission layer may act as an emitter (for example, a thermally activated delayed fluorescence emitter).

The emission layer may not include a phosphorescent dopant. That is, the emission layer may not include a compound capable of emitting light in accordance to a phosphorescence emission mechanism. Therefore, the emission layer may not include a phosphorescence emitter and does not substantially emit phosphorescence. Instead, the emission layer may be a "delayed fluorescence" emission layer that emits delayed fluorescence by transiting a triplet exciton of the heterocyclic compound represented by Formula 1 from a triplet state to a singlet state by reverse intersystem crossing (RISC), followed by transiting to a ground state.

As described above, the "delayed fluorescence" emission layer used herein is distinctly different from a "phosphorescence" emission layer that includes a phosphorescence emitter (for example, a transition metal (for example, an iridium or a platinum) complex) as a dopant and causes an energy transfer from a host to a phosphorescence emitter, without a process of emitting delayed fluorescence by transiting a triplet exciton of the heterocyclic compound represented by Formula 1 from a triplet state to a singlet state by reverse intersystem crossing (RISC), followed by transiting to a ground state.

Second Embodiment

The emission layer may include a host and a dopant. The host may include the heterocyclic compound represented by Formula 1. An amount of the host may be larger than an amount of the dopant. The host and the dopant may be different from each other. The heterocyclic compound included in the emission layer may serve to transfer energy to the dopant, instead of being an emitter.

The emission layer (for example, the emission layer according to the first embodiment or the second embodiment) may emit red light, green light, or blue light. For example, the emission layer may emit blue light, but embodiments of the present disclosure are not limited thereto.

A ratio of a delayed fluorescence component emitted from the heterocyclic compound represented by Formula 1 to a total emission component emitted from the emission layer may be 90% or more, 92% or more, 94% or more, 96% or more, or 98% or more, but embodiments of the present disclosure are not limited thereto.

The host in the emission layer in the first embodiment may include at least one selected from a first material and a second material, in addition to the heterocyclic compound represented by Formula 1, and the host in the emission layer in the second embodiment may further include at least one selected from a first material and a second material.

- the first material may include at least one π electron-rich cyclic group, and may not include an electron transport moiety,
- the second material may include at least one π electron-rich cyclic group and at least one electron transport moiety, and
- the electron transport moiety may be selected from a cyano group, a π electron-depleted nitrogen-containing cyclic group, and a group represented by one selected from the following formulae:

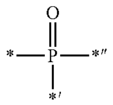
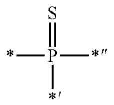
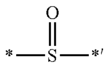
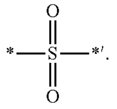

In the formulae, *, *', and *" each indicate a binding site to a neighboring atom.

For example, i) the host may consist of at least one compound of the first material, ii) the host may consist of two different compounds of the first material, iii) the host may consist of one compound of the second material, iv) the host may consist of two different compounds of the second material, or v) the host may consist of at least one compound of the first material and at least one compound of the second material. In this manner, the host may be variously modified.

The term "π electron-depleted nitrogen-containing cyclic group" as used herein refers to a cyclic group having at least one *—N=*' moiety. For example, the π electron-depleted nitrogen-containing cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, an azadibenzosilole group, or a cyclic group condensed with any one of the foregoing groups.

The π electron-rich cyclic group may be, for example, a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group, but embodiments of the present disclosure are not limited thereto.

The first material and the second material may be different from each other.

In an embodiment, the first material and the second material may each independently include at least one carbazole group.

In one or more embodiments, the first material and the second material may each independently include at least two carbazole groups, but embodiments of the present disclosure are not limited thereto.

In one or more embodiments, the second material may include at least one cyano group (for example, one, two, three, or four cyano groups).

In one or more embodiments, the first material may include a cyano group-free benzene group and a cyano group-free carbazole group.

In one or more embodiments, the second material may include at least one cyano group and at least one carbazole ring.

In one or more embodiments, the second material may include at least one of a cyano group-containing benzene group and a cyano group-containing carbazole group.

In one or more embodiments,

- an absolute value of a lowest unoccupied molecular orbital (LUMO) energy level of the first material may be in a range of about 0.90 eV to about 1.20 eV,
- an absolute value of a HOMO energy level of the first material may be in a range of about 5.20 eV to about 5.60 eV,
- an absolute value of a LUMO energy level of the second material may be in a range of about 1.80 eV to about 2.20 eV, an absolute value of a HOMO energy level of the second material may be in a range of about 5.40 eV to about 6.00 eV, but embodiments of the present disclosure are not limited thereto.

When the HOMO and LUMO energy level ranges of the first material and the second material are within these ranges, charge and/or exciton movement and energy flow in the emission layer are smooth, and an organic light-emitting device having high luminescence efficiency and long lifespan may be implemented.

In one or more embodiments, the first material may include at least one selected from a compound represented by Formula H-1(1), a compound represented by Formula H-1(2), and a compound represented by Formula H-1(3):

H-1(1)

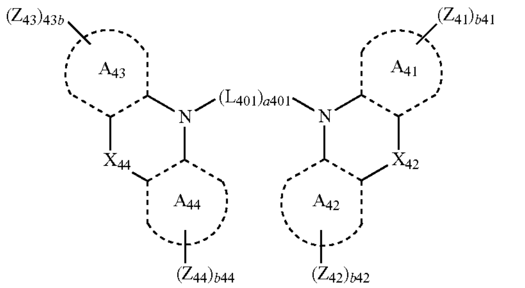

H-1(2)

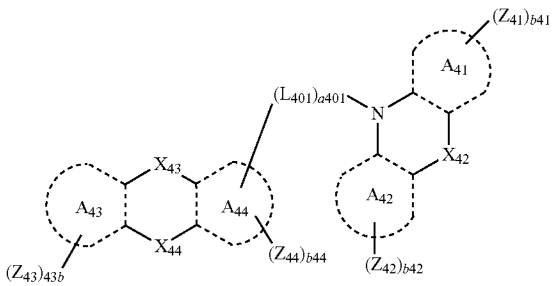

H-1(3)

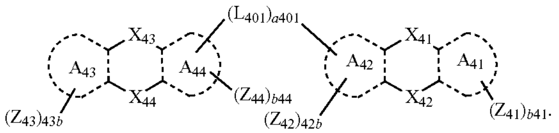

In Formulae H-1(1) to H-1(3), ring $A_{41}$ to ring $A_{44}$ may each independently be a benzene group, a naphthalene group, an indene group, an indole group, a benzofuran group, a benzothiophene group, a benzosilole group, a fluorene group, a carbazole group, a dibenzofuran group, a dibenzothiophene group, or a dibenzosilole group.

For example, ring $A_{41}$ to ring $A_{44}$ may each independently be a benzene group, a fluorene group, a carbazole group, a dibenzofuran group, a dibenzothiophene group, or a dibenzosilole group, wherein at least one of ring $A_{41}$ and ring $A_{42}$ may be a benzene group, and at least one of ring $A_{43}$ and ring $A_{44}$ may be a benzene group.

In Formulae H-1(1) to H-1(3), $X_{41}$ may be N-[$(L_{411})_{c411}$-$Z_{411}$], C($Z_{415}$)($Z_{416}$), O, or S, $X_{42}$ may be a single bond, N-[$(L_{412})_{c412}$-$Z_{412}$], C($Z_{417}$)($Z_{418}$), O, or S, $X_{43}$ may be N-[$(L_{413})_{c413}$-$Z_{413}$], C($Z_{419}$)($Z_{420}$), O, or S, and $X_{44}$ may be a single bond, N-[$(L_{414})_{c414}$-$Z_{414}$], C($Z_{421}$)($Z_{422}$), O, or S.

$L_{401}$ and $L_{411}$ to $L_{414}$ may each independently be selected from:

a single bond; and a π electron-rich cyclic group unsubstituted or substituted with at least one $R_{10d}$ (for example, a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group, each unsubstituted or substituted with at least one $R_{10d}$).

Each of a401 and c411 to c414 indicates the number of each of $L_{401}$ and $L_{411}$ to $L_{414}$, respectively, and may independently be an integer from 1 to 10 (for example, an integer from 1 to 5). When a401 is two or more, two or more of groups $L_{401}$ may be identical to or different from each other, when c411 is two or more, two or more of groups $L_{411}$ may be identical to or different from each other, when c412 is two or more, two or more of groups $L_{412}$ may be identical to or different from each other, when c413 is two or more, two or more of groups $L_{413}$ may be identical to or different from each other, and when c414 is two or more, two or more of groups $L_{414}$ may be identical to or different from each other.

$Z_{41}$ to $Z_{44}$ and $Z_{411}$ to $Z_{422}$ may each independently be selected from:

hydrogen, deuterium, a $C_1$-$C_{20}$ alkyl group, and a $C_1$-$C_{20}$ alkoxy group; and a π electron-rich cyclic group unsubstituted or substituted with at least one $R_{10d}$ (for example, a phenyl group, a biphenyl group, a terphenyl group, a tetraphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, an isoindolyl group, an indolyl group, a furanyl group, a thiophenyl group, a benzofuranyl group, a benzothiophenyl group, a benzosilolyl group, a benzocarbazolyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with at least one $R_{10d}$).

Each of b41 to b44 indicates the number of each of $Z_{41}$ to $Z_{44}$, respectively, and may independently be 1, 2, 3, or 4.

$R_{10d}$ may be defined the same as $R_{10a}$, but $R_{10d}$ is not a cyano group.

In an embodiment, in Formulae H-1(1) to H-1(3), $L_{401}$ and $L_{411}$ to $L_{414}$ may each independently be selected from:

a single bond; and a benzene group, a fluorene group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, an acridine group, or a dihydroacridine group, each unsubstituted or substituted with at least one $R_{10d}$, $Z_{41}$ to $Z_{44}$ and $Z_{411}$ to $Z_{422}$ may each independently be selected from:

hydrogen, deuterium, a $C_1$-$C_{10}$ alkyl group, and a $C_1$-$C_{10}$ alkoxy group; and a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, or a dihydroacridinyl group, each unsubstituted or substituted with at least one $R_{10d}$, but embodiments of the present disclosure are not limited thereto.

In an embodiment, the first material may include at least one compound selected from Compounds H1 to H32, but embodiments of the present disclosure are not limited thereto:

H1

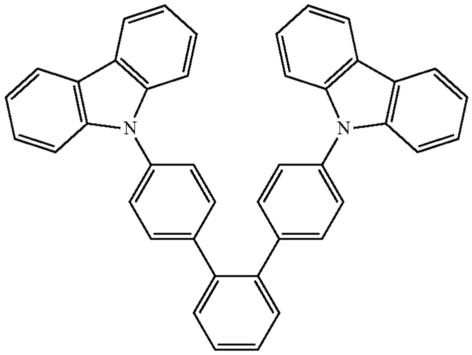

H2

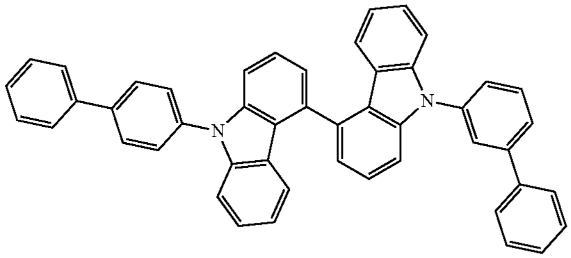

-continued

H3

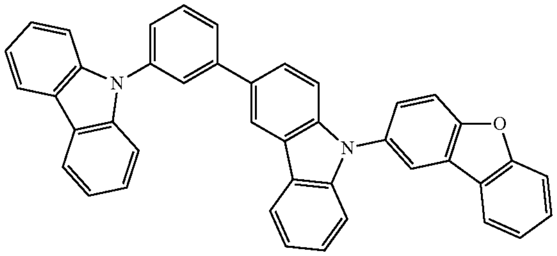

H4

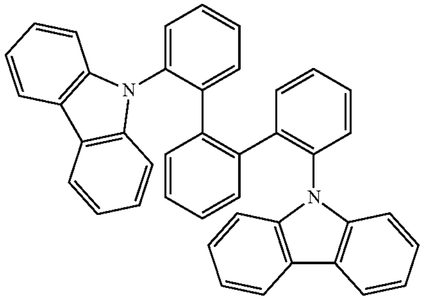

H5

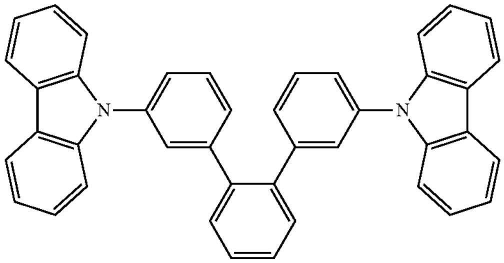

H6

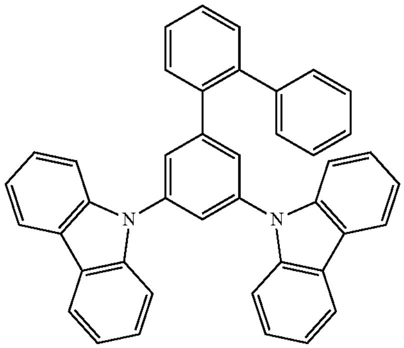

H7

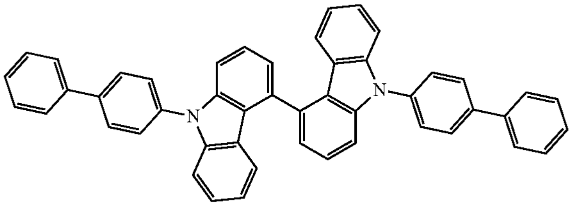

-continued
H8
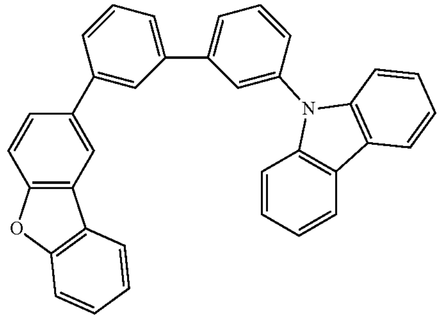
H9
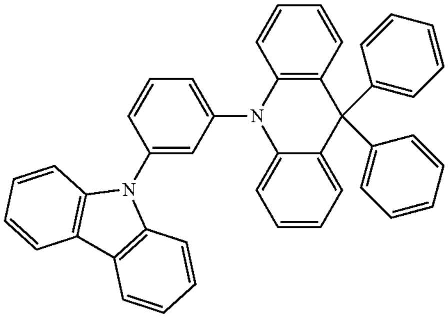
10
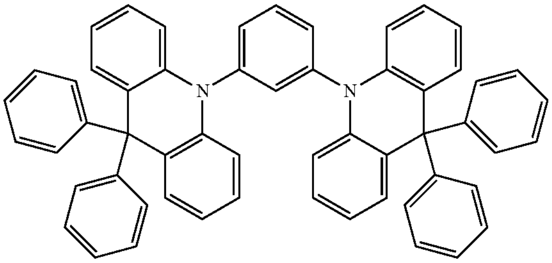
H11
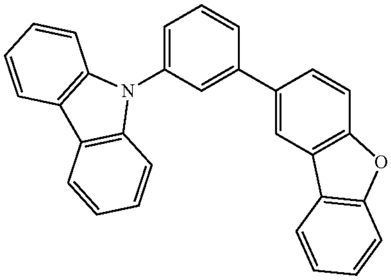
-continued
H12
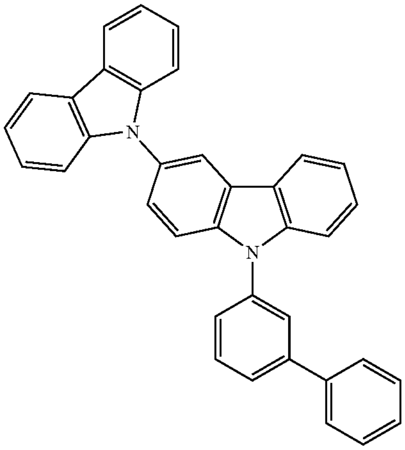
H13
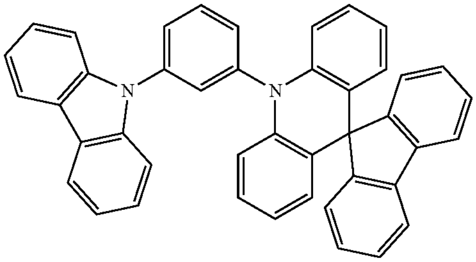
H14
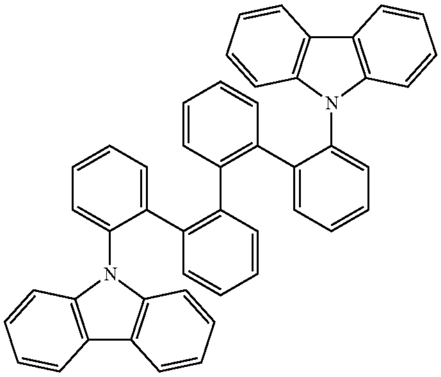
H15
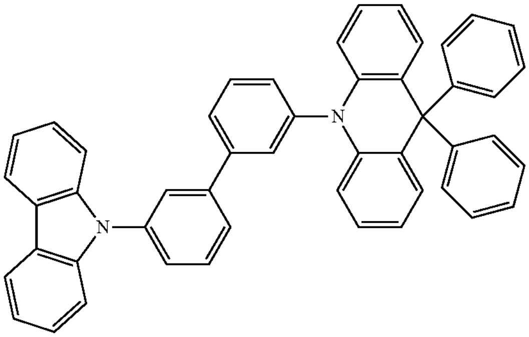

-continued
H16
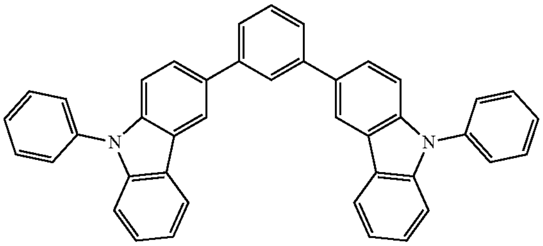
H17
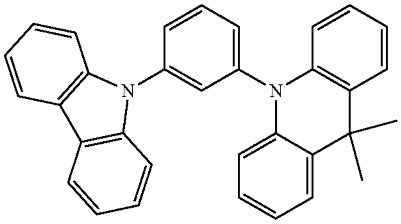
H18
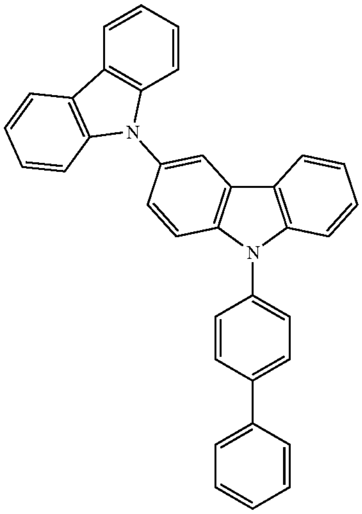
H19
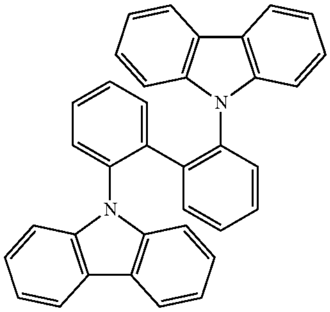
H20
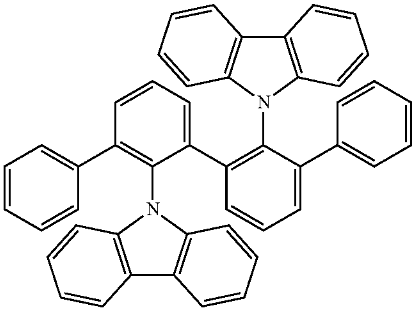
-continued
H21
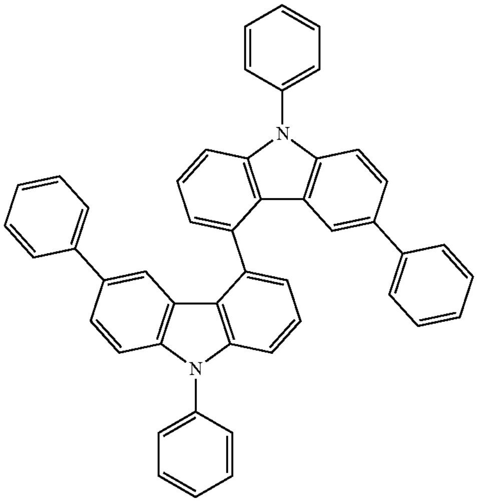
H22
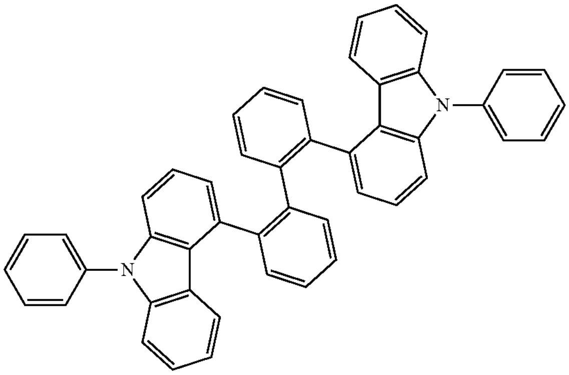
H23
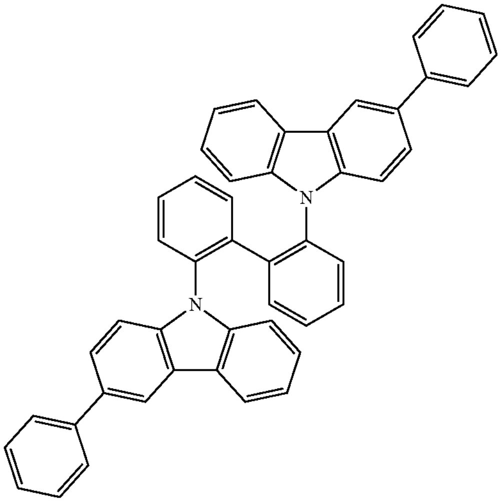

-continued

H24

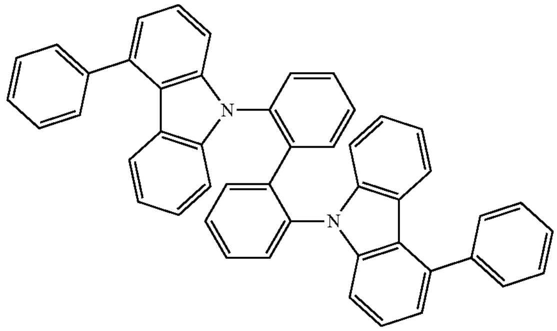

H25

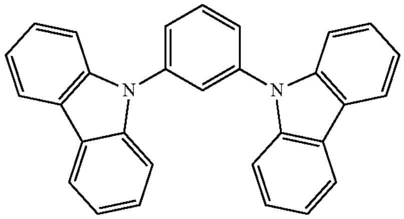

H26

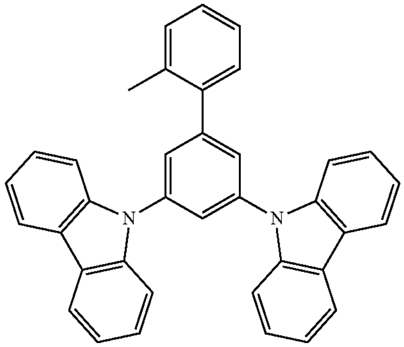

H27

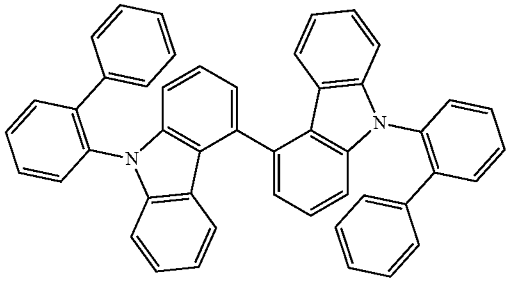

H28

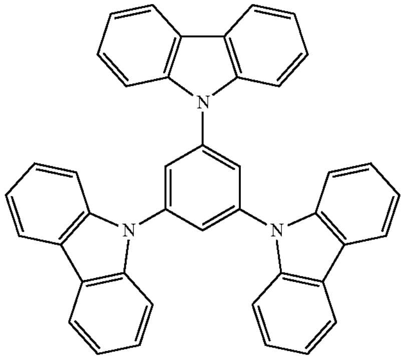

-continued

H29

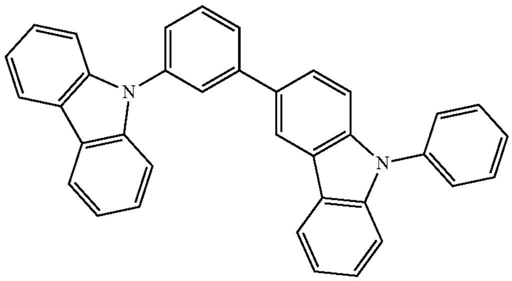

H30

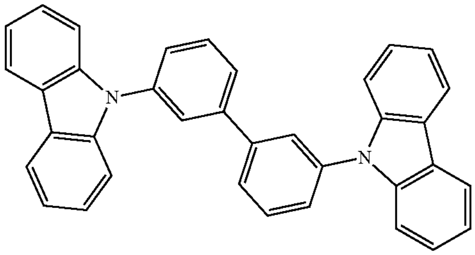

H31

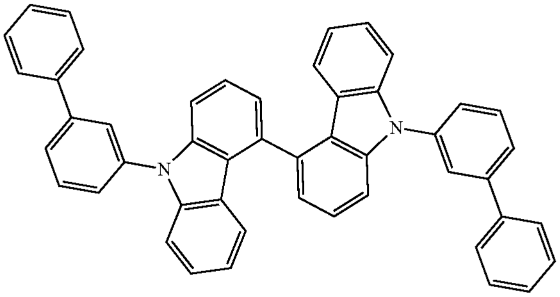

H32

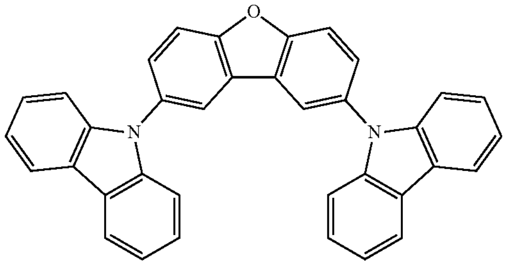

In an embodiment, the first material may not be an amine-based compound.

In one or more embodiments, the first material may not be 1,3-bis(9-carbazolyl)benzene (mCP), tris(4-carbazoyl-9-ylphenyl)amine (TCTA), 4,4'-bis(N-carbazolyl)-1,1'-biphenyl (CBP), 3,3-bis(carbazo-9-yl)biphenyl (mCBP), N,N'-di(1-naphthyl)-N, N'-diphenyl-(1,1'-biphenyl)-4,4'-diamine (NPB), 4,4',4"-tris[phenyl(m-tolyl)amino]triphenylamine (m-MTDATA), or N, N'-bis(3-methylphenyl)-N, N'-diphenylbenzidine (TPD).

In one or more embodiments, the second material may include a compound represented by Formula E-1:

$$[Ar_{301}]_{xb11}\text{-}[(L_{301})_{xb1}\text{-}R_{301}]_{xb21}. \quad \text{Formula E-1}$$

In Formula E-1, $Ar_{301}$ may be selected from a substituted or unsubstituted $C_5$-$C_{60}$ carbocyclic group and a substituted or unsubstituted $C_1$-$C_{60}$ heterocyclic group, xb11 may be 1, 2, or 3, $L_{301}$ may be selected from a single bond, a group represented by one selected from the following formulae, a substituted or unsubstituted $C_5$-$C_{60}$ carbocyclic group, and a substituted or unsubstituted $C_1$-$C_{60}$ heterocyclic group, wherein *, *', and *" in the following formulae each indicate a binding site to a neighboring atom,

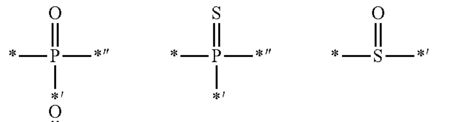

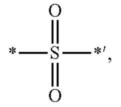

xb1 may be an integer from 1 to 5, $R_{301}$ may be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{10}$ heteroaryl group, a substituted or unsubstituted $C_1$-$C_{60}$ heteroaryloxy group, a substituted or unsubstituted $C_1$-$C_{10}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), —S(=O)($Q_{301}$), —P(=O)($Q_{301}$)($Q_{302}$), and —P(=S)($Q_{301}$)($Q_{302}$), xb21 may be an integer from 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, and satisfies one of Condition 1 to Condition 3:

Condition 1

Each of at least one selected from $Ar_{301}$, $L_{301}$, and $R_{301}$ in Formula E-1 may independently include a π electron-depleted nitrogen-containing cyclic group Condition 2

At least one $L_{301}$ in Formula E-1 may include a group represented by one selected from the following formulae:

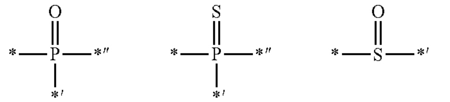

-continued

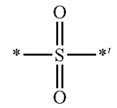

Condition 3

At least one $R_{301}$ in Formula E-1 may be selected from a cyano group, —S(=O)$_2$($Q_{301}$), —S(=O)($Q_{301}$), —P(=O)($Q_{301}$)($Q_{302}$), and —P(=S)($Q_{301}$)($Q_{302}$).

In one or more embodiments, the second material may include at least one selected from a compound represented by Formula E-1(1), a compound represented by Formula E-1(2), and a compound represented by Formula E-1(3):

E-1(1)

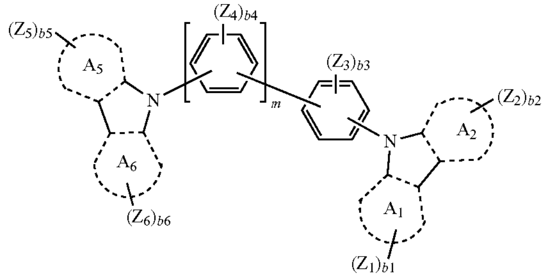

E-1(2)

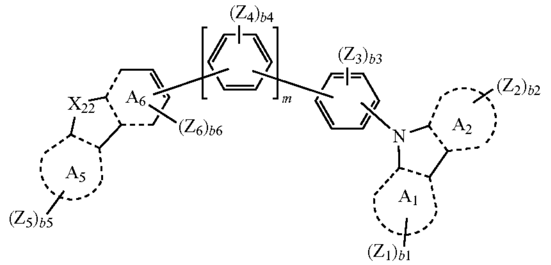

E-1(3)

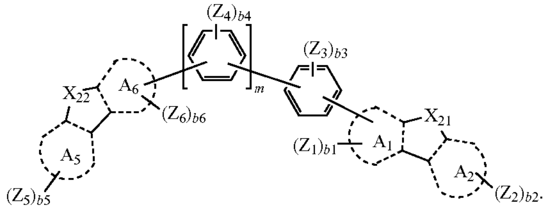

In Formulae E-1(1) to E-1(3), ring $A_1$, ring $A_2$, ring $A_5$, and ring $A_6$ may each independently be selected from a benzene group, a naphthalene group, an anthracene group, a phenanthrene group, a triphenylene group, a pyrene group, a chrysene group, a cyclopentadiene group, a thiophene group, a furan group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, and a phenanthroline group.

For example, ring $A_1$, ring $A_2$, ring $A_5$, and ring $A_6$ may each independently be selected from a benzene group, a carbazole group, a fluorene group, a dibenzothiophene group, and a dibenzofuran group.

In Formulae E-1(1) to E-1(3), $Z_1$ to $Z_6$ may each independently be selected from:

hydrogen, deuterium, and a cyano group; or a $C_1$-$C_{20}$ alkyl group, a phenyl group, a biphenyl group, a terphenyl group, a dibenzofuranyl group, and a dibenzothiophenyl group, each unsubstituted or substituted with at least one selected from deuterium, a cyano group, a $C_1$-$C_{20}$ alkyl group, a phenyl group, and a biphenyl group.

For example, in Formulae E-1(1) to E-1(3), $Z_1$ to $Z_6$ may each independently be selected from:

hydrogen, deuterium, and a cyano group; or a $C_3$-$C_{10}$ alkyl group, a phenyl group, a biphenyl group, a terphenyl group, a dibenzofuranyl group, and a dibenzothiophenyl group, each unsubstituted or substituted with at least one selected from deuterium, a cyano group, a $C_3$-$C_{10}$ alkyl group, a phenyl group, and a biphenyl group.

In an embodiment, in Formulae E-1(1) to E-1(3), $Z_1$ to $Z_6$ may each independently be selected from:

hydrogen, deuterium, and a cyano group; or an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, a biphenyl group, and a terphenyl group, each unsubstituted or substituted with at least one selected from deuterium, a cyano group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a biphenyl group.

In Formulae E-1(1) to E-1(3), b1 to b6 respectively indicate the number of groups $Z_1$ to groups $Z_6$, and may each independently be 1, 2, or 3. When b1 to b6 are two or more, two or more groups $Z_1$ to groups $Z_6$ may be identical to or different from each other.

In an embodiment, in Formulae E-1(1) to E-1(3), at least one selected from groups $Z_1$ in the number of b1, groups $Z_2$ in the number of b2, groups $Z_3$ in the number of b3, groups $Z_4$ in the number of b4, groups $Z_5$ in the number of b5, and groups Re in the number of b6 may be a cyano group.

For example, the number of cyano groups included in the compound represented by Formula E-1(1), the number of cyano groups included in the compound represented by Formula E-1(2), and the number of cyano groups included in the compound represented by Formula E-1(3) may each independently be 1, 2, or 3, but embodiments of the present disclosure are not limited thereto.

In an embodiment, in Formulae E-1(1) to E-1(3), at least one selected from groups $Z_1$ in the number of b1 and groups $Z_2$ in the number of b2 may be a cyano group, at least one selected from groups $Z_3$ in the number of b3 and groups $Z_4$ in the number of b4 may be a cyano group, at least one selected from groups $Z_5$ in the number of b5 and groups $Z_6$ in the number of b6 may be a cyano group, at least one selected from groups $Z_1$ in the number of b1 and groups $Z_2$ in the number of b2 may be a cyano group, and at least one selected from groups $Z_3$ in the number of b3 and groups $Z_4$ in the number of b4 may be a cyano group, at least one selected from groups $Z_1$ in the number of b1 and groups $Z_2$ in the number of b2 may be a cyano group, and at least one selected from groups $Z_5$ in the number of b5 and groups $Z_6$ in the number of b6 may be a cyano group, at least one selected from groups $Z_3$ in the number of b3 and groups $Z_4$ in the number of b4 may be a cyano group, and at least one selected from groups $Z_5$ in the number of b5 and groups $Z_6$ in the number of b6 may be a cyano group, or at least one selected from groups $Z_1$ in the number of b1 and groups $Z_2$ in the number of b2 may be a cyano group, at least one selected from groups $Z_3$ in the number of b3 and groups $Z_4$ in the number of b4 may be a cyano group, and at least one selected from groups $Z_5$ in the number of b5 and groups $Z_6$ in the number of b6 may be a cyano group.

In Formulae E-1(1) to E-1(3), $X_{21}$ and $X_{22}$ may each independently be O or S, and m may be 0 or 1.

In an embodiment, a group represented by

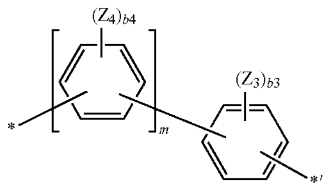

in Formulae E-1(1) to E-1(3) may be one selected from groups represented by Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9:

PO1

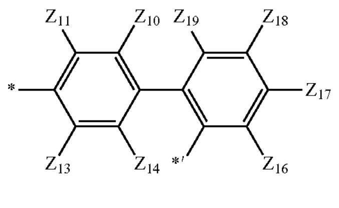

PO2
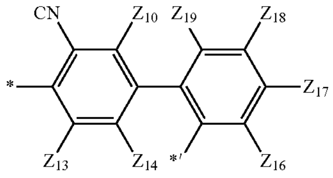
PO3
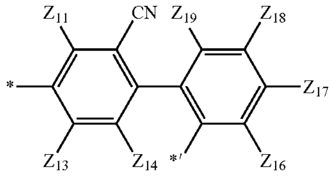
PO4
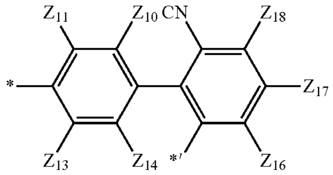
PO5
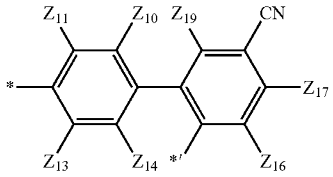
PO6
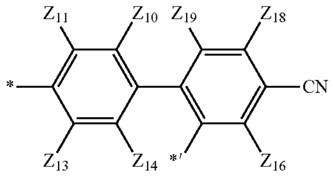
PO7
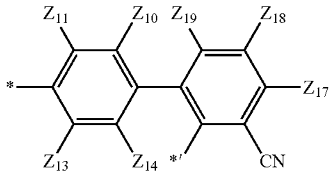
PO8
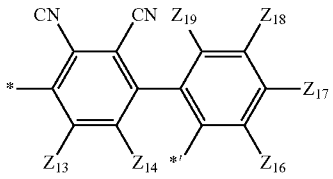
PO9
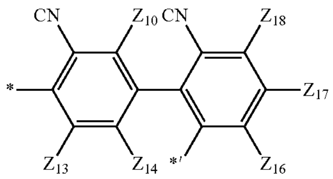
PO10
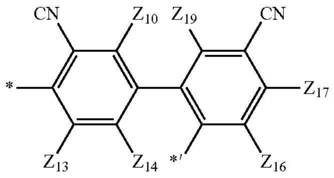
PO11
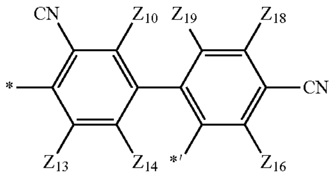
PO12
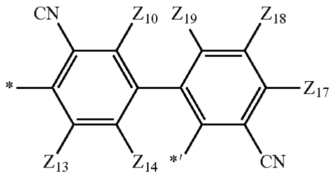
PO13
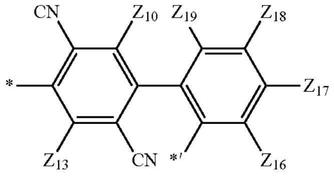
PO14
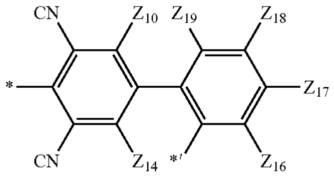
PO15
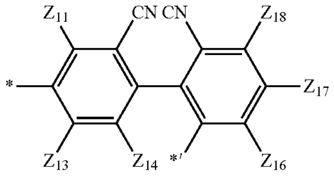
PO16
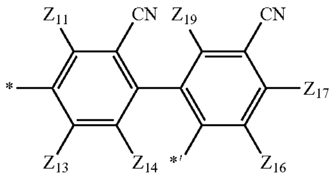
PO17
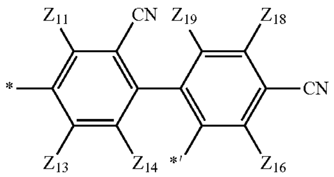

-continued
PO18
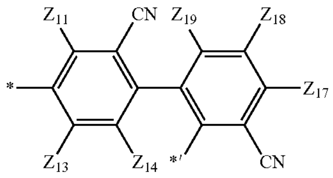
PO19
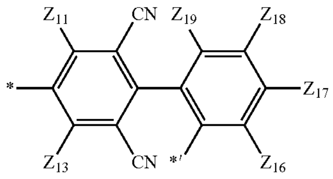
PO20
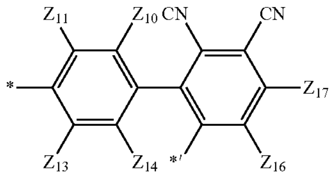
PO21
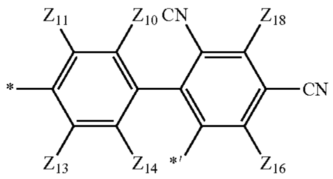
PO22
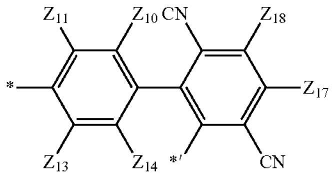
PO23
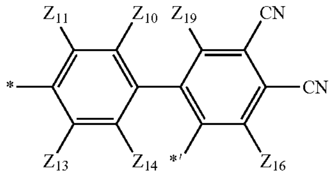
PO24
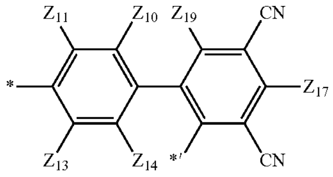
PO25
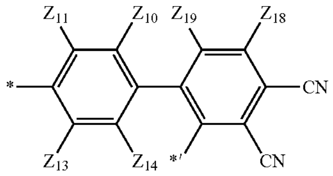
-continued
PM1
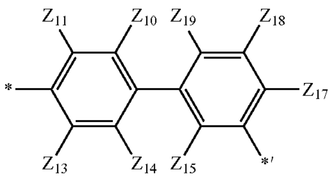
PM2
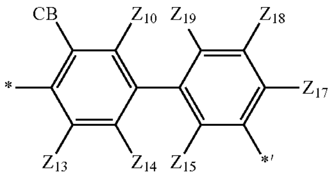
PM3
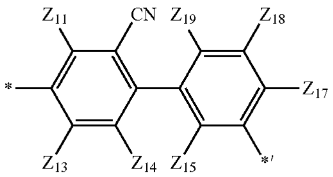
PM4
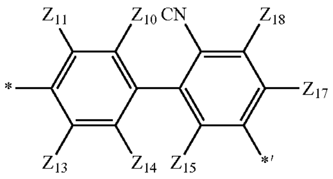
PM5
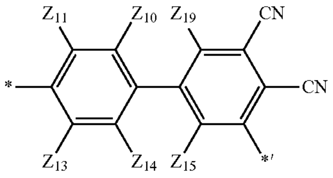
PM6
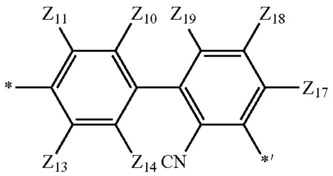
PM7
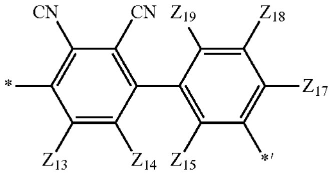
PM8
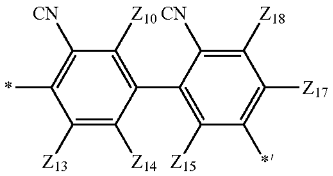

-continued
PM9
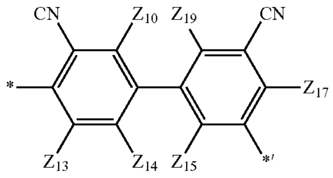
PM10
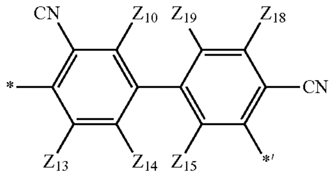
PM11
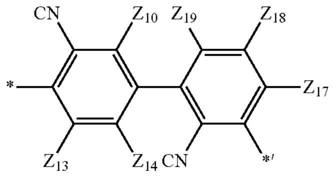
PM12
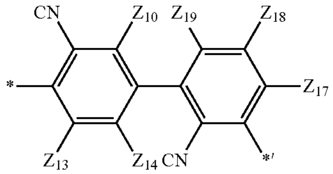
PM13
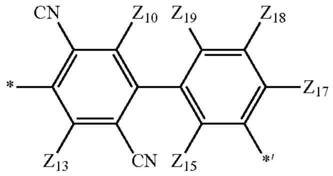
PM14
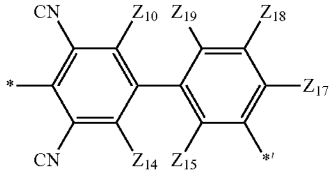
PM15
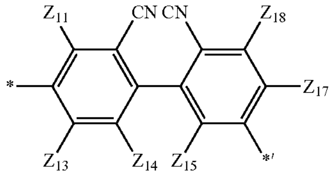
PM16
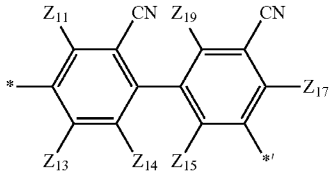
-continued
PM17
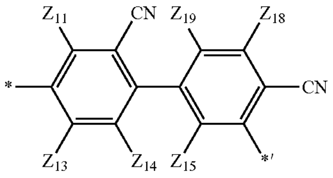
PM18
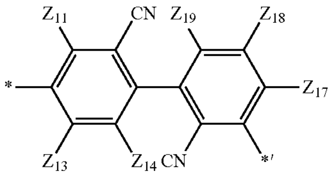
PM19
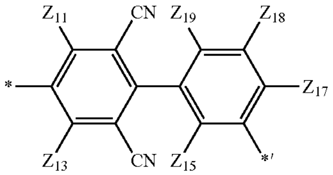
PM20
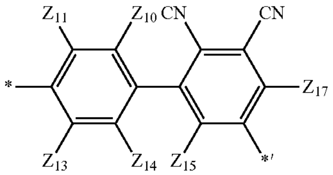
PM21
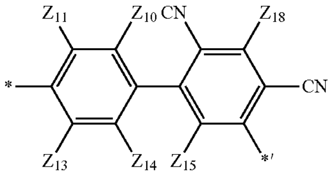
PM22
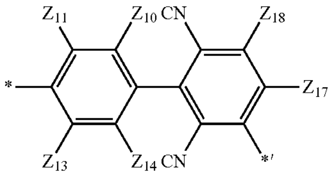
PM23
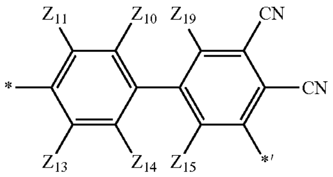
PM24
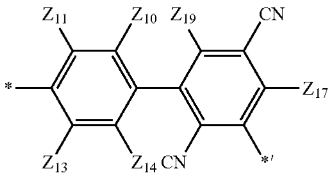

-continued
PM25
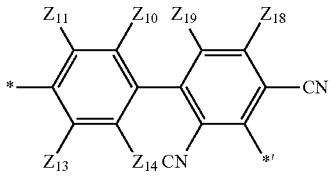
PP1
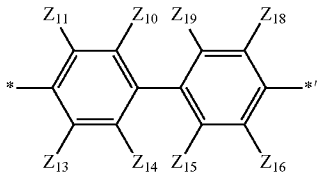
PP2
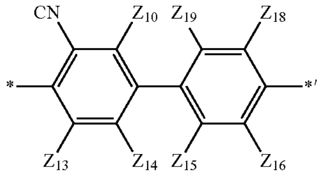
PP3
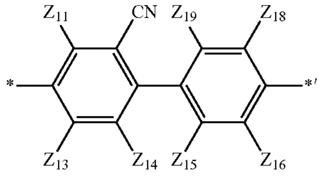
PP4
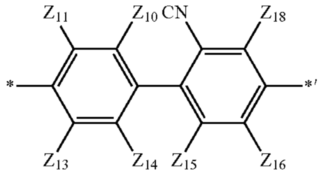
PP5
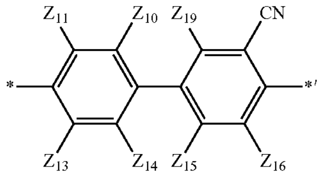
PP6
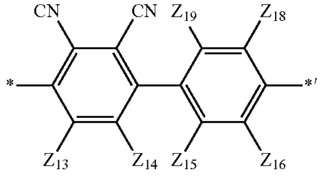
PP7
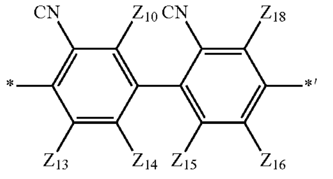
-continued
PP8
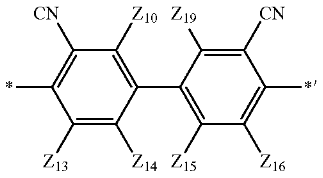
PP9
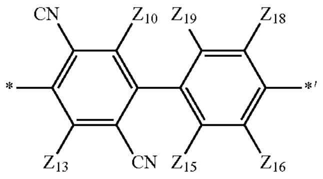
PP10
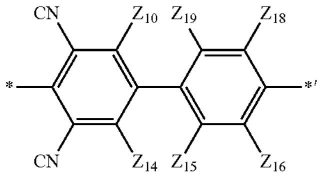
PP11
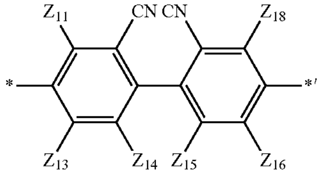
PP12
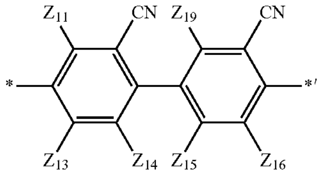
PP13
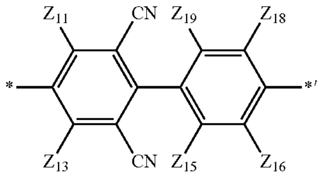
PP14
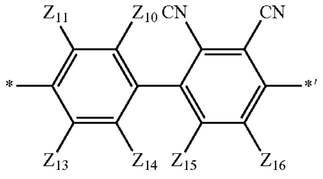
PP15
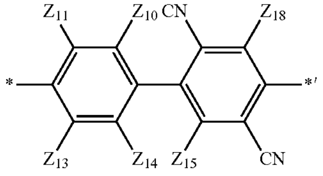

-continued
PP16
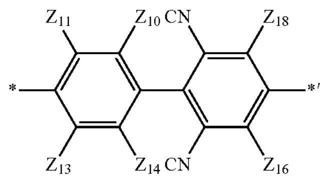
PP17
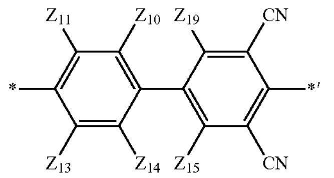
PP18
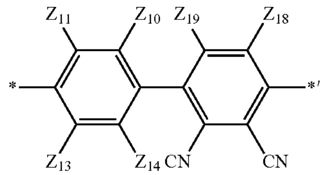
MO1
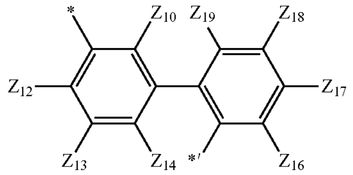
MO2
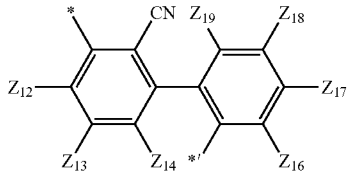
MO3
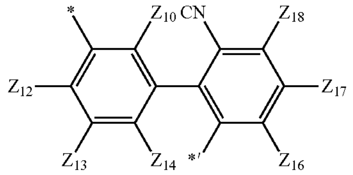
MO4
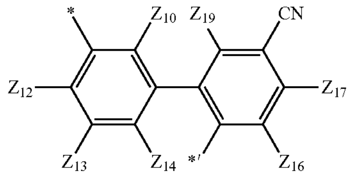
MO5
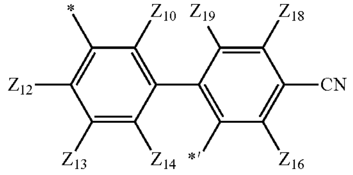
-continued
MO6
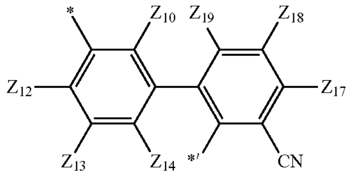
MO7
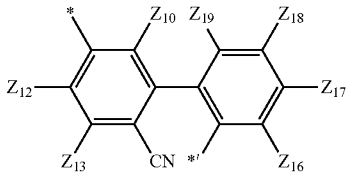
MO8
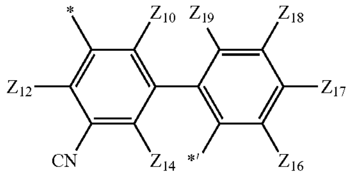
MO9
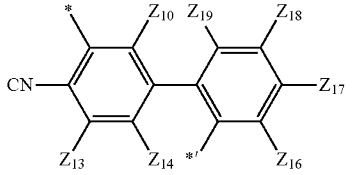
MO10
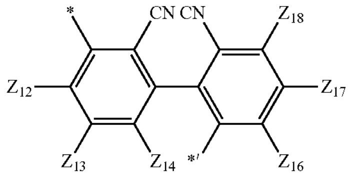
MO11
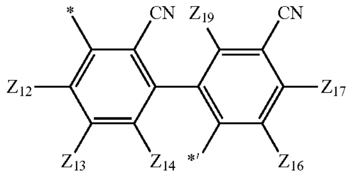
MO12
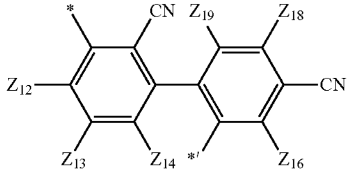
MO13
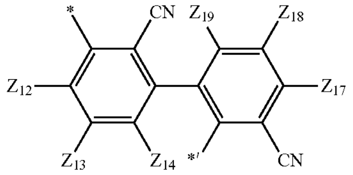

-continued
MO14
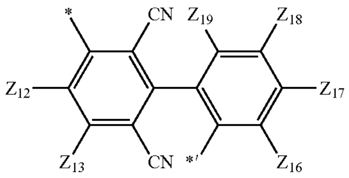
MO15
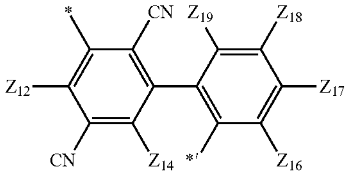
MO16
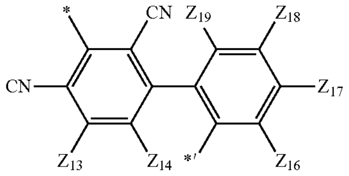
MO17
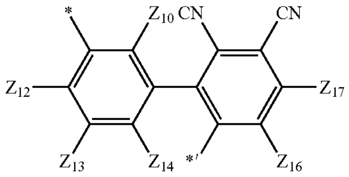
MO18
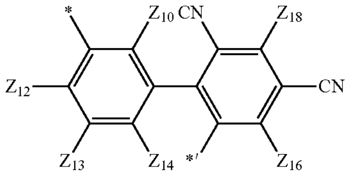
MO19
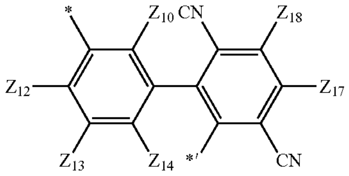
MO20
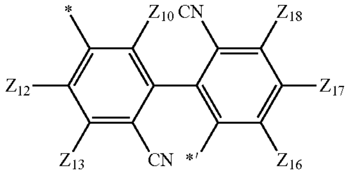
MO21
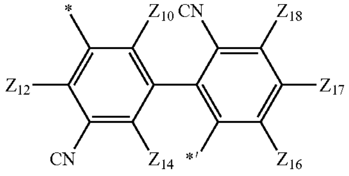
-continued
MO22
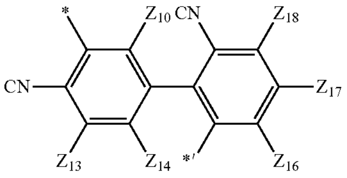
MO23
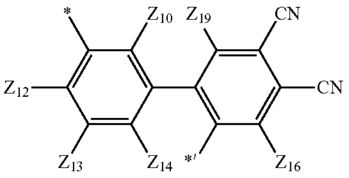
MO24
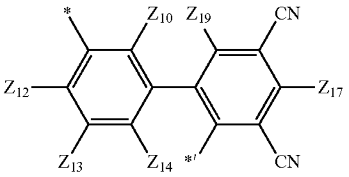
MO25
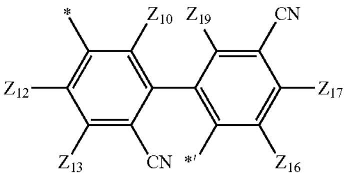
MO26
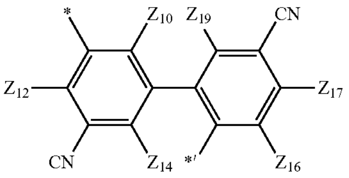
MO27
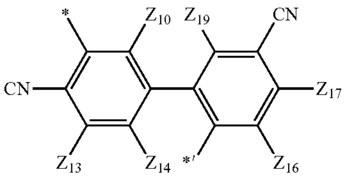
MO28
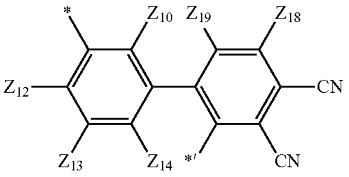
MO29
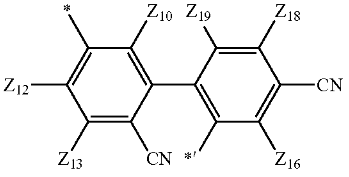

-continued
MO30
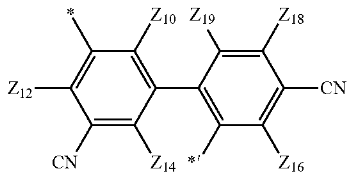
MO31
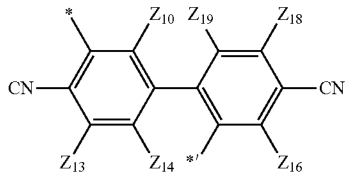
MO32
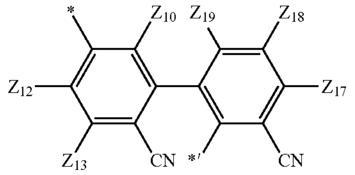
MO33
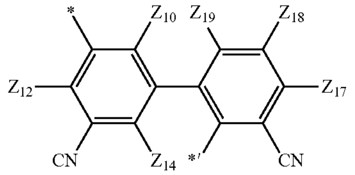
MO34
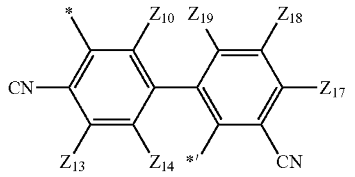
MO35
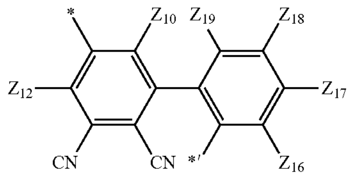
MO36
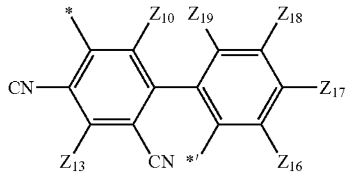
MO37
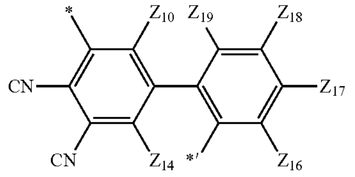
-continued
MM1
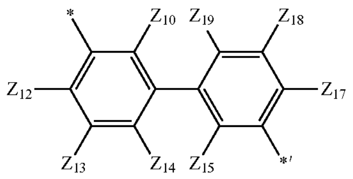
MM2
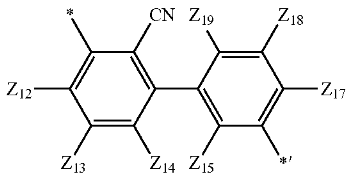
MM3
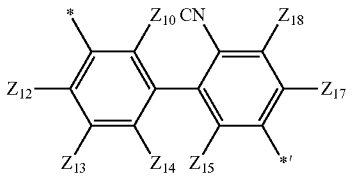
MM4
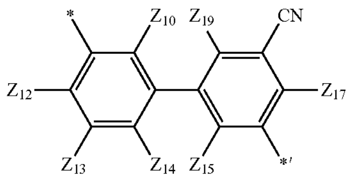
MM5
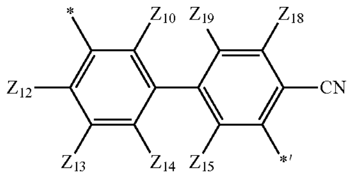
MM6
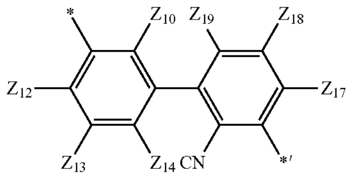
MM7
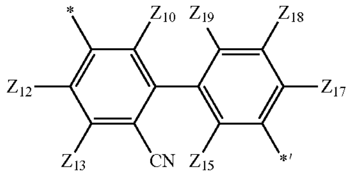
MM8
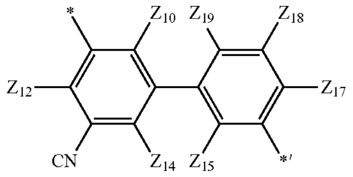

-continued
MM9
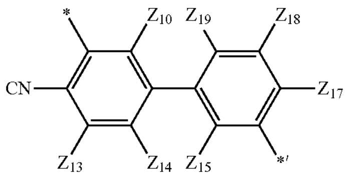
MM10
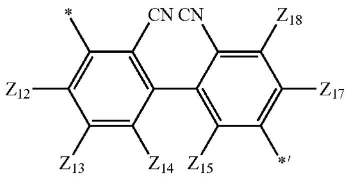
MM11
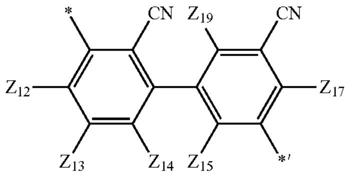
MM12
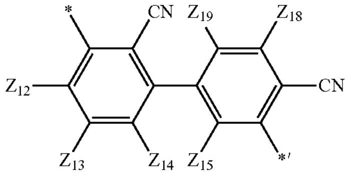
MM13
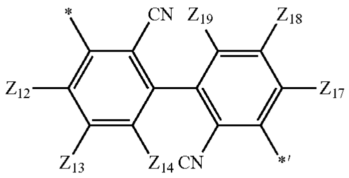
MM14
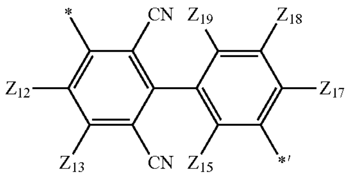
MM15
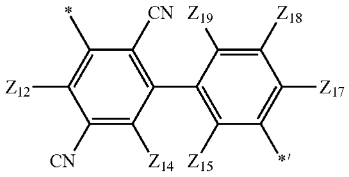
MM16
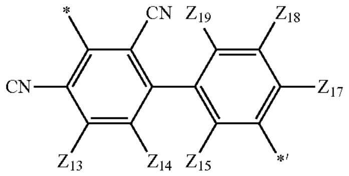
-continued
MM17
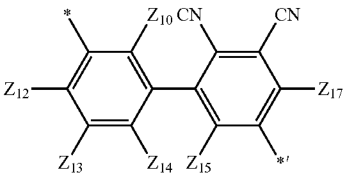
MM18
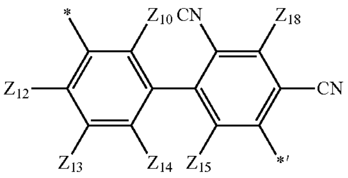
MM19
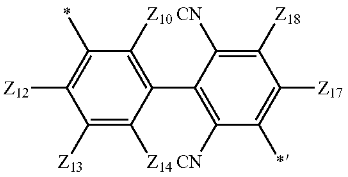
MM20
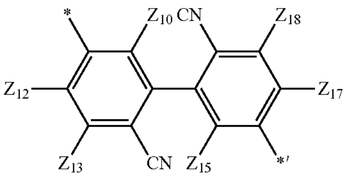
MM21
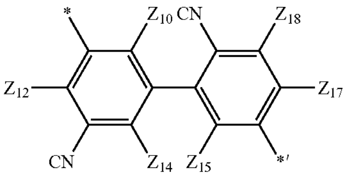
MM22
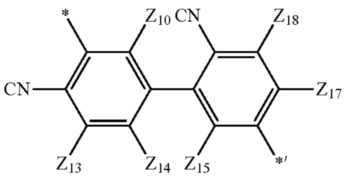
MM23
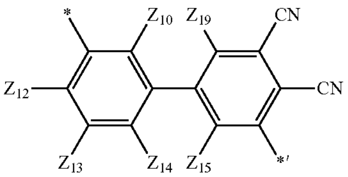
MM24
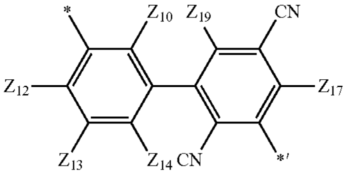

-continued
MM25
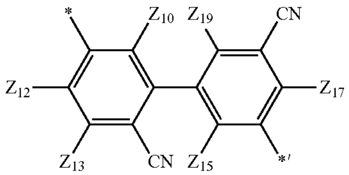
MM26
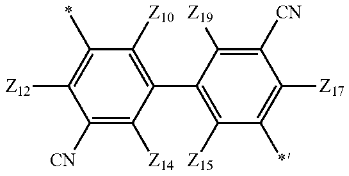
MM27
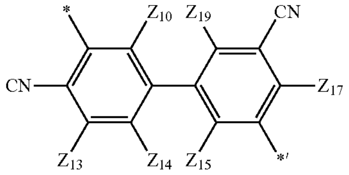
MM28
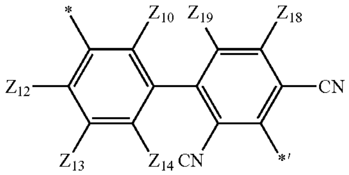
MM29
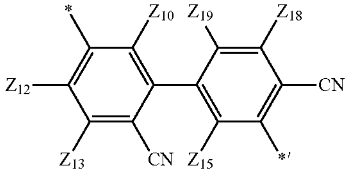
MM30
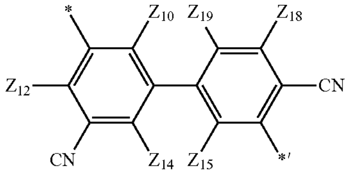
MM31
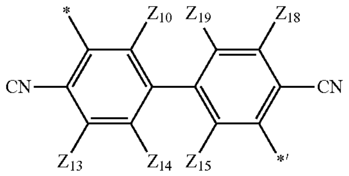
MM32
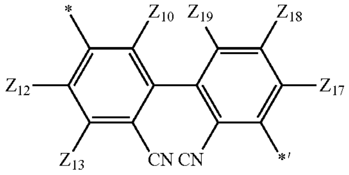
-continued
MM33
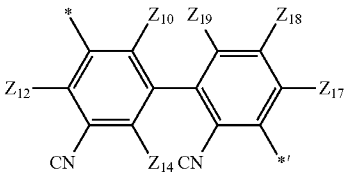
MM34
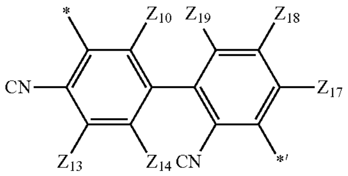
MM35
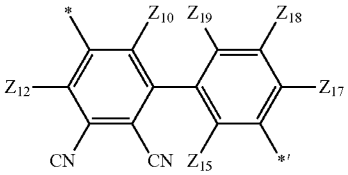
MM36
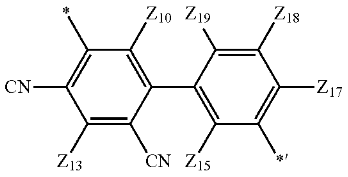
MM37
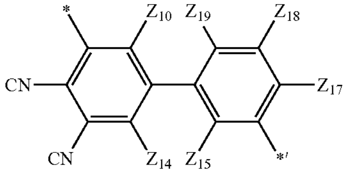
MP1
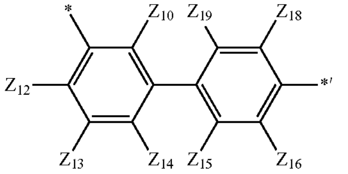
MP2
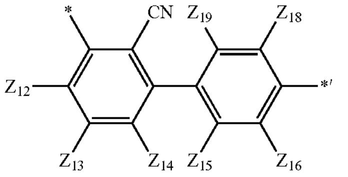
MP3
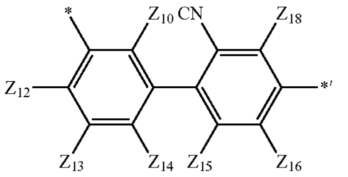

-continued
MP4
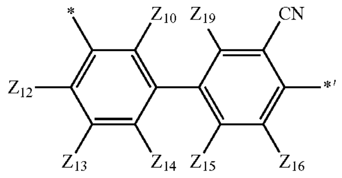
MP5
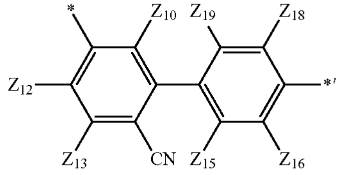
MP6
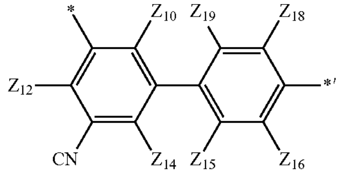
MP7
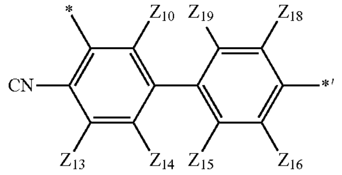
MP8
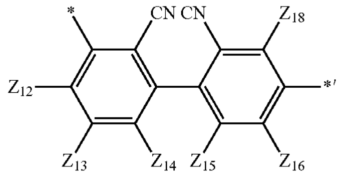
MP9
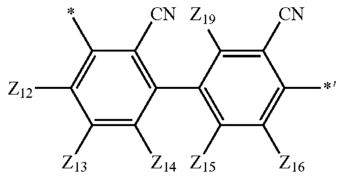
MP10
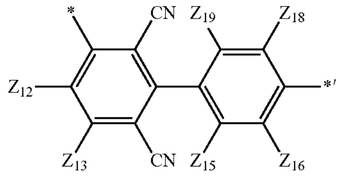
MP11
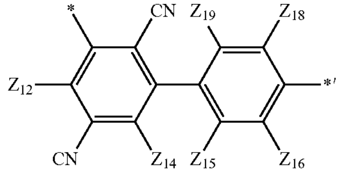
-continued
MP12
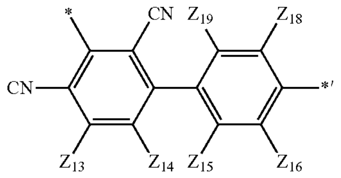
MP13
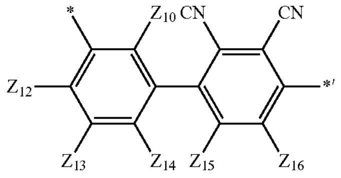
MP14
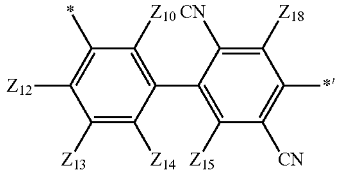
MP15
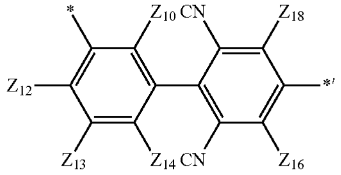
MP16
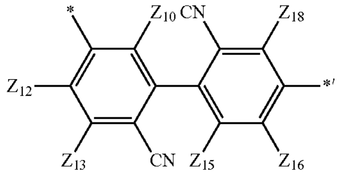
MP17
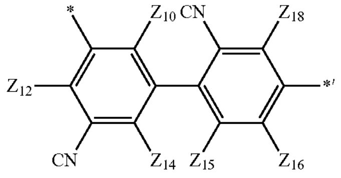
MP18
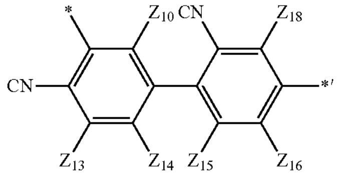
MP19
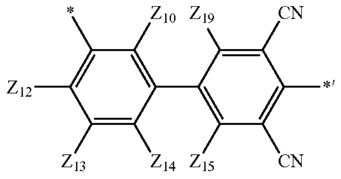

-continued
MP20
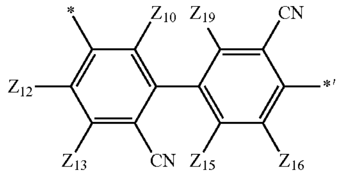
MP21
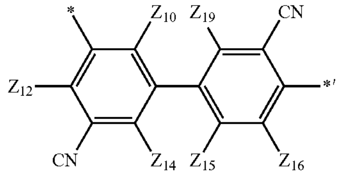
MP22
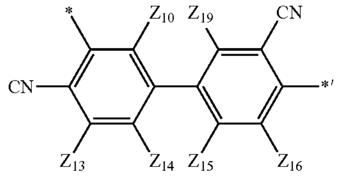
MP23
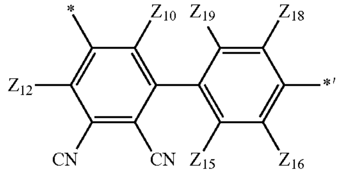
MP24
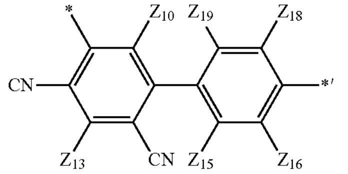
MP25
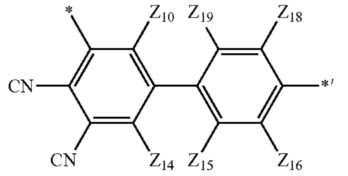
OO1
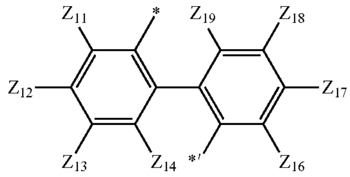
OO2
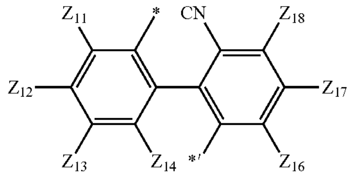
-continued
OO3
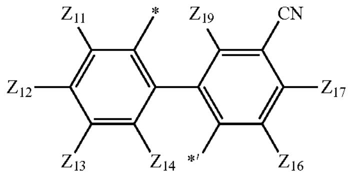
OO4
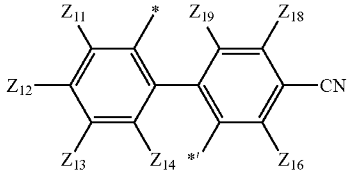
OO5
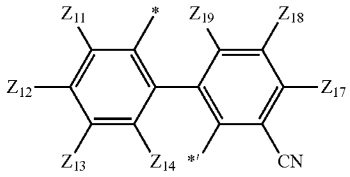
OO6
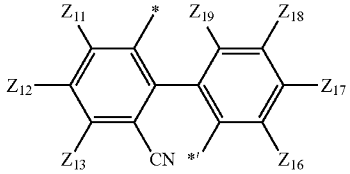
OO7
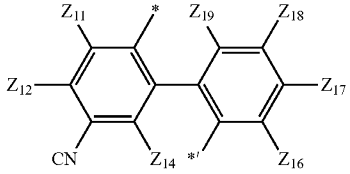
OO8
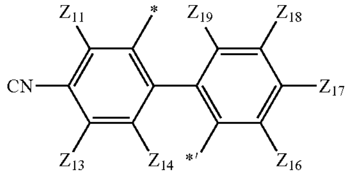
OO9
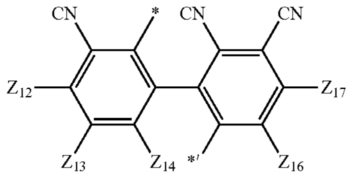
OO10
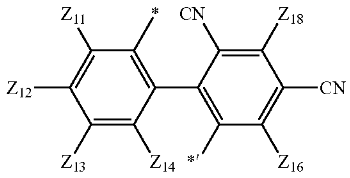

-continued
OO11
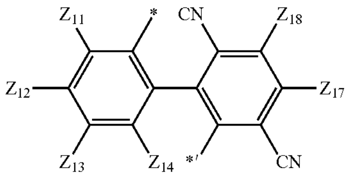
OO12
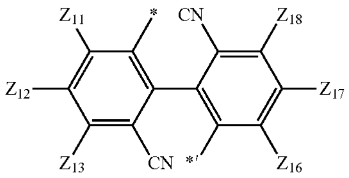
OO13
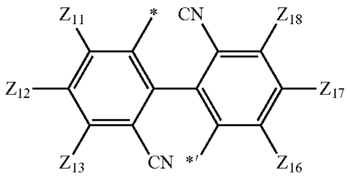
OO14
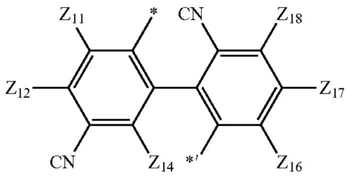
OO15
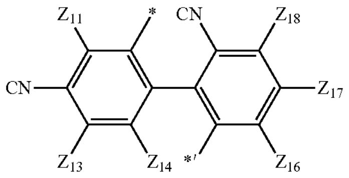
OO16
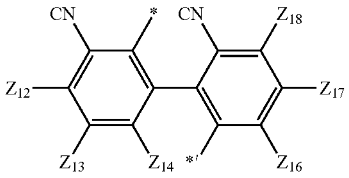
OO17
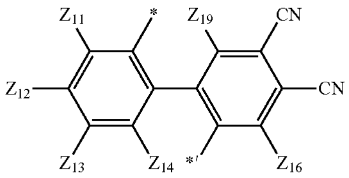
OO18
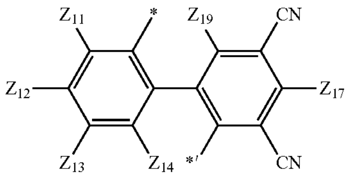
-continued
OO19
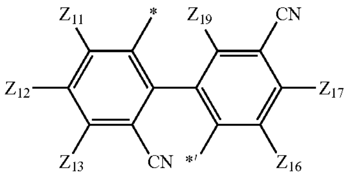
OO20
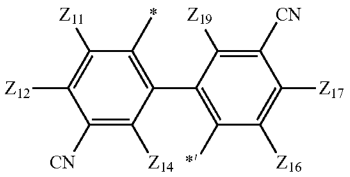
OO21
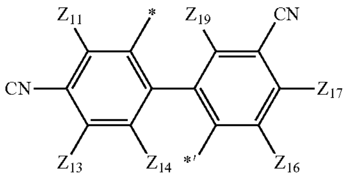
OO22
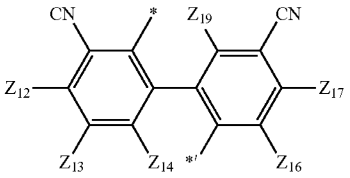
OO23
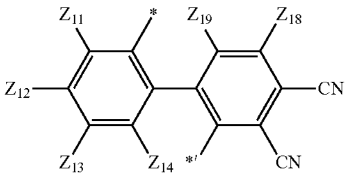
OO24
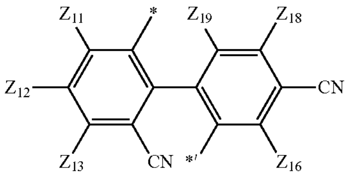
OO25
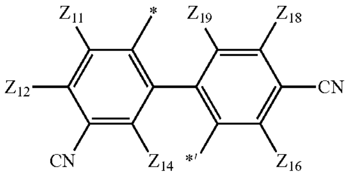
OO26
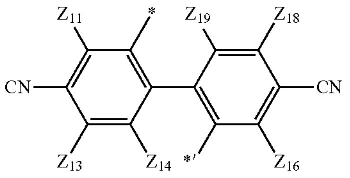

-continued
OO27
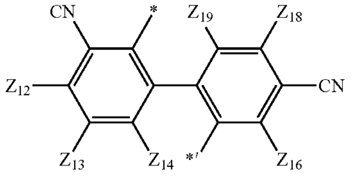
OO28
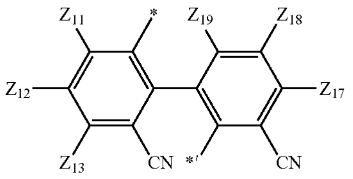
OO29
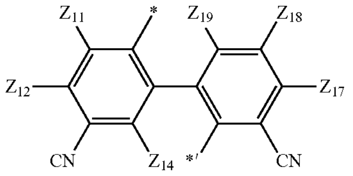
OO30
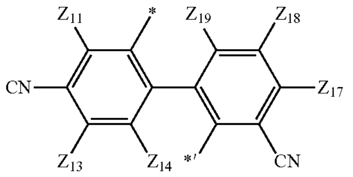
OO31
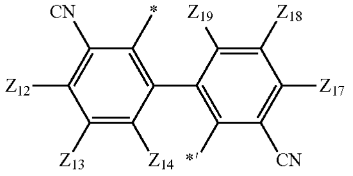
OO32
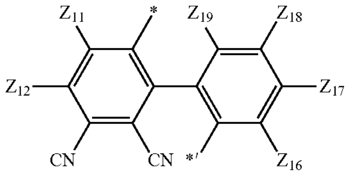
OO33
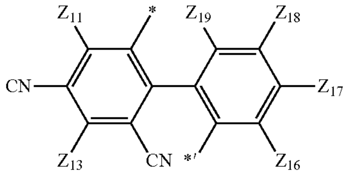
OO34
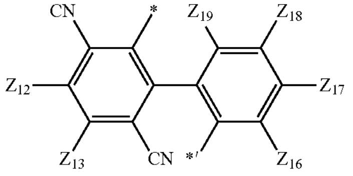
-continued
OO35
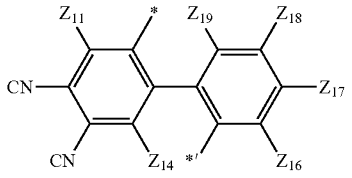
OO36
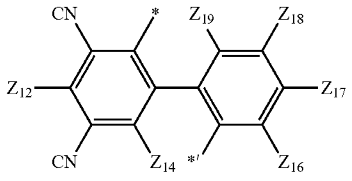
OO37
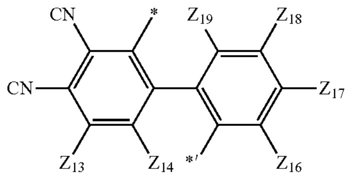
OM1
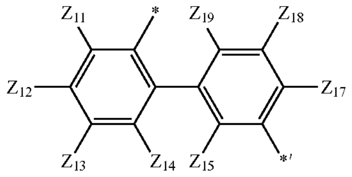
OM2
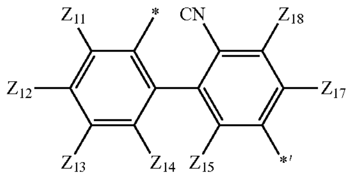
OM3
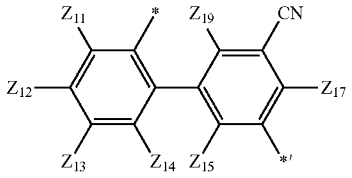
OM4
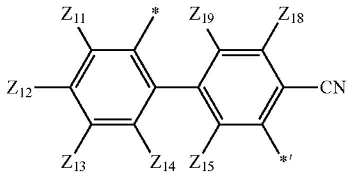
OM5
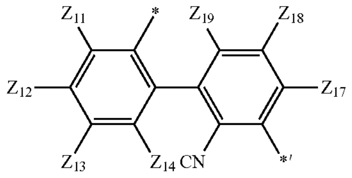

-continued
OM6
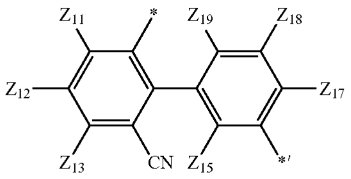
OM7
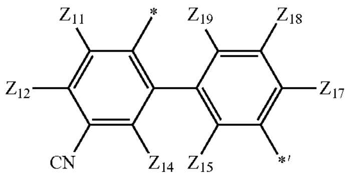
OM8
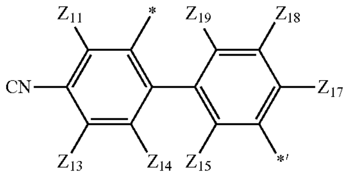
OM9
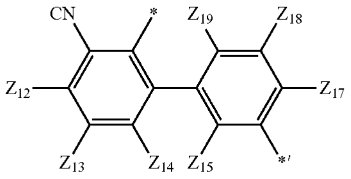
OM10
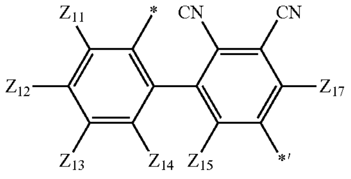
OM11
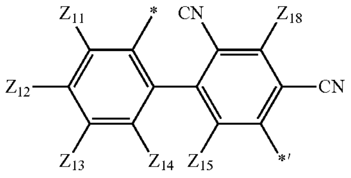
OM12
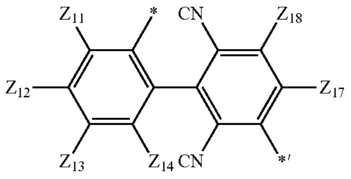
OM13
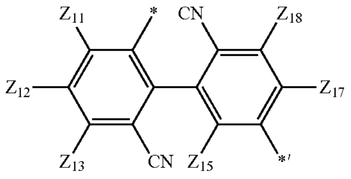
-continued
OM14
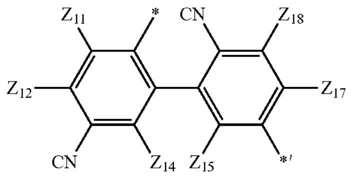
OM15
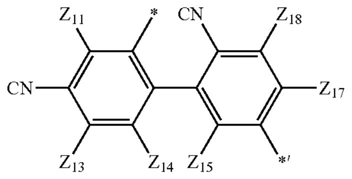
OM16
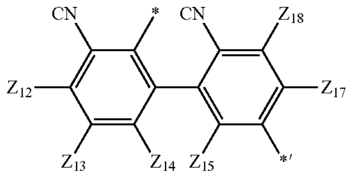
OM17
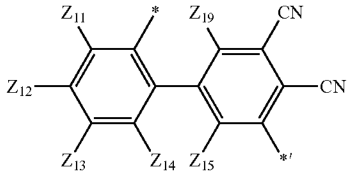
OM18
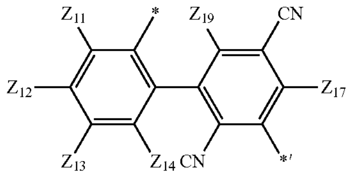
OM19
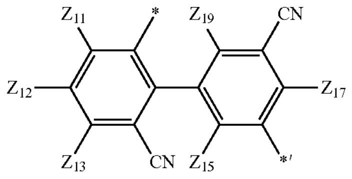
OM20
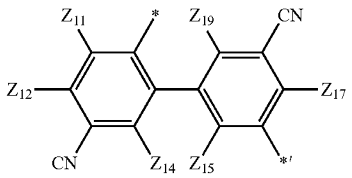
OM21
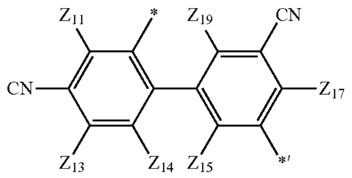

-continued
OM22
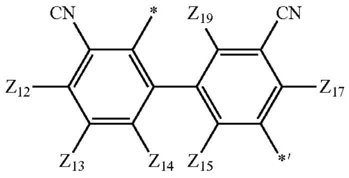
OM23
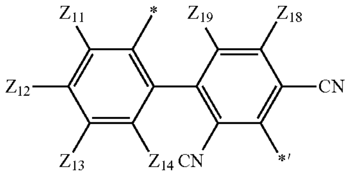
OM24
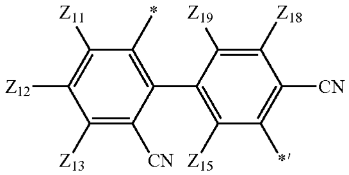
OM25
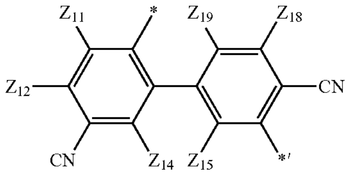
OM26
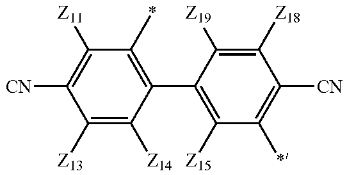
OM27
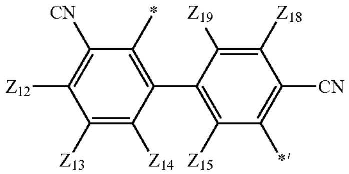
OM28
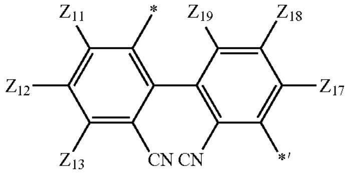
OM29
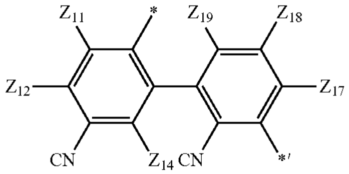
-continued
OM30
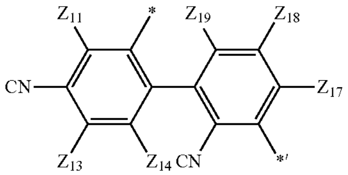
OM31
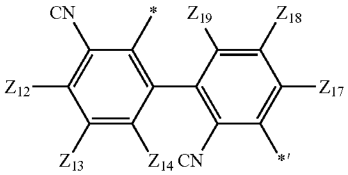
OM32
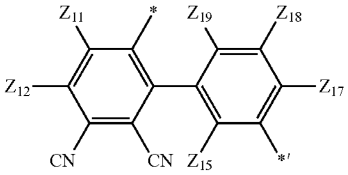
OM33
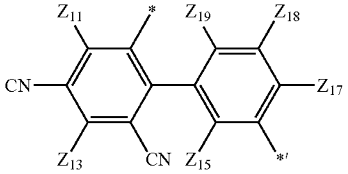
OM34
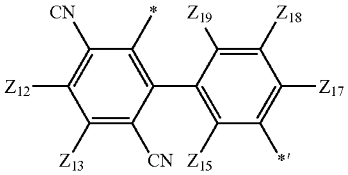
OM35
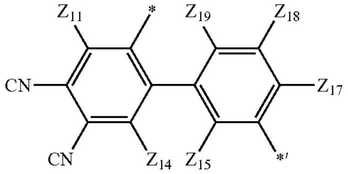
OM36
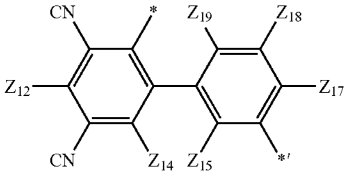
OM37
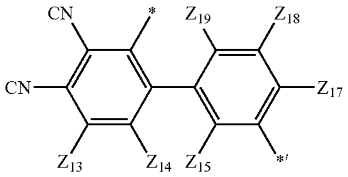

-continued
OP1
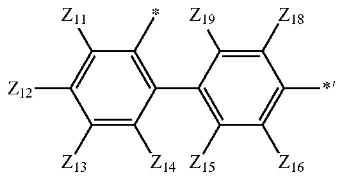
OP2
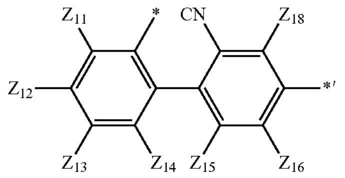
OP3
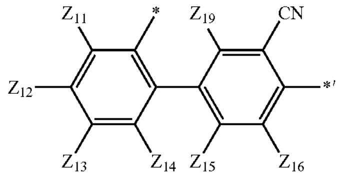
OP4
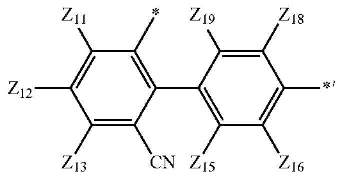
OP5
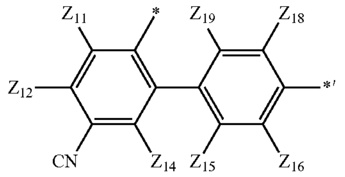
OP6
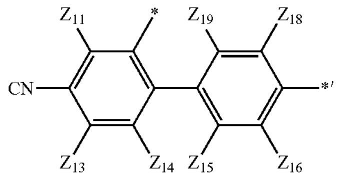
OP7
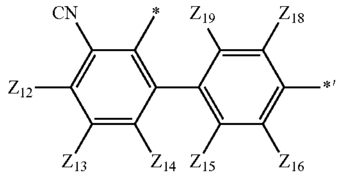
OP8
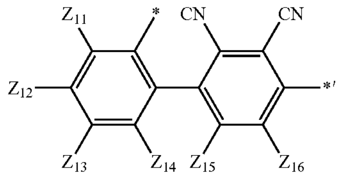
-continued
OP9
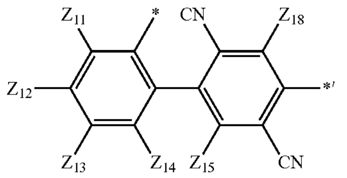
OP10
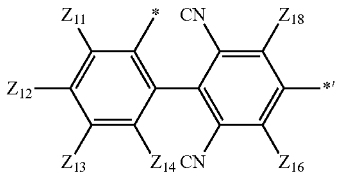
OP11
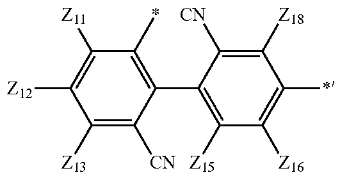
OP12
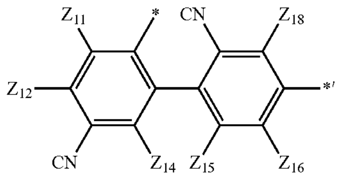
OP13
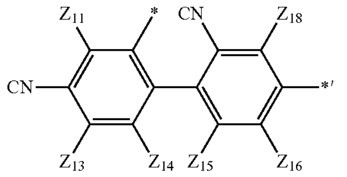
OP14
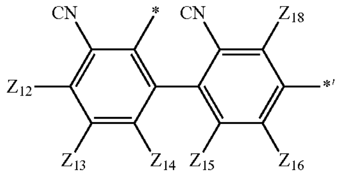
OP15
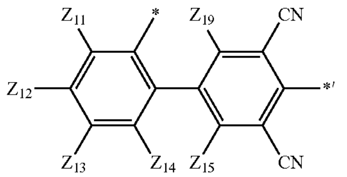
OP16
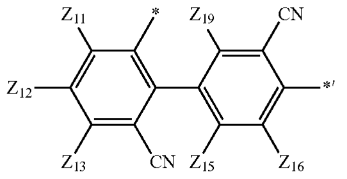

-continued
OP17
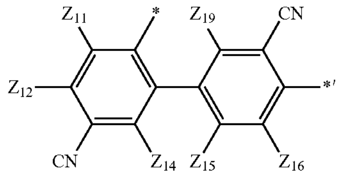
OP18
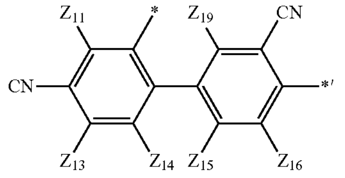
OP19
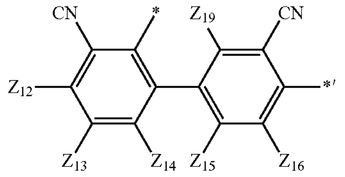
OP20
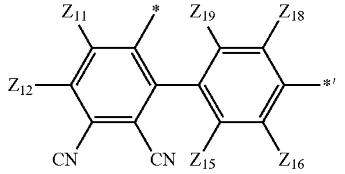
OP21
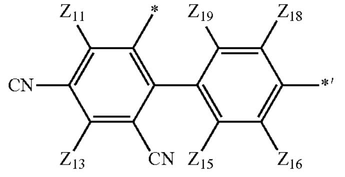
OP22
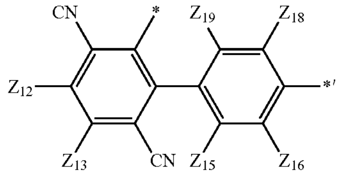
OP23
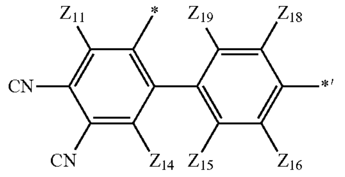
OP24
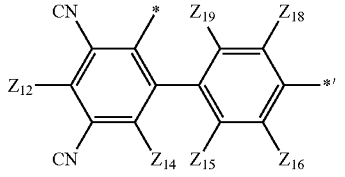
-continued
OP25
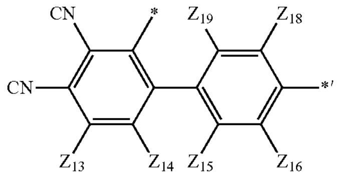
O1
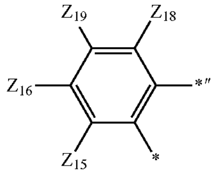
O2
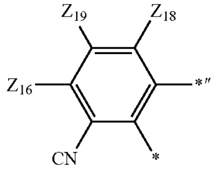
O3
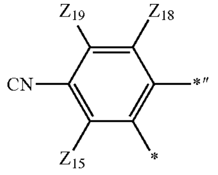
O4
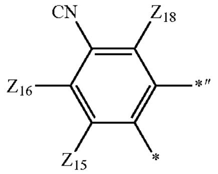
O5
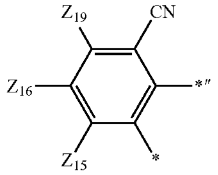
O6
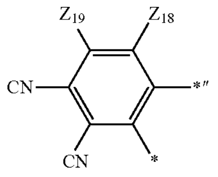
O7
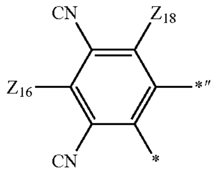

-continued
O8
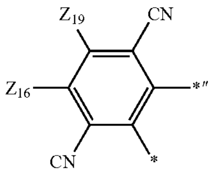
O9
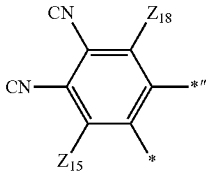
O11
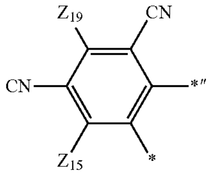
O11
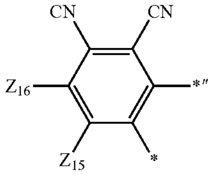
O12
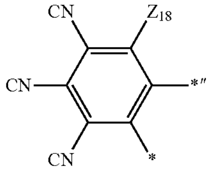
O13
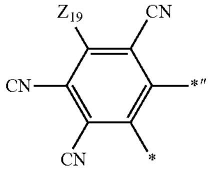
O14
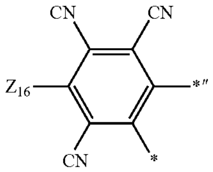
O15
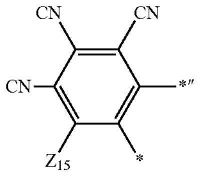
-continued
O16
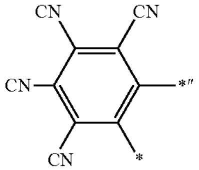
M1
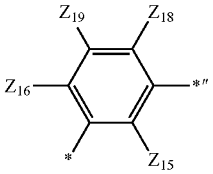
M2
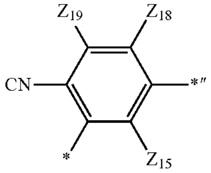
M3
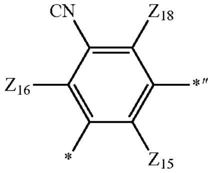
M4
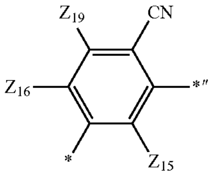
M5
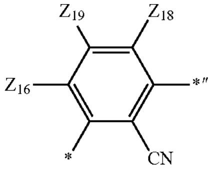
M6
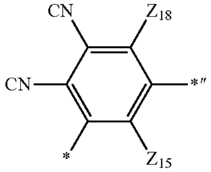
M7
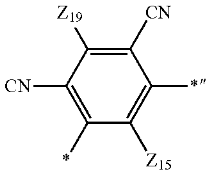

-continued
M8
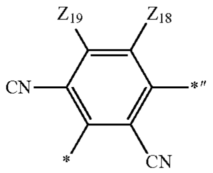
M9
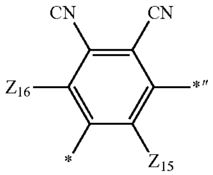
M10
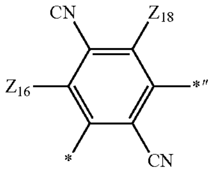
M11
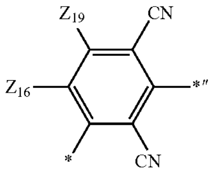
M12
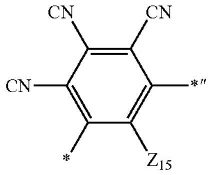
M13
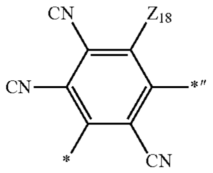
M14
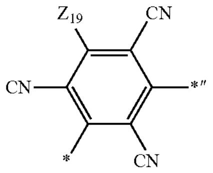
M15
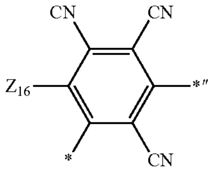
M16
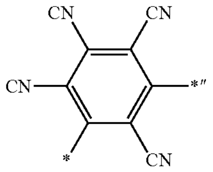
-continued
P1
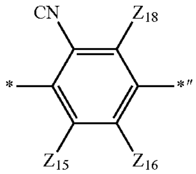
P2
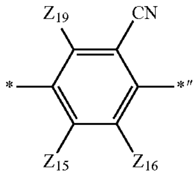
P3
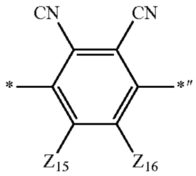
P4
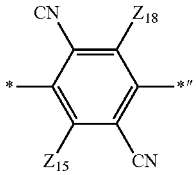
P5
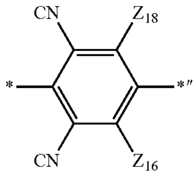
P6
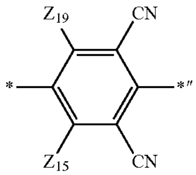
P7
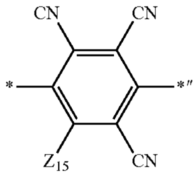
P8
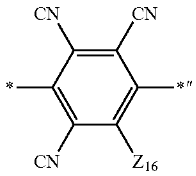

-continued

P9

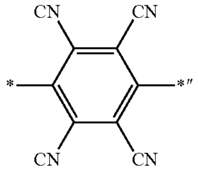

In Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9, $Z_{10}$ to $Z_{10}$ may each independently be the same as described in connection with $Z_3$ and $Z_4$, and * and * each indicate a binding site to a neighboring atom.

In an embodiment, in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16 and P1 to P9, $Z_{10}$ to $Z_{19}$ may not be a cyano group.

In one or more embodiments, in Formulae PO1 to PO25, PM1 to PM25, PP1 to PP18, MO1 to MO37, MM1 to MM37, MP1 to MP25, OO1 to OO37, OM1 to OM37, OP1 to OP25, O1 to O16, M1 to M16, and P1 to P9, $Z_{10}$ to $Z_{19}$ may each independently be selected from:

hydrogen, deuterium, or a cyano group; or a $C_1$-$C_{20}$ alkyl group, a phenyl group, a biphenyl group, a terphenyl group, a dibenzofuranyl group, or a dibenzothiophenyl group, each unsubstituted or substituted with at least one selected from deuterium, a cyano group, a $C_1$-$C_{20}$ alkyl group, a phenyl group, and a biphenyl group.

In an embodiment, the second material may include at least one compound selected from Compounds E1 to E8, but embodiments of the present disclosure are not limited thereto:

E1

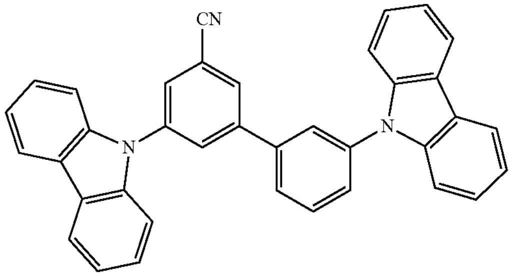

E2

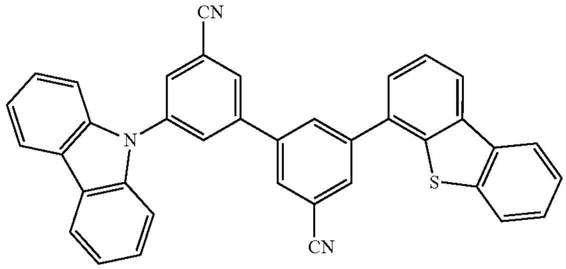

-continued

E3

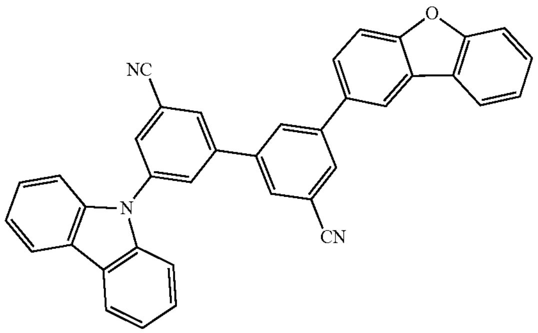

E4

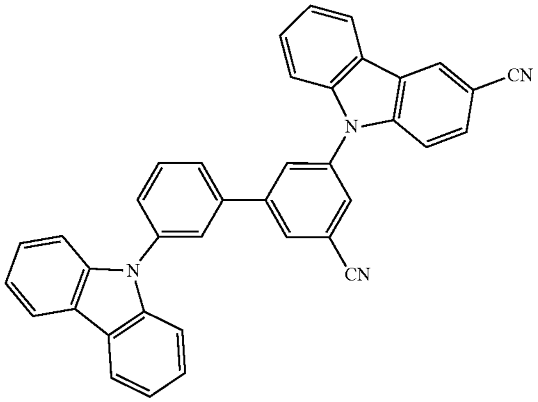

E5

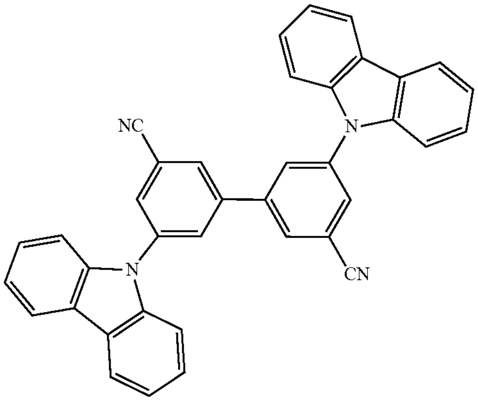

E6

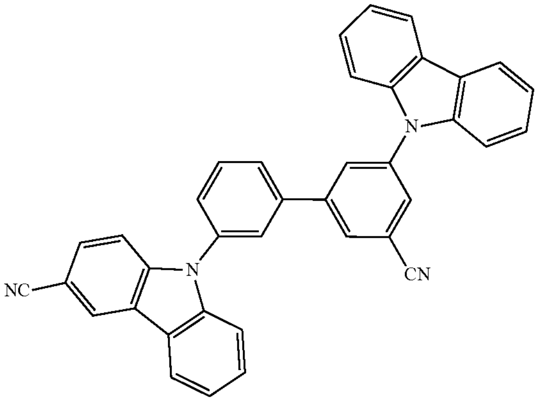

-continued

E7

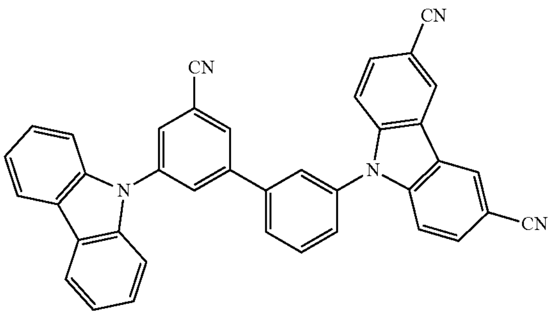

E8

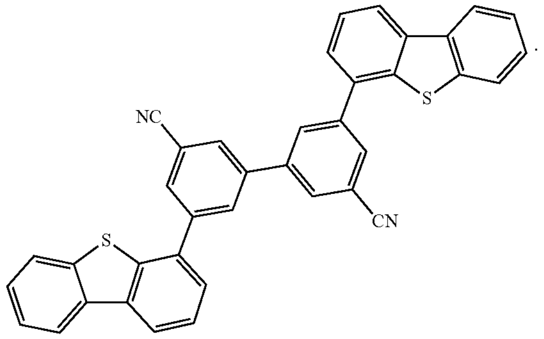

A difference between a triplet energy level (eV) of the host and a triplet energy level (eV) of the heterocyclic compound represented by Formula 1 may be in a range of about 0.2 eV to about 0.5 eV. While not wishing to be bound by theory, it is understood that when the difference between the triplet energy level (eV) of the host and the triplet energy level (eV) of the heterocyclic compound represented by Formula 1 is within this range, it is possible to prevent energy of the triplet exciton generated in the heterocyclic compound represented by Formula 1 from leaking toward the host in the emission layer, thereby implementing efficient light emission. An activated excitation energy level of the host is suppressed, thereby implementing long lifespan driving of the organic light-emitting device.

The triplet energy level is evaluated by using a DFT method (for example, a DFT method of Gaussian program) structurally optimized at a level of B3LYP/6-31G(d,p).

In the first embodiment, an amount of the heterocyclic compound represented by Formula 1 in the emission layer may be in a range of about 0.01 parts by weight to about 30 parts by weight based on 100 pars by weight of the host, but embodiments of the present disclosure are not limited thereto. While not wishing to be bound by theory, it is understood that when the amount of the heterocyclic compound represented by Formula 1 is within this range, a high-quality organic light-emitting device may be implemented without concentration quenching.

The FIGURE a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be disposed on the first electrode 11 by using one or more suitable methods selected from vacuum deposition, spin coating, casting, or Langmuir-Blodgett (LB) deposition.

When the hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, 13-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202:

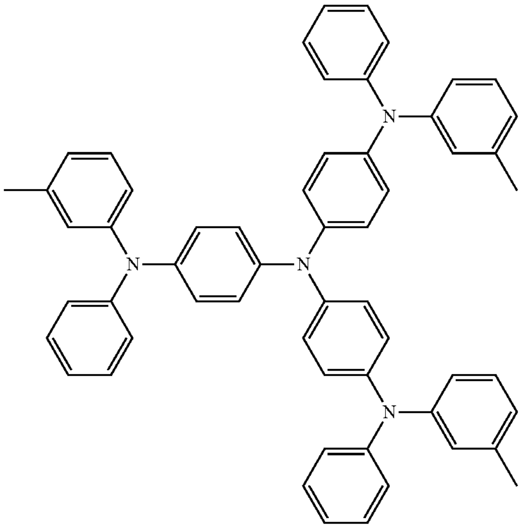

m-MTDATA

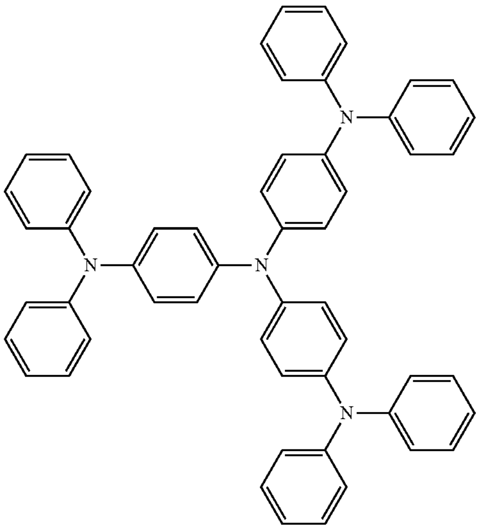

TDATA

-continued

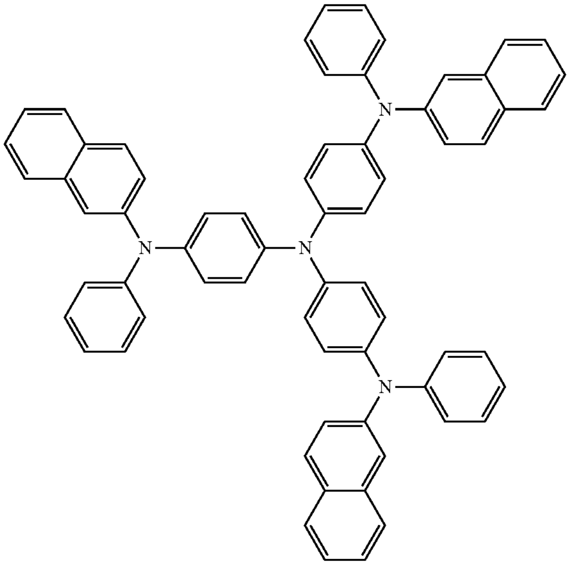

2-TNATA

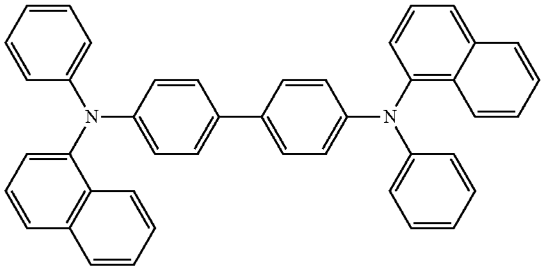

NPB

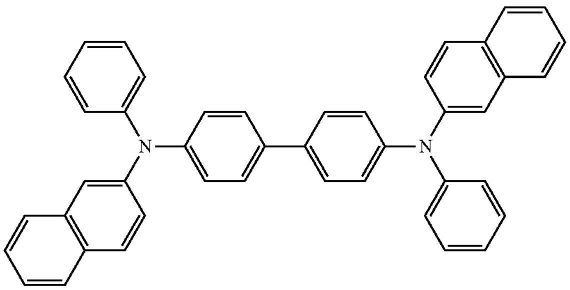

β-NPB

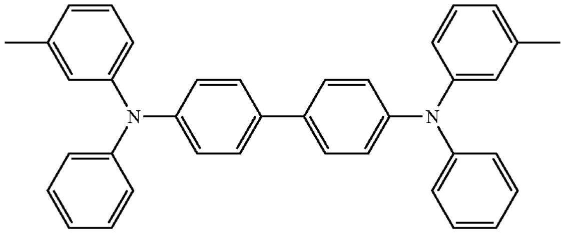

TPD

-continued

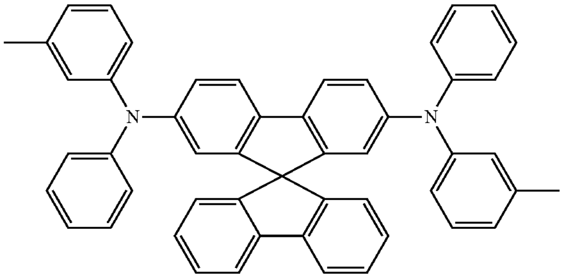

Spiro-TPD

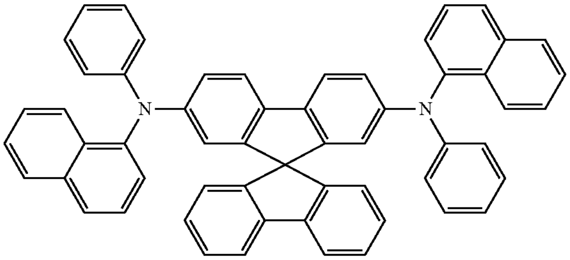

Spiro-NPB

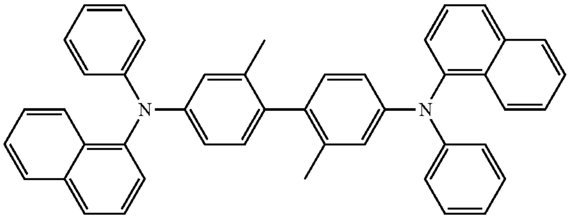

methylated NPB

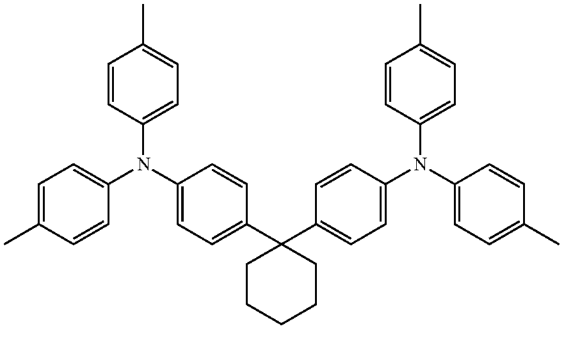

TAPC

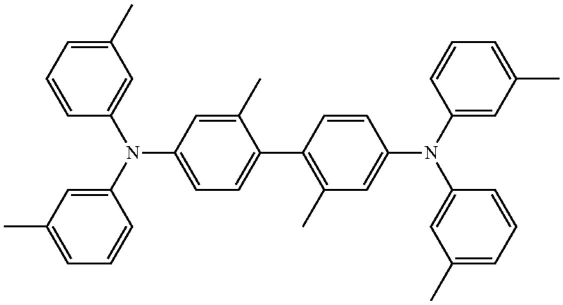

HMTPD

-continued

Formula 201

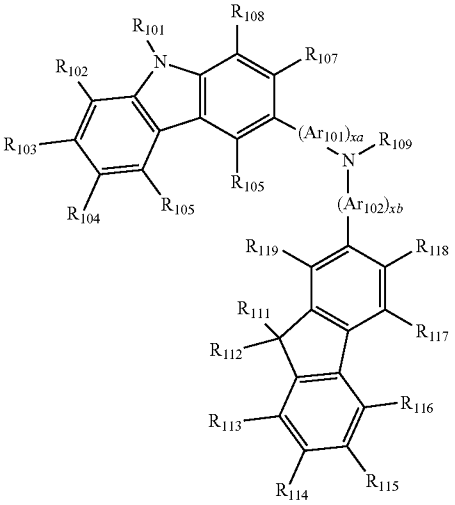

Formula 202

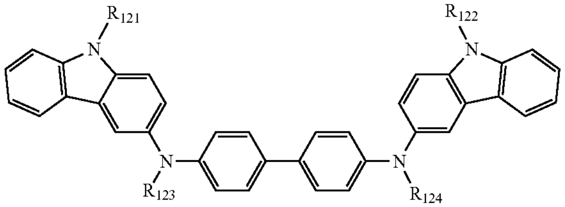

$Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_5$-$C_{60}$ aryl group, a $C_5$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

In Formula 201, xa and xb may each independently be an integer from 0 to 5, or may be 0, 1, or 2. For example, xa may be 1 and xb may be 0, but embodiments of the present disclosure are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments of the present disclosure are not limited thereto:

Formula 201A

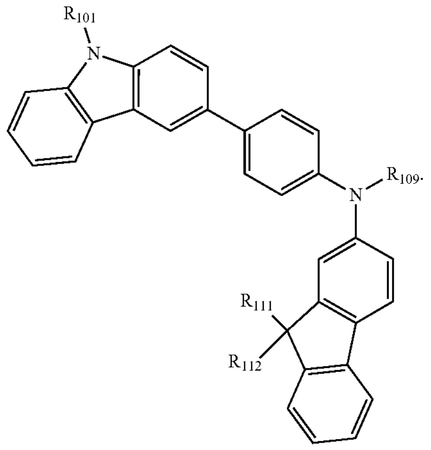

$R_{101}$, $R_{111}$, $R_{112}$, and $R_{109}$ in Formula 201A are the same as described above.

For example, the compound represented by Formula 201, and the compound represented by Formula 202 may include Compounds HT1 to HT20, but embodiments of the present disclosure are not limited thereto:

HT1

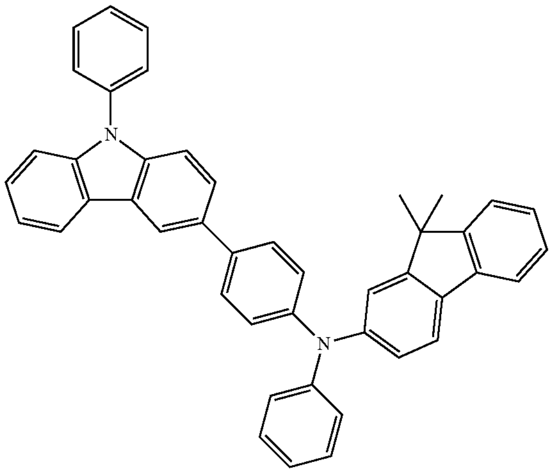

-continued
HT2
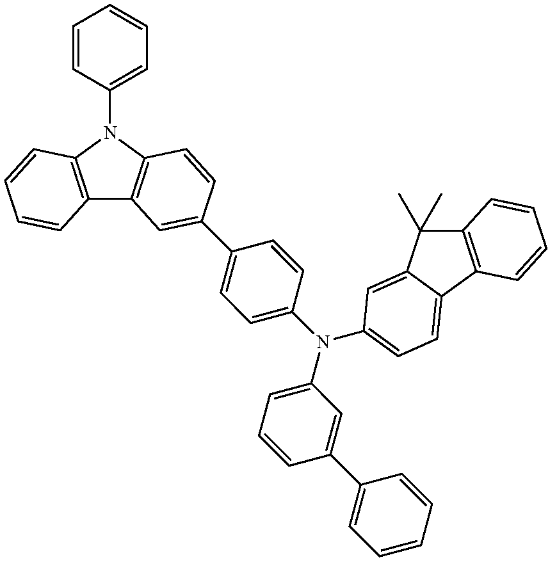
HT3
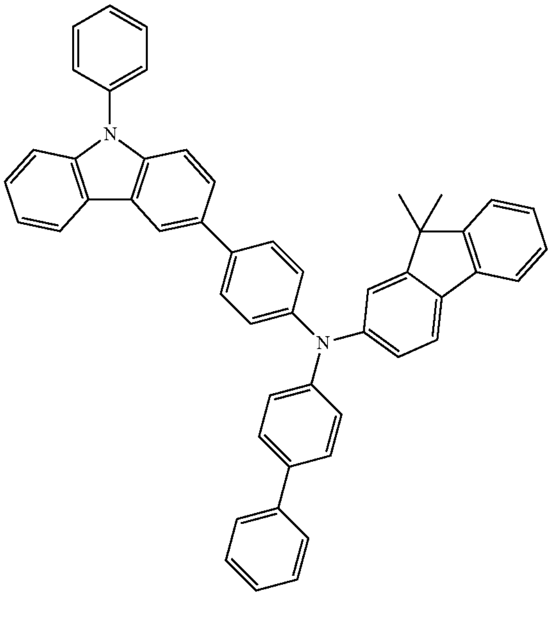
-continued
HT4
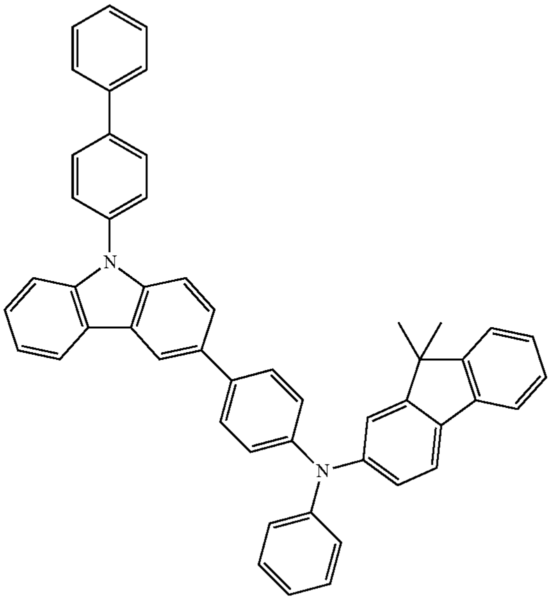
HT5
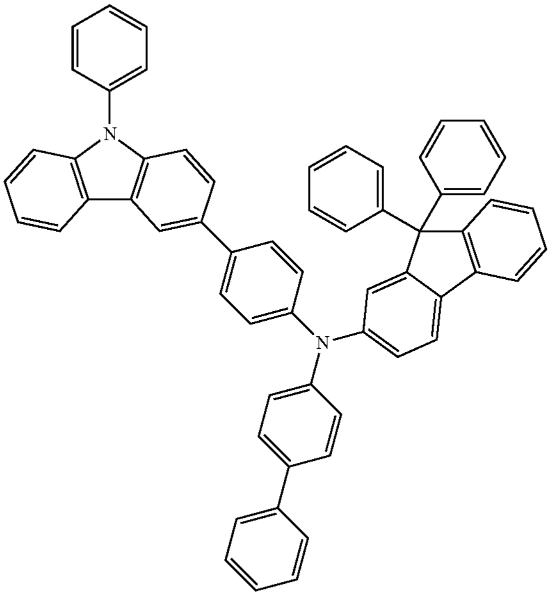

-continued
HT6
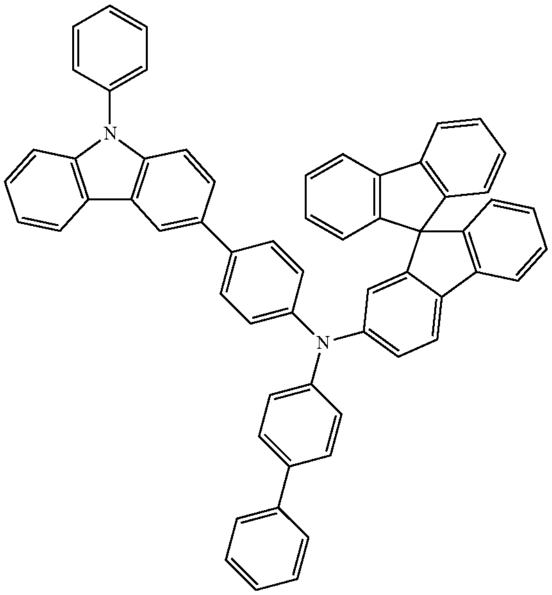
HT7
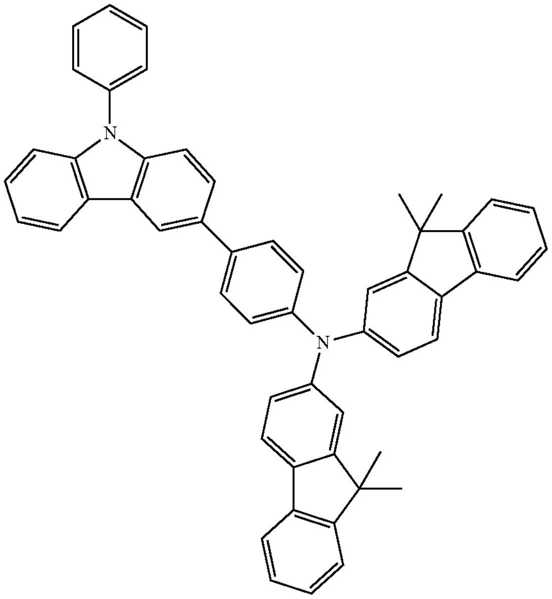
-continued
HT8
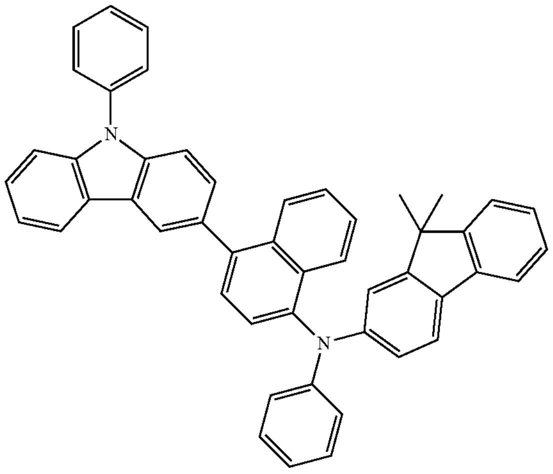
HT9
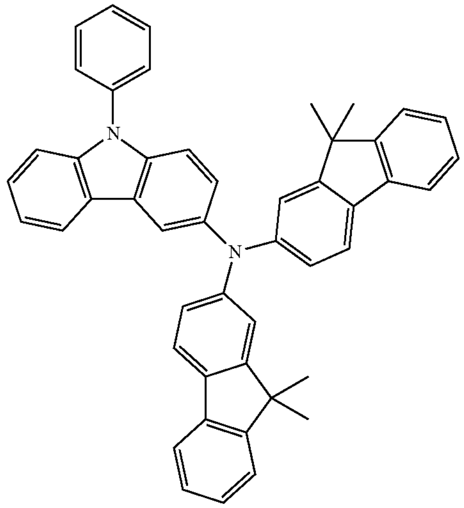
HT10
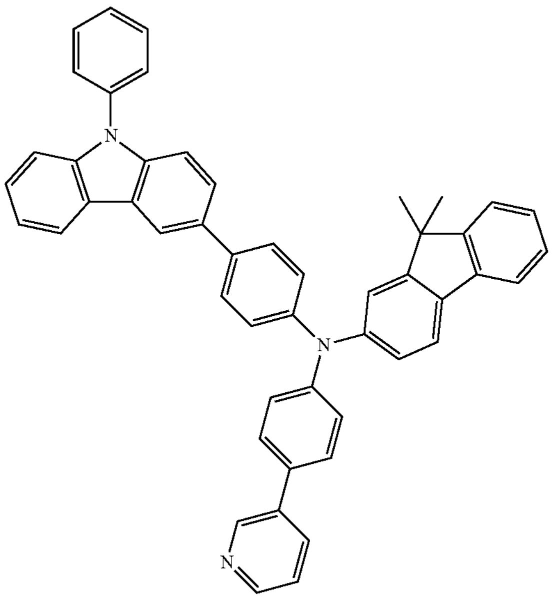

-continued
HT11
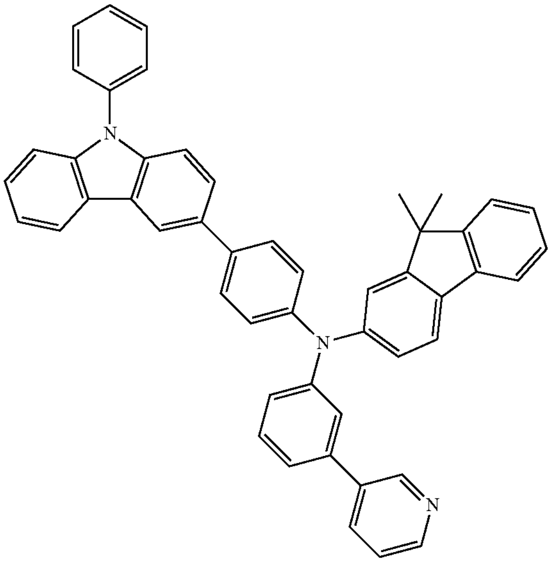
HT12
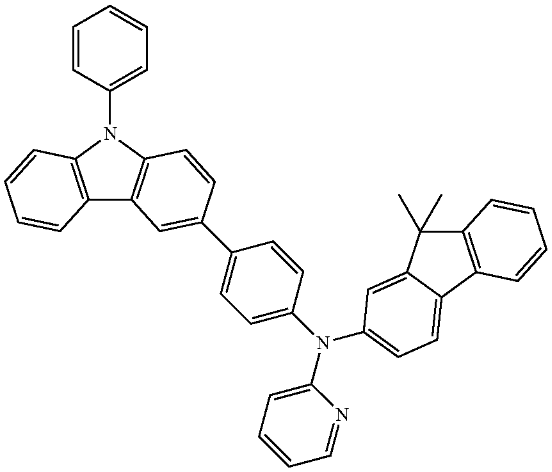
HT13
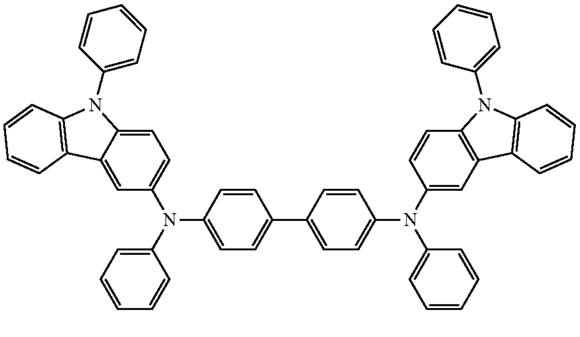
-continued
HT14
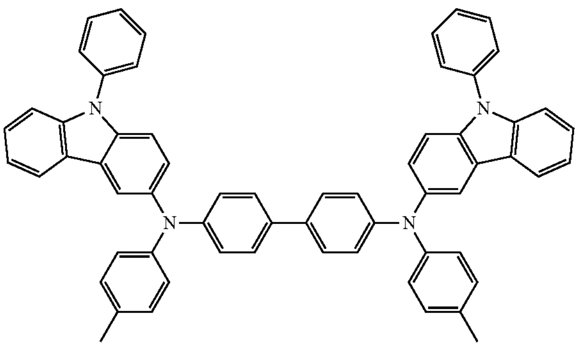
HT15
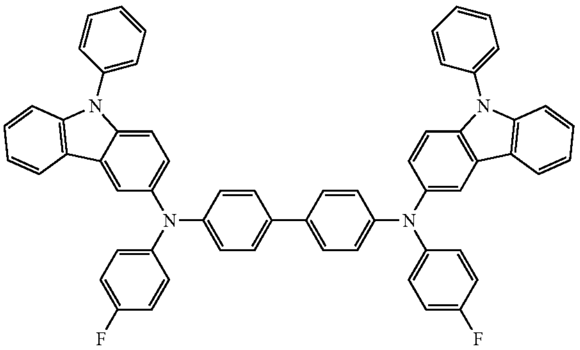
HT16
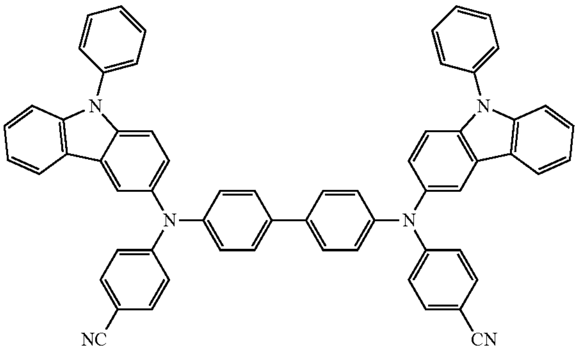
HT17
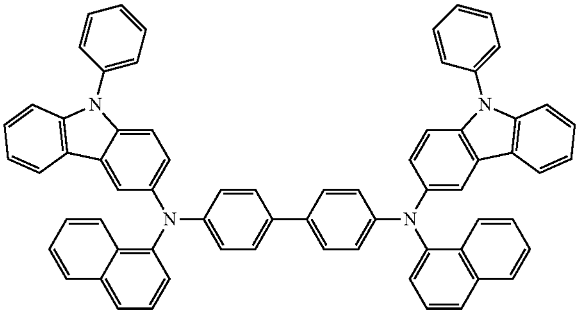

-continued

HT18

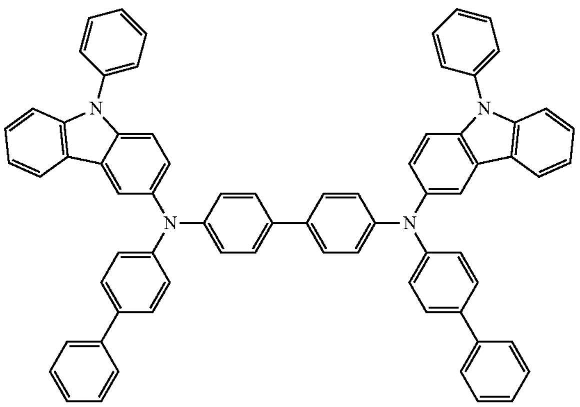

HT19

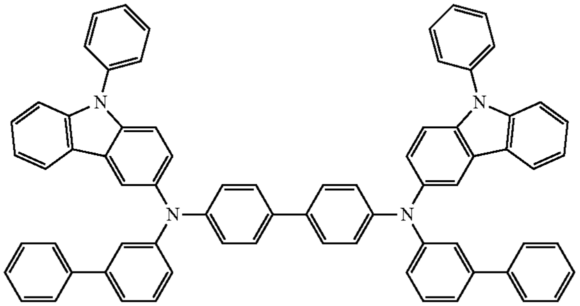

HT20

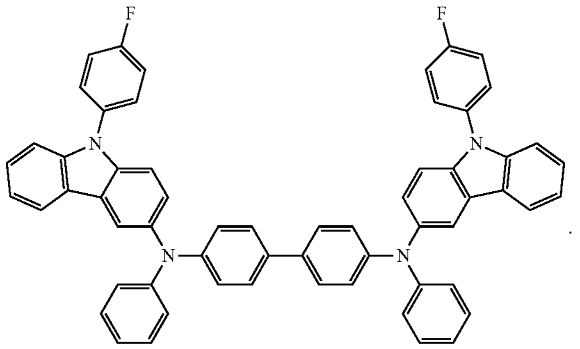

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

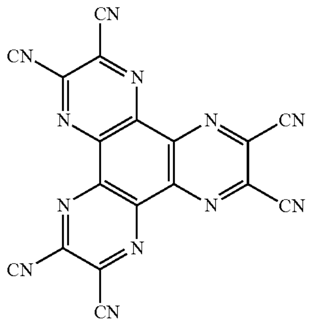

HT-D1

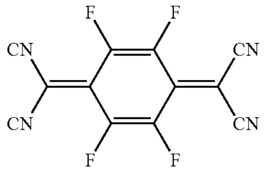

F4-TCNQ

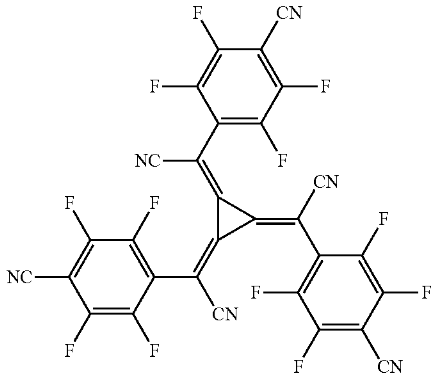

HT-D2

The hole transport region may include a buffer layer.

Also, the buffer layer may compensate for an optical resonance distance according to a wavelength of light emitted from the emission layer, and thus, efficiency of a formed organic light-emitting device may be improved.

The hole transport region may further include an electron blocking layer. The electron blocking layer may include, for example, mCP, but embodiments of the present disclosure are not limited thereto:

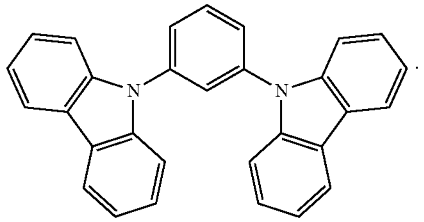

mCP

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer may include a host and a thermally activated delayed fluorescent dopant, and the host and the fluorescent dopant may be the same as described above.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and BPhen, but may also include other materials:

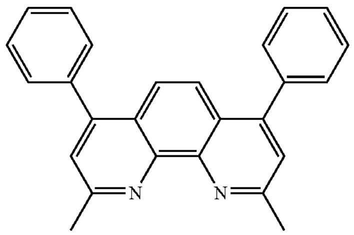

BCP

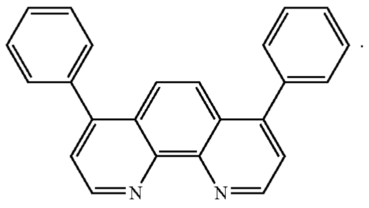

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may include at least one selected from BCP, BPhen, $Alq_3$, BAlq, TAZ, and NTAZ:

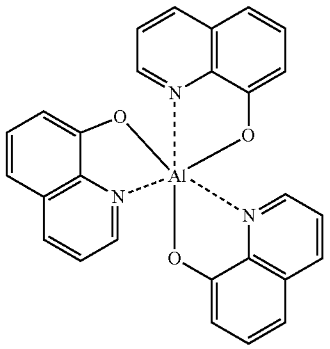

$Alq_3$

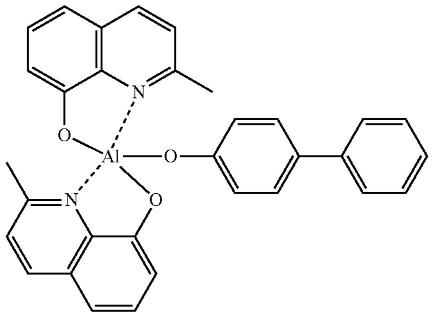

BAlq

-continued
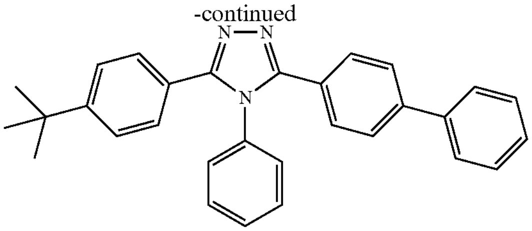
TAZ
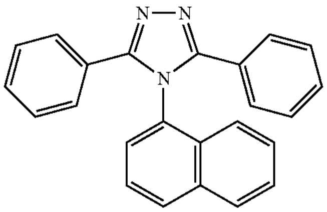
NTAZ
In one or more embodiments, the electron transport layer may include at least one of Compounds ET1 to ET25, but are not limited thereto:
ET1
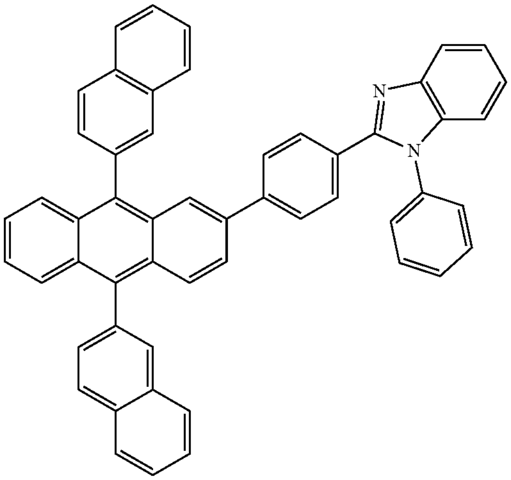
ET2
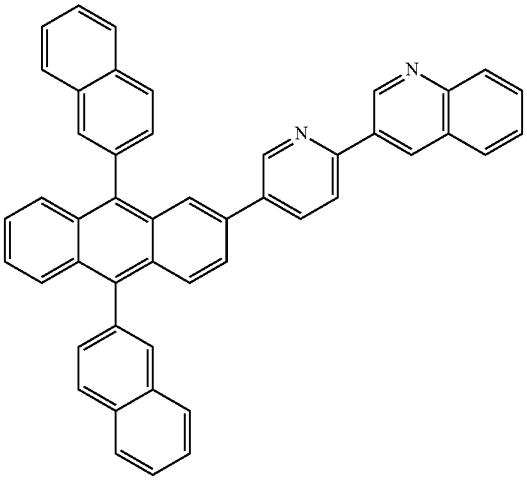
-continued
ET3
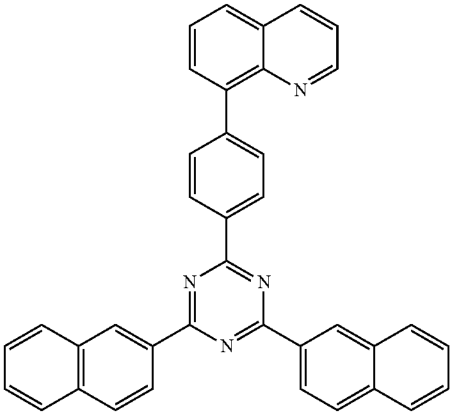
ET4
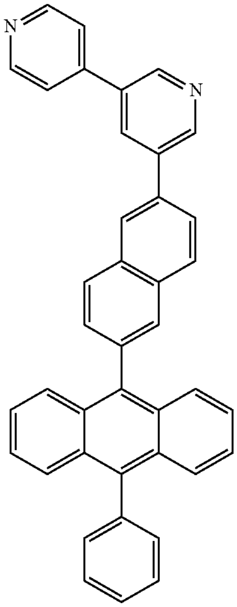
ET5
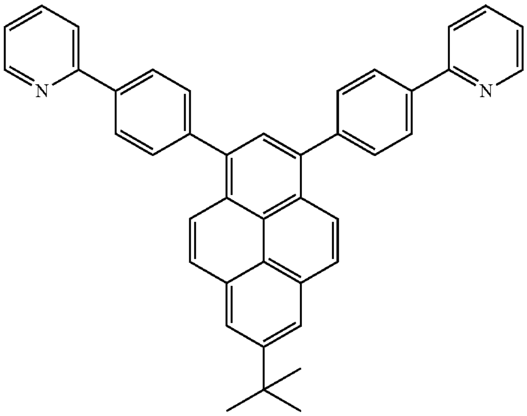

-continued
ET6
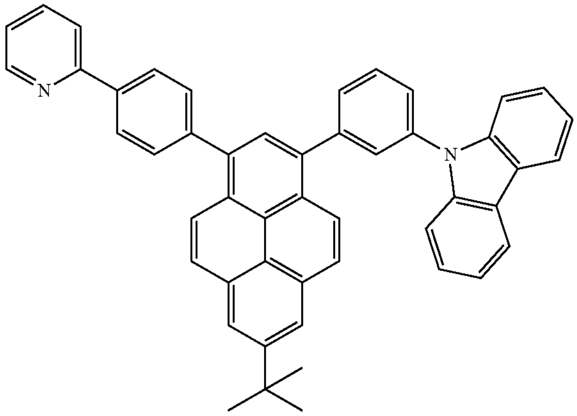
ET7
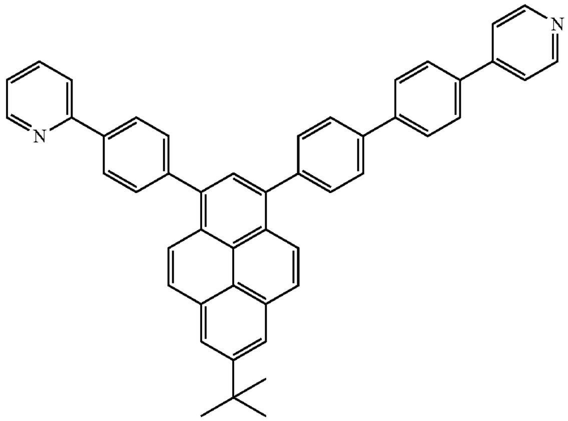
ET8
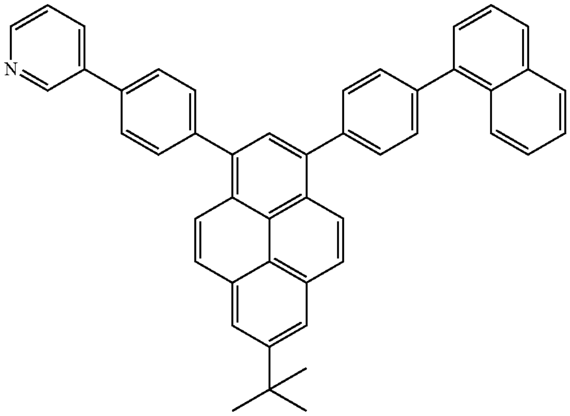
-continued
ET9
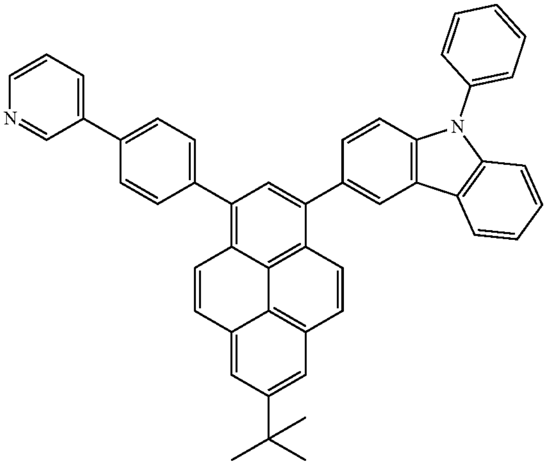
ET10
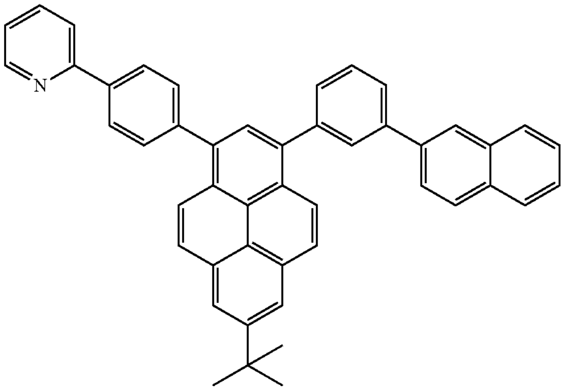
ET11
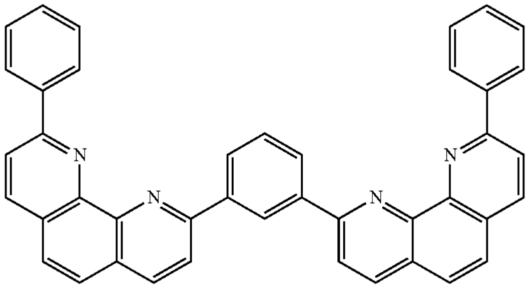
ET12
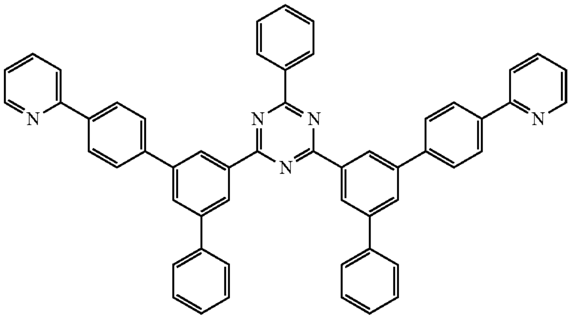

-continued
ET13
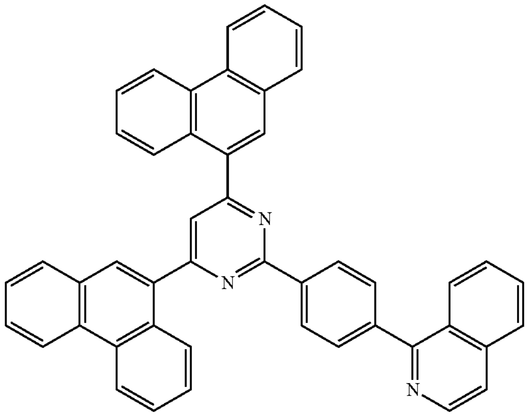
ET14
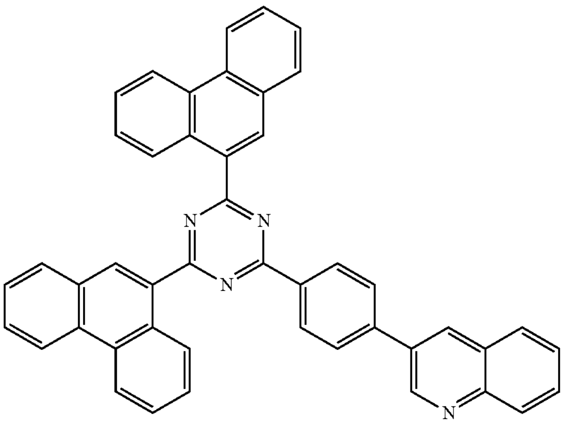
ET15
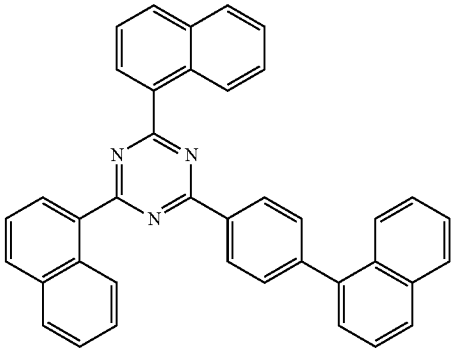
-continued
ET16
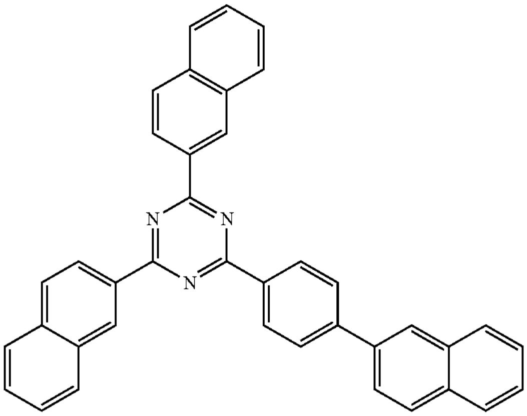
ET17
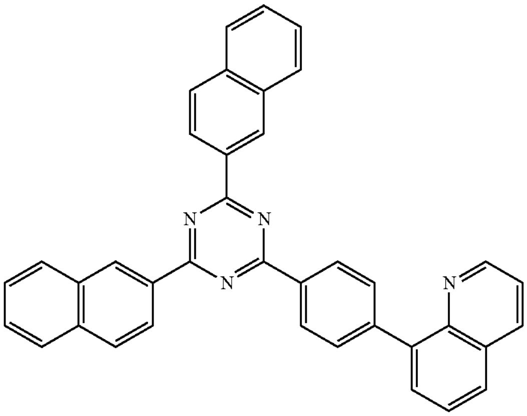
ET18
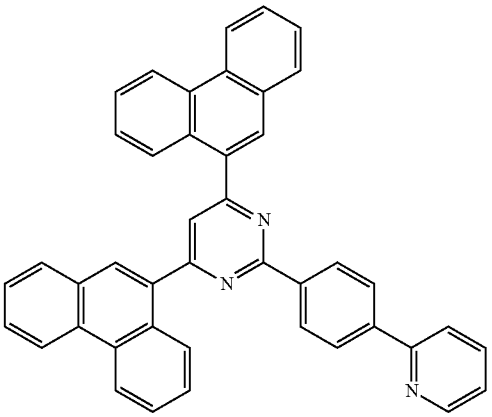

-continued
ET19
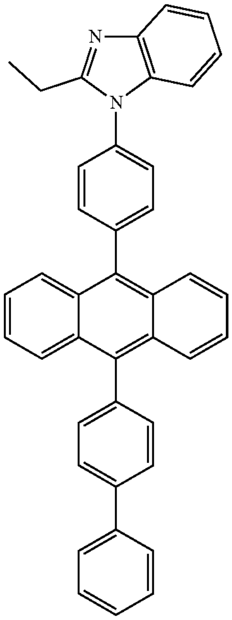
ET20
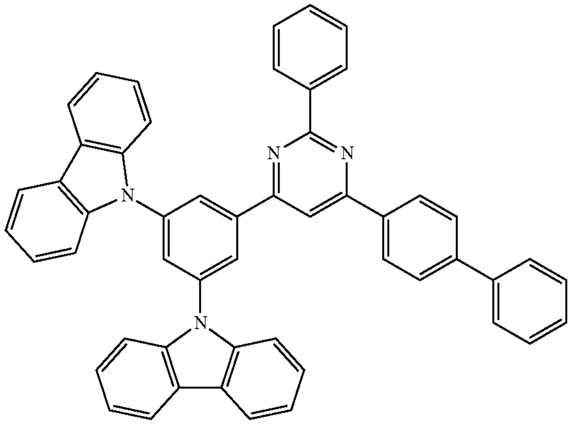
ET21
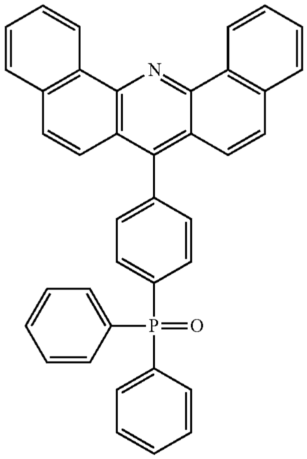
-continued
ET22
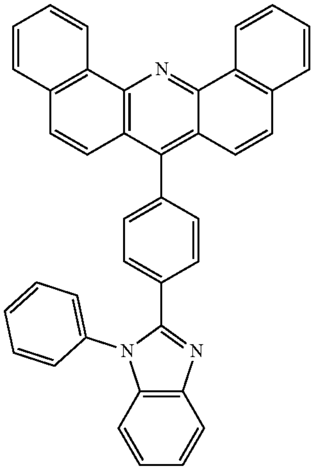
ET23
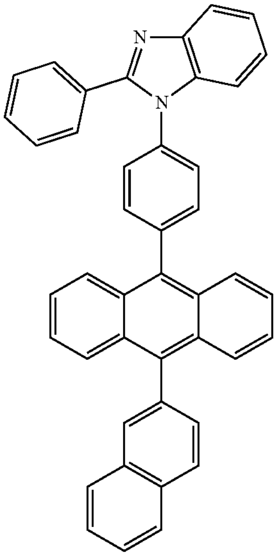
ET24
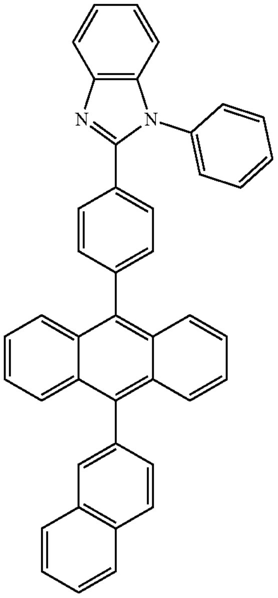

-continued

ET25

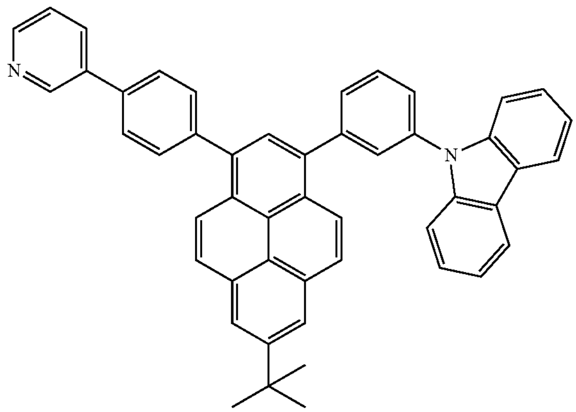

A thickness of the electron transport layer may be in a range of about 100 Å to about 2,000 Å, for example, about 150 Å to about 1,500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium 8-hydroxyquinolate, LiQ) or ET-D2.

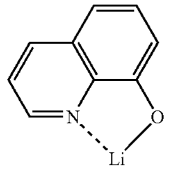

ET-D1

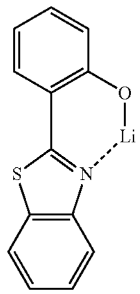

ET-D2

The electron transport region may include an electron injection layer (EIL) that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 may be formed on the organic layer 150. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to FIG. 1, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an iso-propyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-Coo alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having at least one heteroatom selected from N, O, P, Si and S as a ring-forming atom and 2 to 10 carbon atoms, and non-limiting examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, Si, and S as a ring-forming atom, 2 to 10 carbon atoms, and at least one double bond in its ring. Non-limiting examples of the $C_2$-$C_{10}$ heterocycloalkenyl group include a 2,3-dihydrofuranyl group, and a 2,3-dihydrothiophenyl group. The term "$C_2$-$C_{10}$ heterocycloalkenylene group" as used herein refers to a divalent group having the same structure as the $C_2$-$C_{60}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_5$-$C_{60}$ arylene group each include two or more rings, the rings may be fused to each other.

The term "$C_2$-$C_{60}$ heteroaryl group" as used herein refers to a monovalent group having a heterocyclic aromatic system that has at least one heteroatom selected from N, O, P, Si, and S as a ring-forming atom, and 2 to 60 carbon atoms. The term "$C_2$-$C_{60}$ heteroarylene group," as used herein refers to a divalent group having a heterocyclic aromatic system that has at least one heteroatom selected from N, O, P, Si, and S as a ring-forming atom, and 2 to 60 carbon atoms. Non-limiting examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), a $C_6$-$C_{60}$ arylthio group as used herein indicates —$SA_{103}$ (wherein $A_{103}$ is the $C_6$-$C_{60}$ aryl group), and the term "$C_7$-$C_{60}$ arylalkyl group" as used herein indicates -$A_{104}A_{105}$ (wherein $A_{105}$ is the $C_6$-$C_{59}$ aryl group and $A_{104}$ is the $C_1$-$C_{53}$ alkylene group).

The term "$C_1$-$C_{60}$ heteroaryloxy group" as used herein refers to —$OA_{106}$ (wherein $A_{106}$ is the $C_2$-$C_{60}$ heteroaryl group), the term "$C_1$-$C_{60}$ heteroarylthio group" as used herein indicates —$SA_{107}$ (wherein $A_{107}$ is the $C_1$-$C_{60}$ heteroaryl group), and the term "$C_2$-$C_{60}$ heteroarylalkyl group" as used herein refers to -$A_{108}A_{109}$ ($A_{109}$ is a $C_1$-$C_{59}$ heteroaryl group, and $A_{108}$ is a $C_1$-$C_{59}$ alkylene group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$ and —$P(=O)(Q_{28})(Q_{29})$; and —$N(Q_{31})(Q_{32})$, —$Si(Q_{33})(Q_{34})(Q_{35})$, —$B(Q_{36})(Q_{37})$ and —$P(=O)(Q_{38})(Q_{30})$, and $Q_{101}$ to $Q_{103}$, $Q_{111}$ to $Q_{113}$, $Q_{121}$ to $Q_{123}$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

For example, $Q_{101}$ to $Q_{103}$, $Q_{111}$ to $Q_{113}$, $Q_{121}$ to $Q_{123}$, $Q_{11}$ to $Q_{19}$, $Q_{21}$ to $Q_{29}$, and $Q_{31}$ to $Q_{39}$ may each independently be hydrogen, deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, or a tetraphenyl group, but embodiments of the present disclosure are not limited thereto.

The term "room temperature" as used herein refers to about 25° C.

The terms "biphenyl group", "terphenyl group", and "tetraphenyl group" as used herein each refer to a monovalent group in which two, three, or four benzene groups are linked to each other via a single bond, respectively.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1: Synthesis of Compound 2

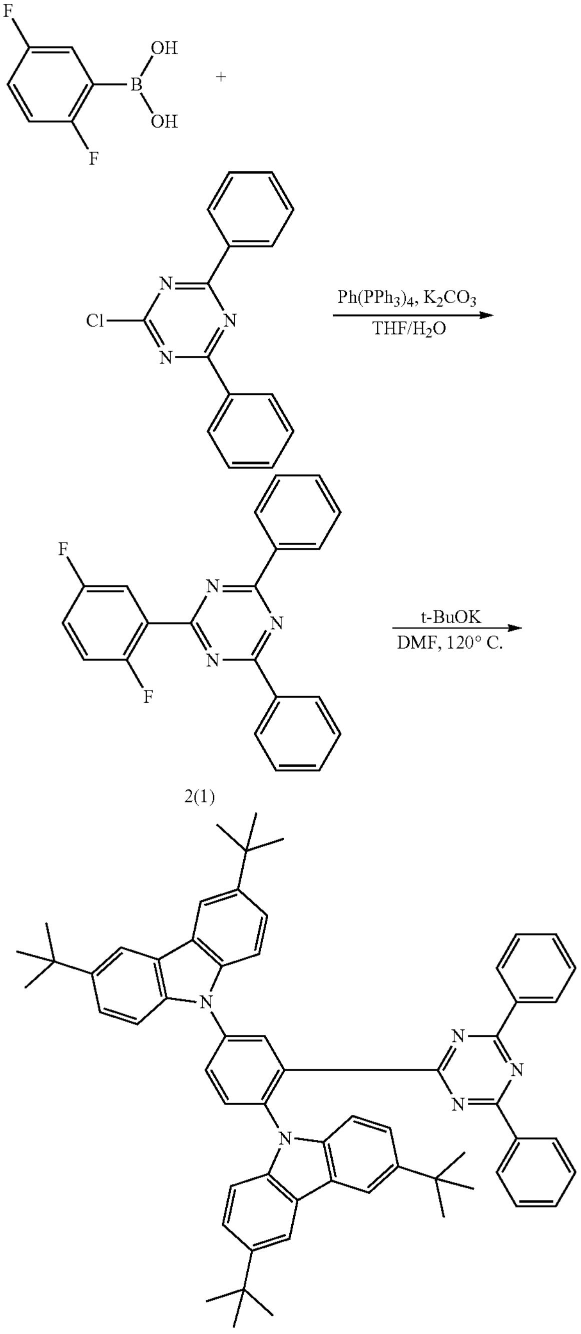

2(1)

2

Synthesis of Intermediate 2(1)

2-chloro-4,6-diphenyl-1,3,5-triazine (3.0 grams (g), 11.21 millimoles, mmol), (2,5-difluorophenyl)boronic acid (2.12 g, 13.45 mmol), palladium tetrakis(triphenylphosphine) (Pd $(PPh_3)_4$) (0.65 g, 0.56 mmol), and potassium carbonate ($K_2CO_3$) (4.65 g, 33.62 mmol) were added to a mixture of 20 milliliters (mL) of tetrahydrofuran and 20 mL of distilled water, and the reaction mixture was heated under reflux. After the reaction was completed, the reaction product was cooled to room temperature, and methanol was added thereto. The reaction solution was filtered through silica gel. An organic layer obtained therefrom was concentrated and precipitated by adding methanol thereto to synthesize Intermediate 2(1) (white solid, 3.23 g, yield of 83%).

Synthesis of Compound 2

Intermediate 2(1) (5.18 g, 15 mmol), 3,6-di-tert-butyl-9H-carbazole (12.57 g, 45 mmol), and potassium-tert-butoxide (t-BuOK) (4.21 g, 37.5 mmol) were added to 30 mL of N,N-dimethylformamide and stirred at a temperature of 120° C. for 12 hours. After the reaction was completed, the reaction product was cooled to room temperature, and methanol was added thereto. The reaction solution was filtered through silica gel. The organic layer obtained therefrom was concentrated, redissolved in toluene, filtered through silica gel, and then concentrated. The resultant obtained therefrom was recrystallized by using toluene to synthesize Compound 2 (yellow solid, 9.39 g, yield of 48%).

LC-MS (Calcd.: 864.19 g/mol. Found: 864.27 g/mol (M+1)).

Synthesis Example 2: Synthesis of Compound 1074

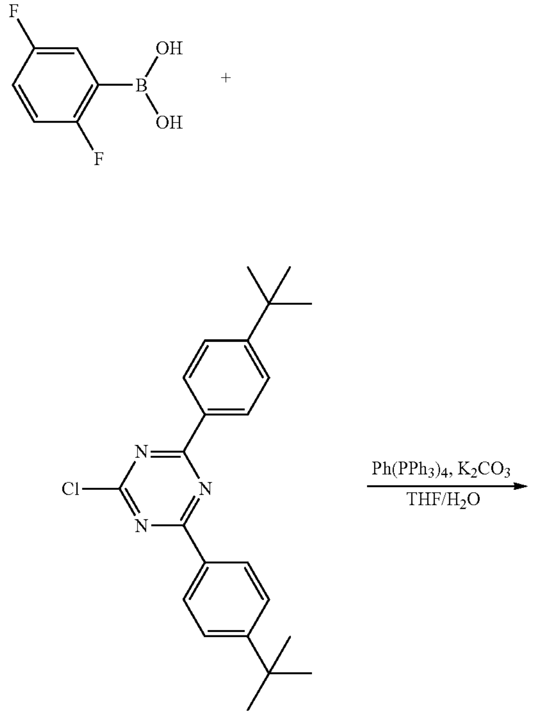

-continued

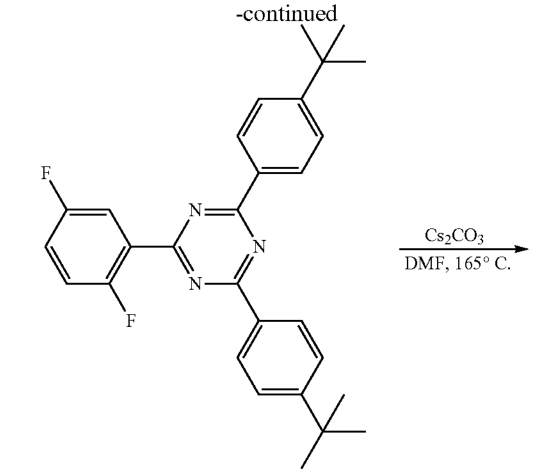

1074(1)

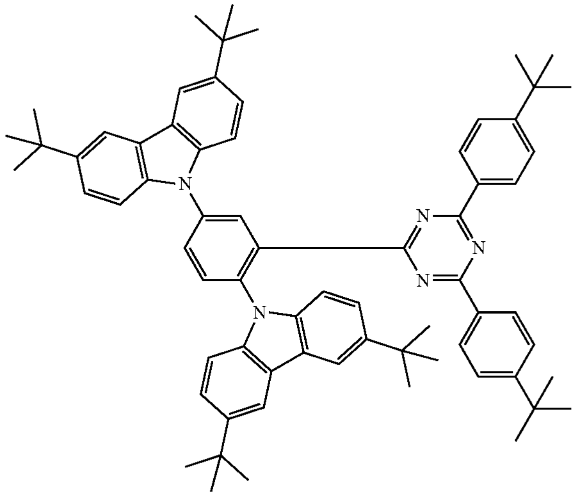

1074

Synthesis of Intermediate 1074(1)

2,4-bis(4-(tert-butyl)phenyl)-6-chloro-1,3,5-triazine (5.0 g, 13.16 mmol), (2,5-difluorophenyl)boronic acid (2.49 g, 15.79 mmol), palladium tetrakis(triphenylphosphine (Pd $(PPh_3)_4$) (0.76 g, 0.66 mmol), and potassium carbonate ($K_2CO_3$) (5.46 g, 39.48 mmol) were added to a mixture of 22 mL of tetrahydrofuran and 22 mL of distilled water, and the reaction mixture was heated under reflux. After the reaction was completed, the reaction product was cooled to room temperature, and the organic layer was extracted therefrom by using dichloromethane and water and filtered through silica gel. The obtained organic layer was concentrated and precipitated by adding methanol thereto to synthesize Intermediate 1074(1) (white solid, 5.0 g, yield of 83%).

Synthesis of Compound 1074

Intermediate 1074(1) (2.62 g, 5.73 mmol), 3,6-di-tert-butyl-9H-carbazole (4.0 g, 14.31 mmol), and cesium carbonate ($Cs_2CO_3$) (9.33 g, 28.63 mmol) were added to 30 mL of N,N-dimethylformamide, and the reaction mixture was stirred at a temperature of 165° C. for 12 hours. After the reaction was completed, the reaction product was cooled to room temperature, and methanol was added thereto. The reaction solution was filtered through silica gel. The organic layer obtained therefrom was concentrated, redissolved in toluene, filtered through silica gel, and then concentrated.

The resultant obtained therefrom was recrystallized by using dichloromethane and methanol to synthesize Compound 1074 (yellow solid, 4.34 g, yield of 78%).

LC-MS (Calcd.: 976.41 g/mol. Found: 976.5 g/mol (M+1)).

Synthesis Example 3: Synthesis of Compound 1075

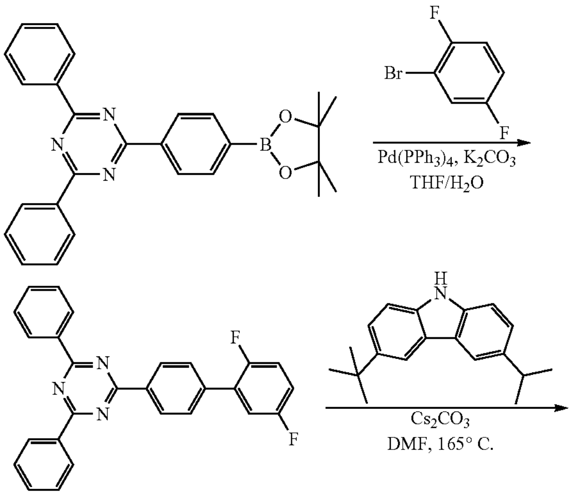

1075(1)

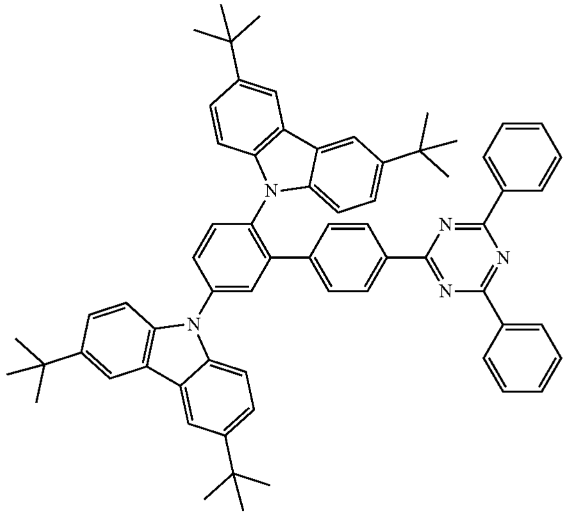

1075

Synthesis of Intermediate 1075(1)

2,4-diphenyl-6-(4-(4,4,5,5-tetramethyl-1,3,2-dioxaborolan-2-yl)phenyl)-1,3,5-triazine (8.12 g, 18.65 mmol), 2-bromo-1,4-difluorobenzene (3.0 g, 15.54 mmol), palladium tetrakis(triphenylphosphine) ($Pd(PPh_3)_4$) (0.89 g, 0.78 mmol), and potassium carbonate ($K_2CO_3$) (6.44 g, 46.63 mmol) were added to a mixture of 20 mL of tetrahydrofuran and 25 mL of distilled water, and the reaction mixture was heated under reflux. After the reaction was completed, the reaction product was cooled to room temperature, and the organic layer was extracted therefrom by using dichloromethane and water and filtered through silica gel. The obtained organic layer was concentrated and recrystallized by using a mixture of dichloromethane and ethyl acetate to synthesize Intermediate 1075(1) (white solid, 4.8 g, yield of 73%).

Synthesis of Compound 1075

Intermediate 1075(1) (1.81 g, 4.29 mmol), 3,6-di-tert-butyl-9H-carbazole (3.0 g, 10.74 mmol), and cesium carbonate ($Cs_2CO_3$) (7.0 g, 21.47 mmol) were added to 43 mL of N,N-dimethylformamide, and the reaction mixture was stirred at a temperature of 165° C. for 12 hours. After the reaction was completed, the reaction product was cooled to room temperature, and methanol was added thereto. The reaction solution was filtered through silica gel. The organic layer obtained therefrom was concentrated, redissolved in toluene, filtered through silica gel, and then concentrated. The resultant obtained therefrom was recrystallized by using a mixture of dichloromethane and hexane to synthesize Compound 1075 (yellow solid, 2.83 g, yield of 70%).

LC-MS (Calcd.: 940.29 g/mol. Found: 976.39 g/mol (M+1)).

Synthesis Example 4: Synthesis of Compound 1076

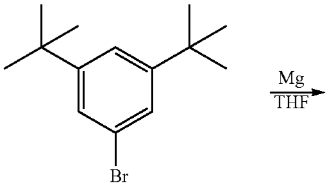

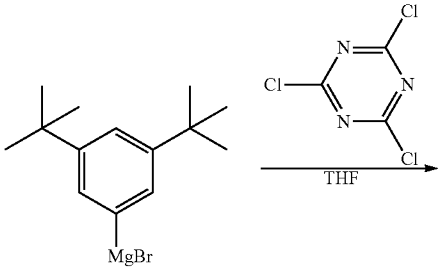

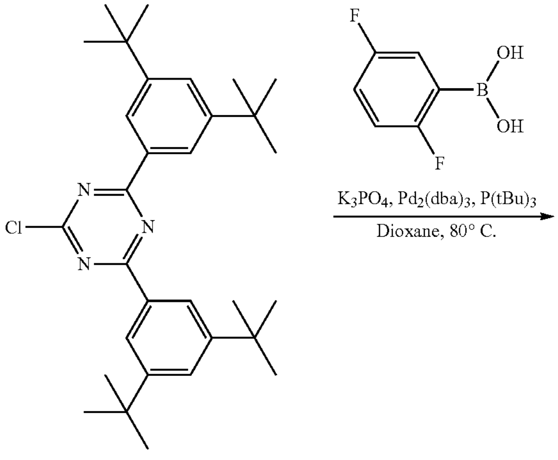

1076(1)

-continued

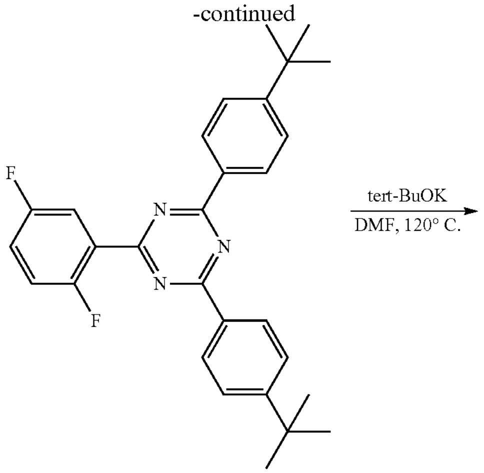

1076(2)

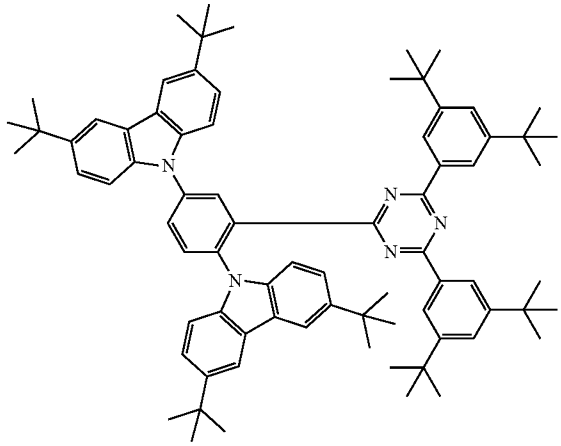

1076

Synthesis of Intermediate 1076(1)

Magnesium (7.76 g, 319.2 mmol) was added to a flask in a nitrogen atmosphere, and 1-bromo-3,5-di-tert-butylbenzene (90.03 g, 334.4 mmol) was dissolved in 300 mL of tetrahydrofuran, slowly added to the flask containing magnesium, and the reaction mixture was stirred at a temperature of 70° C. for 2 hours. After the reaction was completed, the reaction product was cooled to room temperature to obtain (3,5-di-tert-butylphenyl)magnesium bromide Grignard reagent. The Grignard reagent was directly used in a subsequent reaction without any purification. The Grignard reagent was slowly added dropwise to a reaction container in which 2,4,6-trichloro-1,3,5-triazine was dissolved in 300 mL of tetrahydrofuran at a temperature of −40° C. for 20 minutes, and the reaction mixture was stirred at the same temperature for 30 minutes. Then, the reaction container was heated to room temperature and stirred for 16 hours, and was further heated to a temperature of 60° C. and additionally stirred for 4 hours. After the reaction was completed, the reaction product was cooled to room temperature, and the organic layer extracted therefrom by using 1 L of dichloromethane, hydrochloric acid (1 normal (N), 500 mL), and distilled water was concentrated and then recrystallized by using dichloromethane and acetonitrile to synthesize Intermediate 1076(1) (white solid, 53.56 g, yield of 72%).

Synthesis of Intermediate 1076(2)

Intermediate 1076(1) (7.38 g, 15 mmol), (2,5-difluorophenyl)boronic acid (3.55 g, 22.5 mmol), potassium phosphate tribasic ($K_3PO_4$) (4.78 g, 22.5 mmol), tris(dibenzylideneacetone)dipalladium ($Pd_2(dba_3)$) (275 mg, 0.3 mmol), and tri-tert-butylphosphine ($P(tBu)_3$) (242 mg, 12 mmol) were added to 30 mL of dioxane, and the reaction mixture was heated under reflux. After the reaction was completed, the reaction product was cooled to room temperature, the organic layer was extracted therefrom by using toluene and water, filtered through silica gel, concentrated, and then precipitated by using methanol to synthesize Intermediate 1076(2) (white solid, 6.17 g, yield of 72%).

Synthesis of Compound 1076

Compound 1076 (6.8 g, yield of 58%) was synthesized in the same manner as Compound 2 of Synthesis Example 1, except that Intermediate 1076(2) was used instead of Intermediate 2(1).

LC-MS (Calcd.: 1088.63 g/mol. Found: 1088.73 g/mol (M+1)).

Synthesis Example 5: Synthesis of Compound 1

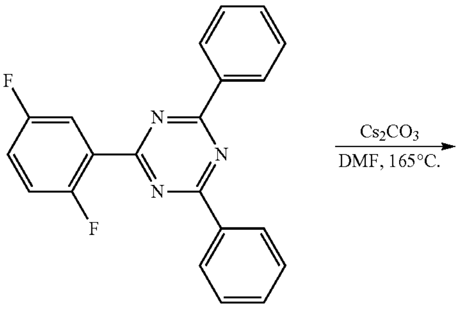

2(1)

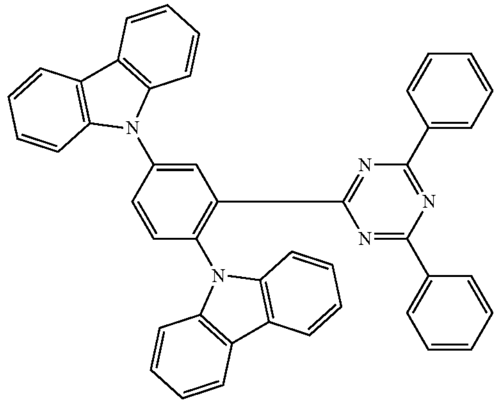

1

Compound 1 (2.4 g, yield of 63%) was synthesized in the same manner as Compound 1074 of Synthesis Example 2, except that carbazole (9H-carbazole) was used instead of 3,6-di-tert-butyl-9H-carbazole, and Intermediate 2(1) was used instead of Intermediate 1074(1).

LC-MS (Calcd.: 716.26 g/mol. Found: 717.26 g/mol (M+1)).

Synthesis Example 6: Synthesis of Compound 1077
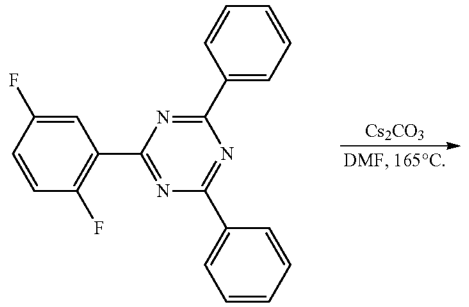
2(1)
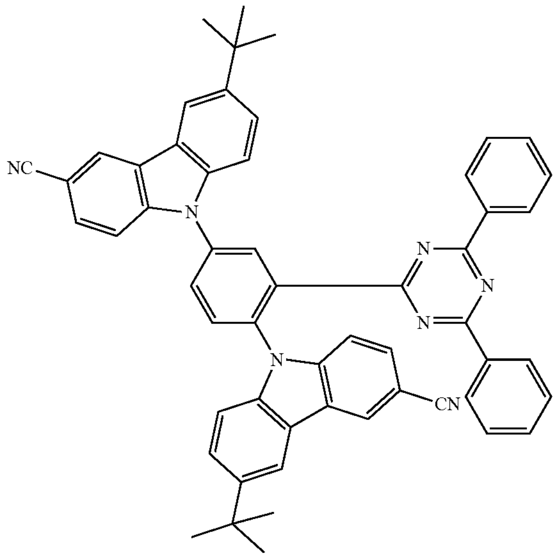
1077
Compound 1077 (2.4 g, yield of 50%) was synthesized in the same manner as in Synthesis Example 5, except that 6-(tert-butyl)-9H-carbazole-3-carbonitrile was used instead of carbazole.
LC-MS (Calcd.: 802.00 g/mol. Found: 802.10 g/mol (M+1)).
Synthesis Example 7: Synthesis of Compound 14
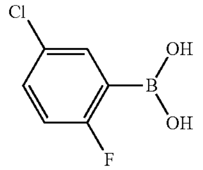
+
-continued
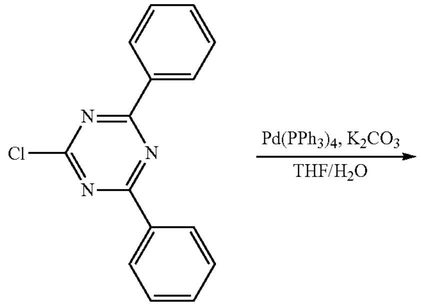
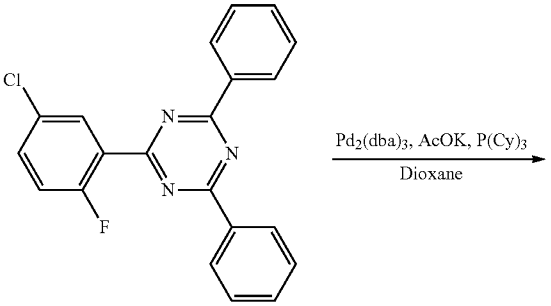
14(1)
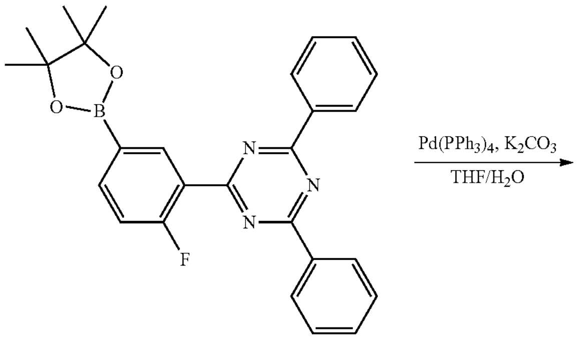
14(2)
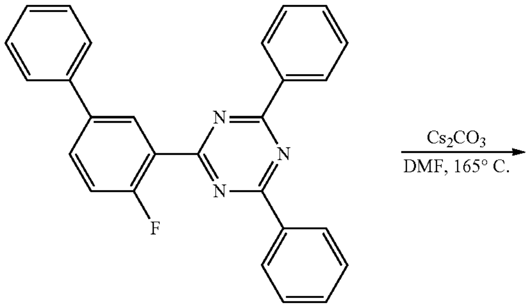
14(3)

-continued

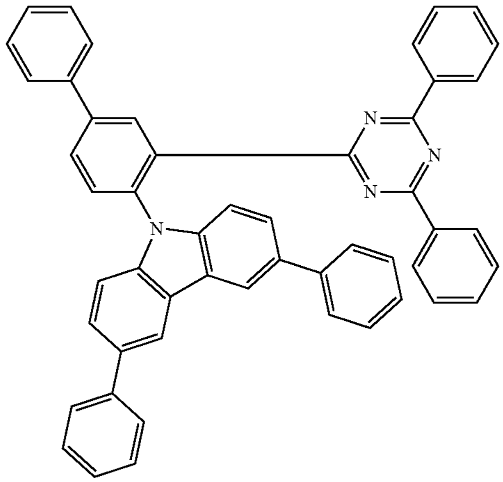

14

Synthesis of Intermediate 14(1)

Intermediate 14(1) (15.30 g, yield of 87%) was synthesized in the same manner as Intermediate 2(1) of Synthesis Example 1, except that (5-chloro-2-fluorophenyl)boronic acid was used instead of (2,5-difluorophenyl)boronic acid.

LC-MS (Calcd.: 361.80 g/mol. Found: 361.90 g/mol (M+1)).

Synthesis of Intermediate 14(2)

Intermediate 14(1) (28.1 g, 77.67 mmol), bis(pinacolato) diboron (39.45 g, 155.33 mmol), potassium acetate (AcOK) (22.87 g, 233.00 mmol), tris(dibenzylideneacetone)dipalladium ($Pd_2(dba)_3$) (7.11 g, 7.77 mmol), and tricyclohexylphosphine ($P(Cy)_3$) (2.178 g, 7.77 mmol) were added to a reaction container, dissolved in 155 mL of dioxane, and the reaction mixture was stirred at a temperature of 120° C. After the reaction was completed, the reaction product was cooled to room temperature, and the organic layer was extracted therefrom by using ethyl acetate and water, filtered through silica gel, and then concentrated. The solid compound (Intermediate 14(2)) (32.40 g, yield of 92%) obtained therefrom was directly used in a subsequent reaction without any purification.

Synthesis of Intermediate 14(3)

Intermediate 14(3) (6 g, yield of 83%) was synthesized in the same manner as Intermediate 2(1) of Synthesis Example 1, except that bromobenzene was used instead of 2-chloro-4,6-diphenyl-1,3,5-triazine.

LC-MS (Calcd.: 403.46 g/mol. Found: 400.56 g/mol (M+1)).

Synthesis of Compound 14

Compound 14 (0.66 g, yield of 30%) was synthesized in the same manner as Compound 1074 of Synthesis Example 2, except that 3,6-diphenyl-9H-carbazole was used instead of 3,6-di-tert-butyl-9H-carbazole, and Intermediate 14(3) was used instead of Intermediate 1074(1).

LC-MS (Calcd.: 702.86 g/mol. Found: 702.96 g/mol (M+1)).

Synthesis Example 8: Synthesis of Compound 13

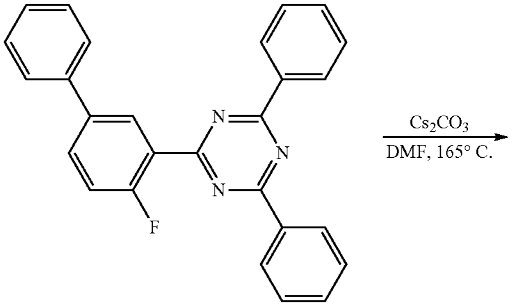

14(3)

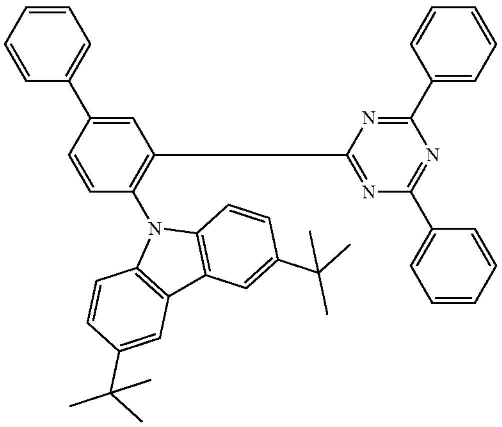

13

Compound 13 (0.70 g, yield of 33%) was synthesized in the same manner as Compound 14 of Synthesis Example 7, except that 3,6-di-tert-butyl-9H-carbazole was used instead of 3,6-diphenyl-9H-carbazole.

LC-MS (Calcd.: 662.88 g/mol. Found: 662.98 g/mol (M+1)).

Synthesis Example 9: Synthesis of Compound 71

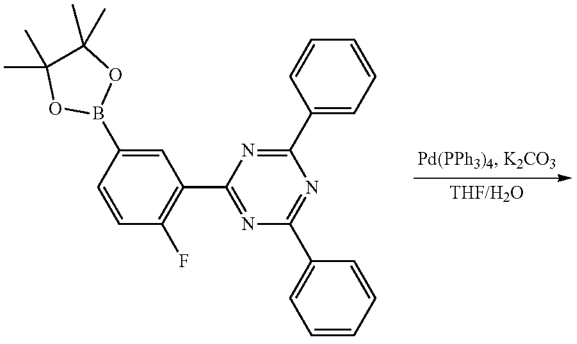

71(A)

-continued

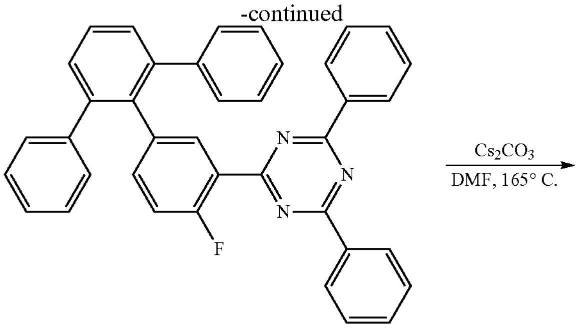

71(1)

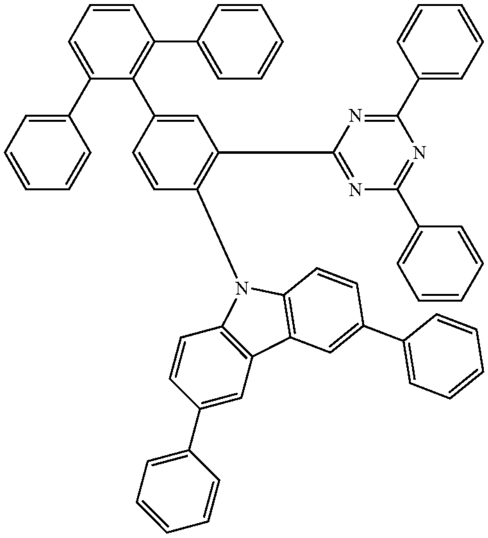

71

Synthesis of Intermediate 71(1)

Compound 71(1) (6 g, yield of 83%) was synthesized in the same manner as Intermediate 2(1) of Synthesis Example 1, except that 2'-bromo-1,1': 3',1"-terphenyl was used instead of 2-chloro-4,6-diphenyl-1,3,5-triazine, and a starting material 71(A) was used instead of (2,5-difluorophenyl) boronic acid.

LC-MS (Calcd.: 555.66 g/mol. Found: 555.76 g/mol (M+1)).

Synthesis of Compound 71

Compound 71 (4.7 g, yield of 70%) was synthesized in the same manner as Compound 14 of Synthesis Example 7, except that Intermediate 71(1) was used instead of Intermediate 14(3).

LC-MS (Calcd.: 855.03 g/mol. Found: 855.13 g/mol (M+1)).

Synthesis Example 10: Synthesis of Compound 70

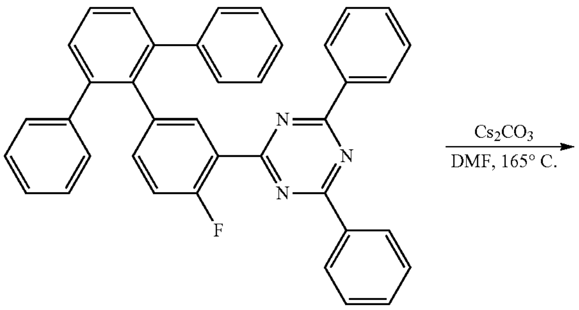

71(1)

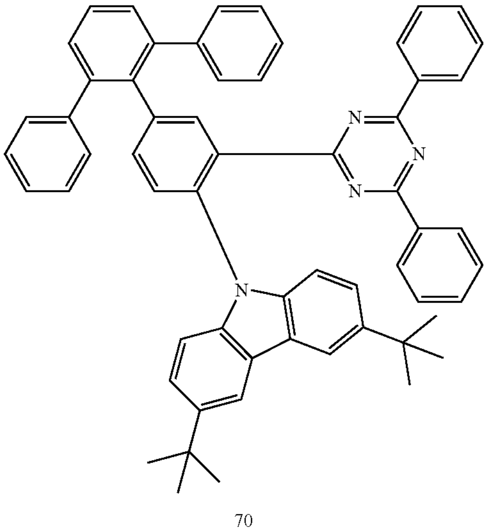

70

Compound 70 (3.8 g, yield of 72%) was synthesized in the same manner as Compound 71 of Synthesis Example 9, except that 3,6-di-tert-butyl-9H-carbazole was used instead of 3,6-diphenyl-9H-carbazole.

LC-MS (Calcd.: 815.06 g/mol. Found: 815.16 g/mol (M+1)).

Synthesis Example 11: Synthesis of Compound 37

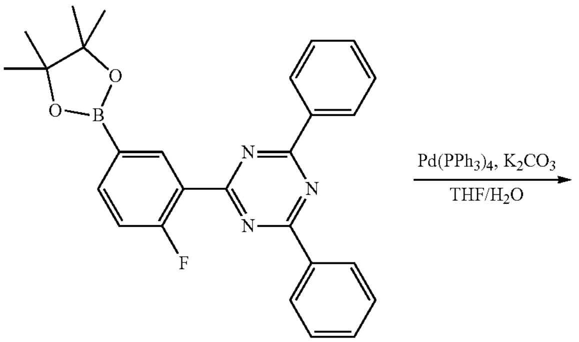

71(A)

-continued

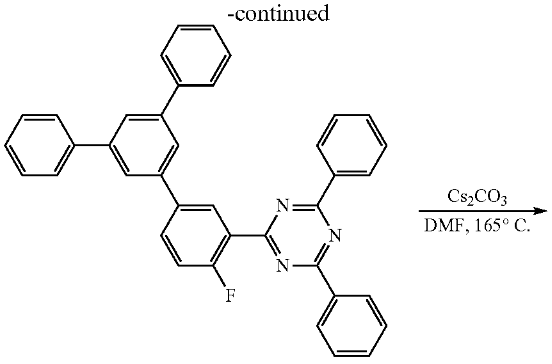

37(1)

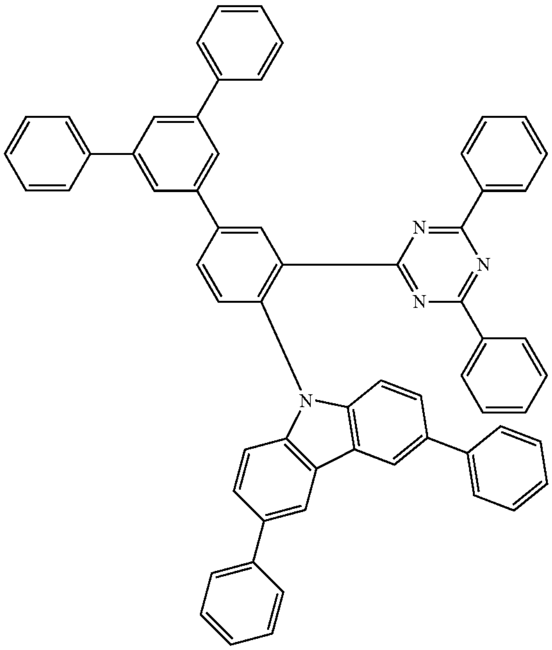

37

Synthesis of Intermediate 37(1)

Intermediate 37(1) (6 g, yield of 83%) was synthesized in the same manner as Intermediate 2(1) of Synthesis Example 1, except that 5'-bromo-1,1':3',1"-terphenyl was used instead of 2-chloro-4,6-diphenyl-1,3,5-triazine, and a starting material 71(A) was used instead of (2,5-difluorophenyl)boronic acid.

LC-MS (Calcd.: 555.66 g/mol. Found: 555.76 g/mol (M+1)).

Synthesis of Compound 37

Compound 37 (4.9 g, yield of 82%) was synthesized in the same manner as Compound 14 of Synthesis Example 7, except that Intermediate 37(1) was used instead of Intermediate 14(3).

LC-MS (Calcd.: 855.03 g/mol. Found: 855.13 g/mol (M+1)).

Synthesis Example 12: Synthesis of Compound 46

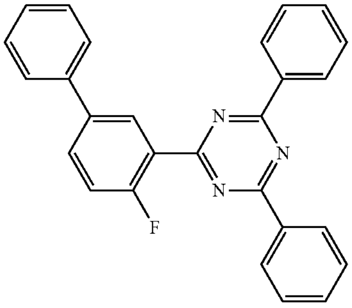

+

14(3)

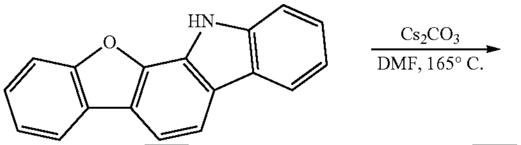

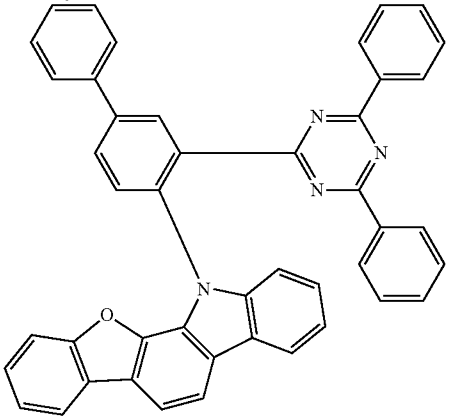

46

Compound 46 (0.7 g, yield of 34%) was synthesized in the same manner as Compound 14 of Synthesis Example 7, except that 12H-benzofuro[2,3-a]carbazole was used instead of 3,6-diphenyl-9H-carbazole.

LC-MS (Calcd.: 640.75 g/mol. Found: 640.85 g/mol (M+1)).

Synthesis Example 13: Synthesis of Compound 21

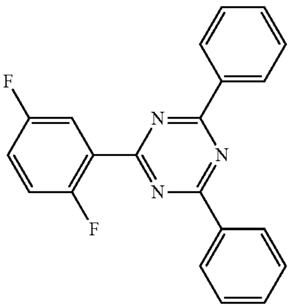

+

2(1)

-continued
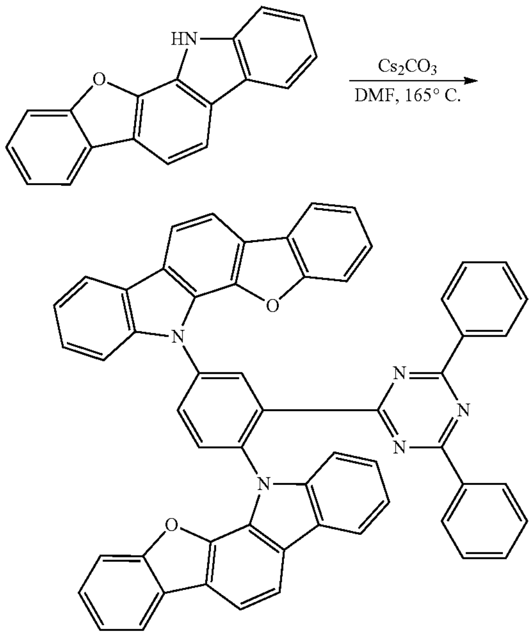
21
Compound 21 (0.7 g, yield of 10%) was synthesized in the same manner as in Synthesis Example 5, except that 12H-benzofuro[2,3-a]carbazole was used instead of carbazole.
LC-MS (Calcd.: 819.92 g/mol. Found: 820.02 g/mol (M+1)).
Synthesis Example 14: Synthesis of Compound 346
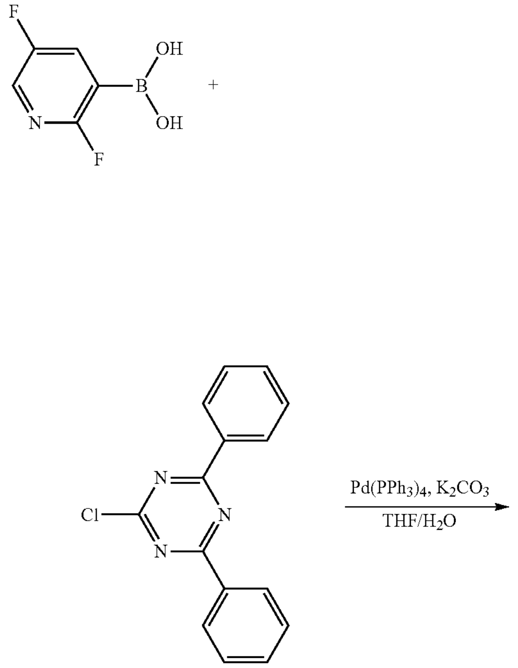
-continued
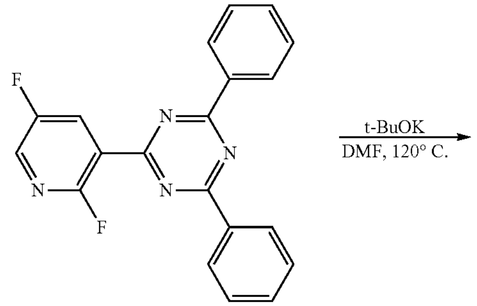
346(1)
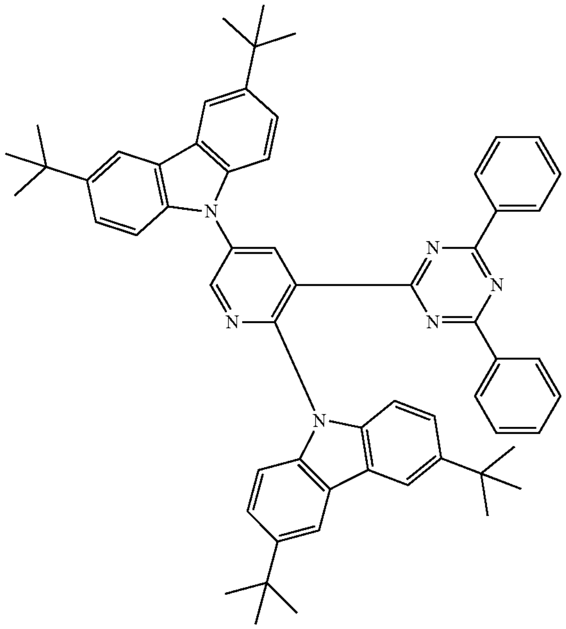
346
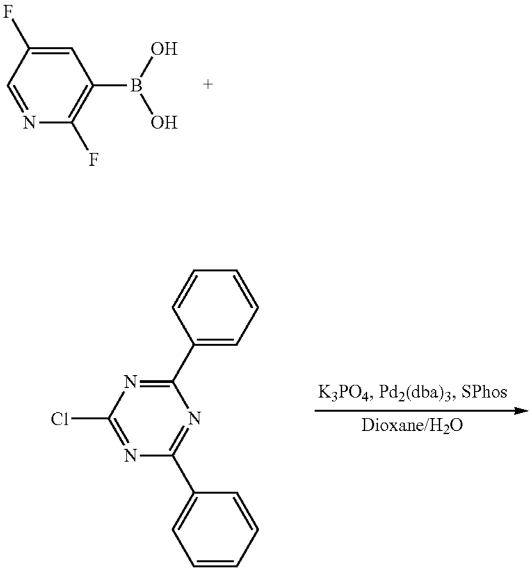

-continued

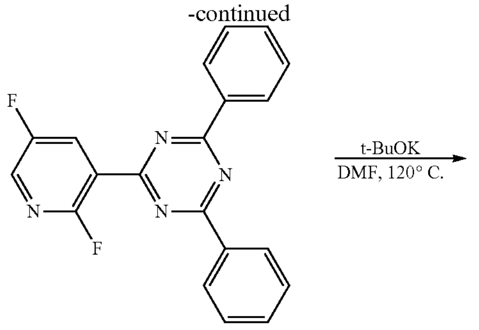

346(1)

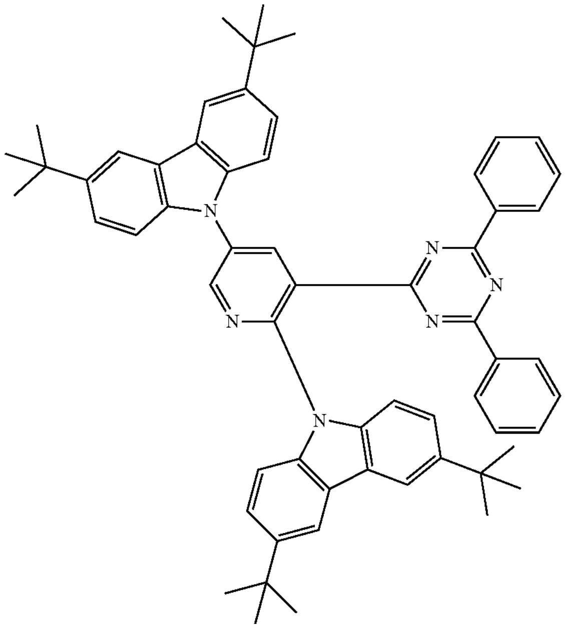

346

Synthesis of Intermediate 346(1)

4-chloro-2,6-diphenyltriazine (10 g, 37.35 mmol), (2,5-difluoropyridin-3-yl)boronic acid (7.122 g, 44.82 mmol), potassium phosphate tribasic ($K_3PO_4$) (15.86 g, 74.70 mmol), tris(dibenzylideneacetone)dipalladium ($Pd_2(dba_3)$) (0.68 g, 0.75 mmol), and a phosphine ligand (SPhos) (1.533 g, 3.74 mmol) were added to a mixture of 60 mL of dioxane and 60 mL of distilled water, and the reaction mixture was heated under reflux. After the reaction was completed, the reaction product was cooled to room temperature, and the organic layer was extracted therefrom by using toluene and water and filtered through silica gel. The obtained organic layer was concentrated and precipitated by using methanol to synthesize Intermediate 346(1) (white solid, 2.32 g, yield of 18%).

LC-MS (Calcd.: 346.34 g/mol. Found: 346.3 g/mol (M+1)).

Synthesis of Compound 346

Compound 346 (3.2 g, yield of 55%) was synthesized in the same manner as Compound 1074 of Synthesis Example 2, except that Intermediate 346(1) was used instead of Intermediate 1074(1).

LC-MS (Calcd.: 865.18 g/mol. Found: 866.2 g/mol (M+1)).

Synthesis Example 15: Synthesis of Compound 25

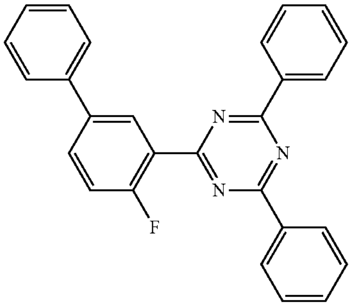

14(3)

+

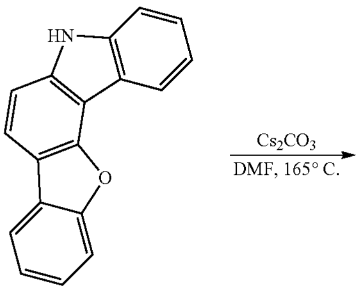

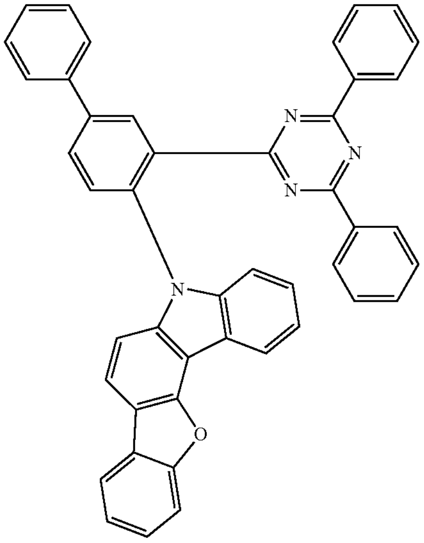

25

Compound 25 (2.9 g, yield of 34%) was synthesized in the same manner as Compound 14 of Synthesis Example 7, except that 5H-benzofuro[3,2-c]carbazole was used instead of 3,6-diphenyl-9H-carbazole.

LC-MS (Calcd.: 640.75 g/mol. Found: 640.85 g/mol (M+1)).

Synthesis Example 16: Synthesis of Compound 1078

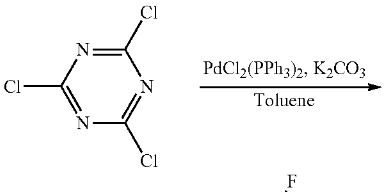

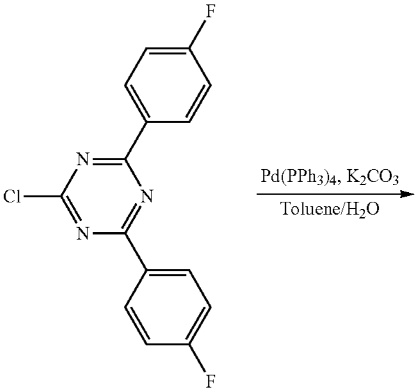

1078(1)

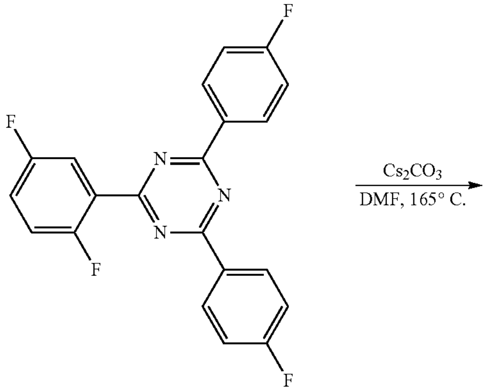

1078(2)

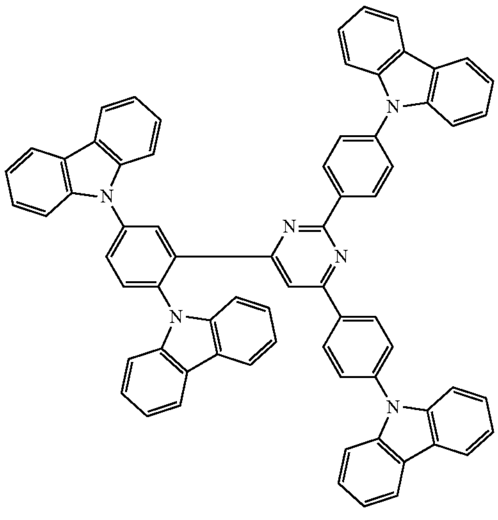

1078

Synthesis of Intermediate 1078(1)

2,4,6-trichloro-1,3,5-triazine (6.0 g, 32.54 mmol), (4-fluorophenyl)boronic acid (9.56 g, 68.33 mmol), potassium carbonate ($K_2CO_3$) (17.98 g, 130.15 mmol), and bis(triphenylphosphine)palladium(II), dichloride $PdCl_2(PPh_3)_4$) (1.14 g, 1.63 mmol) were added to 70 mL of toluene, and the reaction mixture was heated under reflux at a temperature of 60° C. After the reaction was completed, the reaction product was cooled to room temperature, and the organic layer was extracted by using toluene and water and filtered through silica gel. The obtained organic layer was concentrated and precipitated by using methanol to synthesize Intermediate 1078(1) (white solid, 4.01 g, yield of 40%).

LC-MS (Calcd.: 303.54 g/mol. Found: 303.64 g/mol (M+1)).

Synthesis of Intermediate 1078(2)

Intermediate 1078(1) (i.e., 2-chloro-4,6-bis(4-fluorophenyl)-1,3,5-triazine) (3.8 g, 12.51 mmol), (2,5-difluorophenyl)boronic acid (2.37 g, 15.01 mmol), palladium tetrakis (triphenylphosphine) ($Pd(PPh_3)_4$) (0.72 g, 0.63 mmol), and potassium carbonate ($K_2CO_3$) (3.46 g, 25.02 mmol) were added to a mixture of 20 mL of toluene and 7 mL of distilled water, and the reaction mixture was heated under reflux at a temperature of 100° C. After the reaction was completed, the reaction product was cooled to room temperature, and the organic layer was extracted therefrom by using toluene and water and filtered through silica gel. The obtained organic layer was concentrated and precipitated by using methanol to synthesize Intermediate 1078(2) (white solid, 4.2 g, yield of 88%).

Synthesis of Compound 1078

Compound 1078 (2.6 g, yield of 27%) was synthesized in the same manner as Compound 1 of Synthesis Example 5, except that Intermediate 1078(2) was used instead of Intermediate 2(1).

LC-MS (Calcd.: 970.15 g/mol. Found: 970.25 g/mol (M+1)).

Evaluation Example 1: Evaluation of HOMO, LUMO, Ti, and Si Energy Levels

HOMO, LUMO, $T_1$, and $S_1$ energy levels of Compounds shown in Table 2 were measured by using methods described in Table 1, and results thereof are shown in Table 2.

TABLE 1

| | |
|---|---|
| HOMO energy level evaluation method | A voltage-current (V-A) graph of each Compound was obtained by using a cyclic voltammetry (CV) (electrolyte: 0.1 molar (M) $Bu_4NPF_6$/solvent: $CH_2Cl_2$/electrode: 3-electrode system (work electrode: glassy carbon, reference electrode: Ag/AgCl, auxiliary electrode: Pt wire)), and a HOMO energy level of each Compound was calculated from onset reduction potential of the graph. |
| LUMO energy level evaluation method | Each Compound was diluted at a concentration of 1 × $10^{-5}$M in toluene, a UV absorption spectrum was measured at room temperature by using a Shimadzu UV-350 spectrometer, and a LUMO energy level thereof was calculated by using a HOMO energy level and an optical band gap ($E_g$) from the edge of the absorption spectrum. |
| $T_1$ energy level evaluation method | A mixture of toluene and each Compound (each Compound was dissolved in 3 mL of toluene so as to have a concentration of 1 × $10^{-4}$M) was loaded into a quartz cell, and then, the resultant quartz cell was loaded into liquid nitrogen (77 Kelvin, K). A photoluminescence (PL) spectrum thereof was measured by using a photoluminescence measurement |

TABLE 1-continued

| | |
|---|---|
| | device, the obtained spectrum was compared with a PL spectrum measured at room temperature, and the peaks observed only at low temperature were analyzed to calculate an T1 energy level. |
| $S_1$ energy level evaluation method | A PL spectrum of a mixture of toluene and each Compound (diluted at a concentration of 1 × $10^{-4}$M) was measured at room temperature by using a photoluminescence measurement device, and observed peaks were analyzed to calculate an onset S1 energy level. |

TABLE 2

| Compound No. | HOMO (eV) | LUMO (eV) | $T_1$ energy level (eV) | $S_1$ energy level (eV) | $\Delta E_{ST}$ (eV) |
|---|---|---|---|---|---|
| 2 | −5.153 | −1.886 | 2.58 | 2.685 | 0.105 |
| 1075 | −5.205 | −1.933 | 2.767 | 2.833 | 0.066 |
| 1076 | −5.09 | −1.728 | 2.69 | 2.811 | 0.121 |
| 1074 | −5.121 | −1.768 | 2.661 | 2.764 | 0.104 |
| 1077 | −5.803 | −2.274 | 2.815 | 2.925 | 0.111 |
| 1 | −5.354 | −1.942 | 2.705 | 2.806 | 0.102 |
| 13 | −5.134 | −1.807 | 2.632 | 2.725 | 0.093 |
| 70 | −5.108 | −1.756 | 2.668 | 2.75 | 0.082 |
| 14 | −5.155 | −1.863 | 2.655 | 2.72 | 0.064 |
| 71 | −5.13 | −1.802 | 2.704 | 2.76 | 0.056 |
| 21 | −5.328 | −1.859 | 2.764 | 2.873 | 0.109 |
| 37 | −5.154 | −1.865 | 2.651 | 2.716 | 0.065 |
| 46 | −5.276 | −1.811 | 2.75 | 2.854 | 0.104 |
| 346 | −5.23 | −1.952 | 2.626 | 2.734 | 0.108 |
| 25 | −5.183 | −1.856 | 2.692 | 2.759 | 0.067 |
| 1078 | −5.423 | −2.109 | 2.589 | 2.748 | 0.158 |

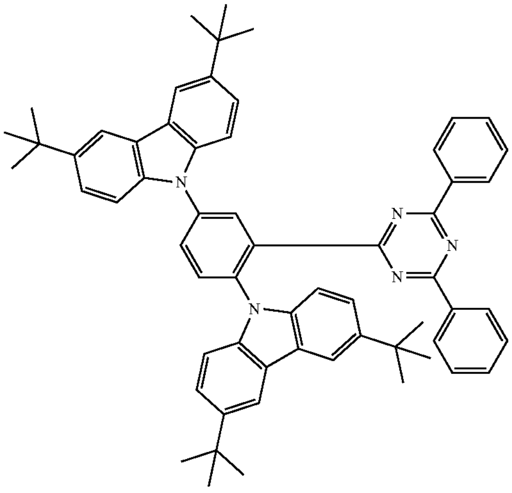

2

TABLE 2-continued

| Compound No. | HOMO (eV) | LUMO (eV) | $T_1$ energy level (eV) | $S_1$ energy level (eV) | $\Delta E_{ST}$ (eV) |
|---|---|---|---|---|---|

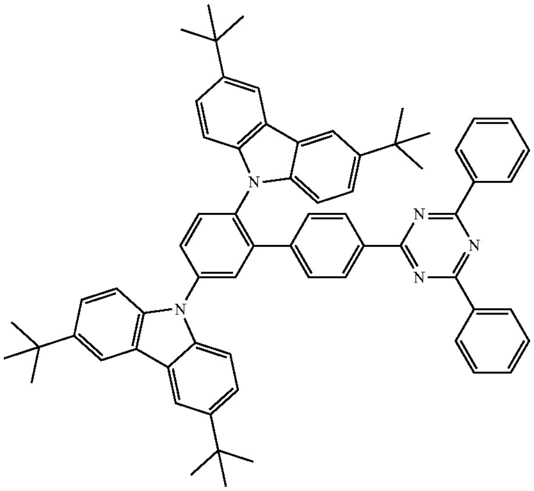

1075

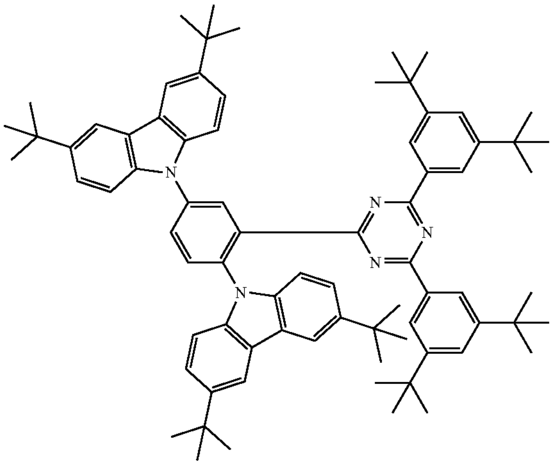

1076

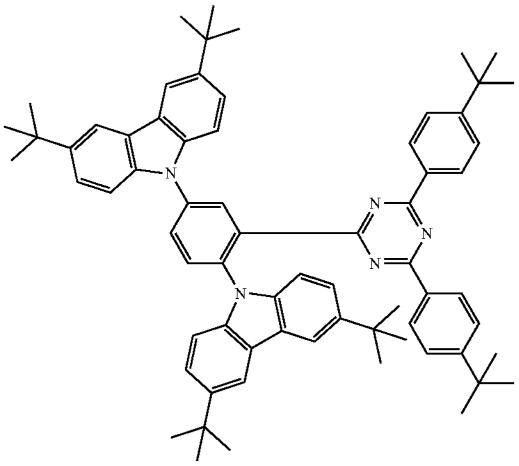

1074

TABLE 2-continued
| Compound No. | HOMO (eV) | LUMO (eV) | $T_1$ energy level (eV) | $S_1$ energy level (eV) | $\Delta E_{ST}$ (eV) |
|---|---|---|---|---|---|
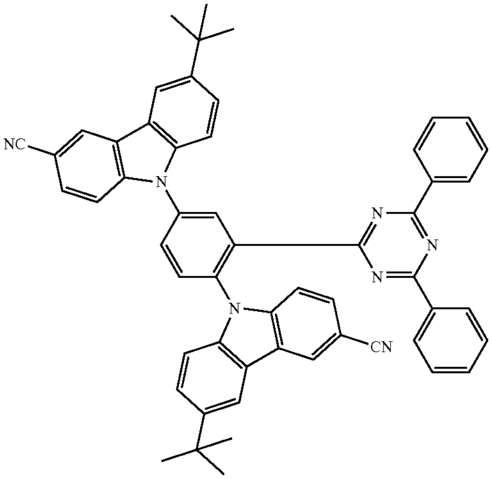
1077
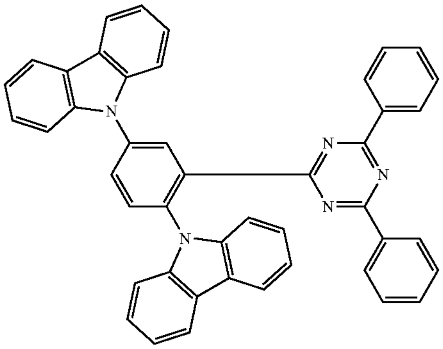
1
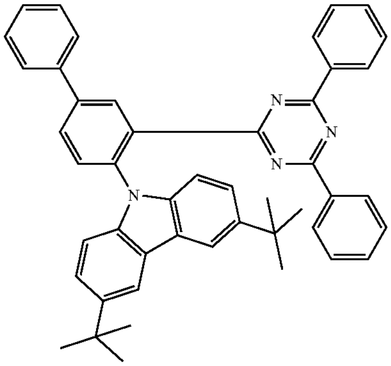
13
TABLE 2-continued
| Compound No. | HOMO (eV) | LUMO (eV) | $T_1$ energy level (eV) | $S_1$ energy level (eV) | $\Delta E_{ST}$ (eV) |
|---|---|---|---|---|---|
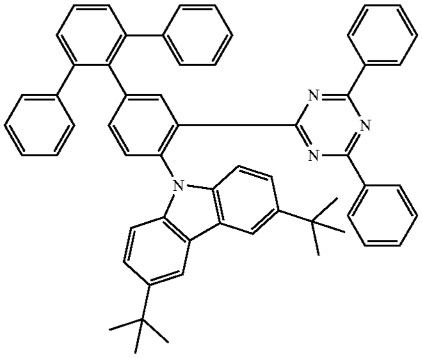
70
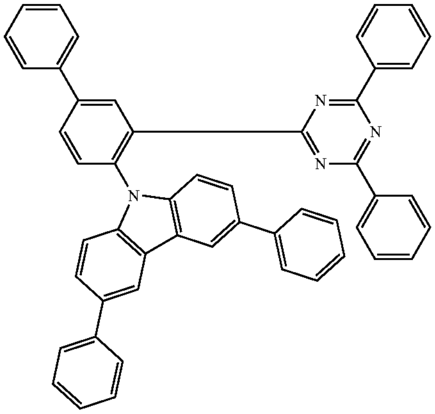
14
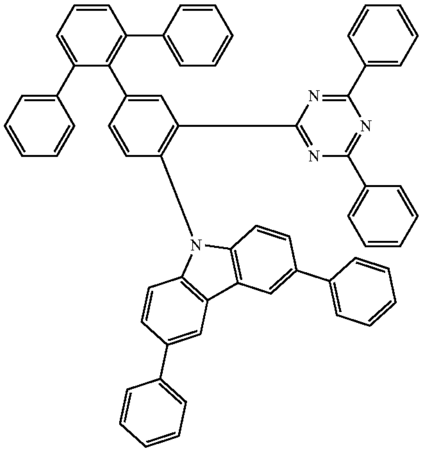
71

TABLE 2-continued
| Compound No. | HOMO (eV) | LUMO (eV) | $T_1$ energy level (eV) | $S_1$ energy level (eV) | $\Delta E_{ST}$ (eV) |
|---|---|---|---|---|---|
| 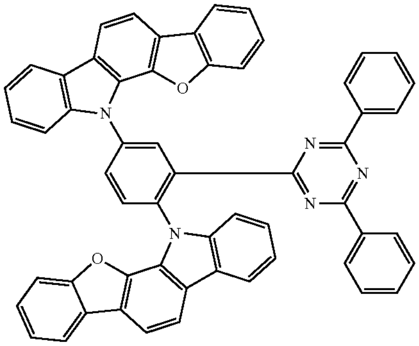 21 | | | | | |
| 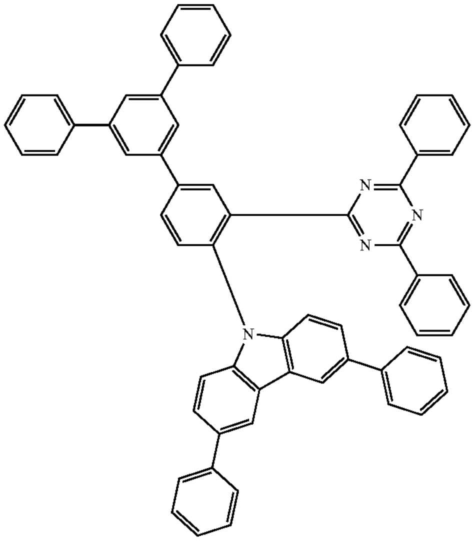 37 | | | | | |
| 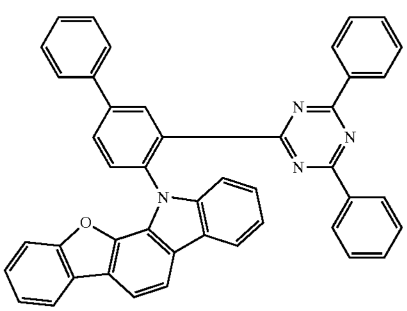 46 | | | | | |
TABLE 2-continued
| Compound No. | HOMO (eV) | LUMO (eV) | $T_1$ energy level (eV) | $S_1$ energy level (eV) | $\Delta E_{ST}$ (eV) |
|---|---|---|---|---|---|
| 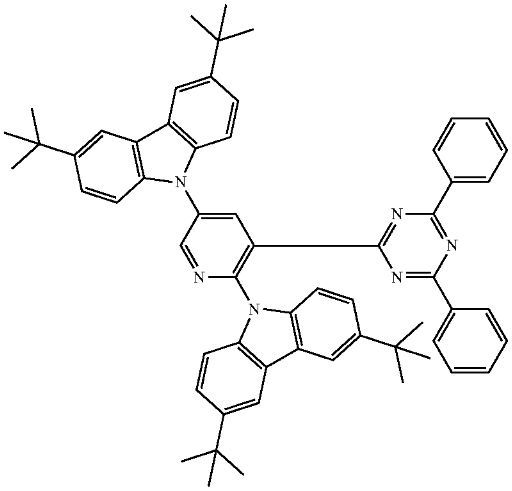 346 | | | | | |
| 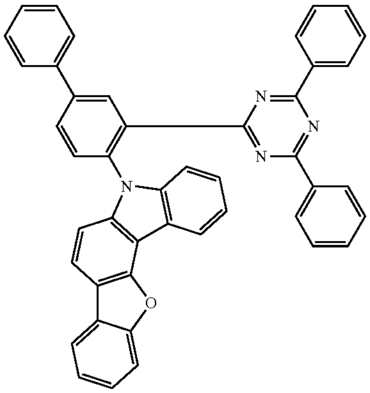 25 | | | | | |
| 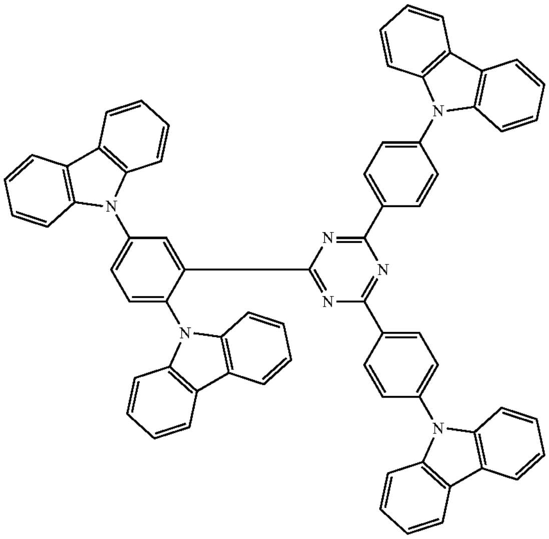 1078 | | | | | |
Referring to Table 2, it is confirmed that Compounds shown in Table 2 have excellent electric characteristics.

Evaluation Example 2: Evaluation of Full Width at Half Maximum (FWHM)

PL spectra of Compounds shown in Table 4 were measured by using methods described in Table 3, and FWHM of each Compound was evaluated. The results thereof are shown in Table 4.

TABLE 3

| | |
|---|---|
| PL spectrum measurement method | Each Compound was diluted at a concentration of $1 \times 10^{-4}$M in toluene, and PL spectrum was measured by using F7000 Spectrofluorometer equipped with a Spxenon (Xenon) lamp (available from Hitachi) (@ 298K). |

TABLE 4

| Compound No. | FWHM (nm) |
|---|---|
| 2 | 65 |
| 1075 | 61 |
| 1076 | 60 |
| 1074 | 65 |
| 1077 | 61 |
| 1 | 62 |
| 13 | 75 |
| 70 | 65 |
| 14 | 72 |
| 71 | 64 |
| 21 | 66 |
| 37 | 65 |
| 46 | 61 |
| 346 | 64 |
| 25 | 69 |
| 1078 | 64 |

Referring to Table 4, it is confirmed that Compounds shown in Table 4 have excellent luminescence characteristics.

Evaluation Example 3: Evaluation of Photoluminescence Quantum Yield (PLQY) and Decay Time (1) Preparation of Thin Film A quartz substrate washed with chloroform and pure water was prepared, and Compound 2 and Compound E4 were co-deposited at a weight ratio of 5:5 at a vacuum degree of $10^{-7}$ torr to manufacture a thin film having a thickness of 50 nanometers (nm).

(2) Evaluation of PLQY

A PLQY of the thin film was evaluated by using Hamamatsu a Photonics absolute PL quantum yield measurement system including a xenon light source, a monochromator, a photonic multichannel analyzer, and an integrating sphere and employing a PLQY measurement software (Hamamatsu Photonics, Ltd., Shizuoka, Japan), and a PLQY of Compound 2 in film was evaluated.

(3) Evaluation of Decay Time

A PL spectrum of the thin film was evaluated at room temperature by using a PicoQuant TRPL measurement system FluoTime 300 and a PicoQuant pumping source PLS340 (excitation wavelength=340 nm, spectral width=20 nm), a wavelength of a main peak of the spectrum was determined, PLS340 repeatedly measured the number of photons emitted from the thin film at the wavelength of the main peak due to a photon pulse (pulse width=500 picoseconds, ps) applied to the thin film according to time based on time-correlated single photon counting (TCSPC), thereby obtaining a sufficiently fittable TRPL curve. $T_{decay}$(Ex) (decay time) of Compound 2 of the thin film was obtained by fitting two or more exponential decay function to the result obtained therefrom. The function used for fitting is expressed by Equation 1, and the greatest value of $T_{decay}$ obtained from each exponential decay function used for fitting was taken as $T_{decay}$(Ex) and shown in Table 5. The remaining values of $T_{decay}$ may be used to determine a lifetime of a decay of a general fluorescence. At this time, a baseline or background signal curve was obtained by repeating the same measurement once more for the same measurement time as the measurement time for obtaining the TRPL curve in a dark state (a state in which a pumping signal applied to the predetermined film was blocked), and the baseline or background signal curve was fitted and used as a baseline.

$$f(t) = \sum_{i=1}^{n} A_i \exp(-t/T_{decay,i}) \quad \text{Equation 1}$$

(4) Table 5

The procedures of the above (1) to (3) were repeated with respect to the remaining Compounds of Table 5, and results thereof are shown in Table 5.

TABLE 5

| Compound No. | PLQY | $T_{decay}$(EX) (μs) (decay time) |
|---|---|---|
| 2 | 0.57 | 12.63 |
| 1075 | 0.41 | 32.679 |
| 1076 | 0.7 | 44.3 |
| 1074 | 0.63 | 25.08 |
| 1077 | 0.38 | 41.5 |
| 1 | 0.45 | 58.6 |
| 13 | 0.51 | 60.1 |
| 70 | 0.47 | 10.3 |
| 14 | 0.66 | 24.2 |
| 71 | 0.52 | 10.6 |
| 21 | 0.34 | 56 |
| 37 | 0.6 | 19 |
| 46 | 0.3 | 86.2 |
| 346 | 0.44 | 20.3 |
| 25 | 0.52 | 20.9 |
| 1078 | 0.44 | 61.1 |

Referring to Table 5, it is confirmed that Compounds shown in Table 5 have excellent PLQY (in film) and decay time characteristics.

Example 1

A glass substrate, on which a 1,500 Å-thick ITO electrode (first electrode, anode) was formed, was sonicated with distilled water. After the washing with distilled water was completed, ultrasonic wave washing was performed by using a solvent such as iso-propyl alcohol, acetone, and methanol, and the glass substrate was dried and then transferred to a plasma cleaner. The glass substrate was cleaned for 5 minutes by using oxygen plasma and provided to a vacuum deposition apparatus.

Compound HT3 and Compound HT-D2 were co-deposited on the ITO electrode of the glass substrate to form a hole injection layer having a thickness of 100 Å, Compound HT3 was deposited on the hole injection layer to form a hole transport layer having a thickness of 1,350 Å, and mCP was deposited on the hole transport layer to form an electron blocking layer having a thickness of 100 Å, thereby forming a hole transport region.

A host and a dopant were co-deposited on the hole transport region at a weight ratio of 85:15 to form an emission layer having a thickness of 300 Å. Compound E4 was used as the host, and Compound 2 was used as the dopant.

Compound BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was deposited on the electron injection layer to form a second electrode (cathode) having a thickness of 1,000 Å, thereby completing the manufacture of an organic light-emitting device.

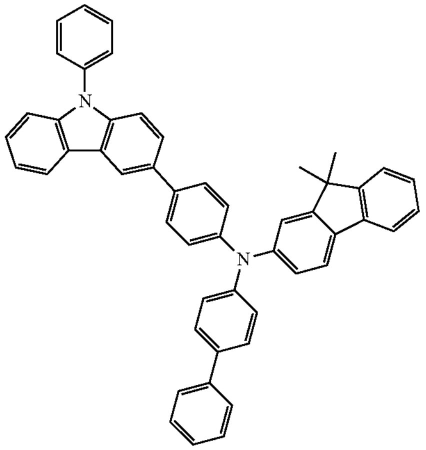

HT3

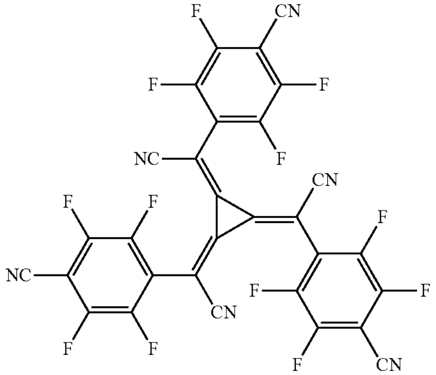

HT-D2

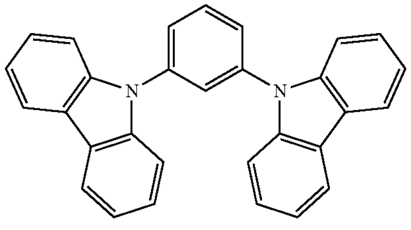

mCP

-continued

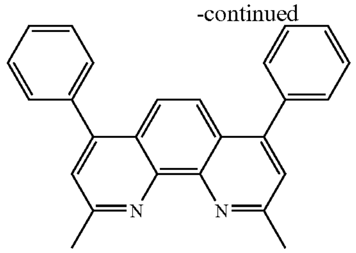

BCP

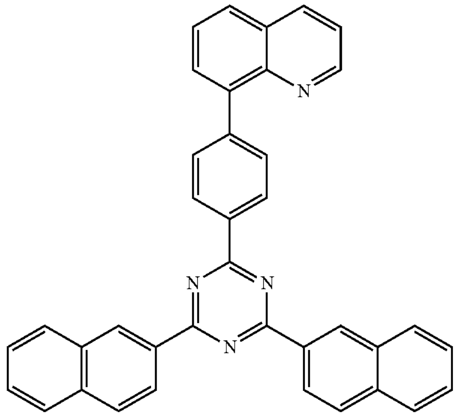

ET3

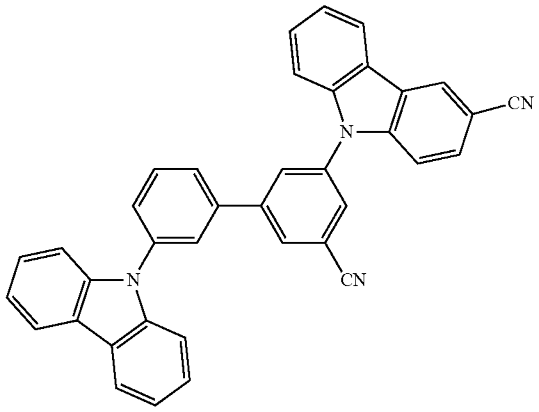

E4

Examples 2 to 8 and Comparative Examples A-1 to D

Organic light-emitting devices were manufactured in the same manner as in Example 1, except that the dopant in the emission layer was changed as shown in Table 6.

Evaluation Example 4: Evaluation of Device Data

The driving voltage, luminescence efficiency, and lifespan ($T_{95}$) of each of Examples 1 to 8 and Comparative Examples A-1 to D were measured by using a current-voltage meter (Keithley 2400) and a luminance meter (Minolta Cs-1000A), and the results thereof are shown in Table 6. The lifespan ($T_{95}$) data (at 500 candelas per square meter, cd/$m^2$) in Table 6 indicates an amount of time (hours, hr) that lapsed when luminance was 95% of initial luminance (100%). The luminescence efficiency and the lifespan are relative values with respect to the luminescence efficiency and the lifespan of Example 2.

TABLE 6

| | Dopant No. | Driving voltage (V) | Luminescence efficiency (relative value, %) | Lifespan ($T_{95}$) (relative value, %) |
|---|---|---|---|---|
| Example 1 | 2 | 4.26 | 129 | 1152 |
| Example 2 | 1076 | 4.503 | 100 | 100 |
| Example 3 | 1074 | 4.249 | 121 | 352 |
| Example 4 | 13 | 4.312 | 127 | 102 |
| Example 5 | 14 | 4.212 | 142 | 1354 |
| Example 6 | 37 | 4.259 | 141 | 1287 |
| Example 7 | 346 | 4.461 | 147 | 585 |
| Example 8 | 25 | 3.89 | 134 | 354 |
| Example 9 | 1078 | 4.561 | 113 | 94 |
| Comparative Example A-1 | A-1 | 5.267 | 18 | 1 |
| Comparative Example A-2 | A-2 | 5.976 | 13 | 7 |
| Comparative Example A-3 | A-3 | 4.193 | 70 | 30 |
| Comparative Example A-4 | A-4 | 4.663 | 81 | 54 |
| Comparative Example A-5 | A-5 | 4.574 | 111 | 61 |
| Comparative Example B-1 | B-1 | 5.2 | 38 | 1 |
| Comparative Example B-2 | B-2 | 5.063 | 33 | 4 |
| Comparative Example B-3 | B-3 | 4.219 | 106 | 41 |
| Comparative Example B-4 | B-4 | 4.12 | 81 | 65 |
| Comparative Example B-5 | B-5 | 4.149 | 97 | 31 |
| Comparative Example B-6 | B-6 | 4.595 | 70 | 9 |
| Comparative Example C-1 | C-1 | 8.2 | 8 | 0 |
| Comparative Example C-2 | C-2 | 10.2 | 8 | 0 |
| Comparative Example C-3 | C-3 | 7.5 | 22 | 0 |
| Comparative Example D | D | 6.1 | 87 | 20 |

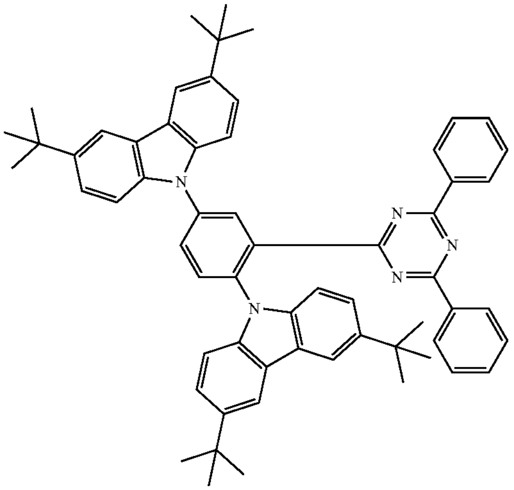

2

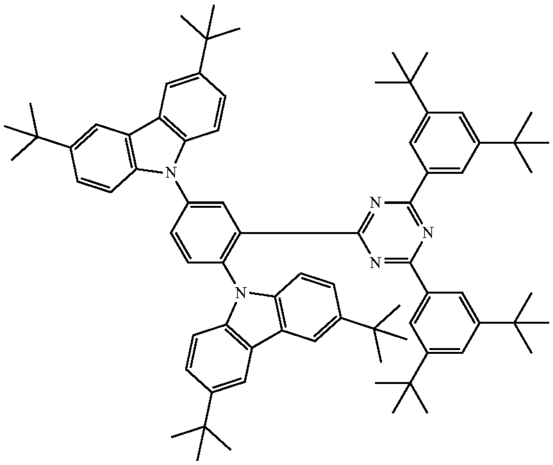

1076

TABLE 6-continued
| | Dopant No. | Driving voltage (V) | Luminescence efficiency (relative value, %) | Lifespan ($T_{95}$) (relative value, %) |
|---|---|---|---|---|
| 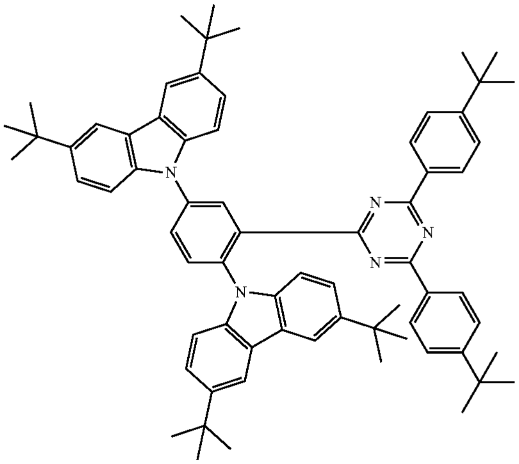 | 1074 | | | |
| 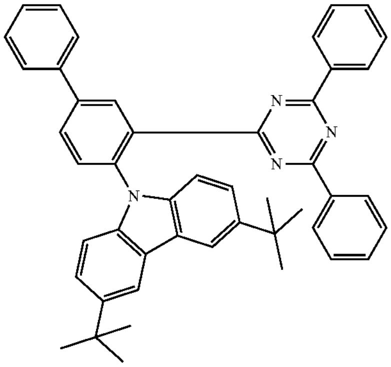 | 13 | | | |
| 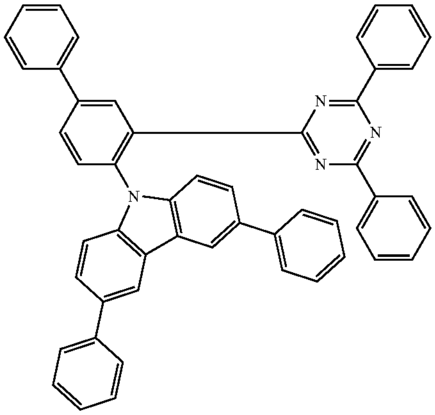 | 14 | | | |

TABLE 6-continued
| | Dopant No. | Driving voltage (V) | Luminescence efficiency (relative value, %) | Lifespan ($T_{95}$) (relative value, %) |
|---|---|---|---|---|
| 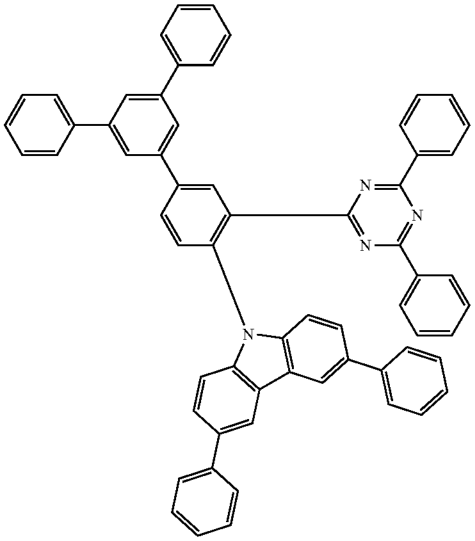 | 37 | | | |
| 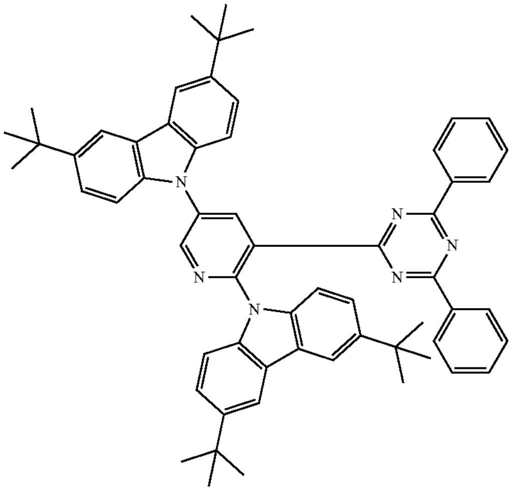 | 346 | | | |
| 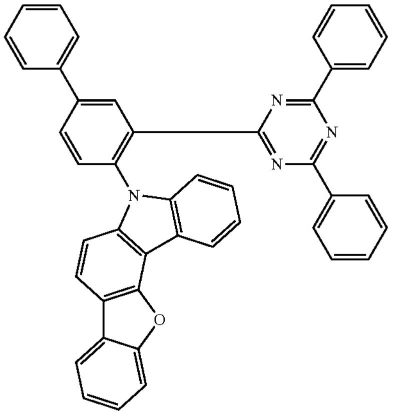 | 25 | | | |

TABLE 6-continued
| | Dopant No. | Driving voltage (V) | Luminescence efficiency (relative value, %) | Lifespan ($T_{95}$) (relative value, %) |
|---|---|---|---|---|
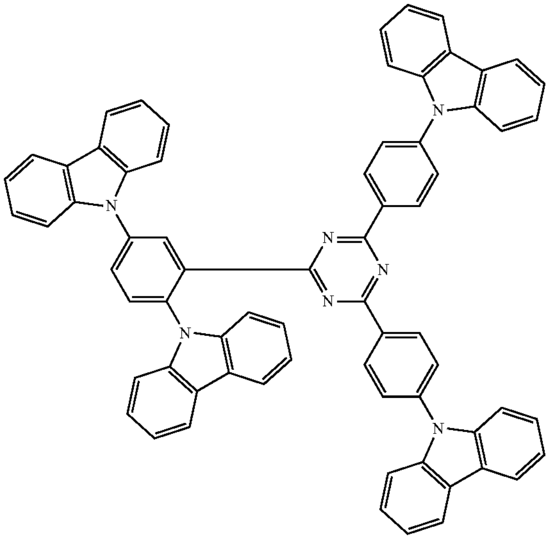
1078
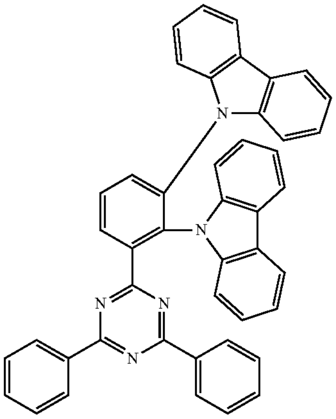
A-1
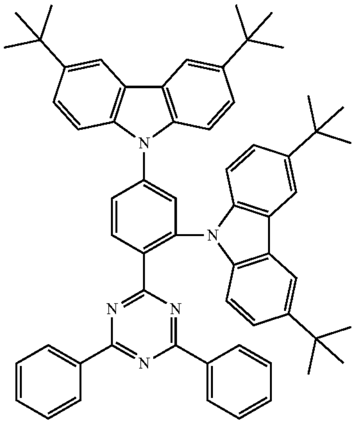
A-2

TABLE 6-continued
| Dopant No. | Driving voltage (V) | Luminescence efficiency (relative value, %) | Lifespan ($T_{95}$) (relative value, %) |
|---|---|---|---|
| 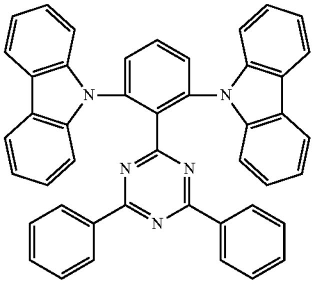 A-3 | | | |
| 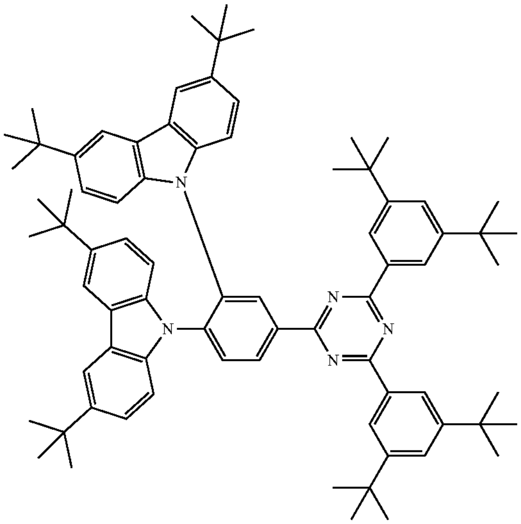 A-4 | | | |
| 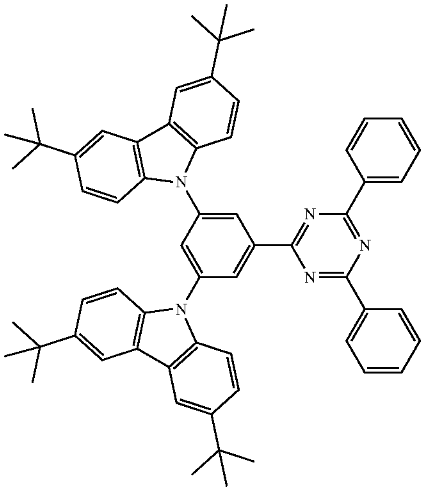 A-5 | | | |

TABLE 6-continued
| | Dopant No. | Driving voltage (V) | Luminescence efficiency (relative value, %) | Lifespan ($T_{95}$) (relative value, %) |
|---|---|---|---|---|
| 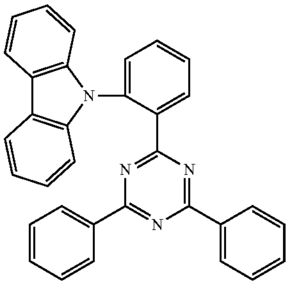 B-1 | | | | |
| 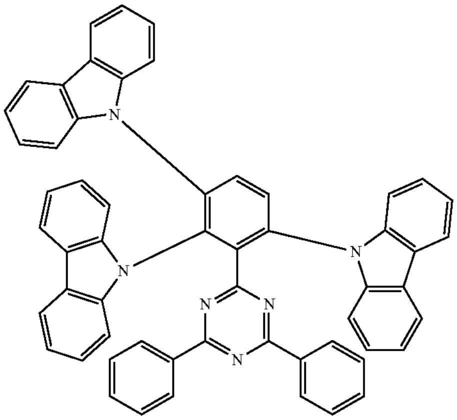 B-2 | | | | |
| 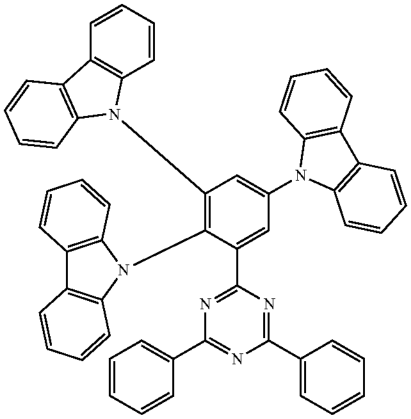 B-3 | | | | |
| 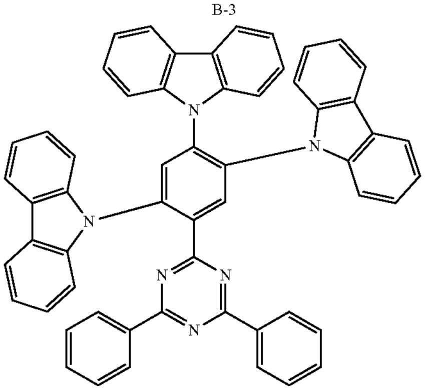 B-4 | | | | |

TABLE 6-continued
| | Dopant No. | Driving voltage (V) | Luminescence efficiency (relative value, %) | Lifespan ($T_{95}$) (relative value, %) |
|---|---|---|---|---|
| 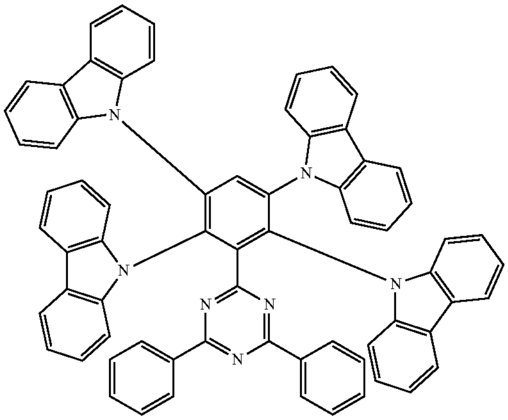 B-5 | | | | |
| 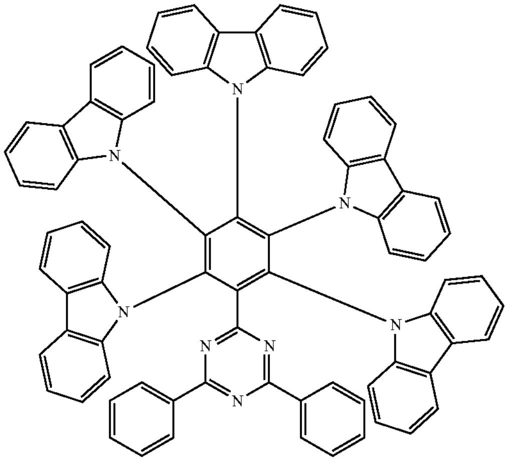 B-6 | | | | |
| 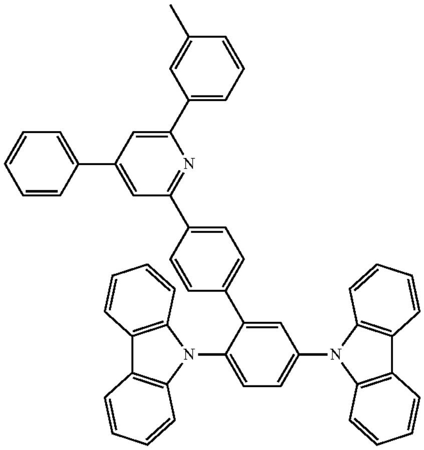 C-1 | | | | |

TABLE 6-continued

| | Dopant No. | Driving voltage (V) | Luminescence efficiency (relative value, %) | Lifespan ($T_{95}$) (relative value, %) |
|---|---|---|---|---|

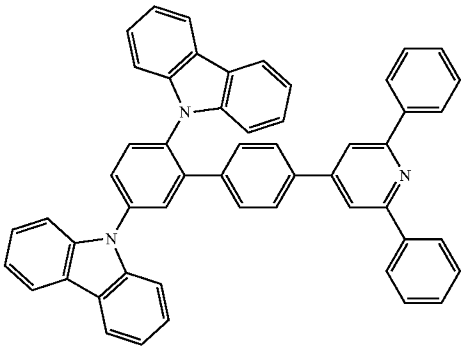

C-2

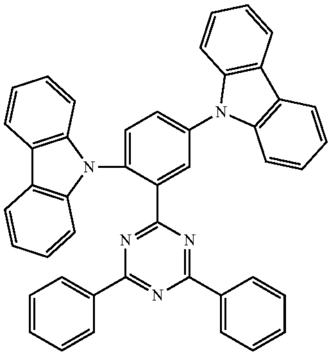

C-3

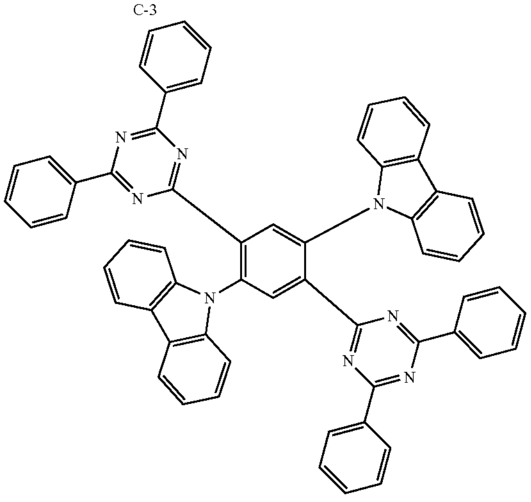

D

Referring to Table 6, it is confirmed that the organic light-emitting devices of Examples 1 to 8 have excellent driving voltage, luminescence efficiency and lifespan "at the same time", as compared with those of the organic light-emitting devices of Comparative Examples A-1 to A-5, B-1 to B-6, C-1 to C-3, and D.

Since the heterocyclic compound has excellent electric characteristics and thermal stability, the organic light-emitting device including the heterocyclic compound may have low driving voltage, low driving voltage, high luminescence efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A heterocyclic compound represented by Formula 1:

Formula 1

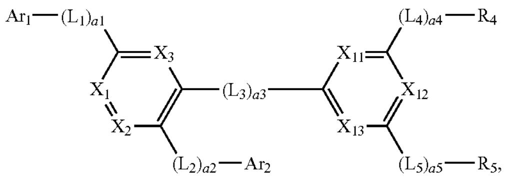

wherein, in Formula 1, $X_1$ is N or $C(R_1)$, $X_2$ is N or $C(R_2)$, and $X_3$ is N or $C(R_3)$, wherein i) one selected from $X_1$ to $X_3$ is N, and the others thereof are not N; or ii) each of $X_1$ to $X_3$ is not N, $R_1$ to $R_3$ are each independently hydrogen, deuterium, a $C_1$-$C_{20}$ alkyl group, a $C_1$-$C_{20}$ alkyl group substituted with at least one deuterium, a $C_1$-$C_{20}$ alkoxy group, a $C_1$-$C_{20}$ alkoxy group substituted with at least one deuterium, or —$Si(Q_{101})(Q_{102})(Q_{103})$, $L_1$ and $L_2$ are each a single bond, $L_3$ to $L_5$ are each independently selected from:

a single bond; and a $C_5$-$C_{60}$ carbocyclic group and a $C_1$-$C_{60}$ heterocyclic group, each unsubstituted or substituted with at least one $R_{10a}$, a1 to a5 are each independently an integer from 1 to 5, and $Ar_2$ is a group represented by Formula 3A, a group represented by Formula 3B, a group represented by Formula 3C, a group represented by Formula 3D, a group represented by Formula 3E, or a group represented by Formula 3F, $Ar_1$ is a group represented by one selected from Formulae D'-1 to D'-7 and D007 to D279:

D'-1

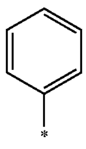

D'-2

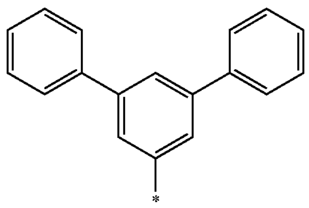

D'-3

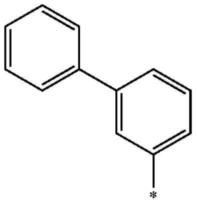

-continued

D'-4

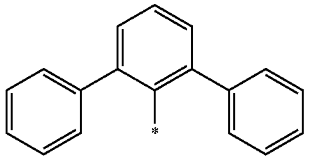

D'-5

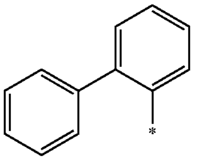

D'-6

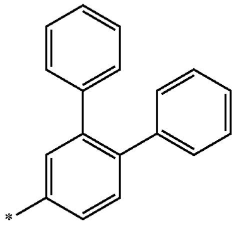

D'-7

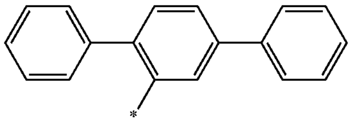

D007

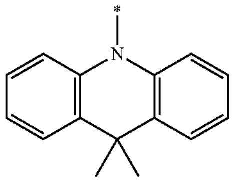

D008

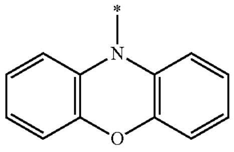

D009

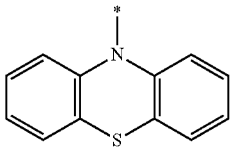

D010

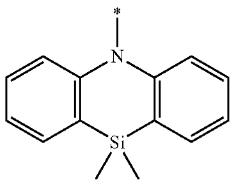

D011

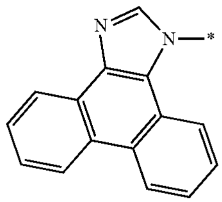

-continued
D012
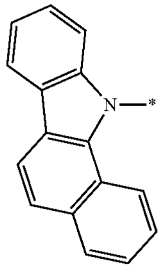
D013
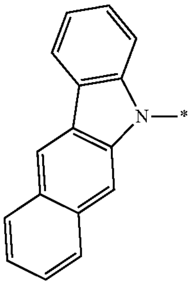
D014
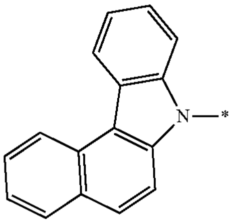
D015
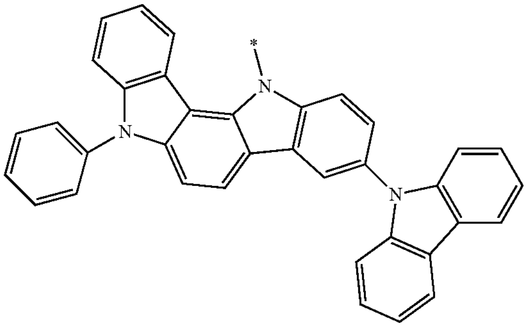
D016
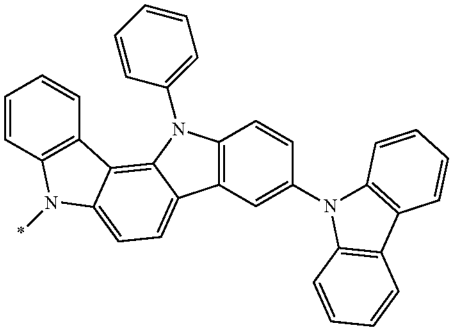
-continued
D017
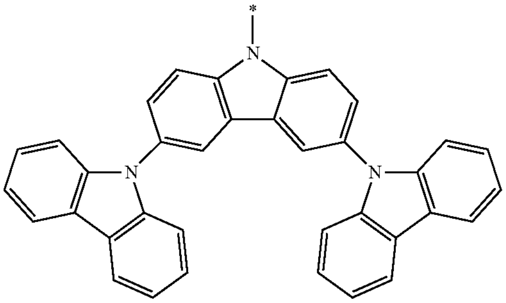
D018
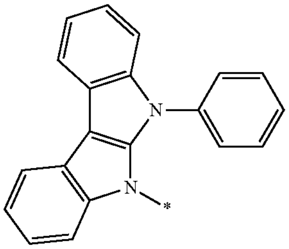
D019
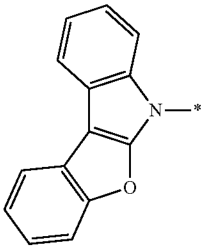
D020
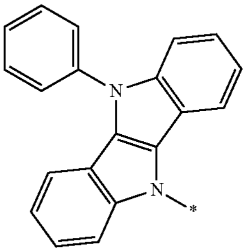
D021
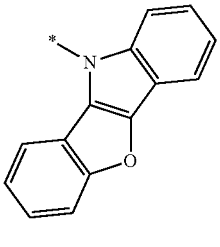
D022
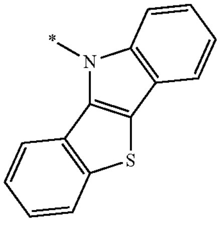

-continued
D023
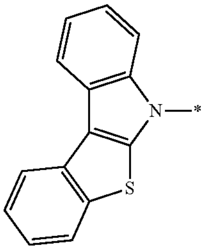
D024
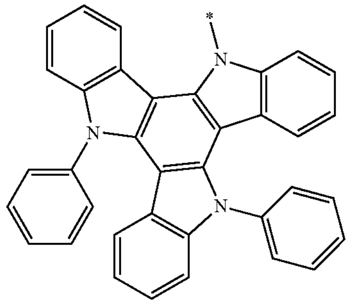
D025
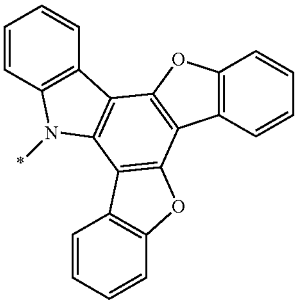
D026
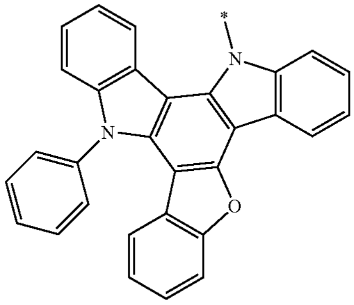
D027
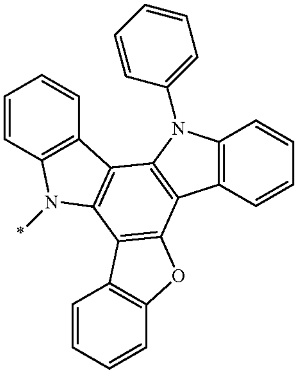
-continued
D028
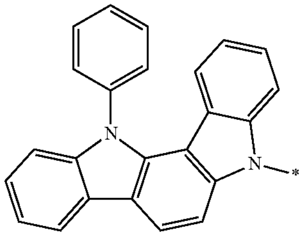
D029
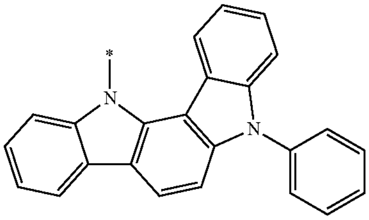
D030
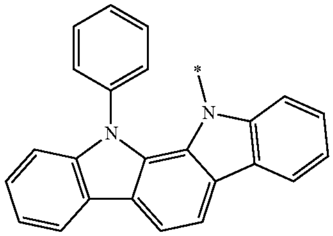
D031
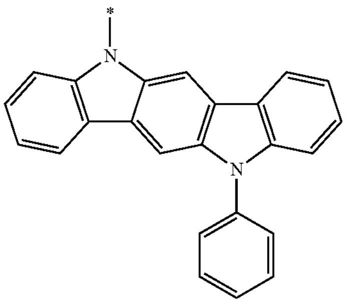
D032
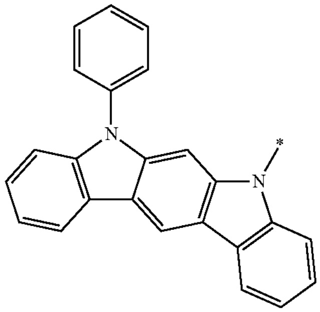

-continued
D033
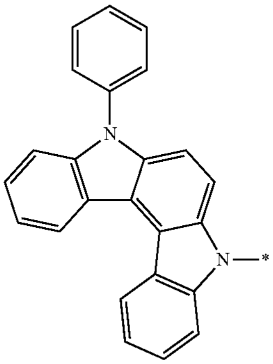
D034
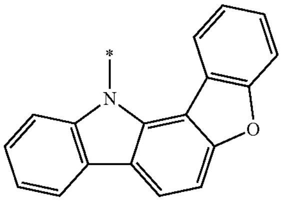
D035
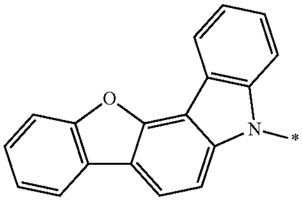
D036
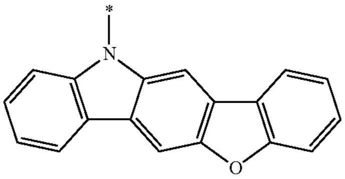
D037
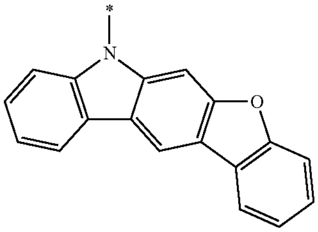
D038
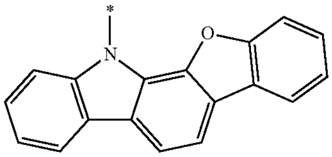
-continued
D039
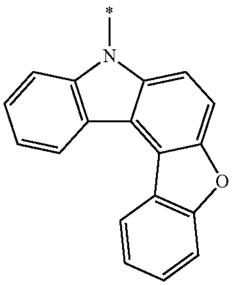
D040
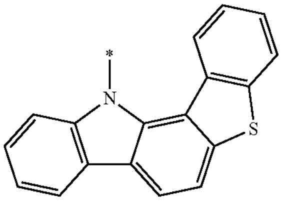
D041
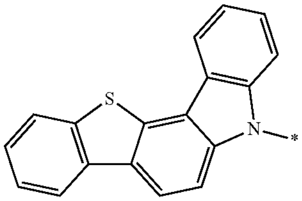
D042
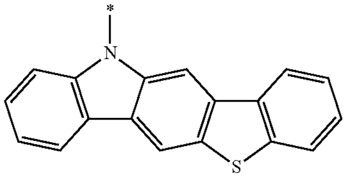
D043
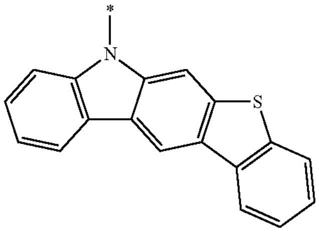
D044
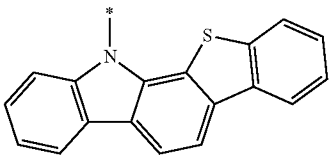
D045
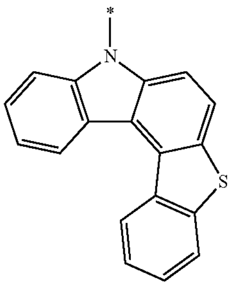

-continued
D046
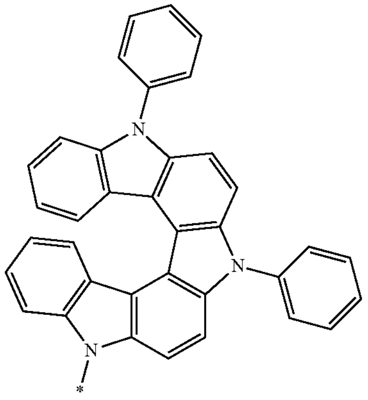
D047
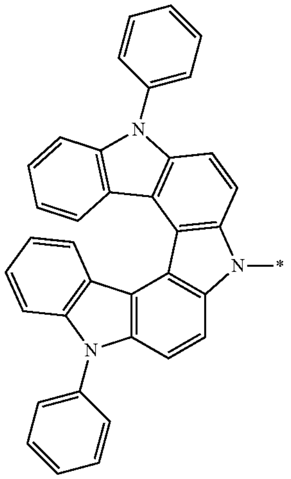
D048
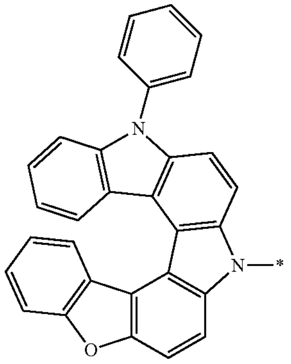
D049
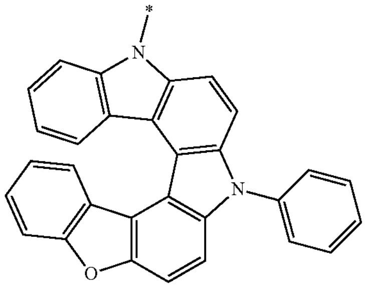
-continued
D050
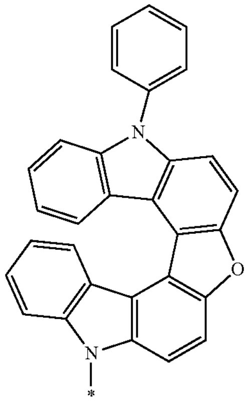
D051
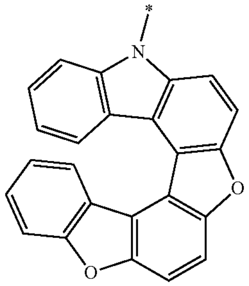
D052
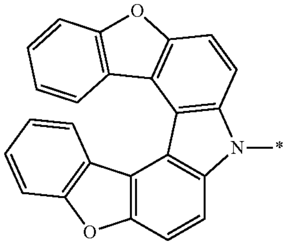
D053
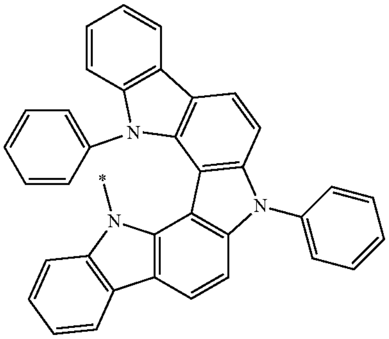
D054
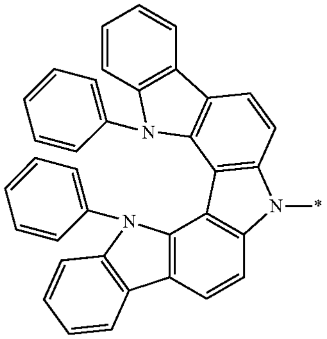

-continued
D055
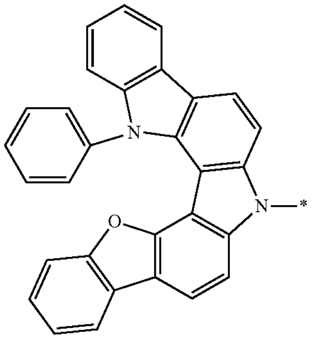
D056
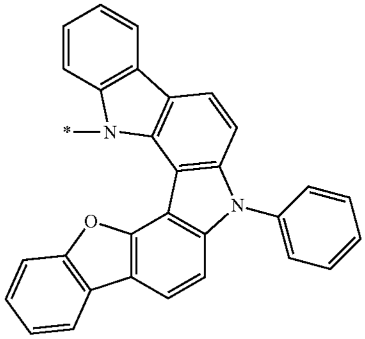
D057
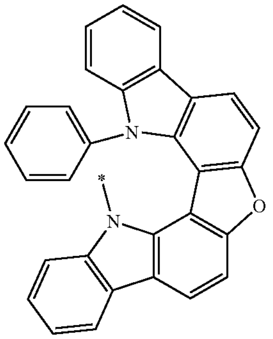
D058
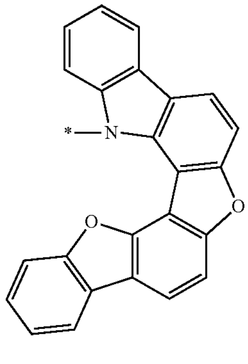
-continued
D059
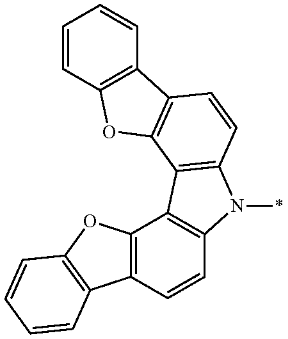
D060
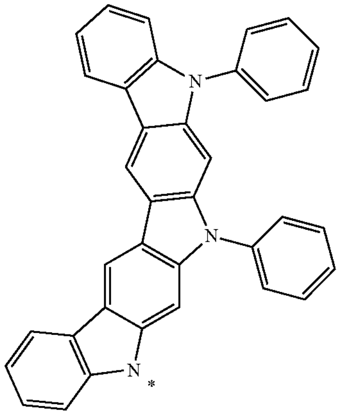
D061
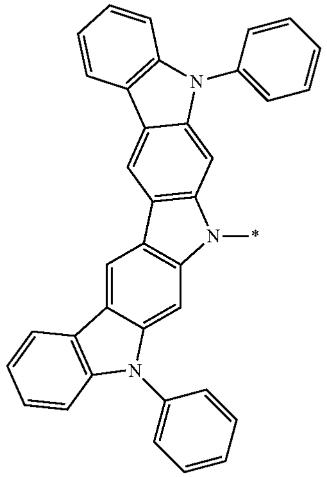
D062
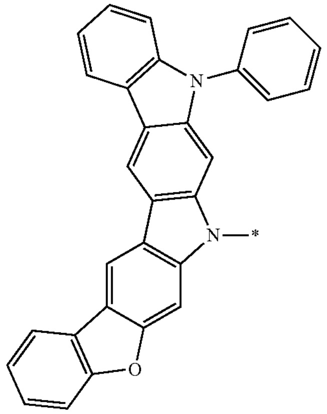

-continued
D063
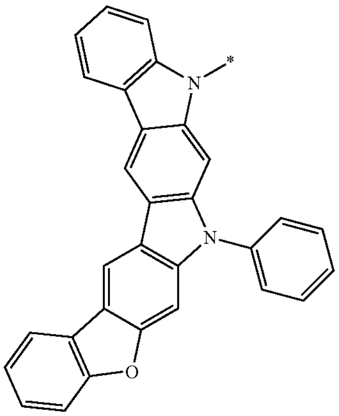
D064
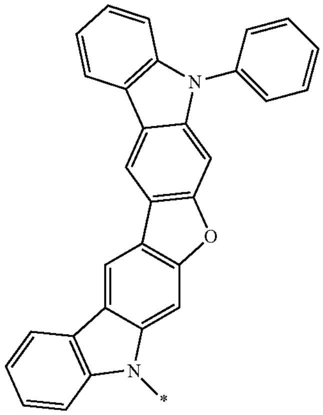
D065
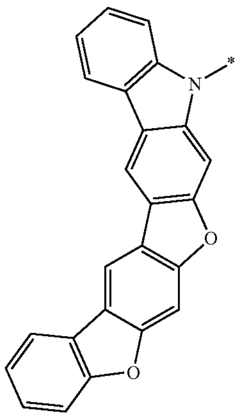
-continued
D066
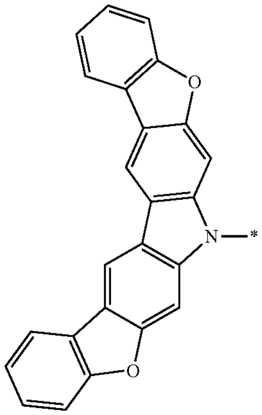
D067
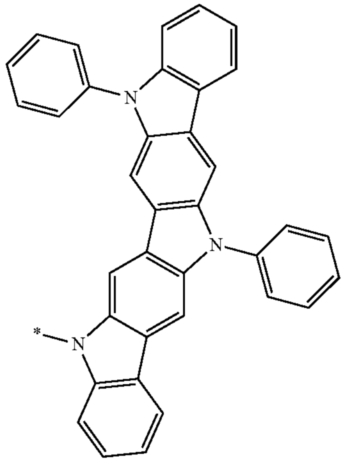
D068
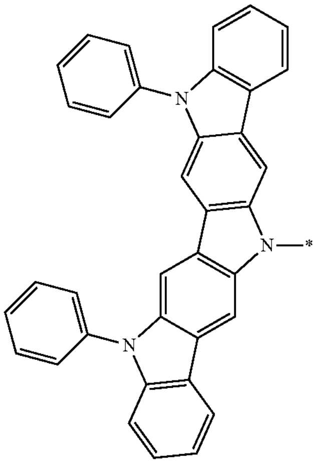

-continued
D069
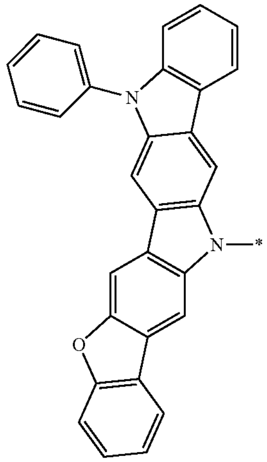
D070
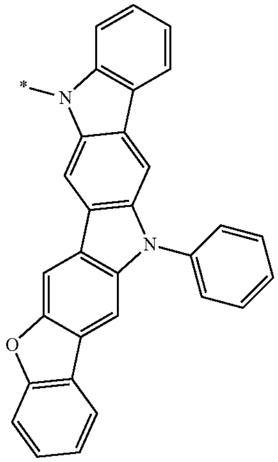
D071
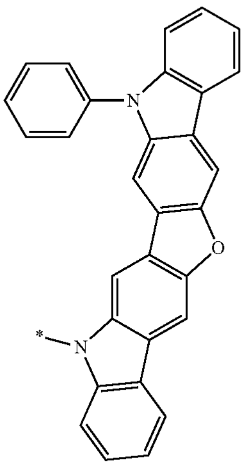
-continued
D072
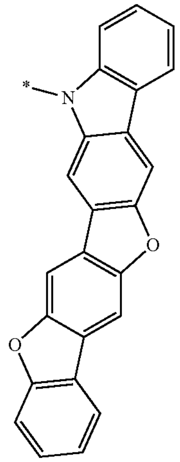
D073
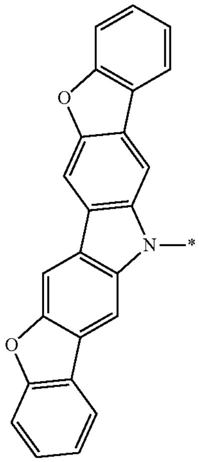
D074
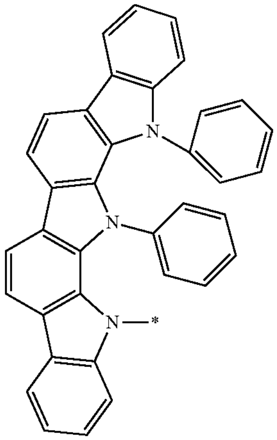

-continued
D075
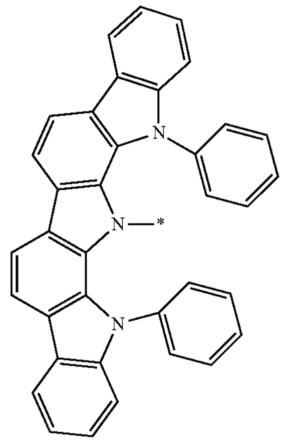
D076
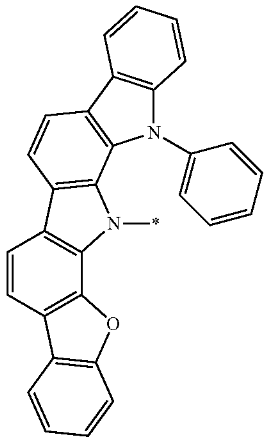
D077
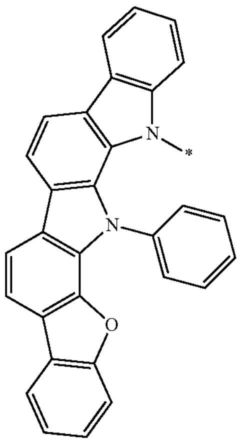
-continued
D078
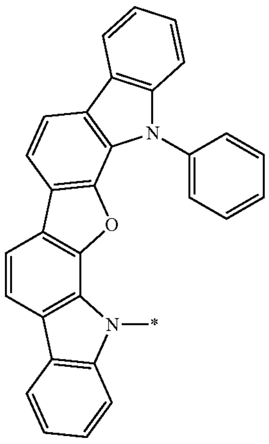
D079
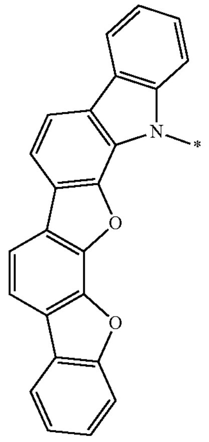
D080
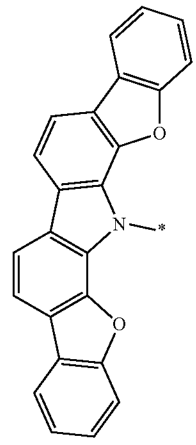

-continued
D081
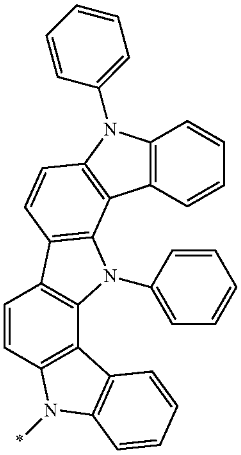
D082
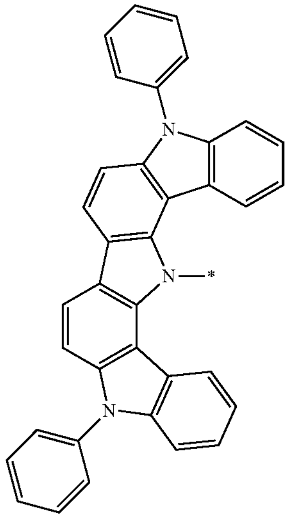
D083
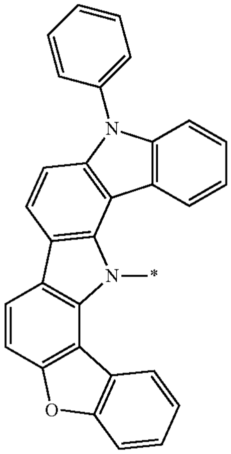
-continued
D084
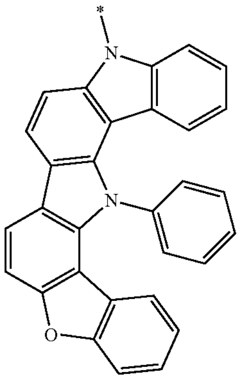
D085
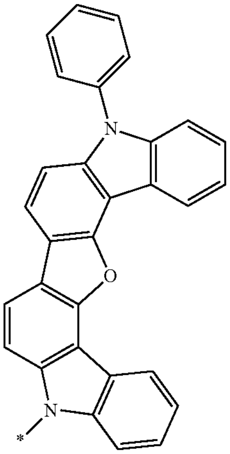
D086
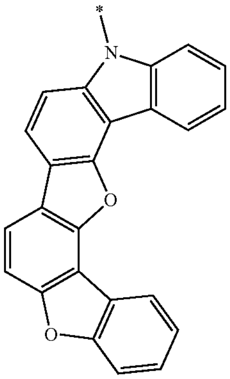
D087
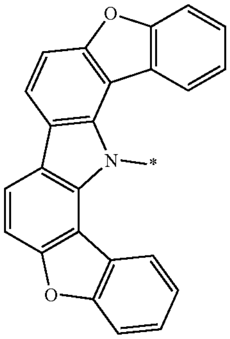

D088
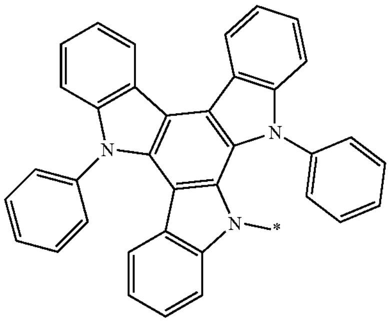
D089
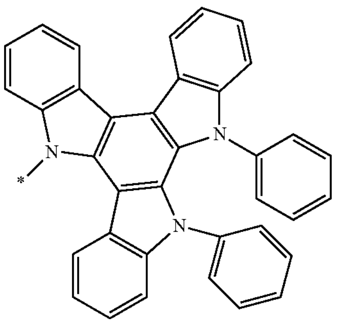
D090
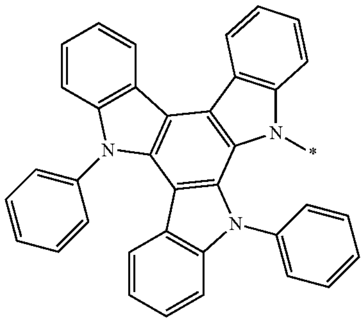
D091
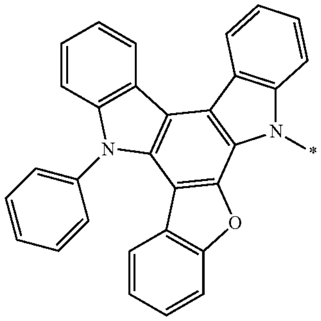
D092
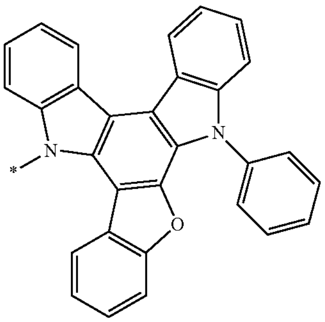
D093
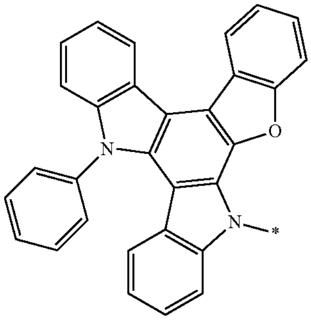
D094
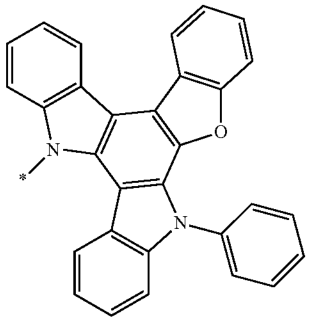
D095
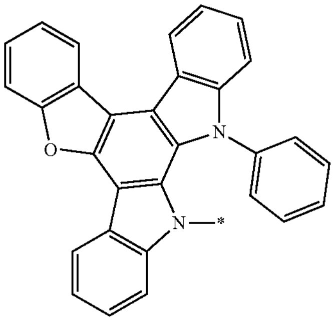
D096
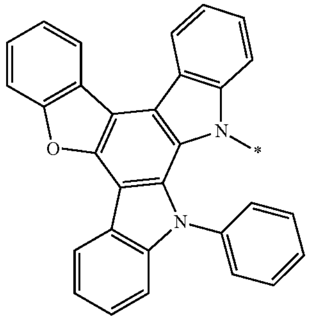
D097
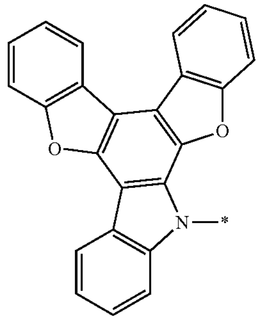

-continued
D098
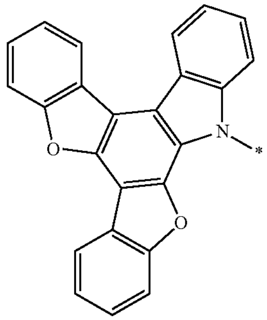
D099
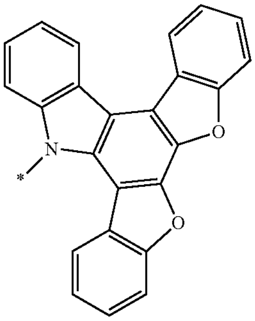
D100
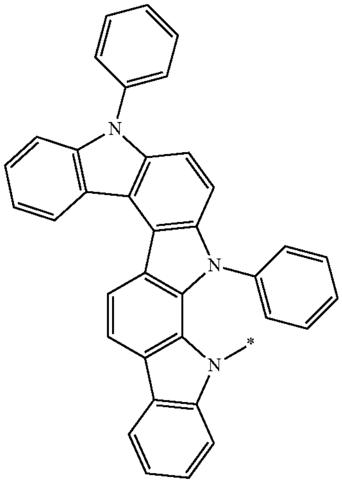
D101
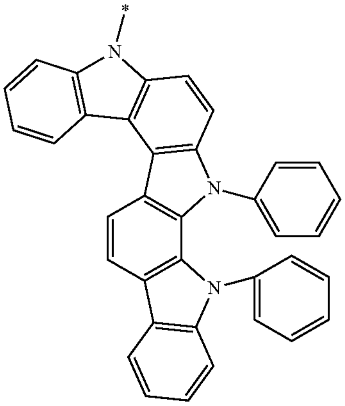
-continued
D102
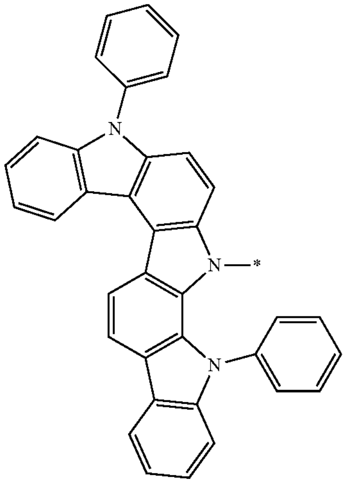
D103
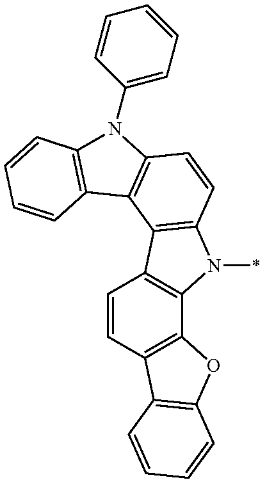
D104
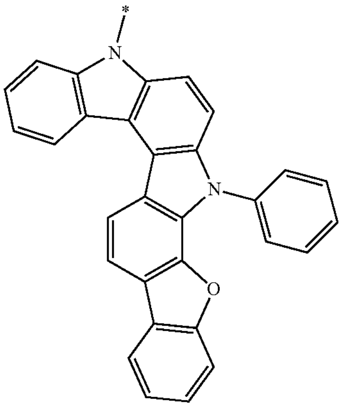

-continued
D105
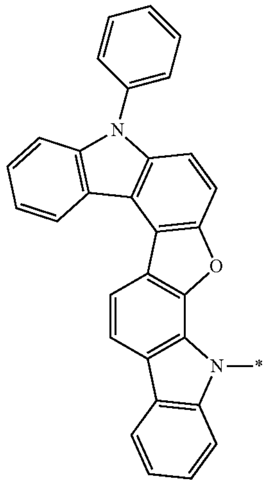
D106
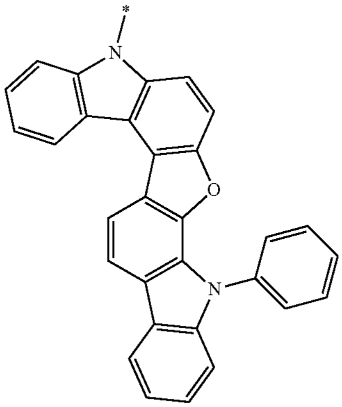
D107
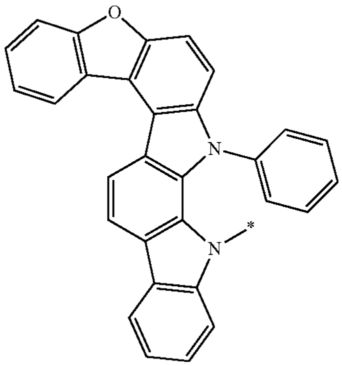
D108
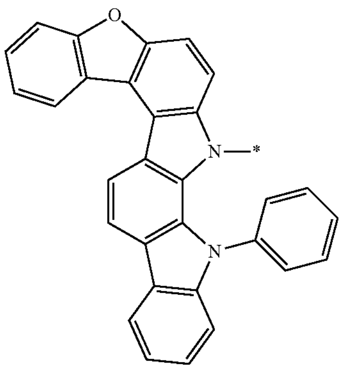
-continued
D109
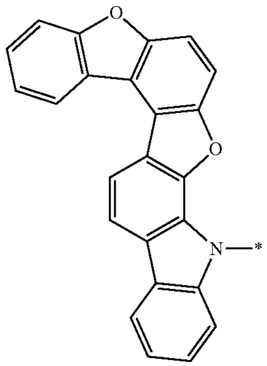
D110
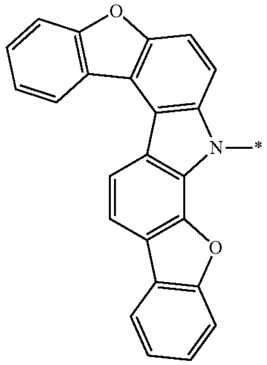
D111
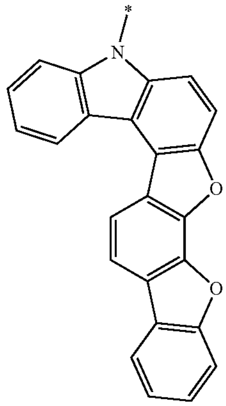
D112
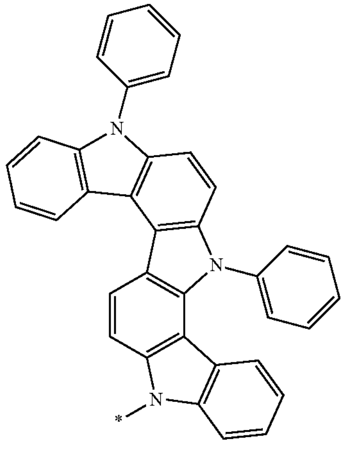

-continued
D113
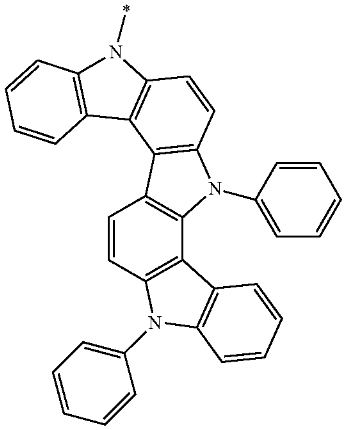
D114
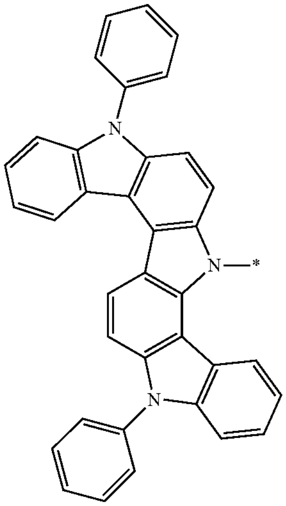
D115
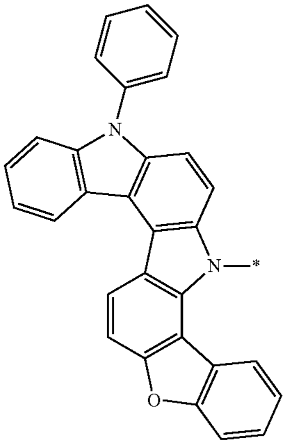
-continued
D116
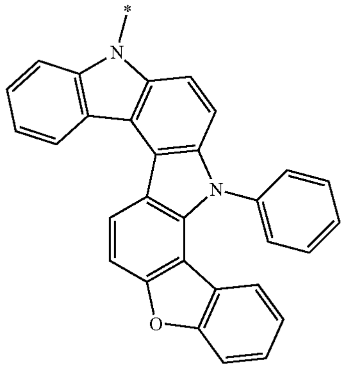
D117
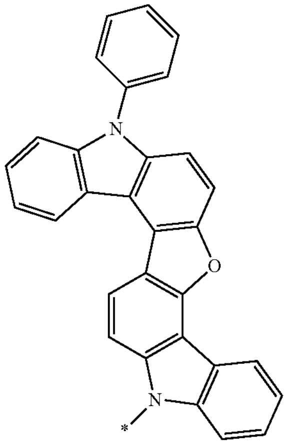
D118
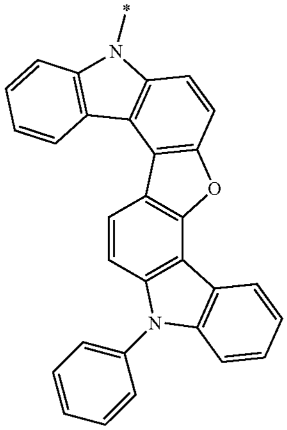
D119
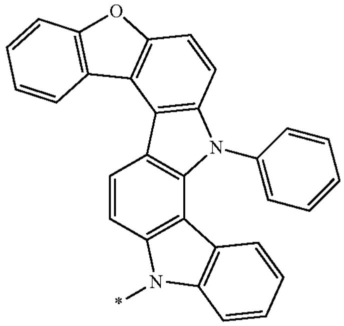

-continued
D120
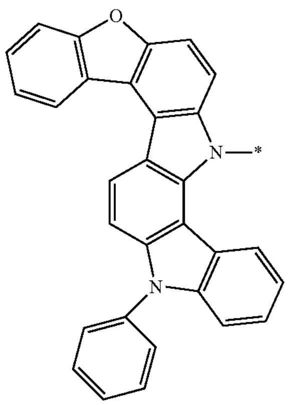
D121
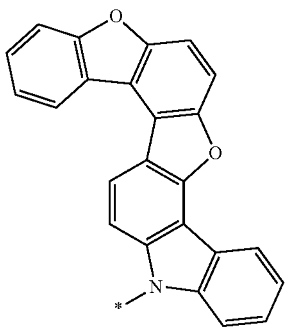
D122
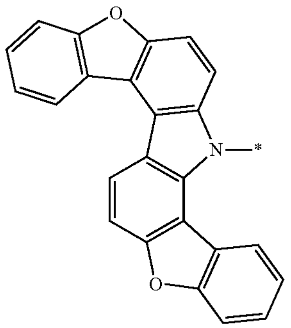
D123
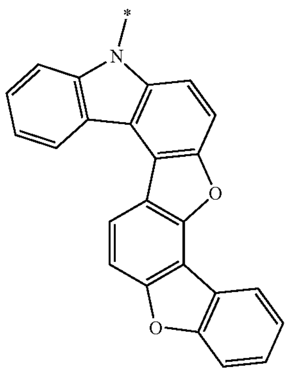
-continued
D124
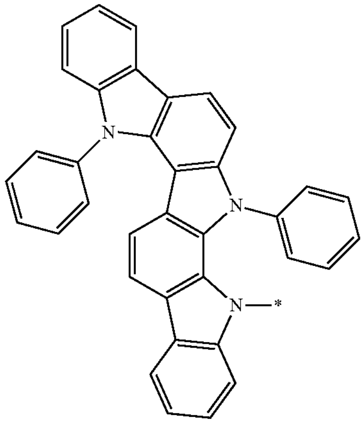
D125
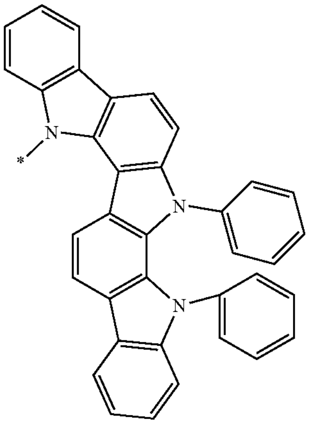
D126
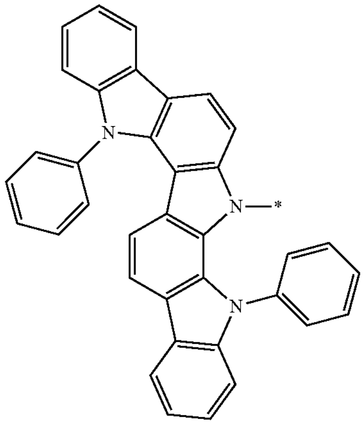

-continued
D127
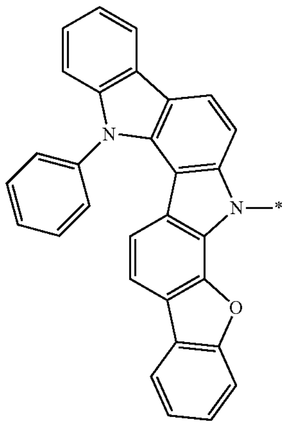
D128
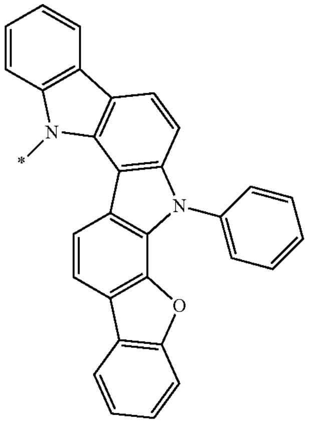
D129
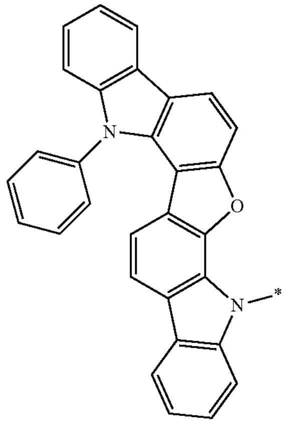
-continued
D130
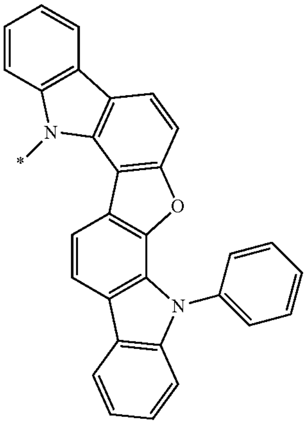
D131
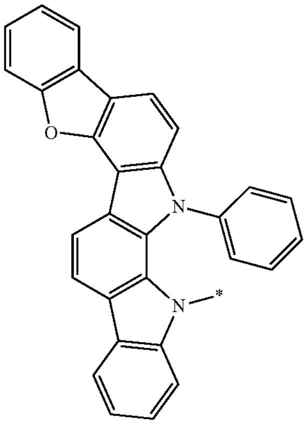
D132
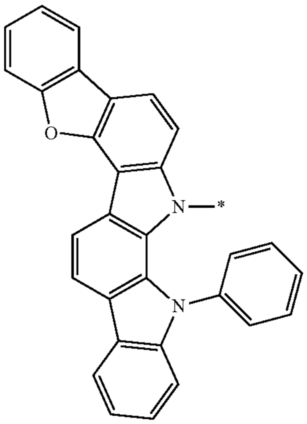

-continued
D133
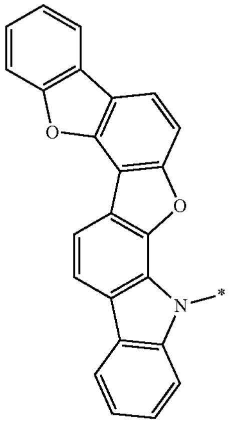
D134
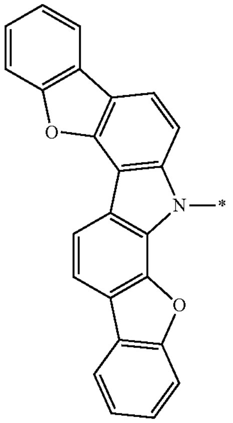
D135
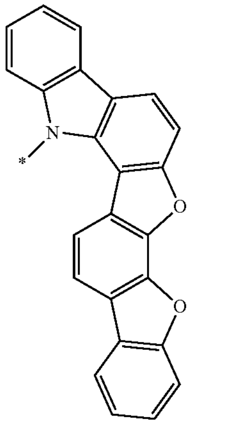
-continued
D136
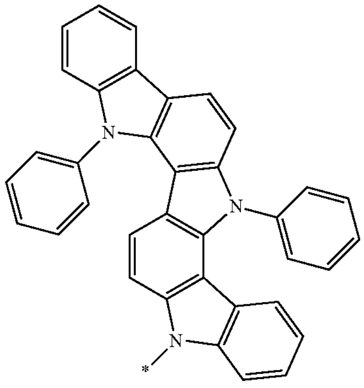
D137
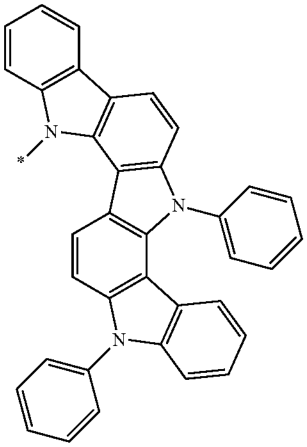
D138
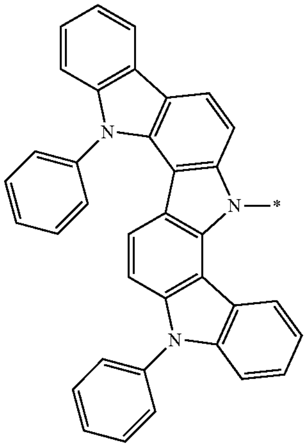

-continued
D139
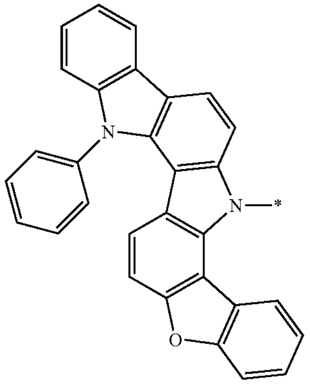
D140
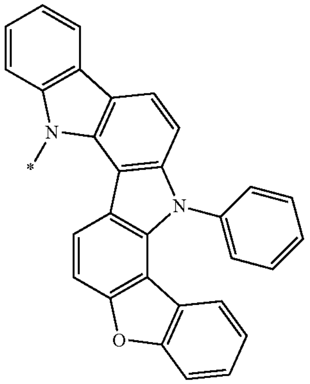
D141
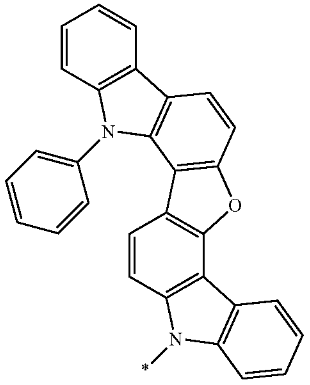
D142
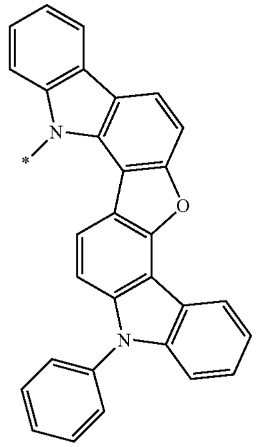
-continued
D143
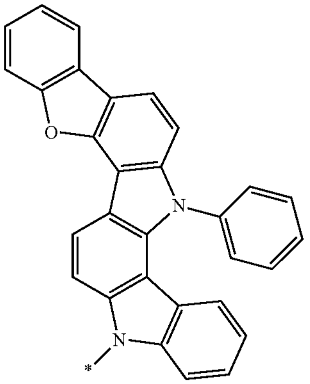
D144
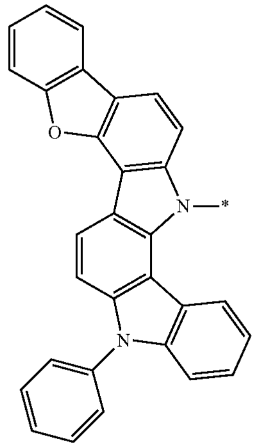
D145
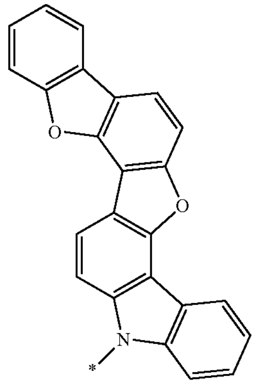
D146
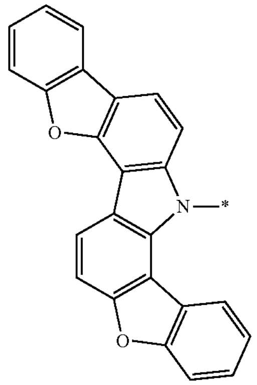

D147
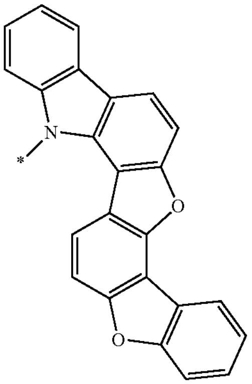
D148
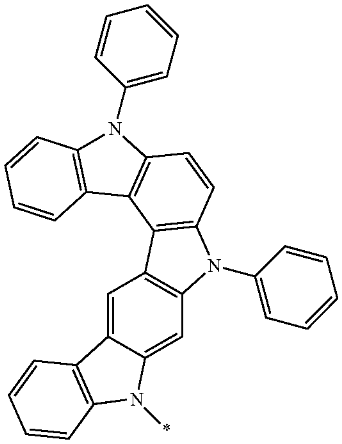
D149
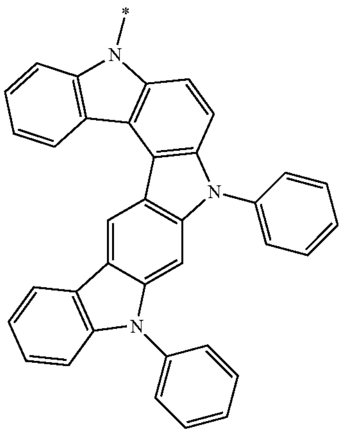
D150
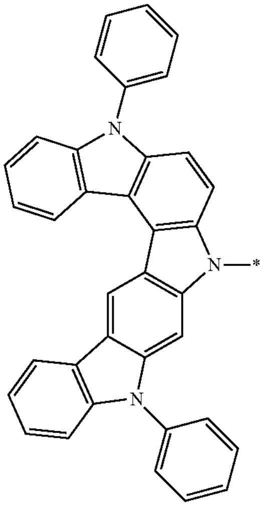
D151
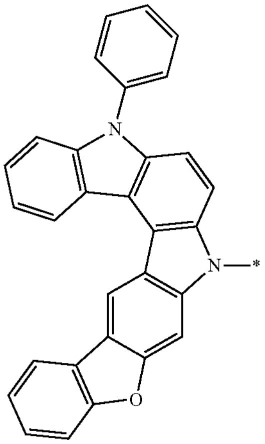
D152
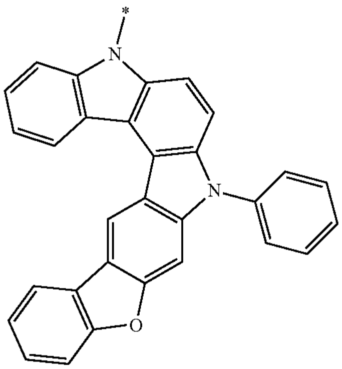

-continued
D153
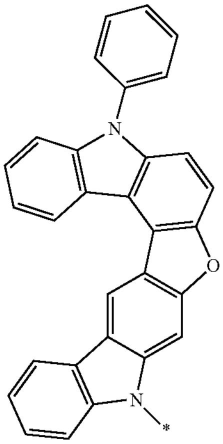
D154
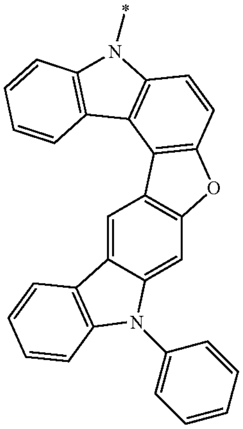
D155
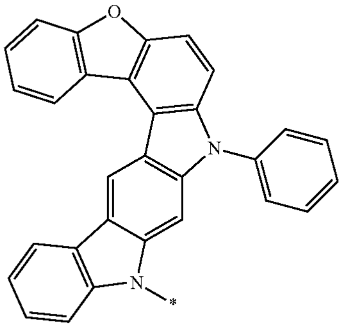
D156
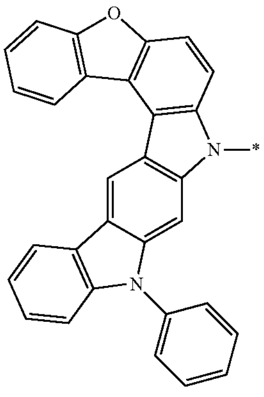
-continued
D157
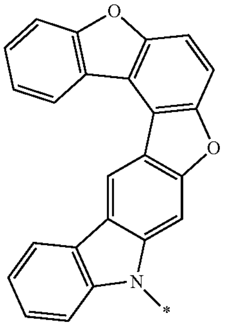
D158
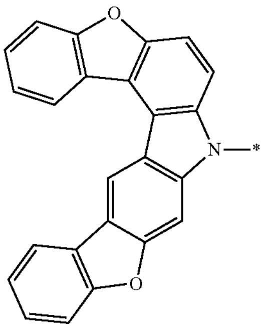
D159
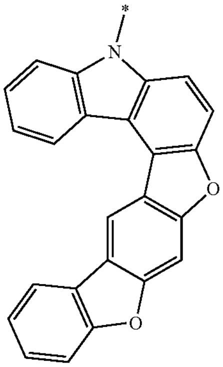
D160
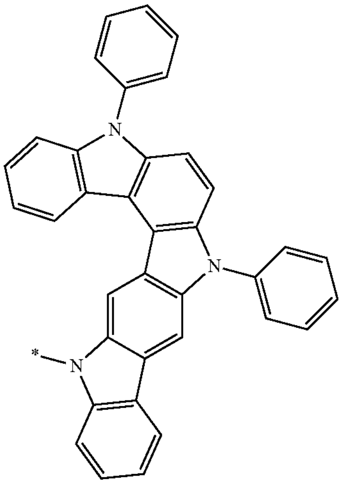

-continued
D161
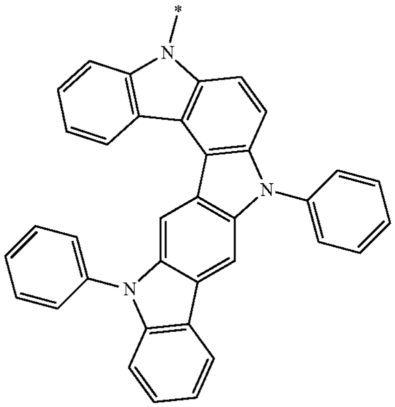
D162
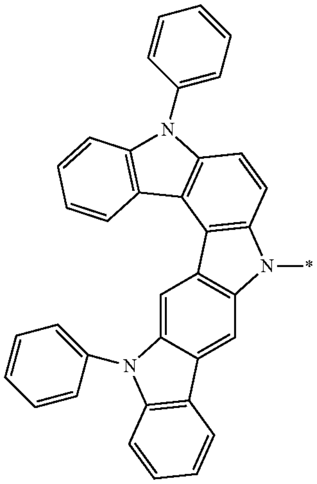
D163
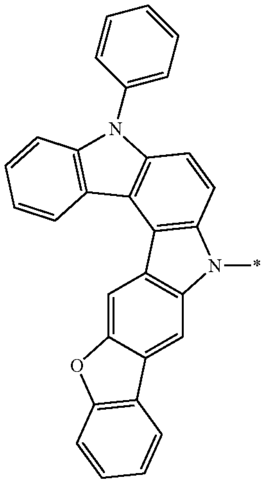
-continued
D164
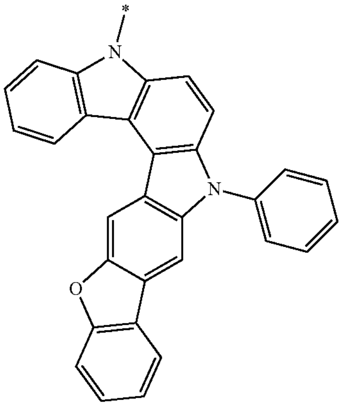
D165
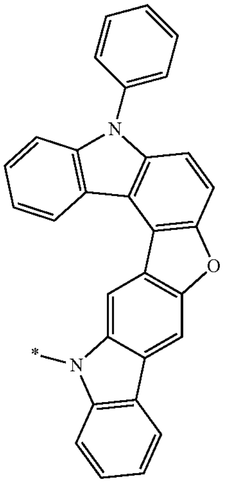
D166
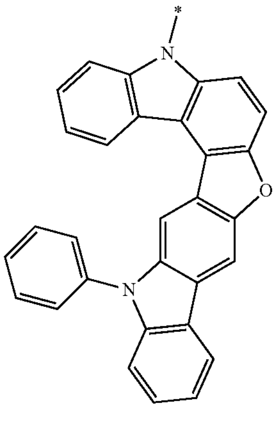

-continued
D167
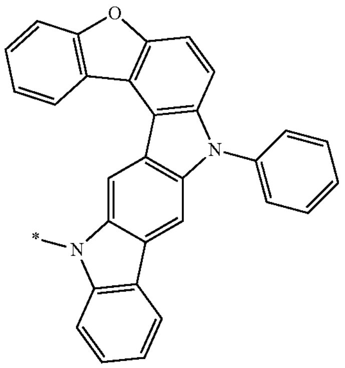
D168
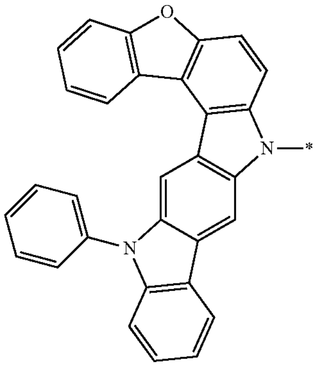
D169
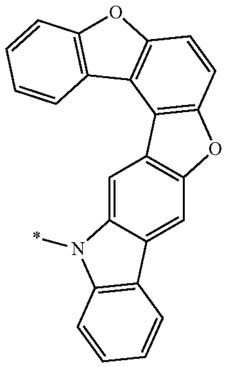
D170
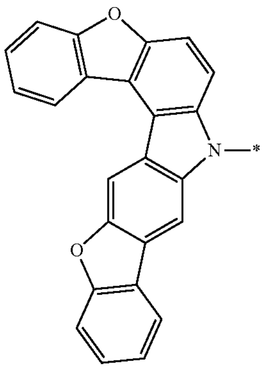
-continued
D171
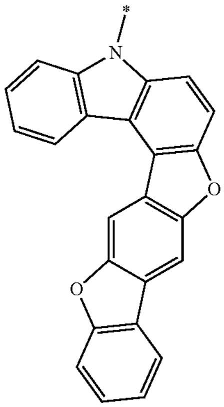
D172
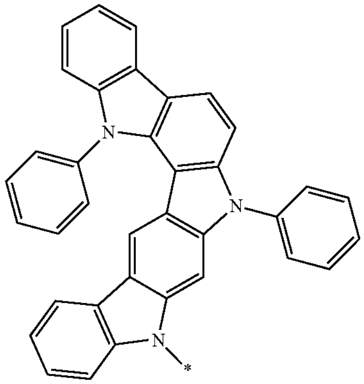
D173
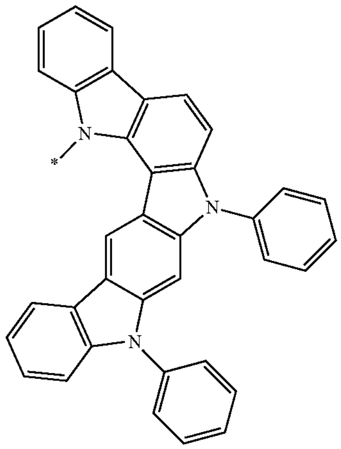

-continued
D174
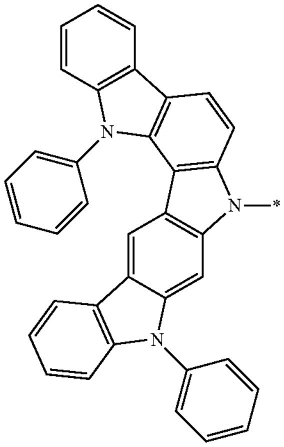
D175
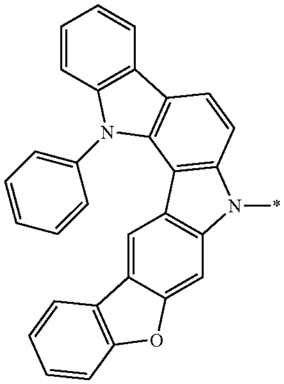
D176
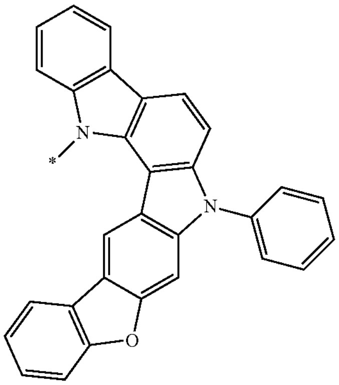
D177
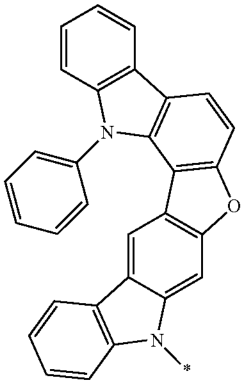
-continued
D178
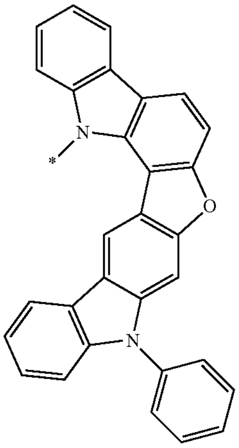
D179
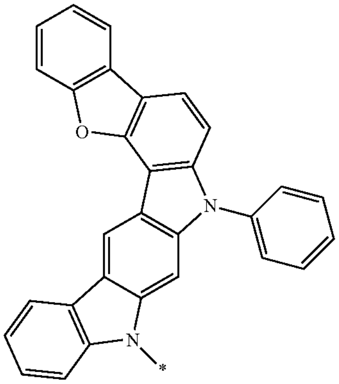
D180
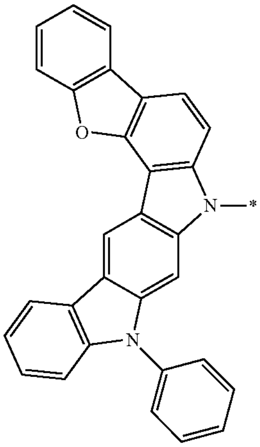

-continued
D181
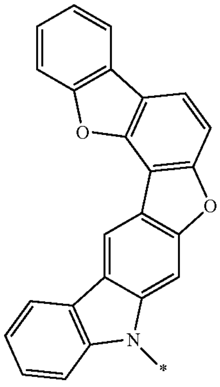
D182
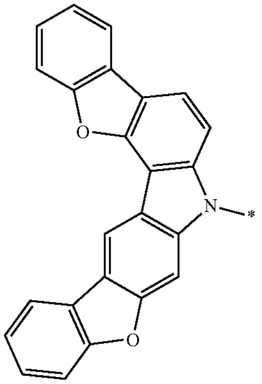
D183
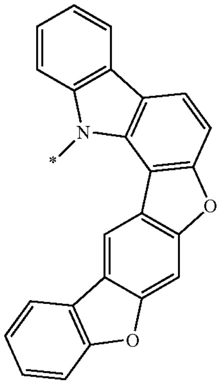
D184
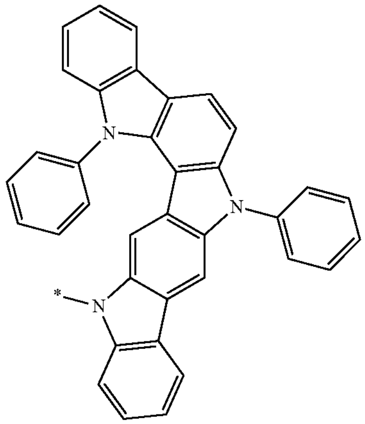
-continued
D185
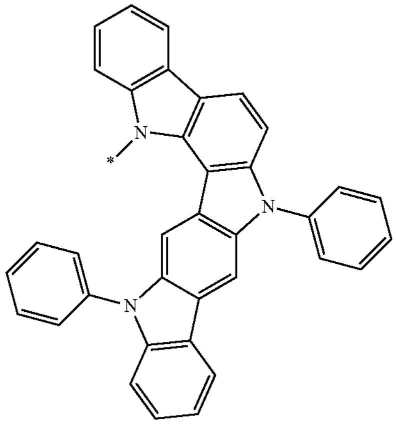
D186
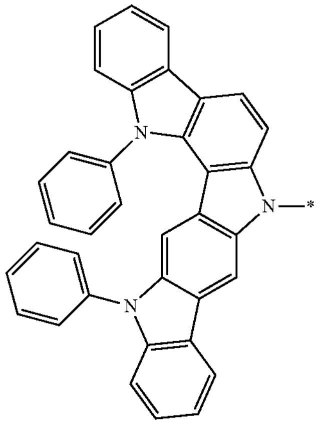
D187
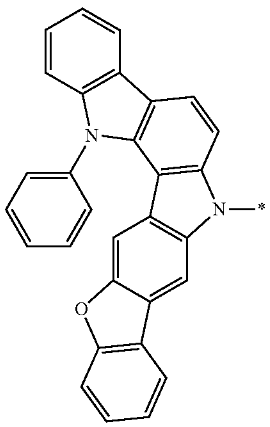

-continued
D188
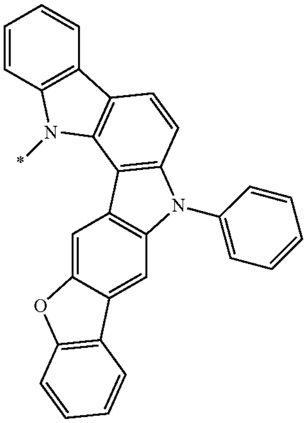
D189
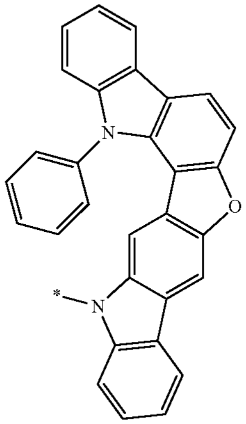
D190
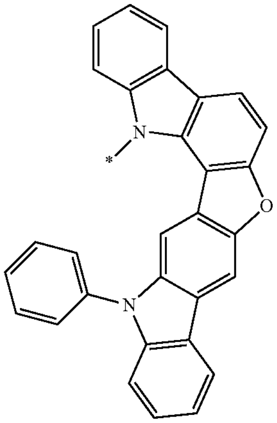
-continued
D191
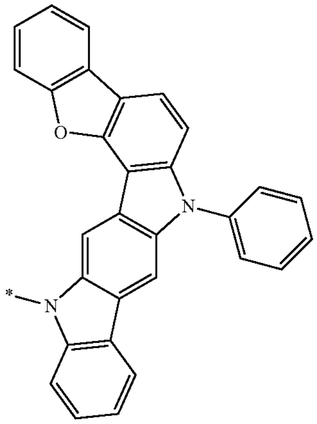
D192
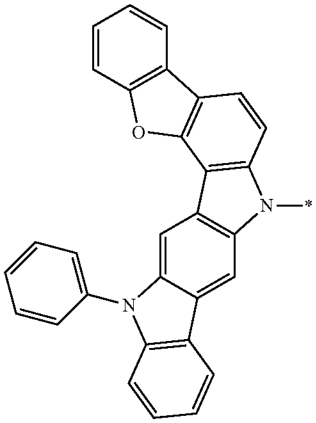
D193
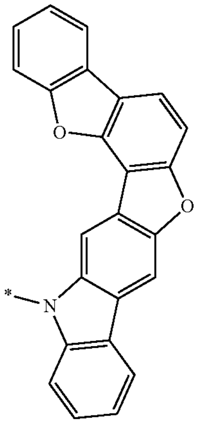

-continued
D194
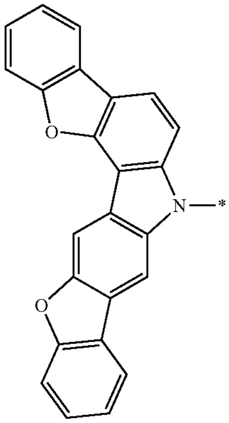
D195
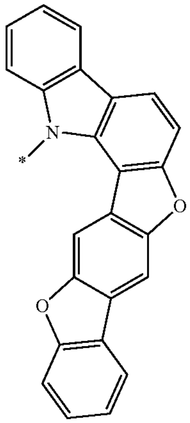
D196
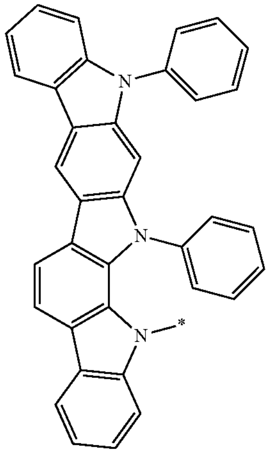
-continued
D197
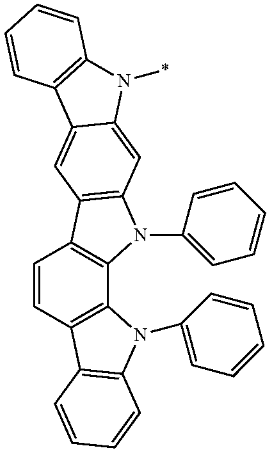
D198
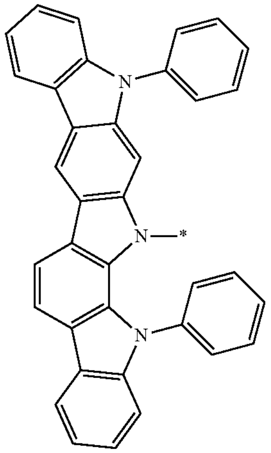
D199
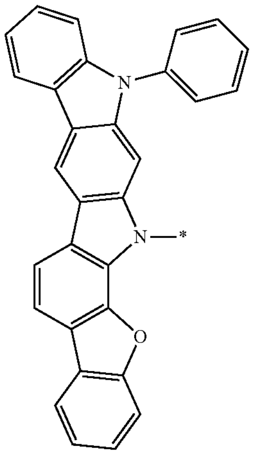

-continued
D200
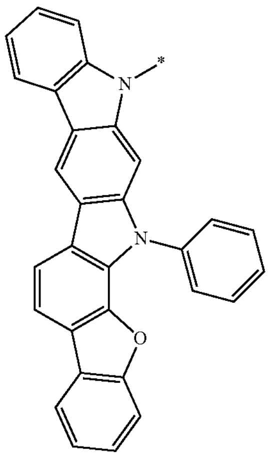
D201
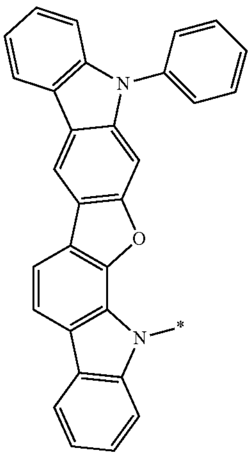
D202
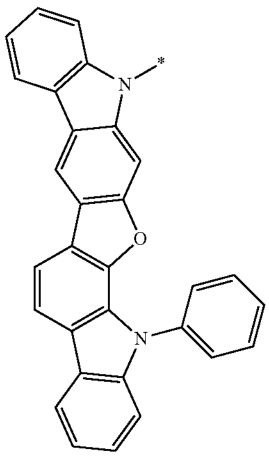
-continued
D203
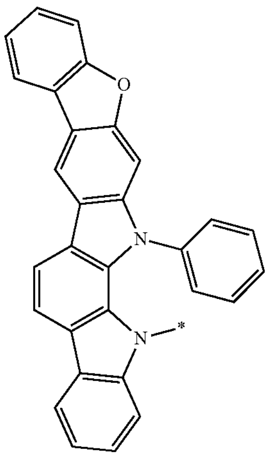
D204
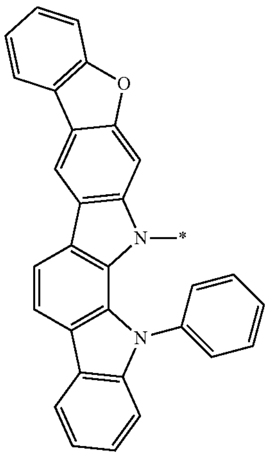
D205
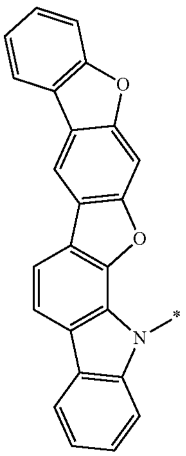

-continued
D206
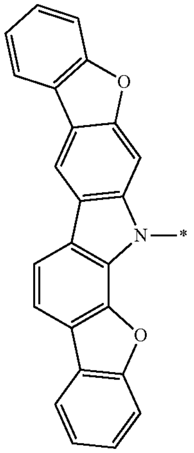
D207
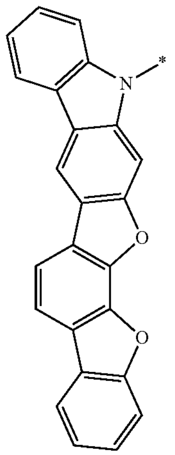
D208
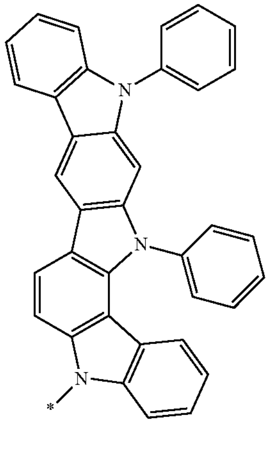
-continued
D209
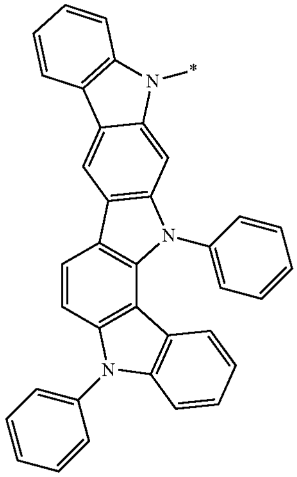
D210
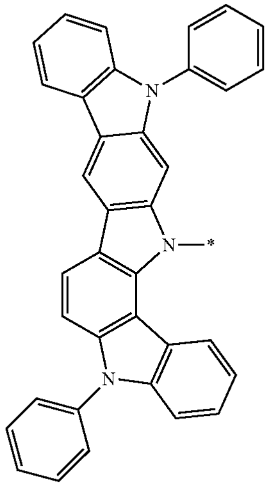
D211
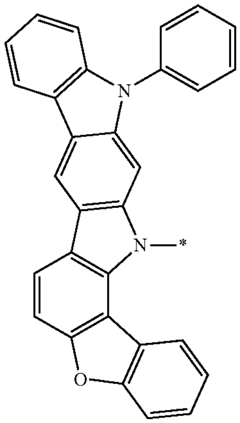

-continued
D212
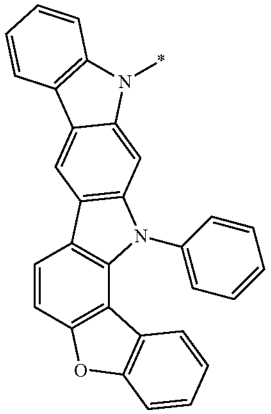
D213
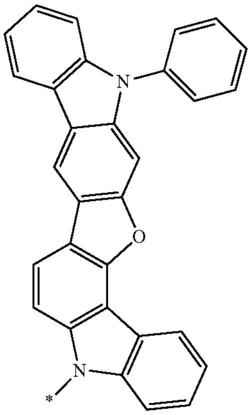
D214
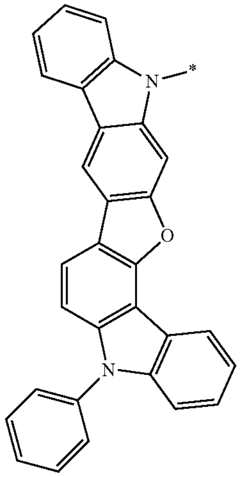
-continued
D215
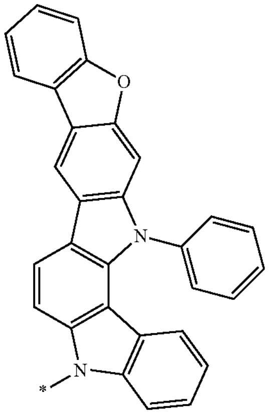
D216
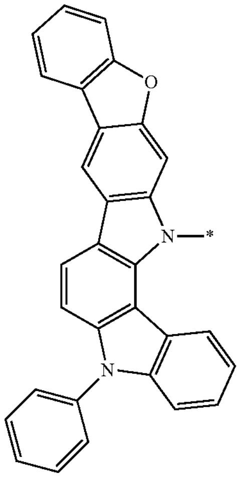
D217
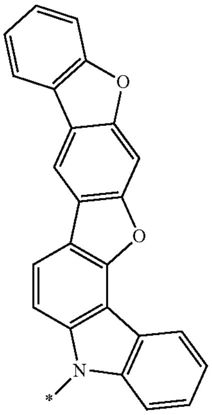

-continued
D218
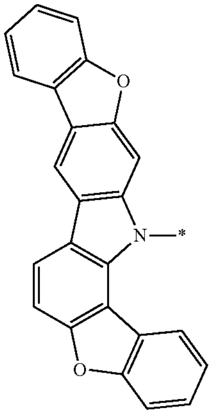
D219
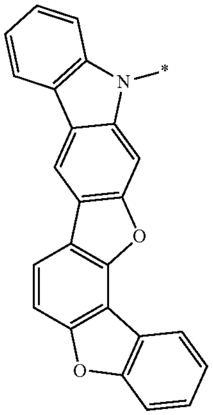
D220
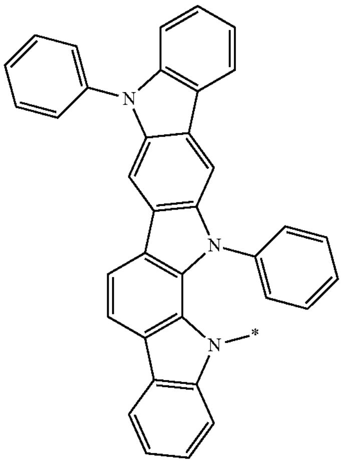
-continued
D221
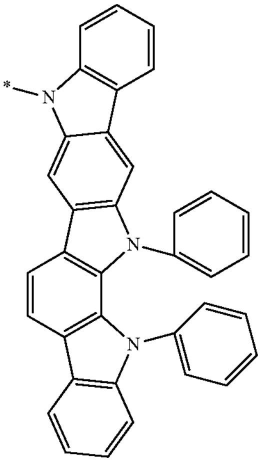
D222
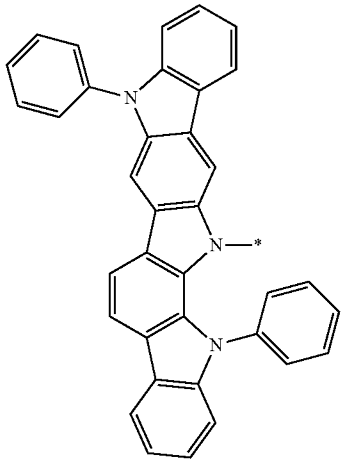
D223
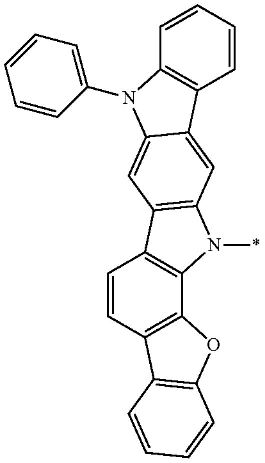

-continued
D224
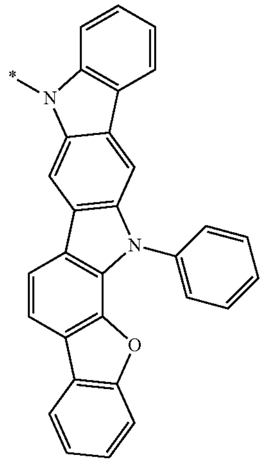
D225
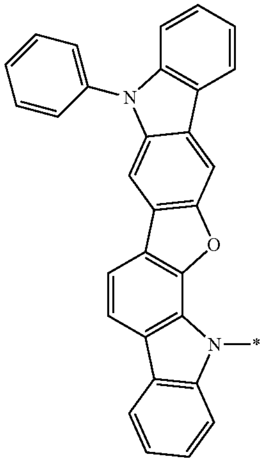
D226
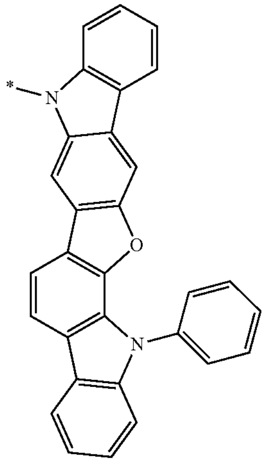
-continued
D227
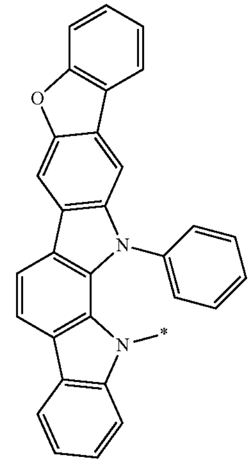
D228
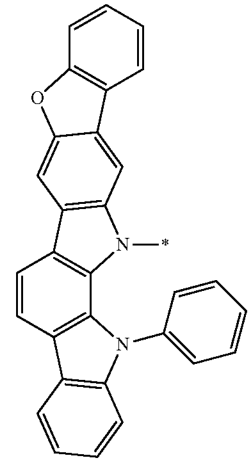
D229
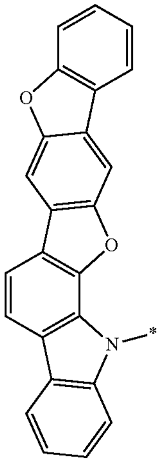

-continued
D230
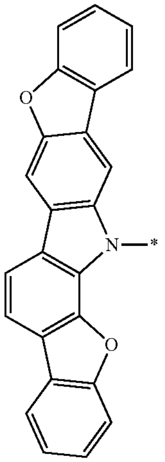
D231
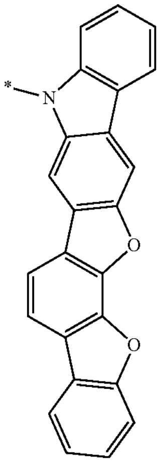
D232
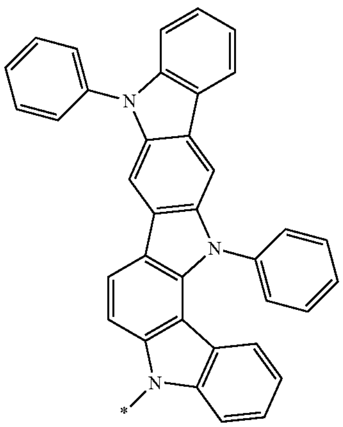
-continued
D233
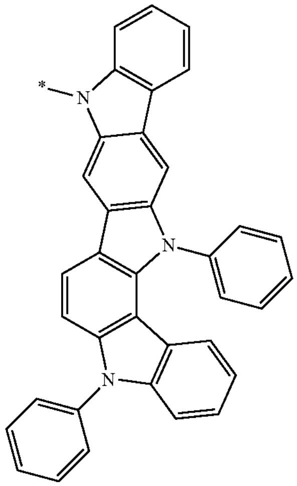
D234
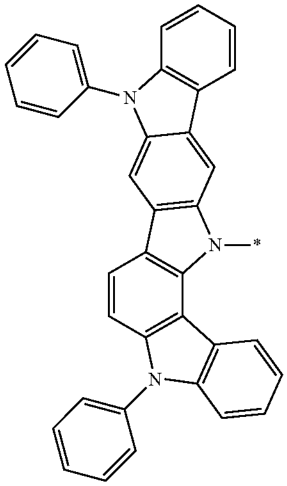
D235
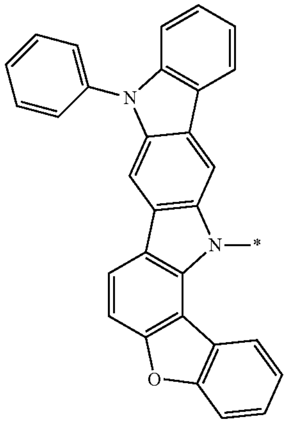

-continued
D236
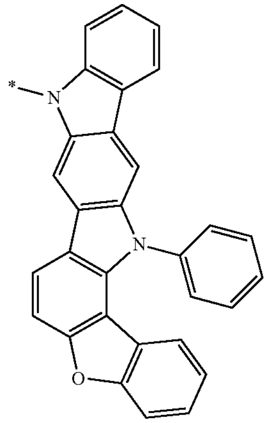
D237
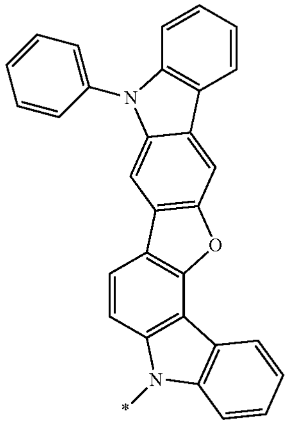
D238
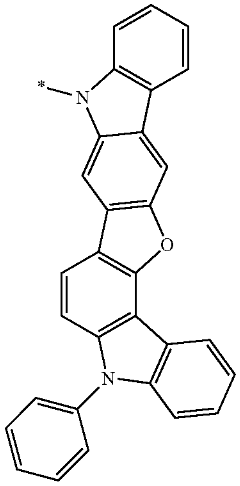
-continued
D239
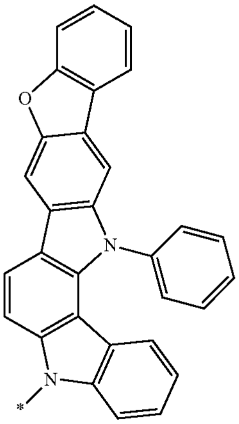
D240
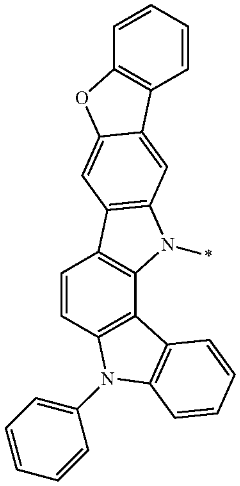
D241
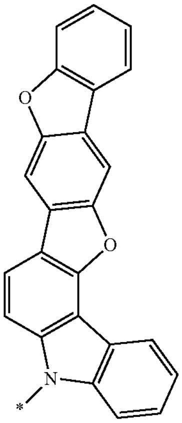

-continued
D242
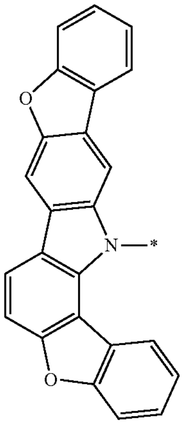
D243
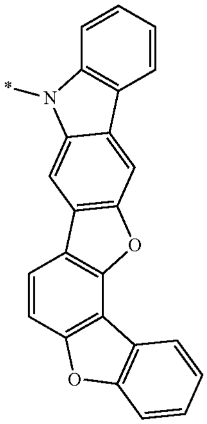
D244
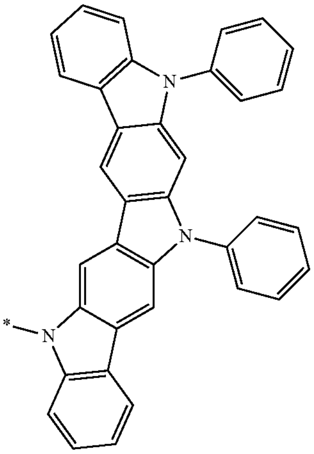
-continued
D245
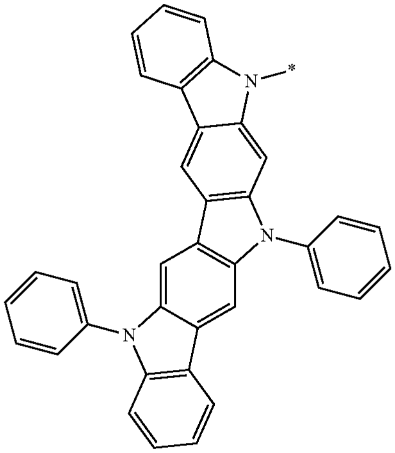
D246
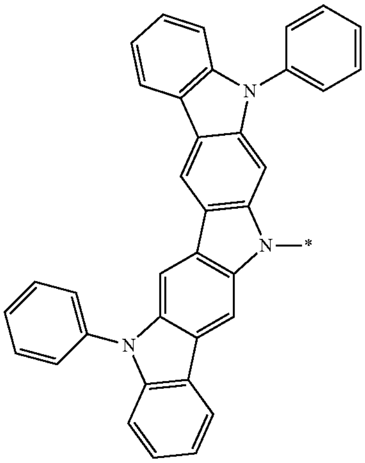
D247
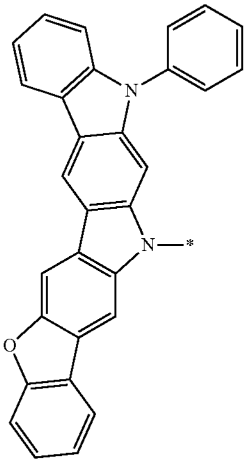

-continued
D248
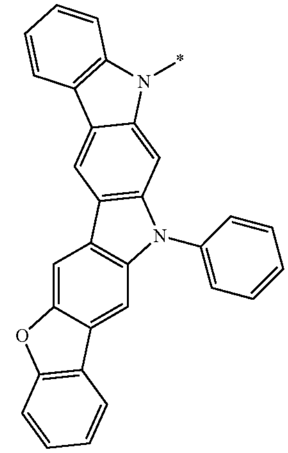
D249
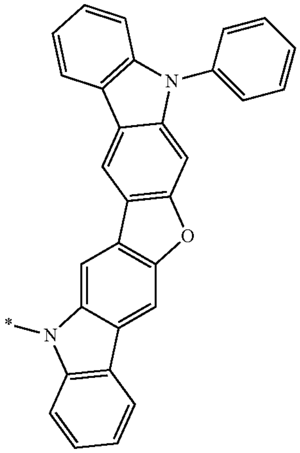
D250
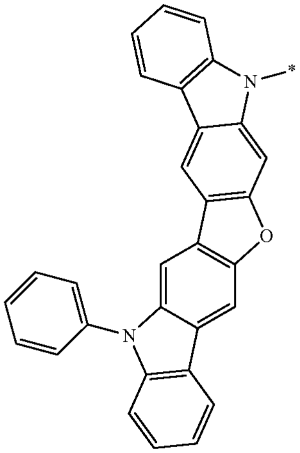
-continued
D251
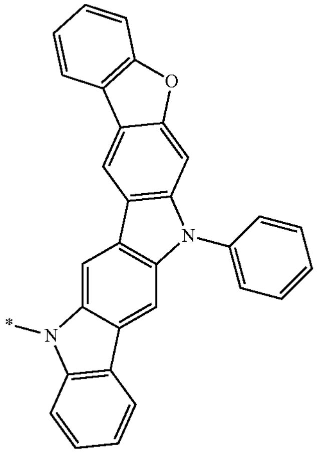
D252
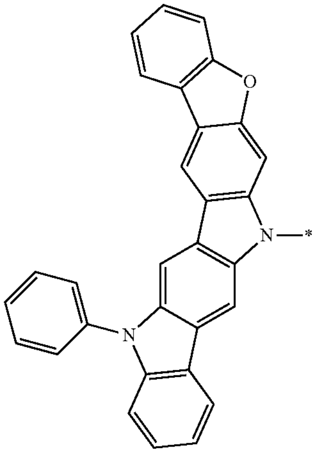
D253
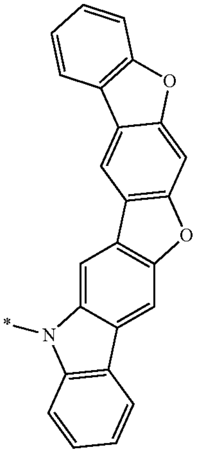

-continued
D254
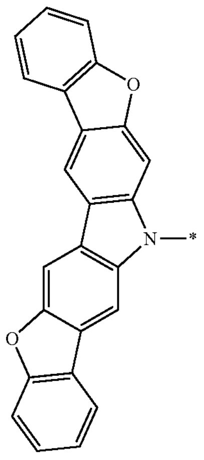
D255
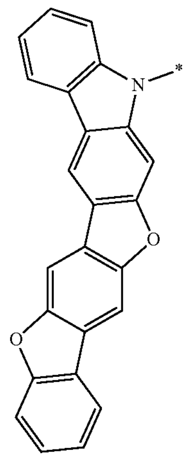
D256
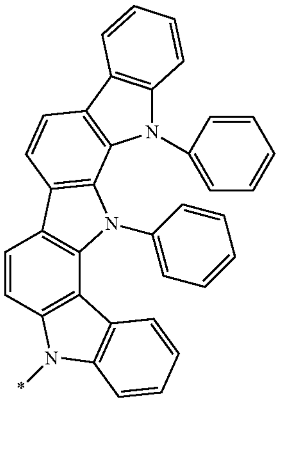
-continued
D257
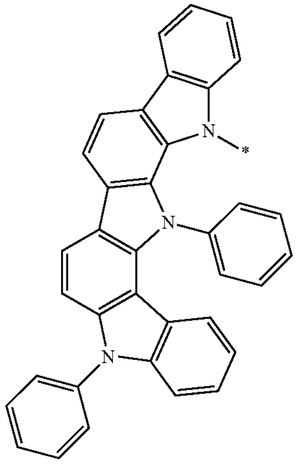
D258
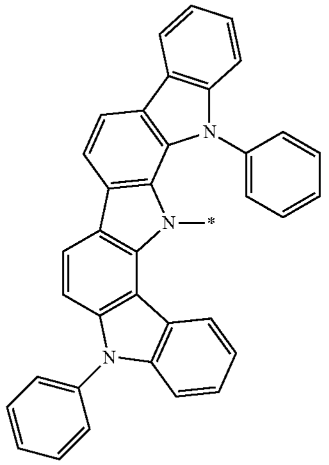
D259
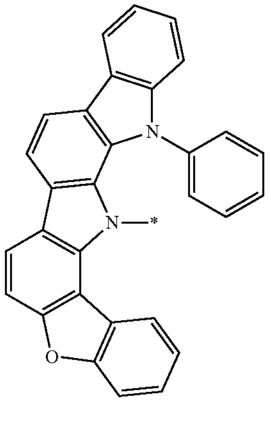

D260
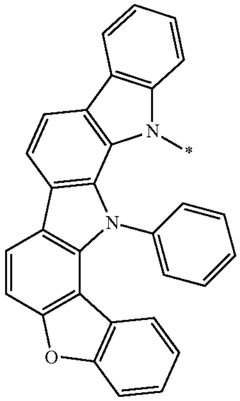
D261
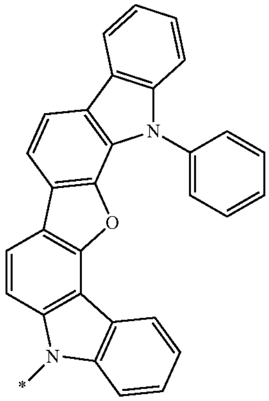
D262
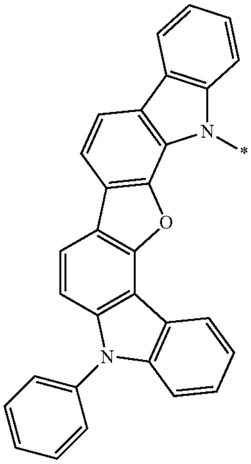
D263
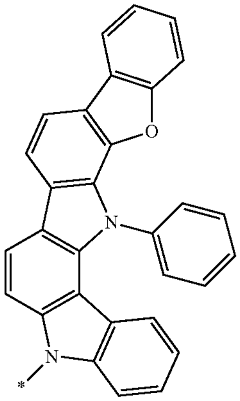
D264
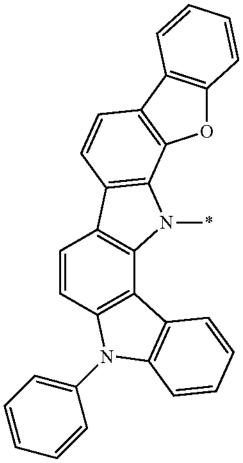
D265
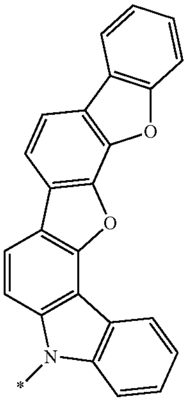

-continued
D266
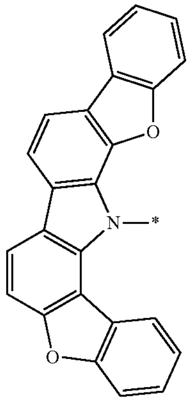
D267
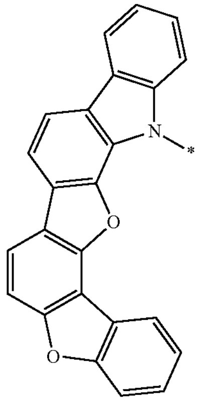
D268
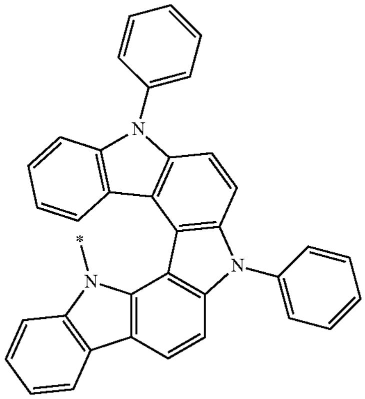
D269
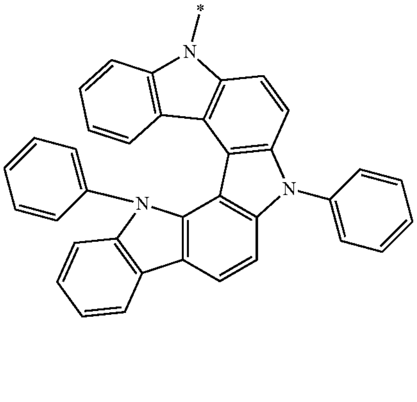
-continued
D270
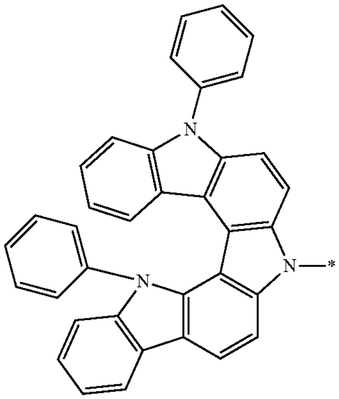
D271
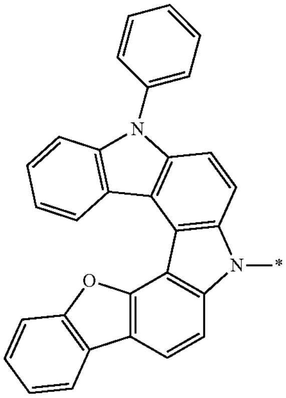
D272
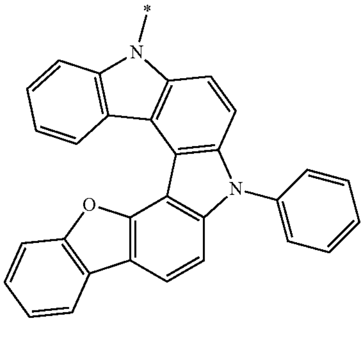
D273
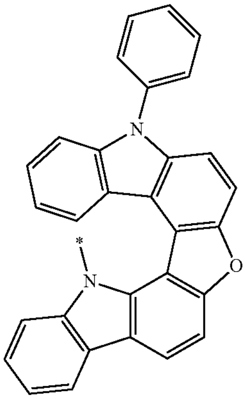

-continued
D274
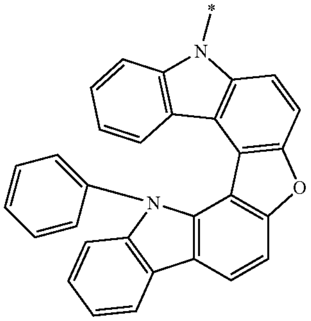
D275
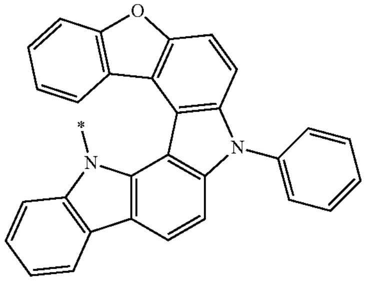
D276
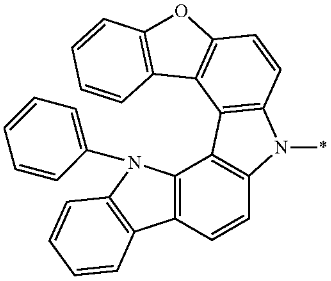
D277
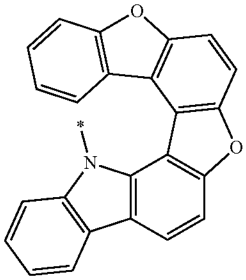
D278
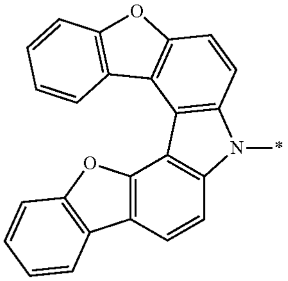
-continued
D279
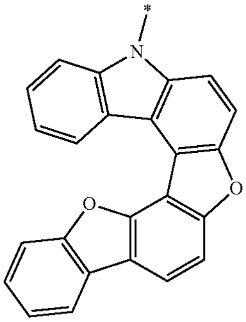
provided that when i) $X_1$ is $C(R_1)$, $X_2$ is $C(R_2)$, and $X_3$ is $C(R_3)$ and ii) $L_3$ is a single bond, then a group represented by
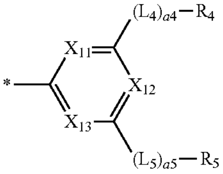
is represented by one selected from Formulae A1 to A38,
A1
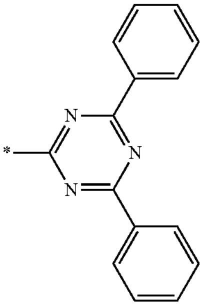
A2
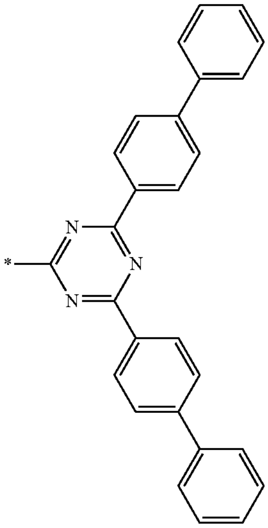

-continued
A3
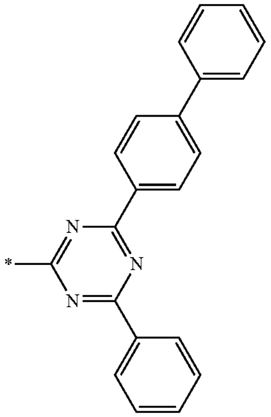
A4
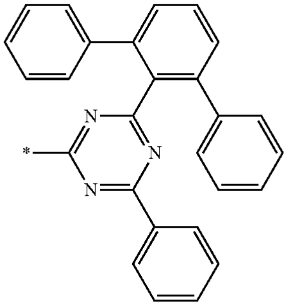
A5
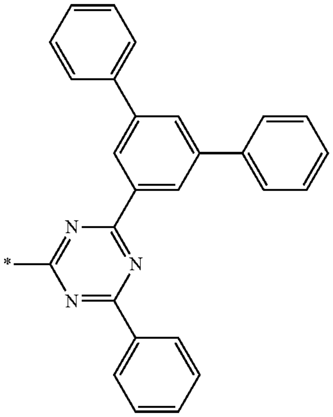
A6
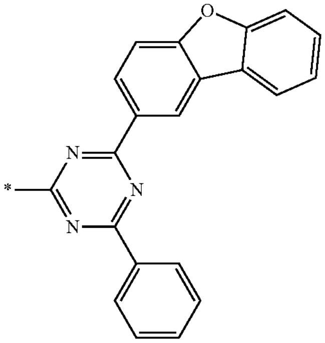
-continued
A7
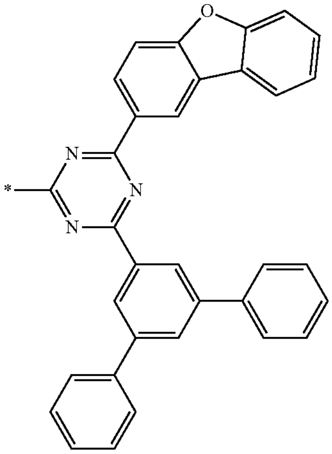
A8
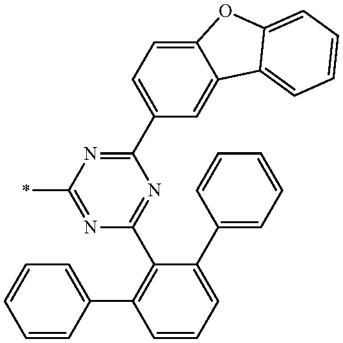
A9
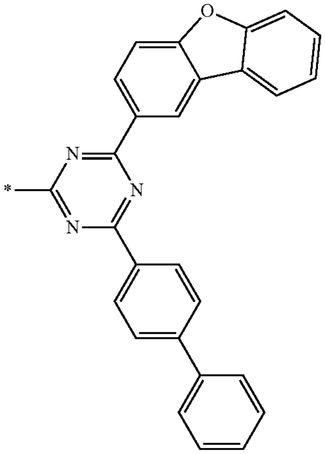

-continued
A10
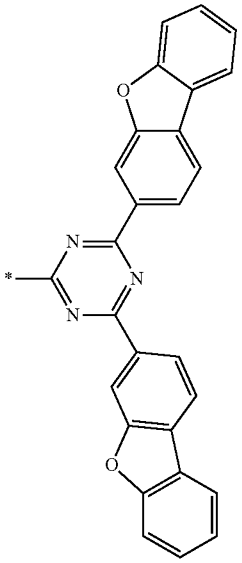
A11
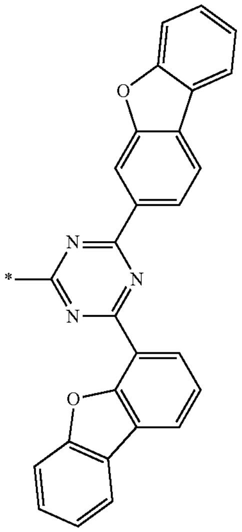
A12
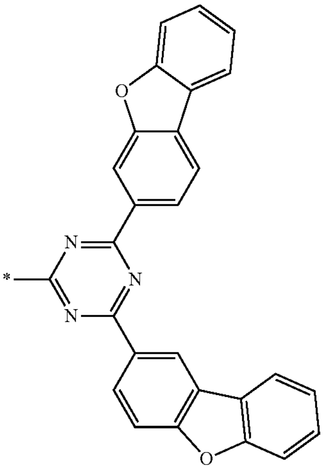
-continued
A13
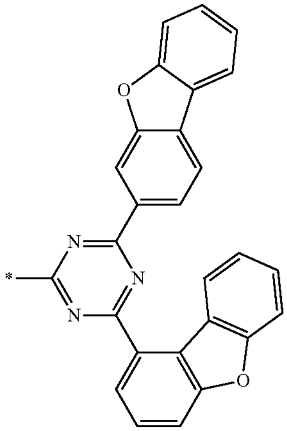
A14
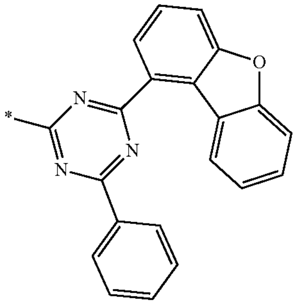
A15
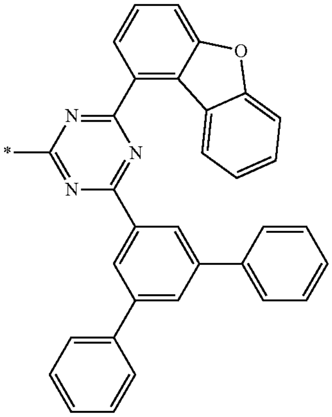
A16
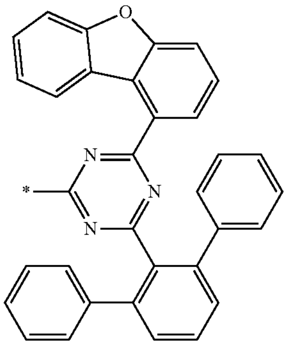

-continued
A17
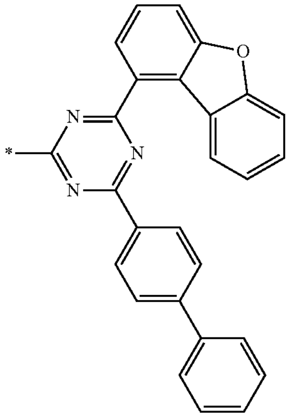
A18
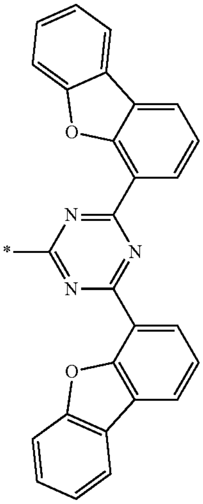
A19
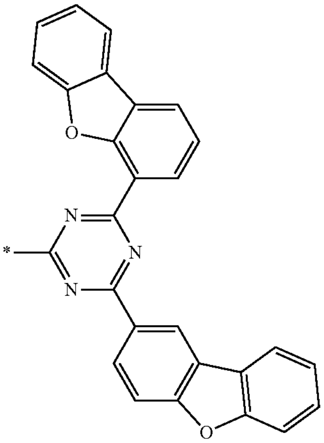
-continued
A20
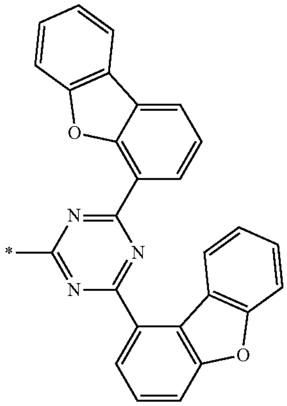
A21
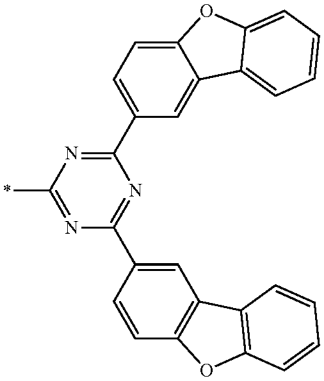
A22
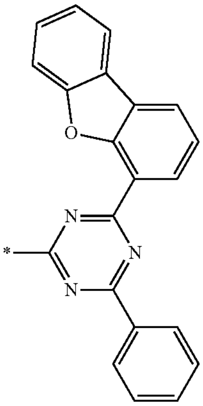

-continued
A23
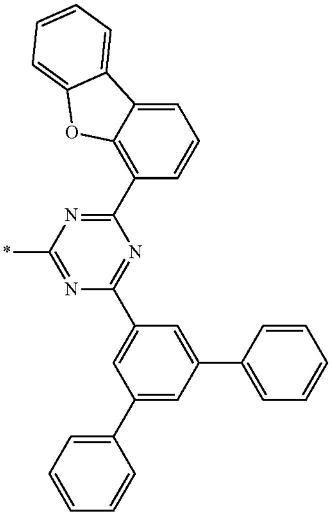
A24
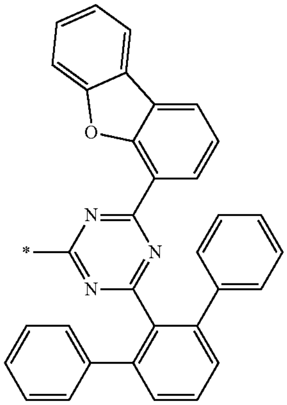
A25
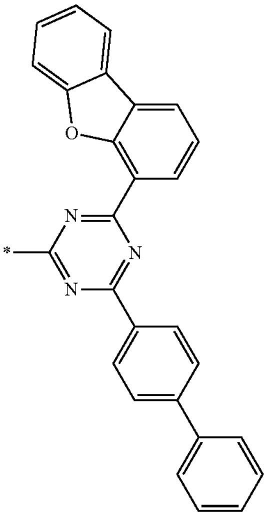
-continued
A26
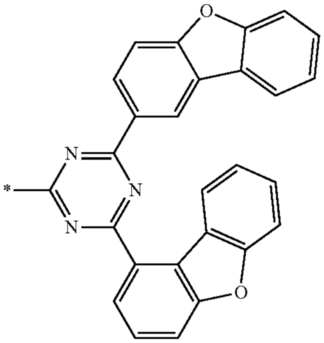
A27
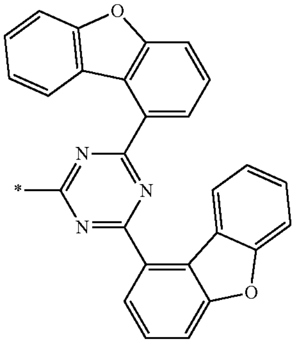
A28
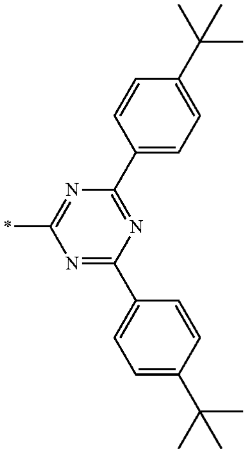
A29
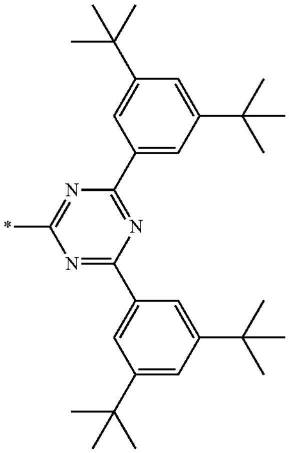

-continued
A30
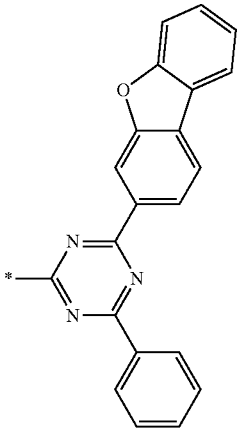
A31
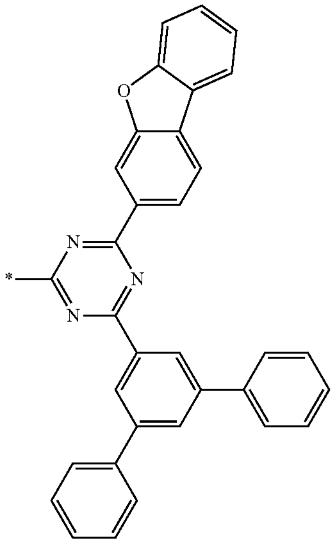
A32
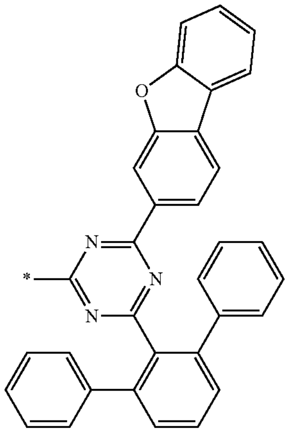
-continued
A33
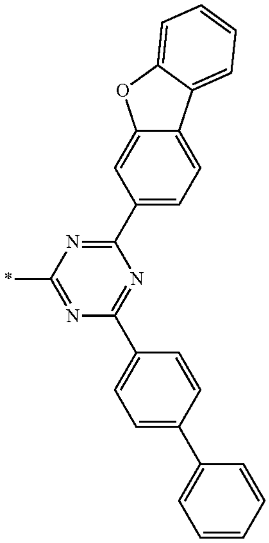
A34
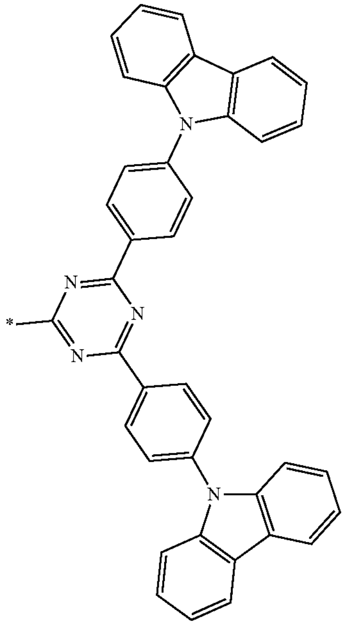
A35
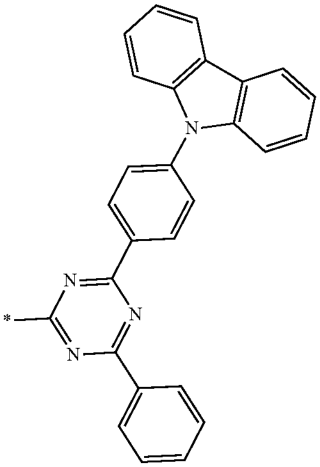

-continued
A36
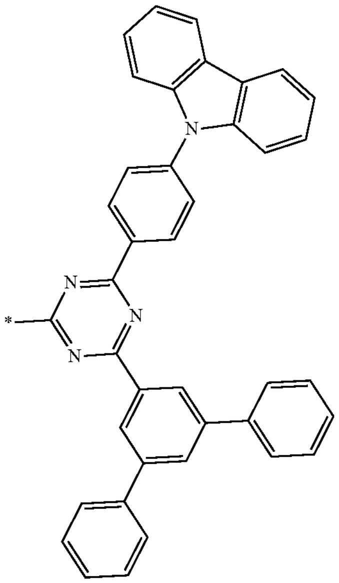
A37
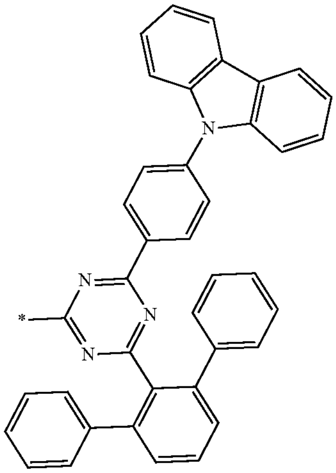
A38
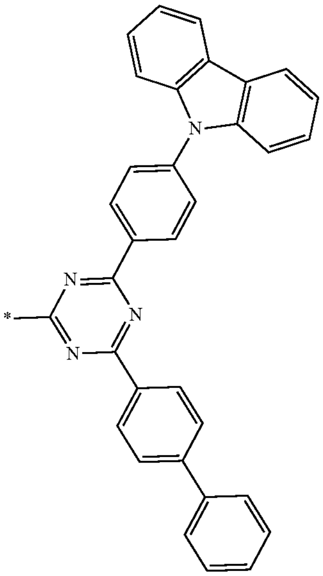
3A
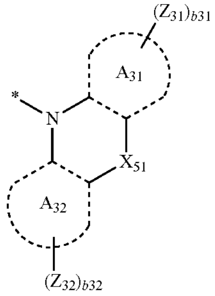
3B
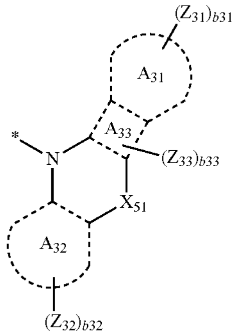
3C
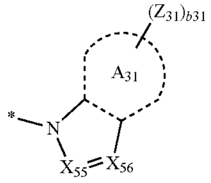
3D
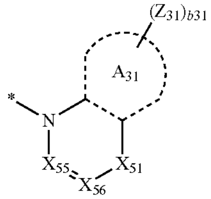
3E
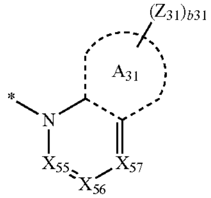
3F
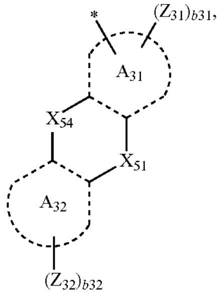

wherein, in Formulae 3A to 3F, ring $A_{31}$ to ring $A_{33}$ are each independently a $C_5$-$C_{60}$ carbocyclic group or a π electron-rich $C_1$-$C_{60}$ heterocyclic group, $X_{51}$ is a single bond, $N(Z_{51a})$, $C(Z_{51a})(Z_{51b})$, $Si(Z_{51a})(Z_{51b})$, O, or S, $X_{54}$ is $N(Z_{54a})$, $C(Z_{54a})(Z_{54b})$, $Si(Z_{54a})(Z_{54b})$, O, or S, $X_{55}$ is N or $C(Z_{55})$, $X_{56}$ is N or $C(Z_{56})$, $X_{57}$ is N or $C(Z_{57})$, $Z_{31}$ to $Z_{33}$, $Z_{51a}$, $Z_{51b}$, $Z_{54a}$, $Z_{54b}$, and $Z_{55}$ to $Z_{57}$ are each independently selected from:

hydrogen, deuterium, a cyano group, a $C_1$-$C_{20}$ alkyl group, and a $C_1$-$C_{20}$ alkoxy group; and a $C_5$-$C_{60}$ carbocyclic group, a pyridine group, and a π electron-rich $C_1$-$C_{60}$ heterocyclic group, each unsubstituted or substituted with at least one $R_{10b}$, b31 to b33 are each independently an integer from 1 to 10,

* indicates a binding site to a neighboring atom, $X_{11}$ to $X_{13}$ are each independently N or C(CN), $R_4$ and $R_5$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and $—Si(Q_{111})(Q_{112})(Q_{113})$, $R_{10a}$ and $R_{10b}$ are each independently deuterium, a cyano group, a $C_1$-$C_{20}$ alkyl group, a $C_1$-$C_{20}$ alkoxy group, a phenyl group, a ($C_1$-$C_{20}$ alkyl)phenyl group, a di($C_1$-$C_{20}$ alkyl)phenyl group, a tri ($C_1$-$C_{20}$ alkyl)phenyl group, a ($C_6$-$C_{20}$ aryl)phenyl group, a di($C_6$-$C_{20}$ aryl) phenyl group, a tri ($C_6$-$C_{20}$ aryl)phenyl group, a terphenyl group, a tetraphenyl group, a fluorenyl group, a ($C_1$-$C_{20}$ alkyl) fluorenyl group, a di($C_1$-$C_{20}$ alkyl) fluorenyl group, a tri ($C_1$-$C_{20}$ alkyl) fluorenyl group, a ($C_6$-$C_{20}$ aryl) fluorenyl group, a di($C_6$-$C_{20}$ aryl) fluorenyl group, a tri ($C_6$-$C_{20}$ aryl) fluorenyl group, a carbazolyl group, a ($C_1$-$C_{20}$ alkyl) carbazolyl group, a di($C_1$-$C_{20}$ alkyl) carbazolyl group, a tri ($C_1$-$C_{20}$ alkyl) carbazolyl group, a ($C_6$-$C_{20}$ aryl) carbazolyl group, a di($C_6$-$C_{20}$ aryl) carbazolyl group, a tri ($C_6$-$C_{20}$ aryl) carbazolyl group, a dibenzofuranyl group, a ($C_1$-$C_{20}$ alkyl)dibenzofuranyl group, a di($C_1$-$C_{20}$ alkyl)dibenzofuranyl group, a tri ($C_1$-$C_{20}$ alkyl)dibenzofuranyl group, a ($C_6$-$C_{20}$ aryl)dibenzofuranyl group, a di($C_6$-$C_{20}$ aryl)dibenzofuranyl group, a tri ($C_6$-$C_{20}$ aryl) dibenzofuranyl group, a dibenzothiophenyl group, a ($C_1$-$C_{20}$ alkyl)dibenzothiophenyl group, a di($C_1$-$C_{20}$ alkyl)dibenzothiophenyl group, a tri ($C_1$-$C_{20}$ alkyl) dibenzothiophenyl group, a ($C_6$-$C_{20}$ aryl)dibenzothiophenyl group, a di($C_6$-$C_{20}$ aryl)dibenzothiophenyl group, a tri ($C_6$-$C_{20}$ aryl)dibenzothiophenyl group, or $—Si(Q_{121})(Q_{122})(Q_{123})$, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group is selected from:

deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, $—N(Q_{11})(Q_{12})$, $—Si(Q_{13})(Q_{14})(Q_{15})$, $—B(Q_{16})(Q_{17})$, and $—P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, $—N(Q_{21})(Q_{22})$, $—Si(Q_{23})(Q_{24})(Q_{25})$, $—B(Q_{26})(Q_{27})$, and $—P(=O)(Q_{28})(Q_{29})$; and $—N(Q_{31})(Q_{32})$, $—Si(Q_{33})(Q_{34})(Q_{35})$, $—B(Q_{36})(Q_{37})$, and $—P(=O)(Q_{38})(Q_{39})$, and $Q_{101}$ to $Q_{103}$, $Q_{111}$ to $Q_{113}$, $Q_{121}$ to $Q_{123}$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a biphenyl group, a terphenyl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, the heterocyclic compound has a singlet energy level in a range of about 2.5 electron volts to about 3.0 electron volts, and the singlet energy level is evaluated by using a density functional theory method structurally optimized at a level of B3LYP/6-31G(d,p).

2. The heterocyclic compound of claim 1, wherein $L_3$ to $L_5$ are each independently selected from:

a single bond; and a benzene group, a fluorene group, a pyridine group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, an acridine group, and a dihydroacridine group, each unsubstituted or substituted with at least one $R_{10a}$.

3. The heterocyclic compound of claim 1, wherein $L_3$ is selected from a single bond and groups represented by Formulae 2-1 to 2-4:

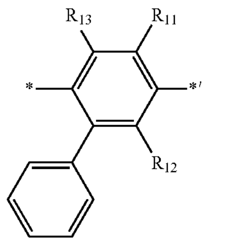
2-1

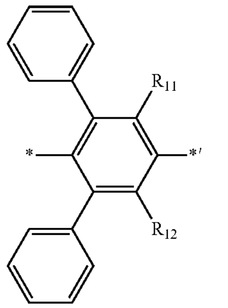
2-2

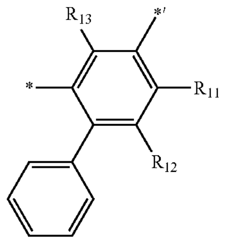
2-3

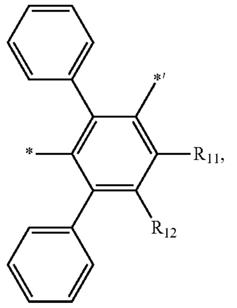
2-4 wherein, in Formulae 2-1 to 2-4, $R_{11}$ to $R_{13}$ are each independently hydrogen, deuterium, or a $C_1$-$C_{10}$ alkyl group,

* indicates a binding site to a 6-membered ring on the left side in Formula 1, and

*' indicates a binding site to a 6-membered ring on the right side in Formula 1.

4. The heterocyclic compound of claim 1, wherein ring $A_{31}$ to ring $A_{33}$ are each independently a benzene group, a naphthalene group, an anthracene group, a phenanthrene group, a triphenylene group, a chrysene group, an indene group, an indole group, a benzofuran group, a benzothiophene group, a benzosilole group, a fluorene group, a carbazole group, a dibenzofuran group, a dibenzothiophene group, a dibenzosilole group, an indenocarbazole group, an indolocarbazole group, a benzofurocarbazole group, a benzothienocarbazole group, a benzosilolocarbazole group, an acridine group, or a dihydroacridine group.

5. The heterocyclic compound of claim 1, wherein a ring represented by
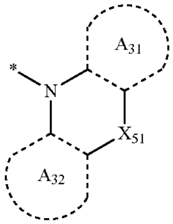
in Formula 3A is selected from groups represented by Formulae 3A-1 to 3A-49,
a ring represented by
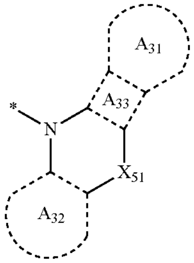
in Formula 3B is selected from groups represented by Formulae 3B-1 to 3B-40, and
a ring represented by
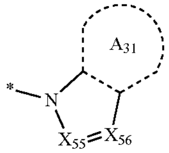
in Formula 3C is a group represented by Formula 3C-1:
3A-1
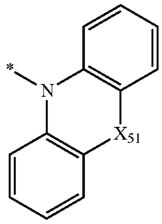
3A-2
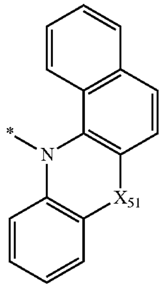
-continued
3A-3
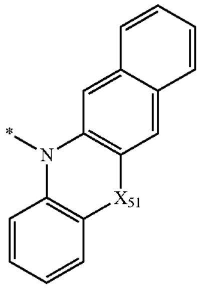
3A-4
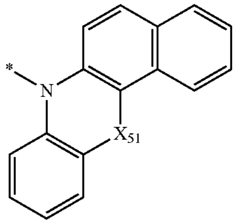
3A-5
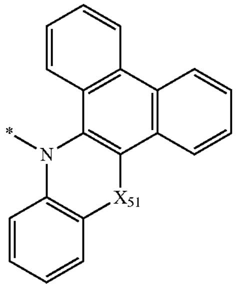
3A-6
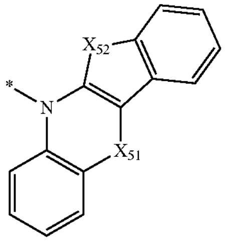
3A-7
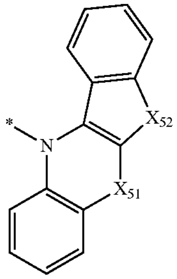

-continued
3A-8
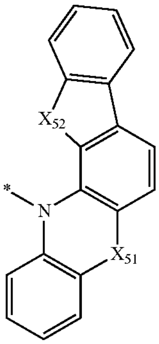
3A-9
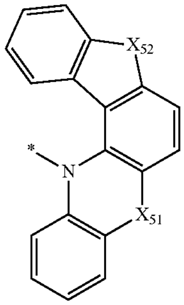
3A-10
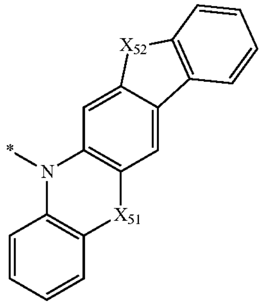
3A-11
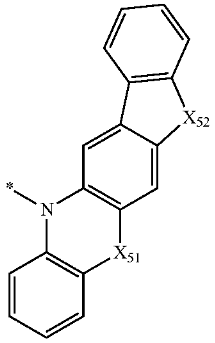
3A-12
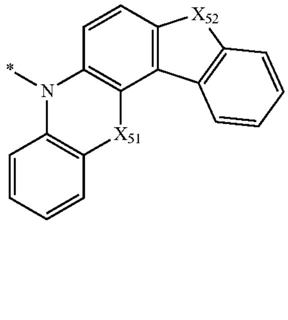
-continued
3A-13
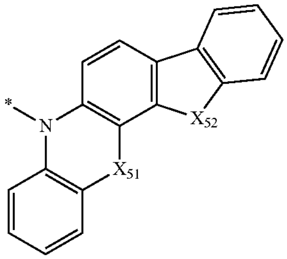
3A-14
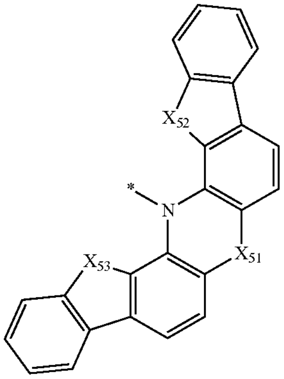
3A-15
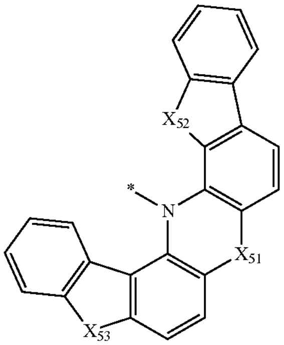
3A-16
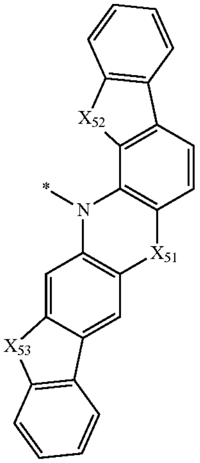

-continued
3A-17
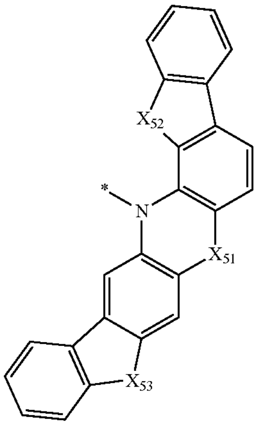
3A-18
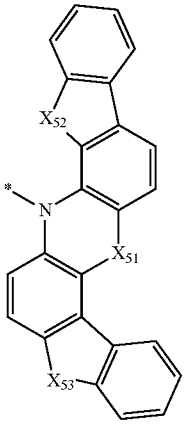
3A-19
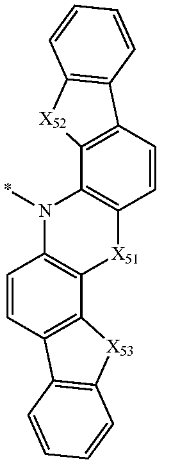
-continued
3A-20
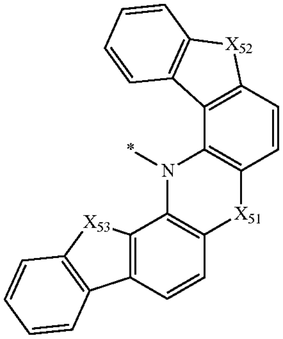
3A-21
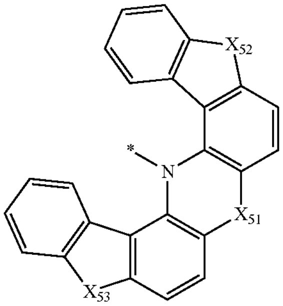
3A-22
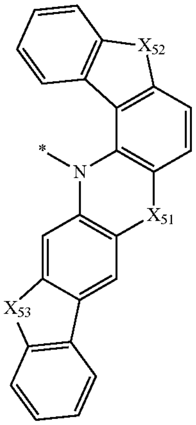
3A-23
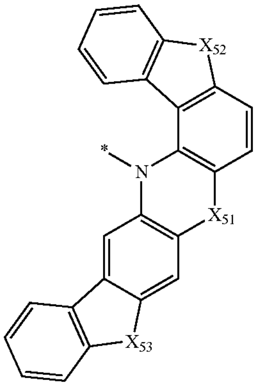

-continued
3A-24
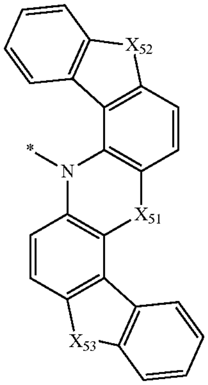
3A-25
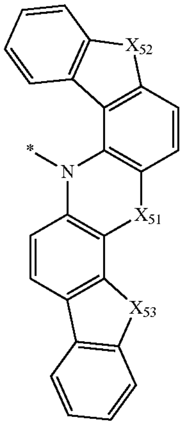
3A-26
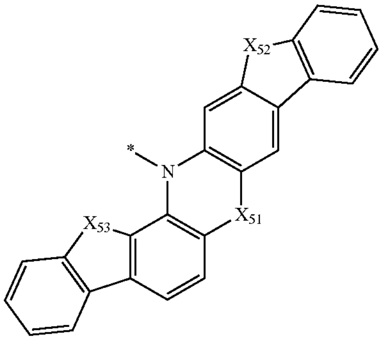
3A-27
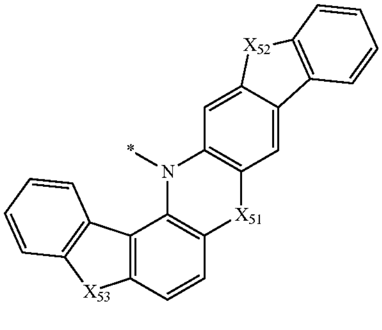
-continued
3A-28
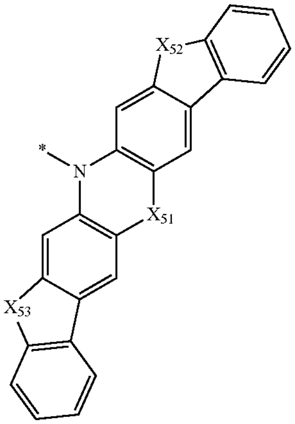
3A-29
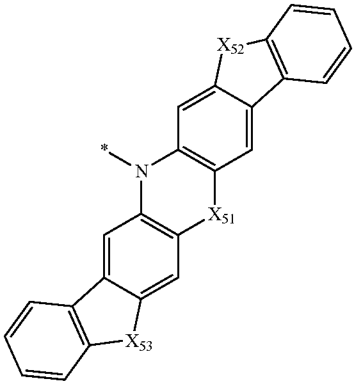
3A-30
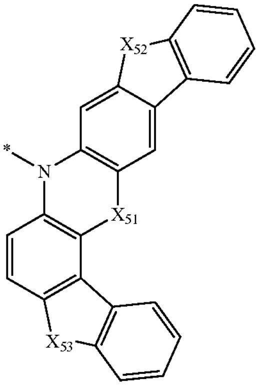
3A-31
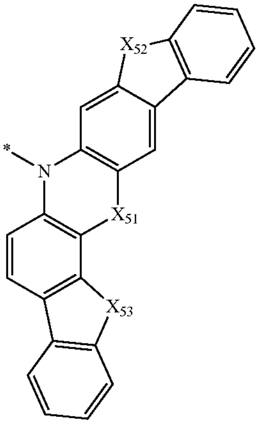

-continued
3A-32
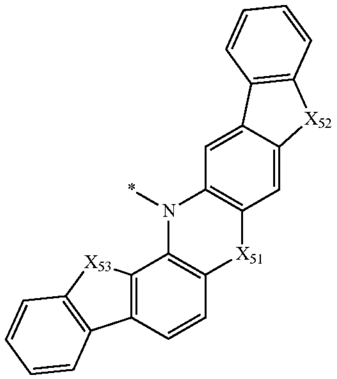
3A-33
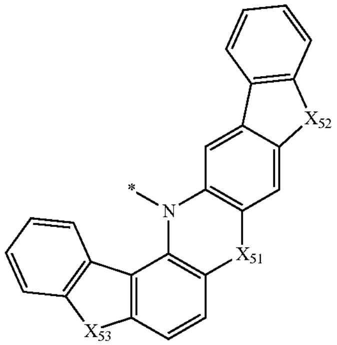
3A-34
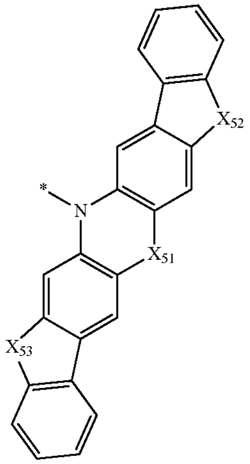
3A-35
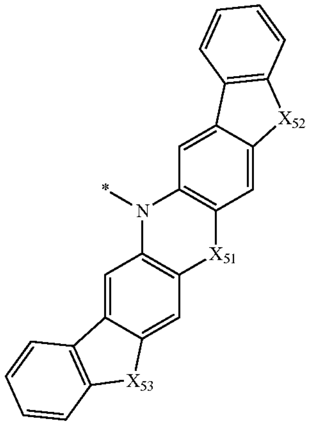
-continued
3A-36
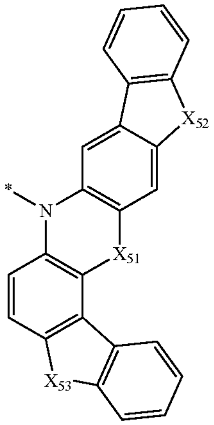
3A-37
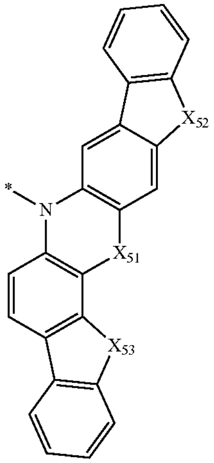
3A-38
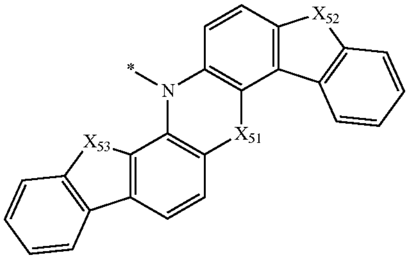
3A-39
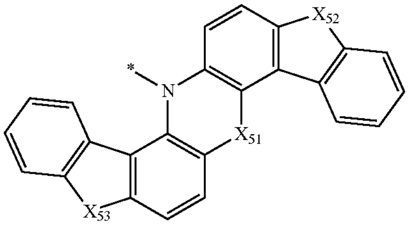

3A-40
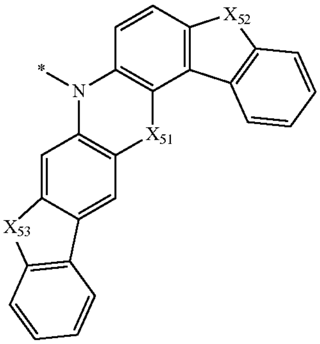
3A-41
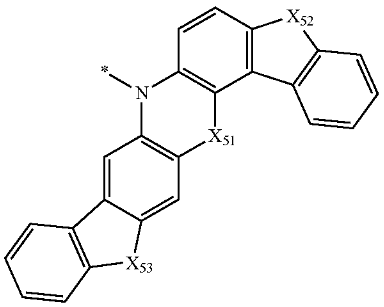
3A-42
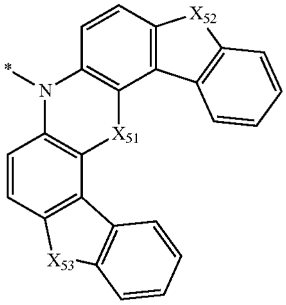
3A-43
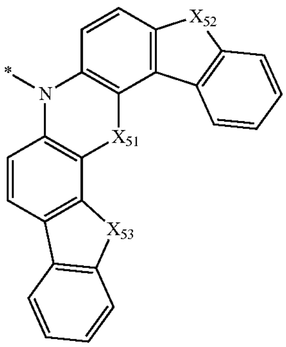
3A-44
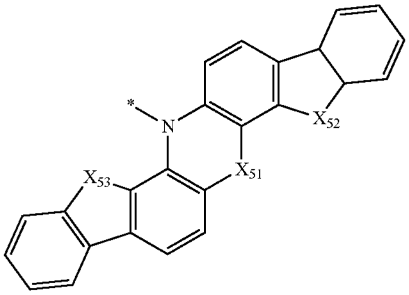
3A-45
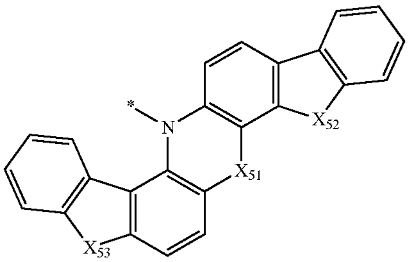
3A-46
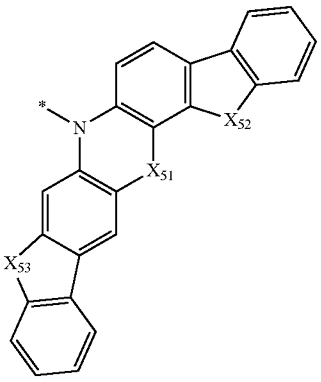
3A-47
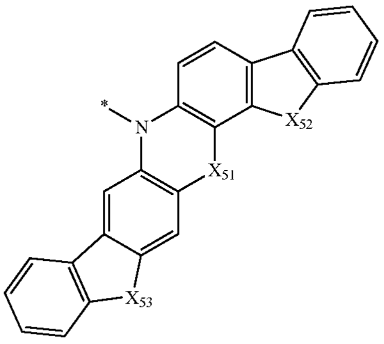
3A-48
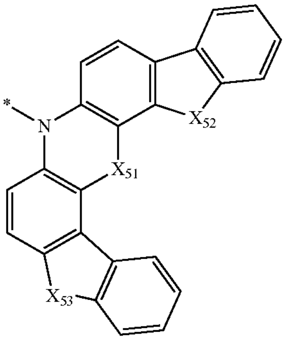

-continued
3A-49
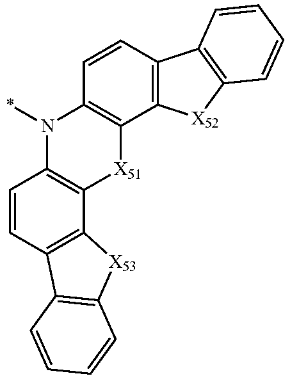
3B-1
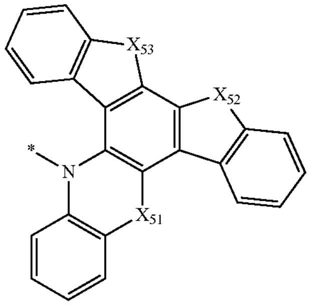
3B-2
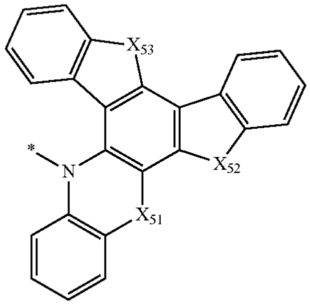
3B-3
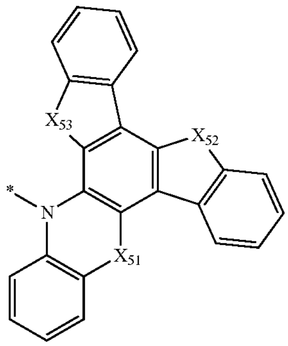
-continued
3B-4
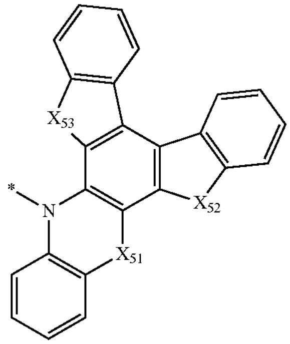
3B-5
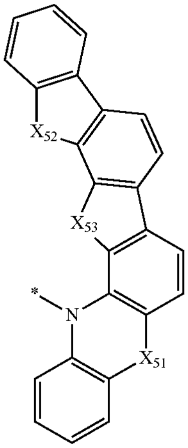
3B-6
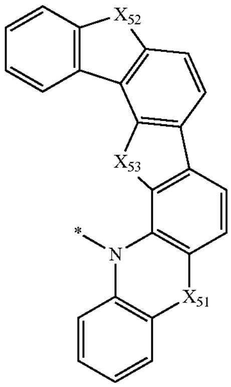
3B-7
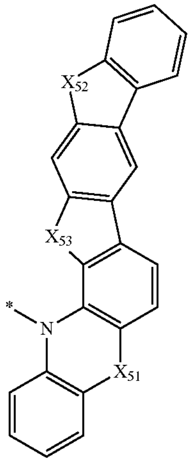

3B-8
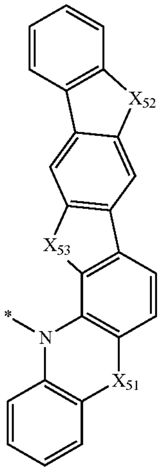
3B-9
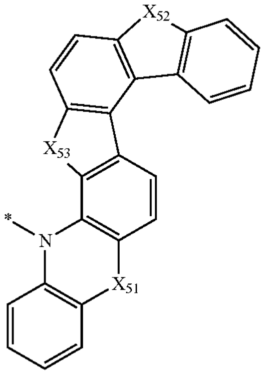
3B-10
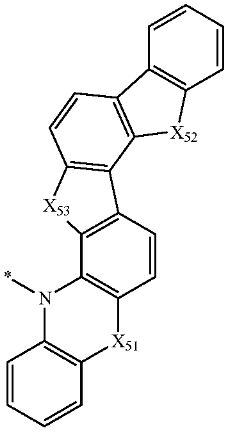
3B-11
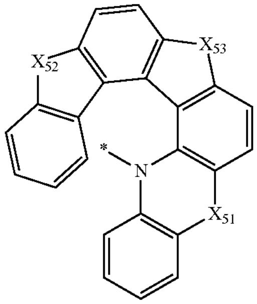
3B-12
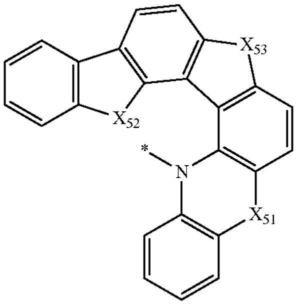
3B-13
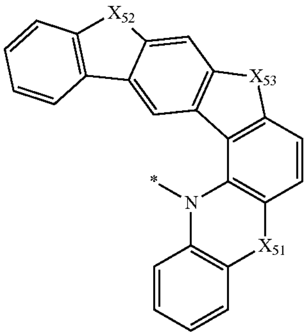
3B-14
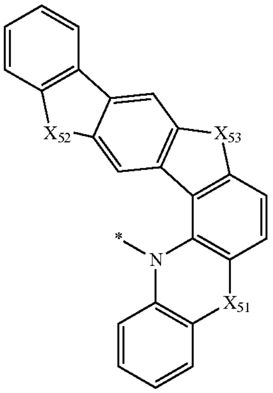
3B-15
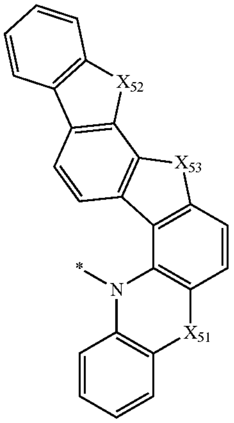

-continued
3B-16
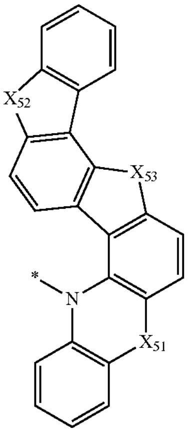
3B-17
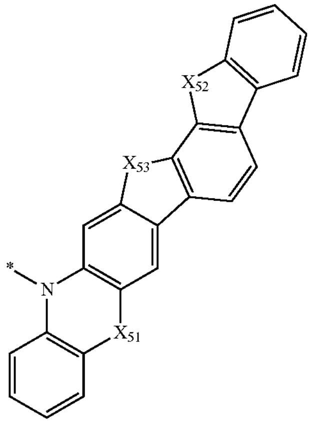
3B-18
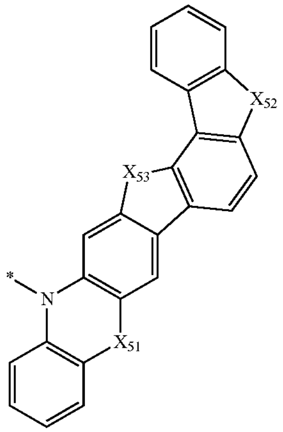
3B-19
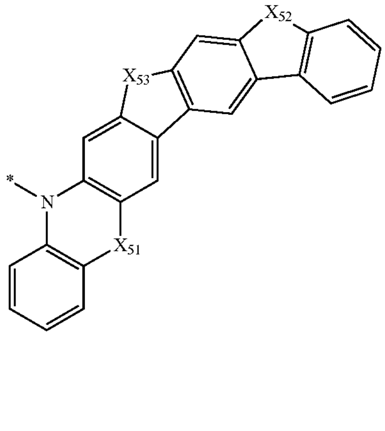
-continued
3B-20
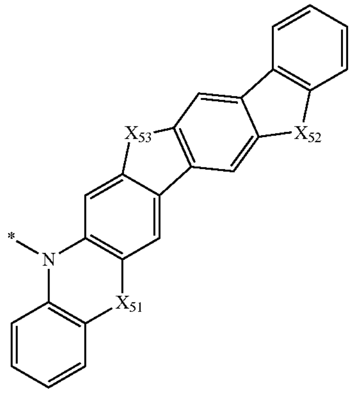
3B-21
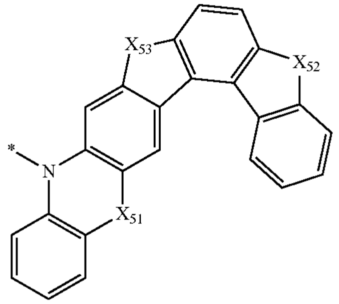
3B-22
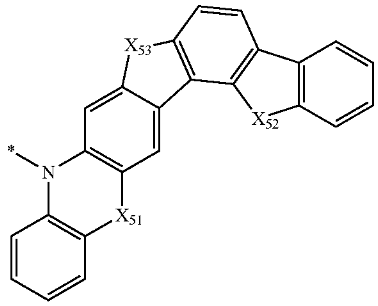
3B-23
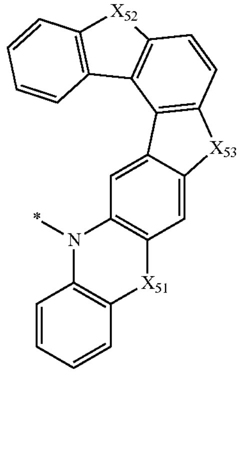

-continued
3B-24
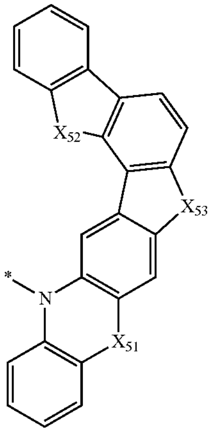
3B-25
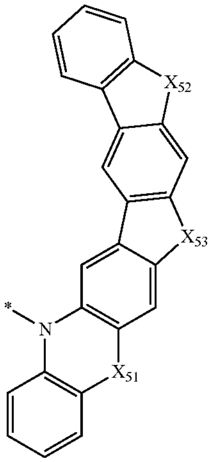
3B-26
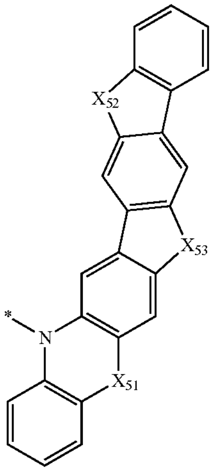
-continued
3B-27
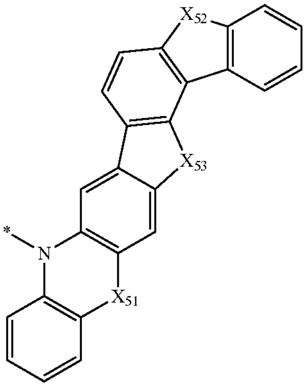
3B-28
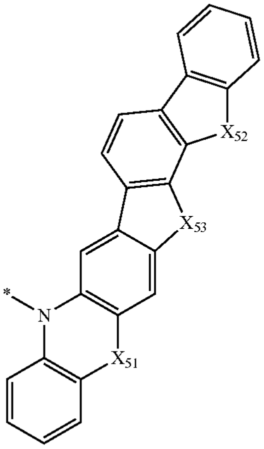
3B-29
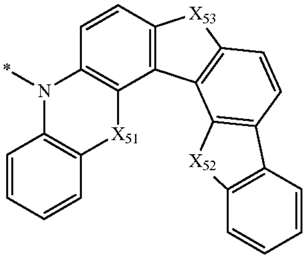
3B-30
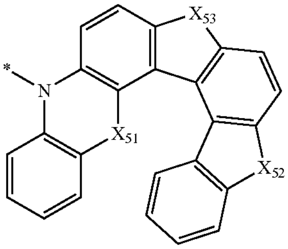
3B-31
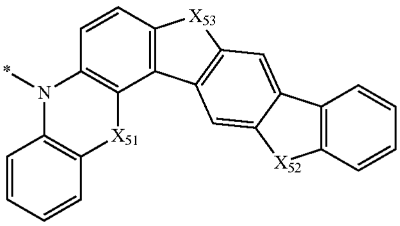

-continued
3B-32
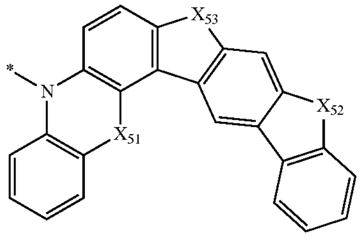
3B-33
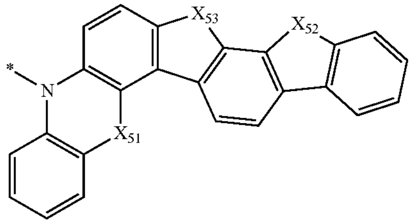
3B-34
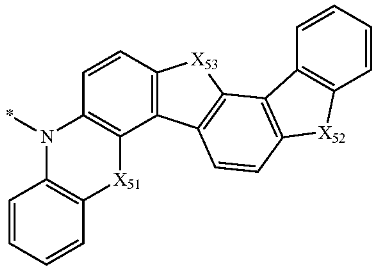
3B-35
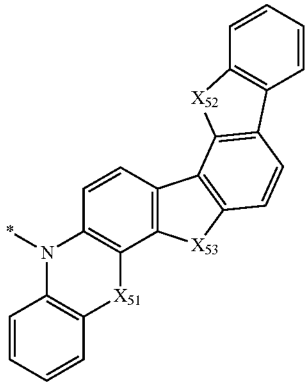
3B-36
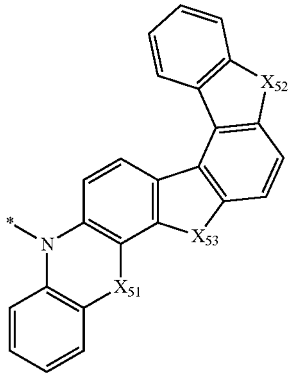
-continued
3B-37
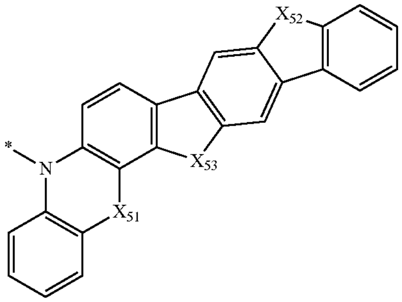
3B-38
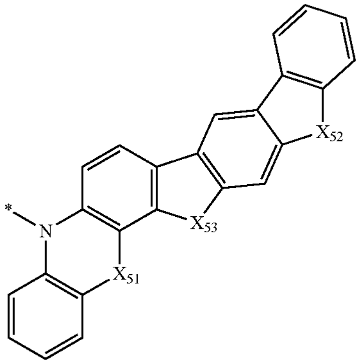
3B-39
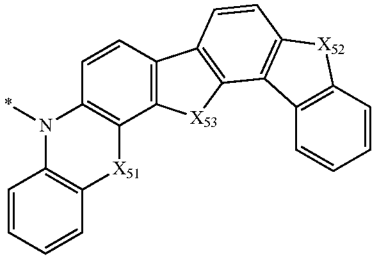
3B-40
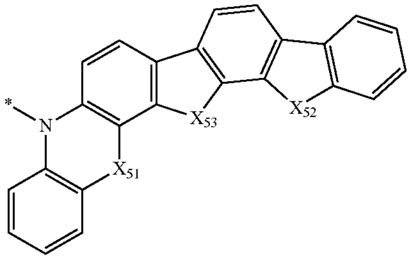
3C-1
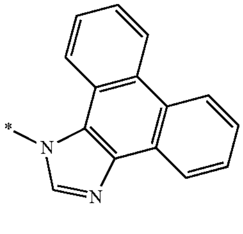
,
wherein, in Formulae 3A-1 to 3A-49, 3B-1 to 3B-40 and 3C-1, $X_{51}$ and * are each independently the same as described in claim 1, $X_{52}$ is $N(Z_{52a})$, $C(Z_{52a})(Z_{52b})$, $Si(Z_{52a})(Z_{52b})$, O, or S, $X_{53}$ is $N(Z_{53a})$, $C(Z_{53a})(Z_{53b})$, $Si(Z_{53a})(Z_{53b})$, O, or S, and $Z_{52a}$, $Z_{52b}$, $Z_{53a}$, and $Z_{53b}$ are each independently the same as described in connection with $Z_{51a}$ in claim 1.

6. The heterocyclic compound of claim 1, wherein $X_{11}$ to $X_{13}$ are each N.

7. The heterocyclic compound of claim 1, wherein $R_4$ and $R_5$ are each independently selected from a phenyl group, a biphenyl group, a terphenyl group, a tetraphenyl group, a fluorenyl group, a dibenzocarbazolyl group, a dibenzofuranyl group, a dibenzothiophenyl group, a carbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group, and a dihydroacridinyl group, each unsubstituted or substituted with at least one $R_{10c}$, and $R_{10c}$ is the same as described in connection with $R_{10a}$ in claim 1.

8. The heterocyclic compound of claim 1, wherein, in Formula 1, a group represented by *-$(L_3)_{a3}$-*' is a single bond or a group represented by one selected from Formulae L-1 to L-5, a group represented by

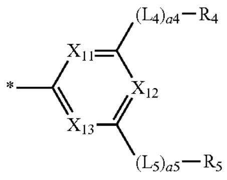

is a group represented by one selected from Formulae A1 to A38,

* in a group represented by

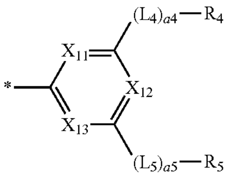

indicates a binding site to a neighboring atom, and in a group represented by *-$(L_3)_{a3}$-*', * indicates a binding site to a 6-membered ring on the left side in Formula 1, and *' indicates a binding site to a 6-membered ring on the right side in Formula 1:

L-1

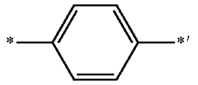

L-2

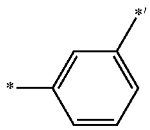

L-3

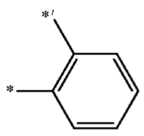

-continued

L-4

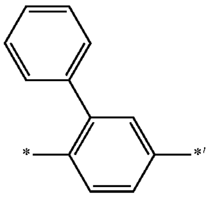

L-5

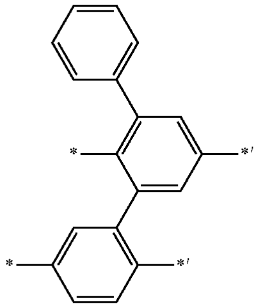

A1

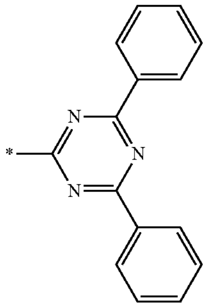

A2

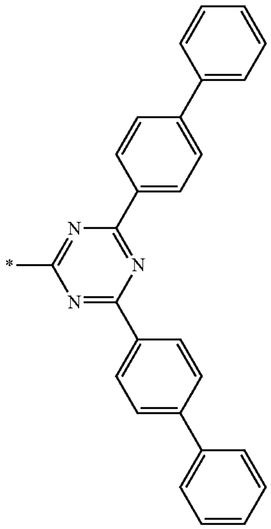

-continued
A3
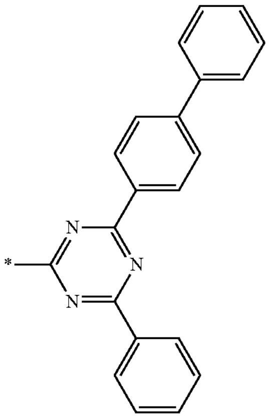
A4
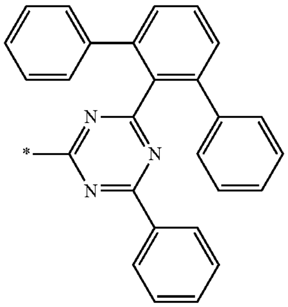
A5
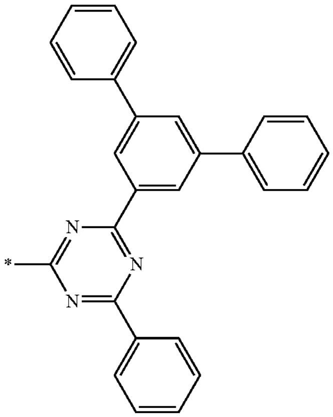
A6
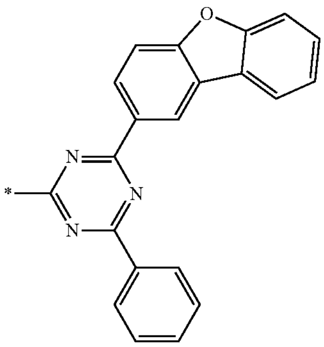
-continued
A7
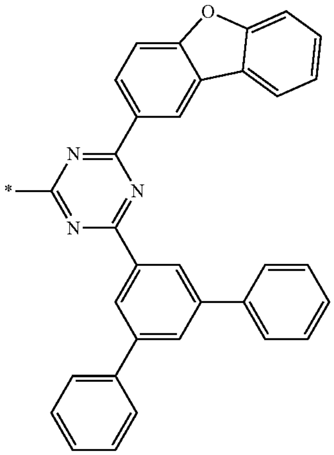
A8
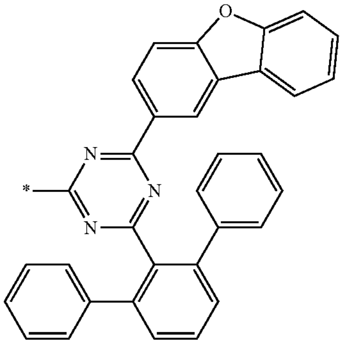
A9
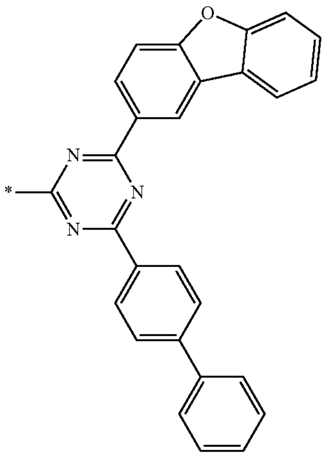

-continued
A10
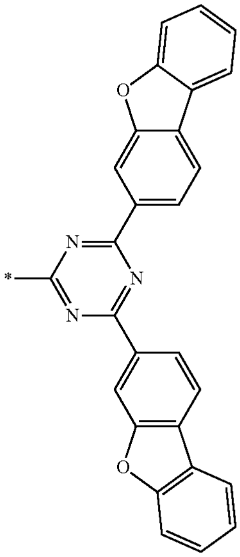
A11
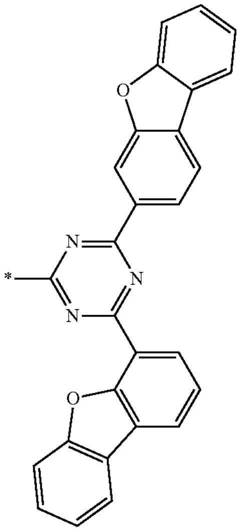
A12
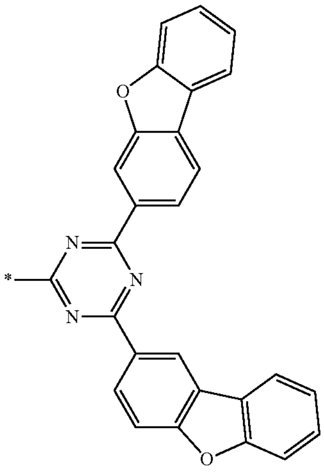
-continued
A13
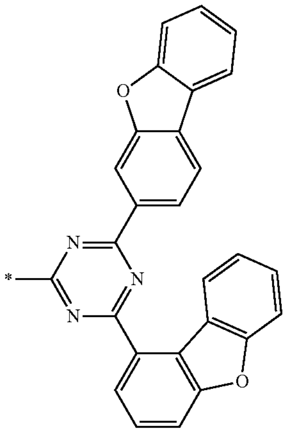
A14
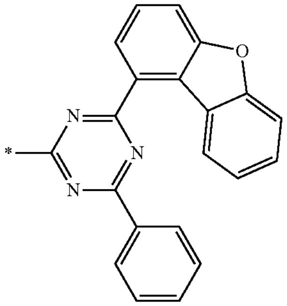
A15
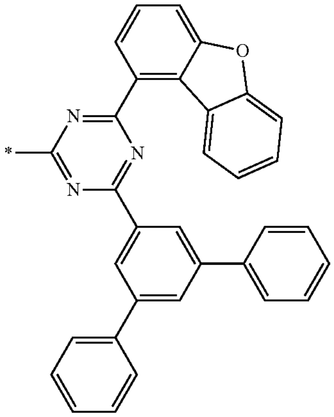
A16
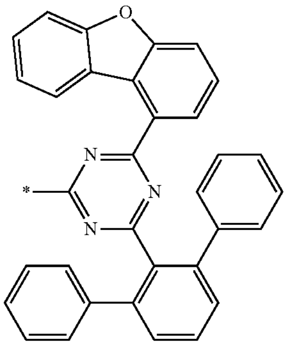

-continued
A17
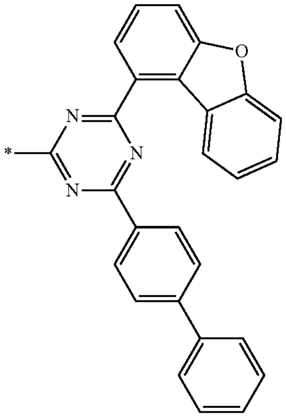
A18
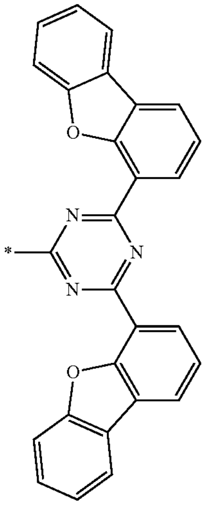
A19
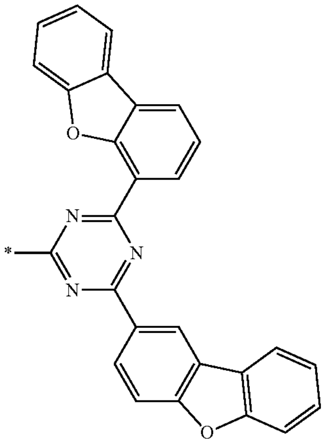
-continued
A20
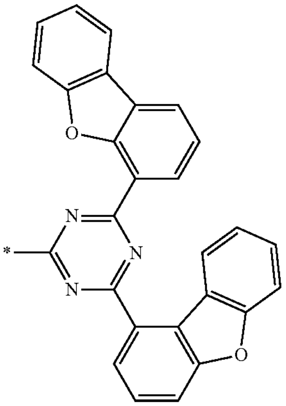
A21
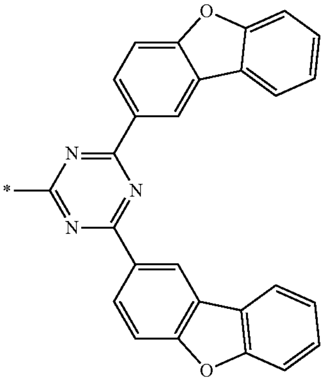
A22
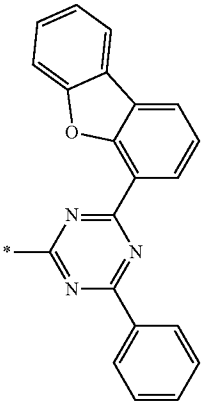

-continued
A23
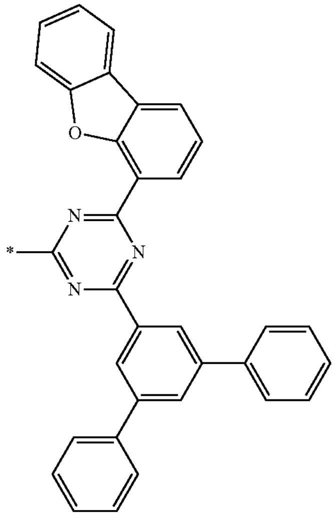
A24
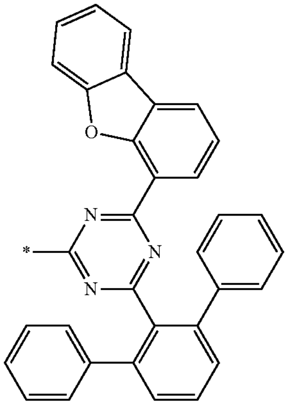
A25
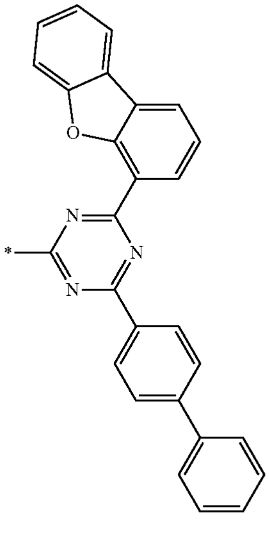
-continued
A26
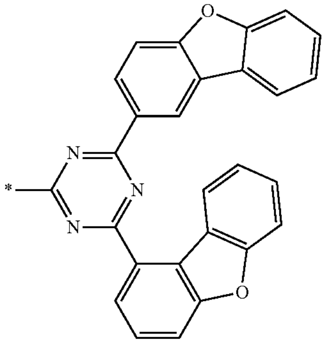
A27
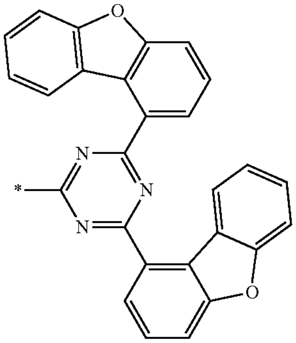
A28
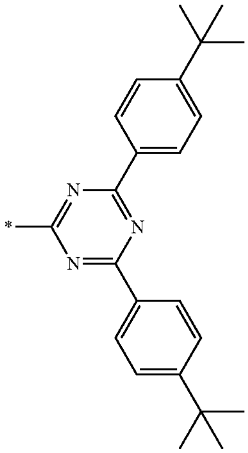
A29
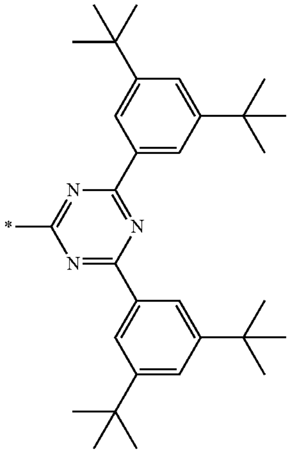

-continued
A30
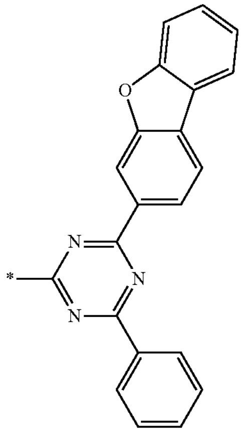
A31
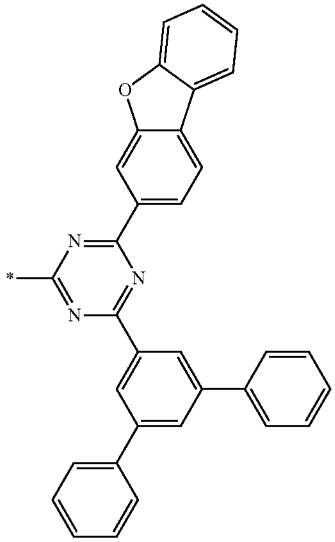
A32
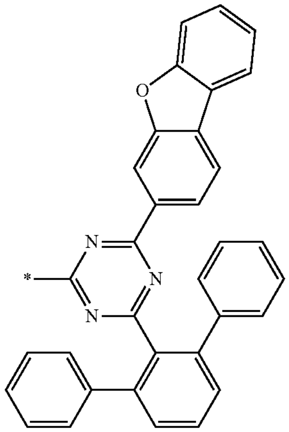
-continued
A33
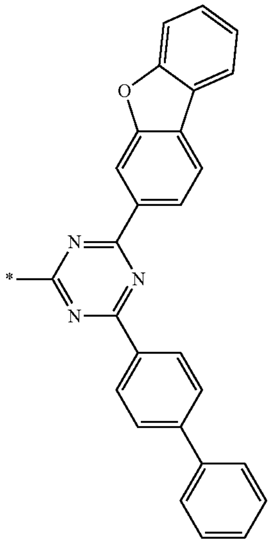
A34
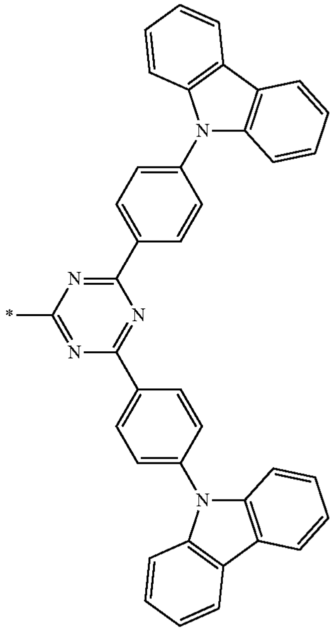
A35
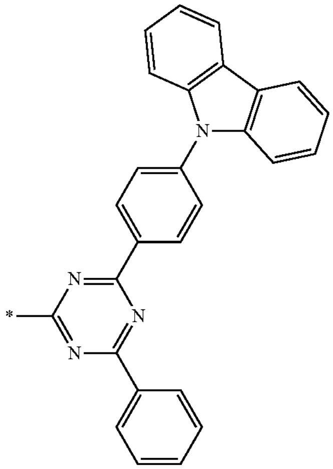

-continued

A36

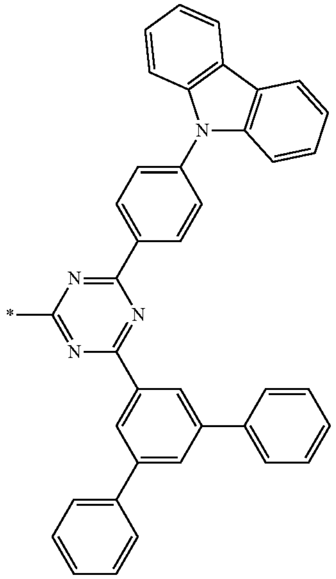

A37

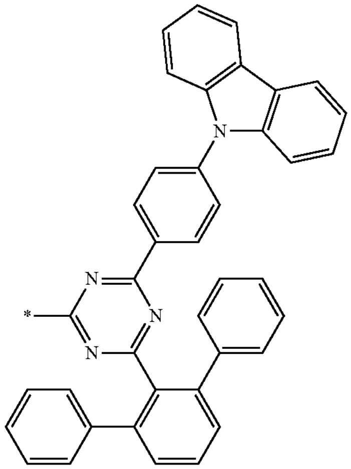

A38

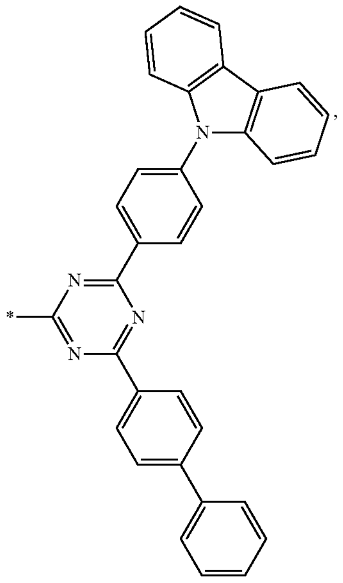

wherein, in the formulae above, * and *' each indicate a binding site to a neighboring atom.

9. The heterocyclic compound of claim 1, wherein a difference between a singlet energy level of the heterocyclic compound and a triplet energy level of the heterocyclic compound is in a range of about 0 electron volts to about 0.5 electron volts, and the singlet energy level and the triplet energy level are evaluated by using a density functional theory method structurally optimized at a level of B3LYP/6-31G(d,p).

10. An organic light-emitting device comprising:

a first electrode;

a second electrode; and an organic layer disposed between the first electrode and the second electrode, wherein the organic layer comprises an emission layer, the emission layer comprises a host and a dopant, the dopant comprises the heterocyclic compound represented by Formula 1, and an amount of the host is larger than an amount of the dopant.

11. The organic light-emitting device of claim 10, wherein the first electrode is an anode, the second electrode is a cathode, the organic layer comprises a hole transport region disposed between the first electrode and the emission layer and an electron transport region disposed between the emission layer and the second electrode, wherein the hole transport region comprises a hole injection layer, a hole transport layer, an electron blocking layer, a buffer layer, or any combination thereof, and wherein the electron transport region comprises a hole blocking layer, an electron transport layer, an electron injection layer, or any combination thereof.

12. The organic light-emitting device of claim 10, wherein the emission layer emits blue light.

13. The organic light-emitting device of claim 10, wherein a ratio of a delayed fluorescence component emitted from the heterocyclic compound of the emission layer to a total emission component emitted from the emission layer is 90% or more.

14. The organic light-emitting device of claim 10, wherein the host comprises at least one selected from a first material and a second material, the first material comprises at least one π electron-rich cyclic group and does not comprise an electron transport moiety, the second material comprises at least one π electron-rich cyclic group and at least one electron transport moiety, and the electron transport moiety is selected from a cyano group, a π electron-depleted nitrogen-containing cyclic group, and a group represented by one selected from the following formulae:

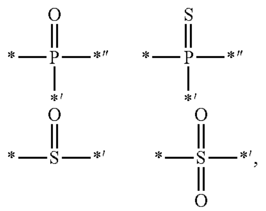

wherein *, *', and *" in the formulae each indicate a binding site to a neighboring atom.

15. The organic light-emitting device of claim 14, wherein the first material comprises a cyano group-free benzene group and a cyano group-free carbazole group, and the second material comprises at least one selected from a cyano group-containing benzene group and a cyano group-containing carbazole group.

* * * * *